(12) United States Patent
Booth et al.

(10) Patent No.: US 7,094,798 B1
(45) Date of Patent: Aug. 22, 2006

(54) INHIBITORS OF CHECKPOINT KINASES (WEE1 AND CHK1)

(75) Inventors: Richard John Booth, Ann Arbor, MI (US); Ellen Myra Dobrusin, Ann Arbor, MI (US); Alan Kraker, Ann Arbor, MI (US); Lorna Helen Mitchell, Dexter, MI (US); William Alexander Denny, Auckland (NZ); Jeffrey Bruce Smaill, Auckland (NZ); Andrew Mark Thompson, Auckland (NZ); Florence Oliver Joseph McCarthy, Auckland (NZ); Ho Huat Lee, Auckland (NZ); Brian Desmond Palmer, Auckland (NZ)

(73) Assignee: Pfizer Inc, New York, NY (US)

( * ) Notice: Subject to any disclaimer, the term of this patent is extended or adjusted under 35 U.S.C. 154(b) by 281 days.

(21) Appl. No.: 10/424,228

(22) Filed: Apr. 25, 2003

Related U.S. Application Data

(60) Provisional application No. 60/375,806, filed on Apr. 26, 2002.

(51) Int. Cl.
*A61K 31/403* (2006.01)
*C07D 209/88* (2006.01)
(52) U.S. Cl. ............ 514/410; 548/420; 514/410
(58) Field of Classification Search ............ 548/420; 514/410
See application file for complete search history.

(56) References Cited

U.S. PATENT DOCUMENTS 4,912,107 A * 3/1990 Kleinschroth et al. ... 514/232.5

5,728,709 A 3/1998 Ikuina et al.

FOREIGN PATENT DOCUMENTS

| EP | 0 362 695 | 4/1990 |
|---|---|---|
| EP | 0 695 755 | 2/1996 |
| WO | WO 00/16781 | 3/2000 |
| WO | WO 01/85686 | 11/2001 |
| WO | WO 03/029482 | 4/2003 |

* cited by examiner

*Primary Examiner*—Kamal A. Saeed
*Assistant Examiner*—Janet L Coppins
(74) *Attorney, Agent, or Firm*—Steve Zelson; David L. Kershner

(57) ABSTRACT

This invention relates to pyrrolocarbazole derivatives according formula I wherein $R^1$, $R^2$, $R^7$, $R^8$, $R^9$, X and Y are as defined in the specification wherein said derivatives specifically inhibit one or both of the checkpoint kinases Wee1 and Chk1

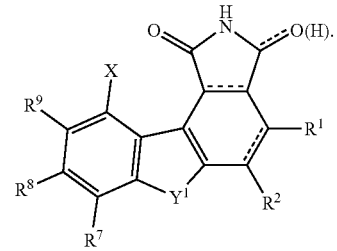

9 Claims, 4 Drawing Sheets

Figure I. Western blot of total Cdc2 and phosphotyrosine 15 from L1210 tumor treated in vivo with Compound of Example 80

INHIBITORS OF CHECKPOINT KINASES (WEE1 AND CHK1)

This application claims the benefit of priority to U.S. provisional application Ser. No. 60/375,806 filed Apr. 26, 2002.

FIELD OF THE INVENTION

This invention relates to small chemical molecules that specifically inhibit one or both of the checkpoint kinases Wee1 and Chk1.

BACKGROUND OF THE INVENTION

The proper orchestration of the steps required for orderly progression of the cell through the cell cycle requires a number of signaling pathways within cells. Many of these pathways utilize protein kinases to effect the transmission of crucial signals at the appropriate time and intracellular location. Cell cycle kinases are naturally occurring enzymes involved in regulation of the cell cycle which is generally divided into four segments: $G_1$ (gap1), S (DNA systhesis), $G_2$ (gap 2) and M (mitosis). Some of these kinases are responsible for inhibiting the cell's normal progression through cell division, while others are normally active in promoting the progression of cells through the cell cycle leading to cell division. Increased activity or temporally abnormal activation of these kinases has been shown to result in development of tumors and other proliferative disorders.

One of the protein kinases involved is a tyrosine specific kinase, Wee1, that has as its substrate another kinase complex called Cdc2/cyclinB. Wee1 kinase is a regulatory kinase that has Cdc2/cyclinB as its substrate and when Wee1 is active, it phosphorylates a specific tyrosine (Tyr15) on Cdc2 that causes an inactivation of the Cdc2/cyclinB complex which in turn results in a pause or checkpoint in the cell cycle at the $G_2$ and M transition. The kinase activity of Cdc2/cyclinB is absolutely required for cells to progress through the $G_2$ stage of the cell division cycle to the M (or mitotic) phase where two daughter cells are formed from the division of the parent cell. Under normal circumstances, as cells are progressing through the cell cycle, the Cdc2/cyclinB complex is assembled in late S phase and through $G_2$. Normally, Wee1 is active and thus phosphorylates the Cdc2/cyclinB complex until the end of $G_2$ when all of the necessary components have been synthesized for the entry of cells into M phase. Wee1 activity then diminishes, a phosphatase removes the inhibitory phosphorylation from Tyr15 of Cdc2/cyclinB, the complex becomes activated and cells move into M phase where the replicated DNA is divided and the daughter cells are formed. Inhibition of Wee1 results in no inhibitory phosphorylation of Tyr15 on Cdc2/cyclinB and the potentially inappropriate and premature entry of the cell into mitosis.

In addition to regulation of the transition of cells between the different phases of the cell cycle under normal conditions, the cell cycle transitions are regulated in response to damage to DNA presumably giving cells opportunities either to repair potentially genotoxic DNA damage before replication using a damaged DNA template or to permanently exit the cell cycle and die.

Another kinase of interest named Chk1 participates in this DNA damage dependent signaling pathway by phosphorylating a phosphatase called Cdc25C which when itself is active and co-localized with Cdc2/cyclinB in the nucleus, dephosphorylates Tyr15 and causes the activation of the Cdc2/cyclinB complex. The Chk1 mediated phosphorylation of Cdc25C causes Cdc25C to be exported from the nucleus at which point it is no longer able to dephosphorylate and thus activate Cdc2/cyclinB. Therefore, if Chk1 is active (in response to DNA damage) it will indirectly contribute to the inactivation of Cdc2/cyclinB (whose activity is required for progression into M phase) through the preservation of the inactivating phosphorylation of Tyr15 on Cdc2/cyclinB. Conversely, inhibition of Chk1 would result in the dephosphorylation of Cdc2/cyclinB by the phosphatase Cdc25C in the nucleus (not exported to the cytoplasm since it is not phosphorylated by Chk1) and the consequent activation of Cdc2/cyclinB with the accompanying entry of the cells in mitosis.

Inhibition of Wee1 or Chk1 or both kinases in the presence of DNA damaged by conventional DNA-directed chemotherapeutic agents or by radiation presents an opportunity to utilize cellular regulatory pathways to inappropriately and prematurely cause cells to progress into M phase. Such cells may be less likely to survive and further divide since the commitment to M phase was made in the presence of potentially catastrophically damaged DNA (Alan J. Kraker and Robert N. Booher, "New Cell Cycle Targets,", *Ann. Rep. Med. Chem.*, 1999; 34:247–256).

Small molecule inhibitors of Wee1 kinase have been reported, WO 0119825 and Cancer Res. (2001), 61(22), 8211–8217. Small molecule inhibitors of Chk1 kinase have also been reported W00016781, Cancer Res. (2000), 60(3), 566–572.

Pyrrolocarbazole derivatives are known to have inhibitory activity against Protein kinase c and anti tumor activity (U.S. Pat. No. 4,912,107) but compared to the compounds of the present invention, the compounds disclosed in U.S. Pat. No. 4,912,107 have very low checkpoint kinase abrogator activity. Pyrrolocarbazole derivatives are also known to stimulate platelet production (WO96/28447) and to promote thrombopoiesis (WO9809967). EP 0695755 discloses another pyrrolocarbazole derivative having Protein kinase c activity. U.S. Pat. No. 5,166,204 discloses antitumor isoindole derivatives having a linkage or lower alkylene group bonded to the 2 and 3 or 3 and 4 of a carbazole skeleton. U.S. Pat. No. 5,728,709 discloses pyrrolocarbazole derivatives that stimulate platelet production. WO01/85686 also discloses pyrrolocarbazole derivatives.

However, there are no reports that any type of pyrrolocarbazole inhibits either Wee1 kinase or Chk1 kinase. Nor have there been any reports that any type of pyrrolocarbazole inhibits both Wee1 kinase and Chk1 kinase.

SUMMARY OF THE INVENTION

Compounds claimed are of the general structure described by Formula I

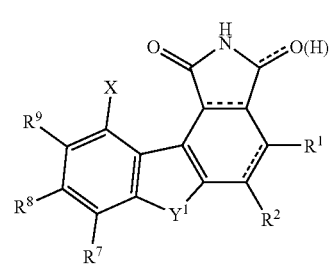

Wherein

Each dashed line represents an optional bond;

$R^1$ is hydrogen, halogen, $C_1$–$C_8$ alkyl, $NR^5R^6$ or an aryl or heteroaryl ring optionally substituted with up to five substituents selected from halogen, alkyl, haloalkyl, hydroxyl, nitro, cyano, C(O)R$^3$, OR$^3$, S(O)$_m$R$^3$, NR$^3$R$^4$, OC(O)R$^3$, NR$^3$(CO)OR$^4$, CH$_2$NR$^3$R$^4$, CH$_2$OR$^3$, COOR$^3$, CONR$^3$R$^4$, NR$^3$COR$^4$, SO$_2$NR$^3$R$^4$, CONHSO$_2$R$^3$, NR$^3$S(O)$_m$R$^4$, NHCONR$^3$R$^4$, NR$^3$CONHR$^4$; or a cycloalkyl or cycloalkenyl ring optionally substituted with up to five substituents selected from, halogen, alkyl, haloalkyl, hydroxyl, nitro, cyano, C(O)R$^3$, OR$^3$, S(O)$_m$R$^3$, NR$^3$R$^4$; OC(O)R$^3$, NR$^3$(CO)OR$^4$, CH$_2$NR$^3$R$^4$, CH$_2$OR$^3$, COOR$^3$, CONR$^3$R$^4$, NR$^3$COR$^4$, SO$_2$NR$^3$R$^4$, CONHSO$_2$,R$^3$, NR$^3$S(O)$_m$R$^4$, NHCONR$^3$R$^4$, NR$^3$CONHR$^4$; or a heterocyclic ring optionally substituted with up to five substituents selected from, halogen, alkyl, haloalkyl, hydroxyl, nitro, cyano, C(O)R$^3$, OR$^3$, S(O)$_m$R$^3$, NR$^3$R$^4$, OC(O)R$^3$, NR$^3$(CO)OR$^4$, CH$_2$NR$^3$R$^4$, CH$_2$OR$^3$, COOR$^3$, CONR$^3$R$^4$, NR$^3$COR$^4$, SO$_2$NR$^3$R$^4$, CONHSO$_2$, R$^3$, NR$^3$S(O)$_m$R$^4$, NHCONR$^3$R$^4$, NR$^3$CONHR$^4$;

m is 0–2;

X is hydrogen or halogen;

Y$^1$ is O, S(O)$_m$, or NR$^{10}$;

R$^9$ is hydrogen, hydroxyl, halogen, NR$^3$C(O)R$^4$, NHCONR$^3$R$^4$, (C=NR$^3$)NHR$^4$, NH(C=NR$^3$)NHR$^4$, NH(C=NH)NR$^3$R$^4$, NH(C=O)O R$^3$, NR$^5$R$^6$, (CR$^5$R$^6$)$_r$—Z;

r is 0–6;

R$^2$, R$^7$, R$^8$ and R$^{10}$ are in each instance independently selected from ((CR$^5$, R$^6$)$_n$T)$_a$(CR$^{11}$ R$^{12}$)$_b$)—Z wherein the sum of n, a and b is in each instance less than 10;

T may be absent, or, when present, is in each instance independently selected from O, CONR$^3$, CONHSO$_2$, S(O)$_m$, NR$^3$, NR$^{3O}$, OS(O)$_m$, S(O)$_m$O, NR$^3$S(O)$_2$, or S(O)$_2$NR$^3$;

n is in each instance independently 0–6;

a is in each instance independently 0–6;

b is in each instance independently 0–6;

Z is selected from hydrogen, halogen, alkyl, haloalkyl, cycloalkyl, cycloalkenyl, heterocyclyl, aryl, heteroaryl, cyano, nitro, hydroxy, C(O)R$^3$, CONHSO$_2$R$^3$, OR$^3$, S(O)$_m$R$^3$, OSO$_2$R$^3$, NR$^3$R$^4$, CO$_2$R$^3$, CONR$^3$, R$^4$, NR$^3$COR$^4$, SO$_2$NR$^3$R$^4$, OPO(OR$^3$)(OR$^4$), CH=CR$^3$R$^4$, CCR$^3$, (C=NR$^3$)NH R$^4$, NH(C=NR$^3$)NHR$^4$, NH(C=NH)NR$^3$R$^4$, wherein the alkyl, cycloalkyl, cycloalkenyl, heterocyclyl, aryl or heteroaryl group may be substituted with up to four groups independently selected from halogen, alkyl, hydroxyl, nitro, cyano, OR$^3$, S(O)$_m$R$^3$, NR$^3$R$^4$, OC(O)R$^3$, NR$^3$(CO)OR$^4$, C(O)R$^3$, COOR$^3$, CONR$^3$R$^4$, NR$^3$COR$^4$, SO$_2$NR$^3$R$^4$, CONHSO$_2$R$^3$ NR$^3$S(O)$_m$R$^4$, CH$_2$NR$^3$R$^4$, CH$_2$OR$^3$ NHCONR$^3$R$^4$, NR$^3$CONHR$^4$;

R$^5$, R$^6$, R$^{11}$ and R$^{12}$ are in each instance independently selected from hydrogen, hydroxyl, alkyl, haloalkyl, cycloalkyl, cycloalkenyl, aryl, heteroaryl, heterocyclyl, halogen, cyano, nitro, CH$_2$NR$^3$R$^4$, CH$_2$OR$^3$, C(O)R$^3$, OR$^3$, S(O)$_m$R$^3$, NR$^3$R$^4$, COOR$^3$, CONR$^3$R$^4$, SO$_2$NR$^3$R$^4$, NHCONR$^3$R$^4$, NR$^3$CONHR$^4$;

wherein the alkyl, haloalkyl, cycloalkyl, cycloalkenyl, heterocyclyl, aryl or heteroaryl group may be substituted with up to four groups independently selected from halogen, alkyl, hydroxyl, nitro, cyano, OR$^3$, S(O)$_m$R$^3$, NR$^3$R$^4$, OC(O)R$^3$, NR$^3$(CO)OR$^4$, C(O)R$^3$, COOR$^3$, CONR$^3$R$^4$, NR$^3$COR$^4$, SO$_2$NR$^3$R$^4$, CONHSO$_2$R$^3$ NR$^3$S(O)$_m$R$^4$, NHCONR$^3$R$^4$, NR$^3$CONHR$^4$;

R$^5$ and R$^6$ or R$^{11}$ and R$^{12}$ together with the carbon atom to which they are attached may form a carbonyl group; or together with the carbon or heteratom to which they are attached may form a cycloalkyl or heterocyclyl group, said carbonyl, cycloalkyl or heterocyclyl group may be substituted with up to four groups independently selected from halogen, hydroxyl, nitro, cyano, alkyl, haloalkyl, halogen, alkyl, nitro, cyano, OR$^3$, S(O)$_m$R$^3$, NR$^3$R$^4$, OC(O) R$^3$, NR$^3$(CO)OR$^4$. C(O)R$^3$, COOR$^3$, CONR$^3$R$^4$, NR$^3$COR$^4$, SO$_2$NR$^3$R$^4$, CONHSO$_2$R$^3$ NR$^3$S(O)$_m$R$^4$, NHCONR$^3$R$^4$, NR$^3$CONHR$^4$;

R$^3$, R$^4$ are independently selected from hydrogen, alkyl, haloalkyl or a substituted or unsubstituted carbocyclic group selected from cycloalkyl, cycloalkenyl, heterocyclyl, aryl, and heteroaryl, wherein the said alkyl, or a substituted carbocyclic group may be substituted with up to 4 groups selected from halogen, hydroxyl, nitro, cyano, alkyl, haloalkyl, alkyloxy, carboxy, COOH, CONH$_2$, NHCOCH$_3$, N(CH$_3$)$_2$, NHCH$_3$, thiomethyl, thioethyl, SOCH$_3$, SO$_2$CH$_3$;

R$^3$ and R$^4$ together with the carbon atom or heteroatom to which they are attached may form a cycloalkyl or heterocyclyl group substituted with up to four groups independently selected from halogen, hydroxyl, nitro, cyano, alkyl, haloalkyl, alkyloxy, formyl, carboxy, acetyl, CH$_2$NH$_2$, CH$_2$OH, COOH, CONH$_2$, NHCOCH$_3$, N(CH$_3$)$_2$, thiomethyl, thioethyl, SOCH$_3$, SO$_2$CH$_3$, alkoxycarbonyl, alkylcarbonyl, alkynylamino, aminoalkyl, aminoalkylcarbonyl, amino, mono- or dialkylamino, or R$^3$ and R$^4$ together with the nitrogen to which they are attached may form a heterocyclic ring containing 3–8 members, up to four of which members are optionally carbonyl groups or heteroatoms independently selected from oxygen, sulfur, S(O), S(O)$_2$, and nitrogen, wherein the carbocyclic group is unsubstituted or substituted with up to four groups independently selected from halogen, hydroxy, hydroxyalkyl, alkyl, haloalkyl, alkoxy, alkoxycarbonyl, alkylcarbonyl, alkynylamino, aminoalkyl, aminoalkylcarbonyl, amino, mono- or dialkylamino.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

DETAILED DESCRIPTION OF THE INVENTION

Figure 1:
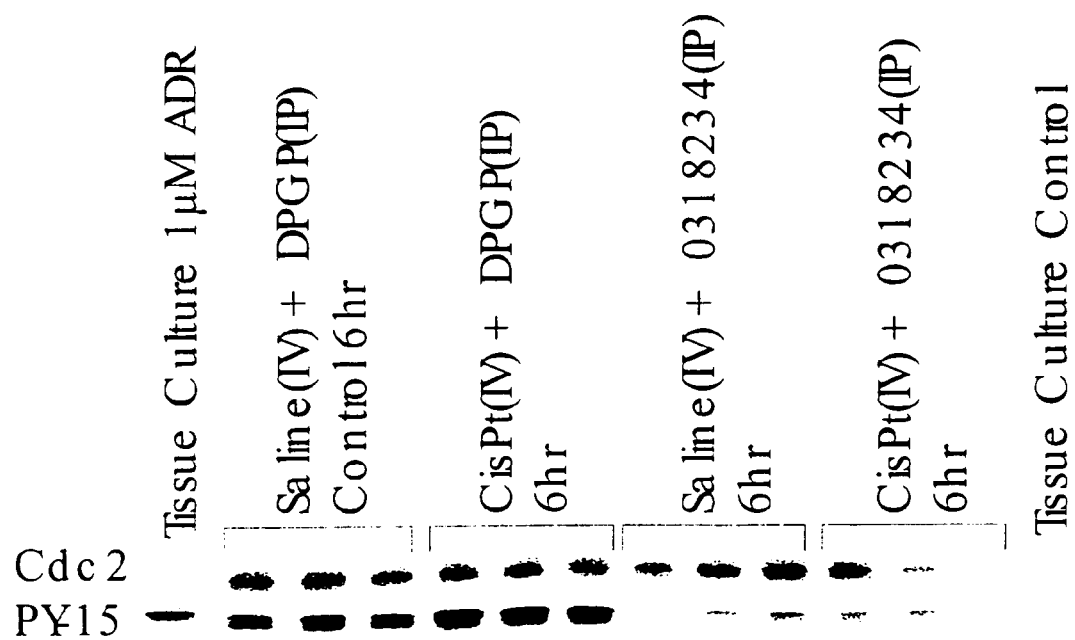
FIG. 1 represents a Western blot of tumor cells treated in vivo with cisplatin and the Compound of Example 80.
Figure 2:
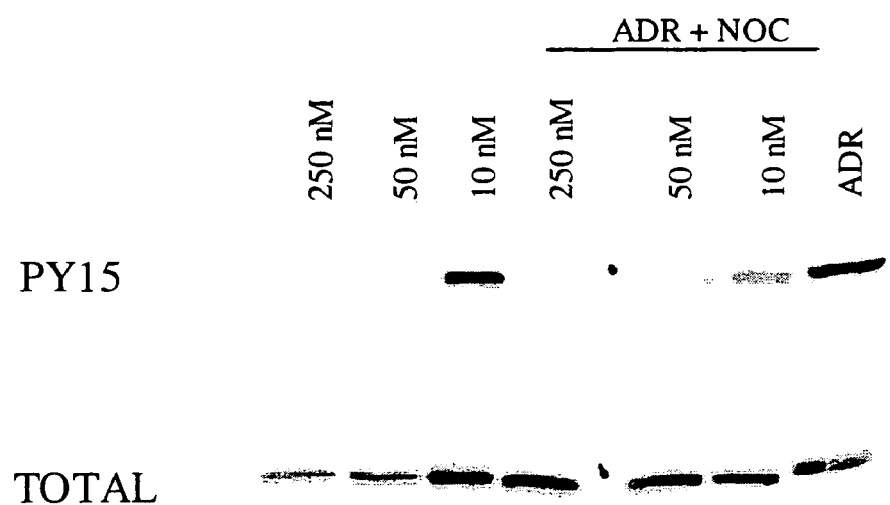
FIG. 2 represent a Western Blot of cells treated in vitro with Adriamycin and the Compound of Example 80
Figure 3:
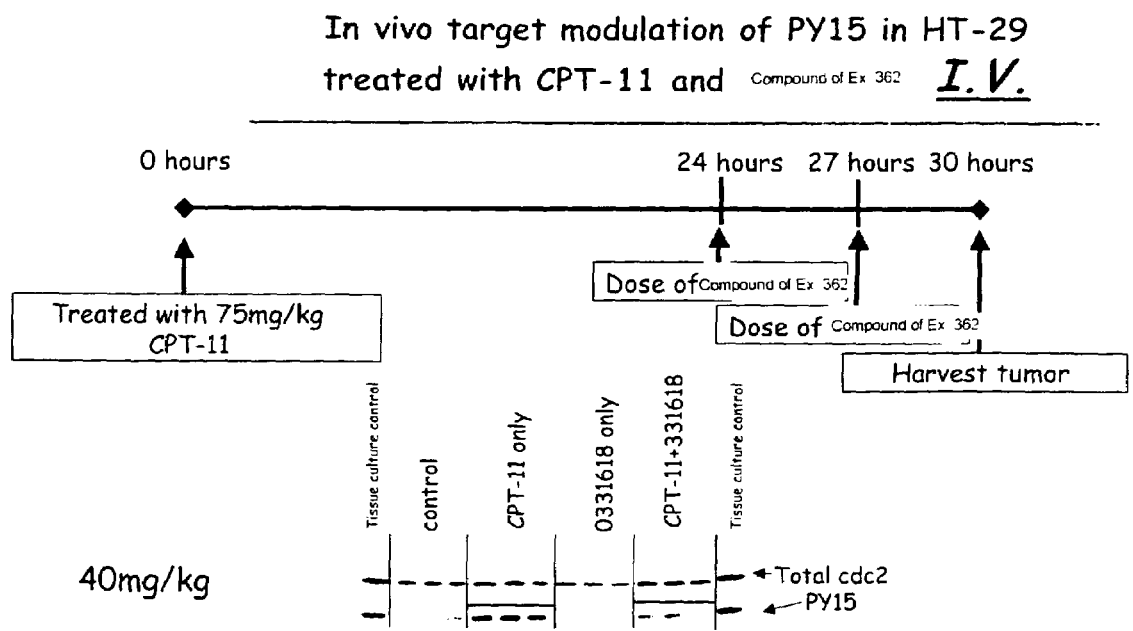
FIG. 3 represents a Western blot of tumor cells treated in vivo with cpt-11 and the Compound of Example 362.
Figure 4:
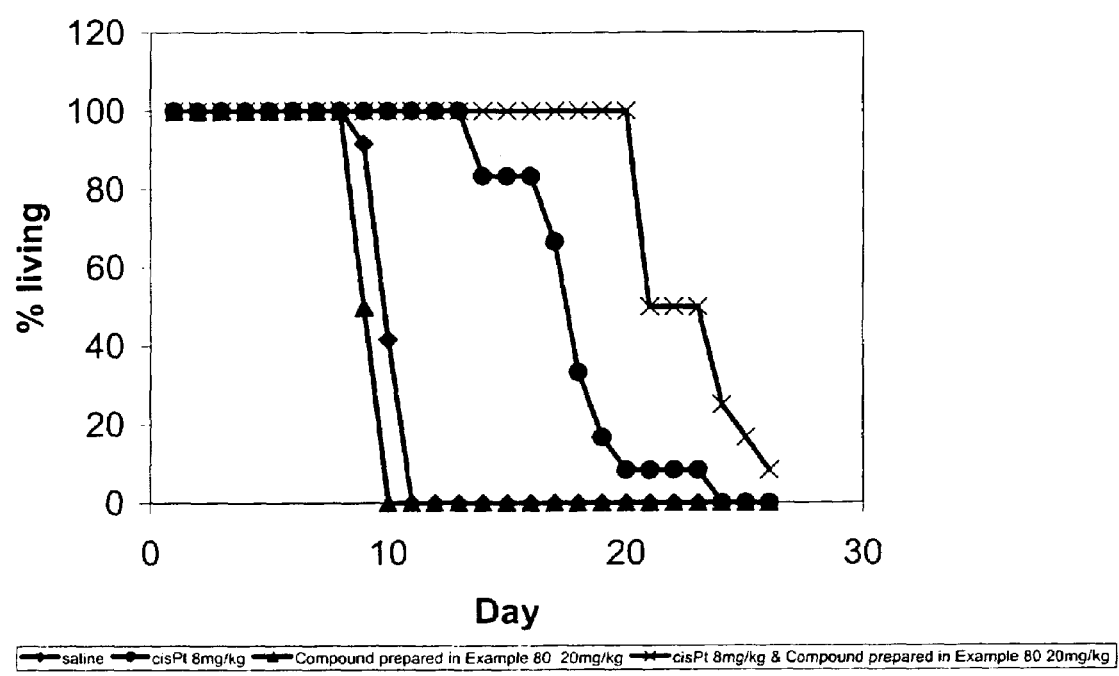
FIG. 4 represents a graph of life span enhancement in animals treated with the Compound of Example 80

Compounds of the present invention are of the general structure described by Formula I

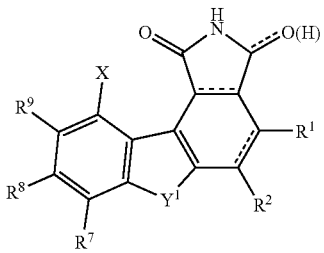

Wherein

Each dashed line represents an optional bond;

$R^1$ is hydrogen, halogen, $C_1$–$C_8$ alkyl; $NR^5R^6$ or an aryl or heteroaryl ring optionally substituted with up to five substituents selected from halogen, alkyl, haloalkyl, hydroxyl, nitro, cyano, $C(O)R^3$, $OR^3$, $S(O)_mR^3$, $NR^3R^4$, $OC(O)R^3$, $NR^3(CO)OR^4$, $CH_2NR^3R^4$, $CH_2OR^3$, $COOR^3$, $CONR^3R^4$, $NR^3COR^4$, $SO_2NR^3R^4$, $CONHSO_2R^3$, $NR^3S(O)_mR^4$, $NHCONR^3R^4$, $NR^3CONHR^4$; or a cycloalkyl or cycloalkenyl ring optionally substituted with up to five substituents selected from, halogen, alkyl, haloalkyl, hydroxyl, nitro, cyano, $C(O)R^3$, $OR^3$, $S(O)_mR^3$, $NR^3R^4$, $OC(O)R^3$, $NR^3(CO)OR^4$, $CH_2NR^3R^4$, $CH_2OR^3$, $COOR^3$, $CONR^3R^4$, $NR^3COR^4$, $SO_2NR^3R^4$, $CONHSO_2R^3$, $NR^3S(O)_mR^4$, $NHCONR^3R^4$, $NR^3CONHR^4$; or a heterocyclic ring optionally substituted with up to five substituents selected from, halogen, alkyl, haloalkyl, hydroxyl, nitro, cyano, $C(O)R^3$, $OR^3$, $S(O)_mR^3$, $NR^3R^4$, $OC(O)R^3$, $NR^3(CO)OR^4$, $CH_2NR^3R^4$, $CH_2OR^3$, $COOR^3$, $CONR^3R^4$, $NR^3COR^4$, $SO_2NR^3R^4$, $CONHSO_2R^3$, $NR^3S(O)_mR^4$ $NHCONR^3R^4$, $NR^3CONHR^4$;

m is 0–2;

X is hydrogen or halogen;

$Y^1$ is O, $S(O)_m$, or $NR^{10}$;

$R^9$ is hydrogen, hydroxyl, halogen, $NR^3C(O)R^4$, $NHCONR^3R^4$, $(C=NR^3)NHR^4$, $NH(C=N\ R^3)NH\ R^4$, $NH(C=NH)N\ R^3$, $R^4$, $NH(C=O)O\ R^3$, $NR^5R^6$, $(CR^5R^6)_r$—Z;

r is 0–6;

$R^2$, $R^7$, $R^8$ and $R^{10}$ are in each instance independently selected from $((CR^5, R^6)_nT)_a(CR^{11}R^{12})_b)$—Z wherein the sum of n, a and b is in each instance less than 10;

T may be absent, or, when present, is in each instance independently selected from O, $CONR^3$, $CONHSO_2$, $S(O)_m$, $NR^3$, $NR^3$—O, O—$S(O)_m$, $S(O)_m$—O, $NR^3$—S $(O)_2$, or $S(O)_2$—$NR^3$;

n is in each instance independently 0–6;

a is in each instance independently 0–6;

b is in each instance independently 0–6;

Z is selected from hydrogen, halogen, alkyl, haloalkyl, cycloalkyl, cycloalkenyl, heterocyclyl, aryl, heteroaryl, cyano, nitro, hydroxy, $C(O)R^3$, $CONHSO_2R^3$, $OR^3$, $S(O)_mR^3$, $OSO_2R^3$, $NR^3R^4$, $CO_2R^3$, $CONR^3R^4$, $NR^3COR^4$, $SO_2NR^3R^4$, $OPO(OR^3)(OR^4)$, $CH=CR^3R^4$, $CCR^3$, $(C=NR^3)NHR^4$, $NH(C=NR^3)NHR^4$, $NH(C=NH)NR^3R^4$, wherein the alkyl, cycloalkyl, cycloalkenyl, heterocyclyl, aryl or heteroaryl group may be substituted with up to four groups independently selected from halogen, alkyl, hydroxyl, nitro, cyano, $OR^3$, $S(O)_mR^3$, $NR^3R^4$, $OC(O)R^3$, $NR^3(CO)OR^4$, $C(O)R^3$, $COOR^3$, $CONR^3R^4$, $NR^3COR^4$, $SO_2NR^3R^4$, $CONHSO_2R^3$ $NR^3S(O)_mR^4$, $CH_2NR^3R^4$, $CH_2OR^3$ $NHCONR^3R^4$, $NR^3CONHR^4$;

$R^5$, $R^6$, $R^{11}$ and $R^{12}$ are in each instance independently selected from hydrogen, hydroxyl, alkyl, haloalkyl, cycloalkyl, cycloalkenyl, aryl, heteroaryl, heterocyclyl, halogen, cyano, nitro, $CH_2NR^3R^4$, $CH_2OR^3$, $C(O)R^3$, $OR^3$, $S(O)_mR^3$, $NR^3R^4$, $COOR^3$, $CONR^3R^4$, $SO_2NR^3R^4$, $NHCONR^3R^4$, $NR^3CONHR^4$;

wherein the alkyl, haloalkyl, cycloalkyl, cycloalkenyl, heterocyclyl, aryl or heteroaryl group may be substituted with up to four groups independently selected from halogen, alkyl, hydroxyl, nitro, cyano, $OR^3$, $S(O)_mR^3$, $NR^3R^4$, $OC(O)R^3$, $NR^3(CO)OR^4$, $C(O)R^3$, $COOR^3$, $CONR^3R^4$, $NR^3COR^4$, $SO_2NR^3R^4$, $CONHSO_2R^3$, $NR^3S(O)_mR^4$, $NHCONR^3R^4$, $NR^3CONHR^4$;

$R^5$ and $R^6$ or $R^{11}$ and $R^{12}$ together with the carbon atom to which they are attached may form a carbonyl group; or together with the carbon or heteroatom to which they are attached may form a cycloalkyl or heterocyclyl group, said carbonyl, cycloalkyl or heterocyclyl group may be substituted with up to four groups independently selected from halogen, hydroxyl, nitro, cyano, alkyl, haloalkyl, halogen, alkyl, nitro, cyano, $OR^3$, $S(O)_mR^3$, $NR^3R^4$, $OC(O)R^3$, $NR^3(CO)OR^4$, $C(O)R^3$, $COOR^3$, $CONR^3R^4$, $NR^3COR^4$, $SO_2NR^3R^4$, $CONHSO_2R^3$, $NR^3S(O)_mR^4$, $NHCONR^3R^4$, $NR^3CONHR^4$;

$R^3$, $R^4$ are independently selected from hydrogen, alkyl, haloalkyl or a substituted or unsubstituted carbocyclic group selected from cycloalkyl, cycloalkenyl, heterocyclyl, aryl, and heteroaryl, wherein the said alkyl, or a substituted carbocyclic group may be substituted with up to 4 groups selected from halogen, hydroxyl, nitro, cyano, alkyl, haloalkyl, alkyloxy, carboxy, COOH, $CONH_2$, $NHCOCH_3$, $N(CH_3)_2$, $NHCH_3$, thiomethyl, thioethyl, $SOCH_3$, $SO_2CH_3$;

$R^3$ and $R^4$ together with the carbon atom or heteroatom to which they are attached may form a cycloalkyl or heterocyclyl group substituted with up to four groups independently selected from halogen, hydroxyl, nitro, cyano, alkyl, haloalkyl, alkyloxy, formyl, carboxy, acetyl, $CH_2NH_2$, $CH_2OH$, COOH, $CONH_2$, $NHCOCH_3$, $N(CH_3)_2$, thiomethyl, thioethyl, $SOCH_3$, $SO_2CH_3$, alkoxycarbonyl, alkylcarbonyl, alkynylamino, aminoalkyl, aminoalkylcarbonyl, amino, mono- or dialkylamino, or $R^3$ and $R^4$ together with the nitrogen to which they are attached may form a heterocyclic ring containing 3–8 members, up to four of which members are optionally carbonyl groups or heteroatoms independently selected from oxygen, sulfur, S(O), $S(O)_2$, and nitrogen, wherein the carbocyclic group is unsubstituted or substituted with up to four groups independently selected from halogen, hydroxy, hydroxyalkyl, alkyl, haloalkyl, alkoxy, alkoxycarbonyl, alkylcarbonyl, alkynylamino, aminoalkyl, aminoalkylcarbonyl, amino, mono- or dialkylamino.

In one preferred embodiment of the invention the compound of Formula I is selected from the group consisting of:

4-(2-Chlorophenyl)-6-(3-hydroxypropyl)-9-methoxypyrrolo[3,4-c]carbazole-1,3(2H,6H)-dione;

4-(5-Amino-2-methoxyphenyl)-9-hydroxypyrrolo[3,4-c] carbazole-1,3(2H,6H)-dione;

9-Hydroxy-4-(2-hydroxyphenyl)-6-(3-hydroxypropyl)pyrrolo[3,4-c]carbazole-1,3(2H,6H)-dione;

4-(2-Chloro-6-methoxyphenyl)-9-hydroxy-6-[2-(4-morpholinyl)ethyl]pyrrolo[3,4-c]carbazole-1,3(2H,6H)-dione;
6-Benzyl-4-(2-chlorophenyl)-9-hydroxypyrrolo[3,4-c]carbazole-1,3(2H,6H)-dione;
9-Hydroxy-6-(3-hydroxypropyl)-4-phenylpyrrolo[3,4-c]carbazole-1,3(2H,6H)-dione;
9-Hydroxy-6-(6-hydroxyhexyl)-4-phenylpyrrolo[3,4-c]carbazole-1,3(2H,6H)-dione;
9-Hydroxy-6-methyl-4-phenylpyrrolo[3,4-c]carbazole-1,3(2H,6H)-dione;
4-(5-Amino-2-chlorophenyl)-9-hydroxypyrrolo[3,4-c]carbazole-1,3(2H,6H)-dione;
3-{[3-(4-(2-Chlorophenyl)-9-hydroxy-1,3-dioxo-2,3-dihydropyrrolo[3,4-c]carbazol-6(1H)-yl)propyl]amino}benzoic acid;
2-{[3-(4-(2-Chlorophenyl)-9-hydroxy-1,3-dioxo-2,3-dihydropyrrolo[3,4-c]carbazol-6 (1H)-yl)propyl]amino benzoic acid;
4-{[3-(4-(2-Chlorophenyl)-9-hydroxy-1,3-dioxo-2,3-dihydropyrrolo[3,4-c]carbazol-6(1H)-yl)propyl]amino}benzoic acid;
4-(2-Chlorophenyl)-6-{3-[(cis)-3,5-dimethylpiperazinyl]propyl}-9-hydroxypyrrolo[3,4-c]carbazole-1,3(2H,6H)-dione;
4-(2,6-Dichlorophenyl)-6-{3-[(cis)-3,5-dimethylpiperazinyl]propyl}-9-hydroxypyrrolo[3,4-c]carbazole-1,3(2H,6H)-dione;
6-(2-aminoethyl)-9-hydroxy-4-phenylpyrrolo[3,4-c]carbazole-1,3(2H,6H)-dione;
9-hydroxy-6-[2-(methylamino)ethyl]-4-phenylpyrrolo[3,4-c]carbazole-1,3(2H,6H)-dione;
6-(3-aminopropyl)-9-hydroxy-4-phenylpyrrolo[3,4-c]carbazole-1,3(2H,6H)-dione;
9-hydroxy-4-phenyl-6-[3-(1-pyrrolidinyl)propyl]pyrrolo[3,4-c]carbazole-1,3(2H,6H)-dione;
6-[3-(diethylamino)propyl]-9-hydroxy-4-phenylpyrrolo[3,4-c]carbazole-1,3(2H,6H)-dione;
9-hydroxy-4-phenyl-6-[3-(1-piperidinyl)propyl]pyrrolo[3,4-c]carbazole-1,3(2H,6H)-dione;
9-hydroxy-6-[3-(4-methyl-1-piperazinyl)propyl]-4-phenylpyrrolo[3,4-c]carbazole-1,3(2H,6H)-dione;
6-[6-(dimethylamino)hexyl]-9-hydroxy-4-phenylpyrrolo[3,4-c]carbazole-1,3(2H,6H)-dione;
9-hydroxy-6-[6-(4-methyl-1-piperazinyl)hexyl]-4-phenylpyrrolo[3,4-c]carbazole-1,3(2H,6H)-dione;
6-(2-aminoethyl)-4-(2-chlorophenyl)-9-hydroxypyrrolo[3,4-c]carbazole-1,3(2H,6H)-dione;
4-(2-chlorophenyl)-9-hydroxy-6-[3-(dimethylamino)ethyl]pyrrolo[3,4-c]carbazole-1,3(2H,6H)-dione;
4-(2-chlorophenyl)-9-hydroxy-6-[2-(1H-imidazol-1-yl)ethyl]pyrrolo[3,4-c]carbazole-1,3(2H,6H)-dione;
4-(2-chlorophenyl)-9-hydroxy-6-[2-(4-morpholinyl)ethyl]pyrrolo[3,4-c]carbazole-1,3(2H,6H)-dione;
4-(2-chlorophenyl)-9-hydroxy-6-[2-(4-methyl-1-piperazinyl)ethyl]pyrrolo[3,4-c]carbazole-1,3(2H,6H)-dione;
6-(2-anilinoethyl)-4-(2-chlorophenyl)-9-hydroxypyrrolo[3,4-c]carbazole-1,3(2H,6H)-dione;
4-(2,6-dichlorophenyl)-9-hydroxy-6-[3-(dimethylamino)ethyl]pyrrolo[3,4-c]carbazole-1,3(2H,6H)-dione;
4-(2,6-dichlorophenyl)-9-hydroxy-6-[2-(4-morpholinyl)ethyl]pyrrolo[3,4-c]carbazole-1,3(2H,6H)-dione;
4-(2,6-dichlorophenyl)-9-hydroxy-6-[2-(4-methyl-1-piperazinyl)ethyl]pyrrolo[3,4-c]carbazole-1,3(2H,6H)-dione;
6-(2-anilinoethyl)-4-(2,6-dichlorophenyl)-9-hydroxypyrrolo[3,4-c]carbazole-1,3(2H,6H)-dione;
4-(2-chlorophenyl)-9-hydroxy-6-[3-(methylamino)propyl]pyrrolo[3,4-c]carbazole-1,3(2H,6H)-dione;
4-(2-chlorophenyl)-6-[3-(dimethylamino)propyl]-9-hydroxypyrrolo[3,4-c]carbazole-1,3(2H,6H)-dione;
4-(2-chlorophenyl)-9-hydroxy-6-[3-(4-morpholinyl)propyl]pyrrolo[3,4-c]carbazole-1,3(2H,6H)-dione;
4-(2-chlorophenyl)-9-hydroxy-6-[3-(4-methyl-1-piperazinyl)propyl]pyrrolo[3,4-c]carbazole-1,3(2H,6H)-dione;
6-(3-anilinopropyl)-4-(2-chlorophenyl)-9-hydroxypyrrolo[3,4-c]carbazole-1,3(2H,6H)-dione;
4-(2,6-dichlorophenyl)-9-hydroxy-6-[3-(methylamino)propyl]pyrrolo[3,4-c]carbazole-1,3(2H,6H)-dione;
4-(2,6-dichlorophenyl)-6-[3-(dimethylamino)propyl]-9-hydroxypyrrolo[3,4-c]carbazole-1,3(2H,6H)-dione;
4-(2,6-dichlorophenyl)-9-hydroxy-6-[3-(1H-imidazol-1-yl)propyl]pyrrolo[3,4-c]carbazole-1,3(2H,6H)-dione;
4-(2,6-dichlorophenyl)-9-hydroxy-6-[3-(4-morpholinyl)propyl]pyrrolo[3,4-c]carbazole-1,3(2H,6H)-dione;
4-(2,6-dichlorophenyl)-9-hydroxy-6-[3-(4-methyl-1-piperazinyl)propyl]pyrrolo[3,4-c]carbazole-1,3(2H,6H)-dione;
6-(3-anilinopropyl)-4-(2,6-dichlorophenyl)-9-hydroxypyrrolo[3,4-c]carbazole-1,3(2H,6H)-dione;
9-Hydroxy-6-[3-(4-morpholinyl)propyl]-4-phenylpyrrolo[3,4-c]carbazole-1,3(2H,6H)-dione;
9-Hydroxy-6-[2-(4-morpholinyl)ethyl]-4-phenylpyrrolo[3,4-c]carbazole-1,3(2H,6H)-dione;
9-Hydroxy-6-[3-(1H-imidazol-1-yl)propyl]-4-phenylpyrrolo[3,4-c]carbazole-1,3(2H,6H)-dione;
9-Hydroxy-6-[2-(1H-imidazol-1-yl)ethyl]-4-phenylpyrrolo[3,4-c]carbazole-1,3(2H,6H)-dione;
9-Hydroxy-6-[3-(methylamino)propyl]-4-phenylpyrrolo[3,4-c]carbazole-1,3(2H,6H)-dione;
9-Hydroxy-4-phenyl-6-[3-(1-piperazinyl)propyl]pyrrolo[3,4-c]carbazole-1,3(2H,6H)-dione;
6-[3-(Benzylamino)propyl]-9-hydroxy-4-phenylpyrrolo[3,4-c]carbazole-1,3(2H,6H)-dione;
6-(3-Anilinopropyl)-9-hydroxy-4-phenylpyrrolo[3,4-c]carbazole-1,3(2H,6H)-dione;
4-(2-Chloro-6-methoxyphenyl)-6-{3-[cis-3,5-dimethylpiperazinyl]propyl}-9-hydroxypyrrolo[3,4-c]carbazole-1,3(2H,6H)-dione;
4-(2-Chlorophenyl)-9-hydroxy-6-[2-(phenylsulfanyl)ethyl]pyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6 (1H)-yl)-N-[2-(dimethylamino)ethyl]-N-methylpropanamide;
3-(4-(2-Chlorophenyl)-9-hydroxy-1,3-dioxo-2,3-dihydropyrrolo[3,4-c]carbazol-6 (1H)-yl)-N-(2,2,6,6-tetramethyl-4-piperidinyl)propanamide (XIII; Ar=2-chlorophenyl, n=2, $R^3$=H, $R^4$=2,2,6,6-tetramethyl-4-piperidinyl);
4-(2-Chlorophenyl)-6-{3-[cis-3,5-dimethylpiperazinyl]-3-oxopropyl}-9-methoxypyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6 (1H)-yl)-N-[2-(1H-imidazol-5-yl)ethyl]propanamide (XIII; Ar=2-chlorophenyl, n=2, $R^3$=H, $R^4$=(1H-imidazol-5-yl)ethyl);
3-(4-(2,6-Dichlorophenyl)-9-hydroxy-1,3-dioxo-2,3-dihydropyrrolo[3,4-c]carbazol-6 (1H)-yl)propanoic acid;
N-[2-(Dimethylamino)ethyl]-3-(9-hydroxy-1,3-dioxo-4-phenyl-2,3-dihydropyrrolo[3,4-c]carbazol-6 (1H)-yl)propanamide;
N-[2-(Dimethylamino)ethyl]-3-(9-hydroxy-4-(2-methoxyphenyl)-1,3-dioxo-2,3-dihydropyrrolo[3,4-c]carbazol-6 (1H)-yl)propanamide;
3,9-dihydroxy-4-phenyl-3,6-dihydropyrrolo[3,4-c]carbazol-1(2H)-one;

4-(2-Chlorophenyl)-1,9-dihydroxy-6-(3-hydroxypropyl)-1,6-dihydropyrrolo[3,4-c]carbazol-3 (2H)-one;

4-(2-chlorophenyl)-3,9-dihydroxy-6-(3-hydroxypropyl)-3,6-dihydropyrrolo[3,4-c]carbazol-1-(2H)-one;

4-(2-Chlorophenyl)-9-hydroxy-6-(3-hydroxypropyl)-4,5,6,10c-tetrahydropyrrolo[3,4-c]carbazole-1,3(2H,3aH)-dione;

8-Hydroxy-4-phenylcyclopenta[c]carbazole-1,3(2H,6H)-dione;

4-(2-Chlorophenyl)-8-hydroxy-6-methylpyrrolo[3,4-c]carbazole-1,3(2H,6H)-dione;

4-(2-Chlorophenyl)-6-[3-(cis-3,5-dimethyl-1-piperazinyl)-2-hydroxypropyl]-9-hydroxypyrrolo[3,4-c]carbazole-1,3(2H,6H)-dione;

4-(2-Chlorophenyl)-6-[3-(dimethylamino)-2-hydroxypropyl]-9-hydroxypyrrolo[3,4-c]carbazole-1,3(2H,6H)-dione;

4-(2-chlorophenyl)-9-hydroxy-6-propylpyrrolo[3,4-c]carbazole-1,3(2H,6H)-dione;

4-(2-chlorophenyl)-9-hydroxy-6-pentylpyrrolo[3,4-c]carbazole-1,3(2H,6H)-dione;

6-allyl-4-(2-chlorophenyl)-9-hydroxypyrrolo[3,4-c]carbazole-1,3(2H,6H)-dione;

4-(2-chlorophenyl)-9-hydroxy-6-(2-phenylethyl)pyrrolo[3,4-c]carbazole-1,3(2H,6H)-dione;

4-(2-chlorophenyl)-9-hydroxy-6-(2-propynyl)pyrrolo[3,4-c]carbazole-1,3(2H,6H)-dione;

4-(2-chlorophenyl)-9-hydroxy-6-isopentylpyrrolo[3,4-c]carbazole-1,3(2H,6H)-dione;

4-(2-chlorophenyl)-9-hydroxy-6-(2,2,2-trifluoroethyl)pyrrolo[3,4-c]carbazole-1,3(2H,6H)-dione;

4-(2-chlorophenyl)-9-hydroxy-6-(4-pentenyl)pyrrolo[3,4-c]carbazole-1,3(2H,6H)-dione;

2-(4-(2-chlorophenyl)-9-hydroxy-1,3-dioxo-2,3-dihydropyrrolo[3,4-c]carbazol-6 (1H)-yl)acetamide;

6-(3-butenyl)-4-(2-chlorophenyl)-9-hydroxypyrrolo[3,4-c]carbazole-1,3(2H,6H)-dione;

4-(2-chlorophenyl)-9-hydroxy-6-isobutylpyrrolo[3,4-c]carbazole-1,3(2H,6H)-dione;

4-(2-chlorophenyl)-9-hydroxy-6-(4,4,4-trifluorobutyl)pyrrolo[3,4-c]carbazole-1,3(2H,6H)-dione;

6-sec-butyl-4-(2-chlorophenyl)-9-hydroxypyrrolo[3,4-c]carbazole-1,3(2H,6H)-dione;

4-(2-chlorophenyl)-6-cyclopentyl-9-hydroxypyrrolo[3,4-c]carbazole-1,3(2H,6H)-dione;

4-(2-Chlorophenyl)-8-[4-(dimethylamino)butyl]-9-hydroxypyrrolo[3,4-c]carbazole-1,3(2H,6H)-dione;

4-(2-Chlorophenyl)-9-hydroxy-8-[4-(1-pyrrolidinyl)butyl]pyrrolo[3,4-c]carbazole-1,3(2H,6H)-dione;

4-(2-Chlorophenyl)-9-hydroxy-6,8-bis(2-hydroxyethyl)pyrrolo[3,4-c]carbazole-1,3(2H,6H)-dione, 4-(2-Chlorophenyl)-9-hydroxy-6-(2-hydroxyethyl)-8-[3-(4-morpholinyl)propoxy]pyrrolo[3,4-c]carbazole-1,3(2H,6H)-dione;

9-Hydroxy-8-(3-hydroxypropyl)-6-methyl-4-phenylpyrrolo[3,4-c]carbazole-1,3(2H,6H)-dione;

8-Ethyl-9-hydroxy-6-methyl-4-phenylpyrrolo[3,4-c]carbazole-1,3(2H,6H)-dione;

8-(2,3-Dihydroxypropyl)-9-hydroxy-6-methyl-4-phenylpyrrolo[3,4-c]carbazole-1,3(2H,6H)-dione;

4-(2-Chlorophenyl)-8-ethyl-9-hydroxy-6-methylpyrrolo[3,4-c]carbazole-1,3(2H,6H)-dione;

9-Hydroxy-8-(2-hydroxyethyl)-6-methyl-4-phenylpyrrolo[3,4-c]carbazole-1,3(2H,6H)-dione;

4-(2-Chlorophenyl)-9-hydroxy-8-(2-hydroxyethyl)-6-methylpyrrolo[3,4-c]carbazole-1,3(2H,6H)-dione;

8-[3-(Dimethylamino)propyl]-9-hydroxy-6-methyl-4-phenylpyrrolo[3,4-c]carbazole-1,3(2H,6H)-dione;

8-[2-(Dimethylamino)ethyl]-9-hydroxy-6-methyl-4-phenylpyrrolo[3,4-c]carbazole-1,3(2H,6H)-dione;

9-Hydroxy-5-methyl-4-phenylpyrrolo[3,4-c]carbazole-1,3(2H,6H)-dione;

9-Hydroxy-4,5-diphenylpyrrolo[3,4-c]carbazole-1,3(2H,6H)-dione;

4-(2-Chlorophenyl)-8-(3-hydroxypropoxy)-9-methoxy-6-methylpyrrolo[3,4-c]carbazole-1,3(2H,6H)-dione;

4-(2-Chlorophenyl)-8-[3-(dimethylamino)propoxy]-9-methoxy-6-methylpyrrolo[3,4-c]carbazole-1,3(2H,6H)-dione;

4-(2-Chlorophenyl)-8-[3-(dimethylamino)propoxy]-9-hydroxy-6-methylpyrrolo[3,4-c]carbazole-1,3(2H,6H)-dione;

8-[3-(Dimethylamino)propoxy]-9-hydroxy-6-methyl-4-phenylpyrrolo[3,4-c]carbazole-1,3(2H,6H)-dione;

4-(2-Chlorophenyl)-9-hydroxy-6-methyl-8-[3-(4-morpholinyl)propoxy]pyrrolo[3,4-c]carbazole-1,3(2H,6H)-dione;

4-(2-Chlorophenyl)-9-hydroxy-6-methyl-8-[3-(1-pyrrolidinyl)propoxy]pyrrolo[3,4-c]carbazole-1,3(2H,6H)-dione;

4-(2-Chlorophenyl)-8-(2-hydroxyethyl)-6-methylpyrrolo[3,4-c]carbazole-1,3(2H,6H)-dione;

4-(2-Chlorophenyl)-8-(1,2-dihydroxyethyl)-6-methylpyrrolo[3,4-c]carbazole-1,3(2H,6H)-dione;

4-(2-Chlorophenyl)-8-(hydroxymethyl)-6-methylpyrrolo[3,4-c]carbazole-1,3(2H,6H)-dione;

4-(2-Chlorophenyl)-8-(3-hydroxypropoxy)-6-methylpyrrolo[3,4-c]carbazole-1,3(2H,6H)-dione;

4-(2-Chlorophenyl)-8-[3-(dimethylamino)propoxy]-6-methylpyrrolo[3,4-c]carbazole-1,3(2H,6H)-dione;

4-(2-Chlorophenyl)-6-methyl-8-[3-(methylamino)propoxy]pyrrolo[3,4-c]carbazole-1,3(2H,6H)-dione;

4-(2-Chlorophenyl)-8-[3-(cis-3,5-dimethyl-1-piperazinyl)propoxy]-6-methylpyrrolo[3,4-c]carbazole-1,3(2H,6H)-dione;

4-(2-Chlorophenyl)-8-(2-hydroxyethoxy)-6-methylpyrrolo[3,4-c]carbazole-1,3(2H,6H)-dione;

4-(2-Chlorophenyl)-8-(2,3-dihydroxypropoxy)-6-methylpyrrolo[3,4-c]carbazole-1,3(2H,6H)-dione;

9-Hydroxy-4-(2-methoxyphenyl)-6-[2-(4-morpholinyl)ethyl]pyrrolo[3,4-c]carbazole-1,3(2H,6H)-dione;

1,3-Dioxo-4-phenyl-1,2,3,6-tetrahydropyrrolo[3,4-c]carbazol-9-yl dihydrogen phosphate;

4-(2-Chlorophenyl)-8-(3-dimethylamino-propoxy)-9-hydroxy-6-(3-hydroxy-propyl)-6H-pyrrolo[3,4-c]carbazole-1,3-dione;

6-(3-Bromo-propyl)-4-(2-chlorophenyl)-8-(3-dimethylamino-propoxy)-9-hydroxy-6H-pyrrolo[3,4-c]carbazole-1,3-dione;

4-(2-Chlorophenyl)-8-(4-dimethylamino-3-hydroxy-butoxy)-6-methyl-6H-pyrrolo[3,4-c]carbazole-1,3-dione;

4-(2-Chlorophenyl)-8-hydroxy-6-(3-hydroxy-propyl)-6H-pyrrolo[3,4-c]carbazole-1,3-dione;

4-(2-Chlorophenyl)-8-(4-dimethylamino-butyl)-6-methyl-6H-pyrrolo[3,4-c]carbazole-1,3-dione;

4-(2-Chlorophenyl)-6-methyl-8-(4-pyrrolidin-1-yl-butyl)-6H-pyrrolo[3,4-c]carbazole-1,3-dione;

4-(2-Chlorophenyl)-6-methyl-8-(4-methylamino-butyl)-6H-pyrrolo[3,4-c]carbazole-1,3-dione;

4-(2-Chlorophenyl)-9-hydroxy-6-(3-hydroxy-propyl)-8-(3-pyrrolidin-1-yl-propoxy)-6H-pyrrolo[3,4-c]carbazole-1,3-dione;

4-(2-Chlorophenyl)-9-hydroxy-8-(4-hydroxy-butyl)-6-methyl-6H-pyrrolo[3,4-c]carbazole-1,3-dione;

8-{3-[Bis-(2-hydroxy-ethyl)-amino]-propoxy}-4-(2-chlorophenyl)-9-hydroxy-6-methyl-6H-pyrrolo[3,4-c]carbazole-1,3-dione;

4-(2-Chloro-phenyl)-9-hydroxy-6-(3-hydroxy-propyl)-8-[3-(4-methyl-piperazin-1-yl)-propoxy]-6H-pyrrolo[3,4-c]carbazole-1,3-dione;

9-Amino-4-(2-chloro-phenyl)-6-(3-hydroxy-propyl)-6H-pyrrolo[3,4-c]carbazole-1,3-dione;

3-[4-(2-Chloro-phenyl)-9-nitro-1,3-dioxo-2,3-dihydro-1H-pyrrolo[3,4-c]carbazol-6-yl]-propionic acid;

4-(2-Chloro-phenyl)-9-hydroxy-8-(4-hydroxy-butoxy)-6-methyl-6H-pyrrolo[3,4-c]carbazole-1,3-dione;

4-(2-Chloro-phenyl)-6-(3-hydroxy-propyl)-8-methoxy-6H-pyrrolo[3,4-c]carbazole-1,3-dione;

4-(2-Chloro-phenyl)-9-fluoro-8-methoxy-6-methyl-6H-pyrrolo[3,4-c]carbazole-1,3-dione;

4-(2-Chloro-phenyl)-9-fluoro-8-hydroxy-6-methyl-6H-pyrrolo[3,4-c]carbazole-1,3-dione;

4-(2-Chloro-phenyl)-9-(3-dimethylamino-propoxy)-6-(3-hydroxy-propyl)-6H-pyrrolo[3,4-c]carbazole-1,3-dione;

4-(2-Chloro-phenyl)-6-(3-hydroxy-propyl)-8-(3-pyrrolidin-1-yl-propoxy)-6H-pyrrolo[3,4-c]carbazole-1,3-dione;

4-(2-Chloro-phenyl)-9-fluoro-8-(3-hydroxy-propoxy)-6-methyl-6H-pyrrolo[3,4-c]carbazole-1,3-dione;

4-(2-Chloro-phenyl)-9-fluoro-6-methyl-8-(3-methylamino-propoxy)-6H-pyrrolo[3,4-c]carbazole-1,3-dione;

4-(2-Chloro-phenyl)-9-hydroxy-6-methyl-8-(4-morpholin-4-yl-butyl)-6H-pyrrolo[3,4-c]carbazole-1,3-dione;

4-(2-Chloro-phenyl)-9-fluoro-6-methyl-8-(3-pyrrolidin-1-yl-propoxy)-6H-pyrrolo[3,4-c]carbazole-1,3-dione;

4-(2-Chloro-phenyl)-9-hydroxy-6-(2-hydroxy-ethyl)-8-[3-(4-methyl-piperazin-1-yl)-propoxy]-6H-pyrrolo[3,4-c]carbazole-1,3-dione;

4-(2-Chloro-phenyl)-8-(3-diethylamino-propoxy)-9-hydroxy-6-(2-hydroxy-ethyl)-6H-pyrrolo[3,4-c]carbazole-1,3-dione;

4-(2-Chloro-phenyl)-8-(3-dimethylamino-propoxy)-9-fluoro-6-methyl-6H-pyrrolo[3,4-c]carbazole-1,3-dione;

N-[4-(2-Chloro-phenyl)-6-(3-hydroxy-propyl)-1,3-dioxo-1,2,3,6-tetrahydro-pyrrolo[3,4-c]carbazol-9-yl]-formamide;

4-(2-Chloro-phenyl)-9-hydroxy-6-(3-hydroxy-propyl)-8-piperidin-4-yl-6H-pyrrolo[3,4-c]carbazole-1,3-dione;

4-(2-Chloro-phenyl)-6-methyl-8-piperidin-4-yl-6H-pyrrolo[3,4-c]carbazole-1,3-dione;

7-(2-Amino-1-hydroxy-ethyl)-4-(2-chlorophenyl)-9-hydroxy-6-oxa-2-aza-cyclopenta[c]fluorene-1,3-dione;

4-(2-Chloro-phenyl)-9-hydroxy-7-(1-hydroxy-2-methylamino-ethyl)-6-oxa-2-aza-cyclopenta[c]fluorene-1,3-dione;

4-(2-Chloro-phenyl)-9-hydroxy-7-(1-hydroxy-2-piperazin-1-yl-ethyl)-6-oxa-2-aza-cyclopenta[c]fluorene-1,3-dione;

4-(2-Chloro-phenyl)-9-hydroxy-7-(1-hydroxy-2-morpholin-4-yl-ethyl)-6-oxa-2-aza-cyclopenta[c]fluorene-1,3-dione;

4-(2-Chloro-phenyl)-9-hydroxy-7-[1-hydroxy-2-(2-methoxy-ethoxy)-ethyl]-6-oxa-2-aza-cyclopenta[c]fluorene-1,3-dione;

7-(2-Amino-1-hydroxy-ethyl)-4-(2-Chlorophenyl)-6-oxa-2-aza-cyclopenta[c]fluorene-1,3-dione;

4-(2-Chlorophenyl)-6-methyl-8-piperidin-3-yl-6H-pyrrolo[3,4-c]carbazole-1,3-dione;

4-(2-Chlorophenyl)-6-methyl-8-piperidin-4-yl-6H-pyrrolo[3,4-c]carbazole-1,3-dione;

4-(2-Chlorophenyl)-8-(4-hydroxy-piperidin-3-yl)-6-methyl-6H-pyrrolo[3,4-c]carbazole-1,3-dione;

8-(1-Aminomethyl-2-hydroxy-ethyl)-4-(2-Chlorophenyl)-6-methyl-6H-pyrrolo[3,4-c]carbazole-1,3-dione;

4-(2-Chlorophenyl)-6-(3-hydroxy-propyl)-8-piperidin-3-yl-6H-pyrrolo[3,4-c]carbazole-1,3-dione;

4-(2-Chlorophenyl)-8-(4-hydroxy-piperidin-3-yl)-6-(3-hydroxy-propyl)-6H-pyrrolo[3,4-c]carbazole-1,3-dione;

4-(2-chlorophenyl)-9-hydroxy-8-[4-(methylamino)butyl]pyrrolo[3,4-c]carbazole-1,3(2H,6H)-dione;

4-(2-chlorophenyl)-9-hydroxy-8-[3-(methylamino)propoxy]pyrrolo[3,4c]carbazole-1,3(2H,6H)-dione;

4-(2-chlorophenyl)-8-[3-(dimethylamino)propoxy]-9-hydroxypyrrolo[3,4-c)carbazole-1,3(2H,6H)-dione;

4-(2-chlorophenyl)-8-[3-(dimethylamino)propoxy]-9-hydroxy-6-(2-hydroxyethyl)pyrrolo[3,4-c]carbazole-1,3(2H,6H)-dione;

4-(2-chlorophenyl)-9-hydroxy-6-(2-hydroxyethyl)-8-[3-(methylamino)propoxy]pyrrolo[3,4-c]carbazole-1,3(2H,6H)-dione;

4-(2-chlorophenyl)-9-hydroxy-6-(2-hydroxyethyl)-8-[4-(methylamino)butyl]pyrrolo[3,4-c]carbazole-1,3(2H,6H)-dione;

4-(2-chlorophenyl)-8-[4-(dimethylamino)butyl]-9-hydroxy-6-(2-hydroxyethyl)pyrrolo[3,4-c]carbazole-1,3(2H,6H)-dione;

4-(2-chlorophenyl)-8-[4-(dimethylamino)butyl]-9-hydroxy-6-(3-hydroxypropyl)pyrrolo[3,4-c]carbazole-1,3(2H,6H)-dione;

4-(2-chlorophenyl)-8-[4-(dimethylamino)butyl]-9-hydroxy-6-(3-hydroxypropyl)pyrrolo[3,4-c]carbazole-1,3(2H,6H)-dione;

4-(2-chlorophenyl)-9-hydroxy-6-(3-hydroxypropyl)-8-[3-(methylamino)propoxy]pyrrolo[3,4-c]carbazole-1,3(2H,6H)-dione;

4-(2-chlorophenyl)-8-[3-(dimethylamino)propoxy]-9-hydroxy-6-(3-hydroxypropyl)pyrrolo[3,4-c]carbazole-1,3(2H,6H)-dione;

4-(2-chlorophenyl)-9-hydroxy-6-(3-hydroxypropyl)-8-[3-(1-pyrrolidinyl)propoxy]pyrrolo[3,4-c]carbazole-1,3(2H,6H)-dione;

4-(2-chlorophenyl)-9-hydroxy-6-methyl-8-[4-(methylamino)butyl]pyrrolo[3,4-c]carbazole-1,3(2H,6H)-dione;

4-(2-chlorophenyl)-9-hydroxy-6-methyl-8-[3-(methylamino)propoxy]pyrrolo[3,4-c]carbazole-1,3(2H,6H)-dione;

4-(2-chlorophenyl)-8-[4-(dimethylamino)butyl]-9-hydroxy-6-methylpyrrolo[3,4-c]carbazole-1,3(2H,6H)-dione;

4-(2-chlorophenyl)-8-{3-[(3,5-dimethylpiperazinyl]propoxy}-9-hydroxy-6-methylpyrrolo[3,4-c]carbazole-1,3(2H,6H)-dione;

6-butyl-4-(2-chlorophenyl)-8-[4-(dimethylamino)butyl]-9-hydroxypyrrolo[3,4-c]carbazole-1,3(2H,6H)-dione;

4-(2-chlorophenyl)-9-hydroxy-8-[4-(methylamino)butyl]-6-propylpyrrolo[3,4-c]carbazole-1,3(2H,6H)-dione;

6-butyl-4-(2-chlorophenyl)-9-hydroxy-8-[3-(methylamino)propoxy]pyrrolo[3,4-c]carbazole-1,3(2H,6H)-dione;

6-butyl-4-(2-chlorophenyl)-8-[3-(dimethylamino)propoxy]-9-hydroxypyrrolo[3,4-c]carbazole-1,3(2H,6H)-dione;

6-butyl-4-(2-chlorophenyl)-9-hydroxy-8-[4-(1-pyrrolidinyl)butyl]pyrrolo[3,4-c]carbazole-1,3(2H,6H)-dione;

4-(2,6-dichlorophenyl)-9-hydroxy-8-[4-(methylamino)butyl]pyrrolo[3,4-c]carbazole-1,3(2H,6H)-dione;

4-(2-chloro-6-methoxyphenyl)-9-hydroxy-8-[4-(methylamino)butyl]pyrrolo[3,4-c]carbazole-1,3(2H,6H)-dione;

4-(2-bromophenyl)-9-hydroxy-8-[4-(methylamino)butyl]pyrrolo[3,4-c]carbazole-1,3(2H,6H)-dione;

4-(2-bromophenyl)-8-[4-(dimethylamino)butyl]-9-hydroxypyrrolo[3,4-c]carbazole-1,3(2H,6H)-dione;

4-(2-chloro-6-methoxyphenyl)-8-[4-(dimethylamino)butyl]-9-hydroxypyrrolo[3,4-c]carbazole-1,3(2H,6H)-dione;
4-(2-chloro-6-methoxyphenyl)-8-[3-(dimethylamino)propoxy]-9-hydroxypyrrolo[3,4-c]carbazole-1,3(2H,6H)-dione;
4-(2,6-dichlorophenyl)-8-[3-(dimethylamino)propoxy]-9-hydroxypyrrolo[3,4-c]carbazole-1,3(2H,6H)-dione;
4-(2-bromophenyl)-8-[3-(dimethylamino)propoxy]-9-hydroxypyrrolo[3,4-c]carbazole-1,3(2H,6H)-dione;
4-(2-bromophenyl)-9-hydroxy-8-[3-(methylamino)propoxy]pyrrolo[3,4-c]carbazole-1,3(2H,6H)-dione;
4-(2-chloro-6-methoxyphenyl)-9-hydroxy-8-[3-(methylamino)propoxy]pyrrolo[3,4-c]carbazole-1,3(2H,6H)-dione;
4-(2-chloro-6-methoxyphenyl)-9-hydroxy-6-methyl-8-[3-(methylamino)propoxy]pyrrolo[3,4-c]carbazole-1,3(2H,6H)-dione;
4-(2,6-dichlorophenyl)-9-hydroxy-6-methyl-8-[3-(methylamino)propoxy]pyrrolo[3,4-c]carbazole-1,3(2H,6H)-dione;
4-(2-bromophenyl)-9-hydroxy-6-methyl-8-[3-(methylamino)propoxy]pyrrolo[3,4-c]carbazole-1,3(2H,6H)-dione;
4-(2-bromophenyl)-8-[3-(dimethylamino)propoxy]-9-hydroxy-6-methylpyrrolo[3,4-c]carbazole-1,3(2H,6H)-dione;
4-(2,6-dichlorophenyl)-8-[4-(dimethylamino)butyl]-9-hydroxy-6-methylpyrrolo[3,4-c]carbazole-1,3(2H,6H)-dione;
4-(2-chloro-6-methoxyphenyl)-8-[4-(dimethylamino)butyl]-9-hydroxy-6-methylpyrrolo[3,4-c]carbazole-1,3(2H,6H)-dione;
4-(2-chloro-6-methoxyphenyl)-8-[3-(dimethylamino)propoxy]-9-hydroxy-6-methylpyrrolo[3,4-c]carbazole-1,3(2H,6H)-dione;
6-butyl-4-(2-chloro-6-methoxyphenyl)-8-[3-(dimethylamino)propoxy]-9-hydroxypyrrolo[3,4-c]carbazole-1,3(2H,6H)-dione;
6-butyl-4-(2-chloro-6-methoxyphenyl)-9-hydroxy-8-[3-(methylamino)propoxy]pyrrolo[3,4-c]carbazole-1,3(2H,6H)-dione;
6-butyl-4-(2-chloro-6-methoxyphenyl)-8-[4-(dimethylamino)butyl]-9-hydroxypyrrolo[3,4-c]carbazole-1,3(2H,6H)-dione;
6-butyl-4-(2,6-dichlorophenyl)-8-[4-(dimethylamino)butyl]-9-hydroxypyrrolo[3,4-c]carbazole-1,3(2H,6H)-dione;
6-butyl-4-(2,6-dichlorophenyl)-8-[3-(dimethylamino)propoxy]-9-hydroxypyrrolo[3,4-c]carbazole-1,3(2H,6H)-dione;
6-butyl-4-(2,6-dichlorophenyl)-9-hydroxy-8-[3-(methylamino)propoxy]pyrrolo[3,4-c]carbazole-1,3(2H,6H)-dione;
6-butyl-4-(2,6-dichlorophenyl)-9-hydroxy-8-[4-(methylamino)butyl]pyrrolo[3,4-c]carbazole-1,3(2H,6H)-dione;
4-(2-chlorophenyl)-9-hydroxy-8-[4-(1-pyrrolidinyl)butyl]-1H-[1]benzofuro[3,2-e]isoindole-1,3(2H)-dione;
8-(4-aminobutyl)-4-(2-chlorophenyl)-9-hydroxy-1H-[1]benzofuro[3,2-e]isoindole-1,3(2H)-dione;
8-(4-aminobutyl)-4-(2-chlorophenyl)-9-hydroxypyrrolo[3,4-c]carbazole-1,3(2H,6H)-dione;
8-(4-aminobutyl)-4-(2-chlorophenyl)-9-hydroxy-6-methylpyrrolo[3,4-c]carbazole-1,3(2H,6H)-dione;
4-(2-chlorophenyl)-9-(hydroxymethyl)pyrrolo[3,4-c]carbazole-1,3(2H,6H)-dione;
4-(2-chlorophenyl)-9-(trifluoromethyl)pyrrolo[3,4-c]carbazole-1,3(2H,6H)-dione;
9-(2-amino-1-hydroxyethyl)-4-(2-chlorophenyl)pyrrolo[3,4-c]carbazole-1,3(2H,6H)-dione;
4-(2-chlorophenyl)-9-[1-hydroxy-2-(methylamino)ethyl]pyrrolo[3,4-c]carbazole-1,3(2H,6H)-dione;
4-(2-chlorophenyl)-9-[2-(dimethylamino)-1-hydroxyethyl]pyrrolo[3,4-c]carbazole-1,3(2H,6H)-dione;
4-(2-chlorophenyl)-9-[1-hydroxy-2-(1-piperidinyl)ethyl]pyrrolo[3,4-c]carbazole-1,3(2H,6H)-dione;
4-(2-chlorophenyl)-9-[1-hydroxy-2-(4-morpholinyl)ethyl]pyrrolo[3,4-c]carbazole-1,3(2H,6H)-dione;
4-(2-chlorophenyl)-8-(4-hydroxybutoxy)-6-methylpyrrolo[3,4-c]carbazole-1,3(2H,6H)-dione;
4-(2-chlorophenyl)-8-(3,4-dihydroxybutoxy)-6-methylpyrrolo[3,4-c]carbazole-1,3(2H,6H)-dione;
4-(2-chlorophenyl)-6-methyl-8-[4-(methylamino)butoxy]pyrrolo[3,4-c]carbazole-1,3(2H,6H)-dione;
4-(2-chlorophenyl)-8-[4-(dimethylamino)-3-hydroxybutoxy]-6-methylpyrrolo[3,4-c]carbazole-1,3(2H,6H)-dione;
4-(2-chlorophenyl)-8-[3-hydroxy-4-(methylamino)butoxy]-6-methylpyrrolo[3,4-c]carbazole-1,3(2H,6H)-dione;
4-(2-chlorophenyl)-8-β-hydroxy-4-(1-pyrrolidinyl)butoxy]-6-methylpyrrolo[3,4-c]carbazole-1,3(2H,6H)-dione;
4-(2-chlorophenyl)-8-[(1E)-4-(dimethylamino)-1-butenyl]-6-methylpyrrolo[3,4-c]carbazole-1,3(2H,6H)-dione;
4-(2-chlorophenyl)-6-methyl-8-[(1E)-4-(methylamino)-1-butenyl]pyrrolo[3,4-c]carbazole-1,3(2H,6H)-dione;
4-(2-chlorophenyl)-6-methyl-8-[4-(methylamino)butyl]pyrrolo[3,4-c]carbazole-1,3(2H,6H)-dione;
4-(2-chlorophenyl)-8-[4-(dimethylamino)butyl]-6-methylpyrrolo[3,4c]carbazole-1,3(2H,6H)-dione;
4-(2-chlorophenyl)-8-[(1E)-4-hydroxy-1-butenyl]-6-methylpyrrolo[3,4-c]carbazole-1,3(2H,6H)-dione;
4-(2-chlorophenyl)-8-[(1E)-4-hydroxy-1-butenyl]pyrrolo[3,4-c]carbazole-1,3(2H,6H)-dione;
4-(2-chlorophenyl)-8-(4-hydroxybutyl)pyrrolo[3,4-c]carbazole-1,3(2H,6H)-dione;
4-(2-chlorophenyl)-8-[4-(methylamino)butyl]pyrrolo[3,4-c]carbazole-1,3(2H,6H)-dione;
4-(2-chlorophenyl)-8-[(1E)-4-(methylamino)-1-butenyl]pyrrolo[3,4-c]carbazole-1,3(2H,6H)-dione;
4-(2-chlorophenyl)-6-(3-hydroxypropyl)-8-[3-(methylamino)propoxy]pyrrolo[3,4-c]carbazole-1,3(2H,6H)-dione;
4-(2-chlorophenyl)-8-[3-(methylamino)propoxy]-6-[3-(methylamino)propyl]pyrrolo[3,4-c]carbazole-1,3(2H,6H)-dione;
4-(2-chlorophenyl)-8-(3-hydroxypropoxy)-6-[3-(methylamino)propyl]pyrrolo[3,4-c]carbazole-1,3(2H,6H)-dione;
4-(2-chlorophenyl)-9-fluoro-8-[3-(methylamino)propoxy]-6-[3-(methylamino)propyl]pyrrolo[3,4-c]carbazole-1,3(2H,6H)-dione;
4-(2-chlorophenyl)-9-fluoro-8-(3-hydroxypropoxy)-6-[3-(methylamino)propyl]pyrrolo[3,4-c]carbazole-1,3(2H,6H)-dione;
4-(2-chlorophenyl)-9-fluoro-6-(3-hydroxypropyl)-8-[4-(methylamino)butyl]pyrrolo[3,4-c]carbazole-1,3(2H,6H)-dione;
4-(2-chlorophenyl)-9-fluoro-8-(4-hydroxybutoxy)-6-methylpyrrolo[3,4-c]-carbazole-1,3(2H,6H)-dione;
4-(2-chlorophenyl)-9-fluoro-6-methyl-8-[3-(methylamino)propoxy]pyrrolo[3,4-c]carbazole-1,3(2H,6H)-dione;
4-(2-chlorophenyl)-9-fluoro-8-(3-hydroxypropoxy)-6-methylpyrrolo[3,4-c]carbazole-1,3(2H,6H)-dione;

4-(2-chloro-3-hydroxyphenyl)-8-[4-(methylamino)butyl]
pyrrolo[3,4-c]carbazole-1,3(2H,6H)-dione;
4-(2-chloro-3-hydroxyphenyl)-9-fluoro-8-[3-(methylamino)
propoxy]pyrrolo[3,4-c]carbazole-1,3(2H,6H)-dione;
4-(2-chloro-3-hydroxyphenyl)-9-fluoro-8-[4-(methylamino)
butyl]pyrrolo[3,4-c]carbazole-1,3(2H,6H)-dione;
4-(2-chloro-3-hydroxyphenyl)-9-fluoro-6-(3-hydroxypropyl)-8-[4-(methylamino)butyl]pyrrolo[3,4-c]carbazole-1,
3(2H,6H)-dione;
4-(3-amino-2-chlorophenyl)-9-fluoro-6-(3-hydroxypropyl)-8-[4-(methylamino)butyl]pyrrolo[3,4-c]carbazole-1,3
(2H,6H)-dione;
4-(3-amino-2-chlorophenyl)-9-fluoro-8-[4-(methylamino)
butyl]pyrrolo[3,4-c]carbazole-1,3(2H,6H)-dione;
4-(3-amino-2-chlorophenyl)-9-fluoro-8-[3-(methylamino)
propoxy]pyrrolo[3,4-c]carbazole-1,3(2H,6H)-dione;
4-(2-chlorophenyl)-9-fluoro-6-methylpyrrolo[3,4-c]carbazole-1,3(2H,6H)-dione;
3-(4-(2-chlorophenyl)-9-(formylamino)-1,3-dioxo-2,3-dihydropyrrolo[3,4-c]carbazol-6(1H)-yl)-N-[2-(dimethylamino)ethyl]propanamide;
3-(9-amino-4-(2-chlorophenyl)-1,3-dioxo-2,3-dihydropyrrolo[3,4-c]carbazol-6 (1H)-yl)-N-[2-(dimethylamino)
ethyl]propanamide;
4-(2-chlorophenyl)-6-methyl-9-{[3-(1-piperidinyl)propyl]
amino}pyrrolo[3,4-c]carbazole-1,3(2H,6H)-dione;
4-(2-chlorophenyl)-9-fluoropyrrolo[3,4-c]carbazole-1,3
(2H,6H)-dione;
9-amino-4-(2-chlorophenyl)-6-(3-hydroxypropyl)pyrrolo[3,
4-c]carbazole-1,3(2H,6H)-dione;
4-(2-chlorophenyl)-6-(3-hydroxypropyl)-1,3-dioxo-1,2,3,6-tetrahydropyrrolo[3,4-c]carbazol-9-ylformamide;
4-(2-chlorophenyl)-9-{[4-(dimethylamino)butyl]amino}-6-methylpyrrolo[3,4-c]carbazole-1,3(2H,6H)-dione;
4-(2-chlorophenyl)-6-methyl-9-{[4-(methylamino)butyl]
amino}pyrrolo[3,4-c]carbazole-1,3(2H,6H)-dione;
4-(2-chlorophenyl)-9-[3-(1-piperidinyl)propyl]amino)pyrrolo[3,4-c]carbazole-1,3(2H,6H)-dione;
4-(2-methoxyphenyl)-6-methyl-1,3-dioxo-1,2,3,6-tetrahydropyrrolo[3,4-c]carbazol-9-ylformamide;
4-(2-methoxyphenyl)-6-methyl-9-(methylamino)pyrrolo[3,
4-c]carbazole-1,3(2H,6H)-dione;
4-(2-chlorophenyl)-6-methyl-8-[3-(methylamino)propoxy]-1,3-dioxo-1,2,3,6-tetrahydropyrrolo[3,4-c]carbazol-9-yl
formamide;
4-(2-chlorophenyl)-9-hydroxy-6-methyl-8-[4-(methylamino)butanoyl]pyrrolo[3,4-c]carbazole-1,3(2H,6H)-dione;
4-(2-chlorophenyl)-8-[4-(dimethylamino)butanoyl]-9-hydroxy-6-methylpyrrolo[3,4-c]carbazole-1,3(2H,6H)-dione;
4-(2-chlorophenyl)-8-[3-(dimethylamino)propoxy]-6-methyl-1,3-dioxo-1,2,3,6-tetrahydropyrrolo[3,4-c]carbazol-9-ylformamide;
4-(2-chlorophenyl)-8-[3-(dimethylamino)propyl]sulfinyl}-9-hydroxy-6-methylpyrrolo[3,4-c]carbazole-1,3(2H,6H)-dione; and
4-(2-chlorophenyl)-9-hydroxy-6-methyl-8-{[3-(methylamino)propyl]sulfonyl}pyrrolo[3,4-c]carbazole-1,3(2H,
6H)-dione.

In another preferred embodiment of the present invention, $R^1$ in compounds according to Formula I is aryl.

In one preferred embodiment are compounds according to Formula I wherein $R^1$ is selected from an unsubstituted aryl ring or an aryl ring substituted with up to 3 substituents selected from the group consisting of halogen, haloalkyl, alkoxy, hydroxyl, nitro or $NR^3R^4$.

In a more preferred embodiment are compounds according to Formula I wherein $R^1$ is an aryl ring substituted with up to 2 halogens or alkoxy groups.

Another preferred embodiment of the present invention comprises compounds according to Formula I in which $R^1$ is selected from Me and I.

In one preferred embodiment of the present invention, $R^9$ in compounds according to Formula I is a hydrogen, hydroxyl, halogen or NHCHO group.

In another embodiment are compounds according to Formula I wherein at least one of X, $R^7$, $R^8$, and $R^9$ is not hydrogen. In another embodiment, when three of X, $R^7$, $R^8$, and $R^9$ are hydrogen and $R^1$ is lower alkyl, then $R^2$ must be hydrogen.

In a more preferred embodiment of the present invention, $R^9$ in compounds according to Formula I is a hydroxyl group.

In a more preferred embodiment of the present invention, $R^9$ in compounds according to Formula I is a fluorine group.

In a more preferred embodiment of the present invention are compounds according to Formula I in which $R^9$ is hydroxyl and $R^1$ is aryl, such as but not limited to:
4-(2-Chloro-3-hydroxyphenyl)-9-hydroxypyrrolo[3,4-c]carbazole-1,3(2H,6H)-dione;
9-Hydroxy-4-(2-iodophenyl)pyrrolo[3,4-c]carbazole-1,3
(2H,6H)-dione;
4-(2-Chloro-6-methoxyphenyl)-9-hydroxypyrrolo[3,4-c]
carbazole-1,3(2H,6H)-dione;
4-(2,6-Dichloro-3-hydroxyphenyl)-9-hydroxypyrrolo[3,4-c]
carbazole-1,3(2H,6H)-dione;
4-(4-Amino-2-bromophenyl)-9-hydroxypyrrolo[3,4-c]carbazole-1,3(2H,6H)-dione);
4-(3-Amino-2-chlorophenyl)-9-hydroxypyrrolo[3,4-c]carbazole-1,3(2H,6H)-dione;
4-(2-Chloro-4-hydroxyphenyl)-9-hydroxypyrrolo[3,4-c]carbazole-1,3(2H,6H)-dione;
4-(2-Bromophenyl)-9-hydroxypyrrolo[3,4-c]carbazole-1,3
(2H,6H)-dione;
9-Hydroxy-4-(2-methoxyphenyl)pyrrolo[3,4-c]carbazole-1,
3(2H,6H)-dione;
4-(4-Amino-2-chlorophenyl)-9-hydroxypyrrolo[3,4-c]carbazole-1,3(2H,6H)-dione;
4-(2,6-Dimethoxyphenyl)-9-hydroxypyrrolo[3,4-c]carbazole-1,3(2H,6H)-dione;
4-(2,6-Dichlorophenyl)-9-hydroxypyrrolo[3,4-c]carbazole-1,3(2H,6H)-dione;
4-(2,3-Dichlorophenyl)-9-hydroxypyrrolo[3,4-c]carbazole-1,3(2H,6H)-dione;
4-(2-Chloro-5-hydroxyphenyl)-9-hydroxypyrrolo[3,4-c]carbazole-1,3(2H,6H)-dione;
9-Hydroxy-4-[2-(methylsulfanyl)phenyl]pyrrolo[3,4-c]carbazole-1,3(2H,6H)-dione;
4-(2,6-Dibromophenyl)-9-hydroxypyrrolo[3,4-c]carbazole-1,3(2H,6H)-dione;
9-Hydroxy-4-(3-thienyl)pyrrolo[3,4-c]carbazole-1,3(2H,
6H)-dione;
4-(2-Chloro-6-hydroxyphenyl)-9-hydroxypyrrolo[3,4-c]carbazole-1,3(2H,6H)-dione;
9-Hydroxy-4-(2-nitrophenyl)pyrrolo[3,4-c]carbazole-1,3
(2H,6H)-dione;
4-(2,6-Dichloro-4-hydroxyphenyl)-9-hydroxypyrrolo[3,4-c]
carbazole-1,3(2H,6H)-dione;
4-(3-Chlorophenyl)-9-hydroxypyrrolo[3,4-c]carbazole-1,3
(2H,6H)-dione;
9-Hydroxy-4-(2-hydroxyphenyl)pyrrolo[3,4-c]carbazole-1,
3(2H,6H)-dione;

9-Hydroxy-4-(4-hydroxyphenyl)pyrrolo[3,4-c]carbazole-1,3(2H,6H)-dione;
4-(3-Aminophenyl)-9-hydroxypyrrolo[3,4-c]carbazole-1,3(2H,6H)-dione;
4-(2,6-Dimethylphenyl)-9-hydroxypyrrolo[3,4-c]carbazole-1,3(2H,6H)-dione;
9-Hydroxy-4-(3-hydroxyphenyl)pyrrolo[3,4-c]carbazole-1,3(2H,6H)-dione;
4-(5-Amino-2-methoxyphenyl)-9-hydroxypyrrolo[3,4-c]carbazole-1,3(2H,6H)-dione;
9-Hydroxy-4-(3-hydroxy-4-methoxyphenyl)pyrrolo[3,4-c]carbazole-1,3(2H,6H)-dione;
9-Hydroxy-4-(2-thienyl)pyrrolo[3,4-c]carbazole-1,3(2H,6H)-dione;
4-(4-Aminophenyl)-9-hydroxypyrrolo[3,4-c]carbazole-1,3(2H,6H)-dione;
2-(9-Hydroxy-1,3-dioxo-1,2,3,6-tetrahydropyrrolo[3,4-c]carbazol-4-yl)benzonitrile;
4-(2-Aminophenyl)-9-hydroxypyrrolo[3,4-c]carbazole-1,3(2H,6H)-dione;
4-(2-Bromo-4-nitrophenyl)-9-hydroxypyrrolo[3,4-c]carbazole-1,3(2H,6H)-dione;
9-Hydroxy-4-[2-(methylsulfinyl)phenyl]pyrrolo[3,4-c]carbazole-1,3(2H,6H)-dione;
4-(2-Ethoxyphenyl)-9-hydroxypyrrolo[3,4-c]carbazole-1,3(2H,6H)-dione;
9-Hydroxy-4-(3-nitrophenyl)pyrrolo[3,4-c]carbazole-1,3(2H,6H)-dione;
4-(2-Ethylphenyl)-9-hydroxypyrrolo[3,4-c]carbazole-1,3(2H,6H)-dione;
9-Hydroxy-4-[2-(hydroxymethyl)phenyl]pyrrolo[3,4-c]carbazole-1,3(2H,6H)-dione;
4-(2-Chloro-4-nitrophenyl)-9-hydroxypyrrolo[3,4-c]carbazole-1,3(2H,6H)-dione;
9-Hydroxy-4-(2-trifluoromethylphenyl)pyrrolo[3,4-c]carbazole-1,3(2H,6H)-dione;
4-[1,1'-Biphenyl]-2-yl-9-hydroxypyrrolo[3,4-c]carbazole-1,3(2H,6H)-dione;
4-(4-Chlorophenyl)-9-hydroxypyrrolo[3,4-c]carbazole-1,3(2H,6H)-dione;
9-Hydroxy-4-(4-hydroxymethylphenyl)pyrrolo[3,4-c]carbazole-1,3(2H,6H)-dione;
9-Hydroxy-4-o-tolyl-6H-pyrrolo[3,4-c]carbazole-1,3-dione;
3-(9-Hydroxy-1,3-dioxo-1,2,3,6-tetrahydro-pyrrolo[3,4-c]carbazol-4-yl)-benzonitrile;
4-Furan-2-yl-9-hydroxy-6H-pyrrolo[3,4-c]carbazole-1,3-dione;
9-Hydroxy-4-m-tolyl-6H-pyrrolo[3,4-c]carbazole-1,3-dione;
9-Hydroxy-4-(2-methylsulfanyl-phenyl)-6H-pyrrolo[3,4-c]carbazole-1,3-dione;
9-Hydroxy-4-(3-trifluoromethoxy-phenyl)-6H-pyrrolo[3,4-c]carbazole-1,3-dione;
9-Hydroxy-4-(3-hydroxymethyl-phenyl)-6H-pyrrolo[3,4-c]carbazole-1,3-dione;
9-Hydroxy-4-(4-trifluoromethoxy-phenyl)-6H-pyrrolo[3,4-c]carbazole-1,3-dione
9-Hydroxy-4-(3-hydroxy-phenyl)-6H-pyrrolo[3,4-c]carbazole-1,3-dione; and
4-(2-Acetyl-phenyl)-9-hydroxy-6H-pyrrolo[3,4-c]carbazole-1,3-dione.

In yet another preferred embodiment of the present invention are compounds according to Formula I in which $Y^1$ is oxygen, such as but not limited to:
4-(2-Chlorophenyl)-7-(1,2-dihydroxyethyl)-9-hydroxy-1H-[1]benzofuro[3,2-e]isoindole-1,3(2H)-dione;
4-(2-Chlorophenyl)-9-hydroxy-1H-[1]benzofuro[3,2-e]isoindole-1,3(2H)-dione;
4-(2-Chlorophenyl)-8-ethyl-9-hydroxy-1H-[1]benzofuro[3,2-e]isoindole-1,3(2H)-dione;
4-(2-Chlorophenyl)-7-ethyl-9-hydroxy-1H-[1 benzofuro[3,2-e]isoindole-1,3(2H)-dione;
9-Hydroxy-4-phenyl-1H-[1]benzofuro[3,2-e]isoindole-1,3(2H)-dione;
4-(2-Chlorophenyl)-8-[3-(dimethylamino)propoxy]-9-hydroxy-1H-[1]benzofuro[3,2-e]isoindole-1,3(2H)-dione; and
4-(2-Chlorophenyl)-9-hydroxy-8-(4-hydroxybutyl)-1H-[1]benzofuro[3,2-e]isoindole-1,3(2H)-dione.

In another preferred embodiment of the present invention are compounds according to Formula I in which $Y^1$ is sulfur, such as but not limited to:
4-(2-Chlorophenyl)-9-hydroxy-1H-[1]benzothieno[3,2-e]isoindole-1,3(2H)-dione.

In another preferred embodiment of the present invention are compounds according to Formula I in which $R^9$ is hydroxyl and $Y^1$ is $NR^{10}$.

In another preferred embodiment of the present invention are compounds according to Formula I in which $R^9$ is $NR^5R^6$, $R^1$ is aryl and $Y^1$ is $NR^{10}$ such as, but not limited to, compounds selected from the group consisting of:
9-Amino-4-(2-methoxyphenyl)-6-methylpyrrolo[3,4-c]carbazole-1,3(2H,6H)-dione;
9-Amino-4-(2-chlorophenyl)-6-methylpyrrolo[3,4-c]carbazole-1,3(2H,6H)-dione;
9-(Dimethylamino)-4-(2-methoxyphenyl)-6-methylpyrrolo[3,4-c]carbazole-1,3(2H,6H)-dione;
9-Amino-4-(2-chlorophenyl)pyrrolo[3,4-c]carbazole-1,3(2H,6H)-dione;
4-(2-Chlorophenyl)-6-methyl-1,3-dioxo-1,2,3,6-tetrahydropyrrolo[3,4-c]carbazol-9-ylformamide;
4-(2-Chlorophenyl)-1,3-dioxo-1,2,3,6-tetrahydropyrrolo[3,4-c]carbazol-9-ylformamide;
4-(2-Chlorophenyl)-6-methyl-9-(methylamino)pyrrolo[3,4-c]carbazole-1,3(2H,6H)-dione;
N-[4-(2-Chlorophenyl)-6-methyl-1,3-dioxo-1,2,3,6-tetrahydropyrrolo[3,4-c]carbazol-9-yl]acetamide;
4-(2-Chlorophenyl)-9-(ethylamino)-6-methylpyrrolo[3,4-c]carbazole-1,3(2H,6H)-dione; and
N-[4-(2-Chlorophenyl)-6-methyl-1,3-dioxo-1,2,3,6-tetrahydropyrrolo[3,4-c]carbazol-9-yl]-3-(1-piperidinyl)propanamide.

In another preferred embodiment of the present invention are compounds according to Formula I in which $R^9$ is hydroxyl and $Y^1$ is $NR^{10}$.

In another preferred embodiment of the present invention are compounds according to Formula I in which $R^9$ is hydroxyl and $Y^1$ is $NR^{10}$, and T may be absent, O, $CONR^3$, or $CONHSO_2$. Such compounds are exemplified below:
9-Methoxy-4-(2-methoxy-5-nitrophenyl)-4,5,6,10c-tetrahydropyrrolo[3,4-c]carbazole-1,3(2H,3aH)-dione;
N-[3-(4-(2-Chlorophenyl)-9-hydroxy-1,3-dioxo-2,3-dihydropyrrolo[3,4-c]carbazol-6(1H)-yl)propanoyl]benzenesulfonamide;
4-(2,6-Dichlorophenyl)-9-hydroxy-6-(3-hydroxypropyl)pyrrolo[3,4-c]carbazole-1,3(2H,6H)-dione;
4-(2,6-Dichlorophenyl)-9-hydroxy-6-(2-hydroxyethyl)pyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6(1H)-yl)-N-(1H-tetraazol-5-yl)propanamide;
4-(2-Chlorophenyl)-9-hydroxy-6-[2-(1H-1,2,4-triazol-5-ylsulfinyl)ethyl]pyrrolo[3,4-c]carbazole-1,3(2H,6H)-dione;

6-(3-Bromopropyl)-4-(2-chlorophenyl)-9-hydroxypyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6(1H)-yl)propanoic acid;
N-[3-(4-(2-Chlorophenyl)-9-hydroxy-1,3-dioxo-2,3-dihydropyrrolo[3,4-c]carbazol-6(1H)-yl)propanoyl]-2-(dimethylamino)ethanesulfonamide;
4-(2-Chlorophenyl)-9-hydroxypyrrolo[3,4-c]carbazole-1,3(2H,6H)-dione;
N-[3-(4-(2-Chlorophenyl)-9-hydroxy-1,3-dioxo-2,3-dihydropyrrolo[3,4-c]carbazol-6(1H)-yl)propanoyl]methanesulfonamide;
4-(4-(2-Chlorophenyl)-9-hydroxy-1,3-dioxo-2,3-dihydropyrrolo[3,4-c]carbazol-6 (1H)-yl)butanoic acid;
N-[4-(4-(2-Chlorophenyl)-9-hydroxy-1,3-dioxo-2,3-dihydropyrrolo[3,4-c]carbazol-6(1H)-yl)butanoyl]methanesulfonamide;
6-Acetyl-4-(2-chlorophenyl)-9-hydroxypyrrolo[3,4-c]carbazole-1,3(2H,6H)-dione;
3-(4-(2,6-Dichlorophenyl)-9-hydroxy-1,3-dioxo-2,3-dihydropyrrolo[3,4-c]carbazol-6(1H)-yl)-N-[2-(dimethylamino)ethyl]propanamide;
3-(4-(2-Chlorophenyl)-9-hydroxy-1,3-dioxo-2,3-dihydropyrrolo[3,4-c]carbazol-6 (1H)-yl)propanenitrile;
4-(2-Chlorophenyl)-9-hydroxy-6-[3-(1H-tetraazol-5-yl)propyl]pyrrolo[3,4-c]carbazole-1,3(2H,6H)-dione;
4-(2-Chlorophenyl)-9-hydroxy-6-[2-(1H-imidazol-2-ylsulfanyl)ethyl]pyrrolo[3,4-c]carbazole-1,3(2H,6H)-dione;
N-[4-(4-(2-Chlorophenyl)-9-hydroxy-1,3-dioxo-2,3-dihydropyrrolo[3,4-c]carbazol-6 (1H)-yl)butanoyl]benzenesulfonamide;
4-(2-Chlorophenyl)-9-hydroxy-6-[2-(1H-1,2,4-triazol-5-ylsulfonyl)ethyl]pyrrolo[3,4-c]carbazole-1,3(2H,6H)-dione;
4-(2-Chlorophenyl)-9-hydroxy-6-[2-(1H-imidazol-2-ylsulfinyl)ethyl]pyrrolo[3,4-c]carbazole-1,3(2H,6H)-dione;
4-(2-Chlorophenyl)-9-hydroxy-6-[2-(1H-tetraazol-5-yl)ethyl]pyrrolo[3,4-c]carbazole-1,3(2H,6H)-dione;
3-(9-Hydroxy-1,3-dioxo-4-phenyl-2,3-dihydropyrrolo[3,4-c]carbazol-6 (1H)-yl)propanamide;
4-(2-Chlorophenyl)-9-hydroxy-6-[2-(1H-imidazol-2-ylsulfonyl)ethyl]pyrrolo[3,4-c]carbazole-1,3(2H,6H)-dione;
3-(9-Hydroxy-1,3-dioxo-4-phenyl-2,3-dihydropyrrolo[3,4-c]carbazol-6 (1H)-yl)propanoic acid;
4-(2-Chlorophenyl)-6-(2,3-dihydroxypropyl)-9-hydroxypyrrolo[3,4-c]carbazole-1,3(2H,6H)-dione;
2-(4-(2,6-Dichlorophenyl)-9-hydroxy-1,3-dioxo-2,3-dihydropyrrolo[3,4-c]carbazol-6 (1H)-yl)ethyl methanesulfonate;
4-(2-Chlorophenyl)-9-hydroxy-6-[2-(4H-1,2,4-triazol-3-ylsulfanyl)ethyl]pyrrolo[3,4-c]carbazole-1,3(2H,6H)-dione;
9-Hydroxy-6-(2-hydroxyethyl)-4-phenylpyrrolo[3,4-c]carbazole-1,3(2H,6H)-dione;
6-(3-Bromopropyl)-4-(2,6-dichlorophenyl)-9-hydroxypyrrolo[3,4-c]carbazole-1,3(2H,6H)-dione;
4-(2-Chlorophenyl)-9-hydroxy-6-(3-methoxypropyl)pyrrolo[3,4-c]carbazole-1,3(2H,6H)-dione;
4-(2-Chlorophenyl)-9-hydroxy-6-(2-hydroxypropyl)pyrrolo[3,4-c]carbazole-1,3(2H,6H)-dione;
4-(2-Chlorophenyl)-9-hydroxy-6-[(2S)-3-hydroxy-2-methylpropyl]pyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6(1H)-yl)-N-[2-(1H-imidazol-5-yl)ethyl]propanamide;
9-Hydroxy-6-(3-hydroxypropyl)-4-(2-methoxyphenyl)pyrrolo[3,4-c]carbazole-1,3(2H,6H)-dione;
Methyl 3-(4-(2-chlorophenyl)-9-hydroxy-1,3-dioxo-2,3-dihydropyrrolo[3,4-c]carbazol-6(1H)-yl)propanoate;
3-(4-(2-Chlorophenyl)-9-hydroxy-1,3-dioxo-2,3-dihydropyrrolo[3,4-c]carbazol-6(1H)-yl)-N-[2-(4-morpholinyl)ethyl]propanamide;
4-(4-(2-Chlorophenyl)-9-hydroxy-1,3-dioxo-2,3-dihydropyrrolo[3,4-c]carbazol-6(1H)-yl)butanenitrile;
4-(2-Chloro-6-methoxyphenyl)-9-hydroxy-6-(2-hydroxyethyl)pyrrolo[3,4-c]carbazole-1,3(2H,6H)-dione;
3-(4-(2-Chlorophenyl)-9-hydroxy-1,3-dioxo-2,3-dihydropyrrolo[3,4-c]carbazol-6(1H)-yl)-N-[2-(dimethylamino)ethyl]propanamide;
4-(2-Chlorophenyl)-6-(3,4-dihydroxybutyl)-9-hydroxypyrrolo[3,4-c]carbazole-1,3(2H,6H)-dione;
3-(4-(2-Chloro-6-methoxyphenyl)-9-hydroxy-1,3-dioxo-2,3-dihydropyrrolo[3,4-c]carbazol-6(1H)-yl)-N-[2-(dimethylamino)ethyl]propanamide;
4-(2-Chlorophenyl)-9-hydroxy-6-[(2R)-3-hydroxy-2-methylpropyl]pyrrolo[3,4-c]carbazole-1,3(2H,6H)-dione;
2-(4-(2-Chlorophenyl)-9-hydroxy-1,3-dioxo-2,3-dihydropyrrolo[3,4-c]carbazol-6(1H)-yl)ethyl methanesulfonate;
4-(2-Chloro-6-methoxyphenyl)-9-hydroxy-6-(3-hydroxypropyl)pyrrolo[3,4-c]carbazole-1,3(2H,6H)-dione;
9-Hydroxy-6-(2-hydroxyethyl)-4-(2-methoxyphenyl)pyrrolo[3,4-c]carbazole-1,3(2H,6H)-dione;
4-(2-Chlorophenyl)-6-(2-hydroxyethyl)-9-hydroxypyrrolo[3,4-c]carbazole-1,3(2H,6H)-dione;
4-(2-Chlorophenyl)-9-hydroxy-6-[3-(methylsulfanyl)propyl]pyrrolo[3,4-c]carbazole-1,3(2H,6H)-dione;
4-(2-Chlorophenyl)-6-ethyl-9-hydroxypyrrolo[3,4-c]carbazole-1,3(2H,6H)-dione (VI; Ar=2-chlorophenyl, R=CH$_2$CH$_3$);
4-(2-Chlorophenyl)-9-hydroxy-6-isopropylpyrrolo[3,4-c]carbazole-1,3(2H,6H)-dione;
4-(2-Chlorophenyl)-9-hydroxy-6-[3-(1H-imidazol-1-yl)propyl]pyrrolo[3,4-c]carbazole-1,3(2H,6H)-dione;
4-(2-Chloro-6-methoxyphenyl)-9-hydroxy-6-[3-(4-morpholinyl)propyl]pyrrolo[3,4-c]carbazole-1,3(2H,6H)-dione;
6-(2-Chloroethyl)-4-(2-chlorophenyl)-9-hydroxypyrrolo[3,4-c]carbazole-1,3(2H,6H)-dione;
6-(3-Bromopropyl)-4-(2-chloro-6-methoxyphenyl)-9-hydroxypyrrolo[3,4-c]carbazole-1,3(2H,6H)-dione;
4-(2-Chlorophenyl)-9-hydroxy-6-[2-hydroxy-3-(methylamino)propyl]pyrrolo[3,4-c]carbazole-1,3(2H,6H)-dione;
4-(2-Chlorophenyl)-9-hydroxy-6-methylpyrrolo[3,4-c]carbazole-1,3(2H,6H)-dione;
4-(2-Chlorophenyl)-9-hydroxy-6-[2-hydroxy-3-(4-morpholinyl)propyl]pyrrolo[3,4-c]carbazole-1,3(2H,6H)-dione;
4-(2,6-Dichlorophenyl)-9-hydroxy-6-[3-(1H-imidazol-1-yl)propyl]pyrrolo[3,4-c]carbazole-1,3(2H,6H)-dione; and
6-Butyl-4-(2-chlorophenyl)-9-hydroxypyrrolo[3,4-c]carbazole-1,3(2H,6H)-dione.

In a more preferred embodiment of the present invention are compounds according to Formula I in which $R^9$ is hydroxyl and $Y^1$ is $NR^{10}$ and the bond represented by the dashed line (C—O) is absent.

In an especially preferred embodiment of the present invention are compounds according to Formula I in which $R^9$ is hydroxyl and $R^8$ is not hydrogen.

In another preferred embodiment of the present invention are compounds according to Formula I in which $R^9$ is hydroxyl and $Y^1$ is $NR^{10}$ and $R^1$ is aryl.

In another especially preferred embodiment of the present invention are compounds according to Formula I in which $R^8$ is not hydrogen, and $R^9$ is hydrogen.

In another especially preferred embodiment of the present invention are compounds according to Formula I in which $R^8$ is not hydrogen, $R^9$ is hydrogen and y1 is $NR^{10}$.

Another especially preferred embodiment of the present invention comprises compounds according to Formula I in which $R^9$ is hydrogen and $R^8$ is $((CR^5, R^6)_n T)_a (CR^{11} R^{12})_b)$—Z; wherein T may be absent or O and Z is $NR^3R^4$.

Another especially preferred embodiment of the present invention comprises compounds according to Formula I in which $R^9$ is selected from halogen or hydroxyl and $R^8$ is $((CR^5R^6)_n T)_a (CR^{11}R^{12})_b)Z$ wherein T is absent and Z is hydrogen.

The following are definitions of terms used in this specification. The initial definition provided for a group or term herein applies to that group or term throughout the present specification, individually or as part of another group, unless otherwise indicated.

Where stereoisomers or enantiomers exist all possible combinations are claimed.

The terms "halogen" and "halo" refer to fluorine, chlorine, bromine and iodine.

The term "unsaturated ring" includes partially unsaturated and aromatic rings.

The term "alkyl" in the present invention means a straight or branched hydrocarbon radical having from 1 to 8 carbon atoms and includes, for example, methyl, ethyl, n-propyl, isopropyl, n-butyl, sec-butyl, isobutyl, tert-butyl, n-pentyl, iso-pentyl, n-hexyl, and the like. The term "aryl" means an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl).

The term "heteroaryl" means an aromatic "heterocycle," "heterocyclic," "heterocyclyl," or "heterocyclo" group as defined below that comprises at least one heteroatom.

The aryl or heteroaryl ring may be optionally substituted with up to five substituents selected from $NH(C_1–C_6$ alkyl), $N(C_1–C_6$ alkyl$)_2$, thio $C_1–C_6$ alkyl, $C_1–C_6$ alkoxy, hydroxy, carboxy, $C_1–C_6$ alkoxycarbonyl, halo, nitrile, and cycloalkyl.

By "alkoxy" is meant straight or branched chain alkoxy groups having 1 to 10 carbon atoms, such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy.

"Alkynyl" means straight and branched hydrocarbon radicals having from 2 to 8 carbon atoms and one triple bond and includes ethynyl, 3-butyn-1-yl, propynyl, 2-butyn-1-yl, 3-pentyn-1-yl, and the like.

The terms "cycloalkyl" and "cycloalkenyl" refer to cyclic hydrocarbon groups of 3 to 8 carbon atoms and includes cyclopropyl, cyclobutyl, cyclopentyl, cyclohexyl, cycloheptyl, cyclooctyl and the like.

"Acyl" means an alkyl, aryl, cycloalkyl, heterocycle, heterocyclic, heterocyclyl, or heterocyclo group bonded through a carbonyl group, i.e., R—C(O)—, Typical acyl groups include acetyl, benzoyl, and the like having from 1–10 carbon atoms, preferably 1–6 carbon atoms.

The term "haloalkyl" means an akyl group substituted with 1 to 6 halogen atoms and include trifluoromethyl, trichloromethyl, tribromomethyl, trifluoroethyl, trifluoropropyl, trifluorobutyl, pentafluoroethyl and the like.

The alkyl, alkenyl, alkoxy, and alkynyl groups described above are optionally substituted, preferably by 1 to 3 groups selected from $NH(C_1–C_6$ alkyl), $N(C_1–C_6$ alkyl$)_2$, phenyl, substituted phenyl, thio $C_1–C_6$ alkyl, $C_1–C_6$ alkoxy, hydroxy, carboxy, $C_1–C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1–C_6$ alkyl or $(CH_2)_p Ph$ where p is 1,2, or 3. Perhalo and polyhalo substitution is also included.

The term "heteroatom" means an oxygen, nitrogen, sulfur, or phosphorous atom.

The terms "heterocycle," "heterocyclic," "heterocyclyl," or "heterocyclo" refer to fully saturated or unsaturated, including aromatic (heteroaryl) or nonaromatic cyclic groups, for example, 4- to 7-membered monocyclic, 7- to 11-membered bicyclic, or 10- to 15-membered tricyclic ring systems, which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Monocyclic heterocyclic groups include, but are not limited to, piperidine, 2,6-dimethylpiperazine, piperazine, n-methylpiperazine, pyrrolidinyl, pyrrolyl, pyrazolyl, oxetanyl, pyrazolinyl, imidazolyl, imidazolinyl, S(O)-imidazoles, $S(O)_2$-imidazoles oxazolyl, oxazolidinyl, isoxazolinyl, isoxazolyl, thiazolyl, thiadiazolyl, thiazolidinyl, isothiazolyl, isothiazolidinyl, morpholine and dimethylmorpoline, 2-thiophene, thiophene, 1-imidazole, 2-imidazole, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, 2-azepinyl, 4-piperidonyl, pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothianyl, tetrazole, SO-triazole, $SO_2$-triazole and the like.

Bicyclic heterocyclic groups include, but are not limited to, indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofaryl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl or furo[2,3-b]pyridinyl), dihydroisoindolyl, dihydroquinazolinyl (such as 3,4-dihydro-4-oxo-quinazolinyl), tetrahydroquinolinyl and the like, tricyclic heterocyclic groups include, but are not limited to, carbazolyl, benzindolyl, phenanthrolinyl, acridinyl, phenanthridinyl, xanthenyl and the like.

The term "cancer" includes, but is not limited to, the following cancers: cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.*, 1977;66:1–19 which is incorporated herein by reference.)

The compounds of Formula I are capable of further forming pharmaceutically acceptable formulations comprising salts, including but not limited to acid addition and/or base salts, solvates and N-oxides of a compound of Formula I. This invention also provides pharmaceutical formulations comprising a compound of Formula I together with a pharmaceutically acceptable carrier, diluent, or excipient therefor. All of these forms are within the present invention.

Pharmaceutically acceptable acid addition salts of the compounds of Formula I include salts derived form inorganic acids such as hydrochloric, nitric, phosphoric, sulfuric, hydrobromic, hydriodic, phosphorus, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science*, 1977;66: 1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra., 1977.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods "March's Advanced Organic Chemistry, 5$^{th}$ Edition". M. B. Smith & J. March, John Wiley & Sons, 2001.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods such as "March's Advanced Organic Chemistry, 5$^{th}$ Edition". M. B. Smith & J. March, John Wiley & Sons, 2001.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

The present invention also includes isotopically labelled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as 2H, $^3$H, $^{13}$C, $^{11}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of Formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I and their pharmaceutically acceptable salts can be administered to mammals via either the oral, parenteral (such as subcutaneous, intraveneous, intramuscular, intrasternal and infusion techniques), rectal, intranasal or topical routes. In general, these compounds are most desirably administered in doses ranging from about 10 to about 10,000 mg per day, in single or divided doses (i.e., from 1 to 4 doses per day), although variations will necessarily occur depending upon the species, weight and condition of the subject being treated and the particular route of administration chosen. However, a dosage level that is in the range of about 0.15 mg to about 150 mg per kg of body weight per day is most desirably employed. Nevertheless, variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such higher dose levels are first divided into several small doses for administration throughout the day.

The compounds of the present invention may be administered alone or in combination with pharmaceutically acceptable carriers or diluents by either of the routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a compound of the present invention in either sesame or peanut oil or in aqueous propylene glycol may be employed. The aqueous solutions should be suitably buffered (preferably pH from about 3 to about 8) if necessary and the liquid diluent first rendered isotonic. These aqueous solutions are suitable for intravenous injection purposes. The oily solutions are suitable for intra-articular, intra-muscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating proliferative cell conditions of the skin and this may be done by way of creams, jellies, gels, pastes, patches, ointments and the like, in accordance with standard pharmaceutical practice.

The activity of the compounds of the present invention is determined by their ability to act as check point abrogators. Checkpoint abrogators inhibit kinases involved in the regulation of the $G_2/M$ checkpoint resulting in the reversal of the imposed checkpoint. Wee1 or Chk1 are examples of such kinases. Utilization in cells either having damaged DNA, for instance, but not limited to, DNA damaged by conventional DNA-directed chemotherapeutic agents or by radiation of cells with undamaged DNA presents an opportunity to utilize cellular regulatory pathways to inappropriately and prematurely cause cells to progress into M phase. Such cells may be less likely to survive and further divide since the commitment to M phase was made in the presence of potentially catastrophically damaged DNA. In the case of undamaged cells having no detectable DNA damage, treatment of these cells with the checkpoint abrogators of the present invention may be forced into M phase prematurely with similar cytotoxic effects. (Alan J. Kraker and Robert N. Booher, "New Cell Cycle Targets,", *Ann. Rep. Med. Chem.,* 1999;34:247–256).

One can identify the checkpoint abrogators of the present invention by measuring the activity in the assays described in Examples 483 (Wee1) and 484 (Chk1) and 486 (PKC) and selecting those compounds that have at least 10-fold less activity in the PKC assay than they have in the Wee1 assay or at least 5-fold less activity in the PKC assay than they have in the Chk1 assay.

The present invention is illustrated by the following examples. It will be understood, however, that the invention is not limited to the specific details of these examples. Melting points are uncorrected. Proton nuclear magnetic resonance spectra ($^1H$ NMR) and $^{13}C$ nuclear magnetic resonance spectra were measured for solutions in deutero-chloroform ($CDCl_3$) or in $CD_3OD$ or $CD_3SOCD_3$ and peak positions are expressed in parts per million (ppm) downfield from tetramethylsilane (TMS). The peak shapes are denoted as follows: s, singlet; d, doublet; t, triplet; q, quartet; m, multiplet; b, broad.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The term "animal" refers to mammals, including rodents, bovine, equine, canine, feline, and human.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis in combination with other conventional therapies. To utilize a compound of the present invention to treat cancer, a patient in need of such treatment, such as one having cancer or another cell proliferative diseases is administered an effective amount of the compound of the invention.

Furthermore, the compounds of the present invention are useful for treating cancers when combined as adjuvant therapy with other clinical treatment agents and modalities such as, but not limited to, X-irradiation, beam therapy, conventional chemotherapeutic agents such as gemcitabine, paclitaxel, docetaxel, cisplatin, carboplatin, etoposide, adriamycin, topotecan, CPT11, capecitabine, or ionizing radiation alkylating agents, antimetabolites, antibodies, DNA intercalators, or other such anti-proliferative agents ultimately leading to DNA damage. As new antineoplastic agents or modalities are discovered, the use of the Wee1 and/or Chk1 inhibitors in combination with these other therapeutic agents or modalities is contemplated.

While the in vivo tests described herein teach administering the compounds according to Formula I simultaneously with or subsequent to the administration of the conventional agent, it is contemplated that the compound of the present invention may also be administered prior to the conventional chemotherapeutic agent or agents.

The following examples illustrate particular embodiments of the invention and are not intended to limit the specification, including the claims, in any way. Those skilled in the art will appreciate that numerous changes and modifications can be made to the preferred embodiments of the invention and that such changes and modifications can be made without departing from the spirit of the invention. It is, therefore, intended that the cover all such equivalent variations as fall within the true spirit and scope of the invention.

The chemical synthesis schemes provided below exemplify the best mode for preparing the compounds of the present invention. This patent describes a number of synthetic transformations known to those skilled in the art. In each case alternative conditions known to one skilled in the art and described in the literature, for instance in Advanced Organic Chemistry 5$^{th}$ Edition, Author: Jerry March,m. b. smith & J. March, John Wiley & Sons 2001; Comprehensive Organic Transformation, Author: Richard C. Larock, The Journal of Organic chemistry, published by the American Chemical Society and the references cited therein) may also lead to the desired product.

Known transformations include, but are not limited to; alkylation, dealkylation, oxidation, reduction, Curtus rearrangement, Suzuki reaction, esterification, Wittig reaction, amide formation, hydrogenation, protection, deprotection, hydrolysis, dihydroxylation., ozonolysis, acetylation, and hydroboration.

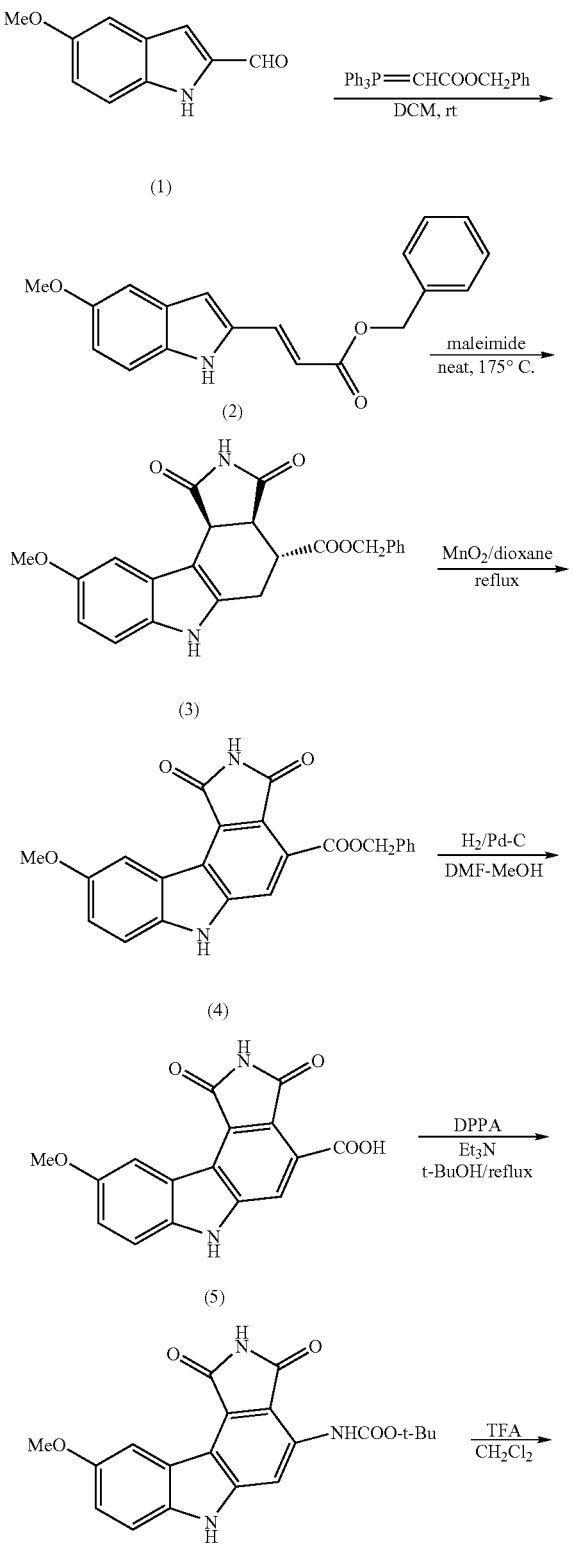

Scheme 1
Preparation of substituted 4-aryl pyrrolo[3,4-c]carbazoles

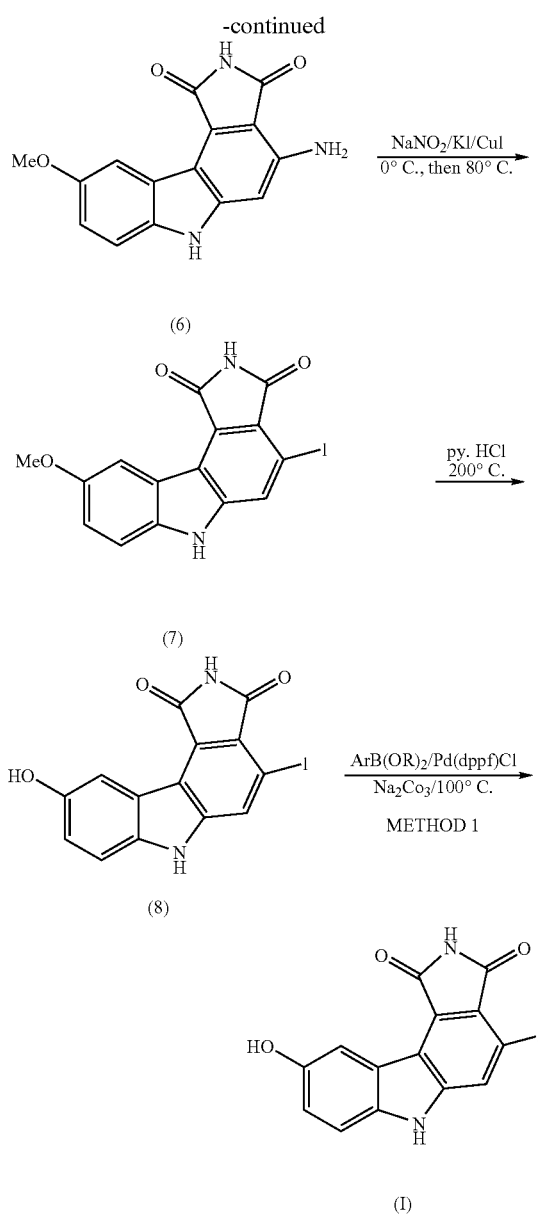

EXAMPLE 1

The Preparation of Benzyl (2E)-3-(5-methoxy-1H-indol-2-yl)-2-propenoate (2)

Benzyl (triphenylphosphoranylidene)acetate (49.2 g, 0.120 mol) was added to a stirred solution of 5-methoxy-1H-indole-2-carbaldehyde (1) (20.0 g, 0.114 mol) in $CH_2Cl_2$ (500 mL) and the solution was stirred at room temperature for 4 h. The solvent was removed in vacuo and the residue slurried with methanol (200 mL), whereupon crystallisation of the product occurred. The mixture was filtered, washed with several portions of cold methanol, and dried to give benzyl (2E)-3-(5-methoxy-1H-indol-2-yl)-2-propenoate (2) in a 30.46 g, 87% yield as pale yellow plates; mp 155–157° C. $^1$H NMR δ ($CDCl_3$) 8.28 (s, 1H), 7.69 (d, J=16.1 Hz, 1H), 7.43–7.32 (m, 5H), 7.23 (d, J=9.1 Hz, 1H), 7.03 (d, J=2.3 Hz, 1H), 6.92 (dd, J=9.1, 2.3 Hz, 1H), 6.74 (d, J=1.8 Hz, 1H), 6.24 (d, J=16.1 Hz, 1H), 5.26 (s, 2H), 3.84 (s, 3H). Found: C, 74.45; H, 5.62; N, 4.58. $C_{19}H_{17}NO_3$ requires C, 74.25; H, 5.57; N, 4.56.

EXAMPLE 2

The Preparation of Benzyl 9-methoxy-1,3-dioxo-1,2,3,3a,4,5,6,10c-octahydropyrrolo[3,4-c]carbazole-4-carboxylate (3)

Maleimide (4.82 g, 0.050 mol) was added to a solution of benzyl (2E)-3-(5-methoxy-1H-indol-2-yl)-2-propenoate, (12.71 g, 0.041 mol) prepared as in example 1 in THF (150 mL) in a 250 mL flat-bottomed flask and the mixture was stirred until homogeneous. The THF was removed in vacuo and the residue dried under high vacuum for 30 min. The flask was immersed in a 175° C. oil bath and the mixture was stirred at this temperature for 3 h. The solid melt was cooled to room temperature and ethyl acetate (100 mL) was added. The solid mass was partially broken up with a spatula and the mixture was stirred vigorously overnight, after which time the product (3) was present as a cream precipitate. Filtration followed by washing with diethyl ether gave benzyl 9-methoxy-1,3-dioxo-1,2,3,3a,4,5,6,10c-octahydropyrrolo[3,4-c]carbazole-4-carboxylate (13.76 g, 83%), mp 179–181° C. $^1$H NMR δ [$(CD_3)_2SO$] 10.98 (br s, 1H), 10.87 (s, 1H), 7.45–7.32 (m, 5H), 7.20 (d, J=2.4 Hz, 1H), 7.17 (d, J=8.7 Hz, 1H), 6.69 (dd, J=8.7, 2.4 Hz, 1H), 5.21 (s, 1H), 4.22 (br d, J=7.8 Hz, 1H), 4.14 (dd, J=7.8, 4.2 Hz, 1H), 3.75 (s, 3H), 3.19–3.13 (m, 1H), 3.00 (dd, J=16.5, 4.8 Hz, 1H), 2.79–2.70 (m, 1H).

EXAMPLE 3

The Preparation of Benzyl 9-methoxy-1,3-dioxo-1,2,3,6-tetrahydropyrrolo[3,4-c]carbazole-4-carboxylate (4)

Activated manganese dioxide (69 g) was added to a solution of benzyl 9-methoxy-1,3-dioxo-1,2,3,3a,4,5,6,10c-octahydropyrrolo[3,4-c]carbazole-4-carboxylate (13.76 g, 0.034 mol), prepared as in example 2, in p-dioxane (300 mL) and the mixture was refluxed with vigorous stirring for 0.5–2 h. The mixture was filtered while hot through a plug of Celite, which was washed exhaustively with a MeOH/p-dioxane (1:1) mixture until the washings were colorless. The combined washings and filtrate were concentrated to dryness and the residue triturated several times with diethyl ether to give benzyl 9-methoxy-1,3-dioxo-1,2,3,6-tetrahydropyrrolo[3,4-c]carbazole-4-carboxylate (4) as a yellow/orange powder (12.47 g, 91.5%), mp 245° C. A small sample was recrystallised from EtOAc to give benzyl 9-methoxy-1,3-dioxo-1,2,3,6-tetrahydropyrrolo[3,4-c]carbazole-4-carboxylate as orange cubes; mp 289–292° C. $^1$H NMR δ ($(CD_3)_2SO$) 12.11 (br s, 1H), 11.27 (br s, 1H), 8.45 (d, J=2.6 Hz, 1H), 7.98 (s, 1H), 7.59 (d, J=8.9 Hz, 1H), 7.55–7.51 (m, 2H), 7.44–7.34 (m, 3H), 7.27 (dd, J=8.9, 2.6 Hz, 1H), 5.41 (s, 2H), 3.88 (s, 3H). Found: C, 68,99; H, 4.09; 6.91. $C_{23}H_{16}N_2O_5$ requires C, 69.00; H, 4.03; N, 6.99.

EXAMPLE 4

The Preparation of 9-Methoxy-1,3-dioxo-1,2,3,6-tetrahydropyrrolo[3,4-c]carbazole-4-carboxylic acid (5)

A solution of benzyl 9-methoxy-1,3-dioxo-1,2,3,6-tetrahydropyrrolo[3,4-c]carbazole-4-carboxylate (2.00 g), prepared as in example 3, in DMF/MeOH (4:1) (50 mL) containing 5% Pd-C (0.50 g) was hydrogenated at 60 psi for 2 h (Parr apparatus). The solution was filtered through a plug of Celite, which was washed 6 times with neat DMF followed by MeOH (several cycles). The combined filtrate and washings were concentrated to dryness in vacuo and the residue was slurried with diethyl ether to give the 9-methoxy-1,3-dioxo-1,2,3,6-tetrahydropyrrolo[3,4-c]carbazole-4-carboxylic acid (5) as a greenish solid. The reaction was repeated 5 times on this scale to and the products were combined to give 9-methoxy-1,3-dioxo-1,2,3,6-tetrahydropyrrolo[3,4-c]carbazole-4-carboxylic acid, (8.1 g, 84%). A portion of the product was purified by adsorption onto silica, followed by chromatography on silica, eluting with EtOAc. The product was triturated with diethyl ether to give 9-methoxy-1,3-dioxo-1,2,3,6-tetrahydropyrrolo[3,4-c]carbazole-4-carboxylic acid as an orange solid; mp>300° C. $^1$H NMR δ [(CD$_3$)$_2$SO] 12.15 (s, 1H), 8.42 (d, J=2.5 Hz, 1H), 7.97 (s, 1H), 7.57 (d, J=8.8 Hz, 1H0, 7.25 (dd, J=8.8, 2.5 Hz, 1H), 3.82 (s, 3H), 3.40 (br, 2H). Found: C, 58.69; H, 3.55; N, 8.40. C$_{16}$H$_{10}$N$_2$O$_5$,H$_2$O requires C, 58.54; H, 3.68; N, 8.53.

EXAMPLE 5

The Preparation of 4-Amino-9-methoxypyrrolo[3,4-c]carbazole-1,3(2H,6H)-dione (6)

Diphenylphosphoryl azide (1.81 mL, 8.38 mmol) was added to a mixture of the 9-methoxy-1,3-dioxo-1,2,3,6-tetrahydropyrrolo[3,4-c]carbazole-4-carboxylic acid (2.55 g, 8.22 mmol), prepared as in example 4, and Et$_3$N (1.17 mL, 8.38 mmol) in anhydrous t-butanol (300 mL) and the mixture was refluxed under an atmosphere of nitrogen for 16 h. The solution was concentrated in vacuo and the residue partitioned between EtOAc and saturated aqueous NaHCO$_3$. Insoluble material was removed by filtration of the two layers through Celite, washing through with more EtOAc. The organic phase was dried, the drying agent was removed and the solution was concentrated to dryness and gave a yellow solid. This material was dissolved in CH$_2$Cl$_2$/trifluoroacetic acid (1:1) (200 mL) and the solution was held at room temperature for 1 h. After concentration in vacuo the residue was partitioned between EtOAc and saturated aqueous NaHCO$_3$ solution. The EtOAc solution was dried, the drying agent was removed and the solution was concentrated to dryness to give an orange solid which was adsorbed onto silica and chromatographed. Elution with ethyl acetate/petroleum ether (1:1) followed by ethyl acetate and then methanol/ethyl acetate (1:9) gave 4-amino-9-methoxypyrrolo[3,4-c]carbazole-1,3(2H,6H)-dione (6) as an orange powder (2.16 g, 93%), mp 342–345° C. $^1$H NMR δ [(CD$_3$)$_2$SO] 11.18 (s, 1H), 10.78 (br s, 1H), 8.18 (d, J=2.5 Hz, 1H), 7.29 (d, J=8.7 Hz, 1H), 7.01 (dd, J=8.7, 2.5 Hz, 1H), 6.83 (s, 1H), 6.28 (br s, 2H), 3.82 (s, 3H). Found: C, 63.05; H, 3.99; N, 14.05. C$_{15}$H$_{11}$N$_3$O$_3$, 1/2H$_2$O requires C, 63.04; H, 4.06; N, 14.7.

EXAMPLE 6

The Preparation of 4-Iodo-9-methoxypyrrolo[3,4-c]carbazole-1,3(2H,6H)-dione (7)

Concentrated H$_2$SO$_4$ (10 mL) was added at room temperature to powdered 4-amino-9-methoxypyrrolo[3,4-c]carbazole-1,3(2H,6H)-dione (0.50 g, 1.78 mmol), prepared as in example 5, and the mixture stirred for 5 min and then cooled in an ice bath. An ice-water slurry (ca 40 mL) was added in one portion with vigorous stirring and the mixture was stirred for a further 15 min to give a tan precipitate. When the internal temperature had reached 3° C. a solution of NaNO$_2$ (0.18 g, 2.65 mmol) in cold water (1 mL) was added dropwise over 30 seconds and the mixture was stirred for an additional 3 minutes. Powdered urea (74 mg, 1.23 mmol) was added and the mixture was stirred for another 3 min. Finally a suspension of KI (1.46 g, 8.79 mmol) and CuI (1.46 g, 7.66 mmol) in cold water (10 mL) was added and the mixture was stirred vigourously for 5 min, and then warmed slowly to 70° C. and held at this temperature for 1 h. Ethyl acetate was added and the two-phase mixture was filtered through a plug of Celite, washing through with more EtOAc. The combined organic portions were washed with 0.5 N aqueous sodium sulfite solution and were dried, the drying agent was removed and the solution was concentrated to dryness to give an oil which was chromatographed on silica. Elution with EtOAc, then crystallisation of the product from THF/petroleum ether as a gave the 4-Iodo-9-methoxypyrrolo[3,4-c]carbazole-1,3(2H,6H)-dione (7) (0.32 g, 46%) as a yellow powder; mp 322–325° C. $^1$H NMR δ [(CD$_3$)$_2$SO] 11.89 (s, 1H), 11.29 (s, 1H), 8.40 (d, J=2.6 Hz, 1H), 8.18 (s, 1H), 7.54 (d, J=8.9 Hz, 1H), 7.24 (dd, J=8.9, 2.6 Hz, 1H), 3.87 (s, 3H). Found: C, 45.49; H, 2.36; N, 6.92. C$_{15}$H$_9$IN$_2$O$_3$,1/4H$_2$O requires C, 45.42; H, 2.41; N, 7.06.

EXAMPLE 7

The Preparation of 9-Hydroxy-4-iodopyrrolo[3,4-c]carbazole-1,3(2H,6H)-dione (8)

Powdered 4-Iodo-9-methoxypyrrolo[3,4-c]carbazole-1,3(2H,6H)-dione (0.50 g, 1.27 mmol) prepared as in example 6 was added in one portion to dry, freshly-prepared pyridine hydrochloride melt at 200° C. under a CaCl$_2$ drying tube and the mixture was stirred at this temperature for 15 min. Water was added and the mixture was extracted with EtOAc. The EtOAc extracts were dried, the drying agent was removed and the solution was concentrated to dryness to give a solid which was chromatographed on silica. Elution with EtOAc gave 9-Hydroxy-4-iodopyrrolo[3,4-c]carbazole-1,3(2H,6H)-dione (8) (0.43 g, 89%) as an orange powder; mp>350° C. $^1$H NMR δ [(CD$_3$)$_2$SO] 11.76 (br s, 1H), 11.24 (br s, 1H), 9.29 (br s, 1H), 8.27 (d, J=2.4 Hz, 1H), 8.13 (s, 1H), 7.44 (d, J=8.7 Hz, 1H), 7.08 (dd, J=8.7, 2.4 Hz, 1H). Found: C, 44.90; H, 1.79; N, 7.14. C$_{14}$H$_{71}$N$_2$O$_3$ requires C, 44.47; H, 1.87; N, 7.40.

EXAMPLE 8

The Preparation of 4-(2-chlorophenyl)-9-hydroxy-pyrrolo[3,4-c]carbazole-1,3(2H,6H)-dione (9) (I, Ar=2-chlorophenyl)

A mixture of the 9-Hydroxy-4-iodopyrrolo[3,4-c]carbazole-1,3(2H,6H)-dione (41.8 mg, 0.110 mmol) prepared as in example 7 and 2-chlorobenzeneboronic acid (52 mg, 0.332 mmol) in p-dioxane (3 mL) and 2N Na$_2$CO$_3$ (0.5 mL) was purged with nitrogen. Pd(dppf)Cl$_2$ (35 mg, 0.011 mmol) was added and the mixture was refluxed under N$_2$ for 4 h and then partitioned between EtOAc and water. The organic layer was dried, the drying agent was removed and the solution was concentrated to dryness, adsorbed onto silica and chromatographed. Elution with EtOAc/petroleum ether (1:4) followed by EtOAc/petroleum ether (2:3) gave a solid the carbazole (50) which crystallised from EtOAc/petroleum ether to yield 4-(2-chlorophenyl)-9-hydroxypyrrolo[3,4-c]

carbazole-1,3(2H,6H)-dione (9) (I, Ar=2-chlorophenyl) (33.1 mg, 83%) as a yellow powder, mp 215–220° C. (dec). $^1$H NMR δ [(CD$_3$)$_2$SO] 11.83 (br s, 1H), 11.01 (br s, 1H), 9.27-(br s, 1H), 8.32 (d, J=2.4 Hz, 1H), 7.65–7.40 m, 5H), 7.08 (dd, J=8.7, 2.4 Hz), 1H). Found: C, 65.72; H, 3.50, N, 6.97. C$_{20}$H$_{11}$ClN$_2$O$_3$,1/4EtOAc requires C, 65.54; H, 3.40; N, 7.28.

EXAMPLE 9

The Preparation of 9-Hydroxy-4-(3-hydroxy-4-methoxyphenyl)pyrrolo[3,4-c]carbazole-1,3(2H,6H)-dione (10)(I, Ar=3-hydroxy-4-methoxyphenyl)

The reaction of 9-hydroxy-4-iodopyrrolo[3,4-c]carbazole-1,3(2H,6H)-dione, prepared as in example 7, with 3-hydroxy-4-methoxybenzeneboronic acid according to the procedure described in example 8 gave 9-hydroxy-4-(3-hydroxy-4-methoxyphenyl)pyrrolo[3,4-c]carbazole-1,3(2H, 6H)-dione (10) (1, Ar=3-hydroxy-4-methoxyphenyl) (51%), mp 265° C. (dec). $^1$H NMR δ [(CD$_3$)$_2$SO] 11.67 (s, 1H), 10.96 (s, 1H), 9.22 (s, 1H), 9.15 (s, 1H), 8.33 (d, J=2.4 Hz, 1H), 7.57 (s, 1H), 7.41 (d, J=8.7 Hz, 1H), 7.22 (d, J=2.0 Hz, 1H), 7.06–6.99 (m, 2H), 6.85 (d, J=8.1 Hz, 1H), 3.81 (s, 3H). EIMS found M$^+$: 374.0900. C$_{21}$H$_{14}$N$_2$O$_5$ requires 374,0903.

EXAMPLE 10

The Preparation of 9-Hydroxy-4-(3-thienyl)pyrrolo[3,4-c]carbazole-1,3(2H,6H)-dione (12) (I, Ar=3-thienyl)

The reaction of 9-hydroxy-4-iodopyrrolo[3,4-c]carbazole-1,3(2H,6H)-dione, prepared as in example 7, with 3-thienylboronic acid according to the procedure described in example 8 gave 9-hydroxy-4-(3-thienyl)pyrrolo[3,4-c]carbazole-1,3(2H,6H)-dione (12) (I, Ar=3-thienyl) in a 74% yield; mp 247° C. (dec). $^1$H NMR δ [(CD$_3$)$_2$SO] 11.73 (br s, 1H), 11.05 (br s, 1H), 9.24 (s, 1H), 9.15 (s, 1H), 8.34 (d, J=2.4 Hz, 1H), 7.92 (dd, J=5.0, 2.7 Hz, 1H), 7.70 (s, 1H), 7.61 (dd, J=5.0, 2.7 Hz, 1H), 7.51 (dd, J=5.0, 0.9 Hz, 1H), 7.42 (d, J=8.7 Hz, 1H), 7.06 (dd, J=8.7, 2.4 Hz, 1H). Found: C, 61.05; H, 2.96; N, 7.60. C$_{18}$H$_{10}$N$_2$SO$_3$,H$_2$O requires C, 61.36; H, 3.43; N, 7.95.

EXAMPLE 11

The Preparation of 4-(3-Aminophenyl)-9-hydroxypyrrolo[3,4-c]carbazole-1,3(2H,6H)-dione (15) (I, Ar=3-aminophenyl)

The reaction of 9-hydroxy-4-iodopyrrolo[3,4-c]carbazole-1,3(2H,6H)-dione, prepared as in example 7, with 3-aminobenzeneboronic acid according to the procedure described in example 8 gave 4-(3-aminophenyl)-9-hydroxypyrrolo[3,4-c]carbazole-1,3(2H,6H)-dione (15) (I, Ar=3-aminophenyl) in a 62% yield; mp 279–284° C. $^1$H NMR δ [(CD$_3$)$_2$SO] 11.70 (s, 1H), 10.96 (s, 1H), 9.22 (s, 1H), 8.33 (d, J=2.4 Hz, 1H), 7.50 (s, 1H), 7.42 (d, J=8.7 Hz, 1H), 7.10–7.03 (m, 2H), 6.77–6.74 (m, 1H), 6.72–6.68 (m, 1H), 6.61 (dd, J=8.1, 2.3 Hz), 1H), 5.11 (br s, 2H). Found: C, 69.41; H, 4.12; N, 10.73. C$_{20}$H$_{13}$N$_3$O$_3$ requires C, 69.96; H, 3.82; N, 12.24.

EXAMPLE 12

The Preparation of 4-(4-Aminophenyl)-9-hydroxypyrrolo[3,4-c]carbazole-1,3(2H,6H)-dione (16) (I, Ar=4-aminophenyl)

The reaction of 9-hydroxy-4-iodopyrrolo[3,4-c]carbazole-1,3(2H,6H)-dione prepared as in example 7 with 4-(4,4,5,5-tetramethyl-1,3,2-dioxaborolan-2-yl)phenylamine according to the procedure described in example 8 gave 4-(4-Aminophenyl)-9-hydroxypyrrolo[3,4-c]carbazole-1,3(2H,6H)-dione (16) (I, Ar=4-aminophenyl) in a 57% yield; mp 256–258° C. $^1$H NMR δ [(CD$_3$)$_2$SO] 11.60 (s, 1H), 10.92 (s, 1H), 9.19 (s, 1H), 8.31 (d, J=2.3 Hz, 1H), 7.48 (s, 1H), 7.39 (d, J=8.6 Hz, 1H), 7.30 (d, J=8.4 Hz, 2H), 7.02 (dd, J=8.6, 2.3 Hz, 1H), 6.62 (d, J=8.4 Hz, 2H), 5.29 (br s, 2H). Found: C, 68.09; H, 4.34; N, 11.03. C$_{20}$H$_{13}$N$_3$O$_3$.1/2H$_2$O requires C, 68.17; H, 4.00; N, 11.92.

EXAMPLE 13

The Preparation of 4-(2,6-Dimethylphenyl)-9-hydroxypyrrolo[3,4-c]carbazole-1,3(2H,6H)-dione (17) (I, Ar=2,6-dimethylphenyl)

The reaction of 9-hydroxy-4-iodopyrrolo[3,4-c]carbazole-1,3(2H,6H)-dione, prepared as in example 7, with 2,6-dimethylbenzeneboronic acid according to the procedure described in example 8 gave 4-(2,6-dimethylphenyl)-9-hydroxypyrrolo[3,4-c]carbazole-1,3(2H,6H)-dione (17) (I, Ar=2,6-dimethylphenyl) in a 62% yield; mp 230–238° C. (dec). $^1$H NMR δ [(CD$_3$)$_2$SO] 11.72 (s, 1H), 10.95 (s, 1H), 9.25 (s, 1H), 8.32 (d, J=2.3 Hz, 1H), 7.44 (d, J=8.7 Hz, 1H), 7.35 (s, 1H), 7.20 (t, J=7.5 Hz, 1H), 7.12 (d, J=7.5 Hz, 2H), 7.06 ((dd, J=8.7, 2.3 Hz, 1H), 1.93 (s, 6H). EIMS found M$^+$: 356,1159, C$_{22}$H$_{16}$N$_2$O$_3$ requires 356,1161.

EXAMPLE 14

The Preparation of 4-(2,3-Dichlorophenyl)-9-hydroxypyrrolo[3,4-c]carbazole-1,3(2H,6H)-dione (18) (I, Ar=2,3-dichlorophenyl)

The reaction of 9-hydroxy-4-iodopyrrolo[3,4-c]carbazole-1,3(2H,6H)-dione, prepared as in example 7, with 2,3-dichlorobenzeneboronic acid according to the procedure described in example 8 gave 4-(2,3-dichlorophenyl)-9-hydroxypyrrolo[3,4-c]carbazole-1,3(2H,6H)-dione (18) (I, Ar=2,3-dichlorophenyl) in a yield 27%; mp 233–235° C. $^1$H NMR δ [(CD$_3$)$_2$SO] 11.87 (br, 1H), 11.05 (br, 1H), 9.29 (br, 1H), 8.31 (d, J=2.5 Hz, 1H), 7.74–7.70 (m, 1H), 7.55 (s, 1H), 7.48–7.45 (m, 3H), 7.09 (dd, J=8.7, 2.5 Hz, 1H). Found: C, 59.19; H, 3.04; N, 6.56, C$_{20}$H$_{10}$Cl$_2$N$_2$O$_3$.1/2H$_2$O requires C, 59.13; H, 2.73; N, 6.89.

EXAMPLE 15

The Preparation of 4-(2,6-Dimethoxyphenyl)-9-hydroxypyrrolo[3,4-c]carbazole-1,3(2H,6H)-dione (19) (I, Ar=2,6-dimethoxyphenyl)

The reaction of 9-hydroxy-4-iodopyrrolo[3,4-c]carbazole-1,3(2H,6H)-dione, prepared as in example 7, with 2,6-dimethoxybenzeneboronic acid according to the procedure described in example 8 gave 4-(2,6-dimethoxyphenyl)-9-hydroxypyrrolo[3,4-c]carbazole-1,3(2H,6H)-dione (19) (I, Ar=2,6-dimethoxyphenyl) in a 43% yield; mp 275–277°

C. (dec). $^1$H NMR δ [(CD$_3$)$_2$SO] 11.62 (br s, 1H), 10.83 (br s, 1H), 9.21 (br s, 1H), 8.29 (d, J=2.4 Hz, 1H), 7.42 (s, 1H), 7.41 (d, J=8.4 Hz, 1H), 7.35 (t, J=8.4 Hz, 1H), 7.04 (dd, J=8.4, 2.4 Hz, 1H), 6.75 (d, J=8.4 Hz, 2H), 3.63 (s, 6H). Found: C, 66.31; H, 4.50, N, 6.70. C$_{22}$H$_{16}$N$_2$O$_5$,1/2H$_2$O requires C, 66.49; H, 4.31; N, 7.04.

EXAMPLE 16

The Preparation of 9-Hydroxy-4-(2-methoxyphenyl)pyrrolo[3,4-c]carbazole-1,3(2H,6H)-dione (20) (I, Ar=2-methoxyphenyl)

The reaction of 9-hydroxy-4-iodopyrrolo[3,4-c]carbazole-1,3(2H,6H)-dione, prepared as in example 7, with 2-methoxybenzeneboronic acid according to the procedure described in example 8 gave 9-hydroxy-4-(2-methoxyphenyl)pyrrolo[3,4-c]carbazole-1,3(2H,6H)-dione (20) (I, Ar=2-methoxyphenyl) in a 75% yield, mp 216° C. $^1$H NMR δ [(CD$_3$)$_2$SO] 11.70 (s, 1H), 10.90 (s, 1H), 9.23 (s, 1H), 8.31 (d, J=2.4 Hz, 1H), 7.50 (s, 1H), 7.43 (d. J=8.0 Hz, 1H), 7.43–7.38 (m, 1H), 7.31 (dd, J=8.0, 2.4 Hz, 1H), 7.11–7.01 (m, 3H), 3.68 (s, 3H). Found: C, 69.21; H, 3.80; N, 7.58. C$_{21}$H$_{14}$N$_2$O$_4$,1/4H$_2$O requires C, 69.51; H, 4.03; N, 7.72.

EXAMPLE 17

The Preparation of 9-Hydroxy-4-(4-hydroxymethylphenyl)pyrrolo[3,4-c]carbazole-1,3(2H,6H)-dione (21) (I, Ar=4-hydroxymethylphenyl)

The reaction of 9-hydroxy-4-iodopyrrolo[3,4-c]carbazole-1,3(2H,6H)-dione, prepared as in example 7, with 4-hydroxymethylbenzeneboronic acid according to the procedure described in example 8 gave 9-hydroxy-4-(4-hydroxymethylphenyl)pyrrolo[3,4-c]carbazole-1,3(2H,6H)-dione (21) (I, Ar=4-hydroxymethylphenyl) in a 34% yield; mp 266–271° C. $^1$H NMR δ [(CD$_3$)$_2$SO] 11.74 (br s, 1H), 11.00 (br s, 1H), 9.25 (br s, 1H), 8.34 (d, J=2.4 Hz, 1H), 7.56 (d, J=8.3 Hz, 2H), 7.56 (s, 1H), 7.43 (d, J=8.7 Hz, 1H), 7.40 (d, J=8.3 Hz, 1H), 7.06 (dd, J=8.7, 2.4 Hz, 1H), 5.27 (t, J=5.7 Hz, 1H), 4.59 (d, J=5.7 Hz, 2H). Found: C, 69.74; H, 4.04; N, 7.57. C$_{21}$H$_{14}$N$_2$O$_4$,1/4H$_2$O requires C, 69.51; H, 4.02; N, 7.72.

EXAMPLE 18

The Preparation of 9-Hydroxy-4-(2-trifluoromethylphenyl)pyrrolo[3,4-c]carbazole-1,3(2H,6H)-dione (22) (I, Ar=2-trifluoromethylphenyl)

The reaction of 9-hydroxy-4-iodopyrrolo[3,4-c]carbazole-1,3(2H,6H)-dione, prepared as in example 7, with 2-trifluoromethylbenzeneboronic acid according to the procedure described in example 8 gave 9-Hydroxy-4-(2-trifluoromethylphenyl)pyrrolo[3,4-c]carbazole-1,3(2H,6H)-dione (22) (I, Ar=2-trifluoromethylphenyl) in a 47% yield, mp 210° C. (dec). $^1$H NMR δ [(CD$_3$)$_2$SO] 11.81 (br s, 1H), 11.01 (br s, 1H), 9.30 (br s, 1H), 8.31 (d, J=2.4 Hz, 1H), 7.86 (br d, J=7.2 Hz, 1H), 7.75–7.64 (m, 2H), 7.51 (s, 1H), 7.49 (br d, J=7.6 Hz, 1H), 7.46 (d, J=8.7 Hz, 1H), 7.09 (dd, J=8.7, 2.4 Hz, 1H). EIMS found M$^+$: 396.0721. C$_{21}$H$_{11}$F$_3$N$_2$O$_3$ requires 396.0722.

EXAMPLE 19

The Preparation of 9-Hydroxy-4-(4-Hydroxy-3-methoxyphenyl)pyrrolo[3,4-c]carbazole-1,3(2H,6H)-dione (23) (I, Ar=4-hydroxy-3-methoxyphenyl)

The reaction of 9-hydroxy-4-iodopyrrolo[3,4-c]carbazole-1,3(2H,6H)-dione, prepared as in example 7, with 2-methoxy-4-(4,4,5,5-tetramethyl-1,3,2-dioxaborolan-2-yl)phenol according to the procedure described in example 8 gave 9-hydroxy-4-(4-hydroxy-3-methoxyphenyl)pyrrolo[3,4-c]carbazole-1,3(2H,6H)-dione (23) (I, Ar=4-hydroxy-3-methoxyphenyl) in a 58% yield; mp 290–295° C. (dec). $^1$H NMR δ [(CD$_3$)$_2$SO] 11.67 (br s, 1H), 10.97 (br s, 1H), 9.22 (br s, 1H), 9.15 (s, 1H), 8.33 (d, J=2.4 Hz, 1H), 7.57 (s, 1H), 7.41 (d, J=8.6 Hz, 1H), 7.23 (d, J=2.0 Hz, 1H), 7.04 (m, 2H), 6.86 (d, J=8.1 Hz, 1H), 3.82 (s, 3H). FABMS found [M+H]$^+$: 375.0973. C$_{21}$H$_{15}$N$_2$O$_5$ requires 375.0981.

EXAMPLE 20

The Preparation of 4-(2-Ethylphenyl)-9-hydroxy-pyrrolo[3,4-c]carbazole-1,3(2H,6H)-dione (501) (I: Ar=2-ethylphenyl)

The reaction of 9-hydroxy-4-iodopyrrolo[3,4-c]carbazole-1,3(2H,6H)-dione, prepared as in example 7, with 2-ethylbenzeneboronic acid according to the procedure described in example 8 gave 4-(2-Ethylphenyl)-9-hydroxy-pyrrolo[3,4-c]carbazole-1,3(2H,6H)-dione (501) (I; Ar=2-ethylphenyl) in a 69% yield; mp (MeOH/CH$_2$Cl$_2$/hexane) 273–275° C. $^1$H NMR [(CD$_3$)$_2$SO] δ 11.73 (br s, 1H), 10.95 (br s, 1H), 9.25 (s, 1H), 8.32 (d, J=2.4 Hz, 1H), 7.44 (s, 1H), 7.44 (d, J=8.6 Hz, 1H), 7.36 (td, J=7.2, 1.5 Hz, 1H), 7.33 (dd, J=8.1, 2.2 Hz, 1H), 7.25 (td, J=7.0, 1.8 Hz, 1H), 7.20 (dd, J=7.5, 1.2 Hz, 1H), 7.07 (dd, J=8.7, 2.5 Hz, 1H), 2.42 (m, 2H), 0.96 (t, J=7.6 Hz, 3H). Found: C, 73.83; H, 4.46; N, 7.82. C$_{22}$H$_{16}$N$_2$O$_3$ requires C, 74.15; H, 4.53; N, 7.86.

EXAMPLE 21

The Preparation of 9-Hydroxy-4-[2-(hydroxymethyl)phenyl]pyrrolo[3,4-c]carbazole-1,3(2H,6H)-dione (503) (I: Ar=2-(hydroxymethyl)phenyl)

The reaction of 9-hydroxy-4-iodopyrrolo[3,4-c]carbazole-1,3(2H,6H)-dione, prepared as in example 7, with 2-(hydroxymethyl)benzeneboronic acid cyclic monoester according to the procedure described in example 8 gave 9-Hydroxy-4-[2-(hydroxymethyl)phenyl]pyrrolo[3,4-c]carbazole-1,3(2H,6H)-dione (503) (I; Ar=2-(hydroxymethyl)phenyl) in a 57% yield, mp (THF/CH$_2$Cl$_2$/hexane) 270–280° C. (dec). $^1$H NMR [(CD$_3$)$_2$SO] δ 11.76 (br s, 1H), 10.96 (br s, 1H), 9.25 (br s, 1H), 8.32 (d, J=2.4 Hz, 1H), 7.57 (d, J=7.6 Hz, 1H), 7.47 (s, 1H), 7.44 (d, J=8.5 Hz, 1H), 7.43 (td, J=7.6, 1.2 Hz, 1H), 7.31 (td, J=7.4, 0.9 Hz, 1H), 7.23 (dd, J=7.5, 1.0 Hz, 1H), 7.06 (dd, J=8.7, 2.5 Hz, 1H), 5.00 (t, J=5.4 Hz, 1H), 4.33 (dd, J=13.6, 5.2 Hz, 1H), 4.24 (dd, J=13.5, 5.3 Hz, 1H). Found: C, 68.41; H, 4.29; N, 7.59. C$_{21}$H$_{14}$N$_2$O$_4$,1/2H$_2$O requires C, 68.66; H, 4.12; N, 7.63.

EXAMPLE 22

The Preparation of 4-(2-Ethoxyphenyl)-9-hydroxy-pyrrolo[3,4-c]carbazole-1,3(2H,6H)-dione (504) (I; Ar=2-ethoxyphenyl)

The reaction of 9-hydroxy-4-iodopyrrolo[3,4-c]carbazole-1,3(2H,6H)-dione, prepared as in example 7, with 2-ethoxybenzeneboronic acid according to the procedure described in example 8 gave 4-(2-ethoxyphenyl)-9-hydroxypyrrolo[3,4-c]carbazole-1,3(2H,6H)-dione (504) (I; Ar=2-ethoxyphenyl) in a 74% yield; mp (THF/CH$_2$Cl$_2$/hexane) 190–193° C. (dec). $^1$H NMR [(CD$_3$)$_2$SO] δ 11.71 (br s, 1H), 10.91 (br s, 1H), 9.23 (s, 1H), 8.31 (d, J=2.4 Hz, 1H), 7.51 (s, 1H), 7.43 (d, J=8.7 Hz, 1H), 7.38 (td, J=7.8, 1.7 Hz, 1H), 7.33 (dd, J=7.5, 1.7 Hz, 1H), 7.07 (br d, J=6.7 Hz, 1H), 7.05 (dd, J=8.7, 2.3 Hz, 1H), 7.02 (dd, J=7.3, 6.6 Hz, 1H), 3.97 (q, J=6.7 Hz, 2H), 1.11 (t, J=6.9 Hz, 3H). Found: C, 70.63; H, 4.74; N, 6.88. C$_{22}$H$_{16}$N$_2$O$_4$.1/4 THF requires C, 70.76; H, 4.65; N, 7.18.

EXAMPLE 23

The Preparation of 9-Hydroxy-4-(2-thienyl)pyrrolo[3,4-c]carbazole-1,3(2H,6H)-dione (505) (I; Ar=2-thienyl)

The reaction of 9-hydroxy-4-iodopyrrolo[3,4-c]carbazole-1,3(2H,6H)-dione prepared as in example 7 with 2-thiopheneboronic acid according to the procedure described in example 8 gave 9-hydroxy-4-(2-thienyl)pyrrolo[3,4-c]carbazole-1,3(2H,6H)-dione (505) (1; Ar=2-thienyl) in a 69% yield; mp (THF/CH$_2$Cl$_2$/hexane) 179–184° C. (dec). $^1$H NMR [(CD$_3$)$_2$SO] δ 11.75 (br s, 1H), 11.11 (br s, 1H), 9.26 (br s, 1H), 8.34 (d, J=2.4 Hz, 1H), 7.75 (s, 1H), 7.73 (dd, J=3.6, 1.0 Hz, 1H), 7.68 (dd, J=5.1, 1.3 Hz, 1H), 7.43 (d, J=8.7 Hz, 1H), 7.20 (dd, J=5.1, 3.6 Hz, 1H), 7.07 (dd, J=8.7, 2.5 Hz, 1H). Found: C, 62.38; H, 3.11; N, 7.74. C$_{18}$H$_{10}$N$_2$O$_3$S.3/4H$_2$O requires C, 62.15; H, 3.33; N, 8.05.

EXAMPLE 24

The Preparation of 3-(9-Hydroxy-1,3-dioxo-1,2,9,3,6-tetrahydropyrrolor[3,4-c]carbazol-4-yl)benzaldehyde (507) (I; Ar=3-formylphenyl)

The reaction of 9-hydroxy-4-iodopyrrolo[3,4-c]carbazole-1,3(2H,6H)-dione, prepared as in example 7, with 3-formylbenzeneboronic acid according to the procedure described in example 8 gave 3-(9-Hydroxy-1,3-dioxo-1,2,3,6-tetrahydropyrrolo[3,4-c]carbazol-4-yl)benzaldehyde (507) (I; Ar=3-formylphenyl) in a 69% yield; mp (THF/CH$_2$Cl$_2$/pentane) 280–286° C. (dec). $^1$H NMR [(CD$_3$)$_2$SO] δ 11.82 (br s, 1H), 11.07 (br s, 1H), 10.11 (s, 1H), 9.27 (br s, 1H), 8.35 (d, J=2.4 Hz, 1H), 8.14 (t, J=1.4 Hz, 1H), 7.97 (m, 2H), 7.70 (t, J=7.7 Hz, 2H), 7.65 (s, 1H), 7.46 (d, J=8.7 Hz, 1H), 7.08 (dd, J=8.7, 2.5 Hz, 1H). FABMS found [M+H]$^+$: 357.0857. C$_{21}$H$_{13}$N$_2$O$_4$ requires 357.0875.

EXAMPLE 25

The Preparation of 9-Hydroxy-4-[2-(methylsulfanyl)phenyl]pyrrolo[3,4-c]carbazole-1,3(2H,6H)-dione (508) (I; Ar=2-(methylsulfanyl)phenyl)

The reaction of 9-hydroxy-4-iodopyrrolo[3,4-c]carbazole-1,3(2H,6H)-dione, prepared as in example 7, with 2-(methylthio)benzeneboronic acid according to the procedure described in example 8 gave 9-hydroxy-4-[2-(methylsulfanyl)phenyl]pyrrolo[3,4-c]carbazole-1,3(2H,6H)-dione (508) (I; Ar=2-(methylsulfanyl)phenyl) in a 72% yield, mp (MeOH/CH$_2$Cl$_2$)/hexane) 208–216° C. $^1$H NMR [(CD$_3$)$_2$SO] δ 11.76 (br s, 1H), 10.95 (br s, 1H), 9.25 (br s, 1H), 8.31 (d, J=2.5 Hz, 1H), 7.47 (s, 1H), 7.44 (d, J=8.6 Hz, 1H), 7.43 (td, J=7.3, 2.2 Hz, 1H), 7.38 (br d, J=7.5 Hz, 1H), 7.27 (dd, J=7.8, 2.2 Hz, 1H), 7.24 (td, J=7.3, 1.3 Hz, 1H), 7.07 (dd, J=8.7, 2.5 Hz, 1H), 2.32 (s, 3H). Found: C, 66.55; H, 3.88; N, 7.38. C$_{21}$H$_{14}$N$_2$O$_3$S.1/4H$_2$O requires C, 66.57; H, 3.86; N, 7.39.

EXAMPLE 26

The Preparation of 4-(9-Hydroxy-1,3-dioxo-1,2,3,6-tetrahydropyrrolo[3,4-c]carbazol-4-yl)benzaldehyde (509) (I; Ar=4-formylphenyl)

The reaction of 9-hydroxy-4-iodopyrrolo[3,4-c]carbazole-1,3(2H,6H)-dione, prepared as in example 7, with 4-formylbenzeneboronic acid according to the procedure described in example 8 gave 4-(9-hydroxy-1,3-dioxo-1,2,3,6-tetrahydropyrrolo[3,4-c]carbazol-4-yl)benzaldehyde (509) (I; Ar=4-formylphenyl) in a 52% yield; mp (THF/CH$_2$Cl$_2$/pentane) 276–280° C. $^1$H NMR [(CD$_3$)$_2$SO] δ 11.84 (br s, 1H), 11.07 (br s, 1H), 10.11 (s, 1H), 9.28 (br s, 1H), 8.34 (d, J=2.3 Hz, 1H), 8.00 (d, J=8.2 Hz, 2H), 7.85 (d, J=8.1 Hz, 2H), 7.65 (s, 1H), 7.46 (d, J=8.7 Hz, 1H), 7.08 (dd, J=8.7, 2.4 Hz, 1H). Found: C, 68.43; H, 4.16; N, 7.26. C$_{21}$H$_{12}$N$_2$O$_4$.3/4H$_2$O requires C, 68.20; H, 3.68; N, 7.57. FABMS found [M+H]$^+$: 357.0841. C$_{21}$H$_{13}$N$_2$O$_4$ requires 357.0875.

EXAMPLE 27

The Preparation of 9-Hydroxy-4-[2-(methylsulfinyl)phenyl]pyrrolo[3,4-c]carbazole-1,3(2H,6H)-dione (510) (I; Ar=2-(methylsulfinyl)phenyl)

A mixture of the 9-hydroxy-4-[2-(methylsulfanyl)phenyl]pyrrolo[3,4-c]carbazole-1,3(2H,6H)-dione (508) (34.5 mg, 0.092 mmol), prepared according to example 25, and 2-phenylsulfonyl-3-phenyloxaziridine (Davis reagent) (26.5 mg, 0.102 mmol) in THF (10 mL) was stirred at 20° C. for 2.5 h, then adsorbed directly onto silica gel and chromatographed. Elution with 0–3% MeOH/CH$_2$Cl$_2$ then 3–4% MeOH/CH$_2$Cl$_2$ gave (after crystallisation from THF/CH$_2$Cl$_2$/pentane) the 9-Hydroxy-4-[2-(methylsulfinyl)phenyl]pyrrolo[3,4-c]carbazole-1,3(2H,6H)-dione (510) (I; Ar=2-(methylsulfinyl)phenyl) in a 86% yield as a yellow solid; mp 321–323° C. $^1$H NMR [(CD$_3$)$_2$SO] δ 11.86, 11.85 (2br s, 1H), 11.09 (br s, 1H), 9.30 (br s, 1H), 8.32 (d, J=2.4 Hz, 1H), 8.04, 7.97 (2d, J=7.6 Hz, 1H), 7.74 (t, J=7.6 Hz, 1H), 7.65, 7.62 (2t, J=7.4 Hz, 1H), 7.62, 7.54 (2s, 1H), 7.47 (d, J=9.1 Hz, 1H), 7.44 (d, J=8.4 Hz, 1H), 7.09 (dd, J=8.7, 2.5 Hz, 1H), 2.43, 2.31 (2s, 3H). Found: C, 64.60; H, 3.88; N, 6.87. C$_{21}$H$_{14}$N$_2$O$_4$S requires C, 64.61; H, 3.61; N, 7.18.

EXAMPLE 28

The Preparation of 9-Hydroxy-4-(4-hydroxyphenyl) pyrrolo[3,4-c]carbazole-1,3(2H,6H)-dione (24) (I, Ar=4-hydroxyphenyl)

The reaction of 9-hydroxy-4-(4-methoxyphenyl)pyrrolo[3,4-c]carbazole-1,3(2H,6H)-dione prepared as decribed in example 34 with BBr$_3$ using the procedure described in example 80 of Scheme 2 gave 9-Hydroxy-4-(4-hydroxyphenyl)pyrrolo[3,4-c]carbazole-1,3(2H,6H)-dione (24) (I, Ar=4-hydroxyphenyl) in a 92% yield; mp 230° C. (dec). $^1$H NMR δ [(CD$_3$)$_2$SO] 11.67 (s, 1H), 10.96 (s, 1H), 9.59 (s, 1H), 9.22 (s, 1H), 8.32 (d, J=2.4 Hz, 1H), 7.51 (s, 1H), 7.43 (d, J=8.7 Hz, 1H), 7.41 (d, J=8.6 Hz, 2H), 7.04 (dd, J=8.7, 2.4 Hz, 1H), 6.84 (d, J=8.6 Hz, 2H). FABMS found [M+H]$^+$: 345.0875. C$_{20}$H$_{13}$N$_2$O$_4$ requires 345.0875.

EXAMPLE 29

The Preparation of 9-Hydroxy-4-(3-hydroxyphenyl) pyrrolo[3,4-c]carbazole-1,3(2H,6H)-dione (25) (I, Ar=3-hydroxyphenyl)

9-Hydroxy-4-(3-methoxyphenyl)pyrrolo[3,4-c]carbazole-1,3(2H,6H)-dione (prepared as decribed in example 35) was reacted with BBr$_3$ using the procedure described in the proceedure described in example 80 of Scheme 2 to give 9-hydroxy-4-(3-hydroxyphenyl)pyrrolo[3,4-c]carbazole-1,3 (2H,6H)-dione (25) (I, Ar=3-hydroxyphenyl) in a yield of 88%; mp 282–285° C. (dec). $^1$H NMR δ [(CD$_3$)$_2$SO] 11.73 (br s, 1H), 11.00 (br s, 1H), 9.48 (br s, 1H), 9.24 (s, 1H), 8.34 (d, J=2.4 Hz, 1H), 7.54 (s, 1H), 7.43 (d, J=8.7 Hz, 1H), 7.24 (dd, J=7.7, 7.7 Hz, 1H), 7.05 (dd, J=8.7, 2.4 Hz, 1H), 7.01–6.96 (m, 2H), 6.82 (dd, J=8.2, 2.1 Hz, 1H). FABMS found [M+H]$^+$: 345.0865. C$_{20}$H$_{13}$N$_2$O$_4$ requires 345.0875.

EXAMPLE 30

The Preparation of 4-(2-Chloro-6-hydroxyphenyl)-9-hydroxypyrrolo[3,4-c]carbazole-1,3(2H,6H)-dione (26) (I, Ar=2-chloro-6-hydroxyphenyl)

4-(2-Chloro-6-methoxyphenyl)-9-hydroxypyrrolo[3,4-c]carbazole-1,3(2H,6H)-dioneprepared as in example 33 was reacted with BBr$_3$ using the procedure described in example 80 of Scheme 2 to give 4-(2-Chloro-6-hydroxyphenyl)-9-hydroxypyrrolo[3,4-c]carbazole-1,3(2H,6H)-dione (26) (I, Ar=2-chloro-6-hydroxyphenyl) in a yield of 70%; m.p. 228–235° C. $^1$H NMR δ [(CD$_3$)$_2$SO] 11.73 (s, 1H), 10.94 (s, 1H), 9.75 (br s, 1H), 9.25 (s, 1H), 8.30 (d, J=2.4 Hz, 1H), 7.45 (s, 1H), 7.44 (d, J=8.7 Hz, 1H), 7.23 (dd, J=8.1, 8.1 Hz, 1H), 7.07 (dd, J=8.7, 2.4 Hz, 1H), 6.99 (d, J=8.1 Hz, 1H), 6.90 (d, J=8.1 Hz, 1H). FABMS found [M+H]$^+$: 381.0461, 379.0479. C$_{20}$H$_{12}$ClN$_2$O$_4$ requires 381.0456, 379.0486.

Compounds described in examples 31–35 were prepared in an array manner by reaction of the iodide (8) prepared as described in Example 7 with the appropriate substituted arylboronic acid using the procedure described in Example 8.

EXAMPLE 31

The Preparation of 4-(3-Chlorophenyl)-9-hydroxypyrrolo[3,4-c]carbazole-1,3(2H,6H)-dione (I; Ar=3-chlorophenyl) (866) by reaction with 3-chlorobenzeneboronic acid Found [M+H]$^+$: 363.

EXAMPLE 32

The Preparation of 4-(4-Chlorophenyl)-9-hydroxypyrrolo[3,4-c]carbazole-1,3(2H,6H)-dione (I; Ar=4-chlorophenyl) (867) by reaction with 4-chlorobenzeneboronic acid Found [M+H]$^+$: 363.

EXAMPLE 33

The Preparation of 4-(2-Chloro-6-methoxyphenyl)-9-hydroxypyrrolo[3,4-c]carbazole-1,3(2H,6H)-dione (I; Ar=2-chloro-6-methoxyphenyl) (868) by reaction with 2-chloro-6-methoxybenzeneboronic acid. Found [M+H]$^+$: 393.

EXAMPLE 34

The Preparation of 9-Hydroxy-4-(4-methoxyphenyl) pyrrolo[3,4-c]carbazole-1,3(2H,6H)-dione (I; Ar=4-methoxyphenyl) (870) by reaction with 4-methoxybenzeneboronic acid. Found [M+H]$^+$: 359

EXAMPLE 35

The Preparation of 9-Hydroxy-4-(3-methoxyphenyl) pyrrolo[3,4-c]carbazole-1,3(2H,6H)-dione (I; Ar=4-methoxyphenyl) by reaction with 4-methoxybenzeneboronic acid. Found [M+H]$^+$: 359

EXAMPLE 36

The Preparation of a series of compounds using multiple parallel synthetic techquires from 9-hydroxy-4-iodopyrrolo[3,4-c]carbazole-1,3(2H,6H)-dione prepared as in Example 7 Combichem Procedure 1

In a 8 ml screw cap vial was added a solution of 9-Hydroxy-4-iodo-6H-pyrrolo[3,4-c]carbazole-1,3-dione, (0.1 mmol) prepared as in example 7 in dioxane (1 ml), a solution of Reagent 1 (see table) (0.1 mmol) in 1:1 dioxane/2.5 M K$_2$CO$_3$ (1 ml) and [1,1'Bis(diphenylphosphino)ferrocene]-dichloropalladium(II) complex with dichloromethane (0.003 g, 0.0037 mmol). The vial was capped and the reaction mixture was shaken for 4 hours at 90° C. After cooling to room temperature, the solution was removed under vacuum. Purification was carried out via reverse-phase HPLC (3% n-propanol in acetonitrile and 3% n-propanol in water as the eluent; C-18 column). The products were characterised by mass spectral analysis (See Table 1).

Combichem Procedure 2

In a 8 ml screw cap vial was added a solution of 9-Hydroxy-4-iodo-6H-pyrrolo[3,4-c]carbazole-1,3-dione, (0.1 mmol) prepared as in example 7 in anhydrous toluene (1 ml), a solution of Reagent 1 (see table) in 1:1 anhydrous toluene/dimethylformamide (1 ml) and a solution of 0.05 M palladium(II) diacetate plus 0.2 M o-dicyclohexylphosphinobiphenyl in anhydrous toluene (20 μl), and 40 mg of K$_3$PO$_4$.2H$_2$O under N$_2$. The vial was capped and the reaction mixture was shaken for 20 hours at 100° C. After cooling to room temperature, the solution was was removed under vacuum. Purification was carried out via reverse-phase HPLC (3% n-propanol in acetonitrile and 3% n-propanol in water as the eluent; C-18 column). The products were characterised by mass spectral analysis (See Table 1).

| Procedure | Reagent 1 | Product | Analytical Data MS-APCI [M + H]+ |
|---|---|---|---|
| Combichem procedure 1 | 2-acetylphenyl boronic acid | 4-(2-Acetylphenyl)-9-hydroxy-6H-pyrrolo[3,4-c]carbazole-1,3-dione | 371.2 |
| Combichem procedure 1 | 4-Fluorophenyl boronic acid | 4-(4-Fluorophenyl)-9-hydroxy-6H-pyrrolo[3,4-c]carbazole-1,3-dione | 347.2 |
| Combichem procedure 1 | 3,4-Methylene dioxybenzene boronic acid | 4-(1,3-Benzodioxol-5-yl-9-hydroxy-6H-pyrrolo[3,4-c]carbazole-1,3-dione | 373.2 |
| Combichem procedure 1 | 2-Naphthalene boronic acid | 9-Hydroxy-4-naphthalen-2-yl-6H-pyrrolo[3,4-c]carbazole-1,3-dione | 379.2 |
| Combichem procedure 1 | 4-Methylthio phenyl boronic acid | 9-Hydroxy-4-(4-methylsulfanylphenyl)-6H-pyrrolo[3,4-c]carbazole-1,3-dione | 375.2 |
| Combichem procedure 1 | 4-biphenylboronic acid | 4-Biphenyl-4-yl-9-hydroxy-6H-pyrrolo[3,4-c]carbazole-1,3-dione | 405.2 |
| Combichem procedure 1 | 3-(trifluoro methoxy) benzene boronic acid | 9-Hydroxy-4-(3-trifluoromethoxy-phenyl)-6H-pyrrolo[3,4-c]carbazole-1,3-dione | 413.2 |
| Combichem procedure 1 | 3-Methoxyphenyl boronic acid | 9-Hydroxy-4-(3-methoxyphenyl)-6H-pyrrolo[3,4-c]carbazole-1,3-dione | 359.2 |
| Combichem procedure 1 | 3-Cyanophenyl boronic acid | 3-(9-Hydroxy-1,3-dioxo-1,2,3,6-tetrahydro-pyrrolo[3,4-c]carbazol-4-yl)-benzonitrile | 354.2 |
| Combichem procedure 1 | 2,5-dichlorophenyl boronic acid | 4-(2,5-Dichlorophenyl)-9-hydroxy-6H-pyrrolo[3,4-c]carbazole-1,3-dione | 398.2 |
| Combichem procedure 1 | 4-trifluoromethoxy phenyl boronic acid | 9-Hydroxy-4-(4-trifluoromethoxy-phenyl)-6H-pyrrolo[3,4-c]carbazole-1,3-dione | 413.2 |
| Combichem procedure 1 | 3-Hydroxymethyl phenyl boronic acid | 9-Hydroxy-4-(3-hydroxymethylphenyl)-6H-pyrrolo[3,4-c]carbazole-1,3-dione | 359.2 |
| Combichem procedure 1 | Furan-3-boronic acid | 4-Furan-2-yl-9-hydroxy-6H-pyrrolo[3,4-c]carbazole-1,3-dione | 319.2 |
| Combichem procedure 1 | Pyridine-3-boronic acid | 9-Hydroxy-4-pyridin-3-yl-6H-pyrrolo[3,4-c]carbazole-1,3-dione | 330.2 |
| Combichem procedure 1 | 2,4-dimethoxy pyrimidin-5-boronic acid | 4-(2,4-Dimethoxy-pyrimidin-5-yl)-9-hydroxy-6H-pyrrolo[3,4-c]carbazole-1,3-dione | 391.2 |
| Combichem procedure 1 | 4-Cyanophenyl boronic acid | 4-(9-Hydroxy-1,3-dioxo-1,2,3,6-tetrahydro-pyrrolo[3,4-c]carbazol-4-yl)-benzonitrile | 354.2 |
| Combichem procedure 1 | 4-(trifluoromethyl) phenyl boronic acid | 9-Hydroxy-4-(4-trifluoromethylphenyl)-6H-pyrrolo[3,4-c]carbazole-1,3-dione | 397.2 |
| Combichem procedure 1 | 3-(trifluoromethyl) phenyl boronic acid | 9-Hydroxy-4-(3-trifluoromethylphenyl)-6H-pyrrolo[3,4-c]carbazole-1,3-dione | 397.2 |
| Combichem procedure 1 | 4-(methylsulfonyl) phenyl boronic acid | 9-Hydroxy-4-(4-methanesulfonylphenyl)-6H-pyrrolo[3,4-c]carbazole-1,3-dione | 407.2 |
| Combichem procedure 1 | 3-acetamidophenyl boronic acid | N-[3-(9-Hydroxy-1,3-dioxo-1,2,3,6-tetrahydro-pyrrolo[3,4-c]carbazol-4-yl)-phenyl]acetamide | 386.2 |
| Combichem procedure 2 | 4-dimethylamino phenyl boronic acid | 4-(4-Dimethylaminophenyl)-9-hydroxy-6H-pyrrolo[3,4-c]carbazole-1,3-dione | 372.2 |
| Combichem procedure 2 | 3-acetylphenyl boronic acid | 4-(3-Acetylphenyl)-9-hydroxy-6H-pyrrolo[3,4-c]carbazole-1,3-dione | 371.2 |
| Combichem procedure 2 | 3-hydroxyphenyl boronic acid | 9-Hydroxy-4-(3-hydroxyphenyl)-6H-pyrrolo[3,4-c]carbazole-1,3-dione | 345.2 |
| Combichem procedure 2 | 3-methylbenzene boronic acid | 9-Hydroxy-4-m-tolyl-6H-pyrrolo[3,4-c]carbazole-1,3-dione | 343.2 |
| Combichem procedure 2 | o-tolylboronic acid | 9-Hydroxy-4-o-tolyl-6H-pyrrolo[3,4-c]carbazole-1,3-dione | 343.2 |
| Combichem procedure 2 | Trans-2-phenylvinyl boronic acid | 9-Hydroxy-4-((E)-styryl)-6H-pyrrolo[3,4-c]carbazole-1,3-dione | 355.2 |
| Combichem procedure 2 | 2-formylphenyl boronic acid | 2-(9-Hydroxy-1,3-dioxo-1,2,3,6-tetrahydro-pyrrolo[3,4-c]carbazol-4-yl)-benzaldehyde | 357.2 |
| Combichem procedure 2 | 2,5-dimethylphenyl boronic acid | 4-(2,5-Dimethylphenyl)-9-hydroxy-6H-pyrrolo[3,4-c]carbazole-1,3-dione | 357.2 |
| Combichem procedure 2 | 4-Methylsulfanyl benzeneboronic acid | 9-Hydroxy-4-(2-methylsulfanylphenyl)-6H-pyrrolo[3,4-c]carbazole-1,3-dione | 375.2 |
| Combichem procedure 2 | 4-Methylbenzene boronic acid | 9-Hydroxy-4-p-tolyl-6H-pyrrolo[3,4-c]carbazole-1,3-dione | 343.2 |

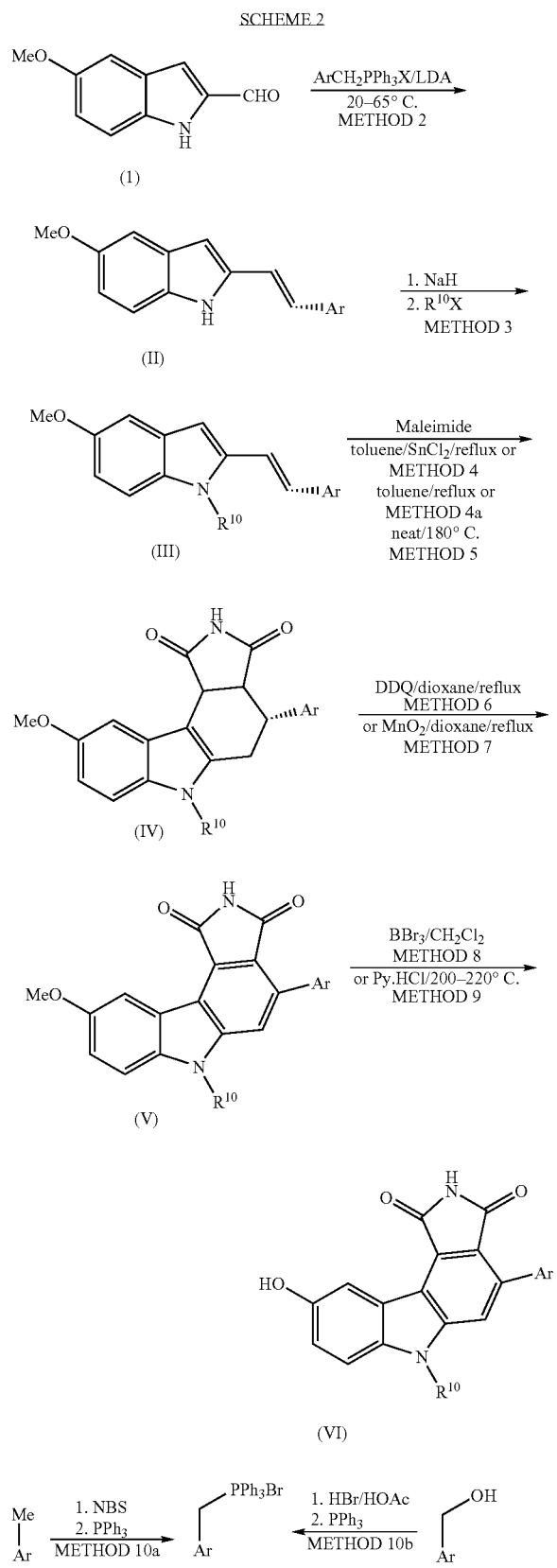

Scheme 2 Procedures

Representative Procedure for Method 2 of Scheme 2

EXAMPLE 37

The Preparation of 2-[2-(2-Chlorophenyl)ethenyl]-5-methoxy-1H-indole (II; Ar=2-chlorophenyl) (27)

Lithium diisopropyl amide (34.4 mL of a 1.5 N solution, 0.052 mol) was added dropwise under nitrogen to a suspension of benzyl(triphenyl)phosphonium chloride (20.17 g, 0.048 mol) in dry THF (200 mL) and the solution was stirred at room temperature for 15 min. A solution of the 5-methoxy-1H-indole-2-carbaldehyde (1) (6.99 g, 0.040 mol) in THF (30 mL) was added and stirring was continued at room temperature for 15 min and then the reaction mixture was heated at reflux for 6 h. The cooled solution was diluted with water, extracted with EtOAc and the organic phase was dried, the drying agent was removed and the solution was concentrated to dryness to give an oil which was adsorbed onto silica and chromatographed on silica. Elution with ethyl acetate/petroleum ether (1:1) gave 2-[2-(2-Chlorophenyl)ethenyl]-5-methoxy-1H-indole (27) as a mixture of E/Z isomers in a yield of 9.76 g, 87%. Crystallisation of a small sample from methanol afforded pure E-isomer, mp 135–137° C. $^1$H NMR δ (CDCl$_3$) 11.39 (s, 1H), 7.86 (dd, J=7.8, 1.5 Hz, 1H), 7.49 (dd, J=8.0, 1.2 Hz, 1H), 7.43 (d, J=16.4 Hz, 1H), 7.37 (m, 1H), 7.31–7.23 (m, 3H), 7.01 (d, J=2.4 Hz, 1H), 6.77 (dd, J=8.7, 2.4 Hz, 1H), 6.56 (s, 1H), 3.75 (s, 3H). Found: C, 72.01; H, 5.03; N, 4.98. C$_{17}$H$_{14}$ClNO requires C, 71.96; H, 4.79; N, 4.94.

Representative Procedure for Method 3 of Scheme 2

EXAMPLE 38

The Preparation of 1-(3-{[tert-Butyl(dimethyl)silyl]oxy}propyl)-2-[2-(2-chlorophenyl) ethenyl]-5-methoxy-1H-indole (III; Ar=2-chlorophenyl, R$^{10}$=CH$_2$CH$_2$CH$_2$OSiMe$_2$t-Bu) (28)

Sodium hydride (1.05 g of a 50% dispersion in mineral oil, 0.022 mol) was added to a solution of the 2-[2-(2-Chlorophenyl)ethenyl]-5-methoxy-1H-indole prepared according to example 37 (4.13 g, 0.014 mol) in DMF (30 mL) and the solution was stirred at room temperature for 5 min. 3-Bromopropyl tert-butyl(dimethyl)silyl ether (4.04 g, 0.016 mol) was added and stirring was continued for 2 h. The solution was diluted with water, extracted with EtOAc which was washed well with brine and the organic phase was dried, the drying agent was removed and the solution was concentrated to dryness to give 1-(3-{[tert-Butyl(dimethyl)silyl]oxy}propyl)-2-[2-(2-chlorophenyl)ethenyl]-5-methoxy-1H-indole (28) as an oily solid (4.98 g) (as a mixture of E/Z isomers) which was used without further purification.

EXAMPLE 39

The Preparation of 6-(3-f [tert-Butyl(dimethyl)silyl]oxy propyl)-4-(2-chlorophenyl)-9-methoxypyrrolo[3,4-c]carbazole-1,3(2H,6H)-dione (V; Ar=2-chlorophenyl, R$^{10}$=CH$_2$CH$_2$CH$_2$OSiMe$_2$t-Bu) (29)

1-(3-{[tert-Butyl(dimethyl)silyl]oxy}propyl)-2-[2-(2-chlorophenyl)ethenyl]-5-methoxy-1H-indole prepared according to example 38 was reacted with maleimide according to the procedure described in example 68 except that the reaction time was 16 h. The resultant product was reacted with $MnO_2$ according to the procedure described in example 81 except that the reaction time was 8 h. Following chromatography on silica the product was triturated with diethyl ether to give 6-(3-{([tert-Butyl(dimethyl)silyl]oxy}propyl)-4-(2-chlorophenyl)-9-methoxypyrrolo[3,4-c]carbazole-1,3(2H,6H)-dione (29) in a 4.87 g, 61% yield, as a yellow solid; mp 199–201° C. $^1$H NMR δ [(CD$_3$)$_2$SO 11.12 (br, 1H), 8.52 (d, J=2.6 Hz, 1H), 7.75 (s, 1H), 7.66 (d, J=8.9 Hz, 1H), 7.57 (dd, J=8.3 Hz, 1H), 7.5–7.4 (m, 3H), 7.30 (dd, J=8.9, 2.6 Hz, 1H), 4.53 (t, J=6.4 Hz, 2H), 3.90 (s, 3H), 3.55 (t, J=5.8 Hz, 2H), 1.94 (m, 2H), 0.77 (s, 9H), –0.06 (s, 3H). Found: C, 65.72; H, 6.09; N, 5.19. $C_{30}H_{32}ClSiN_2O_4$ requires C, 65.74; H, 5.88; N, 5.11.

EXAMPLE 40

The Preparation of 4-(2-Chlorophenyl)-6-(3-hydroxypropyl)-9-methoxypyrrolo[3,4-c]carbazole-1,3(2H,6H)-dione (V; Ar=2-chlorophenyl, $R^{10}$=CH$_2$CH$_2$CH$_2$OH) (31)

3N HCl (50 mL) was added to a solution of 6-(3-{[tert-Butyl(dimethyl) silyl]oxy}propyl)-4-(2-chlorophenyl)-9-methoxypyrrolo[3,4-c]carbazole-1,3(2H,6H)-dione (4.87 g, 8.85 mmol) prepared according to example 39 in 1:1 THF/methanol (200 mL). After stirring at room temperature for 2 h most of the solvents were removed in vacuo, the residue was extracted with ethyl acetate, washed well with water and the organic portion was concentrated to a volume of 60 mL. Petroleum ether was added to precipitate the product, which was filtered off and triturated several times with diethyl ether. The solid was crystallised from THF/petroleum ether and gave 4-(2-Chlorophenyl)-6-(3-hydroxypropyl)-9-methoxypyrrolo[3,4-c]carbazole-1,3(2H,6H)-dione (V; Ar=2-chlorophenyl, $R^{10}$=CH$_2$CH$_2$CH$_2$OH) (31)in a 3.77 g, 88% yield as a yellow powder; mp 228–230° C. $^1$H NMR δ [(CD$_3$)$_2$SO] 11.12 (br s, 1H), 8.52 (d, J=2.5 Hz, 1H), 7.80 (s, 1H), 7.70 (d, J=8.9 Hz, 1H), 7.58 (dd, J=8.1, 22 Hz, 1H), 7.53–7.42 (m, 3H), 7.31 (dd, J=8.9, 2.5 Hz, 1H), 4.63 (br, 1H), 4.53 (t, J=6.9 Hz, 2H), 3.91 (s, 3H), 3.40 (m, 2H), 1.91 (m, 2H). Found: C, 66.00; H, 4.23; N, 6.55. $C_{24}H_{19}ClN_2O_4$ requires C, 66.29; H, 4.40; N, 6.44.

EXAMPLE 41

The Preparation of 2-{2-[2-(2-Chlorophenyl)ethenyl]-5-methoxy-1H-indol-1-yl}ethanol (III; Ar=2-chlorophenyl $R^{10}$=CH$_2$CH$_2$OH) (44)

Alkylation of 2-[2-(2-Chlorophenyl)ethenyl]-5-methoxy-1H-indole (27) prepared according to example 37 with 2-bromoethyl tetrahydro-2H-pyran-2-yl ether using the procedure described in example 38 followed by reaction of the crude product with 2N HCl in methanol gave 2-{2-[2-(2-Chlorophenyl)ethenyl]-5-methoxy-1H-indol-1-yl}ethanol (III; Ar=2-chlorophenyl, $R^{10}$=CH$_2$CH$_2$OH) (44) in a yield of 86% as a mixture of E/Z isomers, which was used without further purification.

EXAMPLE 42

The Preparation of 4-(2-Chlorophenyl)-6-(2-hydroxyethyl)-9-methoxy-4,5,6,10c-tetrahydropyrrolo[3,4-c]carbazole-1,3(2H,3aH)-dione (IV; Ar=2-chlorophenyl, $R^{10}$=CH$_2$CH$_2$OH) (45)

Reaction of 2-{2-[2-(2-Chlorophenyl)ethenyl]-5-methoxy-1H-indol-1-yl}ethanol (III; Ar=2-chlorophenyl, $R^{10}$=CH$_2$CH$_2$OH) (44) prepared according to example 41 with maleimide according to the procedure described in example 68 gave 4-(2-Chlorophenyl)-6-(2-hydroxyethyl)-9-methoxy-4,5,6,1 0c-tetrahydropyrrolo[3,4-c]carbazole-1,3 (2H, 3aH)-dione (IV; Ar=2-chlorophenyl, $R^{10}$=CH$_2$CH$_2$OH) (45) in a 79% yield as an oily solid, which was used without further purification.

EXAMPLE 43

The Preparation of 4-(2-Chlorophenyl)-6-(2-hydroxyethyl)-9-methoxypyrrolo[3,4-c]carbazole-1,3(2H,6H)-dione (V; Ar=2-chlorophenyl. $R^{10}$=CH$_2$CH$_2$OH) (46)

4-(2-Chlorophenyl)-6-(2-hydroxyethyl)-9-methoxy-4,5,6,10c-tetrahydropyrrolo[3,4-c]carbazole-1,3(2H, 3aH)-dione (IV; Ar=2-chlorophenyl, $R^{10}$=CH$_2$CH$_2$OH) (45) prepared according to example 42 was reacted with $MnO_2$ using the procedure described in example 79 except that the reaction time was 18 h gave 4-(2-Chlorophenyl)-6-(2-hydroxyethyl)-9-methoxypyrrolo[3,4-c]carbazole-1,3(2H, 6H)-dione (V; Ar=2-chlorophenyl, $R^{10}$=CH$_2$CH$_2$OH) (46) in a 72% yield as a yellow powder, mp 255–257° C. $^1$H NMR δ [(CD$_3$)$_2$SO] 11.10 (br s, 1H), 8.52 (d, J=2.6 Hz, 1H), 7.80 (s, 1H), 7.71 (d, J=9.0 Hz, 1H), 7.59–7.56 (m, 1H), 7.52–7.43 (m, 4H), 7.29 (dd, J=9.0, 2.2.6 Hz, 1H), 4.84 (t, J=5.0 Hz, 1H), 4.53 (t, J=5.2 Hz, 2H), 3.90 (s, 3H), 3.77 (m, 2H). Found: C, 65.50; H, 4.07; N, 6.59. $C_{23}H_{17}ClN_2O_4$ requires C, 65.64; H, 4.07; N, 6.66.

EXAMPLE 44

The Preparation of 4-(2-Chlorophenyl)-6-(2-hydroxyethyl)-9-hydroxypyrrolo[3,4-c]carbazole-1,3 (2H,6H)-dione (VI; Ar=2-chlorophenyl. $R^{10}$=CH$_2$CH$_2$OH) (47)

The reaction of 4-(2-Chlorophenyl)-6-(2-hydroxyethyl)-9-methoxypyrrolo[3,4-c]carbazole-1,3(2H,6H)-dione (V; Ar=2-chlorophenyl, $R^{10}$=CH$_2$CH$_2$OH) (46) prepared according to example 43 with BBr$_3$ using the procedure described in example 80 gave the 4-(2-Chlorophenyl)-6-(2-hydroxyethyl)-9-hydroxypyrrolo[3,4-c]carbazole-1,3(2H,6H)-dione (VI; Ar=2-chlorophenyl, $R^{10}$=CH$_2$CH$_2$OH) (47) in a yield of 87% as a yellow/orange powder; mp 265° C. (dec). $^1$H NMR δ (CD$_3$)$_2$SO] 11.04 (br, 1H), 9.33 (br s, 1H), 8.38 (d, J=2.4 Hz, 1H), 7.75 (s, 1H), 7.60–7.56 (m, 2H), 7.52–7.43 (m, 4H), 7.12 (dd, J=8.8, 2.4 Hz, 1H), 4.83 (t, J=5.5 Hz, 1H), 4.49 (t, J=5.2 Hz, 2H), 3.77 (dt, J=5.5, 5.2 Hz, 2H), Found: C, 63.41; H, 4.11; N, 6.32. $C_{22}H_{15}ClN_2O_4 \cdot 1/2 H_2O$ requires C, 63.54; H, 3.87; N, 6.73.

EXAMPLE 45

The Preparation of 5-Methoxy-2-[2-(2-methoxy-5-nitrophenyl)ethenyl]-1H-indole (II; Ar=2-methoxy-5-nitrophenyl) (35)

Reaction of 5-methoxy-1H-indole-2-carbaldehyde (1) with 2-methoxy-5-nitrobenzyltriphenylphosphonium chloride using the procedure described in example 37 gave 5-methoxy-2-[2-(2-methoxy-5-nitrophenyl)ethenyl]-1H-indole (II; Ar=2-methoxy-5-nitrophenyl) (35) in a 76% yield as an orange solid (a mixture of E/Z isomers) which was used without further purification.

EXAMPLE 46

The Preparation of 5-Methoxy-2-[2-(3,5-dinitrophenyl)ethenyl]-1H-indole (II; Ar=3,5-dinitrophenyl) (40)

Reaction of 5-methoxy-1H-indole-2-carbaldehyde(1) with 3,5-dinitrobenzyltriphenylphosphonium bromide using the procedure described in example 37 gave 5-Methoxy-2-[2-(3,5-dinitrophenyl)ethenyl]-1H-indole (II; Ar=3,5-dinitrophenyl) (40) in a 26% yield as an orange solid (a mixture of E/Z isomers) which was used without further purification.

EXAMPLE 47

The Preparation of 4-(3,5-Dinitrophenyl)-9-methoxy-4,5,6,10c-tetrahydropyrrolo[3,4-c]carbazole-1,3(2H,3aH)-dione (IV; Ar=3,5-dinitrophenyl. $R^{10}$=H) (41)

The reaction of 5-Methoxy-2-[2-(3,5-dinitrophenyl)ethenyl]-1H-indole (II; Ar=3,5-dinitrophenyl) (40) prepared as described in example 46 with maleimide using the procedure described in example 69 gave 4-(3,5-Dinitrophenyl)-9-methoxy-4,5,6,10c-tetrahydropyrrolo[3,4-c]carbazole-1,3(2H,3aH)-dione (IV; Ar=3,5-dinitrophenyl, $R^{10}$=H) (41) in a 89% yield as a glassy solid which was used without further purification.

EXAMPLE 48

The Preparation of 4-(3,5-Dinitrophenyl)-9-methoxypyrrolo[3,4-c]carbazole-1,3(2H,6H)-dione (V; Ar=3,5-dinitrophenyl, $R^{10}$=H) (42)

The reaction of 4-(3,5-Dinitrophenyl)-9-methoxy-4,5,6,10c-tetrahydropyrrolo[3,4-c]carbazole-1,3(2H,3aH)-dione (IV; Ar=3,5-dinitrophenyl, R=H) (41) prepared as described in example 47 with DDQ according to the procedure described in example 70 gave 4-(3,5-dinitrophenyl)-9-methoxypyrrolo[3,4-c]carbazole-1,3(2H,6H)-dione (V; Ar=3,5-dinitrophenyl, $R^{10}$=H) (42) in a 42% yield as a reddish solid which was used without further purification.

EXAMPLE 49

The Preparation of 4-(3,5-Dinitrophenyl)-9-hydroxypyrrolo[3,4-c]carbazole-1,3(2H,6H)-dione (V; Ar=3,5-dinitrophenyl, $R^{10}$=H) (43)

The reaction of 4-(3,5-dinitrophenyl)-9-methoxypyrrolo[3,4-c]carbazole-1,3(2H,6H)-dione (V; Ar=3,5-dinitrophenyl, $R^{10}$=H) (42) prepared as described in example 48 with pyridinium hydrochloride according to the proceedure described in example 81 gave 4-(3,5-Dinitrophenyl)-9-hydroxypyrrolo[3,4-c]carbazole-1,3(2H,6H)-dione (V; Ar=3,5-dinitrophenyl, $R^{10}$=H) (43) in a 57% yield as an orange powder, mp>330° C. $^1$H NMR δ [(CD$_3$)$_2$SO] 11.94 (br s, 1H), 11.18 (br s, 1H), 9.32 (br s, 1H), 8.91 (s, 3H), 8.35 (d, J=2.3 Hz, 1H), 7.83 (s, 1H), 7.49 (d, J=8.7 Hz, 1H), 7.11 (dd, J=8.7, 2.3 Hz, 1H).

EXAMPLE 50

The Preparation of 5-Methoxy-2-[2-(2-methoxyphenyl)ethenyl]-1H-indole (II; Ar=2-methoxyphenyl) (97)

The reaction of 5-methoxy-1H-indole-2-carbaldehyde (1) with 2-methoxybenzyltriphenylphosphonium chloride using the procedure described in example 37 gave 5-methoxy-2-[2-(2-methoxyphenyl)ethenyl]-1H-indole (II; Ar=2-methoxyphenyl) (97) in a 98% yield as a yellow solid (a mixture of E/Z isomers) which was used without further purification.

EXAMPLE 51

The Preparation of 1-(3-{[tert-Butyl(dimethyl)silyl]oxy}propyl)-5-methoxy-2-[2-(2-methoxyphenyl)ethenyl]-1H-indole (III; Ar=2-methoxyphenyl, $R^{10}$=CH$_2$CH$_2$CH$_2$OSiMe$_2$t-Bu) (98)

Reaction of 5-Methoxy-2-[2-(2-methoxyphenyl)ethenyl]-1H-indole (II; Ar=2-methoxyphenyl) (97) prepared as in example 50 with 3-bromopropyl tert-butyl(dimethyl)silyl ether using the procedure described in example 38 gave 1-(3-{[tert-Butyl(dimethyl)silyl]oxy}propyl)-5-methoxy-2-[2-(2-methoxyphenyl)ethenyl]-1H-indole (III; Ar=2-methoxyphenyl, $R^{10}$=CH$_2$CH$_2$CH$_2$OSiMe$_2$t-Bu) (98) in a 97% yield which was used without further purification.

EXAMPLE 52

The Preparation of 6-(3-{[tert-Butyl(dimethyl)silyl]oxy}propyl)-9-methoxy-4-(2-methoxyphenyl)-4,5,6,10c-tetrahydropyrrolo[3,4-c]carbazole-1,3(2H,3aH)-dione (IV; Ar=2-methoxyphenyl: $R^{10}$=CH$_2$CH$_2$CH$_2$OSiMe$_2$t-Bu) (99)

The reaction of 1-(3-{[tert-Butyl(dimethyl)silyl]oxy}propyl)-5-methoxy-2-[2-(2-methoxyphenyl)ethenyl]-1H-indole (III; Ar=2-methoxyphenyl, $R^{10}$=CH$_2$CH$_2$CH$_2$OSiMe$_2$t-Bu) (98) prepared as described in example 51 with maleimide using the procedure described in example 68 gave 6-(3-{[tert-Butyl(dimethyl)silyl]oxy}propyl)-9-methoxy-4-(2-methoxyphenyl)-4,5,6,10c-tetrahydropyrrolo[3,4-c]carbazole-1,3(2H, 3aH)-dione (IV; Ar=2-methoxyphenyl; $R^{10}$=CH$_2$CH$_2$CH$_2$OSiMe$_2$t-Bu) (99) in a 89% yield as a tan powder, which was used without further purification.

EXAMPLE 53

The Preparation of 6-(3-Hydroxypropyl)-9-methoxy-4-(2-methoxyphenyl)pyrrolo[3,4-c]carbazole-1,3(2H,6H)-dione (V; Ar=2-methoxyphenyl, $R^{10}$=CH$_2$CH$_2$CH$_2$OH) (100).

The reaction of 6-(3-{[tert-Butyl(dimethyl)silyl]oxy}propyl)-9-methoxy-4-(2-methoxyphenyl)-4,5,6,10c-tetrahydropyrrolo[3,4-c]carbazole-1,3(2H,3aH)-dione (IV; Ar=2-methoxyphenyl; $R^{10}$=CH$_2$CH$_2$CH$_2$OSiMe$_2$t-Bu) prepared as described in example 52 with DDQ using the procedure described in example 70 followed reaction with 2N HCl in THF/methanol gave 6-(3-Hydroxypropyl)-9-methoxy-4-(2-methoxyphenyl)pyrrolo[3,4-c]carbazole-1,3 (2H,6H)-dione (V; Ar=2-methoxyphenyl, $R^{10}$=CH$_2$CH$_2$CH$_2$OH) (100) in a 72% yield as an orange powder; mp 223–225° C. $^1$H NMR δ [(CD$_3$)$_2$SO] 10.99 (br s, 1H), 8.53 (d, 2.6 Hz, 1H), 7.74 (s, 1H), 7.67 (d, J=8.9 Hz, 1H), 7.45–7.40 (m, 1H), 7.36 (dd, J=7.4, 1.7 Hz, 1H), 7.29 (dd, J=8.9, 2.7 Hz, 1H), 7.11 (d, J=8.1 Hz, 1H), 7.06 (dd, J=7.2, 7.2 Hz, 1H), 4.63 (t, J=4.8 Hz, 1H), 4.52 (t, J=6.9 Hz, 2H), 3.90 (s, 3H), 3.69 (s, 3H), 3.40 (m, 2H), 1.91 (m, 2H). Found: C, 69.55; H, 5.31; N, 6.30. $C_{25}H_{22}N_2O_5$ requires C69.76; H, 5.15; N, 6.51.

EXAMPLE 54

The Preparation of 9-Hydroxy-4-(2-hydroxyphenyl)-6-(3-hydroxypropyl)pyrrolo[3,4-c]carbazole-1,3 (2H,6H)-dione (VI; Ar=2-hydroxyphenyl, $R^{10}$=CH$_2$CH$_2$CH$_2$OH) (101).

The reaction of 6-(3-Hydroxypropyl)-9-methoxy-4-(2-methoxyphenyl)pyrrolo[3,4-c]carbazole-1,3(2H,6H)-dione (V; Ar=2-methoxyphenyl, $R^{10}$=CH$_2$CH$_2$CH$_2$OH) (100) prepared as described in example 53 with BBr$_3$ using the procedure described in example 80 gave 9-Hydroxy-4-(2-hydroxyphenyl)-6-(3-hydroxypropyl)pyrrolo[3,4-c]carbazole-1,3(2H,6H)-dione (VI; Ar=2-hydroxyphenyl, $R^{10}$=CH$_2$CH$_2$CH$_2$OH) (101) in an 82% yield as an orange powder, mp 306–309° C. $^1$H NMR δ [(CD$_3$)$_2$SO] 10.90 (br, 1H), 9.40 (br, 1H), 8.38 (d, J=2.4 Hz, 1H), 7.67 (s, 1H), 7.56 (d, J=8.8 Hz, 1H), 7.30–7.23 (m, 2H), 7.13 (dd, J=8.8, 2.4 Hz, 1H), 6.94–6.88 (m, 2H), 4.78 (br, 2H), 4.47 (t, J=6.8 Hz, 2H), 3.41 (t, J=6.0 Hz, 2H), 1.91 (m, 2H). Found: C, 66.85; H, 4.61; N, 6.63. $C_{23}H_{18}N_2O_5 \cdot 1/2H_2O$ requires C, 67.14; H, 4.65; N, 6.80.

EXAMPLE 55

The Preparation of 2-[2-(2-Chloro-6-methoxyphenyl)ethenyl]-5-methoxy-1H-indole (II; Ar=2-chloro-6-methoxyphenyl) (102)

The reaction of 5-methoxy-1H-indole-2-carbaldehyde (1) with 2-chloro-6-methoxybenzyltriphenylphosphonium bromide using the procedure described in example 37 gave 2-[2-(2-Chloro-6-methoxyphenyl)ethenyl]-5-methoxy-1H-indole (II; Ar=2-chloro-6-methoxyphenyl) (102) in a 92% yield as a yellow solid (a mixture of E/Z isomers) which was used without further purification.

EXAMPLE 56

The Preparation of 1-(3-{tert-Butyl(dimethyl)silyl]oxy) propyl)-2-[2-(2-chloro-6-methoxyphenyl)ethenyl]-5-methoxy-1H-indole (III; Ar=2-chloro-6-methoxyphenyl $R^{10}$=CH$_2$CH$_2$CH$_2$OSiMe$_2$t-Bu) (103)

The reaction of 2-[2-(2-Chloro-6-methoxyphenyl)ethenyl]-5-methoxy-1H-indole (II; Ar=2-chloro-6-methoxyphenyl) (102) prepared as described in example 55 with 3-bromopropyl tert-butyl(dimethyl)silyl ether using the procedure described in example 38 gave 1-(3-{[tert-Butyl(dimethyl)silyl]oxy}propyl)-2-[2-(2-chloro-6-methoxyphenyl)ethenyl]-5-methoxy-1H-indole (III; Ar=2-chloro-6-methoxyphenyl, $R^{10}$=CH$_2$CH$_2$CH$_2$OSiMe$_2$t-Bu) (103) in a 91% yield which was used without further purification.

EXAMPLE 57

The Preparation of 6-(3-[tert-Butyl(dimethyl)silyl]oxy)propyl)-4-(2-chloro-6-methoxyphenyl)-9-methoxy-4,5,6,10c-tetrahydropyrrolo[3,4-c]carbazole-1,3 (2H,3aH)-dione (IV; Ar=2-chloro-6-methoxyphenyl, $R^{10}$=CH$_2$CH$_2$CH$_2$OSiMe$_2$t-Bu) (104).

The reaction of 1-(3-{[tert-Butyl(dimethyl)silyl]oxy}propyl)-2-[2-(2-chloro-6-methoxyphenyl)ethenyl]-5-methoxy-1H-indole (III; Ar=2-chloro-6-methoxyphenyl, $R^{10}$=CH$_2$CH$_2$CH$_2$OSiMe$_2$t-Bu) (103) prepared as described in example 56 with maleimide using the procedure described in example 68 gave 6-(3-[tert-Butyl(dimethyl)silyl]oxy}propyl)-4-(2-chloro-6-methoxyphenyl)-9-methoxy-4,5,6,10c-tetrahydropyrrolo[3,4-c]carbazole-1,3(2H,3aH)-dione (IV; Ar=2-chloro-6-methoxyphenyl, $R^{10}$=CH$_2$CH$_2$CH$_2$OSiMe$_2$t-Bu) (104) in a 77% yield as a cream powder, which was used without further purification.

EXAMPLE 58

The Preparation of 4-(2-Chloro-6-methoxyphenyl)-6-(3-hydroxypropyl)-9-methoxypyrrolo[3,4-c]carbazole-1,3(2H,6H)-dione (V; Ar=2-chloro-6-methoxyphenyl, $R^{10}$=CH$_2$CH$_2$CH$_2$OH) (105)

The reaction of 6-(3-{[tert-Butyl(dimethyl)silyl]oxy}propyl)-4-(2-chloro-6-methoxyphenyl)-9-methoxy-4,5,6,10c-tetrahydropyrrolo[3,4-c]carbazole-1,3(2H,3aH)-dione (IV; Ar=2-chloro-6-methoxyphenyl, $R^{10}$=CH$_2$CH$_2$CH$_2$OSiMe$_2$t-Bu) (104) prepared as described in example 57 with DDQ using the procedure described in example 70 followed by reaction with 2N HCl in THF/methanol gave 4-(2-Chloro-6-methoxyphenyl)-6-(3-hydroxypropyl)-9-methoxypyrrolo[3,4-c]carbazole-1,3(2H,6H)-dione (V; Ar=2-chloro-6-methoxyphenyl, $R^{10}$=CH$_2$CH$_2$CH$_2$OH) (105) in a 76% yield as an orange powder; mp 224–227° C. $^1$H NMR δ [(CD$_3$)$_2$SO] 11.05 (br, 1H), 8.51 (d, J=2.6 Hz, 1H), 7.75 (s, 1H), 7.69 (d, J=8.9 Hz, 1H), 7.44 (dd, J=8.2, 8.2 Hz, 1H), 7.31 (dd, J=8.9, 2.6 Hz, 1H), 7.18 (d, J=8.2 Hz, 1H), 7.13 (d, J=8.2 Hz, 1H), 4.63 (t, J=4.9 Hz, 1H), 4.51 (t, J=6.8 Hz, 2H), 3.91 (s, 3H), 3.68 (s, 3H), 3.41 (m, 2H), 1.89 (m, 2H). Found: C, 69.71; H, 4.53; N, 6.43. $C_{25}H_{22}N_2O_5$ requires C, 69.76; H, 5.15; N, 6.51.

EXAMPLE 59

The Preparation of 4-(2-Chloro-6-methoxyphenyl)-9-Hydroxy-6-(3-hydroxypropyl)pyrrolo[3,4-c]carbazole-1,3(2H,6H)-dione (VI: Ar=2-chloro-6-methoxyphenyl, $R^{10}$=CH$_2$CH$_2$CH$_2$OH) (106).

The reaction of 4-(2-Chloro-6-methoxyphenyl)-6-(3-hydroxypropyl)-9-methoxypyrrolo[3,4-c]carbazole-1,3(2H, 6H)-dione (V; Ar=2-chloro-6-methoxyphenyl, $R^{10}$=CH$_2$CH$_2$CH$_2$OH) (105) prepared as described in example 58 with BBr$_3$ using the procedure described in example 80 and with a reaction time of 90 minutes gave 4-(2-Chloro-6-methoxyphenyl)-9-hydroxy-6-(3-hydroxypropyl)pyrrolo[3,4-c]carbazole-1,3(2H,6H)-dione (VI; Ar=2-chloro-6-methoxyphenyl, $R^{10}$=CH$_2$CH$_2$CH$_2$OH) (106) in a 64% yield as an orange powder, mp 270–273° C. $^1$H NMR δ [(CD$_3$)$_2$SO] 11.01 (br s, 1H), 9.35 (br s, 1H), 8.37 (d, J=2.4 Hz, 1H), 7.70 (s, 1H), 7.58 (d, J=8.7 Hz, 1H), 7.44 (dd, J=8.3, 8.3 Hz, 1H), 7.20–7.11 (m, 3H), 4.61 (br t, 1H), 4.47 (t, J=6.9 Hz, 2H), 3.68 (s, 3H), 3.42 (m, 2H), 1.88 (m, 2H). Found: C, 64.16; H, 4.55; N, 6.01. $C_{24}H_{19}ClN_2O_5$ requires C, 63.93; H, 4.25; N, 6.21.

EXAMPLE 60

The Preparation of 9-Hydroxy-6-(3-hydroxypropyl)-4-(2-methoxyphenyl)pyrrolo[3,4-c]carbazole-1,3 (2H,6H)-dione (VI: Ar=2-methoxyphenyl. $R^{10}$=CH$_2$CH$_2$CH$_2$OH) (107).

4-(2-Chloro-6-methoxyphenyl)-9-hydroxy-6-(3-hydroxypropyl)pyrrolo[3,4-c]carbazole-1,3(2H,6H)-dione (VI; Ar=2-chloro-6-methoxyphenyl, $R^{10}$=CH$_2$CH$_2$CH$_2$OH) (106) (0.20 g, 0.44 mmol) prepared as described in example 59, potassium acetate (0.20 g) and 5% Pd/C in a solution of ethyl acetate (25 ml) and methanol 1:1 (25 mL) under a atmosphere of hydrogen at 60 psi was reacted for 7 h. The catalyst was filtered off and the filtrate concentrated to dryness. The residue was partitioned between ethyl acetate and water and the organic solution was dried, the drying agent was removed and the solution was concentrated to dryness and chromatographed on silica. Elution with ethyl acetate/petroleum ether (2:1) gave 9-Hydroxy-6-(3-hydroxypropyl)-4-(2-methoxyphenyl)pyrrolo[3,4-c]carbazole-1,3 (2H,6H)-dione (VI; Ar=2-methoxyphenyl, $R^{10}$=CH$_2$CH$_2$CH$_2$OH) (107) in a yield of 51% as an orange powder (from THF/petroleum ether), mp 296–300° C. $^1$H NMR δ [(CD$_3$)$_2$SO] 10.93 (br s, 1H), 9.31 (br s, 1H), 8.38 (d, J=2.4 Hz, 1H), 7.69 (s, 1H), 7.55 (d, J=8.8 Hz, 1H), 7.42 (m, 1H), 7.35 (dd, J=7.5, 1.7 Hz, 1H), 7.13–7.08 (m, 2H), 7.05 (dd, J=7.2, 7.2 Hz, 1H), 4.62 (t, J=4.8 Hz, 1H), 4.48 (t, J=6.8 Hz, 2H), 3.68 (s, 3H), 3.40 (m, 2H), 1.90 (m, 2H). Found: C, 69.29; H, 4.90; N, 6.54. $C_{24}H_{20}N_2O_5$ requires C, 69.22; H, 4.84; N, 6.73.

EXAMPLE 61

The Preparation of 2-{2-[2-(2-Chloro-6-methoxyphenyl)ethenyl]-5-methoxy-1H-indol-1-yl}ethanol (III; Ar=2-chloro-6-methoxyphenyl, $R^{10}$=CH$_2$CH$_2$OH) (109)

The reaction of 2-[2-(2-Chloro-6-methoxyphenyl)ethenyl]-5-methoxy-1H-indole (II; Ar=2-chloro-6-methoxyphenyl) (102) prepared as described in example 55 with 2-bromoethyl tetrahydro-2H-pyran-2-yl ether using the procedure described in example 38 followed by reaction of the crude product with 2N HCl in methanol gave 2-{2-[2-(2-Chloro-6-methoxyphenyl)ethenyl]-5-methoxy-1H-indol-1-yl}ethanol (III; Ar=2-chloro-6-methoxyphenyl, $R^{10}$=CH$_2$CH$_2$OH) (109) in a 91% yield as a mixture of E/Z isomers, which was used without further purification.

EXAMPLE 62

The Preparation of 4-(2-Chloro-6-methoxyphenyl)-6-(2-hydroxyethyl)-9-methoxy-4,5,6,10c-tetrahydropyrrolo[3,4-c]carbazole-1,3(2H,3aH)-dione (IV: Ar=2-chloro-6-methoxyphenyl. $R^{10}$=CH$_2$CH$_2$OH) (110).

Reaction of the 2-{2-[2-(2-Chloro-6-methoxyphenyl)ethenyl]-5-methoxy-1H-indol-1-yl}ethanol (III; Ar=2-chloro-6-methoxyphenyl, R=CH$_2$CH$_2$OH) (109) prepared as described in example 61 with maleimide using the procedure described in example 68 gave 4-(2-Chloro-6-methoxyphenyl)-6-(2-hydroxyethyl)-9-methoxy-4,5,6,10c-tetrahydropyrrolo[3,4-c]carbazole-1,3(2H,3aH)-dione (IV; Ar=2-chloro-6-methoxyphenyl, $R^{10}$=CH$_2$CH$_2$OH) (110) in a 72% yield as a cream powder, which was used without further purification.

EXAMPLE 63

The Preparation of 4-(2-Chloro-6-methoxyphenyl)-6-(2-Hydroxyethyl)-9-methoxypyrrolo[3,4-c]carbazole-1,3(2H,6H)-dione (V; Ar=2-chloro-6-methoxyphenyl. $R^{10}$=CH$_2$CH$_2$OH) (III)

The reaction of 4-(2-Chloro-6-methoxyphenyl)-6-(2-hydroxyethyl)-9-methoxy-4,5,6,10c-tetrahydropyrrolo[3,4-c] carbazole-1,3(2H,3aH)-dione (IV; Ar=2-chloro-6-methoxyphenyl, $R^{10}$=CH$_2$CH$_2$OH) (110) prepared as described in example 62 with MnO$_2$ using the procedure described in example 79 except that the reaction time was 8 h 4-(2-Chloro-6-methoxyphenyl)-6-(2-hydroxyethyl)-9-methoxypyrrolo[3,4-c]carbazole-1,3(2H,6H)-dione (V; Ar=2-chloro-6-methoxyphenyl, $R^{10}$=CH$_2$CH$_2$OH) (111) in a 75% yield as a yellow/orange powder; mp 264–268° C. $^1$H NMR δ [(CD$_3$)$_2$SO] 11.04 (br s, 1H), 8.50 (d, J=2.6 Hz, 1H), 7.75 (s, 1H), 7.69 (d, J=9.0 Hz, 1H), 7.44 (dd, J=8.3, 8.3 Hz, 1H), 7.28 (dd, J=9.0, 2.6 Hz, 1H), 7.18 (d, J=8.3 Hz, 1H), 7.13 (d, J=8.3 Hz, 1H), 4.83 (t, J=5.5 Hz, 1H), 4.51 (t, J=5.3 Hz, 2H), 3.90)s, 3H), 3.75 (m, 2H), 3.67 (s, 3H). Found: C, 63.84; H, 4.32; N, 5.97. $C_{24}H_{19}ClN_2O_5$ requires C, 63.93; H, 4.25; N, 6.21.

EXAMPLE 64

The Preparation of 4-(2-Chloro-6-methoxyphenyl)-9-Hydroxy-6-(2-hydroxyethyl)pyrrolo[3,4-c]carbazole-1,3(2H,6H)-dione (VI; Ar-2-chloro-6-methoxyphenyl, $R^{10}$=CH$_2$CH$_2$OH) (112)

The reaction of 4-(2-Chloro-6-methoxyphenyl)-6-(2-hydroxyethyl)-9-methoxypyrrolo[3,4-c]carbazole-1,3(2H, 6H)-dione (V; Ar=2-chloro-6-methoxyphenyl, $R^{10}$=CH$_2$CH$_2$OH) (111) prepared as described in example 63 with BBr$_3$ using the procedure described in example 80 except that the reaction conditions were 2 h at 0° C. gave 4-(2-Chloro-6-methoxyphenyl)-9-hydroxy-6-(2-hydroxyethyl)pyrrolo[3,4-c]carbazole-1,3(2H,6H)-dione (VI; Ar-2-chloro-6-methoxyphenyl, $R^{10}$=CH$_2$CH$_2$OH) (112) in a 56% yield as a yellow powder (56%); mp 275–278° C. $^1$H NMR δ [(CD$_3$)$_2$SO] 10.98 (br s, 1H). 9.30 (br s, 1H), 8.36 (d, J=2.4 Hz, 1H), 7.70 (s, 1H), 7.57 (d, J=8.7 Hz, 1H), 7.43 (dd, J=8.3, 8.3 Hz, 1H), 7.17 (d, J=7.9 Hz, 1H), 7.14–7.09 (m, 2H), 4.81 (t, J=5.5 Hz, 1H), 4.46 (t, J=5.3 Hz, 2H), 3.74 (dt, J=5.5, 5.3 Hz, 2H), 3.66 (s, 3H). FABMS found [M+H]$^+$: 439.0882, 437.0889. $C_{23}H_{18}ClNO_5$ requires 439.0875, 437.0904.

EXAMPLE 65

The Preparation of 9-Hydroxy-6-(2-Hydroxyethyl)-4-(2-methoxyphenyl)pyrrolo[3,4-c]carbazole-1,3 (2H,6H)-dione (VI; Ar=2-methoxyphenyl. $R^{10}$=CH$_2$CH$_2$OH) (113)

Reaction of 4-(2-Chloro-6-methoxyphenyl)-9-hydroxy-6-(2-hydroxyethyl)pyrrolo[3,4-c]carbazole-1,3(2H,6H)-dione (VI; Ar=2-chloro-6-methoxyphenyl, $R^{10}$=CH$_2$CH,OH) (112) prepared as described in example 64 with hydrogen gas, using a Pd/C catalyst, according to the procedure for example 60 gave 9-Hydroxy-6-(2-hydroxyethyl)-4-(2-methoxyphenyl)pyrrolo[3,4-c]carbazole-1,3(2H,6H)-dione (VI; Ar=2-methoxyphenyl, $R^{10}$=CH$_2$CH$_2$OH) (113) in a 77% yield as a yellow solid; mp 285–289° C. $^1$H NMR δ [(CD$_3$)$_2$SO] 10.91 (br s, 1H), 9.29 (br s, 1H), 8.37 (d, J=2.4 Hz, 1H), 7.70 (s, 1H), 7.55 (d, J=8.8 Hz, 1H), 7.42 (m, 1H), 7.33 (dd, J=8.8, 2.4 Hz, 1H), 7.12–7.02 (m, 3H), 4.84 (t, J=5.5 Hz, 1H), 4.73 (t, J=5.3 Hz, 2H), 3.76 (dt, J=5.5, 5.3 Hz, 2H), 3.68 (s, 3H). Found: C, 67.30; H, 4.47; N, 6.79. C$_{23}$H$_{18}$N$_2$O$_5$.1/2H$_2$O requires C, 67.15; H, 4.65; N, 6.81.

EXAMPLE 66

The Preparation of 2-(4-(2-Chloro-6-methoxyphenyl)-9-Hydroxy-1,3-dioxo-2,3-dihydropyrrolo[3,4-c]carbazol-6 (1H)-yl)ethyl methanesulfonate (VII; Ar=2-chloro-6-methoxyphenyl, n=2, mesylate) (114).

Reaction of 4-(2-Chloro-6-methoxyphenyl)-6-(2-hydroxyethyl)-9-methoxypyrrolo[3,4-c]carbazole-1,3(2H, 6H)-dione (V; Ar=2-chloro-6-methoxyphenyl, $R^{10}$=CH$_2$CH$_2$OH) (111) prepared as described in example 63 with methanesulphonyl chloride, followed by reaction with BBr$_3$ using the procedure described in example 170 of Scheme 3 gave 2-(4-(2-Chloro-6-methoxyphenyl)-9-hydroxy-1,3-dioxo-2,3-dihydropyrrolo[3,4-c]carbazol-6 (1H)-yl)ethyl methanesulfonate (VII; Ar=2-chloro-6-methoxyphenyl, n=2, mesylate) (114), as a yellow solid, which was used without further purification.

EXAMPLE 67

The Preparation of 4-(2-Chloro-6-methoxyphenyl)-9-Hydroxy-6-[2-(4-morpholinyl)ethyl]pyrrolo[3,4-c]carbazole-1,3(2H,6H)-dione (VIII; Ar=2-chloro-6-methoxyphenyl, n=2, Z=4-morpholinyl) (115).

Reaction of 2-(4-(2-Chloro-6-methoxyphenyl)-9-hydroxy-1,3-dioxo-2,3-dihydropyrrolo[3,4-c]carbazol-6 (1H)-yl)ethyl methanesulfonate (VII; Ar=2-chloro-6-methoxyphenyl, n=2, mesylate) (114) prepared as described in example 66 with morpholine using the procedure described in example 179 of Scheme 3 gave 4-(2-Chloro-6-methoxyphenyl)-9-hydroxy-6-[2-(4-morpholinyl)ethyl]pyrrolo[3, 4-c]carbazole-1,3(2H,6H)-dione (VIII; Ar=2-chloro-6-methoxyphenyl, n=2, Z=4-morpholinyl) (115) in an 81% yield as a yellow powder; mp 185° C. $^1$H NMR δ [(CD$_3$)$_2$SO] 10.99 (br s, 1H), 9.34 (br s, 1H), 8.37 (d, J=2.4 Hz, 1H), 7.69 (s, 1H), 7.57 (d, J=8.8 Hz, 1H), 7.44 (dd, J=8.3, 8.3 Hz, 1H), 7.17 (d, J=8.3 Hz, 1H), 7.14–7.10 (m, 2H), 4.53 (t, J=6.1 Hz, 2H), 3.66 (s, 3H), 3.41 (t, J=4.5 Hz, 4H), 2.64 (t, J=6.1 Hz, 2H), 2.37 (m, 4H). Found: C, 63.57; H, 4.71; N, 8.06. C$_{27}$H$_{24}$ClN$_3$O$_5$.1/4H$_2$O requires C, 63.53; H, 4.84; N, 8.23.

Representative Procedure for Method 4 of Scheme 2

EXAMPLE 68

The Preparation of 4-(2-Chlorophenyl)-9-methoxy-4,5,6,10c-tetrahydropyrrolo[3,4-c]carbazole-1,3(2H, 3aH)-dione (IV; Ar=2-chlorophenyl, $R^{10}$=H) (32)

A solution of 2-[2-(2-Chlorophenyl)ethenyl]-5-methoxy-1H-indole (II; Ar=2-chlorophenyl) (27) (1.5 g, 5.29 mmol) prepared according to example 37, maleimide (0.61 g, 6.34 mmol) and SnCl$_2$ (0.20 g, 1.05 mmol) in toluene (25 mL) was refluxed for 6 h. After dilution with ethyl acetate the solution was washed with water and The organic phase was dried, the drying agent was removed and the solution was concentrated to dryness to give 4-(2-Chlorophenyl)-9-methoxy-4,5,6,10c-tetrahydropyrrolo[3,4-c]carbazole-1,3(2H, 3aH)-dione (IV; Ar=2-chlorophenyl, $R^{10}$=H) (32) in a yield of 1.98 g, 98% as a yellow solid (as a mixture of diastereomers), which was used without further purification.

Representative Procedure for Method 5 of Scheme 2

EXAMPLE 69

The Preparation of 9-Methoxy-4-(2-methoxy-5-nitrophenyl)-4,5,6,10c-tetrahydropyrrolo[3,4-c]carbazole-1,3(2H,3aH)-dione (IV; Ar=2-methoxy-5-nitrophenyl, $R^{10}$=H) (185)

A solution of 5-methoxy-2-[2-(2-methoxy-5-nitrophenyl)ethenyl]-1H-indole (II; Ar=2-methoxy-5-nitrophenyl) (0.437 g, 1.35 mmol) prepared as described in example 45 and maleimide (0.156 g, 1.62 mmol) in THF (10 mL) was concentrated to dryness in a 25 mL flask. The resulting solid was placed in an oil bath at 180° C. and the resulting melt was kept at this temperature for 4 h. The residue was cooled and triturated with diethyl ether to give 9-methoxy-4-(2-methoxy-5-nitrophenyl)-4,5,6,10c-tetrahydropyrrolo[3,4-c]carbazole-1,3(2H,3aH)-dione (IV; Ar=2-methoxy-5-nitrophenyl, $R^{10}$=H) (185) in a yield of 0.51 g, 90% as a tan powder, which was used without further purification in the next step.

Representative Procedure for Method 6 of Scheme 2

EXAMPLE 70

The Preparation of 9-Methoxy-4-(2-methoxy-5-nitrophenyl)pyrrolo[3,4-c]carbazole-1,3(2H,6H)-dione (IV; Ar=2-methoxy-5-nitrophenyl, $R^{10}$=H) (36)

A solution of 9-methoxy-4-(2-methoxy-5-nitrophenyl)-4, 5,6,10c-tetrahydropyrrolo[3,4-c]carbazole-1,3(2H,3aH)-dione (IV; Ar=2-methoxy-5-nitrophenyl, $R^{10}$=H) (185) (0.51 g, 1.21 mmol) prepared according to example 69 and DDQ (0.82 g, 3.63 mmol) in dioxane (30 mL) was refluxed for 2 h. After dilution with water the solution was extracted with dichloromethane. The organic extracts were washed with saturated aqueous NaHCO$_3$ solution (3×). The organic phase was dried, the drying agent was removed and the solution was concentrated to dryness to give a solid which was chromatographed on silica. Elution with ethyl acetate/petroleum ether (3:7) followed by ethyl acetate/petroleum ether (1:1) gave a solid which when triturated with diethyl ether gave 9-Methoxy-4-(2-methoxy-5-nitrophenyl)pyrrolo[3,4-c]carbazole-1,3(2H,6H)-dione (V; Ar=2-methoxy-5-nitrophenyl, $R^{10}$=H) (36) in a 0.42 g, 82% yield; mp 302–304° C. $^1$H NMR δ [(CD$_3$)$_2$SO] 11.95 (br s, 1H), 11.06 (br s, 1H), 8.46 (d, J=2.6 Hz, 1H), 8.37 (dd, J=9.2, 3.0 Hz, 1H), 8.22 (d, J=3.0 Hz, 1H), 7.69 (s, 1H), 7.57 (d, J=8.8 Hz, 1H), 7.36 (d, J=9.2 Hz, 1H), 7.24 (dd, J=8.8, 2.6 Hz, 1H), 3.89 (s, 3H), 3.85 (s, 3H). Found: C, 63.90; H, 3.79; N, 9.52. C$_{22}$H$_{15}$N$_3$O$_6$ requires C. 63.61; H, 3.62; N, 10.07.

EXAMPLE 71

The Preparation of 9-Hydroxy-4-(2-hydroxy-5-nitrophenyl)pyrrolo[3,4-c]carbazole-1,3(2H,6H)-dione (VI; Ar=2-Hydroxy-5-nitrophenyl, $R^{10}$=H) (37)

9-Methoxy-4-(2-methoxy-5-nitrophenyl)pyrrolo[3,4-c]carbazole-1,3(2H,6H)-dione (V; Ar=2-methoxy-5-nitrophenyl, R=H) (36) prepared according to example 70 was reacted using the procedure described in example 81 by reaction at 210° C. for 30 min, to give 9-hydroxy-4-(2-hydroxy-5-nitrophenyl)pyrrolo[3,4-c]carbazole-1,3(2H,6H)-dione (VI; Ar=2-hydroxy-5-nitrophenyl, $R^{10}$=H) (37) in a 82% yield as a yellow/orange powder; mp>330° C. $^1$H NMR δ [(CD$_3$)$_2$SO] 11.78 (s, 1H), 10.99 (s, 1H), 9.26 (s, 1H), 8.32 (d, J=2.4 Hz, 1H), 8.21–8.16 (m, 2H), 7.63 (s, 1H), 7.45 (d, J=8.7 Hz, 1H), 7.08 (m, 2H).

EXAMPLE 72

The Preparation of 9-Hydroxy-4-(2-methoxy-5-nitrophenyl)pyrrolo[3,4-c]carbazole-1,3(2H,6H)-dione (VI; Ar=2-methoxy-5-nitrophenyl. $R^{10}$=H) (38)

9-Methoxy-4-(2-methoxy-5-nitrophenyl)pyrrolo[3,4-c]carbazole-1,3(2H,6H)-dione (V; Ar=2-methoxy-5-nitrophenyl, $R^{10}$=H) (36) prepared according to example 70 was reacted using the procedure described in example 80 to give 9-hydroxy-4-(2-methoxy-5-nitrophenyl)pyrrolo[3,4-c]carbazole-1,3(2H,6H)-dione (VI; Ar=2-methoxy-5-nitrophenyl, $R^{10}$=H) (38) in a 76% yield as a yellow powder; mp 265–273° C. (dec). $^1$H NMR δ [(CD$_3$)$_2$SO] 11.86 (br, 1H), 11.01 (br, 1H), 8.38 (dd, J=9.3, 2.8 Hz, 1H), 8.31 (d, J=2.4 Hz, 1H), 8.20 (d, J=2.8 Hz, 1H), 7.65 (s, 1H), 7.48 (d, J=8.7 Hz, 1H), 7.36 (d, J=9.3 Hz, 1H), 7.10 (dd, J=8.7, 2.4 Hz, 1H), 3.84 (s, 3H). EIMS found M$^+$: 403.0794. $C_{21}H_{13}N_3O_6$ requires 403.0804.

EXAMPLE 73

The Preparation of 4-(5-Amino-2-methoxyphenyl)-9-hydroxypyrrolo[3,4-c]carbazole-1,3(2H,6H)-dione (VI; Ar=5-amino-2-methoxyphenyl, $R^{10}$=H) (39)

To a solution of 9-hydroxy-4-(2-methoxy-5-nitrophenyl)pyrrolo[3,4-c]carbazole-1,3(2H,6H)-dione (VI; Ar=2-methoxy-5-nitrophenyl, $R^{10}$=H) (38) (64 mg, 0.159 mmol) prepared according to example 72 in methanol (10 mL) and THF (1 mL) was added 2N HCl (1 mL) Freshly prepared nickel boride (~0.50 g) was added and the mixture was warmed at 60° C. After 1 h HCl (1 mL) and Ni$_2$B (~0.50 g) were added and the reaction mixture was maintained at 60° C. a total of 4 h. The solvents were removed in vacuo and the residue was partitioned between ethyl acetate and 2N HCl. The aqueous layer was basified with conc. ammonia solution and extracted with ethyl acetate. The organic phase was dried, the drying agent was removed and the solvent concentrated to dryness gave a solid which when crystallised from THF/petroleum ether gave 4-(5-Amino-2-methoxyphenyl)-9-hydroxypyrrolo[3,4-c]carbazole-1,3(2H,6H)-dione (VI; Ar=5-amino-2-methoxyphenyl, $R^{10}$=H (39) in a yield of 49.7 mg, 84% as a yellow powder; mp 246–250° C. $^1$H NMR δ [(CD$_3$)$_2$SO] 11.67 (s, 1H), 10.87 (s, 1H), 9.21 (s, 1H), 8.30)d, J=2.4 Hz, 1H), 7.44 (s, 1H), 7.42 (d, J=8.7 Hz, 1H), 7.05 (dd, J=8.6, 2.5 Hz, 1H), 6.80 (d, J=8.7 Hz, 1H), 6.61 (dd, J=8.6, 2.7 Hz, 1H), 6.55 (d, J=2.8 Hz, 1H), 4.68 (br, 2H), 3.53 (s, 3H). FABMS found [M+H]$^+$: 373.1056. $C_{21}H_{15}N_3O_4$ requires 373.1062.

EXAMPLE 74

The Preparation of 2-[(E)-2-(2-Bromo-4-nitrophenyl)ethenyl]-5-methoxy-1H-indole (II, Ar=2-bromo-4-nitrophenyl) (49)

Reaction of 5-methoxy-1H-indole-2-carbaldehyde (1) with 2-bromo-4-nitrobenzyltriphenylphosphonium bromide using the procedure described in example 37 gave the diene 2-[(E)-2-(2-Bromo-4-nitrophenyl)ethenyl]-5-methoxy-1H-indole (II, Ar=2-bromo-4-nitrophenyl) (49) in a 98% yield as a red solid which was used without further purification.

EXAMPLE 75

The Preparation of 4-(2-Bromo-4-nitrophenyl)-9-methoxy-4,5,6,10c-tetrahydropyrrolo[3,4-c]carbazole-1,3(2H,3aH)-dione (IV; Ar=2, bromo-4-nitrophenyl, $R^{10}$=H (50)

Reaction of 2-[(E)-2-(2-Bromo-4-nitrophenyl)ethenyl]-5-methoxy-1H-indole (II, Ar=2-bromo-4-nitrophenyl) (49) prepared as described in example 74 with maleimide using the procedure described in example 69 gave 4-(2-Bromo-4-nitrophenyl)-9-methoxy-4,5,6,10c-tetrahydropyrrolo[3,4-c]carbazole-1,3(2H, 3aH)-dione (IV; Ar=2,bromo-4-nitrophenyl, $R^{10}$=H) (50) in a 54% yield as a tan powder; mp 272° C. (dec), which was used without further purification.

EXAMPLE 76

The Preparation of 4-(2-Bromo-4-nitrophenyl)-9-methoxypyrrolo[3,4-c]carbazole-1,3(2H,6H)-dione (V; Ar=2-bromo-4-nitrophenyl, $R^{10}$=H) (51)

Reaction of 4-(2-bromo-4-nitrophenyl)-9-methoxy-4,5,6,10c-tetrahydropyrrolo[3,4-c]carbazole-1,3(2H,3aH)-dione (IV; Ar=2, bromo-4-nitrophenyl, $R^{10}$=H) (50) prepared as described in example 75 with DDQ using the procedure described in example 70 gave 4-(2-bromo-4-nitrophenyl)-9-methoxypyrrolo[3,4-c]carbazole-1,3(2H,6H)-dione (V; Ar=2-bromo-4-nitrophenyl, $R^{10}$=H) (51), in a 67% yield as a yellow powder, mp 288–292° C. (dec). $^1$H NMR δ [(CD$_3$)$_2$SO] 12.07 (br, 1H), 11.18 (br, 1H), 8.56 (d, J=2.3 Hz, 1H), 8.46 (d, J=2.6 Hz, 1H), 8.33 (dd, J=8.5, 2.6 Hz, 1H), 7.80 (d, J=8.5 Hz, 1H), 7.63 (s, 1H), 7.59 (d, J=8.8 Hz, 1H), 7.27 (dd, J=8.8, 2.3 Hz, 1H), 3.90 (s, 3H). Found: C, 54.06; H, 2.59; N, 8.72. $C_{21}H_{12}BrN_3O_5$ requires C, 54.10; H, 2.59; N, 9.01.

EXAMPLE 77

The Preparation of 4-(2-Bromo-4-nitrophenyl)-9-hydroxypyrrolo[3,4-c]carbazole-1,3(2H,6H)-dione (VI; Ar=2-bromo-4-nitrophenyl, $R^{10}$=H (52).

Reaction of 4-(2-bromo-4-nitrophenyl)-9-methoxypyrrolo[3,4-c]carbazole-1,3(2H,6H)-dione (V; Ar=2-bromo-4-nitrophenyl, $R^{10}$=H) (51) prepared as described in example 76 with pyridinium hydrochloride using the procedure described in the proceedure described in example 81 gave 4-(2-bromo-4-nitrophenyl)-9-hydroxypyrrolo[3,4-c]carbazole-1,3(2H,6H)-dione (VI; Ar=2-bromo-4-nitrophenyl, $R^{10}$=H (52) in a 92% yield as a yellow powder; mp>330° C. $^1$H NMR δ [(CD$_3$)$_2$SO] 11.94 (s, 1H), 11.13 (s, 1H), 9.32 (br s, 1H), 8.55 (d, J=2.3 Hz, 1H), 8.34 (d, J=2.4 Hz, 1H), 8.31 (m, 2H), 7.79 (d, J=8.5 Hz, 1H), 7.58 (s, 1H), 7.48 (d, J=8.7 Hz, 1H), 7.11 (dd, J=8.7, 2.4 Hz, 1H).

EXAMPLE 78

The Preparation of 4-(4-Amino-2-bromophenyl)-9-hydroxypyrrolo[3,4-c]carbazole-1,3(2H,6H)-dione (VI; Ar=4-amino-2-bromophenyl. $R^{10}$=H) (53).

Freshly prepared nickel boride (5.00 g, 0.039 mol) was added in portions to a solution of 4-(2-Bromo-4-nitrophenyl)-9-hydroxypyrrolo[3,4-c]carbazole-1,3(2H,6H)-dione (VI; Ar=2-bromo-4-nitrophenyl, $R^{10}$=H) (52) (0.50 g, 1.10 mmol) prepared as described in example 77 in methanol (80 mL) and 2N HCl (5.0 mL) at 60° C. After 2 h the mixture was cooled, diluted with water, basified with conc. aqueous ammonia and extracted with ethyl acetate. The extract was worked up to give a solid which was chromatographed on silica. Elution with ethyl acetate gave 4-(4-amino-2-bromophenyl)-9-hydroxypyrrolo[3,4-c]carbazole-1,3(2H,6H)-dione (VI; Ar-4-amino-2-bromophenyl, $R^{10}$=H) (53) in a 0.47, 97% yield which crystallised from ethyl acetate/petroleum ether as a yellow powder, mp 324–326° C. $^1$H NMR δ [(CD$_3$)$_2$SO] 11.71 (br s, 1H), 10.93 (br s, 1H), 9.23 (br s, 1H), 8.30 (d. J=2.4 Hz, 1H), 7.43 (d, J=8.6 Hz, 1H), 7.42 (s, 1H), 7.09–7.03 (m, 2H), 6.89 (d, J=2.1 Hz, 1H), 6.61 (dd, J=8.6, 2.4 Hz, 1H), 5.48 (br s, 2H). Found: C, 56.79; H, 3.26; N, 8.77. $C_{20}H_{12}BrN_3O_3$.1/2EtOAc requires C, 56.67; H, 3.46; N, 9.01.

Representative Procedure for Method 7 of Scheme 2

EXAMPLE 79

The Preparation of 4-(2-Chlorophenyl)-9-methoxy-pyrrolo[3,4-c]carbazole-1,3(2H,6H)-dione (V; Ar=2-chlorophenyl, $R^{10}$=H) (33)

Manganese dioxide (12.0 g) was added to a solution of 4-(2-Chlorophenyl)-9-methoxy-4,5,6,10c-tetrahydropyrrolo[3,4-c]carbazole-1,3(2H,3aH)-dione (IV; Ar=2-chlorophenyl, $R^{10}$=H) (32) prepared as described in example 68 (2.1 g, 5.51 mmol) in dioxane (100 mL) and the mixture was refluxed with stirring for 16 h. The mixture was filtered hot through a plug of Celite, washing through with more dioxane and then 10% methanol/dioxane. The combined filtrate and washings were concentrated to dryness and the residue was adsorbed onto silica and chromatographed. Elution with ethyl acetate/petroleum ether (3:7) gave 4-(2-Chlorophenyl)-9-methoxypyrrolo[3,4-c]carbazole-1,3(2H,6H)-dione (V; Ar=2-chlorophenyl, $R^{10}$=H) (33) in a yield of 1.66 g, 79% which crystallised from THF/petroleum ether as a yellow powder, mp 170–175° C. (dec). $^1$H NMR δ [(CD$_3$)$_2$SO 11.96 (br s, 1H), 11.08 (br s, 1H), 8.46 (d, J=2.6 Hz, 1H), 7.60–7.55 (m, 3H), 7.51–7.42 (m, 3H), 7.24 (dd, J=8.9, 2.6 Hz, 1H), 3.89 (s, 3H). Found: C, 65.64; H, 3.63; N, 7.12. $C_{21}H_{13}ClN_2O_3$.1/2H$_2$O requires C, 65.37; H, 3.66; N, 7.26.

Representative Procedure for Method 8 of Scheme 2

EXAMPLE 80

The Preparation of 4-(2-Chlorophenyl)-9-hydroxy-6-(3-hydroxypropyl)pyrrolo[3,4-c]carbazole-1,3(2H,6H)-dione (VI; Ar=2-chlorophenyl, $R^{10}$=CH$_2$CH$_2$CH$_2$OH) (34)

A solution of 1N BBr$_3$ in CH$_2$Cl$_2$ (11.5 mL, 0.011 mol) was added to a solution of 4-(2-Chlorophenyl)-6-(3-hydroxypropyl)-9-methoxypyrrolo[3,4-c]carbazole-1,3(2H,6H)-dione (V; Ar=2-chlorophenyl, $R^{10}$=CH$_2$CH$_2$CH$_2$OH) (31) prepared as described in example 40 (1.00 g, 2.30 mmol) in CH$_2$Cl$_2$ under nitrogen and the reaction mixture was stirred at room temperature for 3 h. Saturated aqueous NaHCO$_3$ solution was added and the solution was diluted with water and extracted with ethyl acetate. The organic phase was dried, the drying agent was removed and the solution was concentrated to dryness, adsorbed onto silica and chromatographed. Elution with ethyl acetate/petroleum ether (1:1) followed by ethyl acetate gave 4-(2-Chlorophenyl)-9-hydroxy-6-(3-hydroxypropyl)pyrrolo[3,4-c]carbazole-1,3(2H, 6H)-dione (VI; Ar=2-chlorophenyl, $R^{10}$=CH$_2$CH$_2$CH$_2$OH) (34) in a yield of 0.90 g, 93%, which crystallised from THF/petroleum ether as a yellow/orange powder, mp 291–294° C. $^1$H NMR δ [(CD$_3$)$_2$SO 11.05 (br s, 1H), 9.36 (s, 1H), 8.38 (d, J=2.5 Hz, 1H), 7.74 (s, 1H), 7.59–7.54 (m, 2H), 7.52–7.42 (m, 3H), 7.14 (dd, J=8.7, 2.5 Hz, 1H), 4.62 (br t, 1H), 4.49 (t, J=6.8 Hz, 2H), 3.41 (m, 2H), 1.90 (m, 2H). Found: C, 64.99; H, 4.13; N, 6.43. $C_{23}H_{17}ClN_2O_4$.1/4H$_2$O requires C, 64.94; H, 4.15; N, 6.58.

Representative Procedure for Method 9 of Scheme 2

EXAMPLE 81

The Preparation of 4-(2-Chlorophenyl)-9-Hydroxy-pyrrolo[3,4-c]carbazole-1,3(2H,6H)-dione (VI; Ar=2-chlorophenyl, $R^{10}$=H (9)

4-(2-Chlorophenyl)-9-methoxypyrrolo[3,4-c]carbazole-1,3(2H,6H)-dione (V; Ar=2-chlorophenyl, $R^{10}$=H) (33) prepared as described in example 79 (0.512 g, 1.36 mmol) was added to a pyridinium hydrochloride melt at 200° C. and the mixture was stirred at this temperature for 20 min. Water was added and the resultant precipitate was filtered off, washed well with water, adsorbed onto silica and chromatographed. Elution with ethyl acetate/petroleum ether (1:1) gave 4-(2-Chlorophenyl)-9-hydroxypyrrolo[3,4-c]carbazole-1,3(2H,6H)-dione (VI; Ar=2-chlorophenyl, $R^{10}$=H) (9) in a 0.42 g, 85% yield; mp 215–220° C. (dec). $^1$H NMR δ [(CD$_3$)$_2$SO] 11.83 (br s, 1H), 11.01 (br s, 1H), 9.27 (br s, 1H), 8.32 (d, J=2.4 Hz, 1H), 7.65–7.40 m, 5H), 7.08 (dd, J=8.7, 2.4 Hz), 1H). Found: C, 65.72; H, 3.50; N, 6.97. $C_{20}H_{11}ClN_2O_3$.1/4CH$_3$COOCH$_2$CH$_3$ requires C, 65.54; H, 3.40; N, 7.28.

EXAMPLE 82

The Preparation of 6-(2-Hydroxyethyl)-9-methoxy-4-phenylpyrrolo[3,4-c]carbazole-1,3(2H,6H)-dione (V: Ar=phenyl. $R^{10}$=(CH)$_2$OH) (201)

5-methoxy-2-[(E,Z)-2-phenylethenyl]-1H-indole (II; Ar=phenyl) (1.93 g, 7.74 mmol was reacted with 2-(2-bromoethoxy)tetrahydro-2H-pyran using the procedure described in example 38. This material was reacted directly with maleimide (0.79 g) using the procedure described in method 4. The product obtained was reacted using the procedure described in example 70 gave crude material that was then dissolved in methanol (100 mL) to which p-toluenesulfonic acid (30 mg) was added before the solution was warmed to 50° C. for 3h. The solution was then diluted with water and extracted with ethyl acetate. The organic phase was dried, the drying agent was removed and the solution was concentrated to dryness before being adsorbed onto silica and chromatographed eluting with ethyl acetate/hexane (1:2 to 1:1) to give 6-(2-Hydroxyethyl)-9-methoxy-4-phenylpyrrolo[3,4-c]carbazole-1,3(2H,6H)-dione (V;

Ar=phenyl, R¹⁰=(CH₂)₂OH) (201) in a yield of 0.51 g, 17% as a yellow powder; mp 262–264° C. ¹H NMR δ [(CD₃)₂SO] 11.09 (br s, 1H), 8.56 (d, J=2.6 Hz, 1H), 7.83 (s, 1H), 7.66 (m, 3H), 7.47 (m, 3H), 7.28 (dd, J=9.0, 2.6 Hz, 1H), 4.86 (t, J=5.5 Hz, 1H), 4.55 (t, J=5.3 Hz, 2H), 3.90 (s, 3H), 3.78 (m, 2H). Found: C, 71.47; H. 4.77; N, 7.32. $C_{23}H_{18}N_2O_4$ requires: C, 71.49; H, 4.70; N, 7.25.

EXAMPLE 83

The Preparation of 6-(3-Hydroxypropyl)-9-methoxy-4-phenylpyrrolo[3,4-c]carbazole-1,3(2H,6H)-dione (V; Ar=phenyl R¹⁰=(CH₂)₃OH) (202)

5-Methoxy-2-[(E,Z)-2-phenylethenyl]-1H-indole (II; Ar=phenyl) (6.85 g, 27.5 mmol) was reacted with with 3-bromopropyl tert-butyl(dimethyl)silyl ether using the procedure described in example 38. The product isolated was reacted directly with maleimide (5.2 g) using the procedure described in example 68. Aromatisation of the crude Diels-Alder adduct using the procedure described in example 79 gave crude material that was then dissolved in methanol (300 mL) to which 1N hydrochloric acid (50 mL) was added. This solution was stirred at rt for 3h before being diluted with water and extracted with ethyl acetate. The organic layer was dried, the drying agent was removed and the solution was concentrated to dryness. The residue was adsorbed onto silica and chromatographed eluting with dichloromethane to ethyl acetate/dichloromethane (7:3). Trituration with diethyl ether gave alcohol (202) as a yellow powder (2.55 g, 23%), mp 241–243° C. ¹H NMR δ [(CD₃)₂SO] 11.10 (br s, 1H), 8.56 (d, J=2.6 Hz, 1H), 7.82 (s, 1H), 7.67 (m, 3H), 7.47 (m, 3H), 7.30 (dd. J=9.0, 2.6 Hz, 1H), 4.66 (t, J=4.9 Hz, 1H), 4.55 (t, J=6.9 Hz, 2H), 3.90 (s, 3H), 3.39 (m. 2H), 1.93 (m, 2H). Found: C, 71.95; H, 5.09; N, 6.93. $C_{24}H_{20}N_2O_4$ requires: C, 71.99; H. 5.03; N. 6.99.

EXAMPLE 84

The Preparation of 6-(6-Hydroxyhexyl)-9-methoxy-4-phenylpyrrolo[3,4-c]carbazole-1,3(2H,6H)-dione (V; Ar=phenyl. R¹⁰=(CH₂)₆OH) (203)

Alkylation of 5-methoxy-2-[(E,Z)-2-phenylethenyl]-1H-indole (II; Ar=phenyl) (0.30 g, 0.71 mmol)) with 6-bromohexyl-tert-butyl(dimethyl)silyl ether according to procedure described in example 38 gave crude material that was reacted directly with maleimide (0.14 g) following Method 4a.

Aromatisation of the crude Diels-Alder adduct using the procedure described in example 79 gave crude material that was then dissolved in methanol (100 mL) to which 1N hydrochloric acid (15 mL) was added. This solution was stirred at rt for 2h before being diluted with water and extracted with ethyl acetate. The organic layer was dried, the drying agent was removed and the solution was concentrated to dryness. Chromatography on silica eluting with dichloromethane to ethyl acetate/hexane (4:1) followed by trituration with diethyl ether gave alcohol (203) as a yellow powder (0.31 g, 98%), mp 170–173° C. ¹H NMR δ [(CD₃)₂SO] 11.10 (br s, 1H), 8.56 (d, J=2.6 Hz, 1H), 7.82 (s, 1H), 7.67 (m, 3H), 7.47 (m, 3H), 7.29 (dd, J=8.9, 2.6 Hz, 1H), 4.50 (t, J=7.0 Hz, 2H), 4.28 (t, J=5.1 Hz, 1H), 3.90 (s, 3H), 3.32 (t, J=6.4 Hz, 2H), 1.76 (m, 2H), 1.36–1.26 (m, 6H). Found: C, 73.57; H, 6.17; N, 6.39. $C_{27}H_{26}N_2O_4$ requires: C, 73.28; H, 5.92; N, 6.33.

EXAMPLE 85

The Preparation of 4-(2,6-Dichlorophenyl)-6-(2-hydroxyethyl)-9-methoxypyrrolo[3,4-c]carbazole-1,3(2H,6H)-dione (V; Ar=2,6-dichlorophenyl R¹⁰=(CH₂)₂OH) (230)

Alkylation of pure trans-diene (512) (3.0 g, 10.6 mmol) prepared as described in example 103 with 2-(2-bromoethoxy)tetrahydro-2H-pyran according to the procedure described in example 38 gave crude material that was dissolved in methanol/tetrahydrofuran (4:1, 250 mL) to which 2N hydrochloric acid (20 mL) was added before the solution was stirred at room temperature for 2h. The solution was then diluted with saturated sodium bicarbonate and concentrated under reduced pressure to precipitate the crude product which was collected by filtration and dried in vacuo. This solid was reacted directly with maleimide (1.26 g) following The procedure described in example 68. Aromatisation of the chromatographed Diels-Alder adduct using the procedure described in example 70 gave material that was then triturated from methanol to give alcohol (230) as a yellow powder (2.14 g, 44%), mp 229–231° C. ¹H NMR δ [(CD₃)₂SO] 11.17 (br s, 1H), 8.50 (d, J=2.6 Hz, 1H), 7.86 (s, 1H), 7.72 (d, J=9.0 Hz, 1H), 7.62 (m, 2H), 7.51 (dd, J=8.9, 7.4 Hz, 1H), 7.31 (dd, J=9.0, 2.6 Hz, 1H), 4.83 (t, J=5.3 Hz, 1H), 4.54 (t, J=5.2 Hz, 2H), 3.91 (s, 3H), 3.77 (m, 2H). Found: C, 60.61; H, 3.85; N, 5.88. $C_{23}H_{16}Cl_2N_2O_4$ requires: C, 60.66; H, 3.54; N, 6.15.

EXAMPLE 86

The Preparation of 4-(2,6-Dichlorophenyl)-6-(3-hydroxypropyl)-9-methoxypyrrolo[3,4-c]carbazole-1,3(2H,6H)-dione (V; Ar=2,6-dichlorophenyl, R¹⁰=(CH₂)₃OH) (232)

Alkylation of diene (512) (3.0 g, 9.43 mmol) prepared as described in example 103 with 3-bromopropyl tert-butyl (dimethyl)silyl ether according to the procedure described in example 38 gave crude material that was dissolved in methanol/dichloromethane (3:1, 300 mL) to which 1N hydrochloric acid (60 mL) was added. This solution was stirred at rt for 2h before being diluted with saturated sodium bicarbonate and concentrated under reduced pressure to precipitate the crude product which was collected by filtration and dried in vacuo. This solid was reacted with maleimide (1.20 g) following The procedure described in example 68. Aromatisation of the crude Diels-Alder adduct using the procedure described in example 70 gave material that was then chromatographed on silica eluting with methanol/dichloromethane (2:98 to 5:95) to give alcohol (232) (2.4 g, 54%) as a yellow powder, mp 254–256° C. ¹H NMR δ [(CD₃)₂SO] 11.18 (br s, 1H), 8.51 (d, J=2.6 Hz, 1H), 7.86 (s, 1H), 7.72 (d, J=9.0 Hz, 1H), 7.63 (m, 2H), 7.51 (dd, J=8.8, 7.4 Hz, 1H), 7.34 (dd, J=9.0, 2.6 Hz, 1H), 4.62 (t, J=5.0 Hz, 1H), 4.54 (t, J=6.9 Hz, 2H), 3.91 (s, 3H), 3.42 (m, 2H), 1.90 (m, 2H). FABMS found M⁺: 468.0630, 470.0628, 472.0626. $C_{24}H_{18}Cl_2N_2O_4$ requires 468.0644, 470.0614, 472.0585.

EXAMPLE 87

The Preparation of 4-(4-(2-Chlorophenyl)-9-methoxy-1,3-dioxo-2,3-dihydropyrrolo[3,4-c]carbazol-6(1H)-yl)butanoic acid (V; Ar=2-chlorophenyl, $R^{10}$=(CH$_2$)$_3$COOH) (262)

Alkylation of diene (27) (0.40 g, 1.41 mmol) prepared as described in example 37 with ethyl bromobutyrate according to the procedure described in example 38 gave crude material that was reacted with maleimide (0.27 g) following the procedure described in example 68. Aromatisation of the Diels-Alder adduct using the procedure described in example 70 gave crude material that was then dissolved in methanol (100 mL) to which 2N potassium hydroxide (2 mL) was added. This solution was stirred at rt for 2h before being diluted with water and acidified by the addition of 1N hydrochloric acid to precipitate the product as a yellow solid, which was collected by filtration and washed with water before being dried in vacuo. Chromatography on silica eluting with ethyl acetate followed by trituration with diethyl ether/hexane, gave acid (262) as a yellow powder (0.10 g, 16%), mp 251–254° C. $^1$H NMR δ [(CD$_3$)$_2$SO] 12.12 (br s, 1H), 11.12 (br s, 1H), 8.53 (d, J=2.6 Hz, 1H), 7.85 (s, 1H), 7.72 (d, J=9.0 Hz, 1H), 7.58 (m, 1H), 7.53–7.45 (m, 3H), 7.32 (dd, J=9.0, 2.6 Hz, 1H), 4.50 (t, J=7.3 Hz, 2H), 3.91 (s, 3H), 2.30 (m, 2H), 1.97 (m, 2H). FABMS found [M+H]$^+$: 463.1025, 465.1034. C$_{25}$H$_{19}$ClN$_2$O$_5$ requires 463.1061, 465.1031.

EXAMPLE 88

The Preparation of 4-(4-(2-Chlorophenyl)-9-hydroxy-1,3-dioxo-2,3-dihydropyrrolo[3,4-c]carbazol-6(1H)-yl)butanoic acid (VI; Ar=2-chlorophenyl, $R^{10}$=(CH$_2$)$_3$COOH) (263)

Demethylation of acid (262) (32 mg, 0.07 mmol) prepared as described in example 87 employing the procedure described in example 80 gave phenol (263) (6 mg, 19%) as an orange powder, mp 274–277° C. $^1$H NMR δ [(CD$_3$)$_2$SO] 12 (v br s, 1H), 11.06 (br s, 1H), 9.38 (br s, 1H), 8.38 (d, J=2.4 Hz, 1H), 7.80 (s, 1H), 7.60 (d, J=8.9 Hz, 1H), 7.58 (m, 1H), 7.52–7.43 (m, 3H), 7.14 (dd, J=8.9, 2.4 Hz, 1H), 4.45 (t, J=7.5 Hz, 2H), 2.27 (m, 2H), 1.95 (m, 2H). FABMS found [M+H]$^+$: 449.0874, 451.0879. C$_{24}$H$_{17}$ClN$_2$O$_5$ requires 449.0904, 451.0875.

EXAMPLE 89

The Preparation of 9-Hydroxy-6-(2-Hydroxyethyl)-4-phenylpyrrolo[3,4-c]carbazole-1,3(2H,6H)-dione (VI; Ar=phenyl, $R^{10}$=(CH$_2$)$_2$OH) (220)

Demethylation of alcohol (201) (135 mg, 0.35 mmol) prepared as described in example 82 employing The procedure described in example 81 gave alcohol (220) (90 mg, 69%) as an orange powder, mp 298–301° C. $^1$H NMR δ [(CD$_3$)$_2$SO] 11.04 (br s, 1H), 9.31 (br s, 1H), 8.40 (d, J=2.5 Hz, 1H), 7.79 (s, 1H), 7.64 (m, 2H), 7.55 (d, J=8.8 Hz, 1H), 7.47 (m, 3H), 7.10 (dd, J=8.8, 2.5 Hz, 1H), 4.85 (t, J=5.3 Hz, 1H), 4.51 (t, J=5.4 Hz, 2H), 3.77 (m. 2H). Found: C, 68.88; H, 4.43; N, 6.76. C$_{22}$H$_{16}$N$_2$O$_4$.3/4H$_2$O requires: C, 68.48; H, 4.57; N, 7.26.

EXAMPLE 90

The Preparation of 9-Hydroxy-6-(3-hydroxypropyl)-4-phenylpyrrolo[3,4-c]carbazole-1,3(2H,6H)-dione (VI; Ar=phenyl, $R^{10}$=(CH$_2$)$_3$OH)(221)

Demethylation of alcohol (202) prepared as described in example 83 (60 mg, 0.15 mmol) employing the procedure described in example 80 gave alcohol (221) (45 mg, 78%) as an orange powder, mp 274–276° C. $^1$H NMR δ [(CD$_3$)$_2$SO] 11.05 (br s, 1H), 9.33 (s, 1H), 8.41 (d, J=2.4 Hz, 1H), 7.77 (s, 1H), 7.64 (m, 2H), 7.56 (d, J=8.8 Hz, 1H), 7.46 (m, 3H), 7.12 (dd, J=8.8, 2.4 Hz, 1H), 4.64 (t, J=4.9 Hz, 1H), 4.51 (t, J=6.9 Hz, 2H), 3.39 (m, 2H), 1.92 (m, 2H). Found: C, 71.59; H, 4.74; N, 7.57. C$_{23}$H$_{18}$N$_2$O$_4$ requires: C, 71.49; H, 4.70; N, 7.25.

EXAMPLE 91

The Preparation of 9-Hydroxy-6-(6-hydroxyhexyl)-4-phenylpyrrolo[3,4-c]carbazole-1,3(2H,6H)-dione (VI; Ar=phenyl, $R^{10}$=(CH$_2$)$_6$OH) (222)

Demethylation of alcohol (203) prepared as described in example 84 (55 mg, 0.12 mmol) employing the procedure described in example 80 gave alcohol (222) (12 mg, 23%) as an orange powder, mp 132–140° C. $^1$H NMR δ [(CD$_3$)$_2$SO] 11.04 (br s, 1H), 9.33 (s, 1H), 8.41 (d, J=2.5 Hz, 1H), 7.77 (s, 1H), 7.64 (m, 2H), 7.54 (d, J=8.8 Hz, 1H), 7.46 (m, 3H), 7.12 (dd, J=8.8, 2.5 Hz, 1H), 4.46 (t, J=7.1 Hz, 2H), 4.29 (t, J=5.1 Hz, 1H), 3.31 (m, 2H), 1.75 (m, 2H), 1.36–1.26 (m, 6H). FABMS found M$^+$: 428.1730. C$_{26}$H$_{14}$N$_2$O$_4$ requires 428.1736.

EXAMPLE 92

The Preparation of 9-Methoxy-6-methyl-4-phenylpyrrolo[3,4-c]carbazole-1,3(2H,6H)-dione (V; Ar=phenyl, $R^{10}$=CH$_3$) (223)

Alkylation of pure trans 5-methoxy-2-[(E)-2-phenylethenyl]-1H-indole (II; Ar=phenyl) (0.20 g, 0.80 mmol) with methyl iodide according to the procedure described in example 38 gave crude material that was reacted with maleimide (92 mg) following Method 4a, except that the reaction time was 24 h. Aromatisation of the crude Diels-Alder adduct using the procedure described in example 79 gave crude material that was chromatographed on silica eluting with ethyl acetate/dichloromethane (1:3). Trituration from methanol gave carbazole (223) (0.20 g, 70%) as a yellow powder, mp 286–291° C. $^1$H NMR δ [(CD$_3$)$_2$SO] 11.11 (br s, 1H), 8.53 (d, J=2.6 Hz, 1H), 7.80 (s, 1H), 7.66 (m, 3H), 7.47 (m, 3H), 7.30 (dd, J=9.0, 2.6 Hz, 1H), 3.96 (s, 3H), 3.90 (s, 3H). Found: C, 74.29; H, 4.67; N, 7.86. C$_{22}$H$_{16}$N$_2$O$_3$ requires: C, 74.15; H, 4.53; N, 7.86.

EXAMPLE 93

The Preparation of 9-Hydroxy-6-methyl-4-phenylpyrrolo[3,4-c]carbazole-1,3(2H,6H)-dione (VI; Ar=phenyl, $R^{10}$=CH$_3$) (224)

Demethylation of alcohol (223) prepared as described in example 92 (180 mg, 0.51 mmol) employing the procedure described in example 81, was followed by chromatography on silica eluting with ethyl acetate/dichloromethane (1:2). Trituration from dichloromethane/hexane gave alcohol (224) (155 mg, 90%) as an orange powder, mp 297–300° C. $^1$H NMR δ [(CD$_3$)$_2$SO] 11.05 (br s, 1H), 9.34 (s, 1H), 8.39 (d, J=2.5 Hz, 1H), 7.76 (s, 1H), 7.65 (m, 2H), 7.54 (d, J=8.8 Hz, 1H), 7.46 (m, 3H), 7.13 (dd, J=8.8, 2.5 Hz, 1H), 3.93 (s, 3H). Found: C, 69.96; H, 4.58; N, 7.70. C$_2$H$_{14}$N$_2$O$_3$.H$_2$O requires: C, 69.99; H, 4.48; N, 7.77.

EXAMPLE 94

The Preparation of 4-(2,6-Dichlorophenyl)-9-Hydroxy-6-(2-hydroxyethyl)pyrrolo[3,4-c]carbazole-1,3(2H,6H)-dione (VI; Ar=2,6-dichlorophenyl. R$^{10}$=(CH$_2$)$_2$OH) (234)

Demethylation of alcohol (230) (0.10 g, 0.22 mmol) prepared as described in example 85 employing the procedure described in example 80 gave phenol (234) (49 mg, 50%) as an orange/yellow powder, mp 254–257° C. $^1$H NMR δ [(CD$_3$)$_2$SO] 11.10 (br s, 1H), 9.35 (s, 1H), 8.36 (d, J=2.4 Hz, 1H), 7.80 (s, 1H), 7.61 (m, 3H), 7.50 (dd, J=8.7, 7.3 Hz, 1H), 7.13 (dd, J=8.8, 2.4 Hz, 1H), 4.82 (t, J=5.5 Hz, 1H), 4.49 (t, J=5.2 Hz, 2H), 3.75 (m, 2H). Found: C, 58.76; H, 3.34; N, 6.25. C$_{22}$H$_{14}$C$_{12}$N O$_4$.1/2H$_2$O requires: C, 58.67; H, 3.36; N, 6.22.

EXAMPLE 95

The Preparation of 4-(2,6-Dichlorophenyl)-9-hydroxy-6-(3-hydroxypropyl)pyrrolo[3,4-c]carbazole-1,3(2H,6H)-dione (VI; Ar=2,6-dichlorophenyl, R$^{10}$=(CH$_2$)$_2$OH) (235)

Demethylation of alcohol (232) (0.36 g, 0.77 mmol) prepared as described in example 86 employing the procedure described in example 80 gave phenol (235) (0.32 g, 92%) as an orange/yellow powder, mp 215–218° C. $^1$H NMR δ [(CD$_3$)$_2$SO] 11.12 (br s, 1H), 9.39 (s, 1H), 8.37 (d, J=2.5 Hz, 1H), 7.80 (s, 1H), 7.61 (m, 3H), 7.51 (dd, J=8.7, 7.2 Hz, 1H), 7.16 (dd. J=8.8, 2.5 Hz, 1H), 4.61 (t, J=5.0 Hz, 1H), 4.49 (t, J=6.9 Hz, 2H), 3.42 (m, 2H), 1.88 (m, 2H). Found: C, 60.36; H, 3.47; N, 6.08. C$_{23}$H$_{16}$Cl$_2$N$_2$O$_4$ requires: C, 60.66; H, 3.54: N, 6.15.

EXAMPLE 96

The Preparation of 3-{2-[(E)-2-(2-Chlorophenyl) ethenyl]-5-methoxy-1H-indol-1-yl}propanenitrile (III; Ar=2-chlorophenyl. R$^{10}$=CH$_2$CH$_2$CN) (236)

To a solution of trans-diene (27) prepared as described in example 37 (1.5 g, 5.25 mmol) in acetonitrile (30 mL) was added acrylonitrile (2.42 mL, 36.8 mmol) and 1,8-diazabicyclo[5,4,0]undec-7-ene (20 drops). The resulting solution was stirred at room temperature under nitrogen for 18 h before being diluted with water and extracted with ethyl acetate. The organic layer was dried, the drying agent was removed and the solution was concentrated to dryness. Chromatography on silica eluting with ethyl acetate/hexane (1:1), followed by trituration from methanol gave the diene (236) (1.36 g, 77%) as an off-white solid, mp 136–138° C. $^1$H NMR δ [(CD$_3$)$_2$SO] 8.05 (dd, J=7.9, 1.5 Hz, 1H), 7.50 (m, 4H), 7.41 (m, 1H), 7.33 (m, 1H), 7.04 (d, J=2.4 Hz, 1H), 6.90 (s, 1H), 6.81 (dd, J=9.0, 2.4 Hz, 1H), 4.68 (t, J=6.6 Hz, 2H), 3.77 (s, 3H), 2.93 (t, J=6.6 Hz, 2H). Found: C, 71.32; H, 5.14; N, 8.51. C$_{20}$H$_{17}$ClN$_2$O requires: C, 71.31; H, 5.09; N, 8.31.

EXAMPLE 97

The Preparation of 3-(4-(2-Chlorophenyl)-9-methoxy-1,3-dioxo-2,3-dihydropyrrolo[3,4-c]carbazol-6 (1H)-yl)propanenitrile (V: Ar=2-chlorophenyl R$^{10}$=CH$_2$CH$_2$CN) (237)

Diene (236) (1.30 g, 3.86 mmol) prepared as described in example 96 was reacted with maleimide (0.49 g) following The procedure described in example 68 and then aromatized according to the procedure described in example 70 to give crude material that was chromatographed on silica eluting with ethyl acetate/hexane (1:1). Trituration from methanol gave nitrile (237) (1.33 g, 80%) as a yellow powder, mp 287–288° C. $^1$H NMR δ [(CD$_3$)$_2$SO] 11.16 (br s, 1H), 8.53 (d, J=2.6 Hz, 1H), 8.02 (s, 1H), 7.83 (d, J=9.0 Hz, 1H), 7.59 (m, 1H), 7.49 (m, 3H), 7.33 (dd, J=9.0, 2.6 Hz, 1H), 4.86 (t, J=6.7 Hz, 2H), 3.91 (s, 3H), 3.04 (t, J=6.7 Hz, 2H). Found: C, 65.32; H, 4.15; N, 9.60. C$_{24}$H$_{16}$ClN$_3$O$_3$.3/4H$_2$O requires: C, 65.01; H, 3.98; N, 9.47.

EXAMPLE 98

The Preparation of 3-(4-(2-Chlorophenyl)-9-Hydroxy-1,3-dioxo-2,3-dihydropyrrolo[3,4-c]carbazol-6 (1H)-yl)propanenitrile (VI; Ar=2-chlorophenyl. R$^{10}$=CH$_2$CH$_2$CN) (238)

Demethylation of nitrile (237) (0.15 g, 0.35 mmol) prepared as described in example 97 employing The procedure described in example 80, followed by trituration from methanol, gave phenol (238) (0.13 g, 89%) as an orange/yellow powder, mp 332–336° C. $^1$H NMR δ [(CD$_3$)$_2$SO] 11.10 (br s, 1H), 9.42 (br s, 1H), 8.39 (d, J=2.4 Hz, 1H), 7.96 (s, 1H), 7.69 (d, J=8.8 Hz, 1H), 7.58 (m, 1H), 7.48 (m, 3H), 7.15 (dd, J=8.8, 2.4 Hz, 1H), 4.82 (t, J=6.7 Hz, 2H), 3.02 (t, J=6.7 Hz, 2H). Found: C, 66.24; H, 3.66; N, 9.93. C$_{23}$H$_{14}$ClN$_3$O$_3$ requires: C, 66.43; H, 3.39; N, 10.10.

EXAMPLE 99

The Preparation of 6-Benzyl-4-(2-chlorophenyl)-9-methoxypyrrolo[3,4-c]carbazole-1,3(2H,6H)-dione (V; Ar=2-chlorophenyl, R$^{10}$=CH$_2$Ph) (239)

Alkylation of pure trans-diene (27) (0.20 g, 0.70 mmol) prepared as described in example 37 with benzyl bromide according to the procedure described in example 38 gave crude material that was reacted directly with maleimide (103 mg) following the procedure described in example 68, except that the reaction time was 24 h. Aromatisation of the crude Diels-Alder adduct using the procedure described in example 70 gave crude material that was chromatographed on silica eluting with ethyl acetate/hexane (1:2). Trituration from ethyl acetate/hexane gave carbazole (239) (0.15 g, 46%) as a yellow powder, mp 234–237° C. $^1$H NMR δ [(CD$_3$)$_2$SO] 11.15 (br s, 1H), 8.55 (d, J=2.6 Hz, 1H), 7.91 (s, 1H), 7.69 (d, J=9.0 Hz, 1H), 7.56 (m, 1H), 7.46 (m, 3H), 7.25 (m, 4H), 7.16 (m, 2H), 5.79 (s, 2H), 3.90 (s, 3H). Found: C, 71.78; H, 4.39; N, 6.18. C$_{28}$H$_{19}$ClN$_2$O$_3$ requires: C, 72.02; H, 4.10; N, 6.00.

EXAMPLE 100

The Preparation of 6-Benzyl-4-(2-chlorophenyl)-9-hydroxypyrrolo[3,4-c]carbazole-1,3(2H,6H)-dione (VI; Ar=2-chlorophenyl, $R^{10}$=CH$_2$Ph) (240)

Demethylation of carbazole (239) (0.10 g, 0.21 mmol) prepared as described in example 99 employing the procedure described in example 80, followed by chromatography on silica eluting with ethyl acetate/hexane (1:2) and trituration from ethyl acetate/hexane, gave carbazole (240) (87 mg, 91%) as an orange/yellow powder, mp 269–271° C. $^1$H NMR δ [(CD$_3$)$_2$SO] 11.09 (br s, 1H), 9.40 (s, 1H), 8.40 (d, J=2.5 Hz, 1H), 7.86 (s, 1H), 7.56 (m, 2H), 7.45 (m, 3H), 7.25 (m, 3H), 7.16 (m, 2H), 7.11 (dd, J=8.9, 2.5 Hz, 1H), 5.75 (s, 2H). Found: C, 72.06; H, 4.18; N, 6.20. C$_{27}$H$_{17}$ClN$_2$O$_3$ requires: C, 71.60; H, 3.78; N, 6.18.

EXAMPLE 101

The Preparation of Methyl 3-(4-(2-chlorophenyl)-9-hydroxy-1,3-dioxo-2,3-dihydropyrrolo[3,4-c]carbazol-6 (1H)-yl)propanoate (VI, Ar=2-chlorophenyl, $R^{10}$=(CH$_2$COOCH$_3$) (264)

Gaseous hydrochloric acid was bubbled through a stirred solution of acid (117) (35 mg, 0.08 mmol) prepared as described in example 230 in methanol (10 mL) for 30 seconds. The resulting solution was stirred for 30 minutes at room temperature before being diluted with water and extracted with ethyl acetate. The organic layer was dried, the drying agent was removed and the solution was concentrated to dryness. Chromatography on silica eluting with ethyl acetate/hexane (1:1) followed by crystallisation from ethyl acetate/hexane gave ester (264) (25 mg, 70%) as an orange powder, mp 218–220° C. $^1$H NMR δ [(CD$_3$)$_2$SO] 11.07 (br s, 1H), 9.39 (br s, 1H), 8.38 (d, J=2.5 Hz, 1H), 7.79 (s, 1H), 7.57 (m, 2H), 7.51–7.44 (m, 3H), 7.14 (dd, J=8.8, 2.5 Hz, 1H), 4.71 (t, J=6.8 Hz, 2H), 3.48 (s, 3H), 2.83 (t, J=6.8 Hz, 2H). Found: C, 62.18; H, 4.04; N, 5.99. C$_{24}$H$_{17}$ClN$_2$O$_5$.3/4H$_2$O requires: C, 62.34; H, 4.03; N, 6.06.

Representative Procedure for Method 10a of Scheme 2

EXAMPLE 102

The Preparation of (2,6-Dichlorobenzyl)(triphenyl)phosphonium bromide (511)

A mixture of 2,6-dichlorotoluene (20.1 g, 0.125 mol), N-bromosuccinimide (24.6 g, 0.138 mol) and 2,2'-azobisisobutyronitrile (0.41 g, 2.50 mmol) in dry benzene (300 mL) under N$_2$ was stirred at reflux for 6 h with continuous irradiation from a 100W lamp. The resulting reaction mixture was concentrated under vacuum (to 50 mL), cooled and filtered, washing with dry benzene. The filtrate (containing the crude benzyl bromide) was treated directly with triphenylphosphine (49.3 g, 0.188 mol), stirring at reflux for 17 h. After cooling, the precipitate was collected by filtration, washing thoroughly with dry benzene, then pentane, and dried under vacuum at 50° C. to give the phosphonium salt (511) as a cream powder (62.1 g, 99%), mp (benzene) 247–250° C. $^1$H NMR (CDCl$_3$) δ 7.76 (m, 9H), 7.64 (m, 6H), 7.18 (s, 3H), 5.50 (d, J=14.3 Hz, 2H). Found: C, 60.03; H, 3.76. C$_{25}$H$_{21}$BrCl$_2$P requires C, 59.79; H, 4.01.

EXAMPLE 103

The Preparation of 2-[(E)-2-(2,6-Dichlorophenyl) ethenyl]-5-methoxy-1H-indole (512) (II, Ar=2,6-dichlorophenyl)

The 5-methoxy-1H-indole-2-carbaldehyde (O) was reacted with (2,6-dichlorobenzyl)(triphenyl)phosphonium bromide (511) prepared as described in example 102 using the procedure described in example 37, except that the LDA and aldehyde were (sequentially) added at 0° C., the ratio of LDA aldehyde was 1.37:1 and the reaction time was 5 h, to give (after crystallisation from CH$_2$Cl$_2$/hexane) the diene (512) as a yellow solid (the pure E isomer) (97%), mp 144–147° C. $^1$H NMR (CDCl$_3$) δ 8.20 (br s, 1H), 7.36 (d, J=8.1 Hz, 1H), 7.27 (m, 1H), 7.25 (d, J=16.8 Hz, 1H), 7.11 (t, J=8.0 Hz, 1H), 7.03 (d, J=2.4 Hz, 1H), 6.93 (d, J=16.8 Hz, 1H), 6.88 (dd, J=8.7, 2.5 Hz, 1H), 6.61 (d, J=1.8 Hz, 1H), 3.86 (s, 3H). Found: C, 64.04; H, 4.13; N, 4.39. C$_{17}$H$_{13}$Cl$_2$NO requires C, 64.17; H, 4.12; N, 4.40.

EXAMPLE 104

The Preparation of 4-(2,6-Dichlorophenyl)-9-methoxy-4,5,6,10c-tetrahydropyrrolo[3,4-c]carbazole-1,3 (2H,3aH)-dione (513) (IV, $R^{10}$=H. Ar=2,6-dichlorophenyl)

The pure E diene (512) prepared as described in example 103 was reacted with maleimide according to the procedure described in example 68 in a foil-covered sealed vial, except that the ratio of diene:maleimide:SnCl$_2$ was 1:4:0.075 and the reaction time was 3 h, to give a crude solid containing the adduct (513), which was used without further purification.

EXAMPLE 105

The Preparation of 4-(2,6-Dichlorophenyl)-9-methoxypyrrolo[3,4-c]carbazole-1,3(2H,6H)-dione (514) (V, $R^{10}$=H, Ar=2,6-dichlorophenyl)

The crude adduct (513) prepared as described in example 104 was aromatised with DDQ (5 equiv.) using the procedure described in example 70, except that the solvent was 1:1 toluene/dioxane and the reaction time was 48 h, to give (after crystallisation from MeOH/CH$_2$Cl$_2$/hexane) the product (514) (78%) as a yellow crystalline solid, mp 299–301° C. $^1$H NMR [(CD$_3$)$_2$SO] δ 12.02 (br s, 1H), 11.15 (br s, 1H), 8.45 (d, J=2.6 Hz, 1H), 7.61 (d, J=7.7 Hz, 2H), 7.61 (s, 1H), 7.59 (d, J=8.9 Hz, 1H), 7.50 (dd, J=8.8, 7.4 Hz, 1H), 7.26 (dd. J=8.9, 2.7 Hz, 1H), 3.90 (s, 3H). Found: C, 61.26; H, 2.92; N, 6.65. C$_{21}$H$_{12}$C$_{12}$N$_2$O$_3$ requires C, 61.33; H, 2.94; N, 6.81.

EXAMPLE 106

The Preparation of 4-(2,6-Dichlorophenyl)-9-hydroxypyrrolo[3,4-c]carbazole-1,3(2H,6H)-dione (515) (V$^1$, $R^{10}$=H, Ar=2,6-dichlorophenyl)

The methyl ether (514) prepared as described in example 105 was demethylated with BBr$_3$ using the procedure described in example 80 to give (after crystallisation from MeOH/CH$_2$Cl$_2$/hexane) the phenol (515) (98%) as an orange solid, mp 205–215° C. (dec). $^1$H NMR [(CD$_3$)$_2$SO] δ 11.89 (br s, 1H), 11.08 (br s, 1H), 9.32 (br s, 1H), 8.30 (d, J=2.4 Hz, 1H), 7.61 (d, J=7.9 Hz, 2H), 7.55 (s, 1H), 7.50 (dd, J=8.7, 7.4 Hz, 1H), 7.47 (d, J=8.7 Hz, 1H), 7.10 (dd, J=8.7, 2.4 Hz, 1H). Found: C, 58.98; H, 2.99; N, 6.68. $C_{20}H_{10}Cl_2N_2O_3$.1/2$H_2O$ requires C, 59.13; H, 2.73; N, 6.90.

EXAMPLE 107

(2,6-Dibromobenzyl)(triphenyl)phosphonium bromide (516)

Bromination of 2,6-dibromotoluene with NBS/AIBN, followed by reaction of the crude bromide with triphenylphosphine, using the procedure described in example 102, except that the reaction time for the bromination was 3 h, gave the phosphonium salt (516) (95%) as a cream powder, mp ($CH_2Cl_2$/benzene) 241–243° C. $^1$H NMR (CDCl$_3$) δ 7.78 (m, 9H), 7.64 (m, 6H), 7.40 (br d, J=7.9 Hz, 2H), 6.99 (td, J=8.0, 2.5 Hz, 1H), 5.58 (d, J=14.1 Hz, 2H). Found: C, 47.06; H, 3.37. $C_{25}H_{20}Br_3P$.3/4 $CH_2Cl_2$ requires C, 47.23; H, 3.31.

EXAMPLE 108

The Preparation of 2-[(E)-2-(2,6-Dibromophenyl)ethenyl]-5-methoxy-1H-indole (517) (II, Ar=2,6-dibromophenyl)

The 5-methoxy-1H-indole-2-carbaldehyde (1) was reacted with (2,6-dibromobenzyl)(triphenyl)phosphonium bromide (516) prepared as described in example 107 using the procedure described in example 37, except that the ratio of LDA:aldehyde was 1.37:1 and the reaction time was 5 h, to give (after crystallisation from $CH_2Cl_2$/hexane) the diene (517) as a yellow solid (the pure E isomer) (80%), mp 140–141° C. $^1$H NMR (CDCl$_3$) δ 8.20 (br s, 1H), 7.60 (d, J=8.1 Hz, 1H), 7.27 (d, J=8.2 Hz, 1H), 7.05 (br s, 1H), 7.03 (d, J=16.7 Hz, 1H), 6.96 (t, J=8.0 Hz, 1H), 6.88 (dd, J=8.7, 2.5 Hz, 1H), 6.82 (d, J=16.7 Hz, 1H), 6.61 (d, J=1.9 Hz, 1H), 3.86 (s, 3H). Found: C, 50.37; H, 3.24; N, 3.37. $C_{17}H_{13}Br_2NO$ requires C, 50.16; H, 3.22; N, 3.44.

EXAMPLE 109

The Preparation of 4-(2,6-Dibromophenyl)-9-methoxy-4,5,6,10c-tetrahydropyrrolo[3,4-c]carbazole-1,3(2H,3aH)-dione (518) (IV, R$^{10}$=H. Ar=2,6-dibromophenyl)

The pure E diene (517) prepared as described in example 108 was reacted with maleimide according to the procedure described in example 68 in a foil-covered sealed vial, except that the ratio of diene:maleimide:SnCl$_2$ was 1:5:0.075 and the reaction time was 3.5 h, to give a crude solid containing the adduct (518), which was used without further purification.

EXAMPLE 110

The Preparation of 4-(2,6-Dibromophenyl)-9-methoxypyrrolo[3,4-c]carbazole-1,3(2H,6H)-dione (519) (V, R$^{10}$=H, Ar=2,6-dibromophenyl)

The crude adduct (518) prepared as described in example 109 was aromatised with DDQ (5 equiv.) using the procedure described in example 70, except that the solvent was 1:1 toluene/dioxane and the reaction time was 24 h, to give (after crystallisation from MeOH/$CH_2Cl_2$/hexane) the product (519) (68%) as an orange crystalline solid, mp 329–331° C. $^1$H NMR [(CD$_3$)$_2$SO] δ 12.02 (br s, 1H), 11.13 (br s, 1H), 8.45 (d, J=2.6 Hz, 1H), 7.80 (d, J=8.1 Hz, 2H), 7.59 (d, J=8.3 Hz, 1H), 7.54 (s, 1H), 7.33 (t, J=8.0 Hz, 1H), 7.26 (dd, J=8.8, 2.6 Hz, 1H), 3.90 (s, 3H). Found: C, 50.29; H, 2.32; N, 5.69. $C_{21}H_{12}Br_2N_2O_3$ requires C, 50.43; H, 2.42; N, 5.60.

EXAMPLE 111

The Preparation of 4-(2,6-Dibromophenyl)-9-Hydroxypyrrolo[3,4-c]carbazole-1,3(2H,6H)-dione (520) (VI, R$^{10}$=H, Ar=2,6-dibromophenyl)

The methyl ether (519) prepared as described in example 110 was demethylated with BBr$_3$ using the procedure described in example 80, except that the reaction time was 1.5 h, to give (after crystallisation from MeOH/$CH_2Cl_2$/EtOAc/hexane) the phenol (520) (98%) as a yellow-orange solid, mp 180–190° C. (dec). $^1$H NMR [(CD$_3$)$_2$SO] δ 11.90 (br s, 1H), 11.08 (br s, 1H), 9.35 (br s, 1H), 8.30 (d. J=2.3 Hz, 1H), 7.80 (d, J=8.1 Hz, 2H), 7.49 (s, 1H), 7.48 (d, J=8.9 Hz, 1H), 7.33 (t, J=8.1 Hz, 1H), 7.11 (dd, J=8.7, 2.5 Hz, 1H). Found: C, 49.13; H, 2.29; N, 6.05. $C_{20}H_{10}Br_2N_2O_3$ requires C, 49.42; H, 2.07; N, 5.76.

Representative Procedure for Method 10b of Scheme 2

EXAMPLE 112

The Preparation of (2,6-Dichloro-4-methoxybenzyl)(triphenyl)phosphonium bromide (521)

A solution of (2,6-dichloro-4-methoxyphenyl)methanol (3.00 g, 14.5 mmol) in 30% HBr in acetic acid (45 mL) was stirred at 20° C. for 3 h, then poured onto ice-water (120 mL) and extracted with pentane (6×100 mL). The extracts were washed with water (3×200 mL), backextracting with pentane (100 mL). Removal of the solvent gave the crude bromide as white crystals, which was immediately redissolved in benzene (80 mL) and treated with triphenylphosphine (5.70 g, 21.7 mmol), stirring at reflux for 15 h. After cooling, the precipitate was collected by filtration, washing thoroughly with dry benzene, then pentane, and dried under vacuum at 50° C. to give the phosphonium salt (521) as a white solid (7.75 g, 100%), mp ($CH_2Cl_2$/benzene) 188–190° C. $^1$H NMR (CDC$_3$) δ 7.83–7.60 (m, 15H), 6.74 (s, 2H), 5.37 (d, J=13.5 Hz, 2H), 3.76 (s, 3H). Found: C, 58.40; H, 4.35. $C_{26}H_{22}BrCl_2OP$ requires C, 58.67; H, 4.17.

EXAMPLE 113

The Preparation of 2-[(E)-2-(2,6-Dichloro-4-methoxyphenyl)ethenyl]-5-methoxy-1H-indole (522) (II, Ar=2,6-dichloro-4-methoxyphenyl)

The 5-methoxy-1H-indole-2-carbaldehyde (1) was reacted with (2,6-dichloro-4-methoxybenzyl)(triphenyl)phosphonium bromide (521), prepared as described in example 112, using the procedure described in example 37, except that the aldehyde was added at 0° C., the ratio of LDA:aldehyde was 1.37:1 and the reaction time was 5 h, to give (after crystallisation from $CH_2Cl_2$/hexane) the diene (522) as a cream solid (the pure E isomer) (70%), mp 128–129° C. $^1$H NMR (CDCl$_3$) δ 8.17 (br s, 1H), 7.25 (d, J=8.7 Hz, 1H), 7.17 (d, J=16.8 Hz, 1H), 7.04 (d, J=2.4 Hz, 1H), 6.93 (s, 2H), 6.88 (d, J=16.8 Hz, 1H), 6.86 (dd, J=8.7, 2.5 Hz, 1H), 6.57 (br d, J=1.7 Hz, 1H), 3.85 (s, 3H), 3.82 (s, 3H). Found: C, 62.01; H, 4.23; N, 4.21. $C_{18}H_{15}Cl_2NO_2$ requires C, 62.09; H, 4.34; N, 4.02.

EXAMPLE 114

The Preparation of 4-(2,6-Dichloro-4-methoxyphenyl)-9-methoxy-4,5,6,10c-tetrahydropyrrolo[3,4-c]carbazole-1,3(2H,3aH)-dione (523) (IV, $R^{10}$=H, Ar=2,6-dichloro-4-methoxyphenyl)

The pure E diene (522) prepared as described in example 113 was reacted with maleimide according to the procedure described in example 68 in a foil-covered sealed vial, except that the ratio of diene:maleimide:$SnCl_2$ was 1:6:0.05 and the reaction time was 1.5 h, to give a crude solid containing the adduct (523), which was used without further purification.

EXAMPLE 115

The Preparation of 4-(2,6-Dichloro-4-methoxyphenyl)-9-methoxypyrrolo[3,4-c]carbazole-1,3(2H,6H)-dione (524) (V, $R^{10}$=H, Ar=2,6-dichloro-4-methoxyphenyl)

The crude adduct (523) prepared as described in example 114 was aromatised with DDQ (6 equiv.) using the procedure described in example 70, except that the solvent was 1:1 toluene/dioxane and the reaction time was 24 h, to give (after crystallisation from MeOH/$CH_2Cl_2$/hexane) the product (524) (74%) as a yellow-orange crystalline solid, mp 272–274° C. $^1$H NMR [$(CD_3)_2SO$] δ 11.98 (br s, 1H), 11.12 (br s, 1H), 8.44 (d, J=2.6 Hz, 1H), 7.58 (d, J=8.7 Hz, 1H), 7.57 (s, 1H), 7.26 (dd, J=8.8, 2.6 Hz, 1H), 7.23 (s, 2H), 3.89 (2s, 2×3H). Found: C, 56.89; H, 3.18; N, 5.94. $C_{22}H_{14}Cl_2N_2O_4.5/4H_2O$ requires C, 56.97; H, 3.59; N, 6.04.

EXAMPLE 116

The Preparation of 4-(2,6-Dichloro-4-hydroxyphenyl)-9-Hydroxypyrrolo[3,4-c]carbazole-1,3(2H,6H)-dione (525) (VI, $R^{10}$=H, Ar=2,6-dichloro-4-hydroxyphenyl)

The methyl ether (524) prepared as described in example 115 was bis-demethylated with $BBr_3$ using the procedure described in example 80, except that the reaction time was 4 h with 10 equiv. $BBr_3$, then a further 9 h with an extra 10 equiv. $BBr_3$, to give (after crystallisation from MeOH/$CH_2Cl_2$/hexane) the phenol (525) (95%) as a yellow-orange solid, mp 300–308° C. $^1$H NMR [$(CD_3)_2SO$] δ 11.82 (br s, 1H), 11.03 (br s, 1H), 10.47 (br s, 1H), 9.28 (br s, 1H), 8.29 (d, J=2.4 Hz, 1H), 7.50 (s, 1H), 7.46 (d, J=8.7 Hz, 1H), 7.08 (dd, J=8.7, 2.5 Hz, 1H), 6.96 (s, 2H). Found: C, 56.28; H, 2.94; N, 6.16. $C_{20}H_{10}Cl_2N_2O_4.3/4H_2O$ requires C, 56.29; H, 2.72; N, 6.56.

EXAMPLE 117

The Preparation of (2,6-Dichloro-3-methoxybenzyl)(triphenyl)phosphonium Bromide (526)

Bromination of (2,6-dichloro-3-methoxyphenyl)methanol with 30% HBr in acetic acid, followed by reaction of the crude bromide with triphenylphosphine, using the procedure described in example 112, except that the reaction time for the displacement was 36 h, gave the phosphonium salt (526) (97%) as a white solid, mp ($CH_2Cl_2$/benzene) 242–244° C. $^1$H NMR ($CDCl_3$) δ 7.83–7.60 (m, 15H), 7.15 (dd, J=9.1, 0.8 Hz, 1H), 6.88 (dd, J=9.0, 2.4 Hz, 1H), 5.41 (d, J=14.3 Hz, 2H), 3.84 (s, 3H). Found: C, 58.68; H, 4.16. $C_{26}H_{22}BrCl_2OP$ requires C, 58.67; H, 4.17.

EXAMPLE 118

The Preparation of 2-[(E)-2-(2,6-Dichloro-3-methoxyphenyl)ethenyl]-5-methoxy-1H-indole (527) (II, Ar=2,6-dichloro-3-methoxyphenyl)

The 5-methoxy-1H-indole-2-carbaldehyde (1) was reacted with (2,6-dichloro-3-methoxybenzyl)(triphenyl)phosphonium bromide (526), prepared as described in example 117, using the procedure described in example 37, except that the aldehyde was added at 0° C., the ratio of LDA:aldehyde was 1.55:1 and the reaction time was 5 h, to give (after crystallisation from $CH_2Cl_2$/hexane) the diene (527) as a cream solid (the pure E isomer) (76%), mp 138–140° C. $^1$H NMR ($CDCl_3$) δ 8.21 (br s, 1H), 7.32 (d, J=8.9 Hz, 1H), 7.26 (d, J=8.7 Hz, 1H), 7.22 (d, J=16.8 Hz, 1H), 7.04 (d, J=2.4 Hz, 1H), 6.92 (d, J=16.8 Hz, 1H), 6.87 (dd, J=8.8, 2.5 Hz, 1H), 6.80 (d, J=8.9 Hz, 1H), 6.61 (d, J=1.7 Hz, 1H), 3.92 (s, 3H), 3.85 (s, 3H). Found: C, 61.92; H, 4.52; N, 3.91. $C_{18}H_{15}Cl_2NO_2$ requires C, 62.09; H, 4.34; N, 4.02.

EXAMPLE 119

The Preparation of 4-(2,6-Dichloro-3-methoxyphenyl)-9-methoxy-4,5,6,10c-tetrahydropyrrolo[3,4-c]carbazole-1,3(2H,3aH)-dione (528) (IV, $R^{10}$=H, Ar=2,6-dichloro-3-methoxyphenyl)

The pure E diene (527) prepared as described in example 118 was reacted with maleimide according to the procedure described in example 68 in a foil-covered sealed vial, except that the ratio of diene:maleimide:$SnCl_2$ was 1:5:0.03 and the reaction time was 2.5 h, to give a crude solid containing the adduct (528), which was used without further purification.

EXAMPLE 120

The Preparation of 4-(2,6-Dichloro-3-methoxyphenyl)-9-methoxypyrrolo[3,4-c]carbazole-1,3(2H,6H)-dione (529) (V, $R^{10}$=H Ar=2,6-dichloro-3-methoxyphenyl)

The crude adduct (528) prepared as described in example 119 was aromatised with DDQ (5 equiv.) using the procedure described in example 70, except that the solvent was 1:1 toluene/dioxane and the reaction time was 24 h, to give (after crystallisation from $CH_2Cl_2$/hexane) the product (529) (70%) as an orange crystalline solid, mp 240–242° C. NMR [$(CD_3)_2SO$] δ 12.00 (br s, 1H), 11.13 (br s, 1H), 8.45 (d, J=2.6 Hz, 1H), 7.58 (d, J=8.2 Hz, 1H), 7.56 (s, 1H); 7.56 (d, J=8.7 Hz, 1H), 7.28 (d, J=9.3 Hz, 1H), 7.26 (dd, J=9.0, 2.4 Hz, 1H), 3.94 (s, 3H), 3.90 (s, 3H). Found: C, 60.11; H, 3.16; N, 6.30. $C_{22}H_{14}Cl_2N_2O_4$ requires C, 59.88; H, 3.20; N, 6.35.

EXAMPLE 121

The Preparation of 4-(2,6-Dichloro-3-hydroxyphenyl)-9-hydroxypyrrolo[3,4-c]carbazole-1,3(2H,6H)-dione (530) (VI, $R^{10}$=H, Ar=2,6-dichloro-3-hydroxyphenyl)

The methyl ether (529) prepared as described in example 120 was bis-demethylated with $BBr_3$ using the procedure described in example 80, except that the reaction time was 6 h with 10 equiv. $BBr_3$, to give (after crystallisation from MeOH/$CH_2Cl_2$/hexane) the phenol (530) (91%) as an orange crystalline solid, mp 313–318° C. $^1$H NMR [$(CD_3)_2$SO] δ 11.84 (br s, 1H), 11.05 (br s, 1H), 10.56 (br s, 1H), 9.29 (br s, 1H), 8.30 (d, J=2.4 Hz, 1H), 7.48 (s, 1H), 7.46 (d, J=8.7 Hz, 1H), 7.36 (d, J=8.8 Hz, 1H), 7.09 (dd, J=8.8, 2.6 Hz, 1H), 7.06 (d, J=8.9 Hz, 1H). Found: C, 57.21; H, 2.65; N, 6.58. $C_{20}H_{10}Cl_2N_2O_4$·1/2 MeOH requires C, 57.36; H, 2.82; N, 6.53.

EXAMPLE 122

The Preparation of 2-[(E)-2-(2-Bromophenyl)ethenyl]-5-methoxy-1H-indole (531) (II, Ar=2-bromophenyl)

The 5-methoxy-1H-indole-2-carbaldehyde (1) was reacted with (2-bromobenzyl)(triphenyl)phosphonium bromide using the procedure described in example 37, except that the aldehyde was added at 0° C., the ratio of LDA: aldehyde was 1.46:1 and the reaction time was 5 h, to give (after crystallisation from $CH_2Cl_2$/hexane) the diene (531) as a yellow solid (the pure E isomer) (88%), mp 120–123° C. $^1$H NMR (CDCl$_3$) δ 8.21 (br s, 1H), 7.66 (dd, J=7.9, 1.5 Hz, 1H), 7.59 (dd, J=8.1, 1.0 Hz, 1H), 7.32 (br t, J=7.1 Hz, 1H), 7.27 (d, J=8.3 Hz, 1H), 7.22 (d, J=16.4 Hz, 1H), 7.12 (td, J=7.6, 1.5 Hz, 1H), 7.05 (d, J=16.4 Hz, 1H), 7.04 (d, J=2.4 Hz, 1H), 6.88 (dd, J=8.8, 2.4 Hz, 1H), 6.59 (d, J=1.7 Hz, 1H), 3.86 (s, 3H). Found: C, 61.97; H, 4.30; N, 4.17. $C_{17}H_{14}BrNO$ requires C, 62.21; H, 4.30; N, 4.27.

Representative Procedure for Combining Method 4a and Method 6 of Scheme 2

EXAMPLE 123

The Preparation of 4-(2-bromophenyl)-9-methoxypyrrolo[3,4-c]carbazole-1,3(2H,6H)-dione (532) (V,$R^{10}$=H, Ar=2-bromophenyl)

A foil-covered mixture of the pure E diene (531) (1.00 g, 3.05 mmol) prepared as described in example 122 and maleimide (1.48 g, 15.2 mmol) in dry toluene (10 mL) was stirred in a sealed vial at reflux for 24 h. The resulting thick suspension was transferred to a flask using further toluene (30 mL) and dioxane (40 mL), then treated with DDQ (3.49 g, 15.4 mmol), stirring under reflux for 24 h. The resulting mixture was treated with saturated aqueous $NaHCO_3$ solution (250 mL) and the product extracted with 15% MeOH/$CH_2Cl_2$. These extracts were washed with aqueous $NaHCO_3$ solution and water. The aqueous $NaHCO_3$ solution and water was extracting several times with 15% MeOH/$CH_2Cl_2$, then the combined extracts were concentrated to dryness. The residue was adsorbed onto silica gel and chromatographed. Elution with 0–0.75% MeOH/$CH_2Cl_2$, then with 0.75% MeOH/$CH_2Cl_2$ gave the crude product (532) which crystallised pure from MeOH/$CH_2Cl_2$/hexane as an orange crystalline solid (1.23 g, 96%), mp 273–275° C. $^1$H NMR [$(CD_3)_2$SO] δ 11.96 (br s, 1H), 11.08 (br s, 1H), 8.46 (d, J=2.6 Hz, 1H), 7.74 (d, J=7.8 Hz, 1H), 7.58 (d, J=8.9 Hz, 1H), 7.55 (s, 1H), 7.48 (m, 2H), 7.39 (m, 1H), 7.25 (dd, J=8.9, 2.7 Hz, 1H), 3.89 (s, 3H). Found: C, 60.08; H, 3.02; N, 6.68. $C_{21}H_{13}BrN_2O_3$ requires C, 59.88; H, 3.11; N, 6.65.

EXAMPLE 124

The Preparation of 4-(2-Bromophenyl)-9-hydroxypyrrolo[3,4-c]carbazole-1,3(2H,6H)-dione (533) (VI, $R^{10}$=H, Ar=2-bromophenyl)

The methyl ether (532) prepared as described in example 123 was demethylated with $BBr_3$ using the procedure described in example 80, except that the reaction time was 4 h. Crystallisation from MeOH/$CH_2Cl_2$/hexane gave the phenol (533) in a yield of 89% as a yellow-orange solid, mp 244–246° C. $^1$H NMR [$(CD_3)_2$SO] δ 11.83 (br s, 1H), 11.01 (br s, 1H), 9.29 (br s, 1H), 8.31 (d, J=2.4 Hz, 1H), 7.73 (brd, J=7.9 Hz, 1H), 7.47 (m, 4H), 7.38 (m, 1H), 7.08 (dd, J=8.7, 2.5 Hz, 1H). Found: C, 57.82; H, 2.90; N, 6.72. $C_{20}H_{11}BrN_2O_3$·1/2$H_2O$ requires C, 57.71; H, 2.91; N, 6.73.

EXAMPLE 125

The Preparation of 4-[1,1-Biphenyl]-2-yl-9-methoxypyrrolo[3,4-c]carbazole-1,3(2H,6H)-dione (534) (V, $R^{10}$=H, Ar=2-biphenyl)

A mixture of the bromo derivative (532) (85.5 mg, 0.203 mmol) prepared as described in example 123, [1,1'-bis(diphenylphosphino)ferrocene]dichloropalladium(II). $CH_2Cl_2$ (85 mg, 0.104 mmol) and tetraphenyltin (0.451, 1.06 mmol) in dry DMF (2.5 mL) was stirred in a sealed vial at 130° C. for 4 d. The resulting mixture was added to aqueous $NaHCO_3$ (100 mL) then extracted with 2:1 $CH_2Cl_2$/EtOAc (5×80 mL). The extracts were washed with water. The water was extracting with 2:1 $CH_2Cl_2$/EtOAc, then the combined organic extracts were concentrated to dryness. The residue was chromatographed several times on silica gel (eluting with $CH_2Cl_2$) to give the crude product (44.5 mg, 54%). This was combined with material from similar reactions and purified by preparative reversed phase C-18 HPLC (using a gradient of 65–99% $CH_3CN$/aqueous $HCO_2NH_4$ buffer, pH 3.45) to give (after crystallisation from MeOH/$CH_2Cl_2$/hexane) the pure product (534) (21% overall) as a yellow solid, mp 220–223° C. $^1$H NMR [$(CD_3)_2$SO] δ 11.76 (br s, 1H), 10.87 (br s, 1H), 8.39 (d, J=2.6 Hz, 1H), 7.50 (m, 5H), 7.38 (s, 1H), 7.20 (dd, J=8.9, 2.6 Hz, 1H), 7.10 (m, 5H), 3.86 (s, 3H). Found: C, 77.37; H, 4.21; N, 6.88. $C_{27}H_{18}N_2O_3$ requires C, 77.50; H, 4.34; N, 6.69.

EXAMPLE 126

The Preparation of 4-[1,1'-Biphenyl]-2-yl-9-hydroxypyrrolo[3,4-c]carbazole-1,3(2H,6H)-dione (535) (VI, $R^{10}$=H, Ar=2-biphenyl)

The methyl ether (534) prepared as described in example 125 was demethylated with $BBr_3$ using the procedure described in example 80, except that the reaction time was 4 h, to give (after crystallisation from MeOH/$CH_2Cl_2$/hexane) the phenol (535) (98%) as a yellow solid, mp 198–203° C. (dec). $^1$H NMR [$(CD_3)_2$SO] δ 11.61 (br s, 1H), 10.82 (br s, 1H), 9.22 (br s, 1H), 8.24 (d, J=2.4 Hz, 1H), 7.52 (m, 1H), 7.45 (m, 3H), 7.37 (d, J=8.7 Hz, 1H), 7.31 (s, 1H), 7.11 (m, 5H), 7.03 (dd, J=8.7, 2.5 Hz, 1H). Found: C, 76.38; H, 3.94; N, 6.99. $C_{26}H_{16}N_2O_3 \cdot 1/4H_2O$ requires C, 76.37; H, 4.07; N, 6.85.

EXAMPLE 127

The Preparation of 5-Methoxy-2-[(E)-2-(2-nitrophenyl)ethenyl]-1H-indole (536) (II, Ar=2-nitrophenyl)

The 5-methoxy-1H-indole-2-carbaldehyde (1) was reacted with (2-nitrobenzyl)(triphenyl)phosphonium chloride using the procedure described in example 37, except that the ratio of LDA:aldehyde was 1.37:1 and the reaction time was 5 h, to give (after crystallisation from $CH_2Cl_2$/hexane) the diene (536) as red-orange crystals (the pure E isomer) (47%), mp 136–138° C. $^1$H NMR (CDCl$_3$) δ 8.25 (br s, 1H), 7.98 (dd, J=8.2, 1.2 Hz, 1H), 7.78 (dd, J=7.9, 1.0 Hz, 1H), 7.61 (td, J=7.6, 0.9 Hz, 1H), 7.41 (d, J=16.3 Hz, 1H), 7.39 (td, J=7.8, 1.3 Hz, 1H), 7.27 (m, 1H), 7.13 (d, J=16.3 Hz, 1H), 7.04 (d, J=2.4 Hz, 1H), 6.90 (dd, J=8.8, 2.5 Hz, 1H), 6.62 (d, J=1.8 Hz, 1H), 3.86 (s, 3H). Found: C, 69.44; H, 4.49; N, 9.70. $C_{17}H_{14}N_2O_3$ requires C, 69.38; H, 4.79; N, 9.52.

EXAMPLE 128

The Preparation of 9-Methoxy-4-(2-nitrophenyl)pyrrolo[3,4-c]carbazole-1,3(2H,6H)-dione (537) (V, $R^{10}$=H, Ar=2-nitrophenyl)

The pure E diene (536) prepared as described in example 127 was subjected to successive reactions with maleimide and then DDQ according to the above representative procedure described in example 123, to give (after crystallisation from MeOH/EtOAc/$CH_2Cl_2$/hexane) the product (537) (97%) as a yellow-orange solid, mp 294–298° C. $^1$H NMR [(CD$_3$)$_2$SO] δ 12.01 (br s, 1H), 11.10 (br s, 1H), 8.44 (d, J=2.5 Hz, 1H), 8.21 (dd, J=8.1, 1.0 Hz, 1H), 7.86 (td, J=7.5, 1.4 Hz, 1H), 7.74 (td, J=7.8, 1.3 Hz, 1H), 7.67 (s, 1H), 7.65 (dd, J=7.6, 1.4 Hz, 1H), 7.59 (d, J=8.9 Hz, 1H), 7.25 (dd, J=8.7, 2.6 Hz, 1H), 3.90 (s, 3H). Found: C, 64.99; H, 3.42; N, 10.79. $C_{21}H_{13}N_3O_5$ requires C, 65.12; H, 3.38; N, 10.85.

EXAMPLE 129

The Preparation of 9-Hydroxy-4-(2-nitrophenyl)pyrrolo[3,4-c]carbazole-1,3(2H,6H)-dione (538) (VI, $R^{10}$=H, Ar=2-nitrophenyl)

The methyl ether (537) prepared as described in example 128 was demethylated with BBr$_3$ using the procedure described in example 80, except that the reaction time was 5 h with 5 equiv. BBr$_3$, then a further 21 h with an extra 5 equiv. BBr$_3$, to give (after crystallisation from MeOH/$CH_2Cl_2$/hexane) the phenol (538) (53%) as an orange solid, mp 322–330° C. $^1$H NMR [(CD$_3$)$_2$SO] δ 11.88 (br s, 1H), 11.05 (br s, 1H), 9.29 (br s, 1H), 8.30 (d, J=2.4 Hz, 1H), 8.20 (dd, J=8.2, 1.1 Hz, 1H), 7.85 (td, J=7.5, 1.2 Hz, 1H), 7.73 (td, J=7.9, 1.4 Hz, 1H), 7.63 (dd, J=7.6, 1.4 Hz, 1H), 7.61 (s, 1H), 7.47 (d, J=8.7 Hz, 1H), 7.09 (dd, J=8.7, 2.5 Hz, 1H). Found: C, 63.03; H, 3.27; N, 10.59. $C_{20}H_{11}N_3O_5 \cdot 1/2$ MeOH requires C, 63.24; H, 3.37; N, 10.79.

EXAMPLE 130

The Preparation of 4-(2-Aminophenyl)-9-methoxypyrrolo[3,4-c]carbazole-1,3(2H,6H)-dione (539) (V, $R^{10}$=H, Ar=2-aminophenyl)

A solution of the nitro derivative (537) (71 mg, 0.183 mmol) prepared as described in example 128 in 2:1 THF/MeOH (45 mL) containing wet 10% Pd-C (71 mg) was hydrogenated at 60 psi for 7 h. The solution was filtered throught celite, the celite and catalyst were washed thoroughly with MeOH and THF, then the filtrate was concentrated to dryness. Crystallisation of the residue from MeOH/$CH_2Cl_2$/hexane gave the amine (539) (67 mg, 97%) as a yellow solid, mp>320° C. $^1$H NMR [(CD$_3$)$_2$SO] δ 11.80 (br s, 1H), 10.94 (br s, 1H), 8.47 (d, J=2.6 Hz, 1H), 7.54 (d, J=8.8 Hz, 1H), 7.51 (s, 1H), 7.21 (dd, J=8.8, 2.6 Hz, 1H), 7.08 (td, J=7.7, 1.5 Hz, 1H), 7.01 (dd, J=7.6, 1.5 Hz, 1H), 6.73 (dd, J=8.1, 0.6 Hz, 1H), 6.61 (td, J=7.4, 0.9 Hz, 1H), 4.70 (s, 2H), 3.89 (s, 3H). Found: C, 67.22; H, 4.50; N, 11.03. $C_{21}H_{15}N_3O_3 \cdot H_2O$ requires C, 67.19; H, 4.56; N, 11.19.

EXAMPLE 131

The Preparation of 4-(2-Aminophenyl)-9-hydroxypyrrolo[3,4-c]carbazole-1,3(2H,6H)-dione (540) (VI, $R^{10}$=H, Ar=2-aminophenyl)

A solution of the nitro derivative (538) (81 mg, 0.217 mmol) prepared as described in example 129 in 2:1 THF/MeOH (60 mL) containing wet 10% Pd-C (81 mg) was hydrogenated at 60 psi for 12 h. The solution was filtered throught celite, the celite and catalyst were washed thoroughly with MeOH and THF, then the filtrate was concentrated to dryness. Crystallisation of the residue from MeOH/$CH_2Cl_2$/hexane gave the amine (540) (60 mg, 81%) as a brown solid, mp>330° C. $^1$H NMR [(CD$_3$)$_2$SO] δ 11.67 (br s, 1H), 10.88 (br s, 1H), 9.21 (s, 1H), 8.32 (d, J=2.4 Hz, 1H), 7.46 (s, 1H), 7.42 (d, J=8.6 Hz, 1H), 7.08 (td, J=7.9, 1.5 Hz, 1H), 7.05 (dd, J=8.7, 2.4 Hz, 1H), 7.00 (dd, J=7.6, 1.4 Hz, 1H), 6.72 (br d, J=8.1 Hz, 1H), 6.60 (td, J=7.4, 0.9 Hz, 1H), 4.69 (s, 2H). Found: C, 66.35; H, 4.06; N, 11.76. $C_{20}H_{13}N_3O_3 \cdot H_2O$ requires C, 66.48; H, 4.18; N, 11.63.

EXAMPLE 132

The Preparation of 4-(2-Hydroxyphenyl)-9-methoxypyrrolo[3,4-c]carbazole-1,3(2H,6H)-dione (541) (V, $R^{10}$=H, Ar=2-Hydroxyphenyl)

A solution of the amine (539) (129 mg, 0.361 mmol) prepared as described in example 130 in 90% $H_2SO_4$ (7.5 mL) was cooled to −10° C. and diluted with ice-water (20 mL). After stirring at −10° C. for 10 min, the resulting suspension was treated dropwise with a solution of NaNO$_2$ (38 mg, 0.551 mmol) in cold water (2×1 mL), and stirred at −10 to −5° C. for 30 min. A solution of urea (13 mg, 0.216 mmol) in cold water (2×0.75 mL) was added and the mixture was stirred at −5° C. for 5 min. Finally, a suspension of KI (400 mg, 2.41 mmol) and CuI (402 mg, 2.11 mmol) in cold water (2×2.5 mL) was added, then the cooling bath was removed and the mixture was stirred for 10 min, then at 60–65° C. for 2 h. An aqueous solution of sodium metabisulfite (100 mL of 5%) was added, then the pH was adjusted to pH=3 with NaHCO$_3$ and the mixture extracted with EtOAc (5×100 mL). The extracts were washed with water (200 mL), the water was extracting with EtOAc, the combined organic extracts were concentrated to dryness. The residue was adsorbed onto silica gel and chromatographed. Elution with 0–0.5% MeOH/CH$_2$Cl$_2$ followed but 0.5% MeOH/CH$_2$Cl$_2$ gave a mixture of crude iodides (543, 544) (24 mg, see experiment below for analytical data). Elution with 1% MeOH/CH$_2$Cl$_2$ gave (after crystallisation from THF/CH$_2$Cl$_2$/pentane) the phenol (541) (31 mg, 24%) as a bright yellow solid, mp 264–267° C. $^1$H NMR [(CD$_3$)$_2$SO] δ 11.82 (br s, 1H), 10.95 (br s, 1H), 9.41 (br s, 1H), 8.47 (d, J=2.6 Hz, 1H), 7.56 (s, 1H), 7.54 (d, J=8.9 Hz, 1H), 7.25 (dd, J=7.4, 1.6 Hz, 1H), 7.23 (td, J=7.9, 1.7 Hz, 1H), 7.22 (dd, J=8.7, 2.6 Hz, 1H), 6.91 (br d, J=7.5 Hz, 1H), 6.87 (td, J=7.4, 0.9 Hz, 1H), 3.89 (s, 3H). Found: C, 70.40; H, 4.06; N, 7.95. C$_{21}$H$_{14}$N$_2$O$_4$ requires C, 70.39; H, 3.94; N, 7.82.

EXAMPLE 133

The Preparation of 9-Hydroxy-4-(2-hydroxyphenyl) pyrrolo[3,4-c]carbazole-1,3(2H,6H)-dione (542) (VI, R$^{10}$=H, Ar=2-hydroxyphenyl)

The methyl ether (541) prepared as described in example 132 was demethylated with BBr$_3$ using the procedure described in example 80, except that the reaction time was 4 h, to give (after crystallisation from MeOH/THF/CH$_2$Cl$_2$/hexane) the phenol (542) (73%) as a yellow-orange solid, mp 291–296° C. $^1$H NMR [(CD$_3$)$_2$SO] δ 11.67 (br s, 1H), 10.88 (br s, 1H), 9.37 (br s, 1H), 9.22 (br s, 1H), 8.31 (d, J=2.4 Hz, 1H), 7.51 (s, 1H), 7.42 (d, J=8.7 Hz, 1H), 7.24 (dd, J=7.5, 1.5 Hz, 1H), 7.22 (td, J=7.7, 1.8 Hz, 1H), 7.05 (dd, J=8.7, 2.5 Hz, 1H), 6.91 (br d, J=8.0 Hz, 1H), 6.86 (td, J=7.4, 0.9 Hz, 1H). Found: C, 66.61; H, 3.67; N, 7.70. C$_{20}$H$_{12}$N$_2$O$_4$.H$_2$O requires C, 66.30; H, 3.89; N, 7.73.

EXAMPLE 134

The Preparation of 4-(2-Iodophenyl)-9-methoxypyrrolo[3,4-c]carbazole-1,3(2H,6H)-dione (543) (V, R$^{10}$=H. Ar=2-iodophenyl)

A solution of the amine (539) (46 mg, 0.129 mmol) prepared as described in example 130 in 90% H$_2$SO$_4$ (2.5 mL) was cooled to −5° C., diluted with ice-water (2.5 mL), then allowed to warm to 7° C. The resulting suspension was treated dropwise with a solution of NaNO$_2$ (13.6 mg, 0.197 mmol) in cold water (2×0.5 mL), and stirred at 7° C. for 8 min. A solution of urea (5 mg, 0.083 mmol) in cold water (2×0.4 mL) was added and the mixture was stirred at 7° C. for 4 min. Finally, a suspension of KI (140 mg, 0.843 mmol) and CuI (140 mg, 0.735 mmol) in cold water (2×1 mL) was added, then the cooling bath was removed and the mixture was stirred for 10 min, then at 60–65° C. for 2 h. An aqueous solution of sodium metabisulfite (100 mL of 0.5%) was added, then the mixture was extracted with 20% THF/EtOAc (5×100 mL). The extracts were washed with water (200 mL), the water was extracting with EtOAc, the combined organic extracts were concentrated to dryness. The residue was adsorbed onto silica gel and chromatographed. Elution with 0–0.5% MeOH/CH$_2$Cl$_2$ followed by 0.5% MeOH/CH$_2$Cl$_2$ gave the crude product (22 mg). This was purified by further chromatography on silica gel (eluting with 1% EtOH/CHCl$_3$) to yield the crude major iodide (543) (18 mg, 30%), which was combined with material from similar reactions, rechromatographed (eluting with 20% EtOAc/petroleum ether) and crystallised from MeOH/THF/CH$_2$Cl$_2$/hexane as yellow-orange crystals, mp 311–315° C.

$^1$H NMR [(CD$_3$)$_2$SO] δ 11.95 (br s, 1H), 11.07 (br s, 1H), 8.46 (d, J=2.6 Hz, 1H), 7.97 (dd, J=7.7, 0.9 Hz, 1H), 7.58 (d, J=8.8 Hz, 1H), 7.50 (td, J=7.6, 0.9 Hz, 1H), 7.48 (s, 1H), 7.44 (dd, J=7.6, 1.8 Hz, 1H), 7.25 (dd, J=8.9, 2.7 Hz, 1H), 7.19 (td, J=7.6, 1.8 Hz, 1H), 3.89 (s, 3H). Found: C, 53.87; H, 2.76; N, 5.98. C$_{21}$H$_{13}$IN$_2$O$_3$ requires C, 53.87; H, 2.80; N, 5.98. FABMS found [M+H]$^+$: 469.0046. C$_{21}$H$_{14}$IN$_2$O$_3$ requires 469.0049.

EXAMPLE 135

The Preparation of 9-Hydroxy-4-(2-iodophenyl) pyrrolo[3,4-c]carbazole-1,3(2H,6H)-dione (545) (VI, R$^{10}$=H, Ar=2-iodophenyl)

The methyl ether (543) prepared as described in example 134 was demethylated with BBr$_3$ using the procedure described in example 80, to give (after crystallisation from MeOH/CH$_2$Cl$_2$/hexane) the phenol (545) (88%) as a yellow-orange solid, mp 217–223° C. $^1$H NMR [(CD$_3$)$_2$SO] δ 11.82 (br s, 1H), 11.01 (br s, 1H), 9.28 (br s, 1H), 8.32 (d, J=2.4 Hz, 1H), 7.96 (br d, J=7.8 Hz, 1H), 7.49 (br t, J=7.7 Hz, 1H), 7.46 (d, J=8.9 Hz, 1H), 7.42 (s, 1H), 7.42 (dd, J=7.4, 1.7 Hz, 1H), 7.19 (td, J=7.6, 1.7 Hz, 1H), 7.08 (dd, J=8.7, 2.5 Hz, 1H). Found: C, 52.93; H, 2.55; N, 6.07. C$_{20}$H$_{11}$N$_2$O$_3$ requires C, 52.89; H, 2.44; N, 6.17. FABMS found [M+H]$^+$: 454.9889. C$_{20}$H$_{12}$IN$_2$O$_3$ requires 454.9893.

EXAMPLE 136

The Preparation of (2-Cyanobenzyl)(triphenyl)phosphonium bromide (547)

Bromination of o-tolunitrile with NBS/AIBN, followed by reaction of the crude bromide with triphenylphosphine (1.2 equiv.), using the procedure described in example 102, except that the reaction time for the bromination was 2 h, gave the phosphonium salt (547) (70%) as a light brown powder, mp (CH$_2$Cl$_2$/benzene) 237–241° C. $^1$H NMR (CDCl$_3$) δ 7.90 (dd, J=7.8, 2.3 Hz, 1H), 7.85–7.63 (m, 15H), 7.52 (br t, J=7.7 Hz, 1H), 7.44 (br d, J=7.5 Hz, 1H), 7.38 (tdd, J=7.6, 2.1, 1.0 Hz, 1H), 5.86 (d, J=14.7 Hz, 2H). Found: C, 67.88; H, 4.42; N, 3.09. C$_{26}$H$_{21}$BrNP requires C, 68.13; H, 4.62; N, 3.06.

EXAMPLE 137

The Preparation of 2-[(E)-2-(5-Methoxy-1H-indol-2-yl)ethenyl]benzonitrile (548) (II, Ar=2-cyanophenyl)

The 5-methoxy-1H-indole-2-carbaldehyde (1) was reacted with (2-cyanobenzyl)(triphenyl)phosphonium bromide (547) prepared as described in example 136 using the procedure described in example 37, except that the LDA and aldehyde were (sequentially) added at 0° C., the ratio of LDA:aldehyde was 1.55:1 and the reaction time was 5 h, to give (after crystallisation from CH$_2$Cl$_2$/hexane) the diene (548) as a yellow solid (the pure E isomer) (60%), mp 192–196° C. $^1$H NMR (CDCl$_3$) δ 8.40 (br s, 1H), 7.79 (d, J=8.1 Hz, 1H), 7.66 (dd, J=8.1, 0.9 Hz, 1H), 7.58 (td, J=7.9, 1.3 Hz, 1H), 7.32 (td, J=8.0, 0.9 Hz, 1H), 7.29 (d, J=8.5 Hz, 1H), 7.28 (d, J=16.9 Hz, 1H), 7.18 (d, J=16.4 Hz, 1H), 7.04 (d, J=2.4 Hz, 1H), 6.91 (dd, J=8.9, 2.4 Hz, 1H), 6.64 (d, J=1.8 Hz, 1H), 3.86 (s, 3H). Found: C, 79.05; H, 5.16; N, 10.31. C$_{18}$H$_{14}$N$_2$O requires C, 78.81; H, 5.14; N, 10.21.

EXAMPLE 138

The Preparation of 2-(9-Methoxy-1,3-dioxo-1,2,3,6-tetrahydropyrrolo[3,4-c]carbazol-4-yl)benzonitrile (549) (V, $R^{10}$=H, Ar=2-cyanophenyl)

The E diene (548) prepared as described in example 137 was subjected to successive reactions with maleimide and then DDQ according to the above representative procedure described in example 123, except that most of the poorly soluble final product was obtained by filtration of the diluted product solution, then washing thoroughly with aqueous $NaHCO_3$ solution, 15% $MeOH/CH_2Cl_2$ and water, with the reminder being obtained by the extraction of the water phase with ethyl acetate. The organic layer was dried, the drying agent was removed and the solution was concentrated to dryness. Crystallization from $THF/CH_2Cl_2$/hexane, to give the product (549) (96%) as a yellow solid, mp 348–350° C. $^1H$ NMR [$(CD_3)_2SO$] δ 12.06 (br s, 1H), 11.19 (br s, 1H), 8.48 (d, J=2.6 Hz, 1H), 7.96 (dd, J=7.7, 1.0 Hz, 1H), 7.82 (td, J=7.7, 1.4 Hz, 1H), 7.71 (br d, J=7.4 Hz, 1H), 7.71 (s, 1H), 7.66 (td, J=7.6, 1.1 Hz, 1H), 7.60 (d, J=8.9 Hz, 1H), 7.27 (dd, J=8.8, 2.6 Hz, 1H), 3.90 (s, 3H). EIMS found $M^+$: 367.0956. $C_{22}H_{13}N_3O_3$ requires 367.0957.

EXAMPLE 139

The Preparation of 2-(9-Hydroxy-1,3-dioxo-1,2,3,6-tetrahydropyrrolo[3,4-c]carbazol-4-yl)benzonitrile (550) (VI, $R^{10}$=H, Ar=2-cyanophenyl)

The methyl ether (549) prepared as described in example 138 was demethylated with $BBr_3$ using the procedure described in example 80, except that the reaction time was 5 h with 5 equiv. $BBr_3$, then a further 4 h with an extra 5 equiv. $BBr_3$, to give (after crystallisation from $THF/CH_2$, $C_2$/hexane) the phenol (550) (83%) as a yellow solid, mp 199–204° C. (dec). $^1H$ NMR [$(CD_3)_2SO$] δ 11.93 (br s, 1H), 11.13 (br s, 1H), 9.31 (br s, 1H), 8.34 (d, J=2.4 Hz, 1H), 7.96 (dd, J=7.6, 0.9 Hz, 1H), 7.82 (td, J=7.7, 1.4 Hz, 1H), 7.70 (br d, J=7.5 Hz, 1H), 7.65 (s, 1H), 7.65 (td, J=7.7, 1.0 Hz, 1H), 7.48 (d, J=8.7 Hz, 1H), 7.10 (dd, J=8.7, 2.5 Hz, 1H). Found: C, 70.17; H, 3.46; N, 11.49. $C_{21}H_{11}N_3O_3.1/4H_2O$ requires C, 70.49; H, 3.24; N, 11.74.

EXAMPLE 140

The Preparation of 5-Methoxy-2-[(E)-2-(3-nitrophenyl)ethenyl]-1H-indole (551) (II, Ar=3-nitrophenyl)

The 5-methoxy-1H-indole-2-carbaldehyde (1) was reacted with (3-nitrobenzyl)(triphenyl)phosphonium bromide using the procedure described in example 37, except that the LDA and aldehyde were sequentially added at 0° C., the ratio of LDA:aldehyde was 1.5:1 and the reaction time was 5 h, to give (after crystallisation from $MeOH/CH_2Cl_2$/hexane) the diene (551) as an orange-red solid (the pure E isomer) (51%), mp 178–182° C. $^1H$ NMR [$(CD_3)_2SO$] δ 11.27 (br s, 1H), 8.34 (t, J=1.9 Hz, 1H), 8.09 (dd, J=8.1, 1.8 Hz, 1H), 7.99 (d, J=7.9 Hz, 1H), 7.67 (t, J=8.0 Hz, 1H), 7.47 (d, J=16.5 Hz, 1H), 7.26 (d, J=8.6 Hz, 1H), 7.25 (d, J=16.6 Hz, 1H), 7.03 (d, J=2.4 Hz, 1H), 6.77 (dd, J=8.8, 2.5 Hz, 1H), 6.61 (d, J=1.6 Hz, 1H), 3.76 (s, 3H). Found: C, 69.36; H, 4.77; N, 9.78. $C_{17}H_{14}N_2O_3$ requires C, 69.38; H, 4.79; N, 9.52.

EXAMPLE 141

The Preparation of 9-Methoxy-4-(3-nitrophenyl)pyrrolo[3,4-c]carbazole-1,3(2H,6H)-dione (552) (V, $R^{10}$=H, Ar=3-nitrophenyl)

The pure E diene-(551) prepared as described in example 140 was subjected to successive reactions with maleimide and then DDQ according to the above representative procedure described in example 123, except that the poorly soluble final product was obtained by filtration of the diluted product solution, then washing thoroughly with aqueous $NaHCO_3$ solution, 15% $MeOH/CH_2Cl_2$ and water, followed by crystallization from MeOH/THF, to give the product (552) (81%) as a brown solid, mp>340° C. $^1H$ NMR [$(CD_3)_2SO$] δ 11.99 (br s, 1H), 11.18 (br s, 1H), 8.50 (d, J=2.5 Hz, 1H), 8.48 (t, J=1.9 Hz, 1H), 8.31 (dd, J=8.1, 1.7 Hz, 1H), 8.11 (br d, J=7.8 Hz, 1H), 7.78 (t, J=8.0 Hz, 1H), 7.75 (s, 1H), 7.58 (d, J=8.8 Hz, 1H), 7.25 (dd, J=8.8, 2.6 Hz, 1H), 3.90 (s, 3H). Found: C, 62.17; H, 3.52; N, 10.33. $C_{21}H_{13}N_3O_5.H_2O$ requires C, 62.22; H, 3.73; N, 10.37.

EXAMPLE 142

The Preparation of 9-Hydroxy-4-(3-nitrophenyl)pyrrolo[3,4-c]carbazole-1,3(2H,6H)-dione (553) (VI, $R^{10}$=H, Ar=3-nitrophenyl)

The methyl ether (552) prepared as described in example 142 was demethylated with pyridinium hydrochloride using the procedure described in example 81, to give (after crystallisation from THF/hexane) the phenol (553) (74%) as an orange-brown solid, mp 300–310° C. (dec). $^1H$ NMR [$(CD_3)_2SO$] δ 11.86 (br s, 1H), 11.11 (br s, 1H), 9.29 (br s, 1H), 8.46 (t, J=1.9 Hz, 1H), 8.35 (d, J=2.4 Hz, 1H), 8.30 (ddd, J=8.2, 2.5, 0.8 Hz, 1H), 8.10 (dt, J=7.8, 1.2 Hz, 1H), 7.77 (t, J=8.0 Hz, 1H), 7.70 (s, 1H), 7.47 (d, J=8.7 Hz, 1H), 7.09 (dd, J=8.7, 2.5 Hz, 1H). FABMS found $M^+$: 373.0692. $C_{20}H_{11}N_3O_5$ requires 373.0699.

EXAMPLE 143

The Preparation of (2-Chloro-3-nitrobenzyl)(triphenyl)phosphonium bromide (554)

Bromination of 2-chloro-3-nitrotoluene with NBS/AIBN, followed by reaction of the crude bromide with triphenylphosphine, using the procedure described in example 102, except that the reaction time for the bromination was 2 h and the displacement reaction was performed at 70° C. for 1 d, gave the phosphonium salt (554) (44%) as a light brown solid, mp ($CH_2Cl_2$/benzene) 224–228° C. $^1H$ NMR ($CDCl_3$) δ 8.09 (br d, J=8.3 Hz, 1H), 7.86–7.63 (m, 16H), 7.34 (t, J=8.1 Hz, 1H), 5.95 (d, J=14.6 Hz, 2H). Found: C, 58.68; H, 4.12; N, 2.79. $C_{25}H_{20}BrClNO_2P$ requires C, 58.56; H, 3.93; N, 2.73.

EXAMPLE 144

The Preparation of 2-[(E)-2-(2-Chloro-3-nitrophenyl)ethenyl]-5-methoxy-1H-indole (555) (II, Ar=2-chloro-3-nitrophenyl)

The 5-methoxy-1H-indole-2-carbaldehyde (1) was reacted with (2-chloro-3-nitrobenzyl)(triphenyl)phosphonium bromide (554) preared as described in example 143 using the procedure described in example 37, except that the LDA and aldehyde were (sequentially) added at 0° C., the ratio of LDA:aldehyde was 1.5:1 and the reaction time was 5 h, to give (after crystallisation from CH$_2$Cl$_2$/pentane) the diene (555) as an orange crystalline solid (the pure E isomer) (50%), mp 131–133° C. $^1$H NMR (CDCl$_3$) δ 8.24 (br s, 1H), 7.86 (dd, J=8.0, 1.4 Hz, 1H), 7.63 (dd, J=7.9, 1.4 Hz, 1H), 7.40 (t, J=8.0 Hz, 1H), 7.28 (d, J=8.5 Hz, 1H), 7.25 (d, J=15.8 Hz, 1H), 7.15 (d, J=16.4 Hz, 1H), 7.05 (d, J=2.4 Hz, 1H), 6.91 (dd, J=8.9, 2.4 Hz, 1H), 6.65 (d, J=1.7 Hz, 1H), 3.86 (s, 3H). Found: C, 61.97; H, 3.92; N, 8.50. C$_{17}$H$_{13}$ClN$_2$O$_3$ requires C, 62.11; H, 3.99; N, 8.52.

EXAMPLE 145

The Preparation of 4-(2-Chloro-3-nitrophenyl)-9-methoxypyrrolo[3,4-c]carbazole-1,3(2H,6H)-dione (556) (V, R$^{10}$=H, Ar=2-chloro-3-nitrophenyl)

The pure E diene (555) prepared as described in example 144 was subjected to successive reactions with maleimide and then DDQ according to the procedure described in example 123, to give (after crystallisation from THF/pentane) the product (556) (93%) as a yellow-brown solid, mp 315–320° C. (dec). $^1$H NMR [(CD$_3$)$_2$SO] δ 12.07 (br s, 1H), 11.16 (br s, 1H), 8.46 (d, J=2.6 Hz, 1H), 8.11 (dd, J=8.1, 1.5 Hz, 1H), 7.82 (dd, J=7.7, 1.6 Hz, 1H), 7.69 (t, J=7.9 Hz, 1H), 7.69 (s, 1H), 7.59 (d, J=8.9 Hz, 1H), 7.26 (dd, J=8.8, 2.6 Hz, 1H), 3.90 (s, 3H). Found: C, 60.47; H, 3.17; N, 9.78. C$_{21}$H$_{12}$ClN$_3$O$_5$.1/4 THF requires C, 60.08; H, 3.21; N, 9.55.

EXAMPLE 146

The Preparation of 4-(2-Chloro-3-nitrophenyl)-9-hydroxypyrrolo[3,4-c]carbazole-1,3(2H,6H)-dione (557) (VI, R$^{10}$=H, Ar=2-chloro-3-nitrophenyl)

The methyl ether (556) prepared as described in example 145 was demethylated with BBr$_3$ using the procedure described in example 80, except that the reaction time was 5 h with 10 equiv. BBr$_3$, to give (after crystallisation from THF/CH$_2$Cl$_2$/pentane) the phenol (557) (84%) as a yellow solid, mp 304–308° C. $^1$H NMR [(CD$_3$)$_2$SO] δ 11.92 (br s, 1H), 11.11 (br s, 1H), 9.30 (s, 1H), 8.31 (d, J=2.4 Hz, 1H), 8.11 (dd, J=8.2, 1.5 Hz, 1H), 7.81 (dd, J=7.6, 1.5 Hz, 1H), 7.68 (t, J=7.9 Hz, 1H), 7.63 (s, 1H), 7.47 (d, J=8.7 Hz, 1H), 7.10 (dd, J=8.7, 2.5 Hz, 1H). Found: C, 58.70; H, 2.72; N, 10.10. C$_{20}$H$_{10}$ClN$_3$O$_5$ requires C, 58.91; H, 2.47; N, 10.30.

EXAMPLE 147

The Preparation of 4-(3-Amino-2-chlorophenyl)-9-hydroxypyrrolo[3,4-c]carbazole-1,3(2H,6H)-dione (558) (VI, R$^{10}$=H, Ar=3-amino-2-chlorophenyl)

A mixture of the nitro derivative (557) (66 mg, 0.162 mmol) prepared as described in example 146 and freshly prepared (wet) nickel boride (202 mg) in MeOH (4.8 mL) and 1M HCl (1.2 mL) was stirred at reflux for 100 min. Conc. aqueous ammonia and aqueous NaHCO$_3$ (100 mL) were added and the mixture extracted with EtOAc (8×100 mL). The extracts were concentrated, adsorbed onto silica gel and chromatographed. Elution with 0–1% MeOH/CH$_2$Cl$_2$ then 1.5% MeOH/CH$_2$Cl$_2$ and THF gave (after crystallisation from THF/CH$_2$Cl$_2$/pentane) the amine (558) (83%) as a yellow-orange solid, mp 348–352° C. $^1$H NMR [(CD$_3$)$_2$SO] δ 11.76 (br s, 1H), 10.96 (br s, 1H), 9.25 (br s, 1H), 8.31 (d, J=2.4 Hz, 1H), 7.45 (s, 1H), 7.44 (d, J=8.7 Hz, 1H), 7.08 (t, J=7.8 Hz, 1H), 7.07 (dd, J=8.7, 2.5 Hz, 1H), 6.86 (dd, J=8.1, 1.5 Hz, 1H), 6.60 (dd, J=7.4, 1.3 Hz, 1H), 5.39 (s, 2H). Found: C, 63.79; H, 3.47; N, 10.37. C$_{20}$H$_{12}$ClN$_3$O$_3$.1/2 THF requires C, 63.85; H, 3.90; N, 10.15.

EXAMPLE 148

The Preparation of (2-Chloro-4-nitrobenzyl)(triphenyl)phosphonium bromide (559)

Bromination of 2-chloro-4-nitrotoluene with NBS/AIBN, followed by reaction of the crude bromide with triphenylphosphine, using the procedure described in example 102, except that the reaction time for the bromination was 24 h and the displacement reaction was performed at 20° C. for 7 d, gave the crude phosphonium salt (559) (34%) as a light brown solid, mp (benzene) 70–75° C. (dec). $^1$H NMR [(CD$_3$)$_2$SO] δ 8.21 (d, J=2.5 Hz, 1H), 8.13 (dd, J=8.7, 2.5 Hz, 1H), 7.94 (td, J=7.5, 1.6 Hz, 3H), 7.80–7.66 (m, 12H), 7.43 (dd, J=8.5, 2.6 Hz, 1H), 5.33 (d, J=15.7 Hz, 2H). FABMS found M$^+$=432.0916, 434.0904. C$_{25}$H$_{20}$ClNO$_2$P requires 432.0921, 434.0891.

EXAMPLE 149

The Preparation of 2-[(E)-2-(2-Chloro-4-nitrophenyl)ethenyl]-5-methoxy-1H-indole (560) (II, Ar=2-chloro-4-nitrophenyl)

The 5-methoxy-1H-indole-2-carbaldehyde (1) was reacted with (2-chloro-4-nitrobenzyl)(triphenyl)phosphonium bromide (559) prepared as described in example 148 using the procedure described in example 37, except that the LDA and aldehyde were (sequentially) added at 0° C., the ratio of LDA:aldehyde was 1.5:1 and the reaction time was 5 h, to give (after crystallisation from CH$_2$Cl$_2$/hexane) the diene (560) as a dark red-brown solid (the pure E isomer) (46%), mp 239–241° C. $^1$H NMR [(CD$_3$)$_2$SO] δ11.57 (br s, 1H), 8.32 (d, J=2.0 Hz, 1H), 8.18 (dd, J=8.8, 2.1 Hz, 1H), 8.15 (d, J=8.9 Hz, 1H), 7.59 (d, J=16.3 Hz, 1H), 7.47 (d, J=16.3 Hz, 1H), 7.29 (d, J=8.9 Hz, 1H), 7.05 (d, J=2.4 Hz, 1H), 6.82 (dd, J=8.7, 2.5 Hz, 1H), 6.70 (s, 1H), 3.76 (s, 3H). Found: C, 62.14; H, 3.91; N, 8.52. C$_{17}$H$_{13}$ClN$_2$O$_3$ requires C, 62.11; H, 3.99; N, 8.52.

EXAMPLE 150

The Preparation of 4-(2-Chloro-4-nitrophenyl)-9-methoxypyrrolo[3,4-c]carbazole-1,3(2H,6H)-dione (561) (V, R$^{10}$=H, Ar=2-chloro-4-nitrophenyl)

The pure E diene (560) prepared as described in example 149 was subjected to successive reactions with maleimide and then DDQ according to the procedure described in example 123, to give (after crystallisation from THF/hexane) the product (561) (98%) as an orange solid, mp 279–282° C. $^1$H NMR [(CD$_3$)$_2$SO] δ 12.06 (br s, 1H), 11.20 (br s, 1H), 8.46 (d, J=2.6 Hz, 1H), 8.43 (d, J=2.2 Hz, 1H), 8.29 (dd, J=8.4, 2.4 Hz, 1H), 7.83 (d, J=8.4 Hz, 1H), 7.66 (s, 1H), 7.59 (d, J=8.9 Hz, 1H), 7.27 (dd, J=8.8, 2.6 Hz, 1H), 3.90 (s, 3H). Found: C, 59.83; H, 3.61; N, 9.57. C$_{21}$H$_{12}$ClN$_3$O$_5$.1/4 THF requires C, 60.08; H, 3.21; N, 9.55.

EXAMPLE 151

The Preparation of 4-(2-Chloro-4-nitrophenyl)-9-hydroxypyrrolo[3,4-c]carbazole-1,3(2H,6H)-dione (562) (VI, $R^{10}$=H, Ar=2-chloro-4-nitrophenyl)

The methyl ether (561) prepared as described in example 150 was demethylated with $BBr_3$ using the procedure described in example 80, except that the reaction time was 5 h with 5 equiv. $BBr_3$, then a further 5 h with an extra 5 equiv. $BBr_3$, to give (after crystallisation from $THF/CH_2Cl_2$/pentane) the phenol (562) (85%) as a red-orange solid, mp 301–305° C. $^1$H NMR [$(CD_3)_2SO$] δ 11.94 (br s, 1H), 11.13 (br s, 1H), 9.32 (br s, 1H), 8.43 (d, J=2.3 Hz, 1H), 8.32 (d, J=2.4 Hz, 1H), 8.29 (dd, J=8.5, 2.3 Hz, 1H), 7.82 (d, J=8.4 Hz, 1H), 7.61 (s, 1H), 7.48 (d, J=8.7 Hz, 1H), 7.10 (dd, J=8.7, 2.5 Hz, 1H). Found: C, 58.81; H, 2.35; N, 10.05. $C_{20}H_{10}ClN_3O_5$ requires C, 58.91; H, 2.47; N, 10.30.

EXAMPLE 152

The Preparation of 4-(4-Amino-2-chlorophenyl)-9-hydroxypyrrolo[3,4-c]carbazole-1,3(2H,6H)-dione (563) (VI, $R^{10}$=H, Ar=4-amino-2-chlorophenyl)

A mixture of the nitro derivative (562) (90 mg, 0.221 mmol) prepared as described in example 151 and freshly prepared (wet) nickel boride (277 mg) in MeOH (7.2 mL) and 1M HCl (1.8 mL) was stirred at reflux for 1 h. Conc. aqueous ammonia and aqueous $NaHCO_3$ (120 mL) were added and the mixture extracted with EtOAc (6×80 mL). The extracts were concentrated, adsorbed onto silica gel and chromatographed. Elution with 0–2% $MeOH/CH_2Cl_2$ then elution with THF gave (after crystallisation from THF/CH,Cl$_2$/pentane) the amine (563) (100%) as an orange solid, mp 293–303° C. (dec). $^1$H NMR [$(CD_3)_2SO$] δ 11.70 (br s, 1H), 10.92 (br s, 1H), 9.23 (br s, 1H), 8.30 (d, J=2.4 Hz, 1H), 7.44 (s, 1H), 7.43 (d, J=8.7 Hz, 1H), 7.09 (d, J=8.2 Hz, 1H), 7.05 (dd, J=8.7, 2.5 Hz, 1H), 6.71 (d, J=2.2 Hz, 1H), 6.58 (dd, J=8.1, 2.2 Hz, 1H), 5.51 (s, 2H). Found: C, 60.42; H, 3.64; N, 10.05. $C_{20}H_{12}ClN_3O_3$.5/4$H_2O$ requires C, 60.01; H, 3.65; N, 10.50.

EXAMPLE 153

The Preparation of (2-Chloro-5-nitrobenzyl)(triphenyl)phosphonium bromide (564)

Bromination of (2-chloro-5-nitrophenyl)methanol with 30% HBr in acetic acid, followed by reaction of the crude bromide with triphenylphosphine, using the procedure described in example 112, gave the phosphonium salt (564) (63%) as a white solid, mp ($CH_2Cl_2$/benzene) 239–243° C. $^1$H NMR ($CDCl_3$) δ 8.22 (br s, 1H), 8.07 (br d, J=8.7 Hz, 1H), 7.87–7.65 (m, 15H), 7.41 (d, J=8.9 Hz, 1H), 5.80 (d, J=14.8 Hz, 2H). Found: C, 58.56; H, 3.93; N, 2.73. $C_{25}H_{20}BrClNO_2P$ requires C, 58.47; H, 3.98; N, 2.66.

EXAMPLE 154

The Preparation of 2-[(E)-2-(2-Chloro-5-nitrophenyl)ethenyl]-5-methoxy-1H-indole (565) (II, Ar=-2-chloro-5-nitrophenyl)

The 5-methoxy-1H-indole-2-carbaldehyde (1) was reacted with (2-chloro-5-nitrobenzyl)(triphenyl)phosphonium bromide (564) prepared as described in example 153 using the procedure described in example 37, except that the LDA and aldehyde were sequentially added at 0° C., the ratio of LDA:aldehyde was 1.5:1 and the reaction time was 5 h, to give (after crystallisation from $CH_2Cl_2$/pentane) the diene (565) as an orange solid (the pure E isomer) (57%), mp 191–193° C. $^1$H NMR ($CDCl_3$) δ 8.54 (d, J=2.6 Hz, 1H), 8.25 (br s, 1H), 8.02 (dd, J=8.8, 2.6 Hz, 1H), 7.56 (d, J=8.9 Hz, 1H), 7.28 (d, J=8.7 Hz, 1H), 7.26 (d, J=16.4 Hz, 1H), 7.20 (d, J=16.5 Hz, 1H), 7.06 (d, J=2.4 Hz, 1H), 6.91 (dd, J=8.8, 2.5 Hz, 1H), 6.70 (br s, 1H), 3.86 (s, 3H). Found: C, 61.44; H, 3.92; N, 8.55. $C_{17}H_{13}ClN_2O_3$.1/4$H_2O$ requires C, 61.27; H, 4.08; N, 8.41.

EXAMPLE 155

The Preparation of 4-(2-Chloro-5-nitrophenyl)-9-methoxypyrrolo[3,4-c]carbazole-1,3(2H,6H)-dione (566) (V, $R^{10}$=H, Ar=2-chloro-5-nitrophenyl)

The pure E diene (565) prepared as described in example 154 was subjected to successive reactions with maleimide and then DDQ according to the above representative procedure described in example 123, to give (after crystallisation from $THF/CH_2Cl_2$/pentane) the product (566) (95%) as a yellow-orange solid, mp 285–287° C. $^1$H NMR [$(CD_3)_2SO$] δ 12.06 (br s, 1H), 11.16 (br s, 1H), 8.46 (d, J=2.6 Hz, 1H), 8.36 (d, J=2.8 Hz, 1H), 8.33 (dd, J=8.7, 2.7 Hz, 1H), 7.91 (d, J=8.7 Hz, 1H), 7.71 (s, 1H), 7.60 (d, J=8.9 Hz, 1H), 7.27 (dd, J=8.9, 2.6 Hz, 1H), 3.90 (s, 3H). Found: C, 57.34; H, 2.68; N, 9.38. $C_{21}H_{12}ClN_3O_5$.1/4 $CH_2Cl_2$ requires C, 57.61; H, 2.84; N, 9.48.

EXAMPLE 156

The Preparation of 4-(2-Chloro-5-nitrophenyl)-9-Hydroxypyrrolo[3,4-c]carbazole-1,3(2H,6H)-dione (567) (VI, $R^{10}$=H, Ar=2-chloro-5-nitrophenyl)

The methyl ether (566) prepared as described in example 155 was demethylated with $BBr_3$ using the procedure described in example 80, except that the reaction time was 6 h with 10 equiv. $BBr_3$, then a further 4 h with an extra 10 equiv. $BBr_3$, to give (after crystallisation from $THF/CH_2Cl_2$/pentane) the phenol (567) (88%) as a yellow-orange solid, mp 268° C. (dec). $^1$H NMR [$(CD_3)_2SO$] δ11.94 (br s, 1H), 11.11 (br s, 1H), 9.31 (br s, 1H), 8.35 (d, J=2.6 Hz, 1H), 8.32 (dd, J=8.6, 2.9 Hz, 1H), 8.32 (d, J=2.4 Hz, 1H), 7.91 (d, J=8.7 Hz, 1H), 7.66 (s, 1H), 7.48 (d, J=8.7 Hz, 1H), 7.10 (dd, J=8.7, 2.5 Hz, 1H). Found: C, 58.31; H, 2.45; N, 9.98. $C_{20}H_{10}ClN_3O_5$.1/4$H_2O$ requires C, 58.27; H, 2.57; N, 10.19.

EXAMPLE 157

The Preparation of 4-(5-Amino-2-chlorophenyl)-9-hydroxypyrrolo[3,4-c]carbazole-1,3(2H,6H)-dione (568) (VI, $R^{10}$=H, Ar=5-amino-2-chlorophenyl)

A mixture of the nitro derivative (567) (70 mg, 0.172 mmol) prepared as described in example 156 and freshly prepared (wet) nickel boride (266 mg) in MeOH (5.6 mL) and 1M HCl (1.4 mL) was stirred at reflux for 3 h. Conc. aqueous ammonia and aqueous $NaHCO_3$ (100 mL) were added and the mixture extracted with EtOAc (5×70 mL). The extracts were washed with water, concentrated, adsorbed onto silica gel and chromatographed. Elution with 0–2% MeOH/CH$_2$Cl$_2$ then 3% MeOH/CH$_2$Cl$_2$ gave (after crystallisation from THF/CH$_2$Cl$_2$/pentane) the amine (568) (97%) as an orange solid, mp 301–306° C. (dec). $^1$H NMR [(CD$_3$)$_2$SO] δ 11.78 (br s, 1H), 10.97 (br s, 1H), 9.26 (br s, 1H), 8.31 (d, J=2.4 Hz, 1H), 7.45 (s, 1H), 7.45 (d, J=8.7 Hz, 1H), 7.13 (d, J=8.3 Hz, 1H), 7.07 (dd, J=8.7, 2.5 Hz, 1H), 6.62 (dd, J=8.2, 2.8 Hz, 1H), 6.60 (d, J=2.3 Hz, 1H), 5.29 (s, 2H). Found: C, 63.09; H, 3.17; N, 10.91. C$_{20}$H$_{12}$ClN$_3$O$_3$.1/4H$_2$O requires C, 62.84; H, 3.30; N, 10.99.

EXAMPLE 158

The Preparation of (2-Chloro-3-methoxybenzyl)(triphenyl)phosphonium bromide (569)

Bromination of 2-chloro-1-methoxy-3-methylbenzene with NBS/AIBN, followed by reaction of the crude bromide with triphenylphosphine, using the procedure described in example 102, except that the reaction time for the bromination was 5 h, gave a mixture of phosphonium salts containing (569) (20%) as a light brown solid which was used without further purification. A small amount of the pure salt (569) was obtained by crystallisation of the mother liquors as white needles, mp (CH$_2$Cl$_2$/benzene) 228–231° C. $^1$H NMR (CDCl$_3$) δ 7.81–7.60 (m, 15H), 7.17 (dt, J=7.8, 2.0 Hz, 1H), 7.11 (t, J=8.0 Hz, 1H), 6.87 (dt, J=8.2, 1.8 Hz, 1H), 5.65 (d, J=14.4 Hz, 2H), 3.81 (s, 3H). Found: C, 62.88; H, 4.64. C$_{26}$H$_{23}$BrClOP requires C, 62.73; H, 4.66.

EXAMPLE 159

The Preparation of 2-[(E)-2-(2-Chloro-3-methoxyphenyl)ethenyl]-5-methoxy-1H-indole (570) (II, Ar=2-chloro-3-methoxyphenyl) and 2-chloro-3-[(E)-2-(5-methoxy-1H-indol-2-yl)ethenyl]phenol (571) (II, Ar=2-chloro-3-hydroxyphenyl)

The 5-methoxy-1H-indole-2-carbaldehyde (1) was reacted with very crude (2-chloro-3-methoxybenzyl)(triphenyl)phosphonium bromide (569) prepared as described in example 158 using the procedure described in example 37, except that the LDA and aldehyde were sequentially added at 0° C., the ratio of LDA:aldehyde was 1.5:1 and the reaction time was 5 h, to give a crude mixture of dienes, which were chromatographed on silica gel. Elution with 0–50% CH$_2$Cl$_2$/petroleum ether then elution with 60% CH$_2$Cl$_2$/petroleum ether gave (after crystallisation from CH$_2$Cl$_2$/pentane) the major product diene (570) as a pale yellow solid (the pure E isomer) (31%), mp 179–183° C. $^1$H NMR (CDCl$_3$) δ 8.22 (br s, 1H), 7.32 (d, J=16.4 Hz, 1H), 7.31 (dd, J=8.2, 1.4 Hz, 1H), 7.26 (d, J=8.7 Hz, 1H), 7.23 (t, J=8.0 Hz, 1H), 7.09 (d, J=16.5 Hz, 1H), 7.04 (d, J=2.4 Hz, 1H), 6.87 (dd, J=8.7, 2.5 Hz, 1H), 6.85 (d, J=7.8, 1.3 Hz, 1H), 6.58 (d, J=1.6 Hz, 1H), 3.93 (s, 3H), 3.85 (s, 3H). Found: C, 68.79; H, 5.22; N, 4.51. C$_{18}$H$_{16}$ClNO$_2$ requires C, 68.90; H, 5.14; N, 4.46. Further elution of the column with 60% CH$_2$Cl$_2$/petroleum ether and CH$_2$Cl$_2$ gave (after crystallisation from CH$_2$Cl$_2$/pentane) the minor product diene (571) as a pale yellow solid (the pure E isomer) (25%), mp 172–175° C. $^1$H NMR (CDCl$_3$) δ 8.20 (br s, 1H), 7.27 (m, 1H), 7.26 (d, J=8.7 Hz, 1H), 7.19 (t, J=7.9 Hz, 1H), 7.18 (d, J=16.4 Hz, 1H), 7.10 (d, J=16.4 Hz, 1H), 7.04 (d, J=2.4 Hz, 1H), 6.95 (dd, J=8.1, 1.5 Hz, 1H), 6.88 (dd, J=8.8, 2.5 Hz, 1H), 6.60 (d, J=1.7 Hz, 1H), 5.65 (s, 1H), 3.86 (s, 3H). Found: C, 67.23; H, 4.72; N, 4.72. C$_{17}$H$_{14}$ClNO$_2$.1/4H$_2$O requires C, 67.11; H, 4.80; N, 4.60.

EXAMPLE 160

The Preparation of 4-(2-Chloro-3-hydroxyphenyl)-9-methoxypyrrolo[3,4-c]carbazole-1,3(2H,6H)-dione (572) (V, R$^{10}$=H, Ar=2-chloro-3-hydroxyphenyl)

A foil-covered mixture of the pure E diene (571) (110 mg, 0.367 mmol) prepared as described in example 159 and maleimide (180 mg, 1.85 mmol) in dry toluene (2 mL) was stirred in a sealed vial at reflux for 24 h (Method 4a). The resulting thick suspension was transferred to a flask using dioxane (5 mL), then treated with manganese dioxide (738 mg, 8.49 mmol), stirring at reflux under N$_2$ for 22 h (as decribed in the procedure for example 79), after addition of water and extraction with ethyl acetate. The organic phase was dried, the drying agent was removed and the solvent concentrated to dryness. Chromatography and crystallisation from THF/CH$_2$Cl$_2$/pentane the product (572) (34%) as an orange-brown solid, mp 280–290° C. (dec). $^1$H NMR [(CD$_3$)$_2$SO] δ 11.92 (br s, 1H), 11.04 (br s, 1H), 10.23 (br s, 1H), 8.46 (d, J=2.6 Hz, 1H), 7.57 (d, J=8.8 Hz, 1H), 7.52 (s, 1H), 7.24 (dd, J=8.9, 2.6 Hz, 1H), 7.21 (t, J=7.8 Hz, 1H), 7.05 (dd, J=8.2, 1.5 Hz, 1H), 6.88 (dd, J=7.5, 1.4 Hz, 1H), 3.89 (s, 3H). Found: C, 64.09; H, 3.48; N, 7.25. C$_{21}$H$_{13}$ClN$_2$O$_4$ requires C, 64.21; H, 3.34; N, 7.13.

EXAMPLE 161

The Preparation of 4-(2-Chloro-3-hydroxyphenyl)-9-hydroxypyrrolo[3,4-c]carbazole-1,3(2H,6H)-dione (573) (VI, R$^{10}$=H, Ar=2-chloro-3-hydroxyphenyl)

The methyl ether (572) prepared as described in example 160 was demethylated with BBr$_3$ using the procedure described in example 80, to give (after crystallisation from THF/CH$_2$Cl$_2$/pentane) the phenol (573) (91%) as a yellow-orange solid, mp 197–203° C. (dec). $^1$H NMR [(CD$_3$)$_2$SO] δ 11.78 (br s, 1H), 10.98 (br s, 1H), 10.17 (br s, 1H), 9.26 (s, 1H), 8.31 (d, J=2.4 Hz, 1H), 7.47 (s, 1H), 7.45 (d, J=8.7 Hz, 1H), 7.20 (t, J=7.8 Hz, 1H), 7.07 (dd, J=8.7, 2.5 Hz, 1H), 7.04 (dd, J=8.3, 1.5 Hz, 1H), 6.87 (dd, J=7.5, 1.4 Hz, 1H). Found: C, 62.06; H, 3.29; N, 7.36. C$_{20}$H$_{11}$ClN$_2$O$_4$.1/2H$_2$O requires C, 61.95; H, 3.12; N, 7.22.

EXAMPLE 162

The Preparation of (2-Chloro-4-methoxybenzyl)(triphenyl)phosphonium bromide (574)

Bromination of (2-chloro-4-methoxyphenyl)methanol with 30% HBr in acetic acid, followed by reaction of the crude bromide with triphenylphosphine, using the procedure described in example 112, except that the reaction time for the bromination was 4 h and the reaction time for the displacement was 28 h, gave the phosphonium salt (574) (100%) as a white solid, mp (CH$_2$Cl$_2$/benzene) 223–226° C. $^1$H NMR (CDCl$_3$) δ 7.82–7.61 (m, 15H), 7.53 (dd, J=8.4, 2.7 Hz, 1H), 6.72 (d, J=2.8 Hz, 1H), 6.70 (dd, J=8.9, 2.5 Hz, 1H), 5.57 (d, J=13.6 Hz, 2H), 3.74 (s, 3H). Found: C, 63.05; H, 4.74. C$_{26}$H$_{23}$BrClOP requires C, 62.73; H, 4.66.

EXAMPLE 163

The Preparation of 2-[(E)-2-(2-Chloro-4-methoxyphenyl)ethenyl]-5-methoxy-1H-indole (575) (II, Ar=2-chloro-4-methoxyphenyl)

The 5-methoxy-1H-indole-2-carbaldehyde (1) was reacted with (2-chloro-4-methoxybenzyl)(triphenyl)phosphonium bromide (574) prepared as described in example 162 using the procedure described in example 37, except that the LDA and aldehyde were sequentially added at 0° C., the ratio of LDA:aldehyde was 1.5:1 and the reaction time was 5 h, to give (after crystallisation from $CH_2Cl_2$/pentane) the diene (575) as a pale yellow solid (the pure E isomer) (64%), mp 129–132° C. $^1H$ NMR ($CDCl_3$) δ 8.17 (br s, 1H), 7.60 (d, J=8.8 Hz, 1H), 7.25 (d, J=8.3 Hz, 1H), 7.19 (d, J=16.5 Hz, 1H), 7.03 (d, J=2.4 Hz, 1H), 6.96 (d, J=17.3 Hz, 1H), 6.94 (d, J=2.4 Hz, 1H), 6.86 (dd, J=8.7, 2.6 Hz, 1H), 6.85 (dd, J=8.7, 2.8 Hz, 1H), 6.54 (d, J=1.7 Hz, 1H), 3.85 (s, 3H), 3.83 (s, 3H). Found: C, 69.05; H, 5.41; N, 4.68. $C_{18}H_{16}ClNO_2$ requires C, 68.90; H, 5.14; N, 4.46.

EXAMPLE 164

The Preparation of 4-(2-Chloro-4-methoxyphenyl)-9-methoxypyrrolo[3,4-c]carbazole-1,3(2H,6H)-dione (576) (V, $R^{10}$=H, Ar=2-chloro-4-methoxyphenyl)

The pure E diene (575) prepared as described in example 163 was subjected to successive reactions with maleimide and then DDQ according to the above representative procedure described in example 123, to give (after crystallisation from THF/pentane) the product (576) (86%) as a yellow-orange solid, mp 284–286° C. $^1H$ NMR [$(CD_3)_2SO$] δ 11.93 (br s, 1H), 11.06 (br s, 1H), 8.46 (d, J=2.6 Hz, 1H), 7.56 (d, J=8.9 Hz, 1H), 7.54 (s, 1H), 7.41 (d, J=8.5 Hz, 1H), 7.24 (dd, J=8.9, 2.6 Hz, 1H), 7.15 (d, J=2.6 Hz, 1H), 7.01 (dd, J=8.5, 2.6 Hz, 1H), 3.89 (s, 3H), 3.86 (s, 3H). Found: C, 65.30; H, 4.79; N, 5.82. $C_{22}H_{15}ClN_2O_4$.THF requires C, 65.20; H, 4.84; N, 5.85.

EXAMPLE 165

The Preparation of 4-(2-Chloro-4-hydroxyphenyl)-9-hydroxypyrrolo[3,4-c]carbazole-1,3(2H,6H)-dione (577) (VI, $R^{10}$=H, Ar=2-chloro-4-hydroxyphenyl)

The methyl ether (576) prepared as described in example 164 was bis-demethylated with $BBr_3$ using the procedure described in example 80, except that the reaction time was 5 h with 10 equiv. $BBr_3$, to give (after crystallisation from THF/$CH_2Cl_2$/pentane) the phenol (577) (90%) as a yellow-orange solid, mp 330–340° C. (dec). $^1H$ NMR [$(CD_3)_2SO$] δ 11.75 (br s, 1H), 10.97 (br s, 1H), 10.00 (br s, 1H), 9.25 (s, 1H), 8.31 (d, J=2.4 Hz, 1H), 7.47 (s, 1H), 7.44 (d, J=8.7 Hz, 1H), 7.27 (d, J=8.4 Hz, 1H), 7.06 (dd, J=8.7, 2.5 Hz, 1H), 6.93 (d, J=2.5 Hz, 1H), 6.82 (dd, J=8.3, 2.4 Hz, 1H). Found: C, 62.63; H, 3.44; N, 7.10. $C_{20}H_{11}ClN_2O_4$.1/4$H_2O$ requires C, 62.68; H, 3.02; N, 7.31.

EXAMPLE 166

The Preparation of (2-Chloro-5-methoxybenzyl)(triphenyl)phosphonium bromide (578)

Bromination of 1-chloro-4-methoxy-2-methylbenzene with NBS/AIBN, followed by reaction of the crude bromide with triphenylphosphine, using the procedure described in example 102, except that the reaction time for the bromination was 4 h, gave the phosphonium salt (578) (76%) as a light brown solid, mp ($CH_2Cl_2$/benzene) 189–190.5° C. $^1H$ NMR ($CDCl_3$) δ 7.82–7.61 (m, 15H), 7.21 (t, J=2.8 Hz, 1H), 7.04 (dd, J=8.8, 0.8 Hz, 1H), 6.76 (dt, J=8.9, 2.7 Hz, 1H), 5.59 (d, J=14.4 Hz, 2H), 3.58 (s, 3H). Found: C, 62.75; H, 4.70. $C_{26}H_{23}BrClOP$ requires-C, 62.73; H, 4.66.

EXAMPLE 167

The Preparation of 2-[(E)-2-(2-Chloro-5-methoxyphenyl)ethenyl]-5-methoxy-1H-indole (579) (II, Ar=2-chloro-5-methoxyphenyl)

The 5-methoxy-1H-indole-2-carbaldehyde (1) was reacted with (2-chloro-5-methoxybenzyl)(triphenyl)phosphonium bromide (578) prepared as described in example 166 using the procedure described in example 37, except that the LDA and aldehyde were (sequentially) added at 0° C., the ratio of LDA:aldehyde was 1.5:1 and the reaction time was 5 h, to give (after crystallisation from $CH_2Cl_2$/hexane) the diene (579) as a pale yellow solid (the pure E isomer) (85%), mp 119–121° C. $^1H$ NMR ($CDCl_3$) δ 8.22 (br s, 1H), 7.29 (d, J=8.9 Hz, 1H), 7.26 (br d, J=8.7 Hz, 1H), 7.22 (d, J=16.5 Hz, 1H), 7.18 (d, J=3.0 Hz, 1H), 7.06 (d, J=16.7 Hz, 1H), 7.04 (br s, 1H), 6.88 (dd, J=8.7, 2.5 Hz, 1H), 6.77 (dd, J=8.8, 3.0 Hz, 1H), 6.59 (d, J=1.8 Hz, 1H), 3.86 (s, 3H), 3.85 (s, 3H). Found: C, 68.70; H, 5.11; N, 4.37. $C_{18}H_{16}ClNO_2$ requires C, 68.90; H, 5.14; N, 4.46.

EXAMPLE 168

The Preparation of 4-(2-Chloro-5-methoxyphenyl)-9-methoxypyrrolo[3,4-c]carbazole-1,3(2H,6H)-dione (580) (V, $R^{10}$=H, Ar=2-chloro-5-methoxyphenyl)

The pure E diene (579) prepared as described in example 167 was subjected to successive reactions with maleimide and then DDQ according to the above representative procedure described in example 123, to give (after crystallisation from MeOH/$CH_2Cl_2$/hexane) the product (580) (84%) as a bright orange solid, mp 284–286° C. $^1H$ NMR [$(CD_3)_2SO$] δ 11.96 (br s, 1H), 11.08 (br s, 1H), 8.46 (d, J=2.6 Hz, 1H), 7.58 (s, 1H), 7.57 (m, 1H), 7.46 (d, J=8.7 Hz, 1H), 7.25 (dd, J=8.8, 2.6 Hz, 1H), 7.07 (d, J=2.9 Hz, 1H), 7.04 (dd, J=8.7, 3.1 Hz, 1H), 3.89 (s, 3H), 3.80 (s, 3H). Found: C, 62.50; H, 3.77; N, 6.54. $C_{22}H_{15}ClN_2O_4$.$H_2O$ requires C, 62.20; H, 4.03; N, 6.59.

EXAMPLE 169

The Preparation of 4-(2-Chloro-5-hydroxyphenyl)-9-hydroxypyrrolo[3,4-c]carbazole-1,3(2H,6H)-dione (581) (VI, $R^{10}$=H, Ar=2-chloro-5-hydroxyphenyl)

The methyl ether (580) prepared as described in example 168 was bis-demethylated with $BBr_3$ using the procedure described in example 80, except that the reaction time was 6.5 h with 10 equiv. $BBr_3$, to give (after crystallisation from MeOH/$CH_2Cl_2$/hexane) the phenol (581) (90%) as an orange-red crystalline solid, mp 335–340° C. $^1H$ NMR [$(CD_3)_2SO$] δ 11.80 (br s, 1H), 11.00 (br s, 1H), 9.78 (br s, 1H), 9.27 (br s, 1H), 8.31 (d, J=2.4 Hz, 1H), 7.49 (s, 1H), 7.45 (d, J=8.7 Hz, 1H), 7.32 (d, J=8.5 Hz, 1H), 7.07 (dd, J=8.7, 2.5 Hz, 1H), 6.84 (dd, J=8.5, 2.9 Hz, 1H), 6.82 (d, J=2.8 Hz, 1H). Found: C, 63.25; H, 3.63; N, 6.73. $C_{20}H_{11}ClN_2O_4$.1/2$H_2O$.1/4

SCHEME 3

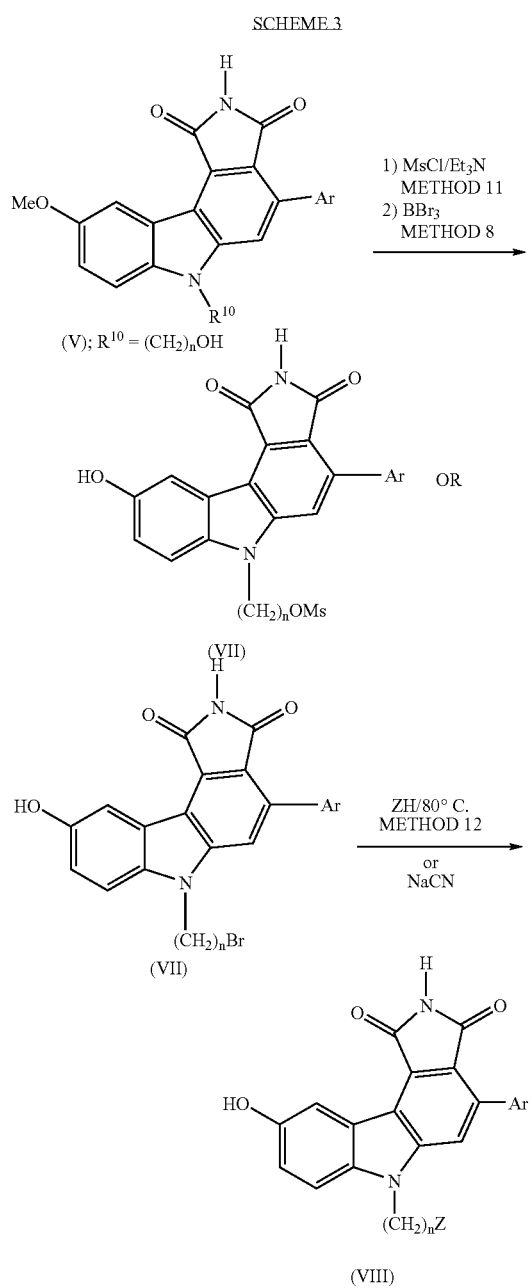

Hexane requires C, 63.09; H, 3.82; N, 6.84.

Scheme 3 Procedures

Representative Procedure for Method 11 of Scheme 3

EXAMPLE 170

The Preparation of 2-(4-(2-Chlorophenyl)-9-methoxy-1,3-dioxo-2,3-dihydropyrrolo[3,4-c]carbazol-6(1H)-yl)ethyl methanesulfonate (V; Ar=2-chlorophenyl, $R^{10}$=CH$_2$CH$_2$OSO$_2$CH$_3$ (228)

Alcohol (46) prepared as described in example 43 (1.10 g, 2.61 mmol) was dissolved in dry tetrahydrofuran (80 mL) under nitrogen. The resulting solution was cooled to 0° C. and triethylamine (2.0 mL) was added followed by methanesulfonyl chloride (263 mL, 3.40 mmol) dropwise. After 30 minutes a further portion of methanesulfonyl chloride (50 mL) was added and then after another 30 minutes the reaction was diluted with saturated sodium bicarbonate and extracted with ethyl acetate. The organic layer was dried, the drying agent was removed and the solution was concentrated to drynessCrystallisation from ethyl acetate/hexane gave mesylate (228) (0.96 g, 74%) as a yellow solid, mp 254° C. (dec). $^1$H NMR δ [(CD$_3$)$_2$SO] 11.15 (s, 1H), 8.53 (d, J=2.6 Hz, 1H), 7.90 (s, 1H), 7.74 (d, J=9.0 Hz, 1H), 7.58 (m, 1H), 7.48 (m, 3H), 7.33 (dd, J=9.0, 2.6 Hz, 1H), 4.89 (t, J=5.0 Hz, 2H), 4.56 (m, 2H), 3.91 (s, 3H), 2.94 (s, 3H). FABMS found [M+H]$^+$: 499.0694, 501.0696. C$_{24}$H$_{19}$ClN$_2$O$_6$S requires 499.0731, 501.0701.

EXAMPLE 171

The Preparation of 2-(4-(2-Chlorophenyl)-9-hydroxy-1,3-dioxo-2,3-dihydropyrrolo[3,4-c]carbazol-6(1H)-yl)ethyl methanesulfonate (VII; Ar=2-chlorophenyl, n=2, mesylate) (229)

Mesylate (228) (1.23 g, 2.48 mmol) prepared as described in example 170 was reacted according to the procedure described in example 80, except that the reaction time was 7 hours, after which chromatography on silica eluting with ethyl acetate/hexane (1:1 to 3:1) and trituration from ethyl acetate/hexane gave phenol (229) (1.05 g, 87%) as a yellow solid, mp 266° C. (dec). $^1$H NMR δ [(CD$_3$)$_2$SO] 11.09 (br s, 1H), 9.40 (s, 1H), 8.39 (d, J=2.5 Hz, 1H), 7.84 (s, 1H), 7.62 (d, J=8.9 Hz, 1H), 7.58 (m, 1H), 7.48 (m, 3H), 7.14 (dd, J=8.9, 2.5 Hz, 1H), 4.85 (t, J=5.0 Hz, 2H), 4.54 (m, 2H), 2.93 (s, 3H). Found: C, 58.13; H, 3.74; N, 5.72. C$_{23}$H$_{17}$ClN$_2$O$_6$S.1/4hexane requires C, 58.10; H, 4.08; N, 5.53.

EXAMPLE 172

The Preparation of 6-(3-Bromopropyl)-4-(2-chlorophenyl)-9-hydroxypyrrolo[3,4-c]carbazole-1,3(2H,6H)-dione (VII, Ar=2-chlorophenyl, n=3, bromide) (58)

Reaction of alcohol (31) prepared as described in example 40 with methanesulfonyl chloride, followed by demethylation with BBr$_3$ following the proceedure described in example 170 gave the bromide (58) (81%), orange powder, mp 278° C. (dec). $^1$H NMR δ [(CD$_3$)$_2$SO] 11.08 (s, 1H), 9.39 (s, 1H), 8.39 (d, J=2.4 Hz, 1H), 7.81 (s, 1H), 7.60 (d, J=8.7 Hz, 1H), 7.60–7.58 (m, 1H), 7.53–7.43 (m, 3H), 7.16 (dd, J=8.7, 2.4 Hz, 1H), 4.55 (t, J=6.9 Hz, 2H), 3.56–3.49 (m, 2H), 2.34–2.24 (m, 2H). Found: C, 56.94; H, 3.45, N, 5.69. C$_{23}$H$_{16}$BrClN$_2$O$_3$ requires C, 57.10; H, 3.33; N, 5.79.

EXAMPLE 173

The Preparation of 6-(3-Bromopropyl)-9-hydroxy-4-phenylpyrrolo[3,4-c]carbazole-1,3(2H,6H)-dione (VII; Ar=phenyl, n=3, bromide) (204)

Alcohol (202) prepared as described in example 83 (0.50 g, 1.25 mmol) was reacted according to the proceedure described in example 170 followed by the procedure described in example 80. Chromatography on silica eluting with ethyl acetate/hexane (1:1 to 4: 1) followed by crystallisation from ethyl acetate/hexane gave bromide (204) (0.54 g, 97%) as an orange powder, mp 280–282° C. $^1$H NMR δ [(CD$_3$)$_2$SO] 11.07 (s, 1H), 9.36 (s, 1H), 8.41 (d, J=2.2 Hz, 1H), 7.83 (s, 1H), 7.66 (m, 2H), 7.58 (d, J=8.8 Hz, 1H), 7.47

(m, 3H), 7.14 (dd, J=8.8, 2.2 Hz, 1H), 4.57 (t, J=6.9 Hz, 2H), 3.53 (t, J=6.5 Hz, 2H), 2.32 (m, 2H). Found: C, 61.87; H, 3.69; N, 6.59. $C_{23}H_{17}BrN_2O_3$ requires: C, 61.48; H, 3.81; N, 6.23.

EXAMPLE 174

The Preparation of 2-(9-Hydroxy-1,3-dioxo-4-phenyl-2,3-dihydropyrrolo[3,4-c]carbazol-6 (1H)-yl) ethyl methanesulfonate (VII; Ar=phenyl, n=2, mesylate) (205)

Alcohol (201) (0.21 g, 0.53 mmol) prepared as described in example 82 was reacted according to the proceedure described in example 170 followed by the procedure described in example 80. Chromatography on silica eluting with ethyl acetate/hexane (1:1 to 4:1) followed by crystallisation from ethyl acetate/hexane gave mesylate (205) (0.19 g, 80%) as a yellow solid, mp 271–276° C. $^1$H NMR δ [(CD$_3$)$_2$SO] 11.08 (s, 1H), 9.37 (br s, 1H), 8.40 (d, J=2.4 Hz, 1H), 7.86 (s, 1H), 7.67 (m, 2H), 7.60 (d, J=8.8 Hz, 1H), 7.46 (m, 3H), 7.13 (dd, J=8.8, 2.4 Hz, 1H), 4.86 (t, J=4.8 Hz, 2H), 4.57 (t, J=4.8 Hz, 2H), 2.97 (s, 3H). FABMS found [M+H]$^+$: 451.0958. $C_{23}H_{18}N_2O_6S$ requires 451.0964.

EXAMPLE 175

The Preparation of 6-(6-Bromohexyl)-9-hydroxy-4-phenylpyrrolo[3,4-c]carbazole-1,3(2H,6H)-dione (VII; Ar=phenyl, n=6, bromide) (206)

Alcohol (203) (0.30 g, 0.67 mmol) prepared as described in example 84 was reacted according to the proceedure described in example 170 followed using the procedure described in example 80. Chromatography on silica eluting with ethyl acetate/hexane (1:1 to 4:1) followed by crystallisation from ethyl acetate/hexane gave bromide (206) (0.29 g, 88%) as a orange solid, mp 214–216° C. $^1$H NMR δ [(CD$_3$)$_2$SO] 11.04 (s, 1H), 9.33 (s, 1H), 8.41 (d, J=2.4 Hz, 1H), 7.78 (s, 1H), 7.65 (m, 2H), 7.56 (d, J=8.8 Hz, 1H), 7.46 (m, 3H), 7.13 (dd, J=8.8, 2.4 Hz, 1H), 4.46 (t, J=7.1 Hz, 2H), 3.46 (t, J=6.7 Hz, 2H), 1.74 (m, 4H), 1.41–1.29 (m, 4H). Found: C, 63.75; H, 4.72; N, 5.94. $C_{26}H_{23}BrN_2O_3$ requires: C, 63.66; H, 4.73; N, 5.71.

EXAMPLE 176

The Preparation of 6-(3-Bromopropyl)-4-(2-chloro-6-methoxyphenyl)-9-hydroxypyrrolo[3,4-c]carbazole-1,3(2H,6H)-dione (VII; Ar=2-chloro-6-methoxyphenyl, n=3, bromide) (207)

Alcohol (105) (0.20 g, 0.43 mmol) prepared as described in example 58 was reacted according to the proceedure described in example 170 followed using the procedure described in example 80, except that the boron tribromide reaction was performed at 0° C. for 2 h and the subsequent worked-up crude was then dissolved in ethyl acetate (100 mL) to which lithium bromide (1.0 g) was added. This solution was warmed to 50° C. for 2 h before being absorbed onto silica and chromatographed eluting with ethyl acetate/hexane (1:3 to 1:1) to give bromide (207) (132 mg, 60%) as a yellow solid, mp 286–288° C. $^1$H NMR δ [(CD$_3$)$_2$SO] 11.03 (s, 1H), 9.38 (s, 1H), 8.38 (d, J=2.4 Hz, 1H), 7.77 (s, 1H), 7.58 (d, J=8.2 Hz, 1H), 7.44 (t, J=8.8 Hz, 1H), 7.18 (d, J=8.8 Hz, 1H), 7.14 (m, 2H), 4.54 (t, J=7.0 Hz, 2H), 3.52 (t, J=6.8 Hz, 2H), 2.27 (m, 2H). FABMS found [M+H]$^+$: 513.0182, 515.0192, 517.0169. $C_{14}H_{18}BrClN_2O_4$ requires 513.0217, 515.0196, 515.0187, 517.0167.

EXAMPLE 177

The Preparation of 2-(4-(2,6-Dichlorophenyl)-9-hydroxy-1,3-dioxo-2,3-dihydropyrrolo[3,4-c]carbazol-6 (1H)-yl)ethyl methanesulfonate (VII; Ar=2,6-dichlorophenyl, n=2, mesylate) (231)

Alcohol (230) (1.0 g, 2.2 mmol) prepared as described in example 85 was reacted according to the proceedure described in example 170 followed by the procedure described in example 80, except that the reaction time with boron tribromide was 30 h. Chromatography on silica eluting with ethyl acetate/hexane (1:1 to 4:1) followed by crystallisation from ethyl acetate/hexane gave mesylate (231) (0.95 g, 83%) as a yellow solid, mp 255–260° C. $^1$H NMR δ [(CD$_3$)$_2$SO] 11.16 (br s, 1H), 9.43 (br s, 1H), 8.38 (d, J=2.5 Hz, 1H), 7.91 (s, 1H), 7.63 (m, 3H), 7.51 (dd, J=8.7, 7.3 Hz, 1H), 7.16 (dd, J=8.9, 2.5 Hz, 1H), 4.85 (t, J=4.9 Hz, 2H), 4.53 (t, J=4.9 Hz, 2H), 2.88 (s, 3H). Found: C, 53.48; H, 3.22; N, 5.23. $C_{23}H_{16}Cl_2N_2O_6S$ requires: C, 53.18; H, 3.10; N, 5.39.

EXAMPLE 178

The Preparation of 6-(3-Bromopropyl)-4-(2,6-dichlorophenyl)-9-hydroxypyrrolo[3,4-c]carbazole-1,3(2H,6H)-dione (VII; Ar=2,6-dichlorophenyl, n=3, bromide) (233)

Alcohol (232) (0.77 g, 1.68 mmol) prepared as described in example 86 was reacted according to the proceedure described in example 170 followed by the procedure described in example 80, except that the reaction time with boron tribromide was 18 h. Chromatography on silica eluting with ethyl acetate/hexane (1:1 to 4:1) followed by crystallisation from ethyl acetate/hexane gave bromide (233) (0.70 g, 80%) as an orange solid, mp 273–276° C. $^1$H NMR δ [(CD$_3$)$_2$SO] 11.15 (br s, 1H), 9.42 (s, 1H), 8.38 (d, J=2.4 Hz, 1H), 7.87 (s, 1H), 7.62 (m, 3H), 7.51 (dd, J=8.9, 7.6 Hz, 1H), 7.18 (dd, J=8.8, 2.4 Hz, 1H), 4.56 (t, J=6.9 Hz, 2H), 3.51 (t, J=6.7 Hz, 2H), 2.27 (m, 2H). Found: C, 53.44; H, 2.96; N, 5.23. $C_{23}H_{15}BrCl_2N_2O_3$ requires: C, 53.30; H, 2.92; N, 5.40.

Representative Procedure for Method 12 of Scheme 3

EXAMPLE 179

The Preparation of 6-[3-(Dimethylamino)propyl]-9-hydroxy-4-phenylpyrrolo[3,4-c]carbazole-1,3(2H,6H)-dione (VIII: Ar=phenyl, n=3, Z=NMe$_2$) (208)

To a solution of bromide (204) prepared as described in example 173 (0.12 g, 0.27 mmol) in dimethylacetamide (4 mL) was added the amine, dimethylamine (25 mol eq., 0.85 mL in this case as an 40% aqueous solution). The reaction vessel was sealed and heated at 80° C. with stirring for 18 h, before being diluted with water. The resulting solution was then acidified by the dropwise addition of concentrated hydrochloric acid and the pH was then adjusted to approximately pH=9 by the addition of solid potassium carbonate. The precipitated product was either collected by filtration and washed with water and diisopropyl ether before being dried or extracted with ethyl acetate. The organic layer was dried, the drying agent was removed and the solution was concentrated to dryness. Chromatography on silica eluting with methanol/dichloromethane (1:9 to 1:4), followed by trituration in ethyl acetate/hexane gave amine (208) (52 mg, 47%) as a yellow powder, mp 185–189° C. $^1$H NMR δ [(CD$_3$)$_2$SO] 11.05 (s, 1H), 9.34 (s, 1H), 8.41 (d, J=2.4 Hz, 1H), 7.78 (s, 1H), 7.64 (m, 2H), 7.56 (d, J=8.9 Hz, 1H), 7.47 (m, 3H), 7.14 (dd, J=8.9, 2.4 Hz, 1H), 4.48 (t, J=6.6 Hz, 2H), 2.16 (t, J=6.5 Hz, 2H), 2.08 (s, 6H), 1.90 (m, 2H). Found: C, 71.98; H, 5.67; N, 10.14. $C_{25}H_{23}N_3O_3 \cdot 1/4H_2O$ requires: C, 71.84; H, 5.67; N, 10.05.

EXAMPLE 180

The Preparation of 6-[2-(Dimethylamino)ethyl]-9-hydroxy-4-phenylpyrrolo[3,4-c]carbazole-1,3(2H, 6H)-dione (VIII; Ar=phenyl, n=2, Z=NMe$_2$) (209)

Mesylate (205) prepared as described in example 174 (70 mg, 0.16 mmol) was reacted with aqueous dimethylamine solution according to the procedure described in example 179 to give amine (209) (30 mg, 48%) as a yellow powder, mp 283–286° C. $^1$H NMR δ [(CD$_3$)$_2$SO] 11.05 (br s, 1H), 9.33 (s, 1H), 8.41 (d, J=2.4 Hz, 1H), 7.77 (s, 1H), 7.65 (m, 2H), 7.54 (d, J=8.8 Hz, 1H), 7.46 (m, 3H), 7.12 (dd, J=8.8, 2.4 Hz, 1H), 4.55 (t, J=6.5 Hz, 2H), 2.62 (t, J=6.5 Hz, 2H), 2.19 (s, 6H). Found: C, 71.92; H, 5.16; N, 10.55. $C_{24}H_{21}N_3O_3$ requires: C, 72.17; H, 5.30; N, 10.52.

EXAMPLE 181

The Preparation of 9-Hydroxy-6-[3-(4-morpholinyl)propyl]-4-phenylpyrrolo[3,4-c]carbazole-1,3(2H, 6H)-dione (VIII; Ar=phenyl, n=3, Z=4-morpholinyl) (210)

Bromide (204) (0.01 g, 0.22 mmol) prepared as described in example 173 was reacted with morpholine according to the procedure described in example 179 to give amine (210) (73 mg, 72%) as a yellow powder, mp 252–255° C. $^1$H NMR δ [(CD$_3$)$_2$SO] 11.04 (br s, 1H), 9.33 (s, 1H), 8.41 (d, J=2.5 Hz, 1H), 7.81 (s, 1H), 7.62 (m, 2H), 7.57 (d, J=8.9 Hz, 1H), 7.47 (m, 3H), 7.12 (dd, J=8.9, 2.5 Hz, 1H), 4.51 (t, J=6.3 Hz, 2H), 3.38 (t, J=4.0 Hz, 4H), 2.18 (br s, 4H), 2.14 (t, J=6.3 Hz, 2H), 1.93 (m, 2H). Found: C, 71.11; H, 5.46; N, 9.29. $C_{27}H_{25}N_3O_4$ requires: C, 71.19; H, 5.53; N, 9.22.

EXAMPLE 182

The Preparation of 9-Hydroxy-6-[2-(4-morpholinyl)ethyl]-4-phenylpyrrolo[3,4-c]carbazole-1,3(2H,6H)-dione (VIII; Ar=phenyl, n=2, Z=4-morpholinyl) (211)

Mesylate (205) (70 mg, 0.16 mmol) prepared as described in example 174 was reacted with morpholine according to the procedure described in example 179 to give amine (211) (53 mg, 75%) as a yellow powder, mp 260–262° C. $^1$H NMR □ [(CD$_3$)$_2$SO] $^1$H NMR δ [(CD$_3$)$_2$SO] 11.04 (br s, 1H), 9.33 (s, 1H), 8.40 (d, J=2.5 Hz, 1H), 7.78 (s, 1H), 7.64 (m, 2H), 7.54 (d, J=8.9 Hz, 1H), 7.47 (m, 3H), 7.12 (dd, J=8.9, 2.5 Hz, 1H), 4.57 (t, J=6.4 Hz, 2H), 3.45 (t, J=4.5 Hz, 4H), 2.67 (t, J=6.4 Hz, 2H), 2.18 (br t, J=4 Hz, 4H). Found: C, 70.55; H, 5.25; N, 9.22. $C_{26}H_{23}N_3O_4$ requires: C, 70.74; H, 5.25; N, 9.51.

EXAMPLE 183

The Preparation of 9-Hydroxy-6-[3-(1H-imidazol-1-yl)propyl]-4-phenylpyrrolo[3,4-c]carbazole-1,3(2H, 6H)-dione (VIII; Ar=phenyl, n=3, Z=1-imidazolyl) (212)

Bromide (204) (80 mg, 0.18 mmol) prepared as described in example 173 was reacted with imidazole according to the procedure described in example 179 to give amine (212) (41 mg, 53%) as a yellow powder, mp 309–311° C. $^1$H NMR δ [(CD$_3$)$_2$SO] 11.06 (s, 1H), 9.36 (s, 1H), 8.40 (d, J=2.3 Hz, 1H), 7.69 (s, 1H), 7.64 (m, 3H), 7.47 (m, 4H), 7.22 (s, 1H), 7.14 (dd, J=8.8, 2.3 Hz, 1H), 6.89 (s, 1H), 4.44 (t, J=7.4 Hz, 2H), 4.07 (t, J=7.3 Hz, 2H), 2.24 (m, 2H). Found: C, 70.31; H, 4.78; N, 12.43. $C_{26}H_{20}N_4O_3 \cdot 1/2H_2O$ requires: C, 70.10; H, 4.75; N, 12.57.

EXAMPLE 184

The Preparation of 9-Hydroxy-6-[2-(1H-imidazol-1-yl)ethyl]-4-phenylpyrrolo[3,4-c]carbazole-1,3(2H, 6H)-dione (VIII; Ar=phenyl, n=2. Z=1-imidazolyl) (213)

Mesylate (205) (70 mg, 0.16 mmol) prepared as described in example 174 was reacted with imidazole according to the procedure described in example 179 to give amine (213) (34 mg, 50%) as a yellow powder, mp>345° C. $^1$H NMR δ [(CD$_3$)$_2$SO] 11.05 (br s, 1H), 9.34 (s, 1H), 8.39 (d, J=2.4 Hz, 1H), 7.59 (m, 2H), 7.45 (m, 5H), 7.27 (s, 1H), 7.06 (dd, J=8.8, 2.4 Hz, 1H), 7.02 (s, 1H), 6.75 (s, 1H), 4.80 (t, J=5.7 Hz, 2H), 4.41 (t, J=5.7 Hz, 2H). Found: C, 70.36; H, 4.38; N, 12.68. $C_{25}H_{18}N_4O_3 \cdot 1/4H_2O$ requires: C, 70.33; H, 4.37; N, 13.12.

EXAMPLE 185

The Preparation of 9-Hydroxy-6-[3-(methylamino)propyl]-4-phenylpyrrolo[3,4-c]carbazole-1,3(2H, 6H)-dione (VIII; Ar=phenyl, n=3, Z=NHMe) (214)

Bromide (204) (40 mg, 0.09 mmol) prepared as described in example 173 was reacted with aqueous methylamine solution (10 mol equiv.) according to the procedure described in example 179 except that the reaction was performed in dimethylsulfoxide at room temperature for 3 h, to give amine (214) (22 mg, 61%) as an orange/yellow powder, mp 265–268° C. $^1$H NMR δ [(CD$_3$)$_2$SO] 9.33 (br s, 1H), 8.41 (d, J=2.5 Hz, 1H), 7.80 (s, 1H), 7.64 (m, 2H), 7.57 (d, J=8.8 Hz, 1H), 7.47 (m, 3H), 7.14 (dd, J=8.8, 2.5 Hz, 1H), 4.51 (t, J=6.8 Hz, 2H), 2.40 (t, J=6.5 Hz, 2H), 2.20 (s, 3H), 1.88 (m, 2H). FABMS found [M+H]$^+$:400.1659. $C_{24}H_{22}N_3O_3$ requires 400.1661.

EXAMPLE 186

The Preparation of 9-Hydroxy-4-phenyl-6-[3-(1-piperazinyl)propyl]pyrrolo[3,4-c]carbazole-1,3(2H, 6H)-dione (VIII; Ar=phenyl, n=3, Z=1-piperazinyl) (215)

Bromide (204) (70 mg, 0.16 mmol) prepared as described in example 173 was reacted with piperazine according to The procedure described in example 179 except that the reaction was performed at room temperature for 20 h, to give amine (215) (40 mg, 55%) as a yellow powder, mp 178–183° C. $^1$H NMR δ [(CD$_3$)$_2$SO] 11.0 (br s, 1H), 9.35 (br s, 1H), 8.40 (d, J=2.4 Hz, 1H), 7.78 (s, 1H), 7.62 (m, 2H), 7.56 (d, J=8.8 Hz, 1H), 7.45 (m, 3H), 7.14 (dd, J=8.8, 2.4 Hz, 1H), 4.49 (t, J=6.3 Hz, 2H), 2.52 (m, 4H), 2.12 (m, 6H), 1.91 (m, 2H). Found: C, 69.31; H, 5.97; N, 11.49. C$_{27}$H$_{26}$N$_4$O$_3$.4/5H$_2$O requires: C, 69.16; H, 5.93; N, 11.94.

EXAMPLE 187

The Preparation of 6-[3-(Benzylamino)propyl-yl-9-hydroxy-4-phenylpyrrolo[3,4-c]carbazole-1,3(2H,6H)-dione (VIII; Ar=phenyl, n=3, Z=NHBn) (216)

Bromide (204) (75 mg, 0.17 mmol) prepared as described in example 173 was reacted with benzylamine according to the procedure described in example 179 except that the reaction was performed at room temperature for 20 h, to give amine (216) (36 mg, 45%) as a yellow powder, mp 139–144° C. $^1$H NMR δ [(CD$_3$)$_2$SO] 11.04 (br s, 1H), 9.33 (br s, 1H), 8.41 (d, J=2.4 Hz, 1H), 7.80 (s, 1H), 7.62 (m, 2H), 7.57 (d, J=8.8 Hz, 1H), 7.44 (m, 3H), 7.24–7.19 (m, 5H), 7.11 (dd, J=8.8, 2.4 Hz, 1H), 4.53 (t, J=6.7 Hz, 2H), 3.57 (s, 2H), 2.46 (t, J=6.4 Hz, 2H), 1.92 (m, 2H). Found: C, 74.84; H, 5.39; N, 8.80. C$_{30}$H$_{25}$N$_3$O$_3$.1/4H$_2$O requires: C, 75.06; H, 5.35; N, 8.75.

EXAMPLE 188

The Preparation of 6-(3-Anilinopropyl)-9-Hydroxy-4-phenylpyrrolo[3,4-c]carbazole-1,3(2H,6H)-dione (VIII; Ar=phenyl, n=3, Z=NHPh) (217)

Bromide (204) (75 mg, 0.17 mmol) prepared as described in example 173 was reacted with aniline according to the procedure described in example 179 except that the reaction was performed at room temperature for 20 h, to give aniline (217) (30 mg, 38%) as a yellow powder, mp 240° C. (dec). $^1$H NMR δ [(CD$_3$)$_2$SO] 11.04 (br s, 1H), 9.33 (s, 1H), 8.40 (d, J=2.4 Hz, 1H), 7.78 (s, 1H), 7.59 (d, J=8.9 Hz, 1H), 7.48 (m, 2H), 7.42 (m, 3H), 7.10 (dd, J=8.8, 2.4 Hz, 1H), 7.05 (m, 2H), 6.52 (m, 3H), 5.70 (t, J=5.3 Hz, 1H), 4.59 (t, J=6.8 Hz, 2H), 2.98 (t, J=6.3 Hz, 2H), 2.07 (m, 2H). Found: C, 74.00; H, 5.22; N, 8.76. C$_{29}$H$_{23}$N$_3$O$_3$.1/2H$_2$O requires: C, 74.03; H, 5.14; N, 8.93.

EXAMPLE 189

The Preparation of 4-(2-Chloro-6-methoxyphenyl)-6-{3-[cis-3,5-dimethylpiperazinyl]propyl}-9-hydroxypyrrolo[3,4-c]carbazole-1,3(2H,6H)-dione (VIII; Ar=2-chloro-6-methoxyphenyl, n=3, Z=1-(cis-3,5-dimethylpiperazinyl)) (218)

Bromide (207) (60 mg, 0.12 mmol), prepared as described in example 176, was reacted with cis-2,6-dimethylpiperazine according to the procedure described in example 179 except that the reaction was performed at room temperature for 20 h, to give amine (218) (63 mg, 98%) as a yellow powder, mp 199–202° C. $^1$H NMR δ [(CD$_3$)$_2$SO] 10.99 (br s, 1H), 9.37 (br s, 1H), 8.36 (d, J=2.4 Hz, 1H), 7.75 (s, 1H), 7.57 (d, J=8.8 Hz, 1H), 7.43 (t, J=8.2 Hz, 1H), 7.15 (m, 3H), 4.45 (t, J=6.1 Hz, 2H), 3.67 (s, 3H), 2.49 (m, 4H), 2.11 (m, 2H), 1.90 (m, 2H), 1.27 (m, 2H), 0.79 (d, 6H). Found: C, 61.35; H, 5.68; N, 9.14. C$_{30}$H$_{31}$ClN$_4$O$_4$.2¼H$_2$O requires: C, 61.32; H, 6.09; N, 9.54.

EXAMPLE 190

The Preparation of 4-(2-Chloro-6-methoxyphenyl)-9-hydroxy-6-[3-(4-morpholinyl)propyl])pyrrolo[3,4-c]carbazole-1,3(2H,6H)-dione (VIII; Ar=2-chloro-6-methoxyphenyl, n=3, Z=4-morpholinyl) (219)

Bromide (207) (60 mg, 0.12 mmol), prepared as described in example 176, was reacted with morpholine according to the procedure described in example 179 except that the reaction was performed at 50° C. for 6 h, to give amine (219) (40 mg, 66%) as a yellow powder, mp 169–174° C. $^1$H NMR δ [(CD$_3$)$_2$SO] 10.99 (br s, 1H), 9.34 (br s, 1H), 8.36 (d, J=2.4 Hz, 1H), 7.77 (s, 1H), 7.58 (d, J=8.8 Hz, 1H), 7.44 (t, J=8.2 Hz, 1H), 7.18 (d, J=8.2 Hz, 1H), 7.12 (m, 2H), 4.47 (t, J=6.1 Hz, 2H), 3.66 (s, 3H), 3.35 (t, J=4.4 Hz, 4H), 2.22–2.11 (m, 6H), 1.91 (m, 2H). Found: C, 63.09; H, 5.26; N, 7.97. C$_{28}$H$_{26}$ClN$_3$O$_5$.3/4H$_2$O requires: C, 63.04; H, 5.20; N, 7.88.

EXAMPLE 191

The Preparation of 4-(4-(2-Chlorophenyl)-9-hydroxy-1,3-dioxo-2,3-dihydropyrrolor[3,4-c]carbazol-6 (1H)-yl)butanenitrile (VIII; Ar=2-chlorophenyl, n=3. Z=CN) (241)

To a solution of bromide 0 (0.13 g, 0.27 mmol) prepared as described in example 172 in dimethylsulfoxide (2 mL) was added a solution of sodium cyanide (15 mg, 0.30 mmol) in dimethylsulfoxide (2 mL) dropwise over 15 minutes. After 30 minutes the reaction was diluted with water and extracted with ethyl acetate. The organic layer was dried, the drying agent was removed and the solution was concentrated to dryness. Chromatography on silica eluting with ethyl acetate/hexane (1:4 to 1:1), followed by crystallization from ethyl acetate/hexane gave nitrile (241) (68 mg, 59%) as an orange powder, mp 262–266° C. $^1$H NMR δ [(CD$_3$)$_2$SO] 11.08 (br s, 1H), 9.39 (s, 1H), 8.39 (d, J=2.4 Hz, 1H), 7.83 (s, 1H), 7.59 (m, 2H), 7.49 (m, 3H), 7.15 (dd, J=8.8, 2.4 Hz, 1H), 4.50 (t, J=7.3 Hz, 2H), 2.57 (m, 2H), 2.07 (m, 2H). FABMS found [M+H]$^+$: 430.0927, 432.0916. C$_{24}$H$_{16}$ClN$_3$O$_3$ requires 430.0958, 432.0929.

EXAMPLE 192

The Preparation of 4-(2-Chlorophenyl)-9-hydroxy-6-[2-(phenylsulfanyl)ethyl]pyrrolo[3,4-c]carbazole-1,3(2H,6H)-dione (VII; Ar=2-chlorophenyl, n=2, Z=SPh) (242)

Mesylate (229) (55 mg, 0.11 mmol) prepared as decribed in example 171 was reacted with excess thiophenol (0.10 mL) according to the procedure described in example 179, except that triethylamine (2.0 mL) was added and the reaction was heated at 110° C. for 4 days. Addition of water was followed by extracted of the compound with with ethyl acetate. The organic layer was dried, the drying agent was removed and the solution was concentrated to dryness. The organic layer was dried, the drying agent was removed and the solution was concentrated to dryness followed by chromatography on silica eluting with ethyl acetate/hexane (1:4 to 1:1) to give carbazole (242) (16 mg, 27%) as an orange powder, mp 262–264° C. $^1$H NMR δ [(CD$_3$)$_2$SO] 11.04 (br s, 1H), 9.37 (br s, 1H), 8.34 (d, J=2.5 Hz, 1H), 7.58 (m, 1H), 7.46 (m, 5H), 7.19 (m, 2H), 7.12 (m, 3H), 7.05 (m, 1H), 4.66 (t, J=6.4 Hz, 2H), 3.46 (t, J=6.4 Hz, 2H). Found: C, 63.64; H, 4.09; N, 4.98. C$_{28}$H$_{19}$ClN$_2$O$_3$S.1¾H$_2$O requires: C, 63.39; H, 4.28; N, 5.28.

EXAMPLE 193

The Preparation of 2-{[3-(4-(2-Chlorophenyl)-9-hydroxy-1,3-dioxo-2,3-dihydropyrrolo[3,4-c]carbazol-6 (1H)-yl)propyl]amino}benzoic acid (VIII; Ar=2-chlorophenyl, n=3, Z=2-carboxyanilino) (60)

Reaction of the bromide (58) prepared as described in example 172 with o-anthranilic acid using the procedure described in example 179 gave the aniline (60) (88%), mp 261–263° C. $^1$H NMR δ [(CD$_3$)$_2$SO] 11.05 (s, 1H), 9.38 (s, 1H), 8.39 (d, J=2.4 Hz, 1H), 7.76 (m, 1H), 7.75 (s, 1H), 7.59 (d, J=8.7 Hz, 1H), 7.55 (m, 1H), 7.46 (m, 1H), 7.40 (m, 1H), 7.33 (m, 1H), 7.27 (m, 1H), 7.12 (dd, J=8.7, 2.4 Hz, 1H), 6.59–6.50 (m, 2H), 4.57 (t, J=6.7 Hz, 2H), 3.22–3.10 (m, 2H), 2.15–2.05 (m, 2H). FABMS found M$^+$: 541.1230, 539.1234. C$_{30}$H$_{22}$ClN$_3$O$_5$ requires 541.1218, 539.1248.

EXAMPLE 194

The Preparation of 3-{[3-(4-(2-Chlorophenyl)-9-hydroxy-1,3-dioxo-2,3-dihydropyrrolo[3,4-c]carbazol-6 (1H)-yl)propyl]amino}benzoic acid (VIII; Ar=2-chlorophenyl, n=3, Z=3-carboxyanilino) (61).

Reaction of the bromide (58) prepared as described in example 172 with m-anthranilic acid using the procedure described in example 179 gave the aniline (61) (82%), mp 160–166° C. (dec). $^1$H NMR δ [(CD$_3$)$_2$SO] 11.04 (s, 1H), 9.38 (s, 1H), 8.39 (d, J=2.4 Hz, 1H), 7.77 (s, 1H), 7.61 (d, J=8.7 Hz, 1H), 7.54 (m, 1H), 7.45 (m, 1H), 7.27 (m, 1H), 7.14–7.08 (m, 4H), 6.67 (m, 1H), 5.92 (br s, 1H), 4.58 (m, 2H), 3.09–2.92 (m, 2H), 2.12–2.02 (m, 2H). FABMS found M$^+$:541.1223, 539.1237. C$_{30}$H$_{22}$ClN$_3$O$_5$ requires 541.1218, 539.1248.

EXAMPLE 195

The Preparation of 4-{[3-(4-(2-Chlorophenyl)-9-hydroxy-1,3-dioxo-2,3-dihydropyrrolo[3,4-c]carbazol-6 (1H)-yl)propyl]amino}benzoic acid (VIII; Ar=2-chlorophenyl, n=3, Z=4-carboxyanilino) (62).

Reaction of the bromide (58) prepared as described in example 172 with p-anthranilic acid using the procedure described in example 179 gave the aniline (62) (77%), mp 160–165° C. (dec). $^1$H NMR δ [(CD$_3$)$_2$SO] 11.06 (br s, 1H), 9.43 (br s, 1H), 8.39 (d, J=2.4 Hz, 1H), 7.75 (s, 1H), 7.65–7.59 (m, 3H), 7.54 (m, 1H), 7.45 (m, 1H), 7.37 (m, 1H), 7.26 (m, 1H), 7.13 (dd, J=8.7, 2.4 Hz, 1H), 6.49 (d, J=8.7 Hz, 2H), 4.58 (m, 2H), 3.11–2.99 (m, 2H), 2.12–2.04 (m, 2H). Found: C, 63.24; H, 4.66; N, 7.95. C$_{30}$H$_{22}$ClN$_3$O$_5$.H$_2$O requires C, 63.55; H, 4.23; N, 7.41.

EXAMPLE 196

The Preparation of 4-(2-Chlorophenyl)-6-{3-[(cis)-3,5-dimethylpiperazinyl]propyl}-9-hydroxypyrrolo[3,4-c]carbazole-1,3(2H,6H)-dione (VIII; Ar=2-chlorophenyl, n=3, Z=cis-3,5-dimethylpiperazinyl) (63).

Reaction of the bromide (58) prepared as described in example 172 with cis-1,3-dimethylpiperazine using the procedure described in example 179 gave (63) (65%), mp 165–172° C. $^1$H NMR δ [(CD$_3$)$_2$SO] 11.04 (br s, 1H), 9.36 (br s, 1H), 8.38 (d, J=2.4 Hz, 1H), 7.80 (s, 1H), 7.59–7.54 (m, 2H), 7.51–7.42 (m, 3H), 7.13 (dd, J=8.7, 2.4 Hz, 1H), 4.47 (m, 2H), 2.58–2.38 (m), 2.09 (t, J=6.2 Hz, 2H), 1.96–1.87 (m, 2H), 1.32–1.23 (m, 2H), 0.81 (d, J=6.1 Hz, 3H), 0.77 (d, J=6.1 Hz, 3H). Found: C, 64.09; H, 5.43; N, 10.08. C$_{29}$H$_{28}$ClN$_4$O$_3$.1.5H$_2$O requires C, 64.14; H, 5.75; N, 10.31.

EXAMPLE 197

The Preparation of 4-(2,6-Dichlorophenyl)-6-{3-[(cis)-3,5-dimethylpiperazinyl]propyl}-9-hydroxypyrrolo[3,4-c]carbazole-1,3(2H,6H)-dione (VIII; Ar=2,6-dichlorophenyl, n=3, Z=cis-3,5-dimethylpiperazinyl) (64).

Reaction of the bromide (233) prepared as described in example 178 with cis-1,3-dimethylpiperazine using the procedure described in example 179 gave (64) (68%), mp 160–165° C. $^1$H NMR δ [(CD$_3$)$_2$SO] 11.11 (br, 1H), 9.39 (br s, 1H), 8.37 (d, J=2.4 Hz, 1H), 7.85 (s, 1H), 7.62 (d, J=8.1 Hz, 2H), 7.59 (d, J=8.7 Hz, 1H), 7.51 (m, 1H), 7.16 (dd, J=8.7, 2.4 Hz, 1H), 4.46 (t, J=5.7 Hz, 2H), 2.55–2.42 (m), 2.10 (t, J=6.4 Hz, 2H), 1.96–1.89 (m, 2H), 1.27 (t, J=10 Hz, 2H), 0.80 (d, J=6.2 Hz, 6H). Found: C, 61.34; H, 5.53; N, 9.56. C$_{29}$H$_{27}$Cl$_2$N$_4$O$_3$.H$_2$O requires C, 61.27; H, 5.14; N, 9.85.

EXAMPLE 198

The following amino-compounds of general structure VIII were prepared in an array manner by reaction of the appropriate mesylate or bromide with the appropriate amine using the procedure described in example 179:

The Preparation of 6-(2-aminoethyl)-9-hydroxy-4-phenylpyrrolo[3,4-c]carbazole-1,3(2H,6H)-dione (VIII; Ar=phenyl, n=2, Z=NH$_2$) (65) by reaction of (205) prepared as described in example 174 with aqueous ammonia. Found: M+H=372

The Preparation of 9-hydroxy-6-[2-(methylamino)ethyl]-4-phenylpyrrolo[3,4-c]carbazole-1,3(2H,6H)-dione (VIII; Ar=phenyl, n=2, Z=NHCH$_3$) (66) by reaction of (205) prepared as described in example 174 with aqueous methylamine. Found: M+H=386

The Preparation of 6-(3-aminopropyl)-9-hydroxy-4-phenylpyrrolo[3,4-c]carbazole-1,3(2H,6H)-dione (VIII, Ar-phenyl, n=3, Z=NH$_2$) (67) by reaction of (204) prepared as described in example 173 with aqueous ammonia. Found: M+H=386

The Preparation of 9-hydroxy-4-phenyl-6-[3-]-pyrrolidinyl)propyl]pyrrolo[3,4-c]carbazole-1,3(2H,6H)-dione (VIII; Ar=phenyl, n=3, Z=1-pyrrolidinyl) (68) by reaction of (204) prepared as described in example 173 with pyrrolidine. Found: M+H=440

The Preparation of 6-[3-(diethylamino)propyl]-9-Hydroxy-4-phenylpyrrolo[3,4-c]carbazole-1,3(2H, 6H)-dione (VIII; Ar=phenyl, n=3, Z=N(CH$_2$CH$_3$)$_2$) (69) by reaction of (204) prepared as described in example 173 with diethylamine. Found: M+H=442.

The Preparation of 9-hydroxy-4-phenyl-6-[3-(1-piperidinyl)propyl]pyrrolo[3,4-c]carbazole-1,3(2H,6H)-dione (VIII; Ar=phenyl, n=3, Z=1-piperidinyl) (70) by reaction of (204) prepared as described in example 173 with piperidine. Found: M+H=454.

The Preparation of 9-hydroxy-6-[3-(4-methyl-1-piperazinyl)propyl]-4-phenylpyrrolo[3,4-c]carbazole-1,3(2H,6H)-dione (VIII; Ar=phenyl, n=3, Z=4-methyl-1-piperazinyl) (71) by reaction of (204) prepared as described in example 173 with 1-methylpiperazine. Found: M+H=469

The Preparation of 6-[6-(dimethylamino)hexyl]-9-hydroxy-4-phenylpyrrolo[3,4-c]carbazole-1,3(2H,6H)-dione (VIII; Ar=phenyl, n=6, Z=N(CH$_3$)$_2$) (72) by reaction of (206) prepared as described in example 175 with aqueous dimethylamine. Found: M+H=456

The Preparation of 9-Hydroxy-6-[6-(4-methyl-1-piperazinyl)hexyl]-4-phenylpyrrolo[3,4-c]carbazole-1,3(2H,6H)-dione (VIII; Ar=phenyl, n=6, Z=4-methyl-1-piperazinyl) (73) by reaction of (206) prepared as described in example 175 with 1-methylpiperazine. Found: M+H=512.

The Preparation of 6-(2-aminoethyl)-4-(2-chlorophenyl)-9-hydroxypyrrolo[3,4-c]carbazole-1,3(2H,6H)-dione (VIII; Ar=2-chlorophenyl, n=2, R=NH$_2$) (74) by reaction of (229) prepared as decribed in example 171 with aqueous ammonia. Found: M−H=404

The Preparation of 4-(2-chlorophenyl)-9-hydroxy-6-[3-(dimethylamino)ethyl]pyrrolo[3,4-c]carbazole-1,3(2H,6H)-dione (VIII, Ar=2-chlorophenyl, n=2, Z=N(CH$_3$)$_2$) (75) by reaction of (229 prepared as decribed in example 171 with aqueous dimethylamine. Found: M+H=434.

The Preparation of 4-(2-chlorophenyl)-9-hydroxy-6-[2-(1H-imidazol-1-yl)ethyl]pyrrolo[3,4-c]carbazole-1,3(2H,6H)-dione (VIII, Ar=2-chlorophenyl, n=2, Z=1H-imidazol-1-yl) (76) by reaction of (229) prepared as decribed in example 171 with imidazole. Found: M+H=457.

The Preparation of 4-(2-chlorophenyl)-9-Hydroxy-6-[2-(4-morpholinyl)ethyl]pyrrolo[3,4-c]carbazole-1,3(2H,6H)-dione (VIII, Ar=2-chlorophenyl, n=2, Z=4-morpholinyl) (77) by reaction of (229) prepared as decribed in example 171 with morpholine. Found: M+H=476.

The Preparation of 4-(2-chlorophenyl)-9-hydroxy-6-[2-(4-methyl-1-piperazinyl)ethyl]pyrrolo[3,4-c]carbazole-1,3(2H,6H)-dione (VIII, Ar=2-chlorophenyl, n=2, Z=4-methyl-1-piperazinyl) (78) by reaction of (229 prepared as decribed in example 171 with 1-methylpiperazine. Found: M+H=489.

The Preparation of 6-(2-anilinoethyl)-4-(2-chlorophenyl)-9-hydroxypyrrolo[3,4-c]carbazole-1,3(2H,6H)-dione (VIII, Ar=2-chlorophenyl, n=2, Z=anilino) (79) by reaction of (229) prepared as decribed in example 171 with aniline. Found: M+H=481

The Preparation of 4-(2,6-dichlorophenyl)-9-hydroxy-6-[3-(dimethylamino)ethyl]pyrrolo[3,4-c]carbazole-1,3(2H,6H)-dione (VIII, Ar=-2,6-dichlorophenyl, n=2, Z=N(CH$_3$)$_2$) (80) by reaction of (231) prepared as decribed in example 177 with aqueous dimethylamine. Found: M+H=468.

The Preparation of 4-(2,6-dichlorophenyl)-9-hydroxy-6-[2-(1H-imidazol-1-yl)ethyl]pyrrolo[3,4-c]carbazole-1,3(2H,6H)-dione (VIII, Ar=2,6-dichlorophenyl, n=2, Z=1H-imidazol-1-yl) (81) by reaction of (231) prepared as decribed in example 177 with imidazole. Found: M+H=491.

The Preparation of 4-(2,6-dichlorophenyl)-9-Hydroxy-6-[2-(4-morpholinyl)ethyl]pyrrolo[3,4-c]carbazole-1,3(2H,6H)-dione (VIII, Ar=2,6-dichlorophenyl, n=2, Z=4-morpholinyl) (82) by reaction of (231) prepared as decribed in example 177 with morpholine. Found: M+H=510.

The Preparation of 4-(2,6-dichlorophenyl)-9-hydroxy-6-[2-(4-methyl-1-piperazinyl)ethyl]pyrrolo[3,4-c]carbazole-1,3(2H,6H)-dione (VIII, Ar=2,6-dichlorophenyl, n=2, Z=4-methyl-1-piperazinyl) (83) by reaction of (231) prepared as decribed in example 177 with 1-methylpiperazine. Found: M+H=523.

The Preparation of 6-(2-anilinoethyl)-4-(2,6-dichlorophenyl)-9-hydroxypyrrolo[3,4-c]carbazole-1,3(2H,6H)-dione (VIII, Ar=2,6-dichlorophenyl, n=2, Z=anilino) (84) by reaction of (231) prepared as decribed in example 177 with aniline. Found: M+H=516

The Preparation of 4-(2-chlorophenyl)-9-hydroxy-6-[3-(methylamino)propyl]pyrrolo[3,4-c]carbazole-1,3(2H,6H)-dione (VIII, Ar=2-chlorophenyl, n=3, Z=NHMe) (85) by reaction of (58) prepared as described in example 172 with aqueous methylamine. Found: M+H=434.

The Preparation of 4-(2-chlorophenyl)-6-[3-(dimethylamino)propyl]-9-hydroxypyrrolo[3,4-c]carbazole-1,3(2H,6H)-dione (VIII, Ar=2-chlorophenyl, n=3, Z=N(CH$_3$)$_2$) (86) by reaction of (58) prepared as described in example 172 with aqueous dimethylamine. Found: M+H=448.

The Preparation of 4-(2-chlorophenyl)-9-hydroxy-6-[3-(1H-imidazol-1-yl)propyl]pyrrolo[3,4-c]carbazole-1,3(2H,6H)-dione (VIII, Ar=2-chlorophenyl, n=3, Z=1H-imidazol-1-yl) (87) by reaction of bromo prepared as described in example 172 with imidazole. Found: M+H=471.

The Preparation of 4-(2-chlorophenyl)-9-hydroxy-6-[3-(4-morpholinyl) c]carbazole-1.3 (2H,6H)-dione (VIII, Ar=2-chlorophenyl, n=3, Z=4-morpholinyl) (88) by reaction of (58) prepared as described in example 172 with morpholine. Found: M+H=490.

The Preparation of 4-(2-chlorophenyl)-9-hydroxy-6-[3-(4-methyl-1-piperazinyl)propyl]pyrrolo[3,4-c]carbazole-1,3(2H,6H)-dione (VIII, Ar=2-chlorophenyl, n=3, Z=4-methyl-1-piperazinyl) (89) by reaction of (58) prepared as described in example 172 with 1-methylpiperazine. Found M+H=503.

The Preparation of 6-(3-anilinopropyl)-4-(2-chlorophenyl)-9-hydroxypyrrolo[3,4-c]carbazole-1,3(2H,6H)-dione (VIII, Ar=2-chlorophenyl, n=3, Z=anilino) (90) by reaction of (58) prepared as described in example 172 with aniline. Found: M+H=495.

The Preparation of 4-(2,6-dichlorophenyl)-9-hydroxy-6-[3-(methylamino)propyl]pyrrolo[3,4-c]carbazole-1,3(2H,6H)-dione (VIII, Ar=2,6-dichlorophenyl, n=3, Z=NHMe) (91) by reaction of (233) prepared as decribed in example 178 with aqueous methylamine. Found: M+H=468.

The Preparation of 4-(2,6-dichlorophenyl)-6-[3-(dimethylamino)propyl]9-hydroxypyrrolo[3,4-c]carbazole-1,3(2H,6H)-dione (VIII, Ar=2,6-dichlorophenyl, n=3, Z=N(CH$_3$)$_2$) (92) by reaction of (233) prepared as decribed in example 178 with aqueous dimethylamine. Found: M+H=482.

The Preparation of 4-(2,6-dichlorophenyl)-9-hydroxy-6-[3-(1H-imidazol-1-yl)propyl]pyrrolo[3,4-c]carbazole-1,3(2H,6H)-dione (VIII, Ar=2,6-dichlorophenyl, n=3, Z=1H-imidazol-1-yl) (93) by reaction of (233) prepared as decribed in example 178 with imidazole. Found: M+H=505.

The Preparation of 4-(2,6-dichlorophenyl)-9-hydroxy-6-[3-(4-morpholinyl)propyl]pyrrolo[3,4-c]carbazole-1,3(2H,6H)-dione (VIII, Ar=2,6-dichlorophenyl, n=3, Z=4-morpholinyl) (94) by reaction of (233) prepared as decribed in example 178 with morpholine. Found: M+H=524.

The Preparation of 4-(2,6-dichlorophenyl)-9-hydroxy-6-[3-(4-methyl-1-piperazinyl)propyl]pyrrolo[3,4-c]carbazole-1,3(2H,6H)-dione (VIII, Ar=2,6-dichlorophenyl, n=3, Z=4-methyl-1-piperazinyl) (95) by reaction of (233) prepared as decribed in example 178 with 1-methylpiperazine. Found M+H=537.

The Preparation of 6-(3-anilinopropyl)-4-(2,6-dichlorophenyl)-9-hydroxypyrrolo[3,4-c]carbazole-1,3(2H,6H)-dione (VIII, Ar=2,6-chlorophenyl, n=3, Z=anilino) (96) by reaction of (233) prepared as decribed in example 178 with aniline. Found: M+H=530.

EXAMPLE 199

Combinatorial Procedure for Aniline Displacements of Br and OMs

To a 8 ml screw cap vial was added a solution of 6-(3-Bromopropyl)-4-(chloro-phenyl)-9-hydroxy-6H-pyrrolo[3,4-c]carbazole-1,3-dione (reagent A), (0.048 g, 0.1 mmol) prepared as described in example 83 or 2-(9-Hydroxy-1,3-dioxo-4-phenyl-2,3-dihydropyrrolo[3,4-c]carbazol-6 (1H)-yl)ethyl methanesulfonate (205) prepared as described in example 174 (reagent B) (See table 2) in anhydrous dimethylacetamide (1 ml), a solution of the appropriate aniline (0.012 g, 0.1 mmol) in anhydrous dimethylacetamide (0.150 ml). The vial was capped and the reaction mixture was shaken for 18 hours at 100° C. After cooling to room temperature, the solvent was removed under vacuum. Purification was carried out via reverse-phase HPLC (3% n-propanol in acetonitrile and 3% n-propanol in water as the eluent; C-18 column). The compounds were analysed by mass spectral analysis.

TABLE 2

Compounds made combinatorially by reaction of the anpropariate commercial anilines

| Reagent | Product | Analytical Data MS-APCI [M + H]$^+$ |
|---|---|---|
| Reagent A | 4-(2-Chloro-phenyl)-9-hydroxy-6-[3-(3-methoxy-phenylamino)-propyl]-6H-pyrrolo[3,4-c]carbazole-1,3-dione | 526.2 |
| Reagent A | 4-(2-Chloro-phenyl)-9-hydroxy-6-[3-(4-hydroxy-phenylamino)-propyl]-6H-pyrrolo[3,4-c]carbazole-1,3-dione | 512.3 |
| Reagent A | 4-(2-Chloro-phenyl)-9-hydroxy-6-[3-(2-trifluoromethyl-phenylamino)-propyl]-6H-pyrrolo[3,4-c]carbazole-1,3-dione | 564.3 |
| Reagent A | 4-(2-Chloro-phenyl)-6-[3-(4-ethyl-phenylamino)-propyl]-9-hydroxy-6H-pyrrolo[3,4-c]carbazole-1,3-dione | 524.3 |
| Reagent A | 6-[3-(4-Bromo-phenylamino)-propyl]-4-(2-chloro-phenyl)-9-hydroxy-6H-pyrrolo[3,4-c]carbazole-1,3-dione | 576.2 |
| Reagent A | 4-(2-Chloro-phenyl)-9-hydroxy-6[3-(3-methylsulfanyl-phenylamino)-propyl]-6H-pyrrolo[3,4-c]carbazole-1,3-dione | 542.3 |
| Reagent A | 4-(2-Chloro-phenyl)-9-hydroxy-6-[3-(3-hydroxy-phenylamino)-propyl]-6H-pyrrolo[3,4-c]carbazole-1,3-dione | 512.3 |
| Reagent A | 6-[3-(3-Bromo-phenylamino)-propyl]-4-(2-chloro-phenyl)-9-hydroxy-6H-pyrrolo[3,4-c]carbazole-1,3-dione | 574.3 |
| Reagent A | ({3-[4-(2-Chloro-phenyl)-9-hydroxy-1,3-dioxo-2,3-dihydro-1H-pyrrolo[3,4-c]carbazol-6-yl]-propyl}-phenyl-amino) acetic acid | 554.3 |
| Reagent A | 4-(2-Chloro-phenyl)-9-hydroxy-6-[3-(1H-indazol-6-ylamino)-propyl]-6H-pyrrolo[3,4-c]carbazole-1,3-dione | 536.3 |
| Reagent A | 3-{3-[4-(2-Chloro-phenyl)-9-hydroxy-1,3-dioxo-2,3-dihydro-1H-pyrrolo[3,4-c]carbazol-6-yl]-propylamino}-benzenesulfonamide | 575.3 |
| Reagent A | 4-(2-Chloro-phenyl)-6-[3-(3-ethyl-phenylamino)-propyl]-9-hydroxy-6H-pyrrolo[3,4-c]carbazole-1,3-dione | 524.3 |
| Reagent A | 6-[3-(1,3-Benzodioxol-5-ylamino)-propyl]-4-(2-chloro-phenyl)-9-hydroxy-6H-pyrrolo[3,4-c]carbazole-1,3-dione | 540.3 |
| Reagent A | 4-(2-Chloro-phenyl)-9-hydroxy-6-[3-(1H-indazol-5-ylamino)-propyl]-6H-pyrrolo[3,4-c]carbazole-1,3-dione | 536.3 |
| Reagent A | 4-(2-Chloro-phenyl)-9-hydroxy-6-[3-(1H-indol-5-ylamino)-propyl]-6H-pyrrolo[3,4-c]carbazoie-1,3-dione | 535.3 |
| Reagent A | 4-(2-Chloro-phenyl)-6-[3-(1,1-dioxo-1H-1$1>6__-benzol[b]thiophen-6-ylamino)-propyl]-9-hydroxy-6H-pyrrolo[3,4-c]carbazole-1,3-dione | 584.3 |
| Reagent A | 4-(2-Chloro-phenyl)-9-hydroxy-6-[3-(indan-5-ylamino)-propyl]-6H-pyrrolo[3,4-c]carbazole-1,3-dione | 536.2 |
| Reagent A | (4-{3-[4-(2-Chloro-phenyl)-9-hydroxy-1,3-dioxo-2,3-dihydro-1H-pyrrolo[3,4-c]carbazol-6-yl]-propylamino}-benzoylamino)-acetic acid | 597.3 |

TABLE 2-continued

Compounds made combinatorially by reaction of the anpropariate commercial anilines

| Reagent | Product | Analytical Data MS-APCI [M + H]+ |
|---|---|---|
| Reagent A | 4-{3-[4-(2-Chloro-phenyl)-9-hydroxy-1,3-dioxo-2,3-dihydro-1H-pyrrolo[3,4-c]carbazol-6-yl]-propylamino}-N-(2-diethylamino-ethyl)-benzamide | 638.4 |
| Reagent A | 6-[3-(Benzothiazol-6-ylamino)-propyl]-4-(2-chloro-phenyl)-9-hydroxy-6H-pyrrolo[3,4-c]carbazole-1,3-dione | 553.2 |
| Reagent A | 4-(2-Chloro-phenyl)-9-hydroxy-6-{3-[(2-hydroxy-ethyl)-phenyl-amino]-propyl}-6H-pyrrolo[3,4-c]carbazole-1,3-dione | 540.3 |
| Reagent A | 4-(2-Chloro-phenyl)-9-hydroxy-6-[3(3 trifluoromethyl-phenylamino)-propyl]-6H-pyrrolo[3,4-c]carbazole-1,3-dione | 564.2 |
| Reagent A | 4-(2-Chloro-phenyl)-9-hydroxy-6-{3-[3-(1,1,2,2-tetrafluoro-ethoxy)-phenylamino]-propyl}-6H-pyrrolo[3,4-c]carbazole-1,3-dione | |
| Reagent A | 3-(3-{3[4-(2-Chloro-phenyl)-9-hydroxy-1,3-dioxo-2,3-dihydro-1H-pyrrolo[3,4-c]carbazol-6-yl]-propylamino}-phenyl)-propionic acid | 568.3 |
| Reagent A | 4-(2-Chloro-phenyl)-9-hydroxy-6-[3-(methyl-phenyl-amino)-propyl]-6H-pyrrolo[3,4-c]carbazole-1,3-dione | 510.3 |
| Reagent B | 4-(2-Chloro-phenyl)-9-hydroxy-6-[2-(3-methoxy-phenylamino)-ethyl]-6H-pyrrolo[3,4-c]carbazole-1,3-dione | 512.3 |
| Reagent B | 4-(2-Chloro-phenyl)-6-[2-(3-ethyl-phenylamino)-ethyl]9-hydroxy-6H-pyrrolo[3,4-c]carbazole-1,3-dione | 510.3 |
| Reagent B | 4-(2-Chloro-phenyl)-9-hydroxy-6-[2-(3-trifluoromethyl-phenylamino)-ethyl]-6H-pyrrolo[3,4-c]carbazole-1,3-dione | 550.3 |
| Reagent B | 4-(2-Chloro-phenyl)-9-hydroxy-6-[2-(2-hydroxy-phenylamino)-ethyl]-6H-pyrrolo[3,4-c)carbazole-1,3-dione | 498.3 |
| Reagent B | 6-[2-(3-Acetyl-phenylamino)-ethyl]-4-(2-chloro-phenyl)-9-hydroxy-6H-pyrrolo[3,4-c]carbazole-1,3-dione | 524.3 |
| Reagent B | 4-(2-Chloro-phenyl)-9-hydroxy-6-[2-(4-methoxy-phenylamino)-ethyl]-6H-pyrrolo[3,4-c]carbazole-1,3-dione | 512.3 |
| Reagent B | 4-(2-Chloro-phenyl)-9-hydroxy-6-[2-(2-methylsulfanyl-phenylamino)-ethyl]-6H-pyrrolo[3,4-c]carbazole-1,3-dione | 528.2 |
| Reagent B | 6-[2-(2-Bromo-phenylamino)-ethyl]-4-(2-chloro-phenyl)-9-hydroxy-6H-pyrrolo[3,4-c]carbazole-1,3-dione | 562.2 |
| Reagent B | 4-(2-Chloro-phenyl)-9-hydroxy-6-[2-(4-hydroxy-phenylamino)-ethyl]-6H-pyrrolo[3,4-c]carbazole-1,3-dione | 498.3 |
| Reagent B | 4-(2-Chloro-phenyl)-6-[2-(4-ethyl phenylamino)-ethyl]-9-hydroxy-6H-pyrrolo[3,4-c]carbazole-1,3-dione | 510.3 |
| Reagent B | 6-[2-(4-Bromo-phenylamino)-ethyl]-4-(2-chloro-phenyl)-9-hydroxy-6H-pyrrolo[3,4-c]carbazole-1,3-dione | 562.1 |
| Reagent B | 4-(2-Chloro-phenyl)-9-hydroxy-6-[2-(3-methylsulfanyl-phenylamino)ethyl]-6H-pyrrolo[3,4-c]carbazole-1,3-dione | 528.2 |
| Reagent B | 4-(2-Chloro-phenyl)-9-hydroxy-6-[2-(3-hydroxy-phenylamino)-ethyl]-6H-pyrrolo[3,4-c]carbazole-1,3-dione | 498.3 |
| Reagent B | 4-(2-Chloro-phenyl)-9-hydroxy-6-[3-(2-hydroxy-phenylamino)-propyl]-6H-pyrrolo[3,4-c]carbazole-1,3-dione | 512.2 |
| Reagent B | 6-[2-(3-Bromo-phenylamino)-ethyl]-4-(2-chloro-phenyl)-9-hydroxy-6H-pyrrolo[3,4-c]carbazole 1,3-dione | 562.2 |
| Reagent B | 4-{2-[4-(2-Chloro-phenyl)-9-hydroxy 1,3-dioxo-2,3-dihydro-1H-pyrrolo[3,4-c]carbazol-6-yl]-ethylamino}-benzonitrile | 507.3 |
| Reagent B | (3-{2-[4-(2-Chloro-phenyl)-9-hydroxy 1,3-dioxo-2,3-dihydro-1H-pyrrolo[3,4-c]carbazol-6-yl]-ethylamino }-phenyl) acetic acid | 540.3 |
| Reagent B | 6-[3-(3-Acetyl-phenylamino)-propyl]-4-(2-chloro-phenyl)-9-hydroxy-6H-pyrrolo[3,4-c]carbazole-1,3-dione | 538.3 |
| Reagent B | 4-(2-Chloro-phenyl)-9-hydroxy-6-[3-(4 methoxy-phenylamino)-propyl]-6H-pyrrolo[3,4-c]carbazole-1,3-dione | 526.3 |
| Reagent B | 4-(2-Chloro-phenyl)-9-hydroxy-6-[3-(2-methylsulfanyl-phenylamino)propyl]-6H-pyrrolo[3,4-c]carbazole-1,3-dione | 542.2 |
| Reagent B | 6-[3-(2-Bromo-phenylamino)-propyl]-4-(2-chloro-phenyl)-9-hydroxy-6H-pyrrolo[3,4-c]carbazole-1,3-dione | 576.2 |

EXAMPLE 200

The Preparation of 4-(2-Chlorophenyl)-9-hydroxy-6-[3-(methylsulfanyl)propyl]pyrrolo[3,4-c]carbazole-1,3(2H,6H)-dione (VIII; Ar=2-chlorophenyl, n=3, Z=SCH$_3$) (130)

A mixture of the bromide (58) (60.0 mg, 0.124 mmol) prepared as described in example 172 and lithium thiomercaptide (13 mg, 0.2481 mmol) in p-dioxane (5 mL) was refluxed for 16 h. A further 10 mg of LiSMe was added and refluxing was continued for a further 9 h. The mixture was diluted with water, extracted with ethyl acetate. The organic layer was dried, the drying agent was removed and the solution was concentrated to drynessto give the sulfide (130 directly (47.1 mg, 84%) which crystallised from ethyl acetate/petroleum ether as an orange powder, mp 218–220° C. $^1$H NMR δ [(CD$_3$)$_2$SO] 11.07 (br s, 1H), 9.39 (br s, 1H), 8.39 (d, J=2.4 Hz, 1H), 7.80 (s, 1H), 7.61–7.56 (m, 2H), 7.53–7.43 (m, 3H), 7.15 (dd, J=8.8, 2.4 Hz, 1H), 4.52 (t, J=6.9 Hz, 2H), 2.45 (t, J=7.0 Hz, 2H), 2.01 (m, 2H), 2.00 (s, 3H). FABMS found [M+H]$^+$: 453.0840, 451.0859. C$_{24}$H$_{20}$ClN$_2$O$_3$S requires 453.0854, 451.0883.

EXAMPLE 201

The Preparation of 4-(2-Chlorophenyl)-9-hydroxy-6-[3-(phenylsulfanyl)propyl]pyrrolo[3,4-c]carbazole-1,3(2H,6H)-dione (VIII; Ar=2-chlorophenyl, n=3, Z=SPh) (131).

A solution of the bromide (58) (41 mg, 0.085 mmol) prepared as described in example 172, thiophenol (9.5 µL, 0.093 mmol) and triethylamine (0.25 mL, 3.40 mmol) in p-dioxane (1.5 mL) was refluxed for 16 h. Water was added and the mixture was extracted with ethyl acetate. The organic layer was dried, the drying agent was removed and the solution was concentrated to dryness the sulfide (131) directly (37.2 mg, 85%), which crystallised from ethyl acetate/petroleum ether as an orange powder, mp 229–231°

C. $^1$H NMR δ [(CD$_3$)$_2$SO] 11.06 (br s, 1H), 9.37 (s, 1H), 8.37 (d, J=2.4 Hz, 1H), 7.76 (s, 1H), 7.60–7.42 (m, 5H), 7.25–7.19 (m, 4H), 7.16–7.10 m, 2H), 4.57 (t, J=6.8 Hz, 2H), 2.98 (m, 2H), 2.01 (m, 2H). Found: C, 67.36; H, 4.29; N, 5.36. C$_{29}$H$_{21}$ClN$_2$SO$_3$.1¼H$_2$O requires C, 67.31; H, 4.19; N, 5.41.

EXAMPLE 202

The Preparation of 4-(2-Chlorophenyl)-9-hydroxy-6-(3-methoxypropyl)pyrrolo[3,4-c]carbazole-1,3(2H, 6H)-dione (VIII; Ar=2-chlorophenyl, n=3, Z=OCH$_3$) (132).

A solution of the bromide (58) (50 mg, 0.103 mmol) prepared as described in example 172 and sodium methoxide (35.2 mg, 0.65 mmol) in methanol (0.5 mL) and p-dioxane (8 mL) was refluxed for 3 h. The solution was acidified with 2N HCl, extracted with ethyl acetate and the organic layer was dried, the drying agent was removed and the solution was concentrated to dryness and chromatographed on silica. Elution with ethyl acetate gave the anhydride, 4-(2-chlorophenyl)-9-hydroxy-6-(3-methoxypropyl)-1H-furo[3,4-c]carbazole-1,3(6H)-dione as an orange powder. $^1$H NMR δ [(CD$_3$)$_2$SO] 9.57 (br, 1H), 8.24 (d, J=2.3 Hz, 1H), 8.00 (s, 1H), 7.66–7.61 (m, 2H), 7.58–7.48 (m, 3H), 7.22 (dd, J=9.0, 2.3 Hz, 1H), 4.56 (t, J=6.7 Hz, 2H), 3.22 (t, J=6.0 Hz, 2H), 3.13 (s, 3H), 2.02 (m, 2H). The product was added to molten ammonium acetate (10 g) at 140° C. and the mixture was warmed at this temperature for 3 h. Water was added and the resultant precipitate was filtered off, adsorbed onto silica from a THF solution, and chromatographed. Elution with ethyl acetate/petroleum ether (1:1) gave (132) (32 mg, 71%) an orange powder, mp 260–262° C. $^1$H NMR δ [(CD$_3$)$_2$SO] 11.07 (br s, 1H), 9.42 (br s, 1H), 8.39 (d, J=2.4 Hz, 1H), 7.69 (s, 1H), 7.60–7.44 (m, 5H), 7.15 (dd, J=8.8, 2.4 Hz, 1H), 4.49 (t, J=6.6 Hz, 2H), 3.22 (t, J=6.0 Hz, 2H), 3.13 (s, 3H), 1.99 (m, 2H). FABMS found [M+H]$^+$: 437.1088, 435.1090. C$_{24}$H$_{20}$ClN$_2$O$_4$ requires 437.1082, 435.1112.

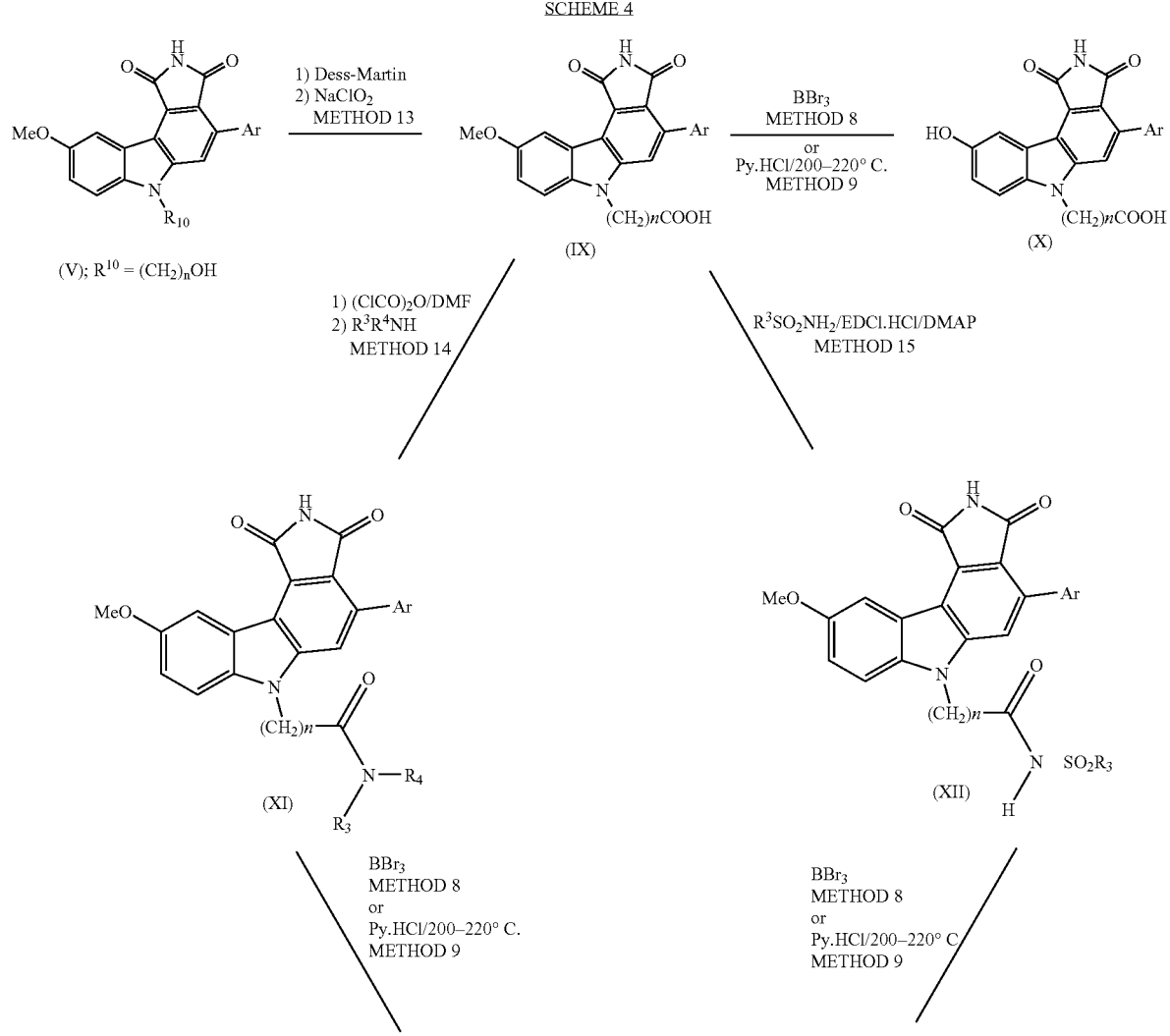

SCHEME 4

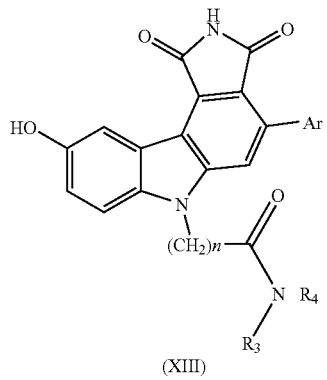

(XIII)

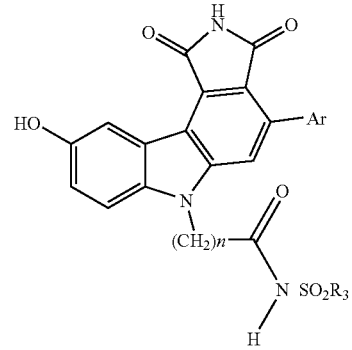

(XIV)

Scheme 4 Procedures

Representative Procedure for Method 13 of Scheme 4

EXAMPLE 203

The Preparation of 3-(9-Methoxy-1,3-dioxo-4-phenyl-1,3-dihydropyrrolo[3,4-c]carbazol-6(1H)-yl)propanoic acid (IX; Ar=phenyl, n=2) (243)

Dess-Martin periodinane (1.91 g, 4.5 mmol) was added to a stirred solution of alcohol (202) (1.20 g, 3.0 mmol) prepared as decribed in example 83 in dry tetrahydrofuran (80 mL) under nitrogen. After 1 hour at room temperature a solution of saturated sodium thiosulphate and saturated sodium bicarbonate (1:1, 100 mL) was added and the reaction mixture was stirred vigorously for 15 minutes before being given extracted with ethyl acetate. The organic layer was dried, the drying agent was removed and the solution was concentrated to dryness. The resulting crude aldehyde was then dissolved in tert-butanol/tetrahydrofuran (9:1, 230 mL) and 2-methyl-2-butene was added (12.0 mmol, 6.0 mL of a 2M solution in tetrahydrofuran). To this solution was added a solution of sodium chlorite (1.09 g, 12.0 mmol) and sodium dihydrogen phosphate (2.5 g, 18.0 mmol) in water (100 mL) containing tert-butanol (4 mL). The resulting solution was stirred at room temperature for 18 hours before being diluted with brine and extracted with ethyl acetate. The organic layer was dried, the drying agent was removed and the solution was concentrated to dryness. Chromatography on silica eluting with ethyl acetate/methanol (1:0 to 9:1), followed by crystallisation from ethyl acetate/hexane gave acid (243) (0.86 g, 69%) as a yellow powder, mp 252–255° C. $^1$H NMR δ [(CD$_3$)$_2$SO] 12.2 (v br s, 1H), 11.13 (br s, 1H), 8.55 (d, J=2.6 Hz, 1H), 7.89 (s, 1H), 7.68 (m, 3H), 7.47 (m, 3H), 7.28 (dd, J=9.0, 2.6 Hz, 1H), 4.73 (t, J=6.6 Hz, 2H), 3.90 (s, 3H), 2.76 (t, J=6.6 Hz, 2H). Found: C, 67.95; H, 4.37; N, 6.47. $C_{24}H_{18}N_2O_5 \cdot 1/2H_2O$ requires C, 68.08; H, 4.52; N, 6.62.

EXAMPLE 204

The Preparation of 3-(4-(2,6-Dichlorophenyl)-9-methoxy-1,3-dioxo-2,3-dihydropyrrolo[3,4-c]carbazol-6 (1H)-yl)propanoic acid (IX; Ar=2,6-dichlorophenyl, n=2) (244)

Oxidation of alcohol (232) prepared as decribed in example 86 (0.50 g, 1.1 mmol) according to the procedure decrsibed in example 203, followed by chromatography on silica eluting with methanol/dichloromethane (3:97 to 1:9) and trituration from ethyl acetate/hexane gave acid (244) (0.35 g, 66%) as a yellow powder, mp 203–209° C. $^1$H NMR δ [(CD$_3$)$_2$SO] 12.3 (v br s, 1H), 11.19 (br s, 1H), 8.50 (d, J=2.6 Hz, 1H), 7.94 (s, 1H), 7.74 (d, J=9.0 Hz, 1H), 7.62 (m, 2H), 7.51 (dd, J=13.3, 6.1 Hz, 1H), 7.33 (dd, J=9.0, 2.6 Hz, 1H), 4.71 (t, J=6.9 Hz, 2H), 3.91 (s, 3H), 2.75 (t, J=6.9 Hz, 2H). Found: C, 59.74; H, 3.62; N, 5.65. $C_{24}H_{16}Cl_2N_2O_5$ requires: C, 59.63; H, 3.34; N, 5.79.

EXAMPLE 205

The Preparation of 3-(4-(2-Chloro-6-methoxyphenyl)-9-methoxy-1,3-dioxo-2,3-dihydropyrrolo[3c]carbazol-6 (1H)-yl)propanoic acid (IX; Ar=2-chloro-6-methoxyphenyl, n=2) (245)

Oxidation of alcohol (105) (2.1 g, 4.5 mmol) prepared as described in example 58 according to the procedure decrsibed in example 203 gave acid (245) (0.81 g, 38%) as a yellow powder, mp 241–243° C. $^1$H NMR δ [(CD$_3$)$_2$SO) 12.5 (v br s, 1H), 11.07 (br s, 1H), 8.50 (d, J=2.6 Hz, 1H), 7.82 (s, 1H), 7.70 (d, J=9.0 Hz, 1H), 7.44 (t, J=8.3 Hz, 1H), 7.30 (dd, J=9.0, 2.6 Hz, 1H), 7.18 (d, J=8.3 Hz, 1H), 7.12 (d, J=8.3 Hz, 1H), 4.68 (t, J=6.8 Hz, 2H), 3.90 (s, 3H), 3.68 (s, 3H), 2.71 (t, J=6.8 Hz, 2H). Found: C, 62.71; H, 4.09; N, 5.62. $C_{25}H_{19}ClN_2O_6$ requires C, 62.70; H, 4.00; N, 5.85.

EXAMPLE 206

The Preparation of 3-(4-(2,6-Dichlorophenyl)-9-hydroxy-1,3-dioxo-2,3-dihydropyrrolo[3,4-c]carbazol-6 (1H)-yl)propanoic acid (X; Ar=2,6-dichlorophenyl, n=2) (246)

Demethylation of acid (244) (90 mg, 0.19 mmol) prepared as described in example 204 employing the procedure described in example 80 gave phenol (246) (63 mg, 71%) as an orange/yellow powder, mp 245–253° C. (dec). $^1$H NMR δ [(CD$_3$)$_2$SO] 12.2 (v br s, 1H), 11.13 (br s, 1H), 9.40 (br s, 1H), 8.36 (d, J=2.5 Hz, 1H), 7.88 (s, 1H), 7.62 (m, 3H), 7.50 (dd, J=8.7, 7.3 Hz, 1H), 7.15 (dd, J=8.9, 2.5 Hz, 1H), 4.66 (t, J=6.9 Hz, 1H), 2.73 (t, J=6.9 Hz, 2H). Found: C, 58.98; H, 3.31; N, 5.81. $C_{23}H_{14}Cl_2N_2O_5$ requires: C, 58.85; H, 3.01; N, 5.97.

Representative Procedure for Method 14 of Scheme 4

EXAMPLE 207

The Preparation of N-[2-(Dimethylamino)ethyl]-3-(9-methoxy-1,3-dioxo-4-phenyl-2,3-dihydropyrrolo[3,4-c]carbazol-6 (1H)-yl)propanamide (XI; Ar=phenyl, n=2, R$^3$=H, R$^4$=CH$_2$CH$_2$N(CH$_3$)$_2$) (247)

To a solution of acid (243) (100 mg, 0.24 mmol) prepared as described in example 203 in dry tetrahydrofuran (20 mL) under nitrogen was added 1 drop of dimethylformamide, followed by oxalyl chloride (84 uL, 0.96 mmol) dropwise. The resulting solution was stirred at room temperature for 2 hours before being reduced to dryness in vacuo. Dry benzene (20 mL) was added to the residue and the suspension was again reduced to dryness in vacuo, before being dissolved in dry tetrahydrofuran (20 uL) and flushed with nitrogen. To this solution was added dimethylethylenediamine (105 mL, 0.96 mmol) via syringe. The reaction mixture was stirred at room temperature for 2 hours and then diluted with water, basified by the addition of solid potassium carbonate and extracted with ethyl acetate. The organic layer was dried, the drying agent was removed and the solution was concentrated to dryness. Chromatography on silica eluting with ethyl acetate/methanol/triethylamine (1:0:0 to 3:1:trace) followed by crystallization from ethyl acetate/hexane, gave amide (247) (85 mg, 73%) as a yellow powder, mp 206–210° C. $^1$H NMR δ ((CD$_3$)$_2$SO) 11.11 (br s, 1H), 8.54 (d, J=2.6 Hz, 1H), 7.81 (s, 1H), 7.73 (t, J=5.6 Hz, 1H), 7.67 (m, 3H), 7.48 (m, 3H), 7.29 (dd, J=8.9, 2.6 Hz, 1H), 4.73 (t, J=6.3 Hz, 2H), 3.89 (s, 3H), 2.93 (dd, J=6.8, 5.6 Hz, 2H), 2.59 (t, J=6.3 Hz, 2H), 1.90 (s, 6H), 1.84 (t, J=6.8 Hz, 2H). Found: C, 67.02; H, 5.80; N, 11.17. $C_{28}H_{28}N_4O_4.H_2O$ requires: C, 66.92; H, 6.02; N, 11.14.

EXAMPLE 208

The Preparation of 3-(9-Methoxy-1,3-dioxo-4-phenyl-2,3-dihydropyrrolo[3,4-c]carbazol-6(1H)-yl)propanamide (XI; Ar=phenyl, n=2, R$^3$=H, R$^4$=H) (248)

Reaction of acid (243) (100 mg, 0.24 mmol) prepared as described in example 203 according to the procedure described in example 207, except that a saturated solution of ammonia gas in tetrahydrofuran (20 mL) was added as the amine, gave amide (248) (61 mg, 62%) as a yellow powder, mp 266–270° C. $^1$H NMR δ [(CD$_3$)$_2$SO] 11.11 (br s, 1H), 8.55 (d, J=2.6 Hz, 1H), 7.87 (s, 1H), 7.68 (m, 3H), 7.48 (m, 3H), 7.33 (br s, 1H), 7.29 (dd, J=9.0, 2.6 Hz, 1H), 6.85 (br s, 1H), 4.71 (t, J=6.5 Hz, 2H), 3.90 (s, 3H), 2.60 (t, J=6.5 Hz, 2H). Found: C, 68.36; H, 4.70; N, 9.99. $C_{24}H_{19}N_3O_4.1/2H_2O$ requires: C, 68.24; H, 4.78; N, 9.94.

EXAMPLE 209

The Preparation of 3-(4-(2-Chlorophenyl)-9-methoxy-1,3-dioxo-2,3-dihydropyrrolo[3,4-c]carbazol-6 (1H)-yl)-N-[2-(dimethylamino)ethyl]propanamide (XI; Ar=2-chlorophenyl, n=2, R$^3$=H, R$^4$=CH$_2$CH$_2$N(CH$_3$)$_2$) (249)

Reaction of acid (116) (95 mg, 0.21 mmol) prepared as described in example 229 according to the procedure described in example 207, followed by trituration in diethyl ether, gave amide (249) (76 mg, 70%) as a yellow powder, mp 250–252° C. $^1$H NMR δ [(CD$_3$)$_2$SO] 11.12 (br s, 1H), 8.51 (d, J=2.6 Hz, 1H), 7.77 (s, 1H), 7.76 (partially obscured t, J=5.9 Hz, 1H), 7.68 (d, J=9.0 Hz, 1H), 7.58 (m, 2H), 7.48 (m, 3H), 7.32 (dd, J=9.0, 2.6 Hz, 1H), 4.71 (t, J=6.4 Hz, 2H), 3.90 (s, 3H), 2.95 (m, 2H), 2.58 (t, J=6.4 Hz, 2H), 1.94 (s, 6H), 1.93 (partially obscured t, J=6±8 Hz, 2H). Found: C, 64.88; H, 5.56; N, 10.70. $C_{28}H_{27}ClN_4O_4$ requires: C, 64.79; H, 5.24; N, 10.79.

EXAMPLE 210

The Preparation of 3-(4-(2,6-Dichlorophenyl)-9-methoxy-1,3-dioxo-2,3-dihydropyrrolo[3,4-c]carbazol-6 (1H)-yl)propanamide (XI; Ar=2,6-dichlorophenyl, n=2, R$^3$=H, R$^4$=H) (250)

Reaction of acid (244) (0.23 g, 0.48 mmol) prepared as described in example 204 according to the procedure described in example 207, except that concentrated ammonia (~30%, 20 mL) was added as the amine, gave amide (250) (0.17 g, 73%) as a yellow powder, mp 261–264° C. $^1$H NMR δ [(CD$_3$)$_2$SO] 11.19 (br s, 1H), 8.50 (d, J=2.6 Hz, 1H), 7.87 (s, 1H), 7.73 (d, J=9.0 Hz, 1H), 7.63 (m, 2H), 7.52 (dd, J=8.8, 7.3 Hz, 1H), 7.38 (br s, 1H), 7.33 (dd, J=9.0, 2.6 Hz, 1H), 6.87 (br s, 1H), 4.69 (t, J=6.7 Hz, 214), 3.91 (s, 3H), 2.57 (t, J=6.7 Hz, 2H). Found: C, 59.55; H, 3.79; N, 8.73. $C_{14}H_{17}Cl_2N_3O_4$ requires: C, 59.75; H, 3.55; N, 8.71.

EXAMPLE 211

The Preparation of 3-(4-(2,6-Dichlorophenyl)-9-methoxy-1,3-dioxo-2,3-dihydropyrrolo[3,4-c]carbazol-6 (1H)-yl)-N-[2-(dimethylamino)ethyl]propanamide (XI; Ar=2,6-dichlorophenyl, n=2, R$^3$=H, R$^4$=CH$_2$CH$_2$N(CH$_3$)$_2$) (251)

Reaction of acid (244) (150 mg, 0.30 mmol) prepared as described in example 204 according to the procedure described in example 207, gave amide (251) (91 mg, 55%) as a yellow powder, mp 141–146° C. $^1$H NMR δ [(CD$_3$)$_2$SO] 11.19 (br s, 1H), 8.50 (d, J=2.6 Hz, 1H), 7.82 (s, 1H), 7.81 (partially obscured t, J=5.6 Hz, 1H), 7.69 (d, J=9.0 Hz, 1H), 7.62 (m, 2H), 7.52 (dd, J=8.8, 7.4 Hz, 1H), 7.34 (dd, J=9.0, 2.6 Hz, 1H), 4.71 (t, J=6.4 Hz, 2H), 3.90 (s, 3H), 2.95 (q, J=6.2 Hz, 2H), 2.58 (t, J=6.4 Hz, 2H), 2.07 (m, 2H), 2.02 (s, 6H). Found: C, 59.13; H, 4.73; N, 9.87. $C_{28}H_{26}Cl_2N_4O_4.H_2O$ requires C, 58.85; H, 4.94; N, 9.80.

EXAMPLE 212

The Preparation of 3-(4-(2-Chloro-6-methoxyphenyl)-9-methoxy-1,3-dioxo-2,3-dihydropyrrolo[3,4-c]carbazol-6 (1H)-yl)-N-[2-(dimethylamino)ethyl]propanamide (XI; Ar=2-chloro-6-methoxyphenyl, n=2, $R^3$=H, $R^4$=$CH_2CH_2N(CH_3)_2$) (252)

Reaction of acid (245) prepared as described in example 205 (160 mg, 0.33 mmol) according to the procedure described in example 207, gave amide (252) (93 mg, 51%) as a yellow powder, mp 164–169° C. $^1$H NMR δ [$(CD_3)_2SO$] 11.06 (br s, 1H), 8.50 (d, J=2.6 Hz, 1H), 7.80 (t, J=5.6 Hz, 1H), 7.72 (s, 1H), 7.66 (d, J=9.0 Hz, 1H), 7.45 (t, J=8.3 Hz, 1H), 7.30 (dd, J=9.0, 2.6 Hz, 1H), 7.18 (d, J=8.3 Hz, 1H), 7.13 (d, J=8.3 Hz, 1H), 4.68 (t, J=6.4 Hz, 2H), 3.90 (s, 3H), 3.68 (s, 3H), 2.98 (dd, J=6.6, 5.6 Hz, 2H), 2.56 (t, J=6.4 Hz, 2H), 2.05 (t, J=6.6 Hz, 2H), 1.90 (s, 6H). Found: C, 61.32; H, 5.28; N, 9.91. $C_{29}H_{29}ClN_4O_5 \cdot H_2O$ requires: C, 61.43; H, 5.51; N, 9.88.

EXAMPLE 213

The Preparation of 3-(4-(2-Chlorophenyl)-9-methoxy-1,3-dioxo-2,3-dihydropyrrolo[3,4-c]carbazol-6 (1H)-yl)-N-(1H-tetraazol-5-yl)propanamide (XI; Ar=2-chlorophenyl, n=2, $R^3$=H, $R^4$=5-tetrazolyl) (253)

Reaction of acid (116) (70 mg, 0.16 mmol) prepared as described in example 229 according to the procedure described in example 207, except that solid 5-aminotetrazole (27 mg, 0.31 mmol) was added as the amine and the reaction was heated at reflux for 2 hours before work-up, gave amide (253) (52 mg, 63%) as a yellow powder, mp 232° C. (dec). $^1$H NMR δ [$(CD_3)_2SO$] 15.8 (v br s, 1H), 11.90 (br s, 1H), 11.13 (br s, 1H), 8.52 (d, J=2.6 Hz, 1H), 7.84 (s, 1H), 7.75 (d, J=9.0 Hz, 1H), 7.57 (d, J=7.4 Hz, 1H), 7.50–7.40 (m, 3H), 7.30 (dd, J=9.0, 2.6 Hz, 1H), 4.83 (t, J=6.8 Hz, 2H), 3.90 (s, 3H), 2.97 (t, J=6.8 Hz, 2H). FABMS found [M=H]$^+$ =516.1174, 518.1154. $C_{12}H_{18}ClN_7O_4$ requires 516.1187, 518.1158.

EXAMPLE 214

The Preparation of N-[2-(Dimethylamino)ethyl]-3-(9-hydroxy-1,3-dioxo-4-phenyl-2,3-dihydropyrrolo[3,4-c]carbazol-6 (1H)-yl)propanamide (XIII; Ar=phenyl, n=2, $R^3$=H, $R^4$=$CH_2CH_2N(CH_3)_2$) (254)

Reaction of methyl ether (247) (70 mg, 0.14 mmol) prepared as described in example 207 according to the procedure described in example 81, except that the reaction mixture was diluted with water, basified by the addition of concentrated ammonia and extracted with ethyl acetate. The organic layer was dried, the drying agent was removed and the solution was concentrated to dryness. Chromatography on silica eluting with ethyl acetate/methanol/triethylamine (1:0:0 to 3:1:trace). Crystallization from ethyl acetate/hexane then gave amide (254) (35 mg, 53%) as an orange powder, mp 176–180° C. $^1$H NMR δ [$(CD_3)_2SO$] 11.06 (br s, 1H), 9.35 (br s, 1H), 8.39 (d, J=2.5 Hz, 1H), 7.77 (s, 1H), 7.74 (t, J=5.6 Hz, 1H), 7.66 (m, 2H), 7.53 (d, J=8.8 Hz, 1H), 7.48 (m, 3H), 7.12 (dd, J=8.8, 2.5 Hz, 1H), 4.69 (t, J=6.4 Hz, 2H), 2.94 (m, 2H), 2.58 (t, J=6.4 Hz, 2H), 1.91 (s, 6H), 1.87 (m, 2H). Found: C, 66.87; H, 5.83; N, 11.47. $C_{27}H_{26}N_4O_4 \cdot 3/4H_2O$ requires: C, 67.00; H, 5.73; N, 11.57.

EXAMPLE 215

The Preparation of 3-(9-Hydroxy-1,3-dioxo-4-phenyl-2,3-dihydropyrrolo[3,4-c]carbazol-6(1H)-yl)propanamide (XIII; Ar=phenyl, n=2, $R_1$=H, $R_2$=H) (255) and 3-(9-hydroxy-1,3-dioxo-4-phenyl-2,3-dihydropyrrolo[3,4-c]carbazol-6 (1H)-yl) propanoic acid (X; Ar=phenyl, n=2) (256)

Reaction of methyl ether (248) (56 mg, 0.14 mmol)) prepared as described in example 208 according to the procedure described in example 81, followed by chromatography on silica eluting with ethyl acetate/hexane (4:1) to ethyl acetate/methanol (9:1) gave initially, amide (255) (11 mg, 20%) as an orange powder, mp 284–288° C. $^1$H NMR δ [$(CD_3)_2SO$] 11.05 (br s, 1H), 9.33 (br s, 1H), 8.40 (d, J=2.5 Hz, 1H), 7.82 (s, 1H), 7.67 (m, 2H), 7.56 (d, J=8.8 Hz, 1H), 7.47 (m, 3H), 7.34 (br s, 1H), 7.12 (dd, J=8.8, 2.5 Hz, 1H), 6.86 (br s, 1H), 4.67 (t, J=6.5 Hz, 2H), 2.58 (t, J=6.5 Hz, 2H). FABMS found [M+H]$^+$: 400.1307. $C_{23}H_{17}N_3O_4$ requires 400.1297. This was followed at lower Rf by the acid (256) (34 mg, 63%) as an orange powder, mp 300–310° C. (dec). $^1$H NMR δ [$(CD_3)_2SO$] 12.1 (v br s, 1H), 11.06 (br s, 1H), 9.34 (br s, 1H), 8.40 (d, J=2.4 Hz, 1H), 7.84 (s, 1H), 7.67 (m, 2H), 7.57 (d, J=8.8 Hz, 1H), 7.46 (m, 3H), 7.12 (dd, J=8.8, 2.4 Hz, 1H), 4.69 (t, J=6.7 Hz, 2H), 2.75 (t, J=6.7 Hz, 2H). Found: C, 67.64; H, 4.29; N, 6.65. $C_{23}H_{16}N_2O_5 \cdot 1/2H_2O$ requires: C, 67.48; H, 4.19; N, 6.84.

EXAMPLE 216

The Preparation of 3-(4-(2-Chlorophenyl)-9-hydroxy-1,3-dioxo-2,3-dihydropyrrolo[3,4-c]carbazol-6 (1H)-yl)-N-[2-(dimethylamino)ethyl]propanamide (XIII; Ar=2-chlorophenyl, n=2, $R^3$=H, $R^4$=$CH_2CH_2N(CH)_2$ (257)

Reaction of methyl ether (249) (65 mg, 0.13 mmol) prepared as described in example 209 according to the proceedure described in example 81, except that the reaction mixture was diluted with water, basified by the addition of concentrated ammonia and extracted with ethyl acetate, The organic layer was dried, the drying agent was removed and the solution was concentrated to dryness. Chromatography on silica eluting with ethyl acetate/methanol/triethylamine (1:0:0 to 3:1:trace). Crystallization from ethyl acetate/hexane then gave amide (257) (28 mg, 44%) as an orange powder, mp 205–215° C. $^1$H NMR δ [$(CD_3)_2SO$] 11.06 (br s, 1H), 9.35 (s, 1H), 8.37 (d, J=2.3 Hz, 1H), 7.81 (br s, 1H), 7.72 (s, 1H), 7.57 (m, 2H), 7.48 (m, 3H), 7.14 (dd, J=8.9, 2.3 Hz, 1H), 4.67 (t, J=6.4 Hz, 2H), 2.99 (m, 2H), 2.57 (t, J=6.4 Hz, 2H), 2.03 (m, 8H). Found: C, 61.32; H, 5.49; N, 10.72. $C_{27}H_{25}ClN_4O_4 \cdot 11/4H_2O$ requires: C, 61.47; H, 5.26; N, 10.62.

EXAMPLE 217

The Preparation of 3-(4-(2,6-Dichlorophenyl)-9-hydroxy-1,3-dioxo-2,3-dihydropyrrolo[3,4-c]carbazol-6 (1H)-yl)propanamide (XIII; Ar=2,6-dichlorophenyl, n=2, $R^3$=H, $R^4$=H) (258)

Reaction of methyl ether (250) (80 mg, 0.17 mmol)) prepared as described in example 210 according to The procedure described in example 80, followed by chromatography on silica eluting with ethyl acetate then tetrahydrofuran and trituration from ethyl acetate, gave amide (258)

(47 mg, 59%) as an orange powder, mp 327–329° C. $^1$H NMR δ [(CD$_3$)$_2$SO] 11.12 (br s, 1H), 9.39 (s, 1H), 8.36 (d, J=2.4 Hz, 1H), 7.82 (s, 1H), 7.61 (m, 3H), 7.51 (dd, J=8.8, 7.4 Hz, 1H), 7.38 (br s, 1H), 7.15 (dd, J=8.9, 2.4 Hz, 1H), 6.87 (br s, 1H), 4.65 (t, J=6.7 Hz, 2H), 2.55 (t, J=6.7 Hz, 2H). Found: C, 57.75; H, 3.83; N, 8.50. $C_{23}H_{15}Cl_2N_3O_4 \cdot 3/4H_2O$ requires: C, 57.33; H, 3.45; N, 8.72.

EXAMPLE 218

The Preparation of 3-(4-(2,6-Dichlorophenyl)-9-hydroxy-1,3-dioxo-2,3-dihydropyrrolo[3,4-c]carbazol-6 (1H)-yl)-N-[2-(dimethylamino)ethyl]propanamide (XIII; Ar=2,6-dichlorophenyl, n=2, R$^3$=H, R$^4$=CH$_2$CH$_2$N(CH$_3$)$_2$) (259)

Reaction of methyl ether (251) (70 mg, 0.13 mmol)) prepared as described in example 211 according to The procedure described in example 80, except that the reaction time was 6 hours and chromatography was performed eluting with ethyl acetate/methanol/triethylamine (1:0:0 to 3:1:trace), gave amide (259) (31 mg, 45%) as a yellow powder, mp 220–226° C. $^1$H NMR δ [(CD$_3$)$_2$SO] 11.13 (br s, 1H), 9.39 (s, 1H), 8.36 (d, J=2.5 Hz, 1H), 7.84 (t, J=5.4 Hz, 1H), 7.76 (s, 1H), 7.62 (m, 2H), 7.58 (d, J=8.9 Hz, 1H), 7.51 (dd, J=8.9, 7.4 Hz, 1H), 7.16 (dd, J=8.9, 2.5 Hz, 1H), 4.67 (t, J=6.5 Hz, 2H), 3.03 (m, 2H), 2.57 (t, J=6.5 Hz, 2H), 2.16 (br s, 2H), 2.08 (m, 6H). Found: C, 58.09; H, 4.44; N, 9.72. $C_{27}H_{24}Cl_2N_4O_4 \cdot H_2O$ requires: C, 58.18; H, 4.70; N, 10.05.

EXAMPLE 219

The Preparation of 3-(4-(2-Chloro-6-methoxyphenyl)-9-hydroxy-1,3-dioxo-2,3-dihydropyrrolo[3,4-c] carbazol-6 (1H)-yl)-N-[2-(dimethylamino)ethyl] propanamide (XIII; Ar=2-chloro-6-methoxyphenyl, n=2, R$^3$=H, R$^4$=CH$_2$CH$_2$N(CH$_3$)$_2$) (260)

Reaction of methyl ether (252) prepared as described in example 212 (80 mg, 0.15 mmol) according to The procedure described in example 80, except that the reaction was performed at 0° C. for 2 hours and chromatography was performed eluting with ethyl acetate/methanol/triethylamine (1:0:0 to 3:1:trace), gave amide (260) (65 mg, 83%) as a yellow/orange powder, mp 200–205° C. $^1$H NMR δ [(CD$_3$)$_2$SO] 11.00 (br s, 1H), 9.34 (s, 1H), 8.36 (d, J=2.4 Hz, 1H), 7.87 (br s, 1H), 7.66 (s, 1H), 7.54 (d, J=8.9 Hz, 1H), 7.44 (t, J=8.2 Hz, 1H), 7.18 (dd, J=8.2, 0.7 Hz, 1H), 7.12 (m, 2H), 4.64 (t, J=6.6 Hz, 2H), 3.68 (s, 3H), 3.05 (m, 2H), 2.56 (t, J=6.6 Hz, 2H), 2.23 (v br s, 2H), 2.15 (br s, 6H). Found: C, 58.98; H, 5.12; N, 9.59. $C_{28}H_{27}ClN_4O_5 \cdot 2H_2O$ requires: C, 58.90; H, 5.47; N, 9.81.

EXAMPLE 220

The Preparation of N-[2-(Dimethylamino)ethyl]-3-(9-hydroxy-4-(2-methoxyphenyl)-1,3-dioxo-2,3-dihydropyrrolo[3,4-c]carbazol-6 (1H)-yl)propanamide (XIII; Ar=2-methoxyphenyl, n=2, R$^3$=H, R$^4$=CH$_2$CH$_2$N(CH$_3$)$_2$) (330)

To a solution of amide (260) (40 mg, 0.07 mmol)) prepared as described in example 219 in ethyl acetate/methanol (1:1, 80 mL) was added 5% Pd-C (catalytic). The resulting suspension was hydrogenated at 60 psi with stirring for 4 days, with additional portions of Pd-C being added every 24 hours. The reaction mixture was then filtered through celite and concentrated under reduced pressure before being chromatographed on silica eluting with methanol/ethyl acetate/triethylamine (1:4:trace), to give amide (330) (6 mg, 16%) as a yellow powder, mp 232–238° C. $^1$H NMR δ [(CD$_3$)$_2$SO] 10.95 (br s, 1H), 9.33 (br s, 1H), 8.37 (d, J=2.4 Hz, 1H), 8.01 (br s, 1H), 7.69 (s, 1H), 7.54 (d, J=8.9 Hz, 1H), 7.43 (m, 1H), 7.34 (dd, J=7.5, 1.8 Hz, 1H), 7.13–7.05 (m, 3H), 4.67 (t, J=6.2 Hz, 2H), 3.69 (s, 3H), –3.2 (obscured m, 2H), 2.60 (t, J=6.2 Hz, 2H), 2.54–2.49 (obscured m, 8H). FABMS found [M+H]$^+$: 501.2142. $C_{28}H_{28}N_4O_5$ requires 501.2138.

EXAMPLE 221

The Preparation of 3-(4-(2-Chlorophenyl)-9-hydroxy-1,3-dioxo-2,3-dihydropyrrolo[3,4-c]carbazol-6 (1H)-yl)-N-(1H-tetraazol-5-yl)propanamide (XIII; Ar=2-chlorophenyl, n=2, R$^3$=H, R$^4$=5-tetrazolyl) (261)

Reaction of methyl ether (253) (40 mg, 0.08 mmol)) prepared as described in example 213 according to the procedure described in example 80, except that the chromatography was performed eluting with ethyl acetate/methanol (1:0 to 9:1), gave amide (261) (11 mg, 27%) as an orange powder, mp 283° C. (dec.). $^1$H NMR δ [(CD$_3$)$_2$SO] 15.82 (br s, 1H), 12.03 (br s, 1H), 11.08 (s, 1H), 9.38 (s, 1H), 8.37 (d, J=2.3 Hz, 1H), 7.79 (s, 1H), 7.62 (d, J=8.8 Hz, 1H), 7.56 (d, J=7.6 Hz, 1H), 7.49–7.38 (m, 3H), 7.13 (dd, J=8.8, 2.3 Hz, 1H), 4.80 (t, J=6.7 Hz, 2H), 2.96 (t, J=6.7 Hz, 2H). FABMS found M$^+$: 501.0955, 503.0956. $C_{24}H_{16}ClN_7O_4$ requires 501.0952, 503.0923.

Representative Procedure for Method 15 of Scheme 4

EXAMPLE 222

The Preparation of N-[3-(4-(2-Chlorophenyl)-9-methoxy-1,3-dioxo-2,3-dihydropyrrolo[3,4-c]carbazol-6 (1H)-yl)propanoyl]methanesulfonamide (XII; Ar=2-chlorophenyl n=2, R$^3$=CH$_3$) (265)

To a stirred solution of acid (116) (0.20 g, 0.45 mmol) prepared as described in example 229, 4-dimethylaminopyridine (DMAP) (165 mg, 1.35 mmol) and methanesulfonamide (86 mg, 0.90 mmol) in dimethylformamide (10 mL) under nitrogen was added 1-(3-dimethylaminopropyl)-3-ethylcarbodiimide hydrochloride (EDCI.HCl) (259 mg, 1.35 mmol). The resulting mixture was stirred at room temperature for 18 hours and then diluted with water, acidified by the addition of 1N hydrochloric acid and extracted with ethyl acetate. The organic phase was dried, the drying agent was removed and the solution was concentrated to dryness. Chromatography on silica eluting with ethyl acetate/hexane (4:1) to ethyl acetate/methanol (1:0 to 9: 1), gave acylsulfonamide (265) (151 mg, 64%) as a yellow powder, mp 293–295° C. $^1$H NMR δ [(CD$_3$)$_2$SO] 11.76 (br s, 1H), 11.14 (br s, 1H), 8.52 (d, J=2.6 Hz, 1H), 7.87 (s, 1H), 7.73 (d, J=9.0 Hz, 1H), 7.58 (m, 1H), 7.53–7.46 (m, 3H), 7.32 (dd, J=9.0, 2.6 Hz, 1H), 4.74 (t, J=6.9 Hz, 2H), 3.91 (s, 3H), 3.08 (s, 3H), 2.81 (t, J=6.9 Hz, 2H). Found: C, 57.30; H, 3.87; N, 7.72. $C_{25}H_{20}ClN_3O_6S$ requires: C, 57.08; H, 3.83; N, 7.99.

EXAMPLE 223

The Preparation of N-[3-(4-(2-Chlorophenyl)-9-hydroxy-1,3-dioxo-2,3-dihydropyrrolo[3,4-c]carbazol-6 (1H)-yl)propanoyl]benzenesulfonamide (XIV; Ar=2-chlorophenyl, n=2, $R^3$=Ph) (266)

Reaction of acid (116) (70 mg, 0.16 mmol) prepared as described in example 229 with benzenesulfonamide according to the procedure described in example 222 followed by demethylation employing the procedure described in example 80 and chromatography on silica eluting with ethyl acetate/hexane (1:1 to 3:1), gave acylsulfonamide (266) (63 mg, 70%) as an orange powder, mp 291–293° C. $^1$H NMR δ [$(CD_3)_2SO$] 12.15 (br s, 1H), 11.07 (br s, 1H), 9.36 (s, 1H), 8.35 (d, J=2.4 Hz, 1H), 7.81 (m, 2H), 7.76 (s, 1H), 7.65 (m, 1H), 7.57–7.46 (m, 7H), 7.06 (dd, J=8.9, 2.4 Hz, 1H), 4.59 (m, 2H), 2.75 (t, J=7.1 Hz, 2H). Found: C, 60.62; H, 3.80; N, 7.20. $C_{29}H_{20}ClN_3O_6S$ requires: C, 60.68; H, 3.51; N, 7.32.

EXAMPLE 224

The Preparation of N-[3-(4-(2-chlorophenyl)-9-methoxy-1,3-dioxo-2,3-dihydropyrrolo[3,4-c]carbazol-6 (1H)-yl)propanoyl]-2-(dimethylamino)ethanesulfonamide (XII; Ar=2-chlorophenyl, n=2, $R^3$=CH$_2$CH$_2$N(CH$_3$)$_2$) (267)

Reaction of acid (116) (70 mg, 0.16 mmol) prepared as described in example 229 with 2-(dimethylamino)ethanesulfonamide according to the procedure described in example 222, except that the reaction mixture was diluted with brine before being extracted with ethyl acetate. The organic phase was dried, the drying agent was removed and the solution was concentrated to dryness, and the chromatography was performed eluting with ethyl acetate/methanol (1:0 to 4:1),gave acylsulfonamide (267) (43 mg, 47%) as a yellow powder, mp 208–213° C. $^1$H NMR δ [$(CD_3)_2SO$] 11.11 (br s, 1H), 8.52 (d, J=2.6 Hz, 1H), 7.80 (s, 1H), 7.72 (d, J=9.0 Hz, 1H), 7.57 (m, 2H), 7.47 (m, 2H), 7.31 (dd, J=9.0, 2.6 Hz, 1H), 4.68 (m, 2H), 3.90 (s, 3H), 3.23 (partially obscured m, 2H), 2.87 (t, J=6.9 Hz, 2H), 2.62 (t, J=6.8 Hz, 2H), 2.43 (s, 6H). Found: C, 59.44; H, 5.57; N, 8.52. $C_{28}H_{27}ClN_4O_6S.1/2C_6H_{14}$ requires: C, 59.47; H, 5.47; N, 8.95.

EXAMPLE 225

The Preparation of N-[4-(4-(2-Chlorophenyl)-9-hydroxy-1,3-dioxo-2,3-dihydropyrrolo[3,4-c]carbazol-6 (1H)-yl)butanoyl]methanesulfonamide (XIV; Ar=2-chlorophenyl, n=3, $R^3$=CH$_3$) (268)

Reaction of acid (262) (50 mg, 0.11 mmol) prepared as described in example 87 according to The procedure described in example 222 followed by demethylation employing the procedure described in example 80 and chromatography on silica eluting with ethyl acetate/hexane (1:1 to 3:1), gave acylsulfonamide (268) (29 mg, 51%) as an orange powder, mp 257–260° C. $^1$H NMR δ [$(CD_3)_2SO$] 11.66 (br s, 1H), 11.06 (br s, 1H), 9.37 (s, 1H), 8.38 (d, J=2.4 Hz, 1H), 7.79 (s, 1H), 7.61–7.45 (m, 5H), 7.15 (dd, J=8.8, 2.4 Hz, 1H), 4.45 (t, J=7.2 Hz, 2H), 3.10 (s, 3H), 2.32 (m, 2H), 1.97 (m, 2H). Found: C, 57.40; H, 3.94; N, 7.73. $C_{25}H_{20}ClN_3O_6S$ requires: C, 57.09; H, 3.83; N, 7.99.

EXAMPLE 226

The Preparation of N-[4-(4-(2-Chlorophenyl)-9-hydroxy-1,3-dioxo-2,3-dihydropyrrolo[3,4-c]carbazol-6 (1H)-yl)butanoyl]benzenesulfonamide (XIV; Ar=2-chlorophenyl, n=3, $R^3$=Ph) (269)

Reaction of acid (262) (45 mg, 0.10 mmol) prepared as described in example 87 with benzenesulfonamide according to the procedure described in example 222 followed by demethylation employing the procedure described in example 80 and chromatography on silica eluting with ethyl acetate/hexane (1:1 to 3:1), gave acylsulfonamide (269) (39 mg, 68%) as an orange powder, mp 224–230° C. $^1$H NMR δ [$(CD_3)_2SO$] 12.09 (br s, 1H), 11.05 (br s, 1H), 9.36 (s, 1H), 8.36 (d, J=2.4 Hz, 1H), 7.88 (m, 2H), 7.73 (s, 1H), 7.67 (m, 1H), 7.57 (m, 3H), 7.52–7.43 (m, 4H), 7.09 (dd, J=8.8, 2.4 Hz, 1H), 4.33 (t, J=7.3 Hz, 2H), 2.29 (t, J=7.2 Hz, 2H), 1.86 (m, 2H). Found: C, 61.10; H, 3.81; N, 6.91. $C_{30}H_{12}ClN_3O_6S$ requires: C, 61.28; H, 3.77; N, 7.15.

EXAMPLE 227

The Preparation of N-[3-(4-(2-Chlorophenyl)-9-hydroxy-1,3-dioxo-2,3-dihydropyrrolo[3,4-c]carbazol-6 (1H)-yl)propanoyl]methanesulfonamide (XIV; Ar=2-chlorophenyl, n=2. $R^3$=CH$_3$) (270)

Reaction of methyl ether (265) (130 mg, 0.25 mmol) prepared according to example 222 according to the procedure described in example 80, except that the chromatography was performed eluting with methanol/dichloromethane (5:95 to 1:9), gave acylsulfonamide (270) (83 mg, 66%) as an orange powder, mp 290–296° C. $^1$H NMR δ [$(CD_3)_2SO$] 11.75 (br s, 1H), 11.08 (br s, 1H), 9.38 (s, 1H), 8.38 (d, J=2.4 Hz, 1H), 7.80 (s, 1H), 7.59 (m, 2H), 7.53–7.46 (m, 3H), 7.14 (dd, J=8.9, 2.4 Hz, 1H), 4.69 (t, J=6.9 Hz, 2H), 3.04 (s, 3H), 2.76 (t, J=6.9 Hz, 2H). Found: C, 54.70; H, 3.81; N, 7.67. $C_{24}H_{18}ClN_3O_6S.3/4H_2O$ requires: C, 54.85; H, 3.74; N, 7.99.

EXAMPLE 228

The Preparation of N-[3-(4-(2-Chlorophenyl)-9-hydroxy-1,3-dioxo-2,3-dihydropyrrolo[3,4-c]carbazol-6 (1H)-yl)propanoyl]-2-(dimethylamino)ethanesulfonamide (XIV; Ar=2-chlorophenyl, n=2, $R^3$=CH$_2$CH$_2$N(CH$_3$)$_2$) (271)

Reaction of methyl ether (267) (35 mg, 0.06 mmol) prepared as described in example 224 according to the proceedure described in example 81, except that the reaction mixture was diluted with saturated sodium bicarbonate and extracted with ethyl acetate. The organic phase was dried, the drying agent was removed and the solution was concentrated to dryness. Chromatography on silica eluting with methanol/dichloromethane (1:9 to 1:3), gave acylsulfonamide (271) (8 mg, 23%) as an orange powder, mp 229–233° C. $^1$H NMR δ [$(CD_3)_2SO$] 11.05 (br s, 1H), 9.37 (br s, 1H), 8.37 (d, J=2.5 Hz, 1H), 7.74 (s, 1H), 7.61–7.52 (m, 3H), 7.50–7.43 (m, 2H), 7.14 (dd, J=8.7, 2.5 Hz, 1H), 4.63 (m, 2H), 3.21 (partially obscured m, 2H), 2.81 (m, 2H), 2.59 (t, J=6.8 Hz, 2H), 2.38 (s, 6H). FABMS found [M+H]$^+$: 569.1255, 571.1204. $C_{27}H_{25}ClN_4O_6S$ requires 569.1262, 571.1232.

EXAMPLE 229

The Preparation of 3-(4-(2-Chlorophenyl)-9-methoxy-1,3-dioxo-2,3-dihydropyrrolo[3,4-c]carbazol-6 (1H)-yl)propanoic acid (IX; Ar=2-chlorophenyl n=2) (116)

Oxidation of the alcohol (31) prepared as described in example 40 using the procedure described in example 203 gave the acid (116) (62%) as a yellow solid, mp 277° C. $^1$H NMR δ [(CD$_3$)$_2$SO] 12.61 (br, 1H), 11.12 (s, 1H), 8.52 (d, J=2.6 Hz, 1H), 7.86 (s, 1H), 7.73 (d, J=9.0 Hz, 1H), 7.58 (m, 1H), 7.54–7.44 (m, 3H), 7.31 (dd, J=9.0, 2.6 Hz, 1H), 4.71 (t, J=6.8 Hz, 2H), 3.93 (s, 3H), 2.80 (t, J=6.8 Hz, 2H). Found: C, 62.90; H, 3.79; N, 5.93. C$_{24}$H$_{17}$ClN$_2$O$_5$.1/2H$_2$O requires C, 62.96; H, 3.96; N, 6.12.

EXAMPLE 230

The Preparation of 3-(4-(2-Chlorophenyl)-9-hydroxy-1,3-dioxo-2,3-dihydropyrrolo[3,4-c]carbazol-6 (1H)-yl)propanoic acid (X; Ar=2-chlorophenyl, n=2) (117)

Demethylation of (116) prepared as described in example 229 with pyridinium hydrochloride using the procedure described in example 81 gave (117) (50%) as a yellow powder, mp 286° C. $^1$H NMR δ [(CD$_3$)$_2$SO] 12.40 (br, 1H), 11.06 (br s, 1H), 9.37 (br s, 1H), 8.37 (d, J=2.4 Hz, 1H), 7.81 (s, 1H), 7.59 (d, J=8.7 Hz, 1H), 7.57 (m, 1H), 7.53–7.43 (m, 3H), 7.13 (dd, J=8.7, 2.4 Hz, 1H), 4.67 (t, J=6.8 Hz, 2H), 2.74 (t, J=6.8 Hz, 2H). Found: C, 60.00; H, 3.65; N, 5.52. C$_{23}$H$_{15}$ClN$_2$O$_5$.1.5H$_2$O requires C, 59.81; H, 3.92; N, 6.06.

EXAMPLE 231

The Preparation of 3-(4-(2-Chlorophenyl)-9-methoxy-1,3-dioxo-2,3-dihydropyrrolo[3,4-c]carbazol-6 (1H)-yl)propanamide (XI; Ar=2-chlorophenyl, n=2, R$^3$=R$^4$=H) (118)

Reaction of acid (117) prepared as described in example 230 with oxalyl chloride followed by ammonia using the procedure described in example 207 gave the amide (118) (78%) as a yellow powder, mp 283–286° C. $^1$H NMR δ [(CD$_3$)$_2$SO] 11.12 (br s, 1H), 8.52 (d, J=2.6 Hz, 1H), 7.82 (s, 1H), 7.71 (d, J=9.0 Hz, 1H), 7.58 (m, 1H), 7.54–7.44 (m, 3H), 7.35 (br, 1H), 7.31 (dd, J=9.0, 2.6 Hz, 1H), 6.86 (br, 1H), 4.69 (t, J=6.6 Hz, 2H), 3.90 (s, 3H), 2.58 (t, J=6.6 Hz, 2H). Found: C, 63.52; H, 4.22; N, 9.04. C$_{14}$H$_{18}$ClN$_3$O$_4$.1/4H$_2$O requires C, 63.72; H, 4.12; N, 9.29.

EXAMPLE 232

The Preparation of 3-(4-(2-Chlorophenyl)-9-hydroxy-1,3-dioxo-2,3-dihydropyrrolo[3,4-c]carbazol-6 (1H)-yl)propanamide (XIII; Ar=2-chlorophenyl, n=2, R$^3$=R$^4$=H) (119).

Demethylation of (118) prepared as described in example 231 with BBr$_3$ using the procedure described in example 80 gave (119) as a yellow/orange powder (77%), mp 319–322° C. $^1$H NMR δ [(CD$_3$)$_2$SO] 11.06 (br s, 1H), 9.36 (br s, 1H), 8.37 (d, J=2.4 Hz, 1H), 7.77 (s, 1H), 7.60–7.55 (m, 2H), 7.52–7.43 (m, 3H), 7.35 (br, 1H), 7.13 (dd, J=8.8, 2.4 Hz, 1H), 6.87 (br, 1H), 4.65 (t, J=6.7 Hz, 2H), 2.57 (t, J=6.7 Hz, 2H). FABMS found M$^+$: 435.0833, 433.0828. C$_{23}$H$_{16}$ClN$_3$O$_4$ requires 435.0800, 433.0829.

EXAMPLE 233

The Preparation of 3-(4-(2-Chlorophenyl)-9-methoxy-1,3-dioxo-2,3-dihydropyrrolo[3,4-c]carbazol-6 (1H)-yl)-N-[2-(4-morpholinyl)ethyl]propanamide (XI; Ar=2-chlorophenyl, n=2, R$^3$=H, R$^4$=CH$_2$CH$_2$N(CH$_2$CH$_2$)$_2$O) (120)

Reaction of acid (117) prepared as described in example 230 with oxalyl chloride followed by N-(2-aminoethyl) morpholine using the procedure described in example 207 gave the amide (120) (73%) as a yellow powder, mp 174–176° C. $^1$H NMR δ [(CD$_3$)$_2$SO] 11.12 (br s, 1H), 8.51 (d, J=2.6 Hz, 1H), 7.77 (s, 1H), 7.74 (t, J=5.6 Hz, 1H), 7.68 (d, J=9.0 Hz, 1H), 7.58 (m, 1H), 7.53–7.44 (m, 3H), 7.31 (dd, J=9.0, 2.6 Hz, 1H), 4.71 (t, J=6.3 Hz, 2H), 3.90 (s, 3H), 3.40 (t, J=4.6 Hz, 4H), 2.97 (m, 1H), 2.58 (t, J=6.3 Hz, 2H), 2.11 (br t, J=4.6 Hz, 4H), 2.00 (t, J=6.7 Hz, 2H). Found: C, 60.46; H, 5.26; N, 9.27. C$_{30}$H$_{29}$ClN$_4$O$_5$.2H$_2$O requires C, 60.35; H, 5.94; N, 9.38.

EXAMPLE 234

The Preparation of 3-(4-(2-Chlorophenyl)-9-hydroxy-1,3-dioxo-2,3-dihydropyrrolo[3,4-c]carbazol-6 (1H)-yl)-N-[2-(4-morpholinyl)ethyl]propanamide (XIII; Ar=2-chlorophenyl, n=2, R$^3$=H, R$^4$=CH$_2$CH$_2$N(CH$_2$CH$_2$)$_2$O) (121)

Demethylation of (120) prepared as described in example 233 with BBr$_3$ using the procedure described in example 80 except that the reaction time was 16 h gave (121) as a yellow powder (64%), mp 143–148° C. (dec). $^1$H NMR δ [(CD$_3$)$_2$SO] 11.05 (s, 1H), 9.35 (s, 1H), 8.36 (d, J=2.4 Hz, 1H), 7.74 (t, J=5.6 Hz, 1H), 7.71 (s, 1H), 7.60–7.55 (m, 2H), 7.52–7.43 (m, 3H), 7.13 (dd, J=8.8, 2.4 Hz, 1H), 4.67 (t, J=6.3 Hz, 2H), 3.40 (t, J=4.7 Hz, 4H), 2.98 (m, 2H), 2.57 (t, J=6.3 Hz, 2H), 2.12 (t, J=4.7 Hz, 4H), 2.02 (t, J=6.7 Hz, 1H). Found: C, 62.37; H, 4.99; N, 9.82. C$_{29}$H$_{27}$ClN$_4$O$_5$.1/2H$_2$O requires C, 62.64; H, 5.08; N, 10.08.

EXAMPLE 235

The Preparation of 3-(4-(2-Chlorophenyl)-9-methoxy-1,3-dioxo-2,3-dihydropyrrolo[3,4-c]carbazol-6 (1H)-yl)-N-[2-(dimethylamino)ethyl]-N-methylpropanamide (XI; Ar=2-chlorophenyl, n=2, R$^3$=CH$_3$, R$^4$=CH$_2$CH$_2$N(CH$_3$)$_2$ (122)

Reaction of acid (117) prepared as described in example 230 with oxalyl chloride followed by N,N,N'-trimethylethylenediamine using the procedure described in example 207 gave the amide (122) (77%) as a yellow powder, mp 146–152° C. (dec). $^1$H NMR δ [(CD$_3$)$_2$SO] 11.10 (br, 1H), 8.51 (d, J=2.6 Hz, 1H), 7.83 (s, 0.5H), 7.79 (s, 0.5H), 7.72 (m, 1H), 7.58 (m, 1H), 7.54–7.43 (m, 3H), 7.31 (m, 1H), 4.72 (m, 2H), 3.90 (s, 1H), 3.25 (m, 1H), 3.09 (m, 1H), 2.83 (m, 2H), 2.72 (s, 1.5H), 2.71 (s, 1.5H), 2.13 (t, J=4.8 Hz, 1H), 2.05 (s, 3H), 2.00 (t, J=4.8 Hz, 1H), 1.88 (s, 3H). Found: C, 63.42; H, 5.46; N, 10.15. C$_{29}$H$_{19}$ClN$_4$O$_4$.H$_2$O requires C, 63.21; H, 5.67; N, 10.17.

EXAMPLE 236

The Preparation of 3-(4-(2-Chlorophenyl)-9-hydroxy-1,3-dioxo-2,3-dihydropyrrolo[3,4-c]carbazol-6 (1H)-yl)-N-[2-(dimethylamino)ethyl]-N-methylpropanamide (XIII; Ar=2-chlorophenyl, n=2, $R^3$=$CH_3$, $R^4$=$CH_2CH_2N(CH_3)$ (123)

Demethylation of (122) prepared as described in example 236 with $BBr_3$ using the procedure described in example 80 except that the reaction time was 48 h gave (123) as a yellow powder (58%), mp 184–188° C. $^1$H NMR δ [$(CD_3)_2SO$] 11.06 (br s, 1H), 9.36 (br s, 1H), 8.37 (d, J=2.4 Hz, 1H), 7.78 (s, 0.5H), 7.74 (s, 0.5H), 7.62–7.54 (m, 2H), 7.53–7.42 (m, 3H), 7.14 (dd, J=8.8, 2.4 Hz, 1H), 4.69 (m, 2H), 3.22 (m, 1H), 3.09 (m, 1H), 2.82 (m, 2H), 2.72 (s, 1.5H), 2.71 (s, 1.5H), 2.14 (t, J=4.8 Hz, 1H), 2.06 (s, 3H), 2.00 (t, J=4.8 Hz, 1H), 1.88 (s, 3H). Found: C, 62.23; H, 5.23; N, 10.24. $C_{28}H_{17}ClN_4O_4$·1.25$H_2O$ requires C, 62.10; H, 5.49; N, 10.35.

EXAMPLE 237

The Preparation of 3-(4-(2-Chlorophenyl)-9-methoxy-1,3-dioxo-2,3-dihydropyrrolo[3,4-c]carbazol-6 (1H)-yl)-N-(2,2,6,6-tetramethyl-4-piperidinyl)propanamide (XI; Ar=2-chlorophenyl, n=2, $R^3$=H, $R^4$=2,2,6,6-tetramethyl-4-piperidinyl) (124)

Reaction of acid (117) prepared as described in example 230 with oxalyl chloride followed by 4-amino-(2,2,6,6-tetramethyl)piperidine using the procedure described in example 207 gave the amide (124) (72%) as a yellow powder, mp 155–160° C. (dec). $^1$H NMR δ [$(CD_3)_2SO$] 11.12 (br, 1H), 8.51 (d, J=2.6 Hz, 1H), 7.78 (s, 1H), 7.67 (d, J=9.0 Hz, 1H), 7.59–7.44 (m, 6H), 7.31 (dd, J=9.0, 2.6 Hz, 1H), 4.71 (m, 2H), 3.90 (s, 3H), 3.82 (m, 1H), 2.52 (t, J=6.2 Hz, 2H), 1.26 (m, 1H), 1.10 (m, 1H), 1.03 (s, 3H), 1.02 (s, 3H), 0.91 (s, 3H), 0.96 (s, 3H), 0.64 (t, J=12.3 Hz, 1H), 0.53 (t, J=12.3 Hz, 1H). Found: C, 64.37; H, 5.97; N, 9.20. $C_{33}H_{35}ClN_4O_4$·1.5$H_2O$ requires C, 64.54; H, 6.24; N, 9.12.

EXAMPLE 238

The Preparation of 3-(4-(2-Chlorophenyl)-9-hydroxy-1,3-dioxo-2,3-dihydropyrrolo[3,4-c]carbazol-6 (1H)-yl)-N-(2,2,6,6-tetramethyl-4-piperidinyl) propanamide (XIII; Ar=2-chlorophenyl, n=2, $R^3$=H, $R^4$=2,2,6,6-tetramethyl-4-piperidinyl) (125)

Demethylation of (124) prepared as described in example 237 with $BBr_3$ using the procedure described in example 80 except that the reaction time was 48 h gave (125) as a yellow powder (47%), mp 293–299° C. (dec). $^1$H NMR δ [$(CD_3)_2$SO] 11.08 (br s, 1H), 9.38 (br s, 1H), 8.72 (br, 1H), 8.37 (d, J=2.4 Hz, 1H), 7.83 (d, J=7.1 Hz, 1H), 7.75 (s, 1H), 7.60–7.44 (m, 5H), 7.14 (dd, J=8.8, 2.4 Hz, 1H), 4.70 (t, J=5.8 Hz, 2H), 3.90 (m, 1H), 2.54 (t, J=5.8 Hz, 2H), 1.45–1.31 (m, 2H), 1.30 (s, 3H), 1.29 (s, 3H), 1.25 (s, 3H), 1.22 (s, 3H), 1.09–9.93 (m, 2H). Found: C, 58.67; H, 5.37; N, 8.41. $C_{32}H_{33}ClN_4O_4$·1.25$CH_2Cl_2$ requires C, 58.79; H, 5.27; N, 8.25.

EXAMPLE 239

The Preparation of 4-(2-Chlorophenyl)-6-{3-[cis-3,5-dimethylpiperazinyl]-3-oxopropyl}-9-methoxypyrrolo[3,4-c]carbazole-1,3(2H,6H)-dione (XI; Ar=2-chlorophenyl, n=2, $R^3$, $R^4$=cis-3,5-dimethylpiperazinyl) (126)

Reaction of acid (117) prepared as described in example 230 with oxalyl chloride followed by cis-2,6-dimethylpiperazine using the procedure described in example 207 gave the amide (126) (76%) as a yellow powder, mp 168–173° C. (dec). $^1$H NMR δ [$(CD_3)_2SO$] 11.13 (br, 1H), 8.52 (d, J=2.6 Hz, 1H), 7.80 (s, 0.5H), 7.76 (s, 0.5H), 7.71 (m, 1H), 7.58 (m, 1H), 7.54–7.43 (m, 3H), 7.31 (dd, J=9.0, 2.6 Hz, 1H), 4.71 (m, 2H), 4.17 (m, 1H), 3.89 (s, 3H), 2.94 (m, 1H), 2.75 (m, 1H), 2.23 (m, 1H), 2.08 (m, 1H), 1.87 (m, 2H), 0.88, 0.86 (2d, J=5.9 Hz, 3H), 0.67 (d, J=6.1 Hz, 3H). Found: C, 64.03; H, 5.47, N, 9.72. $C_{30}H_{29}ClN_4O_4$·$H_2O$ requires C, 64.00; H, 5.55; N, 9.95.

EXAMPLE 240

The Preparation of 4-(2-Chlorophenyl)-6-{3-[(3R,5S)-3,5-dimethylpiperazinyl]-3-oxopropyl}-9-hydroxypyrrolo[3,4-c]carbazole-1,3(2H,6H)-dione (XIII; Ar=2-chlorophenyl, n=2, $R^3$, $R^4$=cis-3,5-dimethylpiperazinyl) (127)

Demethylation of (126) prepared as described in example 239 (with $BBr_3$ using the procedure described in example 80 except that the reaction time was 48 h gave (127) as a yellow powder (38%), mp 220–224° C. (dec). $^1$H NMR δ [$(CD_3)_2$SO] 11.07 (br s, 1H) 9.36 (br s, 1H), 8.72 (br, 1H), 8.34 br, 1H), 7.72 (s, 0.5H), 7.71 (s, 0.5H), 7.60–7.54 (m, 2H), 7.52–7.43 (m, 3H), 7.13 (dd, J=8.8, 2.4 Hz, 1H), 4.68 (m, 3H), 4.15, 4.12 (2s, 2H), 2.94 (m, 1H), 2.72 (m, 1H), 2.19 (m, 1H), 2.00 (m, 1H), 1.84 (m, 1H), 0.86, 0.84 (2d, J=5.8 Hz, 3H), 0.64 (2d, J=6.1 Hz, 3H). Found: C, 63.38; H, 5.38; N, 9.96. $C_{29}H_{17}ClN_4O_4$·$H_2O$ requires C, 63.44; H, 5.32; N, 10.20.

EXAMPLE 241

The Preparation of 3-(4-(2-Chlorophenyl)-9-methoxy-1,3-dioxo-2,3-dihydropyrrolo[3,4-c]carbazol-6 (1H)-yl)-N-[2-(1H-imidazol-5-yl)ethyl]propanamide (XI; Ar=2-chlorophenyl, n=2, $R^3$=H, $R^4$=(1H-imidazol-5-yl)ethyl) (128)

Reaction of acid (117) prepared as described in example 230 with oxalyl chloride followed by histamine using the procedure described in example 207 gave the amide (128) (81%) as a yellow powder, mp 144–149° C. (dec). $^1$H NMR δ [$(CD_3)_2SO$] 11.12 (br, 1H), 8.52 (d, J=2.6 Hz, 1H), 7.91 (t, J=5.5 Hz, 1H), 7.76 (s, 1H), 7.69 (d, J=9.0 Hz, 1H), 7.58 (m, 1H), 7.52–7.42 (m, 4H), 7.32 (dd, J=9.0, 2.6 Hz, 1H), 6.56 (s, 1H), 4.69 (t, J=6.4 Hz, 2H), 3.90 (s, 3H), 3.12 (m, 2H), 2.58 (t, J=6.4 Hz, 2H), 2.39 (t, J=7.4 Hz, 2H). Found: C, 60.73; H, 4.49; N, 11.49. $C_{29}H_{24}ClN_5O_4$·1/2$CH_2Cl_2$ requires C, 60.62; H, 4.31; N, 11.98.

EXAMPLE 242

The Preparation of 3-(4-(2-Chlorophenyl)-9-hydroxy-1,3-dioxo-2,3-dihydropyrrolo[3,4-c]carbazol-6(1H)-yl)-N-[2-(1H-imidazol-5-yl)ethyl]propanamide (XIII; Ar=2-chlorophenyl, n=2, $R^3$=H, $R^4$= (1H-imidazol-5-yl)ethyl) (129)

Demethylation of (128) prepared as described in example 241 with $BBr_3$ using the procedure described in example 80 except that the reaction time was 48 h gave (129) as a yellow powder (46%), mp 158–162° C. (dec). $^1H$ NMR δ [$(CD_3)_2$SO] 11.75 (br, 1H), 11.05 (br s, 1H), 9.36 (br s, 1H), 8.37 (d, J=2.4 Hz, 1H), 7.91 (t, J=5.3 Hz, 1H), 7.71 (s, 1H), 7.59–7.54 (m, 2H), 7.50–7.42 (m, 4H), 7.14 (dd, J=8.8, 2.4 Hz, 1H), 6.57 (br, 1H), 4.65 (t, J=6.5 Hz, 2H), 3.13 (m, 2H), 2.55 (t, J=6.5 Hz, 1H), 2.40 (t, J=6.5 Hz, 1H). FABMS found [M+H]$^+$: 530.1431, 528.1440. $C_{28}H_{23}ClN_5O_4$ requires 530.1409, 528.1439.

Ar=phenyl) (0.50 g, 0.015 mmol) in ethanol (80 mL) and the solution was left overnight. A further four portions of sodium borohydride were added at 1 h intervals and the solution was diluted with water, extracted with ethyl acetate. The organic phase was dried, the drying agent was removed and the solution was concentrated to dryness, which was chromatographed on silica. Ethyl acetate/petroleum ether (2:1) eluted starting material (12 mg), followed by the 3-hydroxy compound (134) (0.07 g, 14%) as a cream powder, mp 300–310° C. (dec). $^1H$ NMR δ [$(CD_3)_2$SO] 11.26 (br s, 1H), 8.98 (s, 1H), 8.83 (s, 1H), 8.50 (d, J=2.3 Hz, 1H), 7.70 (br d, J=7.0 Hz, 2H), 7.53 (s, 1H), 7.49–7.31 (m, 4H), 6.96 (dd, J=8.7, 2.3 Hz, 1H), 6.25 (d, J=9.7 Hz, 1H), 5.87 (d, J=9.7 Hz, 1H). Found: C, 71.77; H, 4.47; N, 8.14. $C_{20}H_{13}N_2O_3 \cdot 1/4H_2O$ requires C, 71.95; H, 4.08; N, 8.39.

Elution with ethyl acetate gave a mixed fraction of (134) and (133) (0.014 g), followed by pure 1-hydroxy compound (133) (0.32 g, 64%) as a white powder, mp 300–310 t ° C. (dec). $^1H$ NMR δ [$(CD_3)_2$SO] 11.38 (br s, 1H), 9.06 (s, 1H),

SCHEME 5

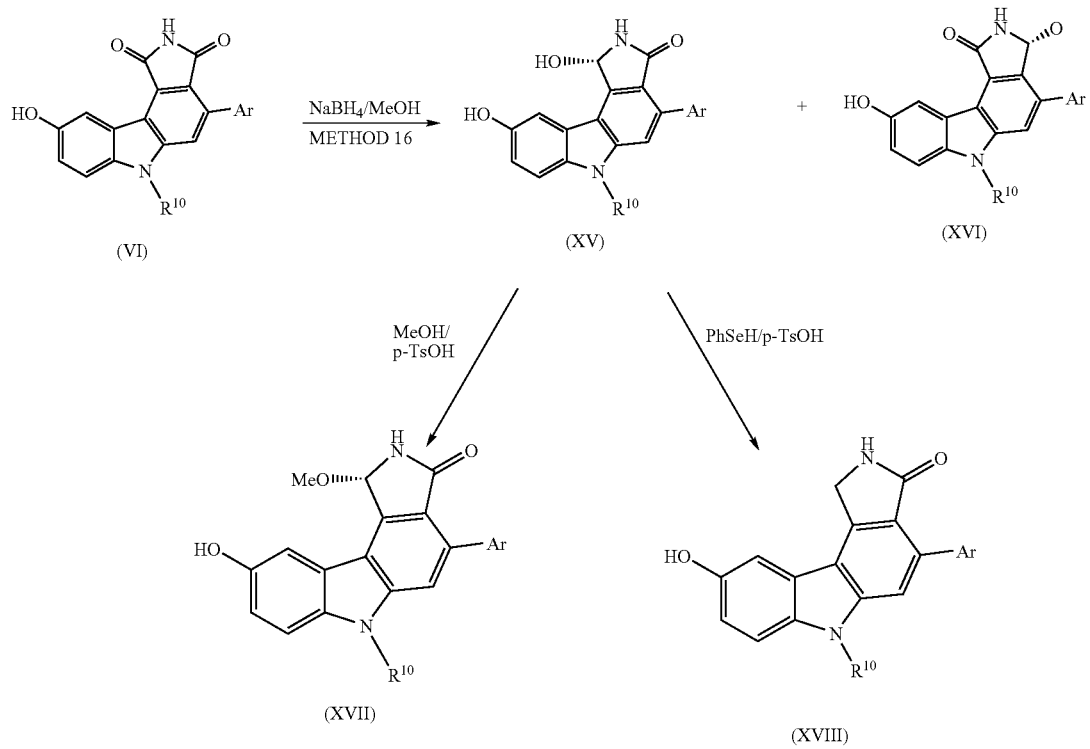

Scheme 5 Procedures

Representative Procedure for Method 16 of Scheme 5

EXAMPLE 243

The Preparation of 1,9-Dihydroxy-4-phenyl-1,6-dihydropyrrolo[3,4-c]carbazol-3 (2H)-one (XV; Ar=phenyl, $R^{10}$=H) (133) and 3,9-dihydroxy-4-phenyl-3,6-dihydropyrrolo[3,4-c]carbazol-1(2H)-one (XVI; Ar=phenyl, $R^{10}$=H) (134).

Sodium borohydride (4 portions of 0.24 g, 0.025 mol total) was added over 5 h to a solution of 9-hydroxy-4-phenylpyrrolo[3,4-c]carbazole-1,3(2H,6H)-dione (I;

8.55 (br s, 1H), 7.72 (d, J=2.2 Hz, 1H), 7.55 (dd, J=7.8, 2.1 Hz, 2H), 7.47–7.35 (m, 4H), 7.32 (s, 1H), 6.98 (dd, J=8.6, 2.2 Hz, 1H), 6.38 (d, J=10.3 Hz, 1H), 6.20 (d, J=10.3 Hz, 1H). Found: C, 68.77; H, 4.66; N, 7.87. $C_{20}H_{13}N_2O_3 \cdot H_2O$ requires C, 69.15; H, 4.35; N, 8.06.

EXAMPLE 244

The Preparation of 9-Hydroxy-1-methoxy-4-phenyl-1,6-dihydropyrrolo[3,4-c]carbazol-3(2H)-one (XVII; Ar=phenyl, $R^{10}$=H (135)

A solution of (133) prepared as described in example 243 (0.050 g, 0.16 mmol) and p-toluenesulphonic acid (15 mg) on methanol (5 mL) was stirred at room temperature for 30 min, then poured into saturated aqueous NaHCO$_3$ solution. The mixture was extracted with ethyl acetate. The organic phase was dried, the drying agent was removed and the solution was concentrated to dryness to give (135), which crystallised from ethyl acetate/petroleum ether as a white solid (0.041 g, 74%), mp 290–300° C. (dec). $^1$H NMR δ [(CD$_3$)$_2$SO] 11.47 (br s, 1H), 9.15 (br s, 1H), 8.75 (s, 1H), 7.57–7.53 (m, 3H), 7.44–7.37 (m, 4H), 7.36 (s, 1H), 7.09 (dd, J=8.7, 2.4 Hz, 1H), 6.26 (s, 1H), 3.25 (s, 3H). Found: C, 71.34; H, 4.79, N, 7.84. C$_{21}$H$_{15}$N$_2$O$_3$.1/2H$_2$O requires C, 71.58; H, 4.57; N, 7.95.

EXAMPLE 245

The Preparation of 9-hydroxy-4-phenyl-1,6-dihydropyrrolo[3,4-c]carbazol-3 (2H)-one (XVIII, Ar=phenyl, R$^{10}$=H) (136).

To a solution of (133) prepared as described in example 243 (0.20 g, 0.605 mmol) in tetrahydrofuran (30 mL) was added p-toluenesulfonic acid (23 mg, 0.121 mmol), followed be PhSeH (1.48 mL, 4.24 mmol) and the solution was stirred at room temperature for 1 h. After diluting with water the mixture was extracted with ethyl acetate and the extract was washed with aqueous NaHCO$_3$ solution. The organic phase was dried, the drying agent was removed and the solution was concentrated to dryness and chromatographed on silica. Elution with ethyl acetate/petroleum ether (1:1) then ethyl acetate followed by ethyl acetate/methanol (95:5) gave (136) as a white powder (0.174 g, 91%), mp 270–280° C. (dec). $^1$H NMR δ [(CD$_3$)$_2$SO] 11.41 (br s, 1H), 9.13 (br s, 1H), 8.27 (br s, 1H), 7.60–7.52 (m, 2H), 7.47–7.36 (m, 4H), 7.34–7.31 (m, 1H), 7.30 (s, 1H), 6.99 (dd, J=8.6, 2,2 Hz, 1H), 4.78 (br s, 2H). Found: C, 75.19; H, 4.88, N, 8.37. C$_{20}$H$_{14}$N$_2$O$_2$.1/4H$_2$O requires C, 75.34; H, 4.58; N, 8.78.

EXAMPLE 246

The Preparation of 4-(2-Chlorophenyl)-1,9-dihydroxy-6-(3-hydroxypropyl)-1,6-dihydropyrrolo[3,4-c]carbazol-3 (2H)-one (XV; Ar=2-chlorophenyl, R$^{10}$=CH$_2$CH$_2$CH$_2$OH) (137) and 4-(2-chlorophenyl)-3,9-dihydroxy-6-(3-hydroxypropyl)-3,6-dihydropyrrolo[3,4-c]carbazol-1(2H)-one (XVI; Ar=2-chlorophenyl, R$^{10}$=CH$_2$CH$_2$CH$_2$OH) (138).

Reduction of alcohol (34) prepared as described in example 243 with sodium borohydride using the procedure described in the procedure described in example 243 of Scheme 5, followed by chromatography of the product on silica gave firstly the 3-hydroxy compound (138) (11%) as a cream powder, mp 160–164° C. (dec). $^1$H NMR δ [(CD$_3$)$_2$SO] 9.08 (br s, 1H), 8.84 (s, 1H), 8.54 (d, J=2.5 Hz, 1H), 7.62–7.36 (m, 6H), 7.03 (dd, J=8.7, 2.5 Hz, 1H), 5.92 (br, 1H), 5.81 (br, 1H), 4.58 (t, J=5.0 Hz, 1H), 4.44 (t, J=6.8 Hz, 2H), 3.38 (m, 2H), 1.88 (m, 2H). Found: C, 64.60; H, 4.82; N, 6.32. C$_{23}$H$_{19}$ClN$_2$O$_4$.1/4H$_2$O requires C, 64.64; H, 4.60; N, 6.55; followed by (137) (67%) as a cream powder, mp 240° C. (dec). $^1$H NMR δ [(CD$_3$)$_2$SO] 9.18 (br s, 1H), 8.53 (br s, 1H), 7.76 (m, 1H), 7.50 (m, 2H), 7.43–7.35 (m, 3H), 7.40 (s, 1H), 7.04 (dd, J=8.7, 2.3 Hz, 1H), 6.52 (d, J=10.0 Hz, 0.5H), 6.40 (d, J=10.0 Hz, 0.5H), 6.25 (d, J=10.0 Hz, 0.5H), 6.21 (d, J=10.0 Hz, 0.5H), 4.61 (t, J=4.7 Hz, 1H), 4.44 (t, J=6.8 Hz, 2H), 3.39 (m, 2H), 1.88 (m, 2H). Found: C, 65.17; H, 4.80; N, 6.46. C$_{23}$H$_{19}$ClN$_2$O$_4$ requires C, 65.33; H, 4.53; N, 6.62.

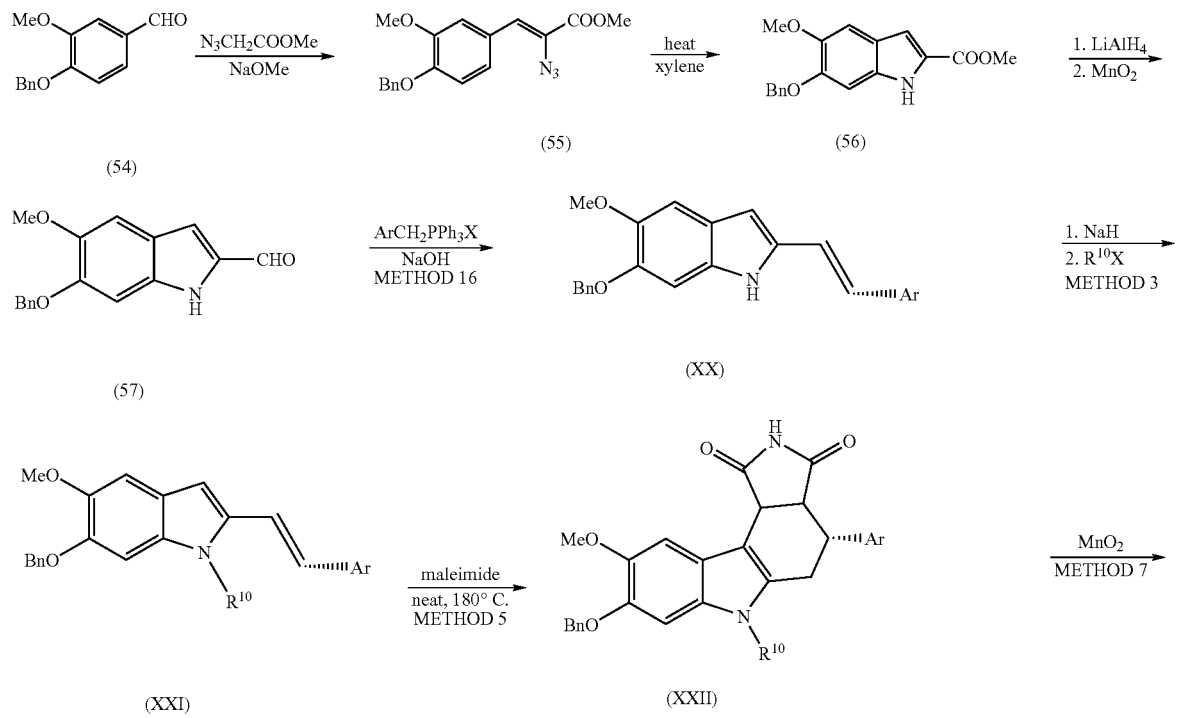

SCHEME 6

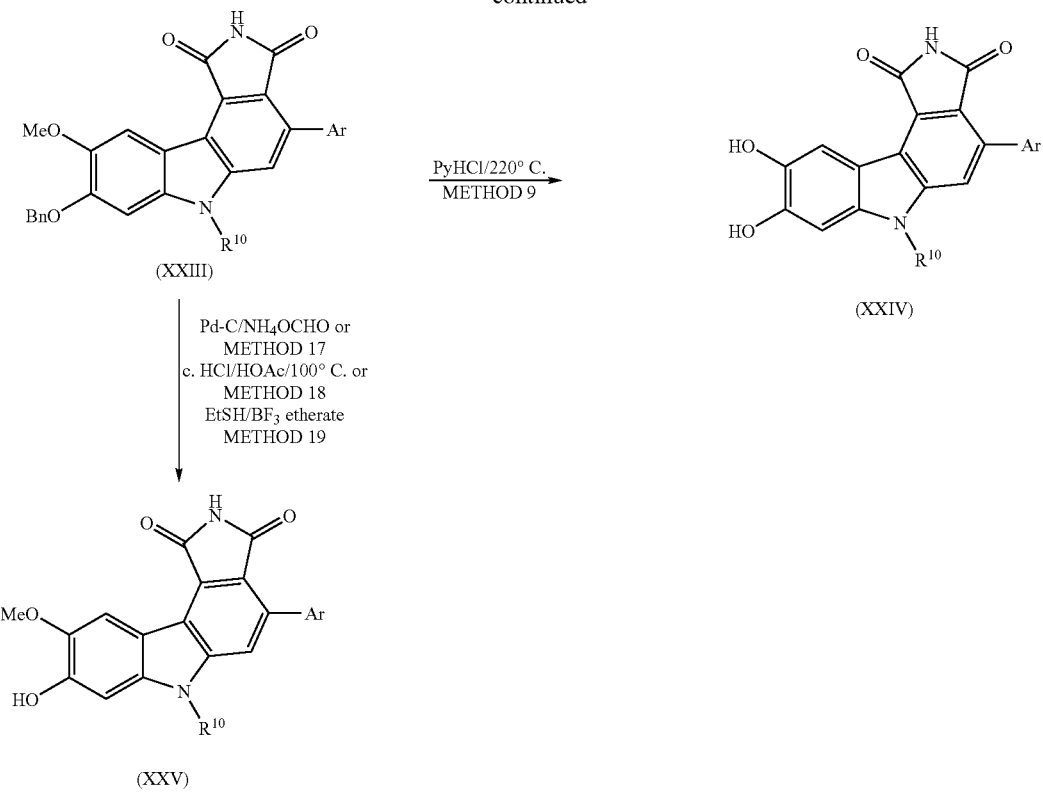

Scheme 6 Procedures

EXAMPLE 247

The Preparation of Methyl-2-azido-3-[4'-(benzyloxy)-3'-methoxyphenyl]prop-2-enoate (55)

A solution of the 4-Benzyloxy-3-methoxy-benzaldehyde (12.0 g, 49.6 mmol) and methyl azidoacetate (23 g, 0.200 mol) in methanol (50 mL) was added over 30 min to a cooled (ice-salt bath) solution of sodium methoxide which had been prepared from addition of methanol (80 mL) to sodium (3.4 g, 0.149 mol). The reaction mixture was stirred at 0° C. for 45 min, during this time a thick cream precipitate formed, and then stood in the freezer overnight. Ice-cold water was added and the precipitate was removed by filtration and dried to give methyl-2-azido-3-[4'-(benzyloxy)-3'-methoxyphenyl]prop-2-enoate (55) (12.2 g, 73%) which was used in the next step without purification.

EXAMPLE 248

The Preparation of methyl-6-(benzyloxy)-5-methoxyindole-2-carboxylate (56)

A solution of the azidocinnamate (55) (12.2 g, 36.0 mmol) prepared as described in example 247 in xylene (300 mL) was added dropwise to refluxing xylene (100 mL) over 1.5 h, the reaction mixture was heated at reflux for a further 15 min and then most of the xylene was removed by distillation. The residue, on cooling to room temperature, formed a fine cream precipitate of methyl-6-(benzyloxy)-5-methoxyindole-2-carboxylate which was collected by filtration. The remaining xylene was removed from the mother liquor azeotropically with ethanol, the residue was recrystallized from ethanol to give further methyl-6-(benzyloxy)-5-methoxyindole-2-carboxylate. The mother liquor was again concentrated and the residue recrystallized. The methyl-6-(benzyloxy)-5-methoxyindole-2-carboxylate (56) (9.9 g total, 88%) was used in the next step without purification. Found: C, 69.38; H, 5.54; N, 4.55. $C_{18}H_{17}NO_4$ requires: C, 69.44; H, 5.50; N, 4.50.

EXAMPLE 249

The Preparation of 6-(Benzyloxy)-5-methoxy-1H-indole-2-carbaldehyde (57)

To a solution of the ester (56) (1.0 g, 3.22 mmol) prepared as described in example 248 in tetrahydrofuran (10 mL) was added a suspension of lithium aluminium hydride (0.150 g, 3.86 mmol) in tetrahydrofuran (10 mL) dropwise, the reaction mixture was stirred at room temperature for 20 min. Water (1 mL) was added dropwise and then dilute sodium hydroxide (1 mL) was added, the solution was stirred for 10 min and then filtered through Celite and concentrated. The resulting yellow oil was dissolved in chloroform (20 mL) and then manganese dioxide (2.2 g, 26.0 mmol) was added, the reaction mixture was heated at 50° C. for 1 h and then filtered through Celite and concentrated. The residue was recrystallized from dichloromethane to give 6-(benzyloxy)-5-methoxy-1H-indole-2-carbaldehyde (57) (0.74 g, 82%) as pale yellow needles. Found: C, 72.53; H, 5.42; N, 4.92. $C_{17}H_{15}NO_3$ requires: C, 72.58; H, 5.37; N, 4.98.

Representative Procedure for Method 16 of Scheme 6

EXAMPLE 250

The Preparation of 6-(Benzyloxy)-5-methoxy-2-[(E)-2-phenylethenyl]-1H-indole (XX; Ar=phenyl) (150)

To a solution of (57) (0.60 g, 2.14 mmol) prepared as described in example 249 and benzyltriphenylphosphonium bromide (1.0 g, 2.35 mmol) in dichloromethane (10 mL) was added a 17 M solution of sodium hydroxide (1.1 mL, 18 mmol) dropwise. The reaction mixture was stirred at room temperature until all the starting material was consumed (30 min), and then it was diluted with water and extracted with dichloromethane (2×40 mL). The combined extracts were dried and concentrated to give an approximately 1:1 mixture of 6-(benzyloxy)-5-methoxy-2-[(E)-2-phenylethenyl]-1H-indole and 6-(benzyloxy)-5-methoxy-2-[(Z)-2-phenylethenyl]-1H-indole (0.75 g, 99%). Recrystallization from dichloromethane cleanly gave the E-isomer (150), mp 140–145° C. (softens), 158–162° C. (melts). $^1$H NMR δ [$(CD_3)_2SO$] 11.08 (s, 1H), 7.52–7.47 (m, 4H), 7.42–7.31 (m, 5H), 7.25–7.15 (m, 2H), 7.05–7.01 (m, 2H), 6.91 (s, 1H), 6.45 (s, 1H), 5.12 (s, 2H), 3.78 (s, 3H). Found: C, 80.84; H, 6.11; N, 3.94. $C_{24}H_{21}NO_2$ requires: C, 81.10; H, 5.96; N, 3.94.

EXAMPLE 251

The Preparation of 6-(Benzyloxy)-5-methoxy-1-methyl-2-[(E)-2-phenylethenyl]-1H-indole (XXI; Ar=phenyl, $R^{10}$=Me) (151)

Reaction of (150) prepared as described in example 250 with sodium hydride followed by iodomethane using the procedure described in method 3 gave (151) (100%), mp 142–145° C. $^1$H NMR δ [$(CD_3)_2SO$] 7.51–7.46 (m, 4H), 7.40–7.34 (m, 6H), 7.31–7.23 (m, 2H), 7.09–7.05 (m, 2H), 7.30 (s, 1H), 5.21 (s, 2H), 3.93 (s, 3H), 3.70 (s, 3H). Found: C, 81.01; H, 6.31; N, 3.79. $C_{25}H_{23}NO_2$ requires: C, 81.27; H, 6.27; N, 3.79.

EXAMPLE 252

The Preparation of 8-(Benzyloxy)-9-methoxy-6-methyl-4-phenyl-4,5,6,10c-tetrahydropyrrolo[3,4-c]carbazole-1,3(2H,3aH)-dione (XXII; Ar=phenyl, $R^{10}$=Me) (152)

Reaction of (151) prepared as described in example 251 with maleimide using the procedure described in example 69 gave the adduct (152) as a yellow solid, which was used without further purification.

EXAMPLE 253

The Preparation of 8-(Benzyloxy)-9-methoxy-6-methyl-4-phenylpyrrolo[3,4-c]carbazole-1,3(2H,6H)-dione (XXIII; Ar=phenyl, $R^{10}$=Me) (153)

Aromatisation of crude (152) prepared as described in example 252 with manganese dioxide using the procedure described in example 79 gave (153) as a yellow solid (69% overall from (151), mp 263–265° C. $^1$H NMR δ [$(CD_3)_2SO$] 11.04 (br s, 1H), 8.48 (s, 1H), 7.73 (s, 1H), 7.66–7.63 (m, 2H), 7.57–7.55 (m, 2H), 7.49–7.36 (m, 7H), 5.28 (s, 2H), 3.95 (s, 3H), 3.90 (s, 3H). Found: C, 74.99; H, 4.67; N, 5.95. $C_{29}H_{22}N_2O_4$ requires: C, 75.31; H, 4.79; N, 6.06.

Representative Procedure for Method 17 of Scheme 6

EXAMPLE 254

The Preparation of 8-Hydroxy-9-methoxy-6-methyl-4-phenylpyrrolo[3,4-c]carbazole-1,3(2H,6H)-dione (XXV; Ar=phenyl, $R^{10}$=Me) (154)

To a solution of (153) (1.0 g, 2.16 mmol) prepared as described in example 253 in a 1:1 mixture of tetrahydrofuran and methanol (100 mL) was added 5% Pd/C (200 mg) and then ammonium formate (1.71 g, 22.0 mmol). The reaction mixture was stirred at room temperature for 2 hr and then filtered through Celite, washing well with tetrahydrofuran. The filtrate was concentrated and then water was added; the resulting yellow precipitate was collected by filtration and dried to give (154) (0.71 g, 88%), mp 298–301° C. $^1$H NMR δ [$(CD_3)_2SO$] 11.01 (s, 1H), 9.70 (s, 1H), 8.46 (s, 1H), 7.71 (s, 1H), 7.65–7.63 (m, 2H), 7.49–7.41 (m, 3H), 3.92 (s, 3H), 3.87 (s, 3H). Found: C, 69.85; H, 4.35; N, 7.15. $C_{22}H_{16}N_2O_4 \cdot 1/3 H_2O$ requires: C, 69.83; H, 4.44; N, 7.40.

EXAMPLE 255

The Preparation of 6-(Benzyloxy)-2-[2-(2-chlorophenyl)ethenyl]-5-methoxy-1H-indole (XX; Ar=2-chlorophenyl) (155)

Reaction of the aldehyde (57) prepared as described in example 249 with 2'-chlorobenzyltriphenylphosphonium chloride using the procedure described in the procedure described in example 243 gave the diene (155) as an E/Z mixture of isomers (78%), green solid, mp 192–194° C. $^1$H NMR δ [$(CD_3)_2SO$] 11.25 (s, 1H), 10.70 (s, minor isomer), 7.83 (dd, J=8.0, 1.4 Hz, 1H), 7.68–7.20 (m), 7.05 (s, 1H), 6.91 (s, 1H), 6.88 (d, J=2.9 Hz, minor isomer), 6.64 (d, J=12.1 Hz, minor isomer), 6.51 (d, J=1.4 Hz, 1H), 6.46 (d, J=12.1 Hz, minor isomer), 5.89 (br s, minor isomer), 5.13 (s, 2H), 5.06 (s, minor isomer), 3.78 (s, 3H), 3.71 (s, minor isomer). Found: C, 73.92; H, 5.23; N, 3.63. $C_{24}H_{19}ClNO_2$ requires C, 74.13; H, 4.92; N, 3.60.

EXAMPLE 256

The Preparation of 6-(Benzyloxy)-2-[2-(2-chlorophenyl)ethenyl]-5-methoxy-1-methyl-1H-indole (XXI; Ar=2-chlorophenyl, $R^{10}$=$CH_3$) (156).

Alkylation of (155) prepared as described in example 255 with sodium hydride and iodomethane using the procedure described in method 3 gave (156) (100%) (mixture of E/Z isomers) as a yellow solid, mp 143–145° C. $^1$H NMR δ [$(CD_3)_2SO$] 7.98 (dd, J=7.9, 1.5 Hz, 1H), 7.55–7.22 (m), 7.19 (s), 7.12 (s), 6.89 (s), 6.85 (d, J=12.2 Hz), 6.80 (s), 6.63 (d, J=12.2 Hz), 5.14 (s), 5.11 (s), 3.81 (s), 3.78 (s), 3.70 (s), 3.64 (s). Found: C, 74.04; H, 5.71; N, 3.49. $C_{25}H_{22}ClNO_2$ requires C, 74.34; H, 5.49; N, 3.47.

EXAMPLE 257

The Preparation of 8-(Benzyloxy)-4-(2-chlorophenyl)-9-methoxy-6-methyl-4,5,6,10c-tetrahydropyrrolo[3,4-c]carbazole-1,3(2H,3aH)-dione (XXII; Ar=2-chlorophenyl, $R^{10}$=CH$_3$) (157).

Reaction of the diene (156) prepared as described in example 256 with maleimide using the procedure described in example 69 gave the adduct (157) (98%) as a cream powder, mp 174° C. (dec), which was used without further purification. Found: C, 68.32; H, 4.94; N, 5.51. $C_{19}H_{24}ClN_2O_4.1/2H_2O$ requires C, 68.43; H, 4.95; N, 5.50.

EXAMPLE 258

The Preparation of 8-(Benzyloxy)-4-(2-chlorophenyl)-9-methoxy-6-methylpyrrolo[3,4-c]carbazole-1,3 (2H,6H)-dione (XXIII) (158)

Aromatisation of (157) prepared as described in example 257 with manganese dioxide using the procedure described in example 79 gave the carbazole (158) (75%) as a yellow powder, mp 282–285° C. $^1$H NMR δ [(CD$_3$)$_2$SO] 11.05 (s, 1H), 8.48 (s, 1H), 7.74 (s, 1H), 7.59–7.54 (m, 3H), 7.52–7.36 (m, 7H), 5.30 (s, 2H), 3.96 (s, 3H), 3.91 (s, 3H). Found: C, 69.89; H, 4.44; N, 5.61. $C_{29}H_{21}ClN_2O_4$ requires C, 70.09; H, 4.26; N, 5.64.

EXAMPLE 259

The Preparation of 4-(2-Chlorophenyl)-8,9-dihydroxy-6-methylpyrrolo[3,4-c]carbazole-1,3(2H,6H)-dione (XXIV; Ar=2-chlorophenyl, $R^{10}$=CH$_3$) (159).

Reaction of (158) prepared as described in example 258 with pyridinium hydrochloride at 220° C. using the procedure described in example 81 gave (159) (76%) as a yellow powder, mp 310–313° C. $^1$H NMR δ [(CD$_3$)$_2$SO)] 10.95 (s, 1H), 9.57 (br, 1H), 9.18 (br, 1H), 8.32 (s, 1H), 7.64 (s, 1H), 7.56 (dd, J=8.1, 2.2 Hz, 1H), 7.50–7.41 (m, 4H), 7.02 (s, 1H), 3.84 (s, 3H). Found: C, 64.11; H, 3.96; N, 6.54. $C_{21}H_{13}ClN_2O_4.1/4CH_3OH$ requires C, 63.67; H, 3.52; N, 6.98.

Representative Procedure for Method 18 of Scheme 6

EXAMPLE 260

The Preparation of 4-(2-Chlorophenyl)-8-hydroxy-9-methoxy-6-methylpyrrolo[3,4-c]carbazole-1,3(2H,6H)-dione (XXV; Ar=2-chlorophenyl, $R^{10}$=CH$_3$) (160)

A mixture of (158) (1.30 g, 2.62 mmol) prepared as described in example 258, conc. HCl (40 mL) and acetic acid (65 mL) was warmed at 100° C. for 2 h. Water was added and the precipitated product was filtered off and dried. The solid was adsorbed onto silica from a tetrahydrofuran solution and chromatographed. Elution with ethyl acetate/petroleum ether (3:2) gave (160) (1.07 g, 85%), which crystallised from terahydrofuran/petroleum ether as a green solid, mp 280–285° C. (dec). $^1$H NMR δ [(CD$_3$)$_2$SO] 11.01 (s, 1H), 9.73 (s, 1H), 8.44 (s, 1H), 7.69 (s, 1H), 7.57 (dd, J=8.0, 2.2 Hz, 1H), 7.51–7.41 (m, 4H), 7.09 (s, 1H), 3.93 (s, 3H), 3.87 (s, 3H). Found: C, 64.53; H, 3.66; N, 6.27. $C_{22}H_{15}ClN_2O_4.1/4H_2O$ requires C, 64.24; H, 3.80; N, 6.81.

EXAMPLE 261

The Preparation of 8-(Benzyloxy)-4-(2-chlorophenyl)-9-methoxy-4,5,6,10c-tetrahydropyrrolo[3,4-c]carbazole-1,3(2H,3aH)-dione (XXII, Ar=2-chlorophenyl, $R^{10}$=H) (161)

Reaction of the diene (155) prepared as described in example 255 with maleimide using the procedure described in example 69 gave the adduct (161) as a tan powder (87%), which was used without further purification.

EXAMPLE 262

The Preparation of 8-(Benzyloxy)-4-(2-chlorophenyl)-9-methoxypyrrolo[3,4-c]carbazole-1,3(2H,6H)-dione (XXIII; Ar=2-chlorophenyl, $R^{10}$=H) (162)

Aromatisation of (161) prepared as described in example 261 with manganese dioxide using the procedure described in example 79 gave the carbazole (162) (93%) as an orange powder, mp 260–264° C. $^1$H NMR δ [(CD$_3$)$_2$SO] 11.86 (s, 1H), 11.01 (s, 1H), 8.43 (s, 1H), 7.58–7.34 (m, 10H), 7.26 (s, 1H), 5.26 (s, 2H), 3.91 (s, 3H). Found: C, 69.65; H, 3.84; N, 5.61. $C_{28}H_{19}ClN_2O_4$ requires C, 69.64; H, 3.97; N, 5.80.

EXAMPLE 263

The Preparation of 4-(2-Chlorophenyl)-8-hydroxy-9-methoxypyrrolo[3,4-c]carbazole-1,3(2H,6H)-dione (XXV; Ar=2-chlorophenyl, $R^{10}$=H) (163).

Debenzylation of (162) prepared as described in example 262 with HCl in acetic acid using the procedure described in example 260 have (163) (77%) as a yellow powder, mp 194–196° C. $^1$H NMR δ [(CD$_3$)$_2$SO] 11.71 (s, 1H), 10.97 (br s, 1H), 9.68 (br s, 1H), 8.38 (s, 1H), 7.56 (dd, J=8.0, 2.2 Hz, 1H), 7.49–7.39 (m, 4H), 7.02 (s, 1H), 3.90 (s, 3H). Found: C, 63.38; H, 3.38; N, 6.20. $C_{21}H_{13}ClN_2O_4.1/4H_2O$ requires C, 63.49; H, 3.42; N, 7.05.

EXAMPLE 264

The Preparation of 6-(Benzyloxy)-2-[2-(2-chlorophenyl)ethenyl]-5-methoxy-1-(2-methoxyethyl)-1H-indole (XXI; Ar=2-chlorophenyl, $R^{10}$=CH$_2$, CH$_2$OCH$_3$) (164).

Alkylation of diene (155) prepared as described in example 255 with sodium hydride and 1-bromo2-methoxyethane using the procedure described in method3 gave (164) (91%) (E/Z mixture of isomers) as an orange solid, which was used without further purification.

EXAMPLE 265

The Preparation of 8-(Benzyloxy)-4-(2-chlorophenyl)-9-methoxy-6-(2-methoxyethyl)-4,5,6,10c-tetrahydropyrrolo[3,4-c]carbazole-1,3(2H,3aH)-dione (XXII; Ar=2-chlorophenyl. $R^{10}$=CH$_2$CH$_2$OCH$_3$) (165)

Reaction of diene (164) prepared as described in example 264 with maleimide using the procedure described in example 69 gave the adduct (165) as a tan solid (74%), which was used without further purification.

EXAMPLE 266

The Preparation of 8-(Benzyloxy)-4-(2-chlorophenyl)-9-methoxy-6-(2-methoxyethyl)pyrrolo[3,4-c]carbazole-1,3(2H,6H)dione (XXIII; Ar=2-chlorophenyl, $R^{10}$=CH$_2$CH$_2$OCH$_3$) (166).

Aromatisation of (165) prepared as described in example 265 with manganese dioxide using the procedure described in example 79 gave the carbazole (166) (89%) as an orange powder, mp 252–254° C. $^1$H NMR δ [(CD$_3$)$_2$SO] 11.04 (br s, 1H), 8.49 (s, 1H), 7.75 (s, 1H), 7.59–7.35 (m, 10H), 5.29 (s, 2H), 4.66 (t, J=5.0 Hz, 2H), 3.91 (s, 3H), 3.68 (t, J=5.0 Hz, 2H), 3.14 (s, 3H). Found: C, 68.72; H, 4.73; N, 5.28. C$_{31}$H$_{25}$ClN$_2$O$_5$ requires C, 68.82; H, 4.66; N, 5.18.

Representative Procedure for Method 19 of Scheme 6

EXAMPLE 267

The Preparation of 4-(2-Chlorophenyl)-8-hydroxy-9-methoxy-6-(2-methoxyethyl)pyrrolo[3,4-c]carbazole-1,3(2H,6H)-dione (XXV; Ar=2-chlorophenyl, $R^{10}$=CH$_2$CH$_2$OCH3) (167).

Ethane thiol (5 mL) and boron trifluoride etherate (2.5 mL) were added to a solution of the benzyl ether (155) (0.840 g, 1.55 mmol) prepared as described in example 255 in dichloromethane (100 mL) and the solution was stirred at room temperature for 16 h. Petroleum ether (500 mL) was added and the mixture was chilled at −20° C. for 3 h. The solid was isolated by decantation of the liquid layer and partitioned between ethyl acetate and saturated aqueous NaHCO$_3$. The organic phase was dried, the drying agent was removed and the solution was concentrated to dryness gave an oily solid which was chromatographed on silica. Elution with ethyl acetate/petroleum ether (1:2) gave foreruns, while ethyl acetate/petroleum ether (1:1) eluted (167) (80 5) which crystallised from ethyl acetate/petroleum ether as a yellow powder, mp 249–252° C. $^1$H NMR δ [(CD$_3$)$_2$SO] 10.98 (br, 1H), 9.70 (br, 1H), 8.44 (s, 1H), 7.70 (s, 1H), 7.57 (dd, J=8.0, 2.2 Hz, 1H), 7.50–7.41 (m, 3H), 7.12 (s, 1H), 4.56 (t, J=5.1 Hz, 2H), 3.92 (s, 3H), 3.68 (t, J=5.1 Hz, 2H), 3.16 (s, 3H). Found: C, 64.19; H, 4.43; N, 5.92. C$_{24}$H$_{19}$ClN$_2$O, requires C, 63.93; H, 4.25; N, 6.21.

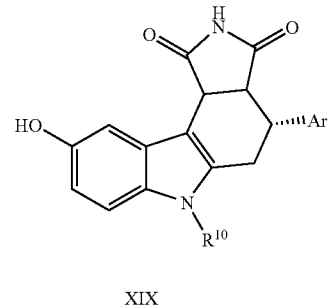

XIX

Scheme 7 Procedures

EXAMPLE 268

The Preparation of 4-(2-Chlorophenyl)-9-hydroxy-6-(3-hydroxypropyl)-4,5,6,10c-tetrahydropyrrolo[3,4-c]carbazole-1,3(2H,3aH)-dione (XIX; Ar=2-chlorophenyl, $R^{10}$=CH—$_2$CH$_2$CH$_2$OH) (139).

Demethylation of 4-(2-Chlorophenyl)-6-(3-hydroxypropyl)-9-methoxy-4,5,6,10c-tetrahydropyrrolo[3,4-c]carbazole-1,3(2H,3aH)-dione (IV; Ar=2-chlorophenyl, $R^{10}$=CH—$_2$CH$_2$CH$_2$OH) (30) prepared by the first step in the procedure described in example 39 with BBr$_3$ using the procedure described in example 80 followed by an acidic workup gave (139) (77%) as a pink powder, mp 190–196° C. (dec). $^1$H NMR δ [(CD$_3$)$_2$SO] 10.82 (br s, 1H), 8.72 (br s, 1H), 7.71 (dd, J=7.7, 1.0 Hz, 1H), 7.46 (dd, J=8.0, 1.4 Hz, 1H), 7.39 (m, 1H), 7.31 (m, 1H), 7.21 (d, J=8.5 Hz, 1H), 7.15 (d, J=2.3 Hz, 1H), 6.62 (dd, J=8.5, 2.3 Hz, 1H), 4.57 (t, J=4.7 Hz, 1H), 4.25 (d, J=7.5 Hz, 1H), 4.11 (t, J=6.9 Hz, 2H), 3.94 (dd, J=7.5, 3.6 Hz, 1H), 3.53 (dt, J=12.6, 3.7 Hz, 1H), 3.22 (m, 2H), 3.03 (dd, J=15.6, 3.6 Hz, 1H), 1.77 (m, 2H). Found: C, 63.57; H, 5.13; N, 6.31. C$_{23}$H$_{21}$ClN$_2$O$_4$.1/2H$_2$O requires C, 63.66; H, 5.11; N, 6.45.

SCHEME 7

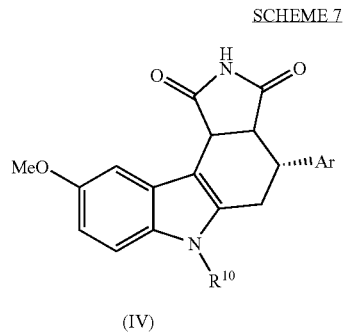

SCHEME 8

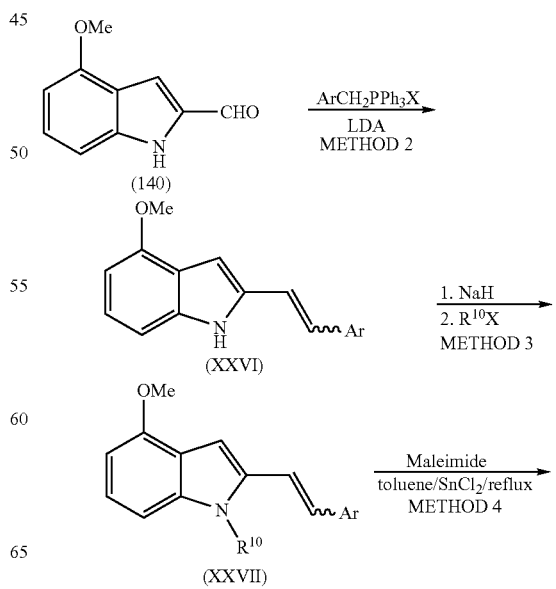

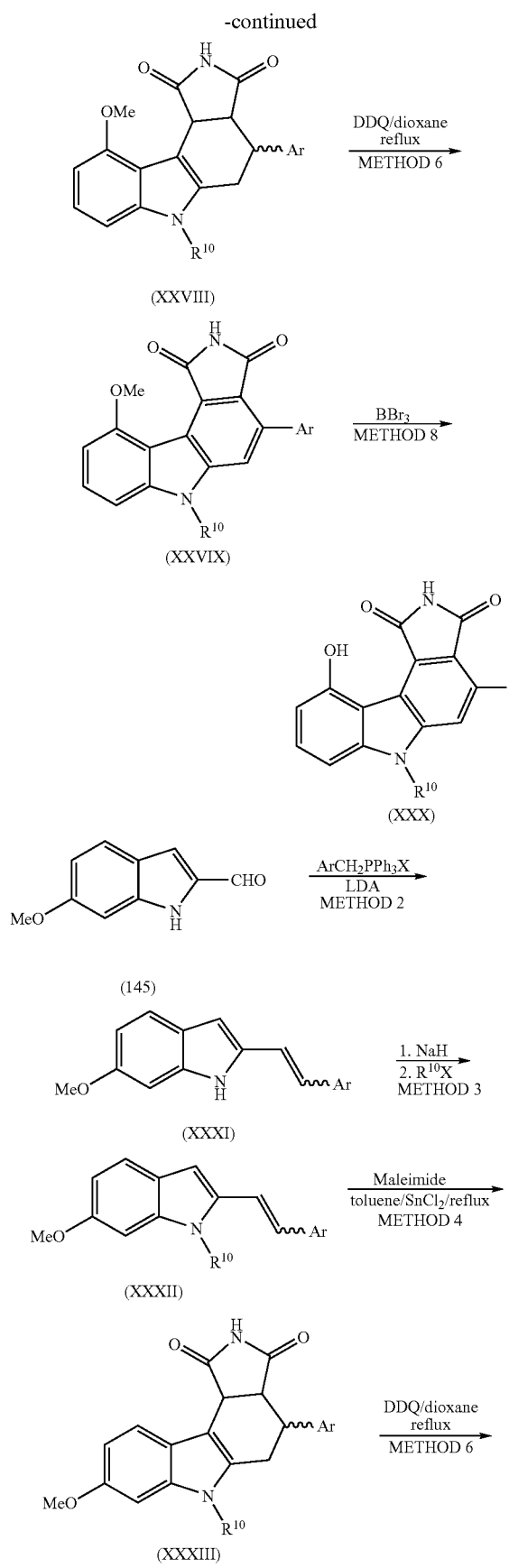

Procedures for Scheme 8

EXAMPLE 269

The Preparation of 4-Methoxy-2-[2-phenylethenyl]-1H-indole (XXVI; Ar=phenyl) (141).

Reaction of 4-methoxyindole-2-carboxaldehyde with benzyltriphenylphosphonium bromide using the procedure described in example 37 gave (141) (89%) as a fluorescent oil, (mixture of E/Z isomers) which was used without further purification.

EXAMPLE 270

The Preparation of 10-Methoxy-4-phenyl-4,5,6,10c-tetrahydrocyclopenta[c]carbazole-1,3(2H,3aH)-dione (XXVIII; Ar=phenyl, $R^{10}$=H (142).

Reaction of the diene (141) prepared by the procedure described in example 269 with maleimide using the procedure described in method4 gave the adduct (142) as a yellow solid (86%), which was used without further purification.

EXAMPLE 271

The Preparation of 10-Methoxy-4-phenylcyclopenta[c]carbazole-1,3(2H,6H)-dione (XXVIX, Ar=phenyl, $R^{10}$=H (143).

Aromatisation of (142) prepared by the procedure described in example 270 with DDQ using the procedure described in example 70 gave the carbazole (143) (78%) as yellow needles, mp 273–276° C. $^1$H NMR δ [(CD$_3$)$_2$SO] 12.10 (s, 1H), 10.78 (s, 1H), 7.59 (s, 1H), 7.57 (dd, J=8.0, 1.8 Hz, 2H), 7.49 (t, J=7.9 Hz, 1H), 7.47–7.39 (m, 3H), 7.16 (d, J=7.9 Hz, 1H), 6.80 (d, J=7.9 Hz, 1H), 3.99 (s, 3H). Found: C, 73.55; H, 4.16; N, 7.93. $C_{21}H_{14}N_2O_3$ requires C, 73.67; H, 4.12; N, 8.18.

EXAMPLE 272

The Preparation of 10-Hydroxy-4-phenylcyclopenta
[c]carbazole-1,3(2H,6H)-dione (XXX; Ar=phenyl,
$R^{10}$=H (144)

Demethylation of (143) prepared by the procedure described in example 271 with BBr$_3$ using the procedure described in example 80 gave (144) as a yellow/orange solid (92%), mp>300° C. $^1$H NMR δ [(CD$_3$)$_2$SO] 12.33 (s, 1H), 12.16 (s, 1H), 11.65 (br, 1H), 7.62 (s, 1H), 7.60 (dd, J=7.9, 1.8 Hz, 2H), 7.51–7.45 (m, 3H), 7.40 (dd, J=7.6 Hz, 1H), 7.03 (d, J=7.6 Hz, 1H), 6.63 (d, J=7.6 Hz, 1H). Found: C, 72.87; H, 3.76; N, 8.44. C$_{20}$H$_{12}$N$_2$O$_3$ requires C, 73.16; H, 3.68; N, 8.53.

EXAMPLE 273

The Preparation of
6-Methoxy-2-[2-phenylethenyl]-1H-indole (XXXI;
Ar=phenyl) (146)

Reaction of 6-methoxyindole-2-carboxaldehyde (145) with benzyltriphenylphosphonium bromide using the procedure described in example 37 gave (146) (94%) as a white solid (mixture of E/Z isomers) which was used without further purification.

EXAMPLE 274

The Preparation of 8-Methoxy-4-phenyl-4,5,6,10c-tetrahydrocyclopenta[c]carbazole-1,3(2H,3aH)-dione
(XXXIII; Ar=phenyl, $R^{10}$=H) (147).

Reaction of the diene (146) prepared by the procedure described in example 273 with maleimide using the procedure described in method4 gave the adduct (147) as a tan solid (61%), which was used without further purification.

EXAMPLE 275

The Preparation of 8-Methoxy-4-phenylcyclopenta
[c]carbazole-1,3(2H,6H)-dione (XXXIV:
Ar=phenyl, $R^{10}$=H (148).

Aromatisation of (147) prepared by the procedure described in example 274 with DDQ using the procedure described in example 70 gave the carbazole (148) (65%) as a yellow powder, mp 154–156° C. $^1$H NMR δ [(CD$_3$)$_2$SO] 11.87 (br, 1H), 11.02 (br, 1H), 8.75 (d, J=8.8 Hz, 1H), 7.61 (dd, J=8.0, 1.8 Hz, 2H), 7.60 (s, 1H), 7.49–7.40 (m, 3H), 7.10 (d, J=2.2 Hz, 1H), 6.94 (dd, J=8.8, 2.2 Hz, 1H), 3.90 (s, 3H). Found: C, 72.49; H, 4.14; N, 8.22. C$_{11}$H$_{14}$N$_2$O$_3$.1/4H$_2$O requires C, 72.71; H, 4.21; N, 8.07.

EXAMPLE 276

The Preparation of 8-hydroxy-4-phenylcyclopenta
[c]carbazole-1,3(2H,6H)-dione (XXXV; Ar=phenyl,
$R^{10}$=H (149)

Demethylation of (148) prepared by the procedure described in example 276 with BBr$_3$ using the procedure described in example 80 gave (149) as a yellow powder (74%), mp>330° C. $^1$H NMR δ [(CD$_3$)$_2$SO] 11.75 (br, 1H), 10.96 (br, 1H), 10.56 (br, 1H), 8.66 (d, J=8.6 Hz, 1H), 7.60 (dd, J=8.0, 1.8 Hz, 2H), 7.53 (s, 1H), 7.49–7.39 (m, 3H), 6.93 (d, J=2.1 Hz, 1H), 6.79 (dd, J=8.6, 2.1 Hz, 1H). Anal. Found: C, 72.36; H, 3.82; N, 8.18. C$_{20}$H$_{12}$N$_2$O$_3$.1/4H$_2$O requires C, 72.17; H, 3.78; N, 8.41.

EXAMPLE 277

The Preparation of 2-[(E,Z)-2-(2-Chlorophenyl)
ethenyl]-6-methoxy-1H-indole (XXXI: Ar=2-chlorophenyl) (841)

Reaction of 6-methoxyindole-2-carboxaldehyde (145) with 2-chlorobenzyltriphenylphosphonium chloride using the procedure described in example 37 gave (841) as a mixture of E/Z isomers as a yellow solid (93%), which was used without further purification.

EXAMPLE 278

The Preparation of 2-[(E,Z)-2-(2-Chlorophenyl)
ethenyl]-6-methoxy-1-methyl-1H-indole (XXXII;
Ar=2-chlorophenyl, $R^{10}$=CH$_3$) (842)

Alkylation of (841) with iodomethane using the procedure described in method3 gave (842) as a yellow solid (77%), which was used without further purification.

EXAMPLE 279

The Preparation of 4-(2-Chlorophenyl)-8-methoxy-6-methylpyrrolo[3,4-c]carbazole-1,3(2H,6H)-dione
(XXXIV: Ar=2-chlorophenyl, $R^{10}$=CH$_3$) (844)

Reaction of (842) prepared as described in example 278 with maleimide using the procedure described in method4 example 68 gave the adduct (XXXIII; Ar=2-chlorophenyl, $R^{10}$=CH$_3$) (843) as a tan powder, which was used without further purification. Aromatisation of (843) with MnO$_2$ using the procedure described in example 79 gave (844) as a yellow powder (78% overall), mp>300° C. $^1$H NMR δ [(CD$_3$)$_2$SO] 11.07 (br s, 1H), 8.77 (d, J=8.7 Hz, 1H), 7.76 (s, 1H), 7.59 (dd, J=8.0, 2.2 Hz, 1H), 7.52–7.43 (m, 3H), 7.27 (d, J=2.2 Hz, 1H), 7.00 (dd, J=8.7, 2.2 Hz, 1H), 3.95 (s, 3H), 3.94 (s, 3H). Found: C, 66.86; H, 4.04; N, 6.90; Cl, 9.26. C$_{22}$H$_{15}$ClN$_2$O$_3$.0.2H$_2$O requires: C, 66.99; H, 3.94; N, 7.10; Cl, 8.99.

EXAMPLE 280

The Preparation of 4-(2-Chlorophenyl)-8-hydroxy-6-methylpyrrolo[3,4-c]carbazole-1,3(2H,6H)-dione
(XXXV; Ar=2-chlorophenyl, $R^{10}$=CH$_3$) (845)

Demethylation of (844) prepared as described in example 279 with BBr$_3$ using the procedure described in example 80 gave (845) (54%) as a yellow solid, mp 304–306° C. $^1$H NMR δ [(CD$_3$)$_2$SO] 11.02 (br, 1H), 10.08 (br, 1H), 8.69 (d, J=8.6 Hz, 1H), 7.71 (s, 1H), 7.58 (m, 1H), 7.51–7.42 (m, 3H), 6.99 (d, J=2.0 Hz, 1H), 6.88 (dd, J=8.6, 2.0 Hz, 1H), 3.87 (s, 3H). Found: C, 63.93; H, 3.95; N, 7.08; Cl, 9.12. C$_{21}$H$_{13}$ClN$_2$O$_3$.H$_2$O requires: C, 63.89; H, 3.83; N, 7.10; Cl, 8.98.

SCHEME 9

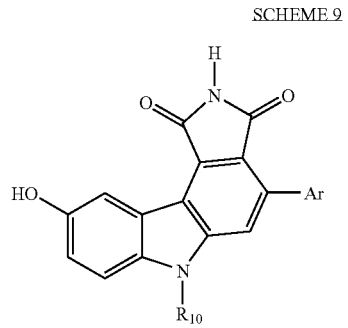

(VI); R$^{10}$ = (CH$_2$)$_n$CN

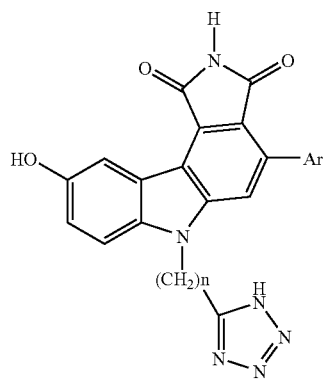

(XXXVI)

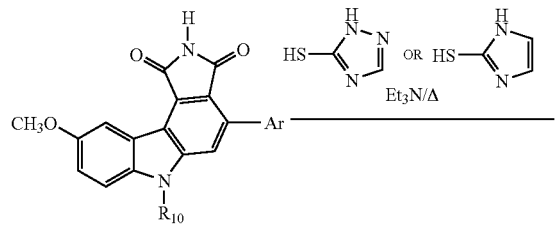

(V); R$^{10}$ = (CH$_2$)$_2$OSO$_2$CH$_3$

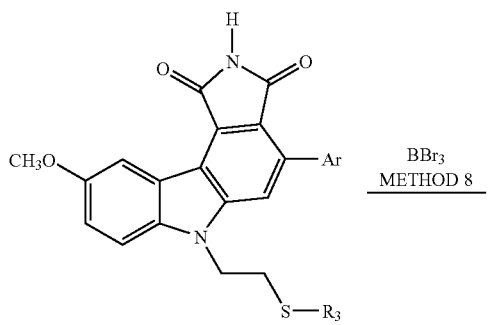

(XXXVII)

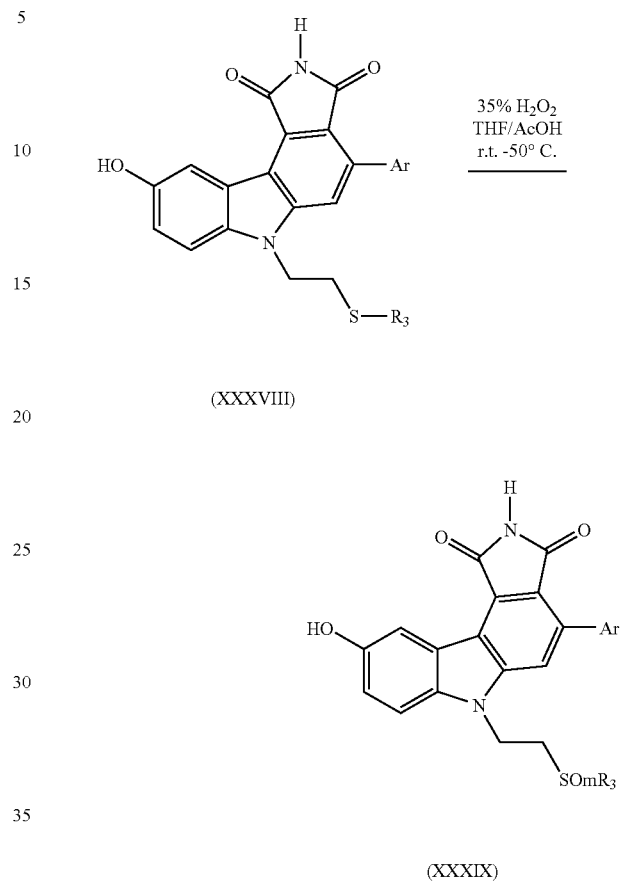

(XXXVIII)

(XXXIX)

Scheme 9 Procedures

EXAMPLE 281

The Preparation of 4-(2-Chlorophenyl)-9-hydroxy-6-[2-(1H-tetraazol-5-yl)ethyl]pyrrolo[3,4-c]carbazole-1,3(2H,6H)-dione (XXXVI; Ar=2-chlorophenyl, n=2) (272)

To a solution of nitrile (238) (0.68 g, 1.63 mmol) prepared as described in example 98 in toluene/dimethylformamide (5:1, 120 mL) was added azidotrimethyl tin (0.67 g, 3.26 mmol). The resulting solution was heated at reflux for 24 hours before a further portion of azidotrimethyl tin (0.34 g, 1.63 mmol) was added. After a further 24 hours at reflux the reaction was diluted with water and extraction with ethyl acetate. The organic phase was dried, the drying agent was removed and the solution was concentrated to dryness. Chromatography on silica eluting with ethyl acetate/hexane (3:1) to ethyl acetate/methanol (9:1), followed by crystallization from ethyl acetate/hexane, gave tetrazole (272) (0.54 g, 72%) as an orange powder, mp 230–234° C. (dec). $^1$H NMR δ [(CD$_3$)$_2$SO] 11.06 (br s, 1H), 9.37 (br s, 1H), 8.36 (d, J=2.4 Hz, 1H), 7.61 (s, 1H), 7.56 (m, 1H), 7.48 (m, 4H), 7.10 (dd, J=8.8, 2.4 Hz, 1H), 4.82 (t, J=6.9 Hz, 2H), 3.32 (obscured t, J=6.9 Hz, 2H). Found: C, 52.69; H, 4.05; N, 15.91. C$_{23}$H$_{15}$ClN$_6$O$_3$.31/2H$_2$O requires: C, 52.93; H, 4.25; N, 16.09.

EXAMPLE 282

The Preparation of 4-(2-Chlorophenyl)-9-hydroxy-6-[3-(1H-tetraazol-5-yl)propyl]pyrrolo[3,4-c]carbazole-1,3(2H,6H)-dione (XXXVI; Ar=2-chlorophenyl, n=3) (273)

To a solution of nitrile (241) (60 mg, 0.14 mmol) prepared as described in example 191 in toluene/dimethylformamide (5:1, 35 mL) was added azidotrimethyl tin (57 mg, 0.28 mmol). The resulting solution was heated at reflux for 72 hours before being diluted with water and extraction with ethyl acetate. The organic phase was dried, the drying agent was removed and the solution was concentrated to dryness. Chromatography on silica eluting with ethyl acetate/hexane (3:1) to ethyl acetate/methanol (9:1), followed by crystallization from tetrahydrofuran/hexane, gave tetrazole (273) (29 mg, 44%) as an orange powder, mp 269–272° C. $^1$H NMR δ [(CD$_3$)$_2$SO]~16 (v br s, 1H), 11.07 (s, 1H), 9.38 (br s, 1H), 8.39 (d, J=2.5 Hz, 1H), 7.84 (s, 1H), 7.61 (d, J=8.9 Hz, 1H), 7.57 (m, 1H), 7.53–7.43 (m, 3H), 7.16 (dd, J=8.9, 2.5 Hz, 1H), 4.59 (t, J=7.1 Hz, 2H), 2.93 (m, 2H), 2.20 (m, 2H). Found: C, 59.71; H, 4.27; N, 16.72. C$_{24}$H$_{17}$ClN$_6$O$_3$.3/4H$_2$O requires: C, 59.26; H, 3.83; N, 17.27.

EXAMPLE 283

The Preparation of 4-(2-Chlorophenyl)-9-methoxy-6-[2-(1H-1,2,4-triazol-5-ylsulfanyl)ethyl]pyrrolo[3,4-c]carbazole-1,3(2H,6H)-dione (XXXVII: Ar=2-chlorophenyl, R$^3$=5-1H-1,2,4-triazolyl) (274)

A solution of mesylate (228) (0.25 g, 0.50 mmol) prepared as described in example 170, 1H-1,2,4-triazole-5-thiol (76 mg, 0.75 nmol) and triethylamine (2.0 mL) in p-dioxane (50 mL) under nitrogen was heated at reflux for 48 hours, before being diluted with water and extraction with ethyl acetate. The organic phase was dried, the drying agent was removed and the solution was concentrated to dryness. Chromatography on silica eluting with ethyl acetate/hexane (1:1 to 1:0), followed by crystallization from ethyl acetate/hexane, gave carbazole (274) (0.24 g, 95%) as a yellow powder, mp 211–213° C. $^1$H NMR δ [(CD$_3$)$_2$SO] 14.09 (br s, 1H), 11.13 (br s, 1H), 8.52 (d, J=2.6 Hz, 1H), 8.43 (v br s, 1H), 7.88 (s, 1H), 7.80 (d, J=9.0 Hz, 1H), 7.57 (m, 1H), 7.48 (m, 3H), 7.31 (dd, J=9.0, 2.6 Hz, 1H), 4.83 (t, J=7.4 Hz, 2H), 3.91 (s, 3H), 3.52 (t, J=7.4 Hz, 2H). Found: C, 59.29; H, 3.77; N, 13.63. C$_{25}$H$_{18}$ClN$_5$O$_3$S.1/4H$_2$O requires: C, 59.29; H, 3.68; N, 13.82.

EXAMPLE 284

The Preparation of 4-(2-Chlorophenyl)-6-[2-(1H-imidazol-2-ylsulfanyl)ethyl]-9-methoxypyrrolo[3,4-c]carbazole-1,3(2H,6H)-dione (XXXVII; Ar=2-chlorophenyl, R$^3$=2-imidazolyl) (275)

A solution of mesylate (228) (0.30 g, 0.60 mmol) prepared as described in example 170, 2-mercaptoimidazole (0.12 g, 1.20 mmol) and triethylamine (2.0 mL) in p-dioxane (25 mL) under nitrogen was heated at reflux for 24 hours, before being diluted with water to precipitate the crude product, which was collected by filtration, washed with water and dried in vacuo. Chromatography on silica eluting with ethyl acetate/hexane (1:1), followed by trituration from ethyl acetate, gave carbazole (275) (0.29 g, 96%) as a yellow powder, mp 245–247° C. $^1$H NMR δ [(CD$_3$)$_2$SO] 12.24 (br s, 1H), 11.13 (br s, 1H), 8.51 (d, J=2.6 Hz, 1H), 7.92 (s, 1H), 7.75 (d, J=9.0 Hz, 1H), 7.58 (m, 1H), 7.48 (m, 3H), 7.29 (dd, J=9.0, 2.6 Hz, 1H), 7.00 (v br s, 2H), 4.78 (t, J=7.5 Hz, 2H), 3.91 (s, 3H), 3.44 (t, J=7.5 Hz, 2H). Found: C, 61.57; H, 4.14; N, 10.85. C$_{26}$H$_{19}$ClN$_4$O$_3$S.1/4H$_2$O requires: C, 61.53; H, 3.87; N, 11.03.

EXAMPLE 285

The Preparation of 4-(2-Chlorophenyl)-9-hydroxy-6-[2-(4H-1,2,4-triazol-3-ylsulfanyl)ethyl]pyrrolo[3,4-c]carbazole-1,3(2H,6H)-dione (XXXVIII; Ar=2-chlorophenyl, R$^3$=5-1H-1,2,4-triazolyl) (276)

Reaction of methyl ether (274) (0.25 g, 0.50 mmol) prepared as described in example 283 according to the procedure described in example 80, followed by chromatography on silica eluting with ethyl acetate/tetrahydrofuran (1:0 to 9:1 to 1:1) and trituration from methanol, gave phenol (276) (0.22 g, 90%) as an orange powder, mp 314–319° C. $^1$H NMR δ [(CD$_3$)$_2$SO] 14.10 (br s, 1H), 11.07 (br s, 1H), 9.39 (s, 1H), 8.42 (v br s, 1H), 8.38 (d, J=2.3 Hz, 1H), 7.83 (s, 1H), 7.68 (d, J=8.8 Hz, 1H), 7.57 (m, 1H), 7.48 (m, 3H), 7.13 (dd, J=8.8, 2.3 Hz, 1H), 4.79 (t, J=7.4 Hz, 2H), 3.50 (t, J=7.4 Hz, 2H). Found: C, 58.56; H, 3.82; N, 13.58. C$_{24}$H$_{16}$ClN$_5$O$_3$S.2/5CH$_4$O requires: C, 58.29; H, 3.53; N, 13.93.

EXAMPLE 286

The Preparation of 4-(2-Chlorophenyl)-9-hydroxy-6-[2-(1H-imidazol-2-ylsulfanyl)ethyl]pyrrolo[3,4-c]carbazole-1,3(2H,6H)-dione (XXXVIII; Ar=2-chlorophenyl, R$^3$=2-imidazolyl) (277)

Reaction of methyl ether (275) (130 mg, 0.24 mmol) prepared as described in example 284 according to The procedure described in example 80, except that the reaction time was 7 hours and the chromatography was performed eluting with ethyl acetate/hexane (1:1 to 3:1), gave phenol (277) (97 mg, 83%) as an orange powder, mp 270–275° C. $^1$H NMR δ [(CD$_3$)$_2$SO] 12.23 (br s, 1H), 11.07 (br s, 1H), 9.39 (br s, 1H), 8.37 (d, J=2.4 Hz, 1H), 7.86 (s, 1H), 7.61 (d, J=8.9 Hz, 1H), 7.57 (m, 1H), 7.48 (m, 3H), 7.12 (dd, J=8.9, 2.4 Hz, 1H), 6.98 (v br s, 2H), 4.74 (t, J=7.7 Hz, 2H), 3.42 (partially obscured t, J=7.7 Hz, 2H). Found: C, 60.87; H, 3.72; N, 11.00. C$_{25}$H$_{17}$ClN$_4$O$_3$S.1/4H$_2$O requires: C, 60.85; H, 3.57; N, 11.35.

EXAMPLE 287

The Preparation of 4-(2-Chlorophenyl)-9-hydroxy-6-[2-(1H-1,2,4-triazol-5-ylsulfinyl)ethyl]pyrrolo[3,4-c]carbazole-1,3(2H,6H)-dione (XXXIX; Ar=2-chlorophenyl, m=1, R$^3$=5-1H-1,2,4-triazolyl) (278)

To a solution of carbazole (276) (70 mg, 0.14 mmol) prepared as described in example 285 in tetrahydrofuran (30 mL) containing glacial acetic acid (8 mL), was added 35% hydrogen peroxide (2 mL). The resulting solution was stirred at room temperature for 10 hours before being poured onto solid sodium bicarbonate, diluted with water and extraction with ethyl acetate. The organic phase was dried, the drying agent was removed and the solution was concentrated to dryness. The combined organic layers were partially concentrated under reduced pressure, then adsorbed directly onto silica and chromatographed eluting with methanol/dichloromethane (5:95 to 1:9). Trituration from diethyl ether gave sulfoxide (278) (29 mg, 41%) as an orange powder, mp 237–242° C. $^1$H NMR δ [(CD$_3$)$_2$SO] 14.7 (v br s, 1H), 11.09 (br s, 1H), 9.41 (br s, 1H), 8.69 (br s, 1H), 8.38 (d, J=2.3 Hz, 1H), 7.79 (d, J=9.6 Hz, 1H), 7.60–7.46 (m, 5H), 7.15 (dd, J=8.8, 2.3 Hz, 1H), 4.89 (m, 2H), 3.71 (m, 2H). Found: C, 56.85; H, 3.79; N, 13.74. $C_{24}H_{16}ClN_5O_4S\cdot1/5C_4H_{10}O$ requires: C, 57.20; H, 3.48; N, 13.45.

EXAMPLE 288

The Preparation of 4-(2-Chlorophenyl)-9-hydroxy-6-[2-(1H-1,2,4-triazol-5-ylsulfonyl)ethyl]pyrrolo[3,4-c]carbazole-1,3(2H,6H)-dione (XXXIX; Ar=2-chlorophenyl, m=2, $R^3$=5-1H-1,2,4-triazolyl) (279)

To a solution of carbazole (276) (60 mg, 0.12 mmol) prepared as described in example 285 in tetrahydrofuran (30 mL) containing glacial acetic acid (10 mL), was added 35% hydrogen peroxide (2 mL). The resulting solution was stirred at room temperature for 30 hours before additional 35% hydrogen peroxide (2 mL) was added and the temperature was increased to 50° C. for 18 hours. The reaction was then poured onto solid sodium bicarbonate, diluted with water and extracted with ethyl acetate. The combined organic layers were partially concentrated under reduced pressure, then adsorbed directly onto silica and chromatographed eluting with ethyl acetate/hexane (1:1 to 1:0). Crystallisation from ethyl acetate/hexane gave sulfone (279) (45 mg, 72%) as an orange powder, mp 301–304° C. $^1$H NMR δ [$(CD_3)_2SO$] 14.9 (v br s, 1H), 11.07 (br s, 1H), 9.38 (br s, 1H), 8.60 (s, 1H), 8.34 (d, J=2.4 Hz, 1H), 7.71 (s, 1H), 7.56 (m, 2H), 7.48 (m, 3H), 7.12 (dd, J=8.8, 2.4 Hz, 1H), 4.89 (m, 2H), 4.03 (m, 2H). Found: C, 55.12; H, 3.52; N, 12.87. $C_{24}H_{16}ClN_5O_5S\cdot1/4C_4H_8O_2$ requires: C, 55.20; H, 3.34; N, 12.88.

EXAMPLE 289

The Preparation of 4-(2-Chlorophenyl)-9-hydroxy-6-[2-(1H-imidazol-2-ylsulfonyl)ethyl]pyrrolo[3,4-c]carbazole-1,3(2H,6H)-dione (XXXIX; Ar=2-chlorophenyl, m=2, $R^3$=2-imidazolyl) (280) and 4-(2-chlorophenyl)-9-hydroxy-6-[2-(1H-imidazol-2-ylsulfinyl)ethyl]pyrrolo[3,4-c]carbazole-1,3(2H,6H)-dione (XXXIX; Ar=2-chlorophenyl, m=1, $R^3$=2-imidazolyl) (281)

To a solution of carbazole (277) (66 mg, 0.14 mmol) prepared as described in example 286 in tetrahydrofuran (30 mL) containing glacial acetic acid (10 mL), was added 35% hydrogen peroxide (2 mL). The resulting solution was stirred at room temperature for 20 hours before being poured onto solid sodium bicarbonate, diluted with water and extracted with ethyl acetate. The combined organic layers were partially concentrated under reduced pressure, then adsorbed directly onto silica and chromatographed eluting with ethyl acetate/hexane (1:1 to 4:1) to ethyl acetate/methanol (99:1) to give at highest $R_f$ sulfone (280) (36 mg, 51%) as an orange powder, mp 263–265° C. $^1$H NMR δ [$(CD_3)_2SO$] 11.09 (br s, 1H), 9.44 (br s, 1H), 8.35 (d, J=2.4 Hz, 1H), 7.63 (s, 1H), 7.58 (m, 1H), 7.52–7.45 (m, 4H), 7.19 (br s, 2H), 7.12 (dd, J=8.8, 2.4 Hz, 1H), 4.85 (t, J=6.6 Hz, 2H), 3.96 (m, 2H). Found: C, 57.44; H, 3.87; N, 9.80. $C_{25}H_{17}ClN_4O_5S\cdot1/2C_4H_8O_2$ requires: C, 57.40; H, 3.75; N, 9.92. This was followed at lower $R_f$ by the sulfoxide (281) (16 mg, 23%) as an orange powder, mp 254–259° C. $^1$H NMR δ [$(CD_3)_2SO$] 13.35 (br s, 1H), 11.10 (br s, 1H), 9.42 (s, 1H), 8.39 (d, J=2.4 Hz, 1H), 7.77 (d, J=12.7 Hz, 1H), 7.58 (m, 2H), 7.53–7.44 (m, 3H), 7.24 (br s, 2H), 7.15 (dd, J=8.8, 2.4 Hz, 1H), 4.85 (m, 2H), 3.69 (m, 2H). FABMS found [M+H]$^+$: 505.0725, 507.0666. $C_{25}H_{17}ClN_4O_4S$ requires 505.0737, 507.0708.

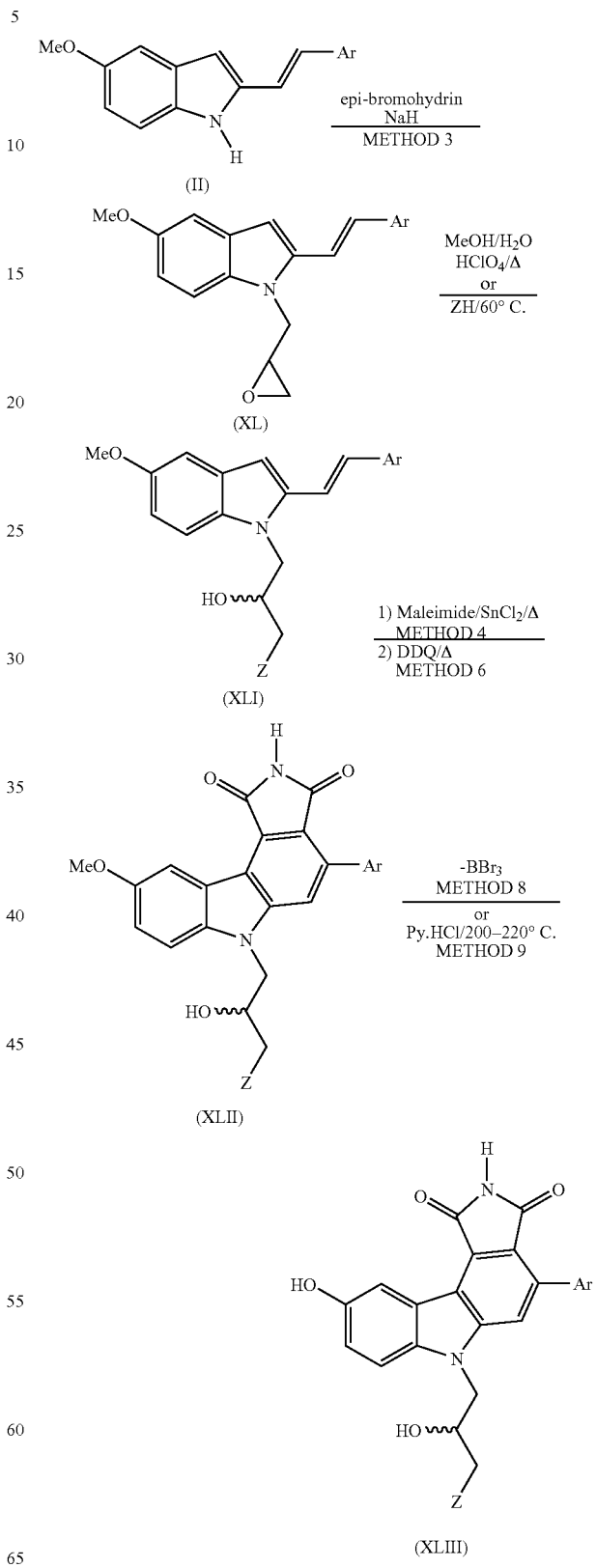

Scheme 10 Procedures

EXAMPLE 290

The Preparation of 6-(2-Hydroxy-3-methoxypropyl)-9-methoxy-4-phenylpyrrolo[3,4-c]carbazole-1,3 (2H,6H)-dione (XLII; Ar=phenyl, Z=OCH₃) (225)

Alkylation of 5-methoxy-2-[(E)-2-phenylethenyl]-1H-indole (11; Ar=phenyl) (0.20 g, 0.80 mmol) with epibromohydrin according to the procedure described in example 38 example 38 gave crude epoxide (XL; Ar=phenyl), which was used without further purification. The epoxide was dissolved in methanol (100 mL) to which 35% perchloric acid (10 mL) was added. The resulting solution was heated at reflux for 3 h before being diluted with water and extraction with ethyl acetate. The organic phase was dried, the drying agent was removed and the solution was concentrated to dryness to give diene (XLI; Ar=phenyl, Z=OCH₃). This crude material was reacted directly with maleimide (92 mg) following Method 4a, except that the reaction time was 18 h. Aromatisation of the crude Diels-Alder adduct using the procedure described in example 79 gave material that was chromatographed on silica eluting with ethyl acetate/hexane (1:1). Crystallisation from ethyl acetate/hexane gave carbazole (225) (0.10 g, 30%) as a yellow powder, mp 128–136° C. $^1$H NMR δ [(CD₃)₂SO] 11.10 (br s, 1H), 8.55 (d, J=2.6 Hz, 1H), 7.81 (s, 1H), 7.64 (m, 3H), 7.47 (m, 3H), 7.29 (dd, J=9.1, 2.6 Hz, 1H), 5.17 (d, J=5.5 Hz, 1H), 4.52 (dd, J=4.2, 15.0 Hz, 1H), 4.43 (dd, J=7.1, 15.0 Hz, 1H), 4.04 (m, 1H), 3.90 (s, 3H), 3.32 (m, 2H), 3.26 (s, 3H). Found: C, 69.94; H, 5.45; N, 6.36. $C_{25}H_{22}N_2O_5$ requires: C, 69.76; H, 5.15; N, 6.51.

EXAMPLE 291

The Preparation of 6-(2,3-Dihydroxypropyl)-9-hydroxy-4-phenylpyrrolo[3,4-c]carbazole-1,3(2H,6H)-dione (XLIII; Ar=phenyl, Z=OH) (226)

Demethylation of alcohol (225) (96 mg, 0.22 mmol) prepared as described in example 290 employing the procedure described in example 80 was followed by chromatography on silica eluting with ethyl acetate/hexane (4:1). Crystallisation from ethyl acetate/hexane gave phenol (226) (28 mg, 31%) as an orange/yellow powder, mp 290–295° C. $^1$H NMR δ [(CD₃)₂SO] 11.04 (br s, 1H), 9.30 (s, 1H), 8.40 (d, J=2.4 Hz, 1H), 7.79 (s, 1H), 7.63 (m, 2H), 7.55 (d, J=8.8 Hz, 1H), 7.47 (m, 3H), 7.11 (dd, J=8.8, 2.4 Hz, 1H), 5.00 (d, J=5.4 Hz, 1H), 4.86 (t, J=5.4 Hz, 1H), 4.51 (dd, J=3.8, 14.9 Hz, 1H), 4.35 (dd, J=7.5, 14.9 Hz, 1H), 3.89 (m, 1H), 3.41 (m, 2H). Found: C, 67.94; H, 4.69; N, 6.50. $C_{23}H_{18}N_2O_5$.1/4H₂O requires: C, 67.89; H, 4.58; N, 6.88.

EXAMPLE 292

The Preparation of 4-(2-Chlorophenyl)-9-hydroxy-6-[2-hydroxy-3-(4-morpholinyl)propyl]pyrrolo[3,4-c]carbazole-1,3(2H,6H)-dione (XLIII; Ar=2-chlorophenyl, Z=4-morpholinyl) (282)

Alkylation of pure trans-diene (27) (0.25 g, 0.88 mmol) prepared as described in example 37 with epibromohydrin according to the procedure described in example 38 gave crude epoxide (XL; Ar=2-chlorophenyl), which was used without further purification. The epoxide was dissolved in tetrahydrofuran (2 mL) to which morpholine (0.5 mL) was added. The resulting solution was heated at 60° C. for 48 hours before being diluted with water and extraction with ethyl acetate. The organic phase was dried, the drying agent was removed and the solution was concentrated to dryness to give diene (XLI; Ar=2-chlorophenyl, Z=4-morpholinyl). This crude material was triturated in diethyl ether/hexane and then reacted directly with maleimide (128 mg) following The procedure described in example 68, except that the reaction time was 18 h and p-dioxane was added as a co-solvent. Aromatisation of the crude Diels-Alder adduct using the procedure described in example 70 gave carbazole (XLII; Ar=2-chlorophenyl, Z=4-morpholinyl) which was demethylated employing the procedure described in example 81, to give crude material that was chromatographed on silica eluting with ethyl acetate. Crystallisation from diethyl,ether/hexane gave carbazole (282) (0.10 g, 22%) as a yellow powder, mp 275–278° C. $^1$H NMR δ [(CD₃)₂SO] 11.05 (br s, 1H), 9.34 (br s, 1H), 8.37 (d, J=2.4 Hz, 1H), 7.79 (s, 1H), 7.63–7.56 (m, 2H), 7.47 (m, 3H), 7.12 (m, 1H), 5.01 (t, J=5.7 Hz, 1H), 4.53 (m, 1H), 4.37 (m, 1H), 4.04 (br s, 1H), 3.38 (m, 4H), 2.39–2.24 (m, 6H). Found: C, 63.90; H, 4.85; N, 8.55. $C_{27}H_{24}ClN_3O_5$ requires: C, 64.10; H, 4.78; N, 8.31.

EXAMPLE 293

The Preparation of 4-(2-Chlorophenyl)-6-[3-(cis-3,5-dimethyl-1-piperazinyl)-2-hydroxypropyl]-9-hydroxypyrrolo[3,4-c]carbazole-1,3(2H,6H)-dione (XLIII; Ar=2-chlorophenyl, Z=cis-3,5-dimethyl-1-piperazinyl) (283)

Alkylation of pure trans-diene (27) (0.25 g, 0.88 mmol) prepared as described in example 37 with epibromohydrin according to the procedure described in example 38 gave crude epoxide (XL; Ar=2-chlorophenyl), which was used without further purification. The epoxide was dissolved in tetrahydrofuran (2 mL) to which cis-2,6-dimethylpiperazine (0.50 g, 4.4 mmol) was added. The resulting solution was heated at 60° C. for 48 hours before being diluted with water and extraction with ethyl acetate. The organic phase was dried, the drying agent was removed and the solution was concentrated to dryness to give diene (XLI; Ar=2-chlorophenyl, Z=cis-3,5-dimethyl-1-piperazinyl). This crude material was triturated in diethyl ether/hexane and then reacted directly with maleimide (0.13 g, 1.5 mmol) following The procedure described in example 68, except that the reaction time was 18 h and p-dioxane was added as a co-solvent. Aromatisation of the crude Diels-Alder adduct using the procedure described in example 70 gave carbazole (XLII; Ar=2-chlorophenyl, Z=cis-3,5-dimethyl-1-piperazinyl) which was demethylated employing The procedure described in example 81 to give crude material that was chromatographed on silica eluting with ethyl acetate/methanol/triethyl amine (4:1 trace). Crystallisation from ethyl acetate/hexane gave carbazole (283) (65 mg, 14%) as a yellow powder, mp 206–210° C. $^1$H NMR δ [(CD₃)₂SO] 11.02 (br s, 1H), 9.33 (br s, 1H), 8.37 (d, J=2.5 Hz, 1H), 7.76 (d, J=9.1, 1H), 7.58 (m, 2H), 7.47 (m, 3H), 7.11 (m, 1H), 4.95 (br s, 1H), 4.52 (m, 1H), 4.34 (m, 1H), 4.04 (m, 1H), 2.71–2.53 (m, 4H), 2.33 (m, 1H), 2.20 (m, 1H), 1.46 (m, 2H), 0.81 (m, 6H). Found: C, 63.76; H, 5.30; N, 10.02. $C_{19}H_{29}ClN_4O_4$.3/4H₂O requires: C, 63.73; H, 5.63; N, 10.25.

EXAMPLE 294

The Preparation of 4-(2-Chlorophenyl)-9-hydroxy-6-[2-hydroxy-3-(methylamino)propyl]pyrrolo[3,4-c]carbazole-1,3(2H,6H)-dione (XLIII; Ar=2-chlorophenyl, Z=NHCH$_3$) (284)

Alkylation of pure trans-diene (27) (0.25 g, 0.88 mmol) prepared as described in example 37 with epibromohydrin according to proceedure described in example 38 gave crude epoxide (XL; Ar=2-chlorophenyl), which was used without further purification. The epoxide was dissolved in tetrahydrofuran (2 mL) to which aqueous methylamine (0.5 mL, 40% solution) was added. The resulting solution was heated at 60° C. for 6 hours before being diluted with water and extraction with ethyl acetate. The organic phase was dried, the drying agent was removed and the solution was concentrated to dryness to give diene (XLI; Ar=2-chlorophenyl, Z=NHCH$_3$). This crude material was triturated in diethyl ether/hexane and then reacted directly with maleimide (0.13 g, 1.5 mmol) following The procedure described in example 68, except that the reaction time was 18 h and p-dioxane was added as a co-solvent. Aromatisation of the crude Diels-Alder adduct using the procedure described in example 70 gave carbazole (XLII; Ar=2-chlorophenyl, Z=NHCH$_3$) which was demethylated employing The procedure described in example 81 to give crude material that was chromatographed on silica eluting with ethyl acetate/methanol/triethylamine (4:1:trace). Crystallisation from ethyl acetate/hexane gave carbazole (284) (61 mg, 15%) as a yellow powder, mp 188–191° C. $^1$H NMR δ [(CD$_3$)$_2$SO] 10.9 (v br s, 1H), 9.36 (br s, 1H), 8.37 (d, J=2.4 Hz, 1H), 7.77 (s, 1H), 7.58 (m, 2H), 7.47 (m, 3H), 7.13 (dd, J=8.8, 2.4 Hz, 1H), 5.09 (br s, 1H), 4.50 (m, 1H), 4.34 (m, 1H), 3.97 (m, 1H), 2.77–2.63 (m, 2H), 2.28 (d, J=2.1 Hz, 3H). Found: C, 62.66; H, 4.64; N, 8.69. C$_{24}$H$_{20}$ClN$_3$O$_4$.2/3H$_2$O requires: C, 62.40; H, 4.66; N, 9.09.

EXAMPLE 295

The Preparation of 4-(2-Chlorophenyl)-6-[3-(dimethylamino)-2-hydroxypropyl-9-hydroxypyrrolo[3,4-c]carbazole-1,3(2H,6H)-dione (XLIII; Ar=2-chlorophenyl, Z=N(CH$_3$)$_2$) (285)

Alkylation of pure trans-diene (27) (0.25 g, 0.88 mmol) prepared as described in example 37 with epibromohydrin according to proceedure described in example 38 gave crude epoxide (XL; Ar=2-chlorophenyl), which was used without further purification. The epoxide was dissolved in tetrahydrofuran (2 mL) to which aqueous dimethylamine (0.5 mL, 40% solution) was added. The resulting solution was heated at 60° C. for 6 hours before being diluted with water and extraction with ethyl acetate. The organic phase was dried, the drying agent was removed and the solution was concentrated to dryness to give diene (XLI; Ar=2-chlorophenyl, Z=N(CH$_3$)$_2$). This crude material was triturated in diethyl ether/hexane and then reacted directly with maleimide (0.13 g, 1.5 mmol) following the procedure described in example 68, except that the reaction time was 18 h and p-dioxane was added as a co-solvent. Aromatisation of the crude Diels-Alder adduct using the procedure described in example 70 gave carbazole (XLII; Ar=2-chlorophenyl, Z=N(CH$_3$)$_2$) which was demethylated employing the procedure described in example 81 to give crude material that was chromatographed on silica eluting with ethyl acetate/methanol/triethylamine (4:1:trace). Crystallisation from ethyl acetate/hexane gave carbazole (285) (165 mg, 40%) as a yellow powder, mp 225–228° C. $^1$H NMR δ [(CD$_3$)$_2$SO] 11.04 (br s, 1H), 9.34 (br s, 1H), 8.38 (d, J=2.4 Hz, 1H), 7.75 (s, 1H), 7.57 (m, 2H), 7.47 (m, 3H), 7.13 (dd, J=8.8, 2.4 Hz, 1H), 4.91 (br s, 1H), 4.50 (m, 1H), 4.34 (m, 1H), 4.00 (m, 1H), 2.35 (m, 1H), 2.24 (m, 1H), 2.17 (s, 6H). Found: C, 63.54; H, 4.60; N, 8.83. C$_{15}$H$_{11}$ClN$_3$O$_4$.1/2H$_2$O requires: C, 63.49; H, 4.90; N, 8.88.

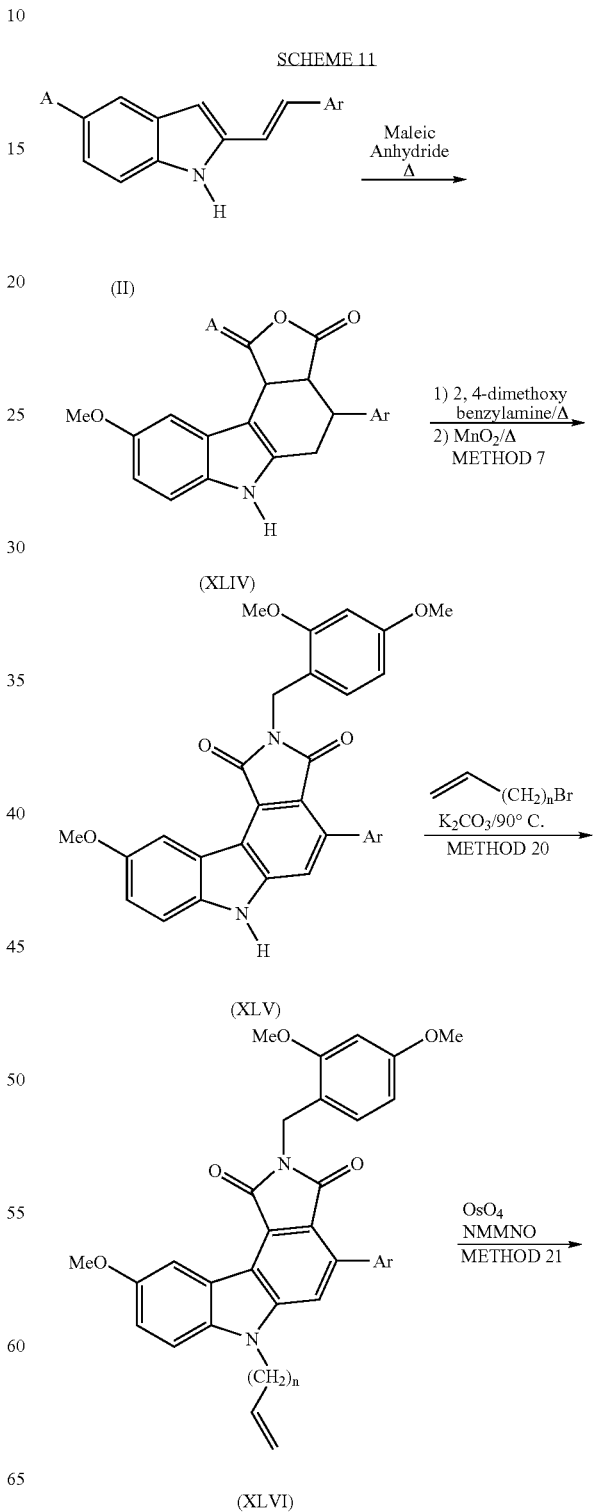

SCHEME 11

Scheme 11 Procedures

EXAMPLE 296

The Preparation of 4-(2-Chlorophenyl)-9-methoxy-4,5,6,10c-tetrahydro-1H-furo[3,4-c]carbazole-1,3(3aH)-dione (XLIV; Ar=2-chlorophenyl) (286)

A solution of trans-diene (27) (0.30 g, 1.06 mmol) prepared as described in example 37 and maleic anhydride (0.16 g, 1.59 mmol) in xylene (30 mL) were heated at reflux for 18 hours, before being concentrated in vacuo and chromatographed on silica eluting with ethyl acetate/hexane (1:2). Crystallisation from ethyl acetate/hexane then gave anhydride (286) (0.29 g, 72%) as a pale brown powder, mp 189–191° C. $^1$H NMR δ (CD$_3$)$_2$SO] 11.16 (br s, 1H), 7.69 (dd, J=7.7, 1.4 Hz, 1H), 7.51 (dd, J=7.7, 1.4 Hz, 1H), 7.43 (ddd, J=7.7, 7.7, 1.4 Hz, 1H), 7.36 (ddd, J=7.7, 7.7, 1.4 Hz, 1H), 7.25 (d, J=8.6 Hz, 1H), 7.15 (d, J=2.4 Hz, 1H), 6.77 (dd, J=8.6, 2.4 Hz, 1H), 4.70 (d, J=7.7 Hz, 1H), 4.47 (dd, J=7.7, 3.5 Hz, 1H), 3.78 (s, 3H), 3.71–3.66 (m, 1H), 3.36 (dd, J=15.9, 13.0 Hz, 1H), 2.99 (dd, J=15.9, 4.1 Hz, 1H). Found: C, 65.85; H, 3.95; N, 3.70. C$_{21}$H$_{16}$ClNO$_4$ requires: C, 66.06; H, 4.22; N, 3.67.

EXAMPLE 297

The Preparation of 4-(2-Chlorophenyl)-2-(2,4-dimethoxybenzyl)-9-methoxypyrrolo[3,4-c]carbazole-1,3(2H,6H)-dione (XLV; Ar=2-chlorophenyl) (287)

To a solution of anhydride (286) (2.80 g, 7.42 mmol) prepared as described in example 296 in glacial acetic acid (70 mL) was added 2,4-dimethoxybenzylamine (1.67 mL, 11.1 mmol). The resulting solution was heated at reflux for 6 hours before being partially concentrated under reduced pressure and diluted with water to precipitate an orange solid, which was collected by filtration, washed with water and dried in vacuo. This crude material was then dissolved in p-dioxane and aromatized according to the procedure for example 79, before being chromatographed on silica eluting with ethyl acetate/hexane (1:1). Crystallisation from methanol then gave carbazole (287) (1.46 g, 37%) as a yellow powder, mp 224–226° C. $^1$H NMR δ [(CD$_3$)$_2$SO] 12.02 (br s, 1H), 8.45 (d, J=2.6 Hz, 1H), 7.62 (s, 1H), 7.58 (m, 2H), 7.53–7.42 (m, 3H), 7.25 (dd, J=8.8, 2.6 Hz, 1H), 6.95 (d, J=8.4 Hz, 1H), 6.57 (d, J=2.3 Hz, 1H), 6.45 (dd, J=8.4, 2.3 Hz, 1H), 4.68 (s, 2H), 3.88 (s, 3H), 3.80 (s, 3H), 3.72 (s, 3H). Found: C, 68.22; H, 4.37; N, 5.29. C$_{30}$H$_{23}$ClN$_2$O$_5$ requires: C, 68.38; H, 4.40; N, 5.32.

Representative Procedure for Method 20 of Scheme 11

EXAMPLE 298

The Preparation of 6-Ally-4-(2-chlorophenyl)-2-(2,4-dimethoxybenzyl)-9-methoxypyrrolo[3,4-c]carbazole-1,3(2H,6H)-dione (XLVI; Ar=2-chlorophenyl, n=1) (288)

To a solution of carbazole (287) (150 mg, 0.28 mmol) prepared as described in example 297 in dimethylformamide (10 mL) under nitrogen was added potassium carbonate (0.39 g, 2.80 mmol) and allyl bromide (720L, 0.84 mmol). The resulting suspension was warmed to 90° C. with stirring for 3 hours before being diluted with water and extraction

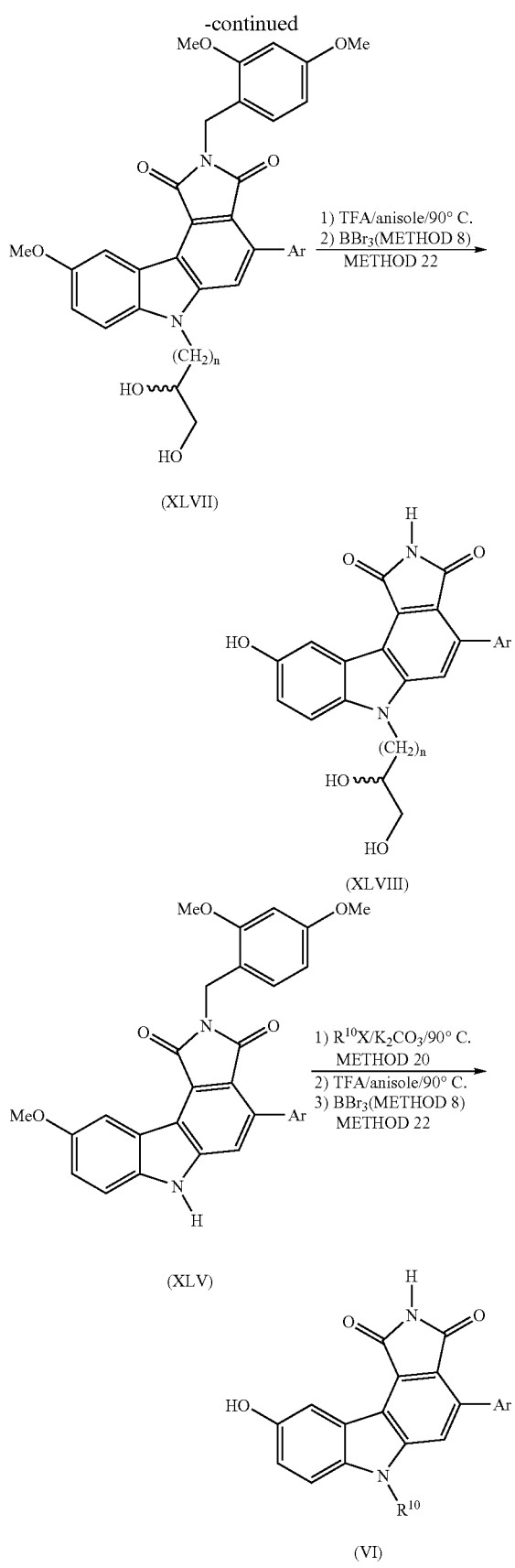

with ethyl acetate. The organic phase was dried, the drying agent was removed and the solution was concentrated to dryness. Chromatography on silica eluting with ethyl acetate/hexane (1:2), followed by crystallization from diethyl ether/hexane gave carbazole (288) (90 mg, 57%) as a yellow powder, mp 171–173° C. $^1$H NMR δ [(CD$_3$)$_2$SO] 8.51 (d, J=2.6 Hz, 1H), 7.84 (s, 1H), 7.67 (d, J=8.9 Hz, 1H), 7.58 (m, 1H), 7.53–7.46 (m, 3H), 7.32 (dd, J=8.9, 2.6 Hz, 1H), 6.97 (d, J=8.4 Hz, 1H), 6.57 (d, J=2.4 Hz, 1H), 6.45 (dd, J=8.4, 2.4 Hz, 1H), 5.99 (m, 1H), 5.18 (d, J=4.9 Hz, 2H), 5.14 (dd, J=10.3, 1.3 Hz, 1H), 4.99 (dd, J=17.2, 1.3 Hz, 1H), 4.69 (s, 2H), 3.90 (s, 3H), 3.80 (s, 3H), 3.72 (s, 3H). Found: C, 69.97; H, 4.75; N, 5.12. C$_{33}$H$_{27}$ClN$_2$O$_5$ requires: C, 69.90; H, 4.80; N, 4.94.

EXAMPLE 299

The Preparation of 6-(3-Butenyl)-4-(2-chlorophenyl)-2-(2,4-dimethoxybenzyl)-9-methoxypyrrolo[3,4-c]carbazole-1,3(2H,6H)-dione (XLVI; Ar=2-chlorophenyl, n=2) (289)

Reaction of carbazole (287) (260 mg, 0.51 mmol) prepared as described in example 297 with 4-bromo-1-butene (155 □L, 1.53 mmol) according to procedure described in example 298 gave carbazole (289) (173 mg, 58%) as a yellow powder, mp 161–164° C. $^1$H NMR δ [(CD$_3$)$_2$SO] 8.50 (d, J=2.6 Hz, 1H), 7.89 (s, 1H), 7.73 (d, J=9.0 Hz, 1H), 7.60–7.46 (m, 4H), 7.31 (dd, J=9.0, 2.6 Hz, 1H), 6.96 (d, J=8.5 Hz, 1H), 6.57 (d, J=2.3 Hz, 1H), 6.44 (dd, J=8.4, 2.3 Hz, 1H), 5.84 (m, 1H), 4.96–4.86 (m, 2H), 4.68 (s, 2H), 4.60 (t, J=6.9 Hz, 2H), 3.89 (s, 3H), 3.80 (s, 3H), 3.72 (s, 3H), 2.54 (partially obscured m, 2H). Found: C, 70.23; H, 5.15; N, 4.91. C$_{34}$H$_{29}$ClN$_2$O$_5$ requires: C, 70.28; H, 5.03; N, 4.82.

Representative Procedure for Method 21 of Scheme 11

EXAMPLE 300

The Preparation of 4-(2-Chlorophenyl)-6-(2,3-dihydroxypropyl)-2-(2,4-dimethoxybenzyl)-9-methoxypyrrolo[3,4-c]carbazole-1,3(2H,6H)-dione (XLVII; Ar=2-chlorophenyl, n=1) (290)

To a solution of carbazole (288) (80 mg, 0.14 mmol) procedure described in example 298 in acetone/water (4:1, 20 mL) was added N-methylmorpholine N-oxide (33 mg, 0.28 mmol) and osmium tetroxide (176 uL, 4% solution in water, ~0.028 mmol). The reaction mixture was stirred at room temperature for 18 hours before being diluted with 1N hydrochloric acid and extraction with ethyl acetate. The organic phase was dried, the drying agent was removed and the solution was concentrated to dryness. Chromatography on silica eluting with ethyl acetatelhexane (2:1), followed by crystallization from diethyl ether/hexane gave diol (290) (80 mg, 94%) as a yellow powder, mp 151–156° C. $^1$H NMR δ [(CD$_3$)$_2$SO] 8.50 (d, J=2.6 Hz, 1H), 7.82 (s, 1H), 7.69 (br d, J=9.0 Hz, 1H), 7.58 (m, 1H), 7.52–7.46 (m, 3H), 7.30 (dd, J=9.0, 2.6 Hz, 1H), 6.95 (d, J=8.4 Hz, 1H), 6.57 (d, J=2.4 Hz, 1H), 6.44 (dd, J=8.4, 2.4 Hz, 1H), 5.02 (d, J=5.0 Hz, 1H), 4.87 (br s, 1H), 4.69 (s, 2H), 4.55 (m, 1H), 4.38 (m, 1H), 3.89 (m, 4H), 3.80 (s, 3H), 3.72 (s, 3H), 3.41 (partially obscured m, 2H). Found: C, 65.32; H, 5.00; N, 4.83. C$_{33}$H$_{29}$ClN$_2$O$_7$.1/4H$_2$O requires: C, 65.45; H, 4.91; N, 4.63.

EXAMPLE 301

The Preparation of 4-(2-Chlorophenyl)-6-(3,4-dihydroxybutyl)-2-(2,4-dimethoxybenzyl)-9-methoxypyrrolo[3,4-c]carbazole-1,3(2H,6H)-dione (XLVII; Ar=2-chlorophenyl, n=2) (291)

Reaction of carbazole (289) (100 mg, 0.17 mmol) procedure described in example 299 according to the procedure described in example 300, except that the reaction time was 48 hours, gave diol (291) (74 mg, 71%) as a yellow powder, mp 126–131° C. $^1$H NMR δ [(CD$_3$)$_2$SO] 8.51 (d, J=2.5 Hz, 1H), 7.83 (s, 1H), 7.72 (d, J=9.0 Hz, 1H), 7.56 (m, 2H), 7.48 (m, 2H), 7.33 (dd, J=9.0, 2.5 Hz, 1H), 6.94 (d, J=8.4 Hz, 1H), 6.57 (d, J=2.3 Hz, 1H), 6.44 (dd, J=8.4, 2.3 Hz, 1H), 4.76 (t, J=5.0 Hz, 1H), 4.69 (s, 2H), 4.60–4.52 (m, 3H), 3.90 (s, 3H), 3.80 (s, 3H), 3.72 (s, 3H), 3.45–3.20 (partially obscured m, 3H), 1.99 (m, 1H), 1.69 (m, 1H). Found: C, 66.39; H, 5.02; N, 4.44. C$_{34}$H$_{31}$ClN$_2$O$_7$ requires: C, 66.39; H, 5.08; N, 4.55.

Representative Procedure for Method 22 of Scheme 11

EXAMPLE 302

The Preparation of 4-(2-Chlorophenyl)-6-(2,3-dihydroxypropyl)-9-hydroxypyrrolo[3,4-c]carbazole-1,3 (2H,6H)-dione (XLVIII; Ar=2-chlorophenyl, n=1) (292)

To a solution of diol (290) (75 mg, 0.13 mmol) prepared as described in example 300 in anisole (0.5 mL) was added trifluoroacetic acid (2.0 mL). The reaction vessel was sealed and heated to 90° C. in an oil bath for 18 h before the trifluoroacetic acid was removed under reduced pressure. The residue was then diluted with water and extracted with diethyl ether (3 times). The combined organic extracts were washed thoroughly with 1N potassium hydroxide and then brine before being dried over anhydrous sodium sulphate and concentrated in vacuo. The aqueous layer was then acidified by the addition of concentrated hydrochloric acid, extracted with diethyl ether and worked-up as above. The combined crude material was triturated with diethyl ether/ hexane and then dissolved in dichloromethane (20 mL) and demethylated according to The procedure described in example 80 to give, after chromatography on silica eluting with ethyl acetate/hexane (1:1 to 1:0), phenol (292) (31 mg, 57%) as an orange powder, mp 305–309° C. $^1$H NMR δ [(CD$_3$)$_2$SO] 11.04 (br s, 1H), 9.33. (s, 1H), 8.38 (d, J=2.4 Hz, 1H), 7.73 (s, 1H), 7.57 (m, 2H), 7.47 (m, 3H), 7.13 (dd, J=8.8, 2.4 Hz, 1H), 4.99 (d, J=5.5 Hz, 1H), 4.83 (t, J=5.4 Hz, 1H), 4.50 (m, 1H), 4.32 (m, 1H), 3.87 (br s, 1H), 3.45–3.36 (m, 2H). Found: C, 63.17; H, 3.94; N, 6.18. C$_{23}$H$_{17}$ClN$_2$O$_5$ requires: C, 63.24; H, 3.92; N, 6.41.

EXAMPLE 303

The Preparation of 4-(2-Chlorophenyl)-6-(3,4-dihydroxybutyl)-9-hydroxypyrrolo[3,4-c]carbazole-1,3 (2H,6H)-dione (XLVIII; Ar=2-chlorophenyl, n=2) (293)

Reaction of diol (291) (35 mg, 0.06 mmol) prepared as described in example 301 according to the procedure described in example 302 gave phenol (293) (25 mg, 92%) as an orange powder, mp 263–267° C. $^1$H NMR δ [(CD$_3$)$_2$SO] 11.05 (br s, 1H), 9.35 (s, 1H), 8.38 (d, J=2.4 Hz, 1H), 7.73 (s, 1H), 7.58 (m, 2H), 7.49 (m, 3H), 7.15 (dd, J=8.8, 2.4 Hz, 1H), 4.73 (t, J=4.9 Hz, 1H), 4.52 (m, 3H), 3.48–3.20 (m, 3H), 1.98 (br s, 1H), 1.67 (br s, 1H). FABMS found [M+H]$^+$=451.1024, 453.1021. $C_{24}H_{19}ClN_2O_5$ requires 451.1061, 453.1031.

EXAMPLE 304

Reaction of carbazole (287) (50 mg, 0.09 mmol per reaction) prepared as described in example 297 with iodomethane, iodoethane, 1-bromopropane, 1-bromobutane, 1-bromopentane, allyl bromide, (2-bromoethyl)benzene, 3-bromopropyne, 1-bromo-3-methylbutane, 2-bromopropane, 2-iodo-1,1,1-trifluoroethane, 5-bromo-1-pentene, iodoacetamide, 4-bromo-1-butene, 1-bromo-2-methylpropane and 1-bromo-4,4,4-trifluorobutane in an array manner according to the procedure described in example 298 except that the reaction time was 18 hours, followed by deprotection according to the procedure described in example 302, except that ethyl acetate was used as the work-up solvent and the 1N potassium hydroxide wash was omitted, gave respectively:

4-(2-chlorophenyl)-9-hydroxy-6-methylpyrrolo[3,4-c]carbazole-1,3(2H,6H)-dione (VI; Ar=2-chlorophenyl, $R^{10}$=$CH_3$) (294). Found: M+H=377.

4-(2-chlorophenyl)-6-ethyl-9-hydroxypyrrolo[3,4-c]carbazole-1,3(2H,6H)-dione (VI; Ar=2-chlorophenyl, $R^{10}$=$CH_2CH_3$) (295). Found: M+H=391.

4-(2-chlorophenyl)-9-Hydroxy-6-propylpyrrolo[3,4-c]carbazole-1,3(2H,6H)-dione (VI; Ar=2-chlorophenyl, $R^{10}$=$(CH_2)_2CH_3$) (296). Found: M+H=405.

6-butyl-4-(2-chlorophenyl)-9-hydroxypyrrolo[3,4-c]carbazole-1,3(2H,6H)-dione (VI; Ar=2-chlorophenyl, $R^{10}$=$(CH_2)_3CH_3$) (297). Found: M+H=419.

4-(2-chlorophenyl)-9-hydroxy-6-pentylpyrrolo[3,4-c]carbazole-1,3(2H,6H)-dione (VI; Ar=2-chlorophenyl, $R^{10}$=$(CH_2)_4CH_3$) (298). Found: M+H=433.

6-allyl-4-(2-chlorophenyl)-9-hydroxypyrrolo[3,4-c]carbazole-1,3(2H,6H)-dione (VI; Ar=2-chlorophenyl, $R^{10}$=$CH_2CH$=$CH_2$) (299). Found: M+H=403.

4-(2-chlorophenyl)-9-hydroxy-6-(2-phenylethyl)pyrrolo[3,4-c]carbazole-1,3(2H,6H)-dione (VI; Ar=2-chlorophenyl, $R^{10}$=$CH_2CH_2Ph$) (300). Found: M+H=467.

4-(2-chlorophenyl)-9-hydroxy-6-(2-propynyl)pyrrolo[3,4-c]carbazole-1,3(2H,6H)-dione (VI; Ar=2-chlorophenyl, $R^{10}$=$CH_2C_2CH$) (301). Found: M+H=401.

4-(2-chlorophenyl)-9-hydroxy-6-isopentylpyrrolo[3,4-c]carbazole-1,3(2H,6H)-dione (VI; Ar=2-chlorophenyl, $R^{10}$=$CH_2CH_2CH(CH_3)_2$) (302). Found: M+H=433.

4-(2-chlorophenyl)-9-hydroxy-6-isopropylpyrrolo[3,4-c]carbazole-1,3(2H,6H)-dione (VI; Ar=2-chlorophenyl, $R^{10}$=$CH(CH_3)_2$) (303). Found: M+H=405.

4-(2-chlorophenyl)-9-hydroxy-6-(2,2,2-trifluoroethyl)pyrrolo[3,4-c]carbazole-1,3(2H,6H)-dione (VI; Ar=2-chlorophenyl, $R^{10}$=$CH_2CF_3$) (304). Found: M+H=445.

4-(2-chlorophenyl)-9-hydroxy-6-(4-pentenyl)pyrrolo[3,4-c]carbazole-1,3(2H,6H)-dione (VI; Ar=2-chlorophenyl, $R^{10}$=$(CH_2)_3CH$=$CH_2$) (305). Found: M+H=431.

2-(4-(2-chlorophenyl)-9-hydroxy-1,3-dioxo-2,3-dihydropyrrolo[3,4-c]carbazol-6(1H)-yl)acetamide (VI; Ar=2-chlorophenyl, $R^{10}$=$CH_2CONH_2$) (306). Found: M+H=420.

6-(3-butenyl)-4-(2-chlorophenyl)-9-hydroxypyrrolo[3,4-c]carbazole-1,3(2H,6H)-dione (VI; Ar=2-chlorophenyl, $R^{10}$=$(CH_2)_2CH$=$CH_2$) (307). Found: M+H=417.

4-(2-chlorophenyl)-9-hydroxy-6-isobutylpyrrolo[3,4-c]carbazole-1,3(2H,6H)-dione (VI; Ar=2-chlorophenyl, $R^{10}$=$CH_2CH(CH_3)_2$) (308). Found: M+H=419.

4-(2-chlorophenyl)-9-hydroxy-6-(4,4,4-trifluorobutyl)pyrrolo[3,4-c]carbazole-1,3(2H,6H)-dione (VI; Ar=2-chlorophenyl, $R^{10}$=$(CH_2)_3CF_3$) (309). Found: M+H=473.

EXAMPLE 305

Reaction of carbazole (287) (50 mg, 0.09 mmol per reaction) prepared as described in example 297 with 2-iodobutane and cyclopentyl bromide in an array manner according to the procedure described in example 298, except that the reaction time was 48 hours, followed by deprotection according to the procedure described in example 302, except that ethyl acetate was used as the work-up solvent and the 1N potassium hydroxide wash was omitted, gave respectively:

6-sec-butyl-4-(2-chlorophenyl)-9-hydroxypyrrolo[3,4-c]carbazole-1,3(2H,6H)-dione (VI; Ar=2-chlorophenyl, $R^{10}$=$CH(CH_3)CH(CH_3)$) (310). Found: M+H=419.

4-(2-chlorophenyl)-6-cyclopentyl-9-hydroxypyrrolo[3,4-c]carbazole-1,3(2H,6H)-dione (VI; Ar=2-chlorophenyl, $R^{10}$=cyclopentyl) (311). Found: M+H=431.

EXAMPLE 306

Reaction of carbazole (287) (50 mg, 0.09 mmol) prepared as described in example 297 with 2-bromoethyl methyl ether in an array manner according to the procedure described in example 298, except that the reaction time was 18 hours, followed by deprotection according to the procedure described in example 302, except that ethyl acetate was used as the work-up solvent, the 1N potassium hydroxide wash was omitted and the demethylation was according to the proceedure described in example 81, gave:

6-(2-chloroethyl)-4-(2-chlorophenyl)-9-hydroxypyrrolo[3,4-c]carbazole-1,3(2H,6H)-dione (VI; Ar=2-chlorophenyl, $R^{10}$=CH$_2$CH$_2$Cl) (312). Found: M+H=425.

Reaction of carbazole (287) (50 mg, 0.09 mmol per reaction) prepared as described in example 297 with 1-chloro-2-propanol, (S)-3-bromo-2-methylpropanol and (R)-3-bromo-2-methylpropanol in an array manner according to the procedure described in example 298 except that the reaction time was 18 hours, followed by deprotection according to the procedure described in example 302 gave:

4-(2-chlorophenyl)-9-hydroxy-6-(2-hydroxypropyl) pyrrolo[3,4-c]carbazole-1,3(2H,6H)-dione (VI; Ar=2-chlorophenyl, $R^{10}$=CH$_2$CH(OH)CH$_3$) (313). Found: M+H=421.

4-(2-chlorophenyl)-9-hydroxy-6-[(2S)-3-hydroxy-2-methylpropyl]pyrrolo[3,4-c]carbazole-1,3(2H,6H)-dione (VI; Ar=2-chlorophenyl, $R^{10}$=CH$_2$CH(CH$_3$) CH$_2$OH) (314). Found: M+H=435.

4-(2-chlorophenyl)-9-hydroxy-6-[(2R)-3-hydroxy-2-methylpropyl]pyrrolo[3,4-c]carbazole-1,3(2H,6H)-dione (VI; Ar=2-chlorophenyl, $R^{10}$=CH$_2$CH(CH$_3$) CH$_2$OH) (315). Found: M+H=435.

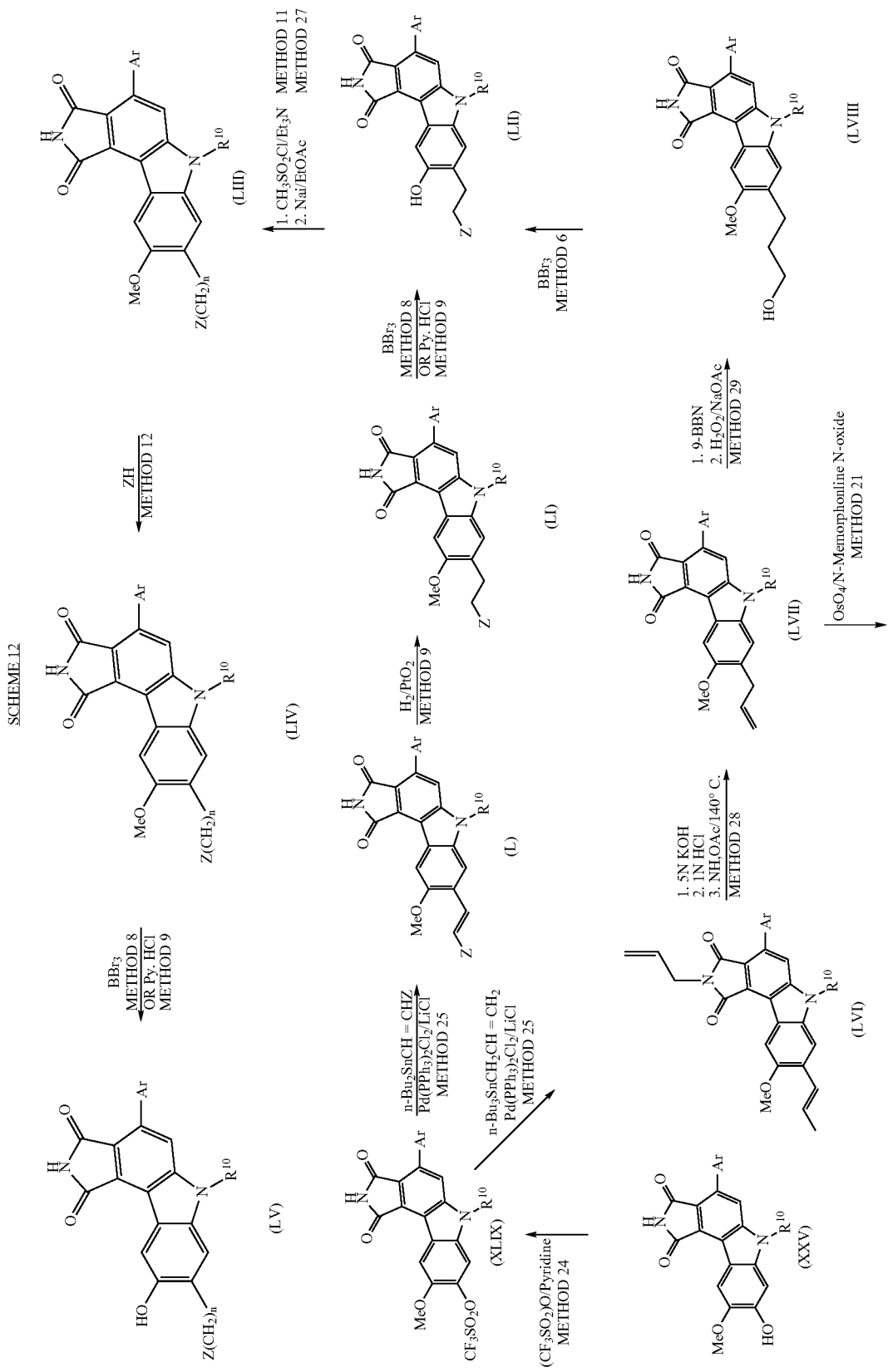

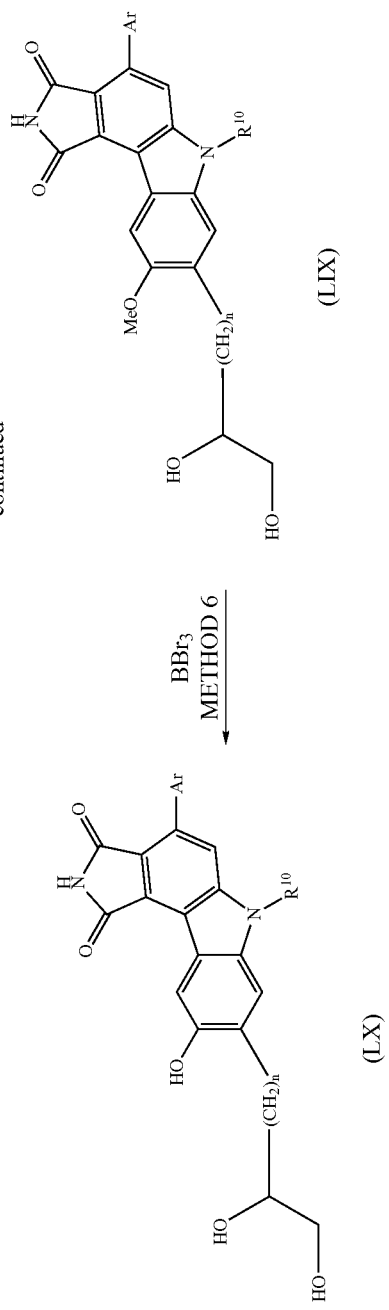

Procedures for Scheme 12

Representative Procedure for Method 24 of Scheme 12

EXAMPLE 307

The Preparation of 4-(2-Chlorophenyl)-9-methoxy-6-(2-methoxyethyl)-1,3-dioxo-1,2,3,6-tetrahydropyrrolo[3,4-c]carbazol-8-yl trifluoromethanesulfonate (XLIX; Ar=2-chlorophenyl, $R^{10}$=CH$_2$CH$_2$OCH$_3$) (168)

Trifluoromethanesulfonic anhydride (1.30 mL, 7.77 mmol) was added dropwise at 0° C. to a solution of the phenol (167) (0.50 g, 1.11. mmol) prepared as described in example 267 and pyridine (6.29 mL, 0.077 mol) in tetrahydrofuran (50 mL). The solution was allowed to warm to room temperature over 1h before dilution with 1N HCl and extraction with ethyl acetate. The extraction was dried, the drying agent was removed and the solution was concentrated to dryness to give a solid which was adsorbed onto silica and chromatographed. Elution with ethyl acetate/petroleum ether (1:1) gave the triflate (168) (0.53 g, 82%) as a pale yellow powder, mp 229–231° C. $^1$H NMR δ [(CD$_3$)$_2$SO] 11.23 (br s, 1H), 8.78 (s, 1H), 8.01 (s, 1H), 7.93 (s, 1H), 7.59 (dd, J=8.0, 2.2 Hz, 1H), 7.54–7.44 (m, 3H), 4.73 (t, J=4.8 Hz, 2H), 4.04 (s, 3H), 3.68 (t, J=4.8 Hz, 2H), 3.14 (s, 3H). Found: C, 49.26; H, 2.91; N, 4.39. C$_{25}$H$_{18}$ClF$_3$SN$_2$O$_7$.1/2CH$_2$Cl$_2$ requires C, 48.97; H, 3.06; N, 4.48.

EXAMPLE 308

The Preparation of 4-(2-Chlorophenyl)-9-methoxy-1,3-dioxo-1,2,3,6-tetrahydropyrrolo[3,4-c]carbazol-8-yl trifluoromethanesulfonate (XLIX; Ar=2-chlorophenyl, $R^{10}$=H) (169)

Reaction of (163) with trifluoromethanesulfonic anhydride using the procedure described in example 307 gave the triflate (169) (87%) as a yellow solid, mp 248–252° C. $^1$H NMR δ [(CD$_3$)$_2$SO] 12.16 (br, 1H), 11.21 (br, 1H), 8.73 (s, 1H), 7.80 (s, 1H), 7.71 (s, 1H), 7.58 (dd, J=8.0, 2.2 Hz, 1H), 7.52–7.43 (m, 3H), 4.03 (s, 3H). Found: C, 52.32; H, 2.87; N, 4.87. C$_{22}$H$_{12}$ClF$_3$N$_2$SO$_6$.THF requires C, 52.31; H, 3.38; N, 4.69.

Representative Procedure for Method 25 of Scheme 12

EXAMPLE 309

The Preparation of 4-(2-Chlorophenyl)-8-[(1E)-4-hydroxy-1-butenyl]-9-methoxypyrrolo[3,4-c]carbazole-1,3(2H,6H)-dione (L; Ar=2-chlorophenyl, $R^{10}$=H, Z=CH$_2$CH$_2$OH) (170).

A solution of the triflate (169) (0.20 g, 0.35 mmol) prepared as described in example 308, (3E)-4-(tributylstannyl)-3-buten-1-ol (0.19 g, 0.53 mmol) and lithium chloride (29 mg, 0.70 mmol) in DMF (10 mL) was purged by bubbling nitrogen through the liquid for 10 min. Bis(triphenylphosphine)palladium dichloride (12 mg, 0.017 mmol) was added last and the solution was flushed with nitrogen for 2 min more, then warmed under an atmosphere of nitrogen for 3 h. The mixture was diluted with brine, extracted with ethyl acetate and worked up to give an oil which was chromatographed on silica. Elution with ethyl acetate/petroleum ether (1:5) gave foreruns, while ethyl acetate/petroleum ether (1:1) increasing to pure ethyl acetate gave (170) as a yellow solid (0.15 g, 95%), mp 271–275° C. $^1$H NMR δ [(CD$_3$)$_2$SO] 11.86 (br s, 1H), 11.07 (br s, 1H), 8.45 (s, 1H), 7.70 (s, 1H), 7.58 (dd, J=8.1, 2.2 Hz, 1H), 7.55 (s, 1H), 7.51–7.41 (m, 3H), 6.87 (d, J=16.0 Hz, 1H), 6.44 (dt, J=16.0, 7.1 Hz, 1H), 4.62 (t, J=5.3 Hz, 1H), 3.94 (s, 3H), 3.58 (m, 2H), 2.42 (m, 2H). Found: C, 67.09; H, 4.36; N, 5.98. C$_{25}$H$_{19}$ClN$_2$O$_4$ requires C, 67.19; H, 4.28; N, 6.27.

Representative Procedure for Method 26 of Scheme 12

EXAMPLE 310

The Preparation of 4-(2-Chlorophenyl)-8-(4-hydroxybutyl)-9-methoxypyrrolo[3,4-c]carbazole-1,3(2H,6H)-dione (LI; Ar=2-chlorophenyl, $R^{10}$=H, Z=CH$_2$CH$_2$OH) (171)

A mixture of (170) (0.15 g, 0.33 mmol) prepared as described in example 309 and PtO$_2$ (20 mg) in 1:1 tetrahydrofuran/methanol (30 mL) was shaken under an atmosphere of hydrogen gas at 40 psi pressure for 30 min. The catalyst was removed by filtration through Celite, washing through with more solvent. The combined filtrates were worked up and chromatographed on silica. Elution with ethyl acetate/petroleum ether (1:1) gave (171) as an orange solid (0.20 g, 100%), mp 256–260° C. (dec). $^1$H NMR δ [(CD$_3$)$_2$SO] 11.90 (br, 1H), 11.10 (br, 1H), 8.34 (s, 1H), 7.64–7.40 (m, 6H), 4.37 (br, 1H), 3.93 (s, 3H), 3.43 (t, J=6.3 Hz, 2H), 2.76 (t, J=7.6 Hz, 2H), 1.66 (m, 1H), 1.50 (m, 2H).

EXAMPLE 311

The Preparation of 4-[4-(2-Chlorophenyl)-9-methoxy-1,3-dioxo-1,2,3,6-tetrahydropyrrolo[3,4-c]carbazol-8-yl]butyl trifluoromethanesulfonate (LIII; Ar=2-chlorophenyl, $R^{10}$=H, n=4, Z=OMs) (172).

Mesylation of (171) prepared as described in example 310 with methanesulfonyl chloride and triethylamine using the procedure described in example 170 of Scheme 3 gave the mesylate (172) as a yellow solid (98%), which was used without further purification.

Representative Procedure for Method 27 of Scheme 12

EXAMPLE 312

The Preparation of 4-(2-Chlorophenyl)-8-(4-iodobutyl)-9-methoxypyrrolo[3,4-c]carbazole-1,3(2H,6H)-dione (LIII; Ar=2-chlorophenyl, $R^{10}$=H, n=4, Z=I) (173)

A mixture of the mesylate (172) 0.12 g, 0.21 mmol) prepared as described in example 311 and sodium iodide (1 g) in ethyl acetate (50 mL) was refluxed for 4 h. The cooled solution was washed with water and worked up to give the iodide (173) which crystallised from tetrahydrofuran/petroleum ether as an orange powder (0.10 g, 85%), mp 142–144° C. $^1$H NMR δ [(CD$_3$)$_2$SO] 11.86 (s, 1H), 11.05 (s, 1H), 8.43 (s, 1H), 7.58 (m, 1H), 7.55 (s, 1H), 7.52–7.43 (m, 3H), 7.42 (s, 1H), 3.94 (s, 3H). EIMS found M$^+$=558.0212, 560.0178. C$_{25}$H$_{20}$ClN$_2$O$_3$ requires 558.0207, 560.0178.

EXAMPLE 313

The Preparation of 4-(2-Chlorophenyl)-8-[4-(dimethylamino)butyl]-9-methoxypyrrolo[3,4-c]carbazole-1,3(2H,6H)-dione (LIV; Ar=2-chlorophenyl, $R^{10}$=H, n=4, Z=N(CH$_3$)$_2$) (174)

Reaction of the iodide (173) prepared as described in example 312 with aqueous dimethylamine using the procedure described in example 179 of Scheme 3 except that the reaction conditions were 6 h at room temperature gave (174) (64%) as an orange powder, mp 162–164° C. $^1$H NMR δ [(CD$_3$)$_2$SO] 11.85 (s, 1H), 11.04 (br s, 1H), 8.42 (s, 1H), 7.57 (dd, J=8.0, 2.2 Hz, 1H), 7.55 (s, 1H), 7.51–7.43 (m, 3H), 7.42 (s, 1H), 3.93 (s, 3H), 2.77 (t, J=7.4 Hz, 2H), 2.24 (t, J=7.3 Hz, 2H), 2.11 (s, 6H), 1.63 (m, 2H), 1.47 (m, 2H). EIMS found M$^+$=475.1657, 477.1650. C$_{27}$H$_{26}$ClN$_3$O$_3$ requires 475.1663, 477.1633.

EXAMPLE 314

The Preparation of 4-(2-Chlorophenyl)-8-[4-(dimethylamino)butyl]-9-hydroxypyrrolo[3,4-c]carbazole-1,3(2H,6H)-dione (LV; Ar=2-chlorophenyl, $R^{10}$=H, n=4, Z=N(CH$_3$)$_2$) (175)

Demethylation of (174 ???) prepared as described in example 313 with pyridine hydrochloride using the procedure described in example 81 gave (176) (67%) as a yellow powder, mp 220–226° C. (dec.). $^1$H NMR δ [(CD$_3$)$_2$SO] 11.72 (s, 1H), 10.98 (s, 1H), 9.33 (br. 1H), 8.32 (s, 1H), 7.56 (dd, J=8.0, 2.2 Hz, 1H), 7.49 (s, 1H), 7.49–7.40 (m, 3H), 7.33 (s, 1H), 2.74 (t, J=7.33 Hz, 2H), 2.54 (m, 2H), 2.34 (br s, 6H), 1.64 (m, 2H), 1.54 (m, 2H). FABMS found [M+H]$^+$: 464.1569, 462.1578. C$_{26}$H$_{25}$ClN$_3$O$_3$ requires 464.1555, 462.1584.

EXAMPLE 315

The Preparation of 4-(2-Chlorophenyl)-9-methoxy-8-[4-(1-pyrrolidinyl)butyl]pyrrolo[3,4-c]carbazole-1,3(2H,6H)-dione (LIV; Ar=2-chlorophenyl, $R^{10}$=H, n=4, Z=1-pyrrolidinyl) (176)

Reaction of the iodide (173) prepared as described in example 312 with pyrrolidine using the procedure described in example 179 except that the reaction conditions were 2 h at room temperature gave (176) (75%) as an orange powder, which was used without further purification, mp 173–178° C. $^1$H NMR δ [(CD$_3$)$_2$SO] 11.85 (s, 1H), 11.04 (br s, 1H), 8.42 (s, 1H), 7.57 (dd, J=8.0, 2.2 Hz, 1H), 7.55 (s, 1H), 7.51–7.43 (m, 3H), 7.42 (s, 1H), 3.93 (s, 3H), 2.77 (t, J=7.4 Hz, 2H), 2.24 (t, J=7.3 Hz, 2H), 2.11 (s, 6H), 1.63 (m, 2H), 1.47 (m, 2H).

EXAMPLE 316

The Preparation of 4-(2-Chlorophenyl)-9-hydroxy-8-[4-(1-pyrrolidinyl)butyl]pyrrolo[3,4-c]carbazole-1,3(2H,6H)-dione (LV; Ar=2-chlorophenyl, $R^{10}$=H, n=4, Z=1-pyrrolidinyl) (177).

Demethylation of (173) prepared as described in example 312 with pyridine hydrochloride using the procedure described in example 81 gave (177) (72%). $^1$H NMR δ [(CD$_3$)$_2$SO] 11.70 (s, 1H), 10.98 (s, 1H), 9.30 (br, 1H), 8.31 (s, 1H), 7.57 (dd, J=8.0, 2.2 Hz, 1H), 7.49 (s, 1H), 7.49–7.40 (m, 3H), 7.32 (s, 1H), 2.73 (t, J=7.5 Hz, 2H), 2.44–2.36 (m, 6H), 1.69–1.61 (m, 6H), 1.51 (m, 2H). The hydrochloride salt had a mp of 173–178° C. (dec). Found: C, 62.27; H, 5.22; N, 7.74. C$_{28}$H$_{26}$ClN$_3$O$_3$.HCl.H$_2$O requires C, 62.00; H, 5.39; N, 7.75.

EXAMPLE 317

The Preparation of 4-(2-Chlorophenyl)-9-methoxy-6-(2-methoxyethyl)-8-vinylpyrrolo[3,4-c]carbazole-1,3(2H,6H)-dione (L; Ar=2-chlorophenyl, $R^{10}$=CH$_2$CH$_2$OCH$_3$, Z=H) (178)

Reaction of the triflate (168) prepared as described in example 307 with tetravinyl tin using the procedure described in example 309 gave the vinyl compound (178) (64%) as a yellow solid, which was used without further purification. $^1$H NMR δ [(CD$_3$)$_2$SO] 11.11 (s, 1H), 8.53 (s, 1H), 7.95 (s, 1H), 7.80 (s, 1H), 7.58 (dd, J=8.1, 2.2 Hz, 1H), 7.52–7.43 (m, 3H), 7.18 (dd, J=17.6, 11.2 Hz, 1H), 6.06 (dd, J=17.6, 1.3 Hz, 1H), 5.42 (dd, J=11.2, 1.3 Hz, 1H), 4.71 (t, J=5.0 Hz, 2H), 3.97 (s, 3H), 3.71 (t, J=5.0 Hz, 2H), 3.16 (s, 3H).

EXAMPLE 318

The Preparation of 4-(2-Chlorophenyl)-8-(2-hydroxyethyl)-9-methoxy-6-(2-methoxyethyl)pyrrolo[3,4-c]carbazole-1,3(2H,6H)-dione (LI; Ar=2-chlorophenyl, $R^{10}$=H, Z=OH) (179).

Hydroboration of (178) prepared as described in example 317 with 9-BBN using the procedure described in example 344 gave (179) (86%) as a yellow solid, mp 271–273° C. $^1$H NMR δ [(CD$_3$)$_2$SO] 11.08 (br, 1H), 8.49 (s, 1H), 7.78 (s, 1H), 7.60 (s, 1H), 7.57 (dd, J=8.0, 2.2 Hz, 1H), 7.52–7.42 (m, 3H), 4.68 (t, J=5.2 Hz, 1H), 4.65 (t, J=5.1 Hz, 2H), 3.94 (s, 3H), 3.70 (m, 4H), 3.15 (s, 3H), 2.96 (t, J=7.2 Hz, 2H).

EXAMPLE 319

The Preparation of 4-(2-Chlorophenyl)-9-hydroxy-6,8-bis(2-hydroxyethyl)pyrrolo[3,4-c]carbazole-1,3(2H,6H)-dione (LII; Ar=2-chlorophenyl, $R^{10}$=CH$_2$CH$_2$OH, Z=OH) (180).

Demethylation of (179) prepared as described in example 318 with BBr$_3$ using the procedure described in example 80 except that the reaction conditions were 12 equiv. of reagent at 0° C. for 6 h gave (180) as a yellow powder (35%), mp 278–280° C. $^1$H NMR δ [(CD$_3$)$_2$SO] 11.00 (br s, 1H), 9.39 (br, 1H), 8.37 (s, 1H), 7.72 (s, 1H), 7.56 (dd, J=8.0, 2.2 Hz, 1H), 7.51–7.42 (m, 4H), 4.82 (t, J=5.5 Hz, 1H), 4.72 (br, 1H), 4.47 (t, J=5.4 Hz, 2H), 3.76 (dt, J=5.5, 5.4 Hz, 2H), 3.69 (t, J=7.2 Hz, 2H), 2.93 (t, J=7.2 Hz, 2H). FABMS found M$^+$: 452.0993, 450.0984. C$_{24}$H$_{19}$ClN$_2$O$_5$ requires 452.0953, 450.0982.

EXAMPLE 320

The Preparation of 9-Methoxy-6-methyl-1,3-dioxo-4-phenyl-1,2,3,6-tetrahydropyrrolo[3,4-c]carbazol-8-yl trifluoromethanesulfonate (XLIX; Ar=phenyl, $R^{10}$=CH$_3$) (185)

Reaction of (154) prepared as described in example 254 with trifluoromethanesulfonic anhydride using the procedure described in example 307 gave 9-methoxy-6-methyl-1,3-dioxo-4-phenyl-1,2,3,6-tetrahydropyrrolo[3,4-c]carbazol-8-yl trifluoromethanesulfonate as a yellow solid (85%), m.p. 244–246° C.; $^1$H NMR δ [(CD$_3$)$_2$SO] 11.22 (br s, 1H), 8.76 (s, 1H), 7.96 (s, 1H), 7.90 (s, 1H), 7.68–7.66 (m, 2H), 7.52–7.46 (m, 3H), 4.02 (s, 3H), 3.99 (s, 3H).

EXAMPLE 321

The Preparation of 4-(2-Chlorophenyl)-9-methoxy-6-methyl-1,3-dioxo-1,2,3,6-tetrahydropyrrolo[3,4-c]carbazol-8-yl trifluoromethanesulfonate (XLIX; Ar=2-chlorophenyl, R$^{10}$=Me) (700)

Reaction of (160) prepared as described in example 260 with trifluoromethanesulfonic anhydride using the procedure described in example 307 gave the triflate (700) (89%) as a yellow solid, mp 251–253° C. $^1$H NMR δ [(CD$_3$)$_2$SO] 11.26 (br s, 1H), 8.80 (s, 1H), 8.02 (s, 1H), 7.87 (s, 1H), 7.61–7.44 (m, 4H). Found: C, 52.51; H, 3.14; N, 4.97. C$_{23}$H$_{14}$N$_2$ClF$_3$O$_6$S.1/4 Hexane requires: C, 52.51; H, 3.15; N, 5.00. FABMS found [M+H]$^+$: 539.0262, 541.0240. C$_{23}$H$_{15}$N$_2$ClF$_3$O$_6$S requires 539.0292, 541.0262.

EXAMPLE 322

The Preparation of 2,8-Diallyl-4-(phenyl)-9-methoxy-6-methylpyrrolo[3,4-c]carbazole-1,3(2H,6H)-dione (LVI; Ar=phenyl, R=Me)(186) and 8-allyl-4-(phenyl)-9-methoxy-6-methylpyrrolo[3,4-c]carbazole-1,3(2H,6H)-dione (LVII; Ar=phenyl, R$^{10}$=Me) (187).

Reaction of triflate (185) prepared as decribed in example 320 and allyltri-n-butyltin at 100° C. for 1 h using the procedure described in example 309 gave a crude product which was chromatographed on silica gel (ethyl acetate/petroleum ether (1:4) to afford (i) pure bis-allyl compound (186) (12%) as an orange solid, mp 188–189° C. $^1$H NMR δ [(CD$_3$)$_2$SO] 8.52 (s, 1H), 7.81 (s, 1H), 7.66 (dd, J=8.0, 1.7 Hz, 2H), 7.53–7.43 (m, 4H), 6.10 (m, 1H), 5.91 (m, 1H), 5.21–5.06 (m, 4H), 4.22 (d, J=5.1 Hz, 2H), 3.95 (s, 6H), 3.56 (d, J=6.6 Hz, 2H). Found: C, 76.43; H, 5.59; N, 6.48. C$_{28}$H$_{24}$N$_2$O$_3$.1/10H$_2$O requires: C, 76.73; H, 5.56; N, 6.39; followed by (ii) pure mono-allyl compound (187) (42%) mp 204–208° C. $^1$H NMR δ (CDCl$_3$) 11.08 (s, 1H), 8.52 (s, 1H), 7.78 (s, 1H), 7.67–7.64 (m, 2H), 7.50 (s, 1H), 7.49–7.43 (m, 3H), 6.09 (ddt, J=6.6 Hz, 1H), 5.15–5.07 (m, 2H), 3.94 (s, 6H), 3.56 (d, J=6.6 Hz, 2H); Found: C, 73.75; H, 5.39; N, 6.76. C$_{25}$H$_{20}$N$_2$O$_3$.3/2H$_2$O requires C, 73.51; H, 5.26; N, 6.86.

EXAMPLE 323

The Preparation of 4-(Phenyl)-9-methoxy-6-methyl-8-vinylpyrrolo[3,4-c]carbazole-1,3(2H,6H)-dione (L; Ar=phenyl, R$^{10}$=Me, Z=H) (701)

Reaction of triflate (185) prepared as decribed in example 320 and tetravinyltin at 100° C. for 1 h using the procedure described in example 309 gave a crude product which was chromatographed on silica gel (ethyl acetate/petroleum ether (1:2) to afford pure 8-vinyl compound (701) (68%) as an orange solid, mp 220° C. (dec). $^1$H NMR δ [(CD$_3$)$_2$SO] 11.12 (br, 1H), 8.57 (s, 1H), 7.92 (s, 1H), 7.79 (s, 1H), 7.69–7.64 (m, 2H), 7.52–7.43 (m, 3H), 7.20 (dd, J=17.7, 11.2 Hz, 1H), 6.09 (dd, J=17.7, 1.2 Hz, 1H), 5.42 (dd, J=11.2, 1.2 Hz, 1H), 4.00 (s, 3H), 3.96 (s, 3H). Found: C, 74.45; H, 4.78; N, 6.94. C$_{24}$H$_{18}$N$_2$O$_3$.1/4H$_2$O requires C, 74.50; H, 4.82; N, 7.24.

EXAMPLE 324

EXAMPLE 325

The Preparation of 2,8-Diallyl-4-(2-chlorophenyl)-9-methoxy-6-methylpyrrolo[3,4-c]carbazole-1,3(2H,6H)-dione (LVI; Ar=2-chlorophenyl, R=Me) (702) and 8-allyl-4-(2-chlorophenyl)-9-methoxy-6-methylpyrrolo[3,4-c]carbazole-13 (2H,6H)-dione (LVII; Ar=2-chlorophenyl, R$^{10}$=Me) (703).

Reaction of triflate (700) prepared as in example 321 and allyltri-n-butyltin at 100° C. for 1 h using the procedure described in example 309 gave a crude product which was chromatographed on silica gel (ethyl acetate/petroleum ether (1:3) to afford (i) pure bis-allyl compound (702) (49%) as an orange solid, mp 183–185° C. $^1$H NMR δ [(CD$_3$)$_2$SO] 8.51 (s, 1H), 7.82 (s, 1H), 7.61–7.44 (m, 5H), 6.16–6.05 (m, 1H), 5.95–5.85 (m, 1H), 5.17–5.07 (m, 4H), 4.21 (br d, J=5.0 Hz, 2H), 3.96 (s, 6H), 3.57 (d, J=6.5 Hz, 2H). Found: C, 71.53; H, 5.14; N, 6.20. C$_{28}$H$_{23}$N$_2$ClO$_3$ requires: C, 71.41; H, 4.92; N, 5.95; followed by (ii) mono-allyl compound (703) (31%) as a yellow solid, mp 269–272° C. $^1$H NMR δ [(CD$_3$)$_2$SO] 11.10 (br, 1H), 8.52 (s, 1H), 7.77 (s, 1H), 7.58–7.43 (m, 4H), 6.16–6.07 (m, 1H), 5.17–5.07 (m, 2H), 3.95 (s, 6H), 3.57 (d, J=6.5 Hz, 2H). Found: C, 69.58; H, 4.55; N, 6.46. C$_{25}$H$_{19}$N$_2$ClO$_3$ requires C, 69.69; H, 4.44; N, 6.50.

EXAMPLE 326

The Preparation of 4-(2-Chlorophenyl)-9-methoxy-6-methyl-8-vinylpyrrolo[3,4-c]carbazole-1,3(2H, 6H)-dione (L; Ar=2-chlorophenyl, R$^{10}$=Me, Z=H) (704).

Reaction of triflate (700) prepared as in example 321 and tetravinyltin at 100° C. for 1 h using the procedure described in example 309 followed by treatment with excess ammonium acetate at 100° C. for another 1H gave a crude product which was chromatographed on silica gel (ethyl acetate/petroleum ether) (1:2) to afford pure 8-vinyl compound (704) (78%) as an orange solid, mp 330° C. (dec). $^1$H NMR δ [(CD$_3$)$_2$SO] 11.12 (br, 1H), 8.53 (s, 1H), 7.94 (s, 1H), 7.78 (s, 1H), 7.60–7.43 (m, 4H), 7.20 (dd, J=17.7, 11.2 Hz, 1H), 6.10 (dd, J=17.7, 1.2 Hz, 1H), 5.43 (dd, J=11.2, 1.2 Hz, 1H), 3.99 (s, 3H), 3.97 (s, 3H).). Found: C, 58.54; H, 4.08; N, 6.65 C$_{24}$H$_{17}$N$_2$ClO$_3$.CH$_2$Cl$_2$.1/2 NH$_3$ requires C, 58.84; H, 4.05; N, 6.86. FABMS found [M+H]$^+$: 417.0982, 419.0955. C$_{24}$H$_{17}$N$_2$ClO$_3$ requires 417.1006, 419.0977.

EXAMPLE 327

The Preparation of 4-(2-Chlorophenyl)-8-[(1E)-3-hydroxy-1-propenyl]-9-methoxy-6-methylpyrrolo[3,4-c]carbazole-1,3(2H,6H)-dione (L; Ar=2-chlorophenyl, R$^{10}$=Me, Z=CH$_2$OH) (710).

Reaction of triflate (700) prepared as in example 321 and 3-hydroxyallyltri-n-butyltin using the procedure described in example 309 at 100° C. for 1 h to gave a crude product which was chromatographed on silica gel (ethyl acetate/petroleum ether) (1:1) to afford pure (710) (42%) as an orange solid, mp 283–285° C. $^1$H NMR δ [(CD$_3$)$_2$SO] 11.11

(s, 1H), 8.51 (s, 1H), 7.89 (s, 1H), 7.76 (s, 1H), 7.59–7.43 (m, 4H), 7.05 (br d, J=16.0 Hz, 1H), 6.67 (dt, J=16.0, 5.0 Hz, 1H), 4.94 (t, J=5.4 Hz, 1H), 4.22 (br t, J=5.0 Hz, 2H), 3.99 (s, 3H), 3.97 (s, 3H). FABMS found M$^+$: 446.1031, 448.1037. $C_{24}H_{17}N_2ClO_3$ requires 446.1033, 448.1004.

Representative Procedure for Method 28 of Scheme 12

EXAMPLE 328

The Preparation of De-alkylation of bisallyl Compound (LVI; Ar=2-chlorophenyl, R=Me) (702) to Give monoallyl Compound (LVII; Ar=2-chlorophenyl, $R^{10}$=Me) (703).

Bisallyl compound (702) (72 mg, 0.153 mmol) prepared as described in example 325 was dissolved in a mixture of acetonitrile (10 mL) and water (1 mL). To this homogeneous solution was added 5M KOH (1 mL) and the mixture was stirred at room temperature for 64 h. Most of the acetonitrile was evaporated in vacuo and the residue was diluted with water (3 mL). After acidification with 1N HCl to pH<1 the acidic solution was stirred at 50–60° C. (bath) for 3 h. After partitioning between ethyl acetate and water the ethyl acetate solution was evaporated and co-evaporated with toluene to give an orange solid which was treated with a large excess of molten ammonium acetate at 140–145° C. (bath) for 3 h. After cooling to room temperature and partitioning between ethyl acetate and water the ethyl acetate solution was evaporated to give a crude product which was chromatographed on silica Cel (ethyl acetate-petroleum ether) (1:3) to give pure monoallyl compound (703) (52 mg, 79%). The $R_f$, mp and $^1$H NMR spectrum were identical with the authentic sample described earlier.

EXAMPLE 329

The Preparation of De-alkylation of Bisallyl Compound (LVI; Ar=phenyl, R=Me) (186) to give monoallyl compound (LVII; Ar-phenyl, $R^{10}$=Me) (187)

Using the procedure described in example 328 bisallyl compound (186) prepared as described in example 322 was converted into monoallyl compound (187) (84%). The $R_f$, mp and $^1$H NMR spectrum were identical with an authentic sample described earlier.

EXAMPLE 330

The Preparation of 8-(2,3-Dihydroxypropyl)-9-methoxy-6-methyl-4-phenylpyrrolo[3,4-c]carbazole-1,3(2H,6H)-dione (LIX; n=1, Ar=phenyl, $R^{10}$=Me) (705).

Reaction of (187) prepared in example 329, N-methylmorpholine N-oxide and osmium tetroxide (at room temperature for 5 h) using the procedure described in example 300 followed by chromatography on silica gel (ethyl acetate) gave (705) (81%) as an orange solid, mp 243–245° C. $^1$H NMR δ [(CD$_3$)$_2$SO] 11.06 (br, 1H), 8.51 (s, 1H), 7.78 (s, 1H), 7.68–7.63 (m, 2H), 7.55 (s, 1H), 7.50–7.42 (m, 3H), 4.58–4.52 (m, 2H), 3.95 (s, 3H), 3.93 (s, 3H), 3.40 (d, J=5.3 Hz, 2H), 3.30 (dd, J=13.5, 5.2 Hz, 1H), 2.77 (dd, J=13.5, 7.8 Hz, 1H). Found: C, 69.02; H, 5.48; N, 6.44. $C_{25}H_{22}N_2O_5 \cdot 1/5H_2O$ requires: C, 69.18; H, 5.20; N, 6.45.

EXAMPLE 331

The Preparation of 8-(1,2-Dihydroxyethyl)-9-methoxy-6-methyl-4-phenylpyrrolo[3,4-c]carbazole-1,3 (2H,6H)-dione (LIX; n=0, Ar=phenyl, $R^{10}$=Me) (706).

Reaction of (701) prepared as described in example 321, N-methylmorpholine N-oxide and osmium tetroxide (at room temperature for 5 h) using the procedure described in example 300 followed by chromatography on silica gel (chloroform/methanol) (10:1) gave (706) (65%) as a yellow solid, mp 242–245° C. $^1$H NMR δ [(CD$_3$)$_2$SO] 11.09 (s, 1H), 8.53 (s, 1H), 7.81 (s, 1H), 7.74 (s, 1H), 7.68–7.64 (m, 2H), 7.50–7.41 (m, 3H), 5.35 (d, J=4.4 Hz, 1H), 5.12–5.06 (m, 1H), 4.75 (t, J=5.3 Hz, 1H), 3.97 (s, 3H), 3.95 (s, 3H), 3.66–3.60 (m, 1H), 3.39–3.33 (m, 1H). Found: C, 69.25; H, 5.14; N, 6.43. $C_{24}H_{20}N_2O_5$ requires: C, 69.22; H, 4.84; N, 6.73.

EXAMPLE 332

The Preparation of 8-(2,3-Dihydroxypropyl)-9-hydroxy-6-methyl-4-phenylpyrrolo[3,4-c]carbazole-1,3 (2H,6H)-dione (LX; n=1, Ar=phenyl, $R^{10}$=Me) (707).

Reaction of (705) prepared as described in example 330 and BBr$_3$ (at 0° C. for 4 h) using the procedure described in example 80 gave the phenol (707) (53%) as an orange solid, mp 283–285° C. $^1$H NMR δ [(CD$_3$)$_2$SO] 11.01 (br, 1H), 9.41 (br, 1H), 8.38 (s, 1H), 7.74 (s, 1H), 7.67–7.62 (m, 2H), 7.50–7.40 (m, 4H), 3.92 (s, 3H), 3.90–3.84 (m, 1H), 3.36 (d, J=5.2 Hz, 2H), 2.98 (dd, J=13.5, 5.0 Hz, 1H), 2.74 (dd, J=13.5, 7.7 Hz, 1H). FABMS found M$^+$: 416.1365. $C_{24}H_{20}N_2O_5$ requires 416.1372.

EXAMPLE 333

The Preparation of 9-Hydroxy-8-(2-hydroxyethyl)-6-methyl-4-phenylpyrrolo[3,4-c]carbazole-1,3(2H,6H)-dione (LII; Ar=phenyl, $R^{10}$=Me, Z=OH) (714).

Reaction of (712) prepared as described in example 340 and BBr$_3$ (at 0° C. for 3 h) using the procedure described in example 80 followed by chromatography on silica gel (chloroform/methanol) (20:1) gave the phenol (714) (31%) as a yellow solid, mp 233–235° C. $^1$H NMR δ [(CD$_3$)$_2$SO] 11.01 (br, 1H), 9.39 (br, 1H), 8.39 (s, 1H), 7.74 (s, 1H), 7.64 (dd, J=7.6, 1.6 Hz, 2H), 7.50–7.42 (m, 4H), 4.73 (br, 1H), 3.92 (s, 3H), 3.70 (t, J=7.1 Hz, 2H), 2.94 (t, J=7.1 Hz, 2H). FABMS found M$^+$: 386.1263. $C_{23}H_{18}N_2O_4$ requires 386.1267.

EXAMPLE 334

The Preparation of 4-(2-Chlorophenyl)-9-hydroxy-8-(2-hydroxyethyl)-6-methylpyrrolo[3,4-c]carbazole-1,3(2H,6H)-dione (LII; Ar=2-chlorophenyl, $R^{10}$=Me, Z=OH) (715)

Reaction of (713) prepared as described in example 341 and BBr$_3$ (at 0° C. for 3 h) using the procedure described in example 80 followed by chromatography on silica gel (chloroform/methanol) (20:1) gave the phenol (715) (81%) as an orange solid, mp 304–306° C. $^1$H NMR δ [(CD$_3$)$_2$SO] 11.00 (br, 1H), 9.30 (br, 1H), 8.37 (s, 1H), 7.71 (s, 1H), 7.57 (dd, J=7.0, 2.0 Hz, 1H), 7.52–7.42 (m, 4H), 4.74 (br, 1H), 3.91 (s, 3H), 3.71 (t, J=7.0 Hz, 2H), 2.94 (t, J=7.0 Hz, 2H). FABMS found M$^+$: 420.0866, 422.0875. C$_{23}$H$_{17}$ClN$_2$O$_4$ requires 420.0877, 422.0847.

EXAMPLE 335

The Preparation of 4-(2-Chlorophenyl)-8-ethyl-9-methoxy-6-methylpyrrolo[3,4-c]carbazole-(1,3(2H,6H)-dione (LI; Ar=2-chlorophenyl, R$^{10}$=Me, Z=H) (708).

Hydrogenation of alkene (704) prepared as in example 326 over PtO$_2$ (45 min reaction time) using the procedure described in example 310 gave 8-ethyl derivative (708) (97%) as an orange solid, mp 262–264° C. $^1$H NMR δ [(CD$_3$)$_2$SO] 11.08 (br, 1H), 8.48 (s, 1H), 7.77 (s, 1H), 7.60–7.42 (m, 5H), 3.95 (s, 6H), 3.90–3.84 (m, 1H), 2.82 (q, J=7.5 Hz, 2H), 1.28 (t, J=7.5 Hz, 3H). Found: C, 68.21; H, 4.38; N, 6.48. C$_{24}$H$_{19}$N$_2$ClO$_3$.1/10H$_2$O requires C, 68.52; H, 4.60; N, 6.66.

EXAMPLE 336

The Preparation of 4-(2-Chlorophenyl)-8-(3-hydroxypropyl)-9-methoxy-6-methylpyrrolo[3,4-c]carbazole-1,3(2H,6H)-dione (LI; Ar=2-chlorophenyl, R$^{10}$=Me, Z=CH$_2$OH) (711)

Hydrogenation of alkene (710) prepared as in example 321 over PtO$_2$ using the procedure described in method26 followed by chromatography on silica gel (ethyl acetate/petroleum ether) (1:1) gave pure 8-(3-hydroxypropyl) compound (711) (44%) as an orange solid, mp 260–263° C. $^1$H NMR δ [(CD$_3$)$_2$SO] 11.08 (s, 1H), 8.48 (s, 1H), 7.77 (s, 1H), 7.59–7.43 (m, 5H), 4.50 (t, J=5.2 Hz, 1H), 3.95 (s, 6H), 3.49 (m, 2H), 2.83 (t, J=7.7 Hz, 2H), 1.82 (m, 2H). FABMS found M$^+$: 448.1194, 450.1200. C$_{25}$H$_{21}$ClN$_2$O$_4$ requires 448.1190, 450.1160.

EXAMPLE 337

The Preparation of 4-(2-Chlorophenyl)-8-ethyl-9-hydroxy-6-methylpyrrolo[3,4-c]carbazole-1,3(2H,6H)-dione (LII; Ar=2-chlorophenyl, R$^{10}$=Me, Z=H) (709).

Reaction of (708) prepared as in example 335 with pyridinium hydrochloride using the procedure described in example 81 followed by chromatography on silica gel (ethyl acetate/petroleum ether) (1:2) gave phenol (709) (78%) as an orange solid, mp 265–268° C. $^1$H NMR δ [(CD$_3$)$_2$SO] 11.01 (s, 1H), 9.39 (s, 1H), 8.37 (s, 1H), 7.71 (s, 1H), 7.59–7.55 (m, 1H), 7.52–7.42 (m, 4H), 3.93 (s, 3H), 2.79 (q, J=7.5 Hz, 2H), 1.27 (t, J=7.5 Hz, 3H). EIMS found M$^+$: 404.0925, 406.0905. C$_{23}$H$_{17}$ClN$_2$O$_3$ requires 404.0928, 406.0898.

EXAMPLE 338

The Preparation of 8-[3-(Dimethylamino)propyl]-9-hydroxy-6-methyl-4-phenylpyrrolo[3,4-c]carbazole-1,3(2H,6H)-dione (LV; n=3, Ar=phenyl, R$^{10}$=Me, Z=NMe$_2$) (720).

Reaction of (717) prepared as described in example 342 with pyridinium hydrochloride using the procedure described in example 81 gave phenol (720) (83%) as an orange solid, mp 315° C. $^1$H NMR δ [(CD$_3$)$_2$SO] 11.01 (br, 1H), 9.79 (br, 1H), 8.38 (s, 1H), 7.72 (s, 1H), 7.64 (dd, J=7.9, 1.4 Hz, 2H), 7.50–7.41 (m, 4H), 3.92 (s, 3H), 2.77 (t, J=7.3 Hz, 2H), 2.25 (t, J=7.0 Hz, 2H) 2.18 (s, 6H), 1.81 (m, 2H). FABMS found [M+H]$^+$: 428.1972. C$_{26}$H$_{26}$N$_3$O$_3$ requires 428.1974.

EXAMPLE 339

The Preparation of 8-[2-(Dimethylamino)ethyl]-9-hydroxy-6-methyl-4-phenylpyrrolo[3,4-c]carbazole-1,3(2H,6H)-dione (LV; n=2, Ar=phenyl, R$^{10}$=Me, Z=NMe$_2$) (721).

Reaction of (719) prepared as described in example 343 with pyridinium hydrochloride using the procedure described in example 81 followed by chromatography on silica gel (chloroform/methanol) (10:1) gave phenol (721) (97%) as an orange solid, mp 278° C. (dec). $^1$H NMR δ [(CD$_3$)$_2$SO] 11.01 (br, 2H), 8.36 (s, 1H), 7.73 (s, 1H), 7.64 (dd, J=7.9, 1.4 Hz, 2H), 7.50–7.41 (m, 4H), 3.92 (s, 3H), 2.94 (t, J=6.9 Hz, 2H), 2.64 (t, J=6.9 Hz, 2H) 2.31 (s, 6H). FABMS found [M+H]$^+$: 414.1821. C$_{25}$H$_{24}$N$_3$O$_3$ requires 414.1818.

EXAMPLE 340

The Preparation of 8-(2-Hydroxyethyl)-9-methoxy-6-methyl-4-phenylpyrrolo[3,4-c]carbazole-1,3(2H,6H)-dione (LI; Ar=phenyl, R$^{10}$=Me, Z=OH) (712).

Reaction of alkene (701) prepared as decribed in example 321 with 9-BBN using the procedure described in method29 gave after chromatography on silica gel (chloroform/methanol) (10:1), the 8-(2-hydroxyethyl) compound (712) (51%) as a yellow solid, mp 284–286° C. $^1$H NMR δ [(CD$_3$)$_2$SO] 11.09 (s, 1H), 8.52 (s, 1H), 7.79 (s, 1H), 7.66 (br d, J=6.4 Hz, 2H), 7.56 (s, 1H), 7.51–7.41 (m, 3H), 4.68 (t, J=5.2 Hz, 1H), 3.96 (s, 3H), 3.94 (s, 3H), 3.69 (m, 2H), 2.98 (t, J=7.2 Hz, 2H).). Found: C, 71.77; H, 5.24; N, 6.81. C$_{24}$H$_{20}$N$_2$O$_4$ requires C, 71.99; H, 5.03; N, 7.00.

EXAMPLE 341

The Preparation of 4-(2-Chlorophenyl)-8-(2-hydroxyethyl)-9-methoxy-6-methylpyrrolo[3,4-c]carbazole-1,3(2H,6H)-dione (LI; Ar=2-chlorophenyl, R$^{10}$=Me, Z=OH) (713).

Reaction of alkene (704) prepared as in example 326 with 9-BBN using the procedure described in method29 gave after chromatography on silica gel (ethyl acetate/petroleum ether) (2:1), the 8-(2-hydroxyethyl) compound (713) (50%) as an orange solid, mp 270–272° C. $^1$H NMR δ [(CD$_3$)$_2$SO] 11.08 (s, 1H), 8.49 (s, 1H), 7.77 (s, 1H), 7.59–7.55 (m, 2H), 7.53–7.43 (m, 3H), 4.69 (t, J=5.3 Hz, 1H), 3.94 (s, 6H), 3.69

(td, J=7.1, 5.3 Hz, 2H), 2.98 (t, J=7.1 Hz, 2H). Found: C, 66.14; H, 4.69; N, 6.51. $C_{24}H_{19}N_2ClO_4$ requires: C, 66.29; H, 4.40; N, 6.44.

EXAMPLE 342

The Preparation of 8-[3-(Dimethylamino)propyl]-9-methoxy-6-methyl-4-phenylpyrrolo[3,4-c]carbazole-1,3(2H,6H)-dione (LIV; n=3 Ar=phenyl, $R^{10}$=Me, Z=NMe$_2$) (717).

Reaction of (188) prepared as described in example 344 with methanesulfonyl chloride using the procedure described in example 170 gave intermediate LIII (n=3, Ar=phenyl, $R^{10}$=Me, Z=OSO$_2$CH$_3$) which was further reacted with aq. 40% dimethylamine (using the procedure described in example 179) at room temperature for 5 h. Usual workup gave a crude product which was refluxed in toluene in the presence of excess ammonium acetate for 23h. After chromatography on silica gel (chloroform/methanol) (10:1) pure dimethylaminopropyl compound (717) (60%) was obtained, mp 175–178° C. $^1$H NMR δ [(CD$_3$)$_2$SO] 11.07 (s, 1H), 8.51 (s, 1H), 7.78 (s, 1H), 7.68–7.63 (m, 2H), 7.55 (s, 1H), 7.51–7.42 (m, 3H), 3.96 (s, 3H), 3.94 (s, 3H), 2.80 (t, J=7.8 Hz, 2H), 2.34 (t, J=7.8 Hz, 2H) 2.20 (s, 6H), 1.80 (m, 2H). Found: C, 69.28; H, 6.64; N, 9.05. $C_{27}H_{27}N_3O_3$.3/2H$_2$O requires C, 69.21; H, 6.45; N, 8.97.

EXAMPLE 343

The Preparation of 8-[2-(Dimethylamino)ethyl]-9-methoxy-6-methyl-4-phenylpyrrolo[3,4-c]carbazole-1,3(2H,6H)-dione (LIV; Ar=phenyl, $R^{10}$=Me, Z=NMe$_2$), n=2) (719)

Reaction of (712) prepared as described in example 340 with methanesulfonyl chloride using the procedure described in example 170 gave intermediate LIII (Ar=phenyl, n=2, $R^{10}$=Me, Z=OSO$_2$CH$_3$) which was further reacted with aq. 40% dimethylamine (using the procedure described in example 179) at room temperature for 25 h. Usual work up gave a crude product which was refluxed in toluene in the presence of excess ammonium acetate for 18 h. After chromatography on silica gel (chloroform/methanol) (10:1) pure dimethylaminoethyl compound (719) (15%) was obtained, mp 233–236° C. $^1$H NMR δ [(CD$_3$)$_2$SO] 11.08 (s, 1H), 8.51 (s, 1H), 7.78 (s, 1H), 7.68–7.63 (m, 2H), 7.58 (s, 1H), 7.50–7.41 (m, 3H), 3.96 (s, 3H), 3.94 (s, 3H), 2.93 (t, J=8.0 Hz, 2H), 2.54 (t, J=8.0 Hz, 2H) 2.23 (s, 6H). EIMS found M$^+$: 427.1890. $C_{26}H_{25}N_3O_3$ requires 427.1896.

Representative Procedure for Method 29 of Scheme 12

EXAMPLE 344

The Preparation of 8-(3-Hydroxypropyl)-9-methoxy-6-methyl-4-phenylpyrrolo[3,4-c]carbazole-1,3 (2H,6H)-dione (LVIII; Ar=phenyl, $R^{10}$=CH$_3$) (188)

A solution of 9-borabicyclo[3,3,1]nonane (1 mL of a 0.5 M solution in tetrahydrofuran, 0.49 mmol) was added to a solution of (187) (65 mg, 0.16 mmol) prepared as described in example 329 in tetrahydrofuran (5 mL). The reaction mixture was stirred at room temperature for 2 hr 20 min and then 3 M sodium acetate (1.5 mL) and 35% hydrogen peroxide (1.0 mL) were added. The mixture was stirred at room temperature for 1 hr 30 min and then diluted with brine and extracted with ethyl acetate (3×30 mL). The combined extracts were dried and concentrated. The residue was purified by column chromatography on silica eluting with ethyl acetate/dichloromethane 1:5 to give 8-(3-hydroxypropyl)-9-methoxy-6-methyl-4-phenylpyrrolo[3,4-c]carbazole-1,3(2H,6H)-dione (58 mg, 85%), mp 105–110° C. softens, 130–134° C. melts. $^1$H NMR δ [(CD$_3$)$_2$SO] 11.06 (s, 1H), 8.51 (s, 1H), 7.78 (s, 1H), 7.66–7.64 (m, 2H), 7.53 (s, 1H), 7.50–7.44 (m, 3H), 4.52 (t, J=5.1 Hz, 1H), 3.96 (s, 3H), 3.94 (s, 3H), 3.52–3.45 (m, 2H), 2.82 (br t, 7.8 Hz, 2H), 1.82 (br dt, J=7.8 Hz, 2H). Found: C, 70.93; H, 5.40; N, 6.54. $C_{25}H_{22}N_2O_4$.1/2H$_2$O requires: C, 70.91; H, 5.47; N, 6.62.

EXAMPLE 345

The Preparation of 9-Hydroxy-8-(3-hydroxypropyl)-6-methyl-4-phenylpyrrolo[3,4-c]carbazole-1,3(2H, 6H)-dione (LII; Ar=phenyl, $R^{10}$=CH$_3$, Z=CH$_2$OH) (189)

Demethylation of (188) prepared as described in example 344 with BBr$_3$ using the procedure described in example 80 gave (189) as a yellow solid. $^1$H NMR δ [(CD$_3$)$_2$SO] 11.00 (br s, 1H), 9.46 (br s, 1H), 8.39 (s, 1H), 7.73 (s, 1H), 7.46–7.63 (m, 2H), 7.49–7.42 (m, 4H), 4.50 (br s, 1H), 3.92 (s, 3H), 3.49–3.44 (m, 2H), 2.78 (br,t, J=7.9 Hz, 2H), 1.82 (br dt, J=7.8 Hz, 2H).

EXAMPLE 346

The Preparation of 8-Ethyl-9-methoxy-6-methyl-4-phenylpyrrolo[3,4-c]carbazole-1,3(2H,6H)-dione (LI; Ar=phenyl, $R^{10}$=CH$_3$, Z=H) (190)

Reaction of the triflate (185) prepared as decribed in example 320 with tetraethyl tin using the procedure described in example 309 gave (190) as a yellow solid (83%), mp 251–253° C. $^1$H NMR δ [(CD$_3$)$_2$SO] 11.07 (s, 1H), 8.53 (s, 1H), 7.77 (s, 1H), 7.67–7.64 (m, 2H), 7.53 (s, 1H), 7.50–7.42 (m, 3H), 3.95 (s, 3H), 3.94 (s, 3H), 2.81 (q, J=7.5 Hz, 2H), 1.27 (t, J=7.5 Hz, 3H). Found: C, 74.48; H, 5.20; N, 7.24. $C_{24}H_{20}N_2O_3$.1/6H$_2$O requires: C, 74.40; H, 5.29; N, 7.23.

EXAMPLE 347

The Preparation of 8-Ethyl-9-hydroxy-6-methyl-4-phenylpyrrolo[3,4-c]carbazole-1,3(2H,6H)-dione (LII; Ar=phenyl, $R^{10}$=CH$_3$, Z=H) (191)

Demethylation of (190) prepared as decried in example 346 with BBr$_3$ using the procedure described in example 80 gave (191) as a yellow solid (92%), mp 278–283° C. $^1$H NMR δ [(CD$_3$)$_2$SO] 11.00 (br s, 1H), 9.36 (s, 1H), 8.40 (s, 1H), 7.73 (s, 1H), 7.66–7.63 (m, 2H), 7.49–7.41 (m, 4H), 3.93 (s, 3H), 2.78 (q, J=7.5 Hz, 2H), 1.27 (t, J=7.5 Hz, 3H). Found: C, 74.36; H, 5.10; N, 7.45. $C_{23}H_{18}N_2O_3$ requires: C, 74.58; H, 4.90; N, 7.56.

SCHEME 13
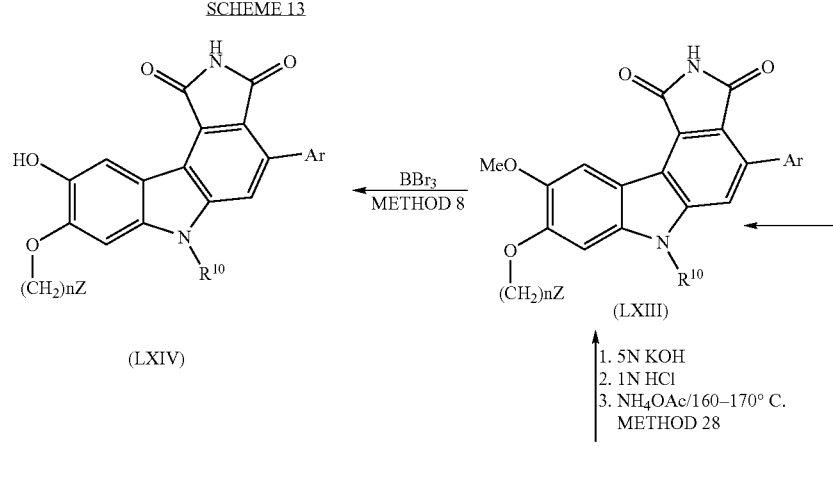
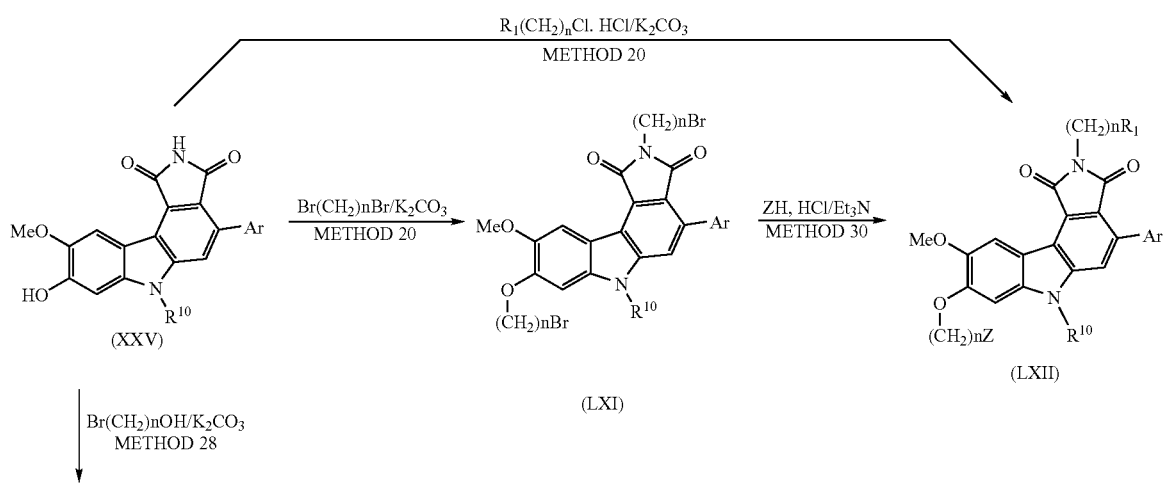
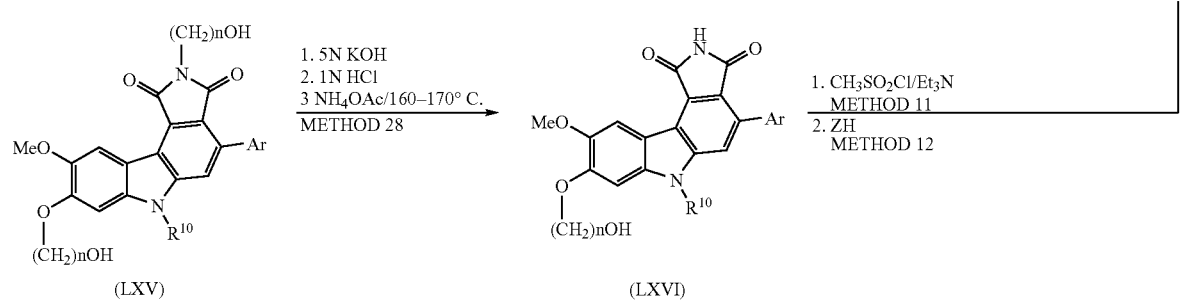

Procedures for Scheme 13

EXAMPLE 348

The Preparation of 4-(2-Chlorophenyl)-8-(3-hydroxypropoxy)-2-(3-hydroxypropyl)-9-methoxy-6-(2-methoxyethyl)pyrrolo[3,4-c]carbazole-1,3(2H,6H)-dione (LXV; Ar=2-chlorophenyl, $R^{10}$=CH$_2$CH$_2$OCH$_3$, n=3) (181)

Alkylation of (167) prepared as described in example 267 with 3-bromopropanol using the procedure described in example 298 gave (181) (92%) as a yellow oil, which was used without further purification.

EXAMPLE 349

The Preparation of 4-(2-Chlorophenyl)-8-(3-hydroxypropoxy)-9-methoxy-6-(2-methoxyethyl)pyrrolo[3,4-c]carbazole-1,3(2H,6H)-dione (LXVI; Ar=2-chlorophenyl, $R^{10}$=CH$_2$CH$_2$OCH, n=3) (182)

Treatment of (182) with the sequence of reactions outlined in the procedure described in example 328 gave (182) (58%) as an orange powder, mp 251–257° C. $^1$H NMR δ [(CD$_3$)$_2$SO] 11.03 (br s, 1H), 8.46 (s, 1H), 7.74 (s, 1H), 7.57 (dd, J=8.0, 2.1 Hz, 1H), 7.51–7.42 (m, 3H), 7.36 (s, 1H), 4.67 (t, J=4.9 Hz, 2H), 4.61 (br, 1H), 4.23 (t, J=6.3 Hz, 2H), 3.90 (s, 3H), 3.70 (t, J=4.9 Hz, 2H), 3.64 (m, 2H), 3.16 (s, 3H), 1.98 (m, 2H). EIMS found: M$^+$=508.1398, 510.1358. C$_{27}$H$_{25}$ClN$_2$O$_6$ requires 508.1401, 510.1371.

EXAMPLE 350

The Preparation of 4-(2-Chlorophenyl)-9-methoxy-6-(2-methoxyethyl)-8-[3-(4-morpholinyl)propoxy]pyrrolo[3,4-c]carbazole-1,3(2H,6H)-dione (LXIII; Ar=2-chlorophenyl, $R^{10}$=CH$_2$CH$_2$OCH$_3$, Z=4-morpholinyl) (183)

Conversion of (182) prepared as described in example 349 to the corresponding mesylate by reaction with methanesulfonyl chloride using the procedure described in example 170 followed by reaction with morpholine using the procedure described in example 179 gave (183) (71%) as a yellow powder, mp 271–275° C., which was immediately demethylated.

EXAMPLE 351

The Preparation of 4-(2-Chlorophenyl)-9-hydroxy-6-(2-hydroxyethyl)-8-[3-(4-morpholinyl)propoxy]pyrrolo[3,4-c]carbazole-1,3(2H,6H)-dione (LXIV; Ar=2-chlorophenyl. $R^{10}$=CH$_2$CH$_2$OCH$_3$, Z=4-morpholinyl) (184)

Demethylation of (183) prepared as decribed in example 350 with BBr$_3$ using the procedure described in example 80 except that the reaction conditions were 0° C. for 2 h gave (184) (36%) as a yellow solid, mp 253–255° C. $^1$H NMR δ [(CD$_3$)$_2$SO] 10.97 (br s, 1H), 8.94 (br s, 1H), 8.34 (s, 1H), 7.69 (s, 1H), 7.56 (dd, J=8.1, 2.2 Hz, 1H), 7.49–7.42 (m, 3H), 7.29 (s, 1H), 4.83 (br, 1H), 4.49 (t, J=5.2 Hz, 2H), 4.18 (t, J=6.2 Hz, 2H), 3.76 (m, 2H), 3.60 (t, J=4.9 Hz, 4H), 2.52 (t, J=7.1 Hz, 2H), 2.41 (m, 4H), 1.99 (m, 2H). FABMS found [M+H]$^+$: 552.1732, 550.1740. C$_{29}$H$_{29}$ClN$_3$O$_6$ requires 552.1715, 550.1745.

EXAMPLE 352

The Preparation of 8-(3-Bromopropoxy)-2-(3-bromopropyl)-9-methoxy-6-methyl-4-phenylpyrrolo[3,4-c]carbazole-1,3(2H,6H)-dione (LXI: Ar=phenyl, $R^{10}$=Me, n=3) (722).

Alkylation of (154) prepared as described in example 254 with 1,3-dibromopropane (3.0 equiv.) using the procedure described in example 298 (at room temperature for 4 d) and after chromatography on silica gel (dichloromethane/petroleum ether) (3:1) gave (722) (47%) as an orange solid, mp 158–160° C. $^1$H NMR δ [(CD$_3$)$_2$SO] 8.50 (s, 1H), 7.76 (s, 1H), 7.69–7.64 (m, 2H), 7.51–7.43 (m, 3H), 7.39 (s, 1H), 4.31 (t, J=6.0 Hz, 2H), 3.98 (s, 3H), 3.92 (s, 3H), 3.77–3.71 (m, 4H), 3.59 (t, J=6.5 Hz, 2H), 2.41–2.34 (m, 2H), 2.23–2.15 (m, 2H). Found: C, 57.16; H, 4.58; N, 4.73. C$_{28}$H$_{26}$N$_2$Br$_2$O$_4$.1/2 hexane requires: C, 56.64; H, 5.06; N, 4.26. FABMS found M$^+$:612.0255, 614.0249, 616.0252. C$_{28}$H$_{26}$Br$_2$N$_2$O$_4$ requires 612.0259. 614.0239, 616.0218.

EXAMPLE 353

The Preparation of 8-(3-Bromopropoxy)-2-(3-bromopropyl)-4-(2-chlorophenyl)-9-methoxy-6-methylpyrrolo[3,4-c]carbazole-1,3(2H,6H)-dione (LXI; Ar=-2-chlorophenyl, $R^{10}$=Me, n=3) (723).

Alkylation of (160) prepared as described in example 260 with 1,3-dibromopropane (15 equiv.) using the procedure described in example 298 (at room temperature for 5 d) and after chromatography on silica gel (dichloromethane/petroleum ether) (3:1) gave (723) (65%) as an orange solid, mp 165–167° C. $^1$H NMR δ [(CD$_3$)$_2$SO] 8.47 (s, 1H), 7.76 (s, 1H), 7.60–7.57 (m, 1H), 7.53–7.43 (m, 3H), 7.41 (s, 1H), 4.31 (t, J=6.0 Hz, 2H), 3.97 (s, 3H), 3.93 (s, 3H), 3.77–3.68 (m, 4H), 3.56 (t, J=6.5 Hz, 2H), 2.42–2.34 (m, 2H), 2.20–2.12 (m, 2H). Found: C, 53.54; H, 4.28; N, 4.20. C$_{28}$H$_{25}$N$_2$ClBr$_2$O$_4$.1/2 hexane requires: C, 53.82; H, 4.66; N, 4.05. FABMS found M$^+$:645.9866, 647.9868, 649.9834. C$_{28}$H$_{25}$N$_2$ClBr$_2$O$_4$ requires 645.9870, 647.9849, 647.9840, 649.9829, 649.9820.

EXAMPLE 354

The Preparation of 4-(2-Chlorophenyl)-8-(3-hydroxypropoxy)-2-(3-hydroxypropyl)-9-methoxy-6-methylpyrrolo[3,4-c]carbazole-1,3(2H,6H)-dione (LXV; Ar=2-chlorophenyl, $R^{10}$=Me, n=3) (724).

Alkylation of (160) prepared as described in example 260 with 3-bromopropanol (2.2 equiv.) using the procedure described in example 298 (at room temperature for 31 h) and after chromatography on silica gel (chloroform/methanol) (20:1) gave (724) (98%) as an orange solid, mp 180–183° C. $^1$H NMR δ [(CD$_3$)$_2$SO] 8.47 (s, 1H), 7.74 (s, 1H), 7.60–7.57 (m, 1H), 7.53–7.43 (m, 3H), 7.36 (s, 1H), 4.60 (t, J=5.1 Hz, 1H), 4.50 (t, J=5.0 Hz, 1H), 4.25 (t, J=6.3 Hz, 2H), 3.96 (s, 3H), 3.92 (s, 3H), 3.67–3.60 (m, 4H), 3.47–3.41 (m, 1H), 2.02–1.95 (m, 2H), 1.79–1.71 (m, 2H). Found: C, 64.03; H, 5.21; N, 5.25. C$_{28}$H$_{27}$N$_2$ClO$_6$ requires C, 64.31; H, 5.20; N, 5.36.

EXAMPLE 355

The Preparation of 4-(2-Chlorophenyl)-8-(3-hydroxypropoxy)-9-methoxy-6-methylpyrrolo[3,4-c]carbazole-1,3(2H,6H)-dione (LXVI; Ar=2-chlorophenyl, $R^{10}$=Me, n=3) (725).

Treatment of (724) prepared as described in example 354 with the sequence of reactions (SM KOH/MeOH/reflux/3h; 1N HCl/100° C./3 h; NH$_4$OAc/150° C./20 min) as described in The procedure described in example 328 gave (725) (85%) as an orange solid, mp 285–287° C. $^1$H NMR δ [(CD$_3$)$_2$SO] 11.02 (br, 1H), 8.46 (s, 1H), 7.72 (s, 1H), 7.59–7.55 (m, 1H), 7.51–7.42 (m, 3H), 7.34 (s, 1H), 4.60 (t, J=5.1 Hz, 1H), 4.25 (t, J=6.3 Hz, 2H), 3.95 (s, 3H), 3.91 (s, 3H), 3.67–3.61 (m, 2H), 2.02–1.95 (m, 2H). Found: C, 64.69; H, 4.60; N, 6.11. $C_{25}H_{21}N_2ClO_5$ requires: C, 64.31; H, 5.20; N, 5.36.

EXAMPLE 356

The Preparation of 8-[3-(Dimethylamino)propoxy]-2-[3-(dimethylamino)propyl]-9-methoxy-6-methyl-4-phenylpyrrolo[3,4-c]carbazole-1,3(2H,6H)-dione (LXII; Ar=phenyl, $R^{10}$=Me, Z|NMe$_2$, n=3) (726).

Reaction of (722) prepared as described in example 352 with excess dimethylamine.HCl in DMF in the presence of triethylamine and 4A molecular sieves at room temperature (Method 30 ??) for 66 h gave (726) (35%) as the d1Hydrochloride salt, mp 278–281° C. (dec). $^1$H NMR δ [(CD$_3$)$_2$SO]] 9.95 (br, 2H), 8.51 (s, 1H), 7.81 (s, 1H), 7.70–7.65 (m, 2H), 7.52–7.43 (m, 3H), 7.40 (s, 1H), 4.28 (t, J=6.1 Hz, 2H), 3.99 (s, 3H), 3.93 (s, 3H), 3.67 (t, J=6.4 Hz, 2H), 3.28 (t, J=7.6 Hz, 2H), 3.10 (t, J=7.6 Hz, 2H), 2.83 (s, 6H), 2.73 (s, 6H), 2.29–2.20 (m, 2H), 2.26–1.97 (m, 2H). Found: C, 59.07; H, 6.68; N, 8.44. $C_{32}H_{40}N_4Cl_2O_4$ requires: C, 58.98; H, 6.81; N, 8.60.

EXAMPLE 357

The Preparation of 4-(2-Chlorophenyl)-8-[3-(dimethylamino)propoxy]-2-[3-(dimethylamino)propyl]-9-methoxy-6-methylpyrrolo[3,4-c]carbazole-1,3(2H, 6H)-dione (LXII; Ar=2-chlorophenyl, $R^{10}$=Me, Z=NMe$_2$, n=3) (727).

Reaction of (723) prepared as described in example 353 with excess dimethylamine.HCl in DMF in the presence of triethylamine and 4A molecular sieves at room temperature (Method 30 ??) for 6 d followed by chromatograpy on silica gel (chloroform/methanol/triethylamine) (10:1:0.1) gave (727) (63%) as the d1Hydrochloride salt, mp 207–210° C. $^1$H NMR δ [(CD$_3$)$_2$SO] 9.89 (br, 2H), 8.48 (s, 1H), 7.79 (s, 1H), 7.61–7.56 (m, 1H), 7.53–7.44 (m, 3H), 7.41 (s, 1H), 4.28 (t, J=6.0 Hz, 2H), 3.97 (s, 3H), 3.94 (s, 3H), 3.65 (t, J=6.6 Hz, 2H), 3.23 (br, 2H), 3.34 (br, 2H), 2.80 (s, 6H), 2.69 (s, 6H), 2.28–2.19 (m, 2H), 2.03–1.92 (m, 2H). Found: C, 58.09; H, 6.13; N, 8.44. $C_{32}H_{37}N_4ClO4.2.2$ HCl requires: C, 58.47; H, 6.01; N, 8.52. Found: C, 59.07; H, 6.68; N, 8.44. $C_{32}H_{40}N_4Cl_2O_4$ requires: C, 58.98; H, 6.81; N, 8.60.

EXAMPLE 358

The Preparation of 4-(2-Chlorophenyl)-8-[3-(dimethylamino)propoxy]-2-[3-(dimethylamino)propyl]-9-methoxy-6-methylpyrrolo[3,4-c]carbazole-1,3(2H, 6H)-dione (LXII; Ar=2-chlorophenyl, $R^{10}$=Me, Z=NMe$_2$, n=3) (727).

On a larger scale (727) was best prepared from (160) prepared as described in example 260 by reaction with 3-dimethylaminopropylchloride hydrochloride (7.3 equiv.) in the presence of excess anhydrous potassium carbonate and 4A molecular sieves at 60–70° C. (bath temperature) for 3 h. The yield of crude product was 96%, which was used for the next step without further purification.

EXAMPLE 359

The Preparation of 4-(2-Chlorophenyl)-8-[3-(dimethylamino)propoxy]-9-methoxy-6-methylpyrrolo[3,4-c]carbazole-1,3(2H,6H)-dione (LXIII; Ar=2-chlorophenyl, $R^{10}$=Me, Z=NMe$_2$, n=3) (728).

Treatment of (727) prepared as described in example 358 with the sequence of reactions (SM KOH/MeOH/reflux/3 h; 1N HCl/100° C./3 h; NH$_4$OAc/170° C./10 h) as described in Example 328, with the modification that after acidic treatment the reaction mixture was evaporated to dryness and fused with NH$_4$OAc, followed by chromatography on silica (dichloromethane/MeOH=5:1) gave (728) (97%) as an orange solid, mp 288–290° C. $^1$H NMR δ [(CD$_3$)$_2$SO] 11.04 (br, 1H), 8.46 (s, 1H), 7.72 (s, 1H), 7.59–7.55 (m, 1H), 7.51–7.42 (m, 3H), 7.33 (s, 1H), 4.21 (t, J=6.5 Hz, 2H), 3.95 (s, 3H), 3.91 (s, 3H), 2.43 (t, J=7.0 Hz, 2H), 2.18 (s, 6H), 2.01–1.93 (m, 2H).). Found: C, 68.22; H, 6.57; N, 7.43. $C_{27}H_{26}N_3ClO_4$, hexane requires: C, 68.58; H, 6.97; N, 7.27. FABMS found [M+H]$^+$:492.1689,494.1675. $C_{27}H_{27}N_3ClO_4$ requires 492.1690, 494.1661.

EXAMPLE 360

The Preparation of 4-(2-Chlorophenyl)-9-methoxy-6-methyl-8-[3-(4-morpholinyl)propoxy]pyrrolo[3,4-c]carbazole-1,3(2H,6H)-dione (LXIII; Ar=2-chlorophenyl, $R^{10}$=Me, Z=4-morpholinyl, n=3) (729).

Conversion of (725) prepared as described in example 355 to the corresponding mesylate by reaction with methanesulfonyl chloride using the procedure described in example 170 example 170 followed by reaction with morpholine using the procedure described in example 179, and treatment of the crude product with NH$_4$OAc at 160–170° C. for 2 h, gave (after a silica column; chloroform/MeOH=10: 1) (729) (76%) as an orange powder, mp 293–295° C. $^1$H NMR δ [(CD$_3$)$_2$SO] 11.04 (br, 1H), 8.47 (s, 1H), 7.72 (s, 1H), 7.59–7.55 (m, 1H), 7.52–7.42 (m, 3H), 7.34 (s, 1H), 4.22 (t, J=6.4 Hz, 2H), 3.96 (s, 3H), 3.91 (s, 3H), 3.59 (br t, J=4.6 Hz, 4H), 2.60–2.36 (m, 6H), 2.03–1.95 (m, 2H). FABMS found [M+H]$^+$:534.1792, 536.1769. $C_{29}H_{29}N_3ClO_5$ requires 534.1796, 536.1766.

EXAMPLE 361

The Preparation of 4-(2-Chlorophenyl)-9-methoxy-6-methyl-8-[3-(1-pyrrolidinyl)propoxy]pyrrolo[3,4-c]carbazole-1,3(2H,6H)-dione (LXIII; Ar=2-chlorophenyl, $R^{10}$=Me, Z=1-pyrrolidinyl, n=3) (730).

Conversion of (725) prepared as described in example 355 to the corresponding mesylate by reaction with methanesulfonyl chloride using the procedure described in example 170 followed by reaction with pyrrolidine using the procedure described in example 179 of Scheme 3, and treatment of the crude product with $NH_4OAc$ at 160–170° C. for 4 h, gave (after a silica column; chloroform/MeOH=10:1) (730) (78%) as an orange solid, 273–275° C. $^1H$ NMR δ [$(CD_3)_2SO$] 11.03 (br, 1H), 8.45 (s, 1H), 7.73 (s, 1H), 7.59–7.55 (m, 1H), 7.52–7.42 (m, 3H), 7.34 (s, 1H), 4.22 (t, J=6.4 Hz, 2H), 3.95 (s, 3H), 3.90 (s, 3H), 2.60 (t, J=7.0 Hz, 2H), 2.42 (m, 4H), 2.03–1.96 (m, 2H), 1.73–1.67 (m, 4H). Found: C, 66.40; H, 5.47; N, 7.85. $C_{29}H_{28}N_3ClO_4 \cdot 1/2H_2O$ requires C, 66.09; H, 5.55; N, 7.97.

EXAMPLE 362

The Preparation of 8-[3-(Dimethylamino)propoxy]-9-methoxy-6-methyl-4-phenylpyrrolo[3,4-c]carbazole-1,3(2H,6H)-dione (LXIII; Ar=2-phenyl, $R^{10}$=Me$_2$, Z=NMe$_2$, n=3) (731).

Treatment of (726) prepared as described in example 356 with the sequence of reactions (5M KOH/MeOH/reflux/3 h; 1N HCl/100° C./3 h; $NH_4OAc/170°$ C./10 h) in the proceedure described example 328 with the modification that after acidic treatment the reaction mixture was evaporated to dryness and fused with $NH_4OAc$, gave (731) (37%), after a silica column (dichloromethane/MeOH=5:1) as a hygroscopic solid, $^1H$ NMR δ [$(CD_3)_2SO$] 11.04 (br, 1H), 8.48 (s, 1H), 7.75 (s, 1H), 7.68–7.62 (m, 2H), 7.51–7.42 (m, 3H), 7.33 (s, 1H), 4.21 (t, J=6.9 Hz, 2H), 3.97 (s, 3H), 3.90 (s, 3H), 2.43 (t, J=7.1 Hz, 2H), 2.19 (s, 6H), 2.01–1.93 (m, 2H). LCMS(APCI) m/z: 458.101 [M+H]$^+$.

EXAMPLE 363

The Preparation of 4-(2-Chlorophenyl)-8-[3-(dimethylamino)propoxy]-9-hydroxy-6-methylpyrrolo[3,4-c]carbazole-1,3(2H,6H)-dione (LXIV; Ar=2-chlorophenyl, $R^{10}$=Me, Z=NMe$_2$, n=3) (732).

Demethylation of (728) prepared as described in example 359 with BBr$_3$ using the procedure described in example 80 except that the reaction conditions were 0° C. for 2 h gave (732) (83%) as an orange solid, mp 259–262° C. $^1H$ NMR δ [$(CD_3)_2SO$] 10.99 (s, 1H), 9.22 (br, 1H), 8.35 (s, 1H), 7.70 (s, 1H), 7.58–7.54 (m, 1H), 7.51–7.42 (m, 3H), 7.29 (s, 1H), 4.22 (t, J=6.0 Hz, 2H), 3.92 (s, 3H), 2.89 (br, 2H), 2.50 (br, 6H), 2.13–2.03 (m, 2H). FABMS found [M+H]$^+$:478.1532, 480.1519. $C_{26}H_{25}N_3ClO_4$ requires 478.1534, 480.1504.

EXAMPLE 364

The Preparation of 8-[3-(Dimethylamino)propoxy]-9-hydroxy-6-methyl-4-phenylpyrrolo[3,4-c]carbazole-1,3(2H,6H)-dione (LXIV; Ar=phenyl, $R^{10}$=Me, Z=NMe, n=3) (733).

Demethylation of (731) prepared as described in example 362 with BBr$_3$ using the procedure described in example 80 except that the reaction conditions were 0° C. for 2 h gave (733) (56%), mp 303–304° C. $^1H$ NMR δ [$(CD_3)_2SO$] 11.00 (s, 1H), 9.00 (br, 2H), 8.39 (s, 1H), 7.73 (s, 1H), 7.66–7.61 (m, 2H), 7.50–7.41 (m, 3H), 7.29(s, 1H), 4.26 (t, J=5.7 Hz, 2H), 3.94 (s, 3H), 3.24 (t, J=7.1 Hz, 2H), 2.80 (s, 6H), 2.23–2.14 (m, 2H). Found: C, 60.61; H, 5.05; N, 7.82. $C_{26}H_{25}N_3O_4$ requires: C, 60.48; H, 5.06; N, 8.14.

EXAMPLE 365

The Preparation of 4-(2-Chlorophenyl)-9-hydroxy-6-methyl-8-[3-(4-morpholinyl)propoxyl]pyrrolo[3,4-c]carbazole-1,3(2H,6H)-dione (LXIV; Ar=2-chlorophenyl, $R^{10}$=Me, Z=4-morpholinyl, n=3) (734).

Demethylation of (729) prepared as described in example 360 with BBr$_3$ using the procedure described in example 80 except that the reaction conditions were 0° C. for 2 h gave (734) (60%) as an orange solid, mp 235–237° C. $^1H$ NMR δ [$(CD_3)_2SO$] 10.98 (s, 1H), 8.97 (br, 1H), 8.33 (s, 1H), 7.69 (s, 1H), 7.59–7.54 (m, 1H), 7.51–7.42 (m, 3H), 7.28 (s, 1H), 4.21 (t, J=6.1 Hz, 2H), 3.92 (s, 3H), 3.61 (br, 4H), 2.58–2.37 (m, 6H), 2.05–1.95 (m, 2H). FABMS found [M+H]$^+$: 520.1648, 522.1635. $C_{28}H_{27}N_3ClO_5$ requires 520.1639, 522.1610.

EXAMPLE 366

The Preparation of 4-(2-Chlorophenyl)-9-hydroxy-6-methyl-8-[3-(1-pyrrolidinyl)propoxy]pyrrolo[3,4-c]carbazole-1,3(2H,6H)-dione (LXIV; Ar=2-chlorophenyl, $R^{10}$=Me, Z=1-pyrrolidinyl, n=3) (735).

Demethylation of (730) prepared as described in example 361 with BBr$_3$ using the procedure described in example 80 except that the reaction conditions were 0° C. for 2 h gave (735) (60%) as an orange solid, mp 234–236° C. $^1H$ NMR δ [$(CD_3)_2SO$] 10.98 (br, 1H), 9.27 (br, 1H), 8.33 (s, 1H), 7.68 (s, 1H), 7.58–7.55 (m, 1H), 7.51–7.42 (m, 3H), 7.30 (s, 1H), 4.20 (t, J=6.2 Hz, 2H), 3.92 (s, 3H), 2.66 (t, J=6.8 Hz, 2H), 2.54–2.35 (m, 4H), 2.04–1.96 (m, 2H), 1.75–1.68 (m, 4H). FABMS found [M+H]$^+$:504.1687, 506.1661. $C_{28}H_{27}N_3ClO_4$ requires 504.1690, 506.1661.

SCHEME 14

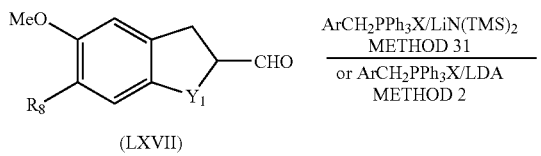

(LXVII)

ArCH$_2$PPh$_3$X/LiN(TMS)$_2$
METHOD 31
or ArCH$_2$PPh$_3$X/LDA
METHOD 2

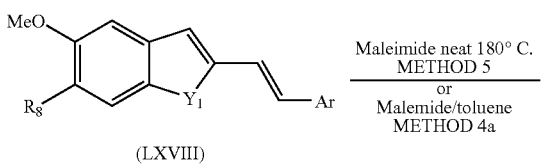

(LXVIII)

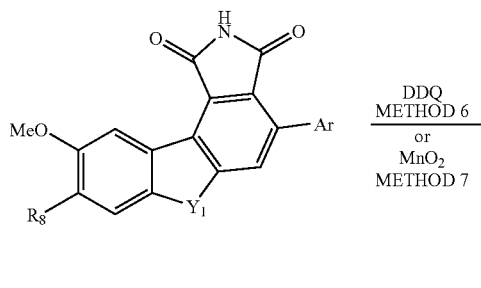

(LXIX)

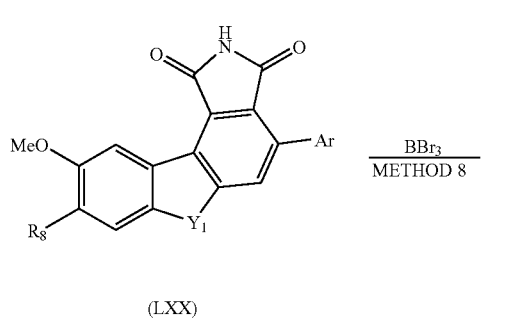

(LXX)

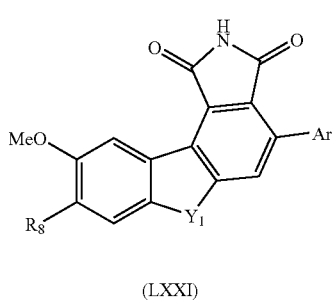

(LXXI)

Procedures for Scheme 14

Representative Procedure for Method 31 of Scheme 14

EXAMPLE 367

The Preparation of 5-Methoxy-2-[(E,Z)-2-phenylethenyl]-1-benzofuran (LXVIII; Ar=phenyl, $R^8$=H, $Y^1$=O) (828)

To a suspension of benzyltriphenylphosphonium bromide (1.85 g, 4.26 mmol) in tetrahydrofuran (30 mL) was added a solution of lithium bis(trimethylsilyl)amide (4 mL of a 1 M solution in tetrahydrofuran, 3.98 mmol), the solution turned a bright orange/red color. The reaction mixture was stirred at room temperature for 30 min and then a solution of 5-methoxy-1-benzofuran-2-carbaldehyde (827) (0.50 g, 2.84 mmol) in tetrahydrofuran (10 mL) was added. After 20 min water was then added and the tetrahydrofuran removed at reduced pressure. The residue was extracted with ethyl acetate (2×50 mL), the combined extracts were dried and concentrated. The residue was purified by column chromatography on silica eluting with dichloromethane to give (828) as a 1:2 mixture of Z- and E-isomers, (0.63 g, 89%), m.p. 124–128° C. Found: C, 81.60; H, 5.61. $C_{17}H_{14}O_2$ requires: C, 81.58, H, 5.64.

EXAMPLE 368

The Preparation of 9-Methoxy-4-phenyl-1H-[1]benzofuro[3,2-e]isoindole-1,3(2H)-dione (LXX; Ar=phenyl, $R^8$=H, $Y^1$=O) (830)

The diene mixture (828) prepared as described in example 367 was reacted with maleimide using the procedure described in example 69 to give the adduct (LXIX; Ar=phenyl, $R^8$=H, $Y^1$=O) (829), which was used without further purification. The crude Diels-Alder adduct was aromatised with $MnO_2$ using the procedure described in example 79 of Scheme 2 to give the dibenzofuran (830) as a yellow solid (53%), mp 271–275° C. $^1$H NMR δ [$(CD_3)_2$SO] 11.41 (br s, 1H), 8.24 (d, J=2.7 Hz, 1H), 7.98 (s, 1H), 7.77 (d, J=9.0 Hz, 1H), 7.67–7.65 (m, 2H), 7.51–7.45 (m, 3H), 7.30 (dd, J=9.0, 2.7 Hz, 1H), 3.91 (s, 3H). Found: C, 72.09; H, 3.84; N, 4.04. $C_{21}H_{13}NO_4.1/3H_2O$ requires: C, 72.20; H, 3.94; N, 4.01.

EXAMPLE 369

The Preparation of 9-Hydroxy-4-phenyl-1H-[1]benzofuro[3,2-e]isoindole-1,3(2H)-dione (LXXI; Ar=phenyl, $R^{10}$=H, $Y^1$=O) (831)

Demethylation of (830) prepared as described in example 368 with $BBr_3$ using the procedure described in example 80 gave (831) as a yellow solid (100%), mp 288–290° C. $^1$H NMR δ [$(CD_3)_2$SO] 11.37 (br s, 1H), 9.74 (s, 1H), 8.13 (d, J=2.6 Hz, 1H), 7.94 (s, 1H), 7.66–7.63 (m, 3H), 7.51–7.44 (m, 3H), 7.11 (dd, J=8.9, 2.6 Hz, 1H). Found: C, 71.17; H, 3.48; N, 4.07. $C_{20}H_{11}NO_4.1/2H_2O$ requires: C, 71.00; H, 3.58; N, 4.14.

EXAMPLE 370

The Preparation of 2-[(E,Z)-2-(2-Chlorophenyl)ethenyl]-5-methoxy-1-benzofuran (LXVIII; Ar=2-chlorophenyl, $R^8$=H, $Y^1$=O) (832)

Reaction of 5-methoxy-1-benzofuran-2-carbaldehyde (827) prepared as described in example with 2-chlorobenzyltriphenylphosphonium bromide using the procedure described in method gave (832) as a 1:2 mixture of Z:E isomers (24%), mp 90–92° C., which was used without further purification.

EXAMPLE 371

The Preparation of 4-(2-Chlorophenyl)-9-methoxy-1H-[1]benzofuro[3,2-e]isoindole-1,3(2H)-dione (LXX; Ar=2-chlorophenyl, $R^8$=H, $Y^1$=O) (834)

The diene mixture (832) prepared as described in example 370 was reacted with maleimide using the procedure described in example 69 to give the adduct (LXIX; Ar=2-chlorophenyl, $R^8$=H, $Y^1$=O) (833), which was used without further purification. The crude Diels-Alder adduct was aromatised with $MnO_2$ using the procedure described in example 79 of Scheme 2 to give the dibenzofuran (834) as a yellow solid (49%), mp 246–248° C. $^1$H NMR δ [$(CD_3)_2$SO] 11.46 (br s, 1H), 8.22 (d, J=2.7 Hz, 1H), 7.99 (s, 1H), 7.80 (d, J=9.0 Hz, 1H), 7.61–7.58 (m, 1H), 7.53–7.44 (m, 3H), 7.33 (dd, J=9.0, 2.7 Hz, 1H), 3.92 (s, 3H). Found: C, 66.53; H, 3.41; N, 3.54. $C_{21}H_{12}ClNO_4$ requires: C, 66.77; H, 3.20; N, 3.71.

EXAMPLE 372

The Preparation of 4-(2-Chlorophenyl)-9-hydroxy-1H-[1]benzofuro[3,2-e]isoindole-1,3(2H)-dione (LXXI; Ar=2-chlorophenyl, $R^8$=H, $Y^1$=O) (835)

Demethylation of (834) prepared as described in example 371 with $BBr_3$ using the procedure described in example 80 gave (835) as a yellow solid (89%), mp 140–145° C. $^1$H NMR δ [$(CD_3)_2$SO] 11.39 (br s, 1H), 9.78 (s, 1H), 8.12 (d, J=2.6 Hz, 1H), 7.93 (s, 1H), 7.66 (d, J=8.9 Hz, 1H), 7.60–7.58 (m, 1H), 7.52–7.43 (m, 3H), 7.13 (dd, J=8.9, 2.6 Hz, 1H); EIMS found M$^+$:363.0294, 365.0269. $C_{20}H_{10}ClNO_4$ requires: 363.0298, 365.0289.

EXAMPLE 373

The Preparation of 2-[(E,Z)-2-(2-Chlorophenyl)ethenyl]-5-methoxy-1-benzothiophene (LXVIII; Ar=2-chlorophenyl, $R^8$=H, $Y^1$=S) (837)

Reaction of 5-methoxy-1-benzothiophene-2-carbaldehyde (836) with 2-chlorobenzyltriphenylphosphonium chloride using the procedure described in example 37 gave the diene (837) as an E/Z mixture (63%). $^1$H NMR δ (CDCl$_3$) Minor isomer: 7.6 (d, 1H), 7.4 (m, 5H), 7.15 (s, 1H), 7.05 (s, 1H), 6.9 (d, 1H), 6.75 (m, 2H), 3.85 (s, 3H). Major isomer: 7.75 (d, J=9 Hz, 1H), 7.55 (m, 2H), 7.25–7.4 (m, 3H), 7.18 (m, 2H), 7.05 (s, 1H), 6.95 (m, 2H).

EXAMPLE 374

The Preparation of 4-(2-Chlorophenyl)-9-methoxy-1H-[1]benzothieno[3,2-e]isoindole-1,3(2H)-dione (LXX; Ar=2-chlorophenyl, $R^8$=H, $Y^1$=S) (839)

Reaction of (837) prepared as described in example 373 with maleimide using the procedure described in method4 except that the reaction time was 6 days gave the adduct (LXIX; Ar=2-chlorophenyl, $R^8$=H, $Y^1$=S) (838) which was used without further purification. Aromatisation of (838) with DDQ using the procedure described in example 70 of Scheme 2 except that the solvent was chloroform, and the reaction conditions were 5 days at 40° C. gave (839) as a yellow solid (44%). $^1$H NMR δ [$(CD_3)_2$SO] 11.46 (s, 1H), 9.37 (d, J=2.5 Hz, 1H), 8.38 (s, 1H), 8.2 (d, J=9 Hz, 1H), 7.62 (m, 2H), 7.48 (m, 3H), 7.31 (dd, J=2.5, 9.0 Hz, 1H), 3.94 (s, 3H).

EXAMPLE 375

The Preparation of 4-(2-Chlorophenyl)-9-hydroxy-1H-[1]benzothieno[3,2-e]isoindole-1,3(2H)-dione (LXXI; Ar=2-chlorophenyl, $R^8$=H, $Y^1$=S) (840).

Demethylation of (839) prepared as described in example 374 with $BBr_3$ using the procedure described in example 80 except that the reaction time was 48 h gave (840) (65%) as a yellow solid, mp 311–313° C. $^1$H NMR δ [$(CD_3)_2$SO] 11.42 (s, 1H), 9.85 (s, 1H), 9.17 (d, J=2.5 Hz, 1H), 8.32 (s, 1H), 7.9 (d, J=9 Hz, 1H), 7.62 (m, 2H), 7.5 (m, 3H), 7.17 (dd, J=2.5, 9 Hz, 1H). MH$^+$346. Found C, 68.75; H, 3.43; N, 3.89; S, 9.35. $C_{20}H_{11}NO_3S.0.2H_2O$ requires: C, 68.83; H, 3.29; N, 4.01; S, 9.19.

EXAMPLE 376

The Preparation of 6-(Benzyloxy)-2-[(E,Z)-2-(chlorophenyl)ethenyl]-5-methoxy-1-benzofuran (LXVIII; $R^8$=OCH$_2$Ph, $Y^1$=O, Ar=2-chlorophenyl) (601)

Reaction of 6-(benzyloxy)-5-methoxy-1-benzofuran-2-carbaldehyde (LXVIII; $Y^1$=O, $R^8$=OCH$_2$Ph) with 2-chlorobenzyltriphenylphosphonium chloride using the procedure described in method 2 with a reaction time of 4 hours gave (601) as a pale yellow solid (83%), mp 130–135° C. $^1$H NMR δ [$(CD_3)_2$SO] 7.88 (d, J=6.4 Hz, 1H), 7.51–7.31 (m, 12H), 7.18 (s, 1H), 6.93 (s, 1H), 5.17 (s, 2H), 3.78 (s, 3H). EIMS found: M$^+$=390.1021. $C_{24}H_{19}ClO_3$ requires 390.1023.

EXAMPLE 377

The Preparation of 8-(Benzyloxy)-4-(2-chlorophenyl)-9-methoxy-1H-[1]benzofuro[3,2-e]isoindole-1,3(2H)-dione (LXX; $R^8$=OCH$_2$PH, $Y^1$=O, Ar=2-chlorophenyl) (603)

Compound (602) (LXIX; $R^8$=OCH$_2$Ph, $Y^1$=O, Ar=2-chlorophenyl) was prepared from (601) using the procedure described in method 4a using xylene as the solvent to give a brown solid which was used without further purification. The crude Diels-Alder adduct was aromatised with $MnO_2$ using the procedure described in example 79, to give (603) as a bright yellow solid (24%), mp 296–300° C. $^1$H NMR δ [$(CD_3)_2$SO] 11.38 (s, 1H), 8.17 (s, 1H), 7.94 (s, 1H), 7.67 (s, 1H), 7.58–7.36 (m, 13H), 5.28 (s, 2H), 3.93 (s, 3H). EIMS found: M$^+$=483.0871. $C_{28}H_{18}ClNO_5$ requires 483.0873.

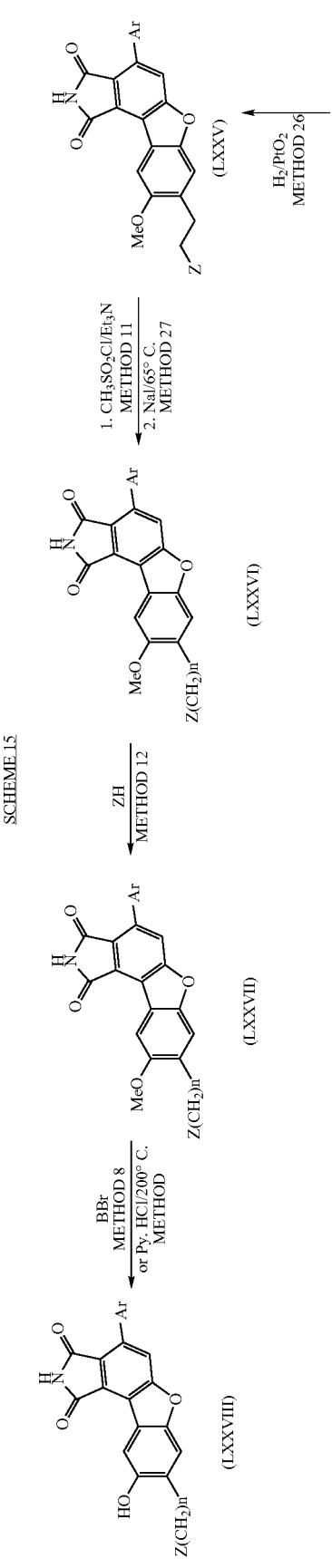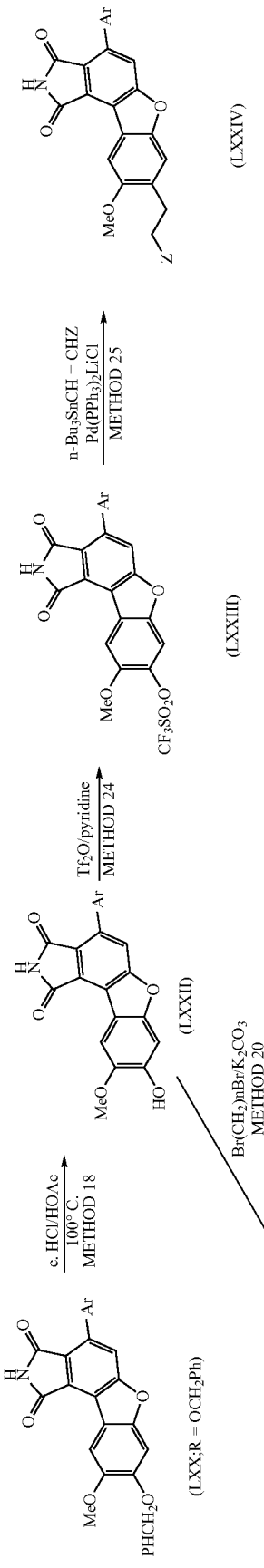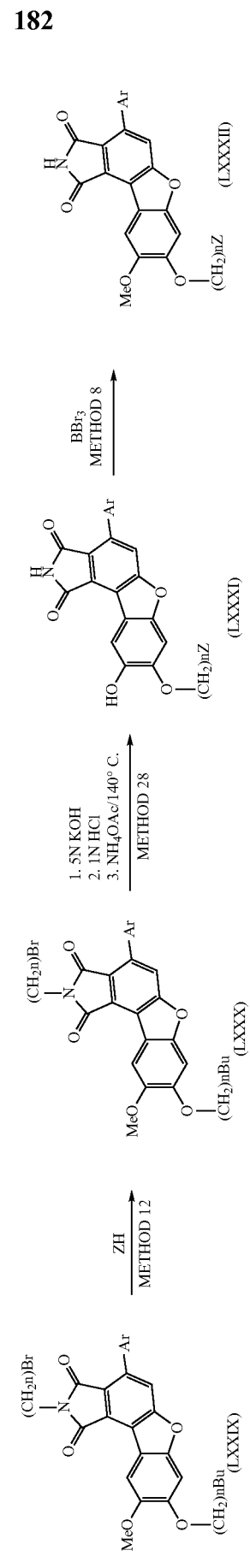
SCHEME 15

Scheme 15 Procedures

EXAMPLE 378

The Preparation of 4-(2-Chlorophenyl)-8-hydroxy-9-methoxy-1H-[1]benzofuro[3,-e]isoindole-1,3(H)-dione (LXXII; Ar=2-chlorophenyl) (604)

Removal of the benzyl ether group of (603) prepared as described in example 377 using the procedure described in example 260 gave (604) as a yellow solid (86%), mp 294–298° C. $^1$H NMR δ [(CD$_3$)$_2$SO] 11.34 (s, 1H), 10.40 (s, 1H), 8.12 (s, 1H), 7.87 (s, 1H), 7.59–7.30 (m, 4H), 7.23 (s, 1H), 3.96 (s, 3H). EIMS found: M$^+$=393.0400. C$_{21}$H$_{12}$ClNO$_5$ requires 393.0404.

EXAMPLE 379

The Preparation of 4-(2-Chlorophenyl)-9-hydroxy-1,3-dioxo-2,3-dihydro-1H-[1]benzofuro[3,2-e]isoindol-8-yl trifluoromethanesulfonate (LXXIII; Ar=2-chlorophenyl) (605)

Compound (605) was prepared from (604) using the procedure described in example 307 as a pale brown solid (88%), mp 237–240° C. $^1$H NMR δ [(CD$_3$)$_2$SO] 11.55 (s, 1H), 8.47 (s, 1H), 8.29 (s, 1H), 8.11 (s, 1H), 7.62–7.45 (m, 4H), 4.07 (s, 3H). FABMS found: [M+H]$^+$=525.9958, 527.9940. C$_{22}$H$_{12}$ClF$_3$NSO$_7$ requires 525.9975, 527.9946.

EXAMPLE 380

The Preparation of 4-(2-Chlorophenyl)-8-ethyl-9-methoxy-1H-[1]benzofuro[3,2-e]isoindole-1,3(2H)-dione (LXXV; Z=H, Ar=2-chlorophenyl) (606)

Compound 606 was prepared from (605) prepared as described in example 379 using the procedure described in example 309 and tetraethyl tin as the stannane, as a yellow solid (87%), mp 252–257° C. $^1$H NMR δ [(CD$_3$)$_2$SO] 11.45–11.15 (br, 1H), 8.16 (s, 1H), 7.91 (s, 1H), 7.60–7.56 (m, 1H), 7.54 (s, 1H), 7.52–7.41 (m, 3H), 4.23 (s, 3H), 3.92 (m, 2H), 2.16–2.09 (m, 3H). EIMS found: M$^+$=405.0766. C$_{23}$H$_{16}$ClNO$_4$ requires 405.0768.

EXAMPLE 381

The Preparation of 4-(2-Chlorophenyl)-8-ethyl-9-hydroxy-1H-[1]benzofuro[3,2-e]isoindole-1,3(2H)-dione (LXXVIII; n=2, Z=H, Ar=2-chlorophenyl) (607)

Demethylation of (606) prepared as described in example 380 via The procedure described in example 80 gave (607) as a yellow solid (32%), mp 265–268° C. $^1$H NMR δ [(CD$_3$)$_2$SO] 8.13 (s, 1H), 7.68 (s, 1H), 7.57–7.52 (m, 3H), 7.44–7.31 (m, 4H), 2.85 (q, J=7.6 Hz, 2H), 1.35 (t, J=7.6 Hz, 3H). EIMS found: M$^+$=391.0612. C$_{22}$H$_{14}$ClNO$_4$ requires 391.0611.

EXAMPLE 382

The Preparation of 4-(2-Chlorophenyl)-8-[(1E)-4-hydroxy-1-butenyl]-9-methoxy-1H-[1]benzofuro[3,2-e]isoindole-1,3(2H)-dione (LXXIV; Z=CH$_2$CH$_2$OH, Ar=2-chlorophenyl) (608)

Compound 608 was prepared from triflate (605) prepared as described in example 379 using the procedure described in example 309 and (3E)-4-(tributylstannyl)-3-buten-1-ol as the stannane as a yellow solid (84%), mp 247–250° C. $^1$H NMR δ [(CD$_3$)$_2$SO] 11.43 (s, 1H), 8.23 (s 1H), 7.92 (s, 1H), 7.86 (s, 1H), 7.58 (d, J=6.5 Hz, 1H), 7.48–7.42 (m, 3H), 6.85 (d, J=16.0 Hz, 1H), 6.53 (m, 1H), 4.35 (br, 1H), 3.97 (s, 3H), 3.57 (t, J=6.6 Hz, 2H), 2.41 (m, 2H). EIMS found: M$^+$=447.0886. C$_{25}$H$_{18}$ClNO$_5$ requires 447.0873.

EXAMPLE 383

The Preparation of 4-(2-Chlorophenyl)-8-(4-hydroxybutyl)-9-methoxy-1H-[1]benzofuro[3,2-e]isoindole-1,3(2H)-dione (LXXV; Z=CH$_2$CH$_2$OH, Ar=2-chlorophenyl) (609)

Hydrogenation of (608) prepared as described in example 382 using the procedure described in example 310 gave (609) as a yellow solid (96%), mp 158–162° C. $^1$H NMR δ [(CD$_3$)$_2$SO] 11.40 (s, 1H), 8.29 (s, 1H), 7.71 (s, 1H), 7.60 (s, 1H), 7.56–7.39 (m, 4H), 4.36 (br, 1H), 3.95 (s, 3H), 3.39 (m, 2H), 2.75 (t, J=7.6 Hz, 2H), 1.65 (m, 2H), 1.51 (m, 2H). FABMS found: [M+H]$^+$=450.1083, 452.1078. C$_{25}$H$_{21}$ClNO$_5$ requires 450.1108, 452.1079.

EXAMPLE 384

The Preparation of 4-(2-Chlorophenyl)-9-hydroxy-8-(4-hydroxybutyl)-1H-[1]benzofuro[3,2-e]isoindole-1,3(2H)-dione (LXXVIII; n=4, Z=OH, Ar=2-chlorophenyl) (610)

Demethylation of (609) prepared as described in example 383 using the procedure described in example 80 gave (610) as a yellow solid (38%), mp 256–259° C. $^1$H NMR δ [(CD$_3$)$_2$SO] 11.40 (br, 1H), 9.80 (s, 1H), 8.13 (s, 1H), 7.90 (s, 1H), 7.60–7.56 (m, 1H), 7.54 (s, 1H), 7.52–7.42 (m, 3H), 4.38 (s, 1H), 3.44 (m, 2H), 2.72 (t, J=7.4 Hz, 2H), 1.66 (m, 2H), 1.50 (m, 2H). FABMS found: [M+H]$^+$=436.0942, 483.0922. C$_{24}$H$_{19}$ClNO$_5$ requires 436.0952, 438.0915.

EXAMPLE 385

The Preparation of 8-(3-Bromopropoxy)-2-(3-bromopropyl)-4-(2-chlorophenyl)-9-methoxy-1H-[1]benzofuro[3,2-e]isoindole-1,3(2H)-dione (LXXIX; Ar=2-chlorophenyl, n=3) (331)

Reaction of phenol (604) (245 mg, 0.62 mmol) prepared as described in example 378 with 1,3-dibromopropane (excess, 3.0 mL) according to the procedure described in example 298, except that the reaction was performed in refluxing acetone (80 mL), gave dibromide (331) (300 mg, 76%) as a yellow powder, mp 180–182° C. $^1$H NMR δ [(CD$_3$)$_2$SO] 8.16 (s, 1H), 7.96 (s, 1H), 7.60 (m, 2H), 7.53–7.44 (m, 3H), 4.26 (t, J=6.0 Hz, 2H), 3.95 (s, 3H), 3.72 (t, J=6.4 Hz, 4H), 3.57 (t, J=6.6 Hz, 2H), 2.35 (m, 2H), 2.17 (m, 2H). Found: C, 51.25; H, 3.52; N, 2.37. C$_{27}$H$_{22}$Br$_2$ClNO$_5$ requires: C, 51.01; H, 3.49; N, 2.20.

EXAMPLE 386

The Preparation of 4-(2-Chlorophenyl)-8-[3-(dimethylamino)propoxy]-9-methoxy-1H-[1]benzofuro[3,2-e]isoindole-1,3(2H)-dione (LXXXI; Ar=2-chlorophenyl, n=3, Z=N(CH$_3$)$_2$) (332)

Reaction of dibromide (331) (100 mg, 0.16 mmol) prepared as described in example 385 with aqueous dimethylamine solution (40%, 5.0 mL) according to The procedure described in example 179, except that the reaction was performed in tetrahydrofuran (50 mL) at room temperature for 30 hours, gave the crude diamine (LXXX; Ar=2-chlorophenyl, n=3, Z=N(CH$_3$)$_2$), which was used without further purification as a tetrahydrofuran solution. To this solution was added 5N potassium hydroxide (2.5 mL), then the procedure outlined in example 328 was followed except that the HCl treatment was for 24 hours and the chromatography was performed eluting with methanol/dichloromethane/concentrated ammonia (15:85:trace). Trituration from ethyl acetate gave amine (332) (64 mg, 84%) as a yellow powder, mp 251–253° C. $^1$H NMR δ [(CD$_3$)$_2$SO] 11.37 (br s, 1H), 8.15 (s, 1H), 7.93 (s, 1H), 7.59 (m, 1H), 7.55 (s, 1H), 7.52–7.43 (m, 3H), 4.18 (t, J=6.4 Hz, 2H), 3.93 (s, 3H), ~2.5 (obscured m, 2H), 2.23 (br s, 6H), 1.96 (m, 2H). Found: C, 65.03; H, 4.79; N, 6.00. C$_{26}$H$_{23}$ClN$_2$O$_5$ requires: C, 65.21; H, 4.84; N, 5.85.

EXAMPLE 387

The Preparation of 4-(2-Chlorophenyl)-9-methoxy-8-[3-(1-pyrrolidinyl)propoxy]-1H-[1]benzofuro[3,2-e]isoindole-1,3(2H)-dione (LXXXI; Ar-2-chlorophenyl, n=3, Z=1-pyrrolidinyl) (333)

Reaction of dibromide (331) (110 mg, 0.17 mmol) prepared as described in example 385 with pyrrolidine (361 uL, 4.33 mmol) according to The procedure described in example 179, except that the reaction was performed in tetrahydrofuran (50 mL) at room temperature for 3 days, gave the crude diamine (LXXX; Ar=2-chlorophenyl, n=3, Z=1-pyrrolidinyl), which was used without further purification as a tetrahydrofuran solution. To this solution was added 5N potassium hydroxide (2.5 mL), then the procedure outlined in example 328 was followed except that the HCl treatment was for 24 hours and the chromatography was performed eluting with methanol/dichloromethane/concentrated ammonia (15:85:trace). Crystallisation from ethyl acetate/hexane, gave amine (333) (51 mg, 59%) as a yellow powder, mp 252–255° C. $^1$H NMR δ [(CD$_3$)$_2$SO] 11.35 (br s, 1H), 8.15 (s, 1H), 7.91 (s, 1H), 7.58 (m, 1H), 7.54 (s, 1H), 7.52–7.43 (m, 3H), 4.19 (t, J=6.4 Hz, 2H), 3.93 (s, 3H), 2.57 (t, J=7.1 Hz, 2H), 2.46 (m, 4H), 1.97 (m, 2H), 1.69 (m, 4H). Found: C, 66.46; H, 5.15; N, 5.43. C$_{28}$H$_{25}$ClN$_2$O$_5$ requires C, 66.60; H, 4.99; N, 5.55.

EXAMPLE 388

The Preparation of 4-(2-Chlorophenyl)-8-[3-(dimethylamino)propoxy]-9-hydroxy-1H-[1]benzofuro[3,2-e]isoindole-1,3(2H)-dione (LXXXII; Ar=2-chlorophenyl, n=3, Z=N(CH$_3$)$_2$) (334)

Demethylation of amine (332) (70 mg, 0.15 mmol) prepared as described in example 386 according to the procedure described in example 80, except that the reaction was performed at 0° C. for 8 hours and the chromatography was performed eluting with methanol/dichloromethane/triethylamine (15:85:trace), gave amine (334) (48 mg, 71%) as a yellow powder, which was converted to the hydrochloride salt, mp 255–258° C. $^1$H NMR δ [(CD$_3$)$_2$SO] 11.34 (br s, 1H), 9.96 (br s, 1H), 9.44 (br s, 1H), 8.10 (s, 1H), 7.91 (s, 1H), 7.58 (m, 1H), 7.51–7.43 (m, 4H), 4.23 (t, J=5.9 Hz, 2H), ~3.3 (obscured m, 2H), 2.81 (s, 6H), 2.21 (m, 2H). Found: C, 58.86; H, 4.68; N, 5.35. C$_{25}$H$_{21}$ClN$_2$O$_5$·HCl·1/2H$_2$O requires: C, 58.84; H, 4.54; N, 5.49.

EXAMPLE 389

The Preparation of 4-(2-Chlorophenyl)-9-hydroxy-8-[3-(1-pyrrolidinyl)propoxy]-1H-[1]benzofuro[3,2-e]isoindole-1,3(2H)-dione (LXXXII; Ar=2-chlorophenyl, n=3. Z=1-pyrrolidinyl) (335)

Demethylation of amine (333) (50 mg, 0.10 mmol) prepared as described in example 387 according to the procedure described in example 80, except that the reaction was performed at 0° C. for 6 hours and the chromatography was performed eluting with methanol/dichloromethane/triethylamine (15:85:trace), gave amine (335) (mg, %) as a yellow powder, which was converted to the hydrochloride salt, mp 302–304° C. $^1$H NMR δ [(CD$_3$)$_2$SO] 11.34 (s, 1H), 9.99 (br, 1H), 9.47 (br, 1H), 8.10 (s, 1H), 7.90 (s, 1H), 7.58 (m, 1H), 7.51 (s, 1H), 7.52–7.42 (m, 3H), 4.24 (t, J=5.7 Hz, 2H), 3.6 (br, 2H), 3.03 (br, 2H), 2.22 (m, 2H), 2.08–1.81 (m, 6H). Found: C, 61.18; H, 4.56; N, 5.16. C$_{27}$H$_{23}$ClN$_2$O$_5$·HCl requires C, 61.49; H, 4.59; N, 5.31.

SCHEME 16
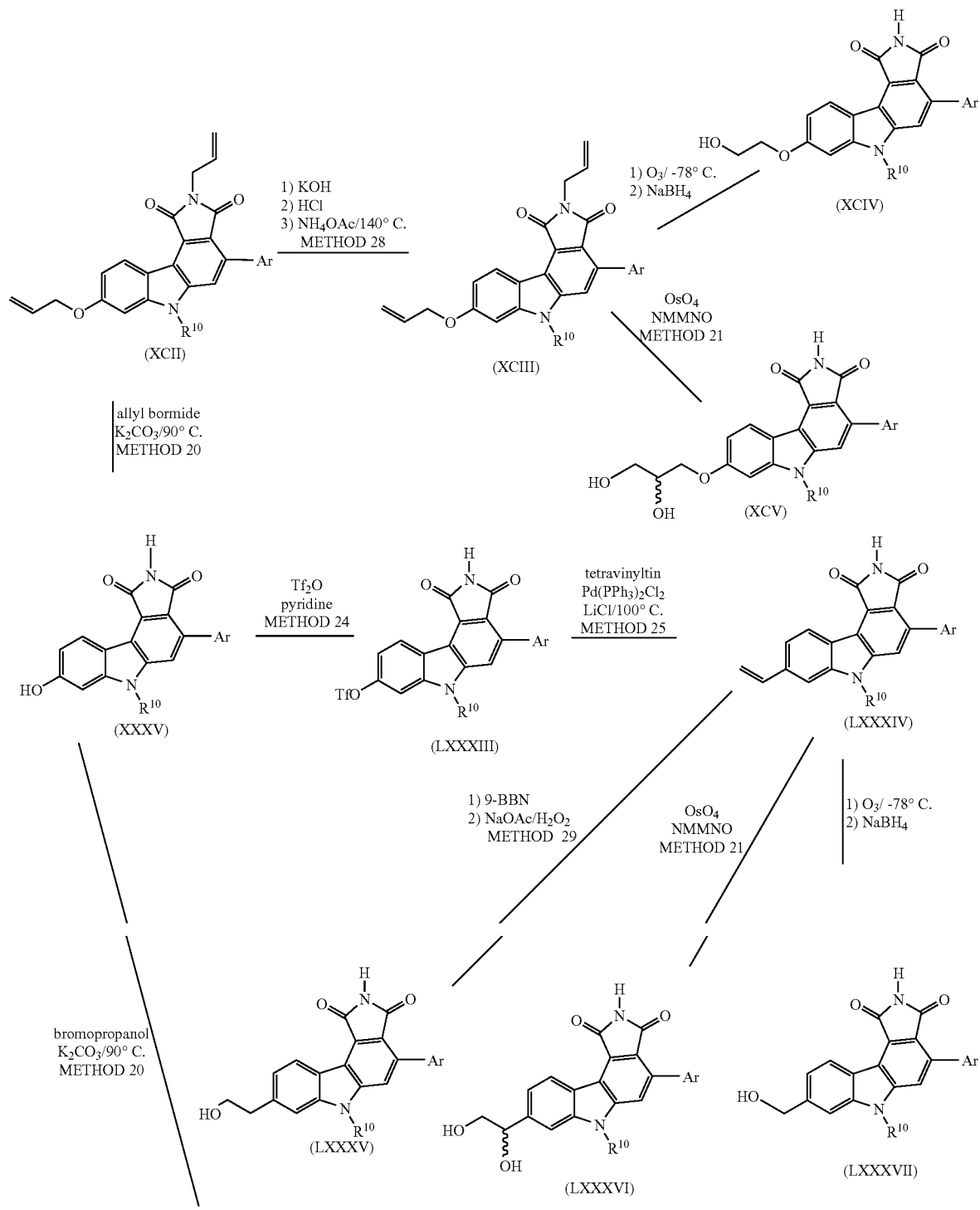

-continued

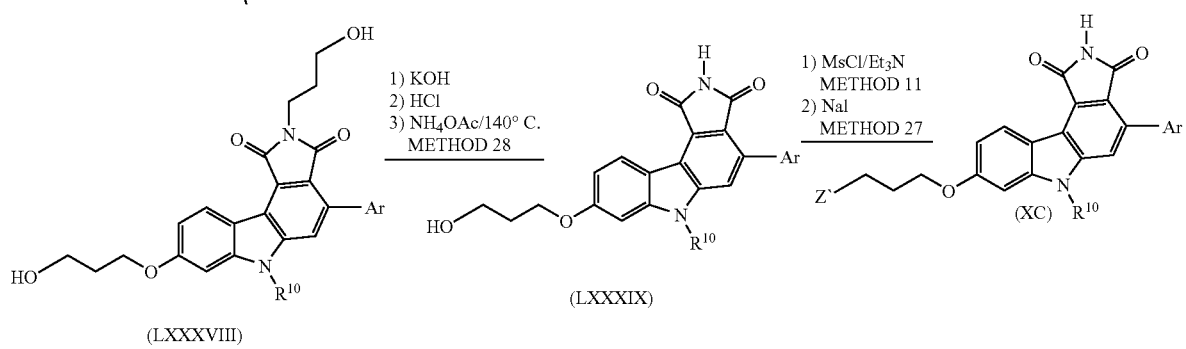

Scheme 16 Procedures

EXAMPLE 390

The Preparation of 4-(2-Chlorophenyl)-6-methyl-1,3-dioxo-1,2,3,6-tetrahydropyrrolo[3,4-c]carbazol-8-yl trifluoromethanesulfonate (LXXXIII; Ar=2-chlorophenyl, $R^{10}$=CH$_3$) (316)

Reaction of phenol (845) (0.25 g, 0.66 mmol) prepared as described in example 280 according to the procedure described in example 307 gave triflate (316) (323 mg, 96%) as a pale yellow solid, mp 230–233° C. $^1$H NMR δ [(CD$_3$)$_2$SO] 11.26 (br s, 1H), 9.04 (d, J=8.7 Hz, 1H), 8.03 (d, J=2.3 Hz, 1H), 7.94 (s, 1H), 7.59 (m, 1H), 7.50 (m, 4H), 4.04 (s, 3H). Found: C, 51.98; H, 2.29; N, 5.41. C$_{22}$H$_{12}$ClF$_3$N$_2$O$_5$S requires C, 51.93; H, 2.38; N, 5.51.

EXAMPLE 391

The Preparation of 4-(2-Chlorophenyl)-6-methyl-8-vinylpyrrolo[3,4-c]carbazole-1,3(2H,6H)-dione (LXXXIV; Ar=2-chlorophenyl, $R^{10}$=CH$_3$) (317)

Reaction of triflate (316) (0.32 g, 0.63 mmol) prepared as described in example 390 with tetravinyltin (172 □L, 0.94 mmol) according to the procedure described in example 309 gave alkene (317) (193 mg, 79%) as a pale yellow solid, mp 276–282° C. $^1$H NMR δ [(CD$_3$)$_2$SO] 11.13 (br s, 1H), 8.86 (d, J=8.2 Hz, 1H), 7.84 (m, 2H), 7.60–7.46 (m, 5H), 6.98 (dd, J=17.6, 10.9 Hz, 1H), 6.09 (d, J=17.6 Hz, 1H), 5.42 (d, J=10.9 Hz, 1H), 4.00 (s, 3H). Found: C, 69.64; H, 4.03; N, 6.88. C$_{23}$H$_{15}$ClN$_2$O$_2$.1/2H$_2$O requires: C, 69.79; H, 4.07; N, 7.08.

EXAMPLE 392

The Preparation of 4-(2-Chlorophenyl)-8-(2-hydroxyethyl)-6-methylpyrrolo[3,4-c]carbazole-1,3(2H,6H)-dione (LXXXV; Ar=2-chlorophenyl, $R^{10}$=CH$_3$) (318)

Reaction of alkene (317) (60 mg, 0.16 mmol) prepared as described in example 391 according to to the procedure described in example 344 gave alcohol (318) (36 mg, 57%) as a pale yellow solid, mp 289–292° C. $^1$H NMR δ [(CD$_3$)$_2$SO] 11.10 (br s, 1H), 8.81 (d, J=8.1 Hz, 1H), 7.82 (s, 1H), 7.58 (m, 2H), 7.49 (m, 3H), 7.27 (d, J=8.1 Hz, 1H), 4.73 (t, J=5.2 Hz, 1H), 3.97 (s, 3H), 3.75 (m, 2H), 2.99 (t, J=7.0 Hz, 2H). Found: C, 67.47; H, 4.37; N, 6.51. C$_{23}$H$_{17}$ClN$_2$O$_3$.1/4H$_2$O requires: C, 67.49; H, 4.31; N, 6.84.

EXAMPLE 393

The Preparation of 4-(2-Chlorophenyl)-8-(1,2-dihydroxyethyl)-6-methylpyrrolo[3,4-c]carbazole-1,3(2H,6H)-dione (LXXXVI; Ar=2-chlorophenyl, $R^{10}$=CH$_3$) (319)

Reaction of alkene (317) (50 mg, 0.13 mmol) prepared as described in example 391 according to the procedure described in example 300 gave diol (319) (40 mg, 74%) as a pale yellow solid, mp 252–255° C. $^1$H NMR δ [(CD$_3$)$_2$SO] 11.11 (br s, 1H), 8.84 (d, J=8.2 Hz, 1H), 7.84 (s, 1H), 7.71 (br s, 1H), 7.58 (m, 1H), 7.49 (m, 3H), 7.39 (br d, J=8.2 Hz, 1H), 5.46 (d, J=4.2 Hz, 1H), 4.79 (m, 2H), 3.98 (s, 3H), 3.57 (m, 2H). Found: C, 65.72; H, 4.50; N, 6.32. C$_{23}$H$_{17}$ClN$_2$O$_4$ requires: C, 65.64; H, 4.07; N, 6.66.

EXAMPLE 394

The Preparation of 4-(2-Chlorophenyl)-8-(hydroxymethyl)-6-methylpyrrolo[3,4-c]carbazole-1,3(2H,6H)-dione (LXXXVII; Ar=2-chlorophenyl, $R^{10}$=CH$_3$) (320)

Ozone was bubbled through a solution of alkene (317) (60 mg, 0.16 mmol) prepared as described in example 391 in methanol/dichloromethane (1:1, 40 mL) at −78° C. for 10 minutes, by which time the solution had gone from yellow to yellow/green. Excess ozone was purged from the solution by bubbling nitrogen through it for 2 minutes and then a solution of sodium borohydride (180 mg, 4.76 mmol) in methanol (20 mL) was added. The resulting solution was allowed to warm to room temperature over 20 minutes and then it was diluted with water and extraction with ethyl acetate. The organic phase was dried, the drying agent was removed and the solution was concentrated to dryness. Chromatography on silica eluting with ethyl acetate/hexane (3:1 to 1:0), followed by crystallization from ethyl acetate/hexane, gave alcohol (320) (39 mg, 62%) as a pale yellow solid, mp 291–294° C. $^1$H NMR δ [(CD$_3$)$_2$SO] 11.11 (br s, 1H), 8.85 (d, J=8.1 Hz, 1H), 7.84 (s, 1H), 7.70 (br s, 1H), 7.58 (m, 1H), 7.49 (m, 3H), 7.35 (br d, J=8.1 Hz, 1H), 5.42 (t, J=5.6 Hz, 1H), 4.77 (d, J=5.6 Hz, 2H), 3.98 (s, 3H). Found: C, 67.74; H, 4.11; N, 7.13. C$_{22}$H$_{15}$ClN$_2$O$_3$ requires: C, 67.61; H, 3.87; N, 7.17.

EXAMPLE 395

The Preparation of 4-(2-Chlorophenyl)-8-(3-hydroxypropoxy)-2-(3-hydroxypropyl)-6-methylpyrrolo[3,4-c]carbazole-1,3(2H,6H)-dione (LXXXVIII; Ar=2-chlorophenyl, $R^{10}$=$CH_3$)

(321)

Reaction of phenol (845) (0.53 g, 1.41 mmol) prepared as described in example 280 with 3-bromopropan-1-ol (280 □L, 3.10 mmol) according to the procedure described in example 298 gave diol (321) (0.29 g, 42%) as a yellow powder, mp 136–140° C. $^1$H NMR δ [$(CD_3)_2SO$] 8.77 (d, J=8.7 Hz, 1H), 7.76 (s, 1H), 7.58 (m, 1H), 7.49 (m, 3H), 7.28 (d, J=2.0 Hz, 1H), 7.00 (dd, J=8.7, 2.0 Hz, 1H), 4.61 (t, J=5.1 Hz, 1H), 4.49 (t, J=5.0 Hz, 1H), 4.24 (t, J=6.3 Hz, 2H), 3.94 (s, 3H), 3.63 (m, 4H), 3.43 (m, 2H), 1.96 (m, 2H), 1.75 (m, 2H). Found: C, 64.91; H, 5.13; N, 5.63. $C_{27}H_{25}ClN_2O_4 \cdot 1/4H_2O$ requires C, 65.19; H, 5.17; N, 5.63.

EXAMPLE 396

The Preparation of 4-(2-Chlorophenyl)-8-(3-hydroxypropoxy)-6-methylpyrrolo[3,4-c]carbazole-1,3(2H,6H)-dione (LXXXIX; Ar=2-chlorophenyl, $R^{10}$=$CH_3$) (322)

Reaction of diol (321) (270 mg, 0.55 mmol) prepared as described in example 395 according to the proceedure described example 328, except that ethanol was used instead of acetonitrile and the HCl treatment was for 18 hours, gave crude material that was dissolved in methanol/dichloromethane (4:1, 80 mL), to which 1M potassium carbonate (2.0 mL) was added (to hydrolyse a small amount of acetate present by tlc). The resulting solution was stirred at room temperature for 2 hours before being diluted with water and extraction with ethyl acetate. The organic phase was dried, the drying agent was removed and the solution was concentrated to dryness. Chromatography on silica eluting with ethyl acetate/hexane (2:1), followed by crystallization from ethyl acetate/hexane, gave alcohol (322) (136 mg, 57%) as a yellow solid, mp 274–276° C. $^1$H NMR δ [$(CD_3)_2SO$] 11.06 (br s, 1H), 8.75 (d, J=8.7 Hz, 1H), 7.75 (s, 1H), 7.57 (m, 1H), 7.48 (m, 3H), 7.27 (d, J=2.1 Hz, 1H), 7.00 (dd, J=8.7, 2.1 Hz, 1H), 4.61 (t, J=4.9 Hz, 1H), 4.24 (t, J=6.3 Hz, 2H), 3.94 (s, 3H), 3.63 (m, 2H), 1.96 (m, 2H). Found: C, 66.01; H, 4.41; N, 6.41. $C_{24}H_{19}ClN_2O_4$ requires C, 66.29; H, 4.40; N, 6.44.

EXAMPLE 397

The Preparation of 4-(2-Chlorophenyl)-8-(3-iodopropoxy)-6-methylpyrrolo[3,4-c]carbazole-1,3(2H,6H)-dione (XC; Ar=2-chlorophenyl, $R^{10}$=$CH_3$) (323)

Reaction of alcohol (322) (82 mg, 0.19 mmol) prepared as described in example 396 according to the proceedure described in example 170 followed using the procedure described in method27, gave after chromatography on silica eluting with ethyl acetate/hexane (2:1), iodide (323) (92 mg, 89%) as a yellow solid, mp 264–266° C. $^1$H NMR δ [$(CD_3)_2SO$] 11.07 (br s, 1H), 8.77 (d, J=8.7 Hz, 1H), 7.76 (s, 1H), 7.58 (m, 1H), 7.47 (m, 3H), 7.31 (d, J=2.1 Hz, 1H), 7.02 (dd, J=8.7, 2.1 Hz, 1H), 4.23 (t, J=6.0 Hz, 2H), 3.95 (s, 3H), 3.46 (t, J=6.7 Hz, 2H), 2.30 (m, 2H). Found: C, 53.30; H, 3.27; N, 5.08. $C_{24}H_{18}ClIN_2O_3$ requires: C, 52.91; H, 3.33; N, 5.14.

EXAMPLE 398

The Preparation of 4-(2-Chlorophenyl)-8-[3-(dimethylamino)propoxy]-6-methylpyrrolo[3,4-c]carbazole-1,3(2H,6H)-dione (XCI: Ar=2-chlorophenyl, $R^{10}$=$CH_3$, Z=$N(CH_3)_2$) (324)

Reaction of iodide (323) (50 mg, 0.09 mmol) prepared as described in example 397 with dimethylamine according to the procedure described in example 179, except that the reaction was performed at room temperature for 2 hours and the chromatography was performed on alumina (grade II–III) eluting with ethyl acetate/methanol (1:0 to 9:1) gave amine (324) as a yellow powder, which was crystallized as the hydrochloride salt (43 mg, 96%) from methanol/diethyl ether/hexane, mp 262–265° C. $^1$H NMR □[$(CD_3)_2SO$] 11.08 (br s, 1H), 10.0 (br s, 1H), 8.78 (d, J=8.7 Hz, 1H), 7.78 (s, 1H), 7.58 (m, 1H), 7.48 (m, 3H), 7.29 (d, J=2.1 Hz, 1H), 7.02 (dd, J=8.7, 2.1 Hz, 1H), 4.26 (t, J=6.0 Hz, 2H), 3.96 (s, 3H), 3.28 (partially obscured m, 2H), 2.82 (s, 6H), 2.22 (m, 2H). Found: C, 59.62; H, 5.01; N, 8.02. $C_{26}H_{24}ClN_3O_3 \cdot HCl \cdot 1.5H_2O$ requires: C, 59.43; H, 5.37; N, 8.00.

EXAMPLE 399

The Preparation of 4-(2-Chlorophenyl)-6-methyl-8-[3-(methylamino)propoxy]pyrrolo[3,4-c]carbazole-1,3(2H,6H)-dione (XCI: Ar=2-chlorophenyl, $R^{10}$=$CH_3$, Z=$NHCH_3$) (325)

Reaction of iodide (323) (17 mg, 0.03 mmol) prepared as described in example 397 with aqueous methylamine solution (40%, 54 uL) according to The procedure described in example 179, except that the reaction was performed at room temperature in tetrahydrofuran for 20 hours, gave amine (325) (6 mg, 43%) as a yellow powder, mp 269–271° C. $^1$H NMR δ [$(CD_3)_2SO$] 8.75 (d, J=8.7 Hz, 1H), 7.76 (s, 1H), 7.57 (m, 1H), 7.47 (m, 3H), 7.27 (d, J=2.1 Hz, 1H), 8.99 (dd, J=8.7, 2.1 Hz, 1H), 4.22 (t, J=6.4 Hz, 2H), 3.94 (s, 3H), 2.67 (t, J=6.7 Hz, 2H), 2.32 (s, 3H), 1.94 (m, 2H). FABMS found: [M+H]+=448.1447, 450.1428. $C_{25}H_{22}ClN_3O_3$ requires 448.1428, 450.1398.

EXAMPLE 400

The Preparation of 4-(2-Chlorophenyl)-8-[3-(cis-3,5-dimethyl-1-piperazinyl)propoxy]-6-methylpyrrolo[3,4-c]carbazole-1,3(2H,6H)-dione (XCI; Ar=2-chlorophenyl, $R^{10}$=$CH_3$, Z=cis-3,5-dimethyl-1-piperazinyl) (326)

Reaction of iodide (323) (17 mg, 0.03 mmol) prepared as described in example 397 with cis-2,6-dimethylpiperazine (71 mg, 0.62 mmol) according to The procedure described in example 179, except that the reaction was performed at room temperature in tetrahydrofuran for 20 hours and the chromatography was performed on alumina (grade II–III) eluting with ethyl acetate/methanol (1:0 to 9:1), gave amine (326) (15 mg, 91%) as a yellow powder, mp 225–227°C. $^1$H NMR δ [$(CD_3)_2SO$] 11.06 (br s, 1H), 8.75 (d, J=8.7 Hz, 1H), 7.76 (s, 1H), 7.57 (m, 1H), 7.47 (m, 3H), 7.25 (d, J=2.1 Hz, 1H), 8.99 (dd, J=8.7, 2.1 Hz, 1H), 4.19 (t, J=6.3 Hz, 2H), 3.94 (s, 3H), 2.73 (m, 4H), 2.44 (t, J=7.1 Hz, 2H), 1.96 (m, 2H), 1.46 (t, J=10.6 Hz, 2H), 0.92 (d, J=6.2 Hz, 6H). FABMS found: [M+H]+=531.2166, 533.2162. $C_{30}H_{31}ClN_4O_3$ requires 531.2163, 533.2133.

EXAMPLE 401

The Preparation of 8-(Allyloxy)-4-(2-chlorophenyl)-6-methylpyrrolo[3,4-c]carbazole-1,3(2H,6H)-dione (XCIII; Ar=2-chlorophenyl, $R^{10}$=CH$_3$) (327)

Reaction of phenol (845) (250 mg, 0.66 mmol) prepared as described in example 280 with allyl bromide according to the procedure described in example 298 gave the bis-allyl derivative (XCII; Ar=2-chlorophenyl, R=CH$_3$), which was used without further purification. Reaction of the crude material according to the proceedure described example 328 gave alkene (327) (216 mg, 79%) as a yellow powder, mp 253–256° C. $^1$H NMR □ [(CD$_3$)$_2$SO] 11.07 (br s, 1H), 8.77 (d, J=8.7 Hz, 1H), 7.76 (s, 1H), 7.57 (m, 1H), 7.47 (m, 3H), 7.30 (d, J=2.2 Hz, 1H), 7.03 (dd, J=8.7, 2.2 Hz, 1H), 6.20–6.11 (m, 1H), 5.51 (m, 1H), 5.33 (m, 1H), 4.77 (m, 2H), 3.92 (s, 3H). Found: C, 69.42; H, 4.27; N, 6.50. C$_{24}$H$_{17}$ClN$_2$O$_3$ requires: C, 69.15; H, 4.11; N, 6.72.

EXAMPLE 402

The Preparation of 4-(2-Chlorophenyl)-8-(2-hydroxyethoxy)-6-methylpyrrolo[3,4-c]carbazole-1,3 (2H,6H)-dione (XCIV; Ar=2-chlorophenyl. $R^{10}$=CH$_3$) (328)

Ozone was bubbled through a solution of alkene (327) (50 mg, 0.12 mmol) prepared as described in example 401 in methanol/dichloromethane (1:1, 40 mL) at −78° C. for 10 minutes, by which time the solution had gone from yellow to yellow/green. Excess ozone was purged from the solution by bubbling nitrogen through it for 2 minutes and then a solution of sodium borohydride (136 mg, 3.60 mmol) in methanol (20 mL) was added. The resulting solution was allowed to warm to room temperature over 45 minutes and then it was diluted with water and extraction with ethyl acetate. The organic phase was dried, the drying agent was removed and the solution was concentrated to dryness. Chromatography on silica eluting with ethyl acetate/hexane (1:1 to 3:1), followed by trituration from diethyl ether, gave alcohol (328) (11 mg, 22%) as a yellow solid, mp 309–312° C. $^1$H NMR δ [(CD$_3$)$_2$SO] 11.06 (br s, 1H), 8.77 (d, J=8.7 Hz, 1H), 7.75 (s, 1H), 7.57 (m, 1H), 7.47 (m, 3H), 7.28 (d, J=2.0 Hz, 1H), 7.01 (dd, J=8.7, 2.0 Hz, 1H), 4.94 (t, J=5.4 Hz, 1H), 4.19 (t, J=5.1 Hz, 2H), 3.95 (s, 3H), 3.81 (m, 2H). FABMS found [M+H]$^+$:421.0932, 423.0912. C$_{23}$H$_{17}$ClN$_2$O$_4$ requires 421.0955, 423.0926.

EXAMPLE 403

The Preparation of 4-(2-Chlorophenyl)-8-(2,3-dihydroxypropoxy)-6-methylpyrrolo[3,4-c]carbazole-1,3 (2H.6H)-dione (XCV; Ar=2-chlorophenyl. $R^{10}$=CH$_3$) (329)

Reaction of alkene (327) (30 mg, 0.07 mmol) prepared as described in example 401 according to the procedure described in example 300 gave diol (329) (19 mg, 60%) as a yellow solid, mp 287–290° C. $^1$H NMR δ [(CD$_3$)$_2$SO] 11.06 (br s, 1H), 8.77 (d, J=8.7 Hz, 1H), 7.76 (s, 1H), 7.57 (m, 1H), 7.47 (m, 3H), 7.27 (d, J=2.2 Hz, 1H), 7.00 (dd, J=8.7, 2.2 Hz, 1H), 5.04 (d, J=5.1 Hz, 1H), 4.73 (t, J=5.6 Hz, 1H), 4.20 (dd, J=8.8, 4.5 Hz, 1H), 4.07 (dd, J=9.9, 6.1 Hz, 1H), 3.95 (s, 3H), 3.89 (m, 2H), 3.52 (t, J=5.6 Hz, 2H). FABMS found [M+H]$^+$:451.1052, 453.1039. C$_{24}$H$_{19}$ClN$_2$O$_5$ requires 451.1061, 453.1031.

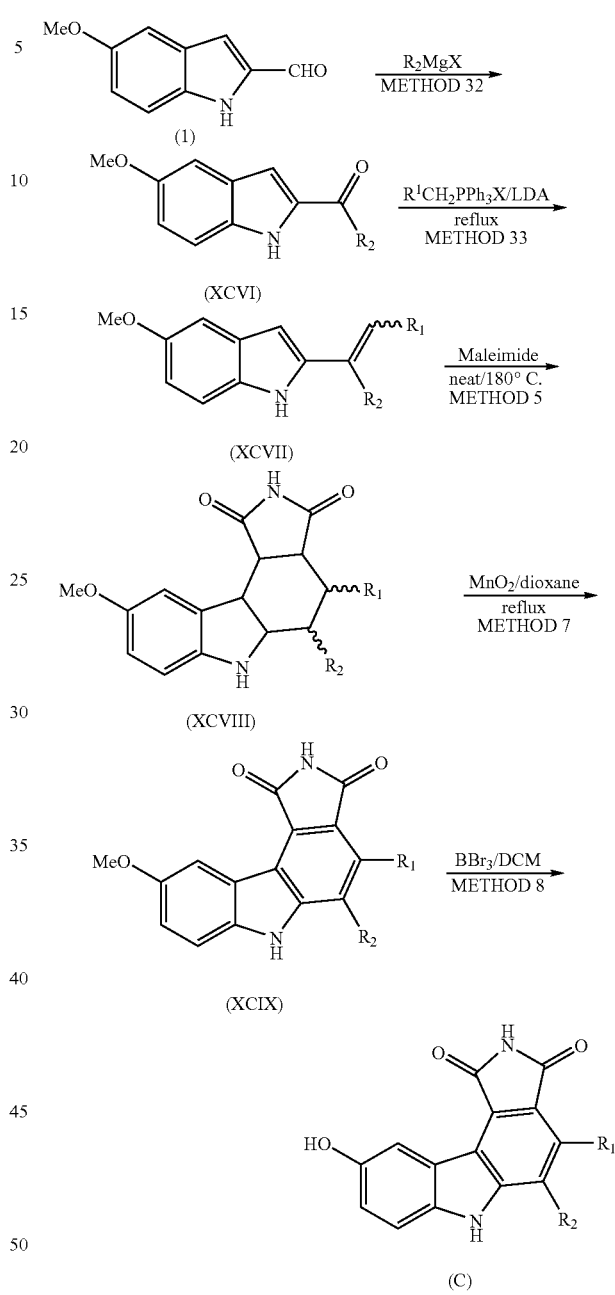

Procedures for Scheme 17

Representative Procedure for Method 32 of Scheme 17

EXAMPLE 404

The Preparation of 1-(5-Methoxy-1H-indol-2-yl)ethanone (XCVI; $R^2$=CH$_3$) (800)

To a solution of the 5-methoxy-1H-indole-2-carbaldehyde (1) (2.0 g, 11.0 mmol) in tetrahydrofuran (30 mL) at 0° C. was added a solution of methyl magnesium bromide (11 mL of a 3 M solution in ether, 34.0 mmol) dropwise. The cold-bath was removed and the reaction mixture allowed to warm to room temperature over 50 min. Saturated ammonium chloride was added and then the tetrahydrofuran was removed at reduced pressure. The residue was extracted with ethyl acetate (2×60 mL), the combined extracts were washed, dried, and concentrated. The crude alcohol was dissolved in chloroform (40 mL) and manganese dioxide (15 g, 0.171 mol) was added, the reaction mixture was heated at reflux for 40 min. The mixture was filtered through Celite and then concentrated to give an off-white solid. The solid was purified by recrystallization from dichloromethane to give (800) (1.80 g, 83%), mp 170–172° C. $^1$H NMR δ [(CD$_3$)$_2$SO] 11.58 (br s, 1H), 7.34 (d, J=9.0 Hz, 1H), 7.23 (s, 1H), 7.12 (d, J=2.4 Hz, 1H), 6.94 (dd, J=9.0, 2.4 Hz, 1H), 3.77 (s, 3H), 2.52 (s, 3H). Found: C, 69.77; H, 5.95; N, 7.54. C$_{11}$H$_{11}$NO$_2$ requires: C, 69.83; H, 5.86; N, 7.40.

Representative Procedure for Method 33 of Scheme 17

EXAMPLE 405

The Preparation of Methyl 2-[(E,Z)-1-methyl-2-phenylethenyl]-1H-indol-5-yl ether (XCVII; R$^2$=CH$_3$, R$^1$=phenyl) (801)

To a suspension of benzyltriphenylphosphonium bromide (3.4 g, 7.9 mmol) in tetrahydrofuran (30 mL) was added a solution of LDA (4.9 mL of a 1.5 M solution in cyclohexane, 7.4 mmol). The red/orange reaction mixture was stirred for 10 min and then a solution of the ketone (1.0 g, 5.3 mmol) in tetrahydrofuran (15 mL) was added. The mixture was heated at reflux overnight and then water was added and the solvent was removed at reduced pressure. The organic material was extracted with ethyl acetate (3×50 mL). The combined extracts were dried and concentrated. The residue was purified by column chromatography on silica eluting with dichloromethane to give methyl (801) (0.26 g, 19%) as a mixture of E- and Z-isomers, which was used without further purification.

EXAMPLE 406

The Preparation of 9-Methoxy-5-methyl-4-phenylpyrrolo[3,4-c]carbazole-1,3(2H,6H)-dione (XCIX; R$^2$=CH$_3$, R$^1$=phenyl) (803)

Reaction of (801) prepared as described in example 405 with maleimide at 180° C. for 40 min using the procedure described in example 69 gave the adduct (XCVIII; R$^2$=CH$_3$, R$^1$=phenyl) (802), which was used without further purification. The crude Diels-Alder adduct was aromatised with MnO$_2$ using the procedure described in example 79 of Scheme 2 to give (803) (69%).

EXAMPLE 407

The Preparation of 9-Hydroxy-5-methyl-4-phenylpyrrolo[3,4-c]carbazole-1,3(2H,6H)-dione (C; R$^2$=CH$_3$, R$^1$=phenyl) (804)

Demethylation of (803) prepared as described in example 406 with BBr$_3$ using the procedure described in example 69 gave (804) (90%), mp 270–280° C. $^1$H NMR δ [(CD$_3$)$_2$SO] 11.60 (s, 1H), 10.82 (s, 1H), 9.22 (s, 1H), 8.31 (d, J=2.0 Hz, 1H), 7.47–7.42 (m, 4H), 7.36–7.23 (m, 2H), 7.06 (dd, J=8.7, 2.0 Hz, 1H), 2.32 (s, 3H). EIMS found M$^+$:342.1005. C$_{21}$H$_{14}$N$_2$O$_3$ requires: 342.1004.

EXAMPLE 408

The Preparation of (5-Methoxy-1H-indol-2-yl)(phenyl)methanone (XCVI; R$^2$=phenyl) (805)

Reaction of 5-methoxy-1H-indole-2-carbaldehyde with phenylmagnesium bromide using the procedure described in example 404 gave (805) (91%), mp 159–161° C. $^1$H NMR δ [(CD$_3$)$_2$SO] 11.86 (s, 1H), 7.94–7.91 (m, 2H), 7.71–7.66 (m, 1H), 7.61–7.57 (m, 2H), 7.42 (d, J=8.9 Hz, 1H), 7.16 (d, J=2.4 Hz, 1H), 7.03 (s, 1H), 6.99 (dd, J=8.9, 2.4 Hz, 1H), 3.77 (s, 3H). Found: C, 76.28; H, 5.21; N, 5.42. C$_{16}$H$_{13}$NO$_2$ requires: C, 76.48; H, 5.21; N, 5.57.

EXAMPLE 409

The Preparation of 2-[(E)-1,2-Diphenylethenyl]-5-methoxy-1H-indole (XCVII; R$^1$=R$^2$=phenyl) (806)

To freshly washed magnesium turnings (0.29 g, 12 mmol) and an iodine crystal in ether (20 mL) was added benzyl chloride (1.4 mL, 12 mmol) at such a rate as to maintain the reaction mixture at reflux. After addition of the benzyl chloride was complete the reaction mixture was heated at reflux for a further 3 h, it was then added to a solution of the ketone (1.0 g, 3.98 mmol) in tetrahydrofuran (20 mL). The reaction mixture was stirred at room temperature for 1 h and then 2 M hydrochloric acid (2 mL) was added. The mixture was filtered and then the solvent was removed at reduced pressure. The crude oily yellow alcohol was dissolved in ethanol/tetrahydrofuran/2 M HCl (2:2:1) and stirred at room temperature for 15 min, water was added and the organic solvents removed at reduced pressure. The organic material was extracted with ethyl acetate (3×50 mL), the combined extracts were dried and concentrated. The residue was purified by recrystallization from dichloromethane (0.95 g, 73%), mp 144–147° C. $^1$H NMR δ [(CD$_3$)$_2$SO] 11.24 (s, 1H), 7.49–7.42 (m, 3H), 7.29–7.26 (m, 4H), 7.17–7.08 (m, 3H), 6.97–6.95 (m, 2H), 6.92 (d, J=2.4 Hz, 1H), 6.75 (dd, J=8.7, 2.4 Hz, 1H), 5.81 (s, 1H), 3.70 (s, 3H). Found: C, 84.30; H, 5.85; N, 4.36. C$_{23}$H$_{19}$NO.1/10H$_2$O requires: C, 84.43; H, 5.91; N, 4.28.

EXAMPLE 410

The Preparation of 9-Methoxy-4,5-diphenylpyrrolo[3,4-c]carbazole-1,3(2H,6H)-dione (XCIX; R$^1$|R$^2$=phenyl) (808).

Reaction of (806) prepared as described in example 409 with maleimide at 180° C. using the procedure described in example 69 gave the adduct (XCVIII; R$^1$=R$^2$=phenyl) (807), which was used without further purification. The crude Diels-Alder adduct was aromatised with MnO$_2$ using the procedure described in example 79 of Scheme 2 to give (808) (77%). $^1$H NMR 1H NMR δ [(CD$_3$)$_2$SO] 11.08 (s, 1H), 11.02 (br s, 1H), 8.52 (d, J=2.6 Hz, 1H), 7.50 (d, J=8.9 Hz, 1H), 7.36–7.28 (m, 3H), 7.21–7.11 (m, 8H), 3.89 (s, 3H).

EXAMPLE 411

The Preparation of 9-Hydroxy-4,5-diphenylpyrrolo[3,4-c]carbazole-1,3(2H,6H)-dione (C; R$^1$=R$^2$=phenyl) (809)

Demethylation of (807) prepared as described in example 410 with BBr$_3$ using the procedure described in example 80 gave (809) as a yellow powder (87%), mp>300° C. ¹H NMR δ [(CD$_3$)$_2$SO] 10.96 (s, 1H), 10.94 (s, 1H), 9.23 (s, 1H), 8.37 (d, J=2.4 Hz, 1H), 7.39 (d, J=8.7 Hz, 1H), 7.35–7.29 (m, 3H), 7.22–7.10 (m, 7H), 7.03 (dd, J=8.7, 2.4 Hz, 1H). Found: C, 77.16; H, 4.00; N, 6.83. C$_{26}$H$_{16}$N$_2$O$_3$ requires: C, 77.22; H, 3.99; N, 6.93.

EXAMPLE 412

The Preparation of 5-Methoxy-2-[(1E)-1-phenyl-1-propenyl]-1H-indole (XCVII; R$^2$=phenyl, R$^1$=CH$_3$)(810)

Reaction of (805) prepared as described in example 408 with ethyltriphenylphosphonium bromide using the procedure described in example 405 gave (810) (72%), mp 128–130° C. ¹H NMR δ [(CD$_3$)$_2$SO] 10.97 (s, 1H), 7.47–7.39 (m, 3H), 7.28–7.19 (m, 3H), 6.88 (d, J=2.4 Hz, 1H), 6.69 (dd, J=8.7, 2.4 Hz, 1H), 6.38 (q, J=6.9 Hz, 1H), 5.69 (s, 1H), 3.69 (s, 3H), 1.67 (d, J=6.9 Hz, 3H) Found: C, 81.78; H, 6.26; N, 5.33. C$_{18}$H$_{17}$NO requires: C, 82.10; H, 6.51; N, 5.32.

EXAMPLE 413

The Preparation of 9-Methoxy-4-methyl-5-phenylpyrrolo[3,4-c]carbazole-1,3(2H,6H)-dione (XCVIII; R$^2$=phenyl, R$^1$=CH$_3$) (812)

Reaction of (810) prepared as described in example 412 with maleimide at 180° C. using the procedure described in example 69 gave the adduct (XCIV; R$^2$=phenyl, R$^1$=CH$_3$) (811), which was used without further purification. The crude Diels-Alder adduct was aromatised with MnO$_2$ using the procedure described in example 79 of Scheme 2 to give (812) (74%), mp 284–286° C. ¹H NMR δ [(CD$_3$)$_2$SO] 11.06 (br s, 1H), 10.93 (s, 1H), 8.43 (d, J=2.6 Hz, 1H), 7.64–7.54 (m, 3H), 7.45–7.42 (m, 3H), 7.14 (dd, J=8.9, 2.6 Hz, 1H), 3.32 (s, 3H), 2.48 (s, 3H). Found: C, 73.13; H, 4.32; N, 7.72. C$_{22}$H$_{16}$N$_2$O$_3$.1/3H$_2$O requires: C, 72.92; H, 4.64; N, 7.73.

EXAMPLE 414

The Preparation of 9-Hydroxy-4-methyl-5-phenylpyrrolo[3,4-c]carbazole-1,3(2H,6H)-dione (C; R$^2$=phenyl, R$^1$=CH$_3$)

Demethylation of (812) prepared as described in example 413 with BBr$_3$ using the procedure described in example 80 gave (813) (85%), mp>300° C. ¹H NMR δ [(CD$_3$)$_2$SO] 11.01 (s, 1H), 10.79 (s, 1H), 9.17 (s, 1H), 8.28 (d, J=2.4 Hz, 1H), 7.34–7.60 (m, 2H), 7.57–7.52 (m, 1H), 7.43–7.41 (m, 2H), 7.34 (d, J=8.7 Hz, 1H), 6.98 (dd, J=8.7, 2.4 Hz, 1H), 2.26 (s, 3H). EIMS found M$^+$:342.1003. C$_{21}$H$_{14}$N$_2$O$_3$ requires: 342.1004.

EXAMPLE 415

The Preparation of 5-Methoxy-2-vinyl-1H-indole (XCVII; R$^1$=R$^2$=H) (814)

Reaction of 5-methoxy-1H-indole-2-carbaldehyde with methyltriphenylphosphonium bromide using the procedure described in method33 gave (814) (87%), mp 80–81° C. ¹H NMR δ [(CD$_3$)$_2$SO] 11.09 (s, 1H), 7.21 (d, J=8.7 Hz, 1H), 6.97 (d, J=2.3 Hz, 1H), 6.75–6.66 (m, 2H), 6.37 (s, 1H), 5.76 (d, J=17.3 Hz, 1H), 5.21 (d, J=11.6, 1H), 3.73 (s, 3H). Found: C, 76.34; H, 6.24; N, 8.11. C$_{11}$H$_{11}$NO requires: C, 76.28; H, 6.40; N, 8.09.

EXAMPLE 416

The Preparation of 9-Methoxypyrrolo[3,4-c]carbazole-1,3(2H,6H)-dione (XCIX; R$^1$=R$^2$=H) (816)

Reaction of (814) prepared as described in example 415 with maleimide at 180° C. using the procedure described in example 69 gave the adduct (XCVIII; R$^1$=R$^2$=H) (814), which was used without further purification. The crude Diels-Alder adduct was aromatised with MnO$_2$ using the procedure described in example 79 to give (815 ??) (76%), mp 260–270° C. ¹H NMR δ [(CD$_3$)$_2$SO] 11.91 (s, 1H), 11.10 (s, 1H), 8.38 (d, J=2.6 Hz, 1H), 7.81 (d, J=8.2 Hz, 1H), 7.76 (d, J=8.2 Hz, 1H), 7.54 (d, J=8.8 Hz, 1H), 7.22 (dd, J=8.8, 2.6 Hz, 1H), 3.88 (s, 3H). Found: C, 65.44; H, 3.96; N, 10.30. C$_{15}$H$_{10}$N$_2$O$_3$.1/2H$_2$O requires: C, 65.45; H, 4.03; N, 10.18.

EXAMPLE 417

The Preparation of 9-Hydroxypyrrolo[3,4-c]carbazole-1,3(2H,6H)-dione (C; R$^1$=R$^2$=H) (817)

Demethylation of (816) prepared as described in example 416 with BBr$_3$ using the procedure described in example 80 gave (817) (79%), mp 335–345° C. ¹H NMR δ [(CD$_3$)$_2$SO] 11.77 (s, 1H), 11.04 (s, 1H), 9.23 (s, 1H), 8.24 (d, J=2.3 Hz, 1H), 7.75 (2d, J=8.2 Hz, 2H), 7.43 (d, J=8.7 Hz, 1H), 7.05 (dd, J=8.7, 2.3 Hz, 1H). Found: C, 64.44; H, 3.45; N, 10.41. C$_{14}$H$_8$N$_2$O$_3$.1/2H$_2$O requires: C, 64.37; H, 3.47; N, 10.72.

EXAMPLE 418

The Preparation of Methyl 2-(1-phenylvinyl)-1H-indol-5-yl ether (XCVII; R$^2$=phenyl, R$^1$=H) (818)

Reaction of (805) prepared as described in example 408 with methyltriphenylphosphonium bromide using the procedure described in example 405 gave (818) (95%), mp 119–121° C. ¹H NMR δ [(CD$_3$)$_2$SO] 11.13 (s, 1H), 7.47–7.39 (m, 5H), 7.26 (d, J=8.8 Hz, 1H), 6.97 (d, J=2.4 Hz, 1H), 6.76 (dd, J=8.8, 2.4 Hz, 1H), 6.12 (s, 1H), 5.77 (s, 1H), 5.30 (s, 1H), 3.72 (s, 3H). Found: C, 81.83; H, 6.22; N, 5.59. C$_{17}$H$_{15}$NO requires: C, 81.90; H, 6.06; N, 5.62.

EXAMPLE 419

The Preparation of 9-Methoxy-5-phenylpyrrolo[3,4-c]carbazole-1,3(2H,6H)-dione (XCIX; R=phenyl, R$^1$=H) (820)

Reaction of (818) prepared as described in example 418 with maleimide at 180° C. using the procedure described in example 69 gave the adduct (XCVIII; R=phenyl, R'=H) (819), which was used without further purification. The crude Diels-Alder adduct was aromatised with MnO$_2$ using the procedure described in example 79 to give (820) (73%), mp 281–285° C. ¹H NMR δ [(CD$_3$)$_2$SO] 11.63 (br s, 1H), 11.15 (br s, 1H), 8.45 (d, J=2.5 Hz, 1H), 7.78–7.76 (m, 2H), 7.68 (s, 1H), 7.65–7.62 (m, 2H), 7.57–7.53 (m, 2H), 7.22

(dd, J=8.8, 2.5 Hz, 1H), 3.89 (s, 3H). Found: C, 72.06; H, 4.57; N, 7.69. $C_{21}H_{14}N_2O_3 \cdot 1/3H_2O$ requires: C, 72.41; H, 4.24; N, 8.04.

EXAMPLE 420

The Preparation of 9-Hydroxy-5-phenylpyrrolo[3,4-c]carbazole-1,3(2H,6H)-dione (C; $R^2$=phenyl, $R^1$=H) (821)

Demethylation of 820 prepared as described in example 419 with $BBr_3$ using the procedure described in example 80 gave (821) (89%), mp 335–345° C. $^1$H NMR δ [(CD$_3$)$_2$SO] 11.50 (s, 1H), 11.10 (s, 1H), 9.26 (d, J=2.4 Hz, 1H), 8.30 (d, J=2.4 Hz, 1H), 7.77–7.75 (m, 2H), 7.65–7.61 (m, 3H), 7.56–7.52 (m, 1H), 7.46 (d, J=8.7 Hz, 1H), 7.06 (dd, J=8.7, 2.4 Hz, 1H). Found: C, 72.71; H, 3.55; N, 8.16. $C_{20}H_{12}N_2O_3$ requires: C, 73.16; H, 3.68; N, 8.53.

EXAMPLE 421

The Preparation of 1-(5-Methoxy-1H-indol-2-yl)-1-propanone (XCVI; $R^2$=CH$_2$CH$_3$) (822)

Reaction of 5-methoxy-1H-indole-2-carbaldehyde with ethylmagnesium bromide using the procedure described in example 404 gave (822) (82%), mp 170–171.5° C. $^1$H NMR δ [(CD$_3$)$_2$SO] 11.56 (s, 1H), 7.34 (d, J=9.1 Hz, 1H), 7.22 (d, J=1.7 Hz, 1H), 7.11 (d, J=2.4 Hz, 1H), 6.93 (d, J=9.1, 2.4 Hz, 1H), 3.77 (s, 3H), 2.96 (q, J=7.3 Hz, 2H), 1.13 (t, J=7.3 Hz, 3H). Found: C, 71.15; H, 6.45; N, 7.07. $C_{12}H_{13}NO_2$ requires: C, 70.92; H, 6.45; N, 6.89.

EXAMPLE 422

The Preparation of 2-[(E,Z)-1-Ethyl-2-phenylethenyl]-5-methoxy-1H-indole (XCVII; $R^2$=CH$_2$CH$_3$, $R^1$=phenyl) (823)

Reaction of (822) prepared as described in example 421 with benzyltriphenylphosphonium bromide using the procedure described in example 404 gave (823) (38%), mp 95–97° C. Found: C, 82.28; H, 6.98; N, 5.07. $C_{19}H_{19}NO$ requires: C, 82.28; H, 6.90; N, 5.05.

EXAMPLE 423

The Preparation of 5-Ethyl-9-methoxy-4-phenylpyrrolo[3,4-c]carbazole-1,3(2H,6H)-dione (XCIX; $R^2$=CH$_2$CH$_3$, $R^1$=phenyl) (825)

Reaction of (823) prepared as described in example 422 with maleimide at 180° C. using the procedure described in example 69 gave the adduct (XCVIII; R=CH$_2$CH$_3$, R'=phenyl) (824), which was used without further purification. The crude Diels-Alder adduct was aromatised with $MnO_2$ using the procedure described in example 79 to give (825) (68%), mp 301–303° C. $^1$H NMR δ [(CD$_3$)$_2$SO] 11.78 (s, 1H), 10.87 (s, 1H), 8.47 (d, J=2.6 Hz, 1H), 7.56 (d, J=8.8 Hz, 1H), 7.48–7.41 (m, 3H), 7.32–7.30 (m, 2H), 7.23 (dd, J=8.8, 2.6 Hz, 1H), 3.89 (s, 3H), 2.76 (q, J=7.4 Hz, 2H), 1.07 (t, J=7.4 Hz, 3H).

EXAMPLE 424

The Preparation of 5-Ethyl-9-hydroxy-4-phenylpyrrolo[3,4-c]carbazole-1,3(2H,6H)-dione (C; $R^2$=CH$_2$CH$_3$, $R^1$=phenyl) (826)

Demethylation of (825) prepared as described in example 423 with $BBr_3$ using the procedure described in example 80 gave (826) (97%), mp 190–196° C. $^1$H NMR δ [(CD$_3$)$_2$SO] 11.63 (s, 1H), 10.81 (s, 1H), 9.21 (s, 1H), 8.31 (d, J=2.4 Hz, 1H), 7.48–7.40 (m, 4H), 7.31–7.29 (m, 2H), 7.06 (dd, J=8.7, 2.4 Hz, 1H), 2.74 (q, J=7.4 Hz, 2H), 1.06 (t, J=7.4 Hz, 3H). Found: C, 72.43; H, 4.54; N, 7.54. $C_{22}H_{16}N_2O_3 \cdot 1/2H_2O$ requires: C, 72.32; H, 4.69; N, 7.67.

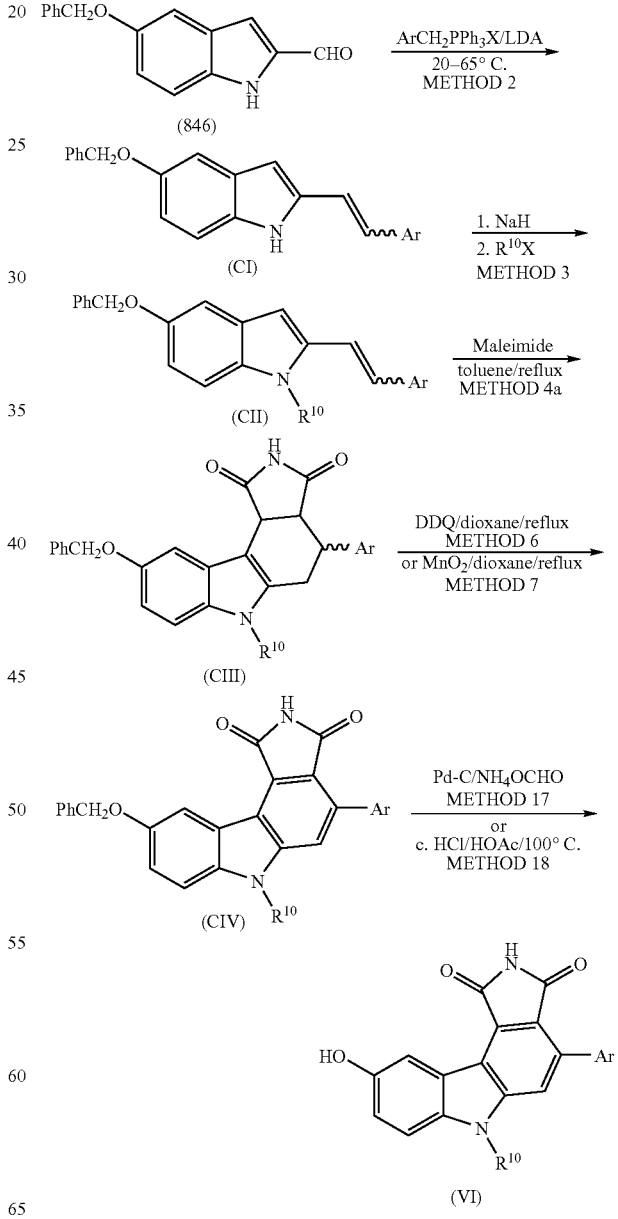

SCHEME 18

Procedures for Scheme 18

EXAMPLE 425

The Preparation of 5-(Benzyloxy)-2-[(E,Z)-2-(2-methoxyphenyl)ethenyl]-1H-indole (CI; Ar=2-methoxyphenyl) (847)

Reaction of 5-(benzyloxy)-1H-indole-2-carbaldehyde (846) with 2-methoxybenzyltriphenylphosphonium bromide using the procedure described in example 37 gave (847) as a cream-colored solid (mixture of E/Z isomers) (89%), which was used without further purification. $^1$H NMR δ [(CD$_3$)$_2$SO] (major isomer) 11.26 (s, 1H), 7.62 (d, J=6.8 Hz, 1H), 7.48 (m), 7.41–7.15 (m), 7.08–7.02 (m), 6.97 (m, 1H), 6.81 (dd, J=8.7, 2.4 Hz, 1H), 6.45 (s, 1H), 5.08 (s, 2H), 3.87 (s, 3H).

EXAMPLE 426

The Preparation of 5-(Benzyloxy)-2-[(E,Z)-2-(2-methoxyphenyl)ethenyl]-1-[2-(4-morpholinyl)ethyl]-1H-indole (CII; Ar=2-methoxyphenyl, R$^{10}$=CH$_2$CH$_2$N(CH$_2$CH$_2$)$_2$O) (848)

Alkylation of (847) prepared as described in example 425 with 4-(2-chloroethyl)morpholine using the procedure described in method 3 gave (848) (87%) as a pale yellow solid, which was used without further purification.

EXAMPLE 427

The Preparation of 9-(Benzyloxy)-4-(2-methoxyphenyl)-6-[2-(4-morpholinyl)ethyl]pyrrolo[3,4-c]carbazole-1,3(2H,6H)-dione (CIV; Ar=2-methoxyphenyl, R$^{10}$=CH$_2$CH$_2$N(CH$_2$CH$_2$)$_2$O) (850)

Reaction of (848) prepared as described in example 426 with maleimide using the procedure described in method 4a gave the adduct (CIII; Ar=2-methoxyphenyl, R$^{10}$=CH$_2$CH$_2$N(CH$_2$CH$_2$)$_2$O) (849), which was used without further purification. Aromatisation of (849) with MnO$_2$ using the procedure described in example 79 gave (850) (36%) as a yellow solid, mp 170–172° C.

EXAMPLE 428

The Preparation of 9-Hydroxy-4-(2-methoxyphenyl)-6-[2-(4-morpholinyl)ethyl]pyrrolo[3,4-c]carbazole-1,3(2H,6H)-dione (VI; Ar=2-methoxyphenyl, R$^{10}$=CH$_2$CH$_2$N(CH$_2$CH$_2$)$_2$O(851)

Removal of the benzyl ether group of (850) prepared as described in example 427 by hydrogenolysis using the procedure described in example 254 gave (851) (66%) as a yellow powder, mp 262–264° C. $^1$H NMR δ [(CD$_3$)$_2$SO] 10.92 (br s, 1H), 9.31 (br s, 1H), 8.37 (d, J=2.5 Hz, 1H), 7.69 (s, 1H), 7.54 (d, J=8.8 Hz, 1H), 7.42 (m, 1H), 7.33 (dd, J=7.4, 1.7 Hz, 1H), 7.12–7.08 (m, 2H), 7.05 (m, 1H), 4.54 (t, J=6.3 Hz, 2H), 3.68 (s, 3H), 3.45 (t, J=4.4 Hz, 4H), 2.65 (t, J=6.3 Hz, 2H), 2.41 (br t, 4H). Found EIMS M$^+$:471.1789. C$_{27}$H$_{25}$N$_3$O$_5$ requires 471.1794.

EXAMPLE 429

The Preparation of 5-(Benzyloxy)-2-{(E)-2-[2-(2-methoxyethoxy)phenyl]ethenyl}-1H-indole (CI; Ar=2-(2-methoxyethoxy)phenyl) (852)

Reaction of 5-(benzyloxy)-1H-indole-2-carbaldehyde (846) with 2-(2-methoxyethoxy)benzyltriphenylphosphonium bromide using the procedure described in example 37 gave (847) as a cream-colored solid (mixture of E/Z isomers) (86%), which was used without further purification.

EXAMPLE 430

The Preparation of 9-(Benzyloxy)-4-[2-(2-methoxyethoxy)phenyl]pyrrolo[3,4-c]carbazole-1,3(2H,6H)-dione (CIV; Ar=2-(2-methoxyethoxy)phenyl, R$^{10}$=H) (854)

Reaction of (852) with maleimide using the procedure described in method 4a gave the adduct (CIII; Ar=2-(2-methoxyethoxy)phenyl, R$^{10}$=H (853), which was used without further purification. Aromatisation of (853) with MnO$_2$ using the procedure described in example 79 gave (854) (46%) as an orange solid, mp 157–159° C., which was used without further purification.

EXAMPLE 431

The Preparation of 9-Hydroxy-4-[2-(2-methoxyethoxy)phenyl]pyrrolo[3,4-c]carbazole-1,3(2H,6H)-dione (VI; Ar=2-(2-methoxyethoxy)phenyl, R$^{10}$=H) (855).

Removal of the benzyl ether group of (854) prepared as described in example 430 by hydrogenolysis using the procedure described in example 254 gave (855) (53%) as a yellow powder, mp 275–279° C. $^1$H NMR δ [(CD$_3$)$_2$SO] 11.71 (br s, 1H), 10.89 (br s, 1H), 9.22 (br s, 1H), 8.31 (d, J=2.2 Hz, 1H), 7.51 (s, 1H), 7.43 (d, J=8.5 Hz, 1H), 7.39 (m, 1H), 7.34 (dd, J=7.5 Hz, 1H), 1.7 Hz, 1H), 7.10 (d, J=7.7 Hz, 1H), 7.05 (m, 2H), 4.04 (m, 2H), 3.45 (t, J=4.7 Hz, 2H), 3.10 (s, 3H). EIMS Found M$^+$:402.1213. C$_{23}$H$_{18}$N$_2$O$_5$ requires 402.1215.

EXAMPLE 432

The Preparation of (2-Methoxy-4-nitrobenzyl)(triphenyl)phosphonium bromide (582)

Bromination of (2-methoxy-4-nitrophenyl)methanol with 30% HBr in acetic acid, followed by reaction of the crude bromide with triphenylphosphine, using the procedure described in example 112, except that the conditions for the displacement were 3 days at 20° C. followed by 1 day at 55° C., gave the phosphonium salt (582) (84%) as a yellow solid, mp (CH$_2$Cl$_2$/benzene) 194–196° C. $^1$H NMR (CDCl$_3$) δ 7.83–7.63 (m, 17H), 7.45 (br s, 1H), 5.52 (d, J=15.0 Hz, 2H). Found: C, 61.10; H, 4.73; N, 3.05. C$_{26}$H$_{23}$BrNO$_3$P requires C, 61.43; H, 4.56; N, 2.76.

EXAMPLE 433

The Preparation of 5-(Benzyloxy)-2-[(E)-2-(2-methoxy-4-nitrophenyl)ethenyl]-1H-indole (583) (CI, Ar=2-methoxy-4-nitrophenyl)

The aldehyde (846) was reacted with (2-methoxy-4-nitrobenzyl) (triphenyl)phosphonium bromide (582) prepared as described in example 432 using the procedure described in method 2, except that the LDA and aldehyde were (sequentially) added at 0° C., the ratio of LDA:aldehyde was 1.5:1 and the reaction time was 5 h, to give (after crystallisation from $CH_2Cl_2$/pentane) the diene (583) as an orange solid (the pure E isomer) (63%), mp 156–159° C. $^1$H NMR ($CDCl_3$) δ 8.23 (br s, 1H), 7.87 (dd, J=8.5, 2.1 Hz, 1H), 7.76 (d, J=2.2 Hz, 1H), 7.68 (d, J=8.6 Hz, 1H), 7.48 (d, J=7.3 Hz, 2H), 7.39 (t, J=7.3 Hz, 2H), 7.32 (t, J=7.2 Hz, 1H), 7.28 (d, J=17.1 Hz, 1H), 7.26 (d, J=8.7 Hz, 1H), 7.20 (d, J=16.7 Hz, 1H), 7.12 (d, J=2.4 Hz, 1H), 6.97 (dd, J=8.7, 2.5 Hz, 1H), 6.63 (br s, 1H), 5.11 (s, 2H), 4.01 (s, 3H). Found: C, 71.69; H, 4.94; N, 7.11. $C_{24}H_{20}N_2O_4$ requires C, 71.99; H, 5.03; N, 7.00.

EXAMPLE 434

The Preparation of 9-(Benzyloxy)-4-(2-methoxy-4-nitrophenyl)-4,5,6,10c-tetrahydropyrrolo[3,4-c]carbazole-1,3(2H,3aH)-dione (584) (CIII, $R^{10}$=H, Ar=2-methoxy-4-nitrophenyl) and 9-benzyloxy-4-(2-methoxy-4-nitrophenyl)pyrrolo[3,4-c]carbazole-1, 3(2H,6H)-dione (585) (CIV, $R^{10}$=H, Ar=2-methoxy-4-nitrophenyl)

A foil-covered mixture of the pure E diene (583) (185 mg, 0.463 mmol) prepared as described in example 433 and maleimide (260 mg, 2.68 mmol) in dry toluene (3 mL) was stirred in a sealed vial at reflux for 22 h (Method 4a). The resulting thick suspension was transferred to a flask using dioxane (7 mL), then treated with manganese dioxide (900 mg, 10.4 mmol), stirring at reflux for 24 h (according to the procedure for example 79), to give (after workup) a mixture, which was adsorbed onto silica gel and chromatographed. Elution with 0–0.25% MeOH/$CH_2Cl_2$ gave foreruns, then further elution with 0.25–33% MeOH/$CH_2Cl_2$ gave (after crystallisation from THF/$CH_2Cl_2$/pentane) the crude product (585) (64 mg). This was further purified by chromatography on silica gel (eluting with 20% EtOAc/petroleum ether) to give (after crystallisation from THF/$CH_2Cl_2$/pentane) the pure material (585) (58 mg, 25%) as a yellow solid, mp 301–303° C. $^1$H NMR [$(CD_3)_2SO$] δ 11.97 (br s, 1H), 11.08 (br s, 1H), 8.54 (d, J=2.5 Hz, 1H), 7.94 (dd, J=8.3, 2.2 Hz, 1H), 7.88 (d, J=2.2 Hz, 1H), 7.64 (d, J=8.2 Hz, 1H), 7.63 (s, 1H), 7.58 (d, J=8.8 Hz, 1H), 7.56 (br d, J=7.1 Hz, 2H), 7.42 (t, J=7.4 Hz, 2H), 7.35 (t, J=7.4 Hz, 1H), 7.32 (dd, J=8.9, 2.7 Hz, 1H), 5.23 (s, 2H), 3.83 (s, 3H). Found: C, 68.14; H, 3.89; N, 8.41. $C_{28}H_{19}N_3O_6$ requires C, 68.15; H, 3.88; N, 8.52.

Further elution with 1% MeOH/$CH_2Cl_2$ gave (after crystallisation from MeOH/$CH_2Cl_2$/petroleum ether) recovered adduct (584) (72 mg, 31%) as a pale yellow solid (which was aromatised directly with 5 equiv. DDQ using the procedure described in example 70 to give further product in 79% yield), $^1$H NMR [$(CD_3)_2SO$] δ 10.96 (br s, 1H), 10.86 (br s, 1H), 7.90 (dd, J=8.5, 2.3 Hz, 1H), 7.78 (d, J=2.2 Hz, 1H), 7.72 (d, J=8.6 Hz, 1H), 7.50 (d, J=7.1 Hz, 2H), 7.40 (t, J=7.3 Hz, 2H), 7.34 (d, J=2.4 Hz, 1H), 7.33 (t, J=7.4 Hz, 1H), 7.21 (d, J=8.7 Hz, 1H), 6.80 (dd, J=8.7, 2.5 Hz, 1H), 5.09 (s, 2H), 4.27 (d, J=7.6 Hz, 1H), 3.98 (dd, J=7.6, 3.6 Hz, 1H), 3.97 (s, 3H), 3.54 (dt, J=12.9, 3.8 Hz, 1H), 3.24 (br dd, J=15.7, 13.5 Hz, 1H), 2.89 (dd, J=15.4, 3.6 Hz, 1H). FABMS found: $M^+$=497.1601. $C_{28}H_{23}N_3O_6$ requires 497.1587.

EXAMPLE 435

The Preparation of 9-Hydroxy-4-(2-methoxy-4-nitrophenyl)pyrrolo[3,4-c]carbazole-1,3(2H,6H)-dione (586) (VI, $R^{10}$=H, Ar=2-methoxy-4-nitrophenyl)

A suspension of the benzyl ether (585) (55 mg, 0.112 mmol) prepared as described in example 434 in glacial AcOH (11.2 mL) was treated with concentrated HCl (6.7 mL of 36%), stirring at 100° C. for 50 min (Using the procedure described in example 260 of Scheme 18). The cooled solution was added slowly to ice/aqueous $NaHCO_3$ (150 mL), then extracted with EtOAc (5×100 mL). The extracts were washed with water, then adsorbed onto silica gel and chromatographed. Elution with 0–1% MeOH/$CH_2Cl_2$ gave foreruns, then elution with 1.5% MeOH/$CH_2Cl_2$ gave (after crystallisation from THF/$CH_2Cl_2$/pentane) the phenol (586) (86%) as an orange solid, mp 242–244° C. $^1$H NMR [$(CD_3)_2SO$] δ11.84 (br s, 1H), 11.02 (br s, 1H), 9.28 (br s, 1H), 8.31 (d, J=2.4 Hz, 1H), 7.93 (dd, J=8.2, 2.1 Hz, 1H), 7.87 (d, J=2.1 Hz, 1H), 7.63 (d, J=8.2 Hz, 1H), 7.58 (s, 1H), 7.45 (d, J=8.7 Hz, 1H), 7.08 (dd, J=8.7, 2.4 Hz, 1H), 3.83 (s, 3H). Found: C, 62.55; H, 3.22; N, 10.13. $C_{21}H_{13}N_3O_6$ requires C, 62.53; H, 3.25; N, 10.42.

EXAMPLE 436

The Preparation of 4-(4-Amino-2-methoxyphenyl)-9-hydroxypyrrolo[3,4-c]carbazole-1,3(2H,6H)-dione (587) (VI, $R^{10}$=H, Ar=4-amino-2-methoxyphenyl)

A mixture of the nitro derivative (586) (31 mg, 0.0769 mmol) prepared as described in example 435 and freshly prepared (wet) nickel boride (242 mg) in MeOH (2.4 mL) and 1M HCl (0.6 mL) was stirred at reflux for 1 h. Six drops of conc. HCl were added, then the mixture was stirred at reflux for a further 1 h. Conc. aqueous ammonia and aqueous $NaHCO_3$ (100 mL) were added and the mixture extracted with EtOAc (8×100 mL). The extracts were concentrated, adsorbed onto silica gel and chromatographed. Elution with 0–2% MeOH/$CH_2Cl_2$ gave foreruns, then further elution with 2–3% MeOH/$CH_2Cl_2$ gave (after crystallisation from MeOH/THF/$CH_2Cl_2$/pentane) the amine (587) (77%) as a yellow-orange solid, mp 308–316° C. $^1$H NMR [$(CD_3)_2SO$] δ 11.57 (br s, 1H), 10.79 (br s, 1H), 9.17 (br s, 1H), 8.29 (d, J=2.4 Hz, 1H), 7.43 (s, 1H), 7.39 (d, J=8.7 Hz, 1H), 7.02 (dd, J=8.7, 2.5 Hz, 1H), 6.95 (d, J=7.9 Hz, 1H), 6.30 (d, J=2.0 Hz, 1H), 6.22 (dd, J=8.0, 1.9 Hz, 1H), 5.26 (br s, 2H), 3.59 (s, 3H). Found: C, 67.65; H, 4.06; N, 11.01. $C_{21}H_{15}N_3O_4$ requires C, 67.56; H, 4.05; N, 11.25.

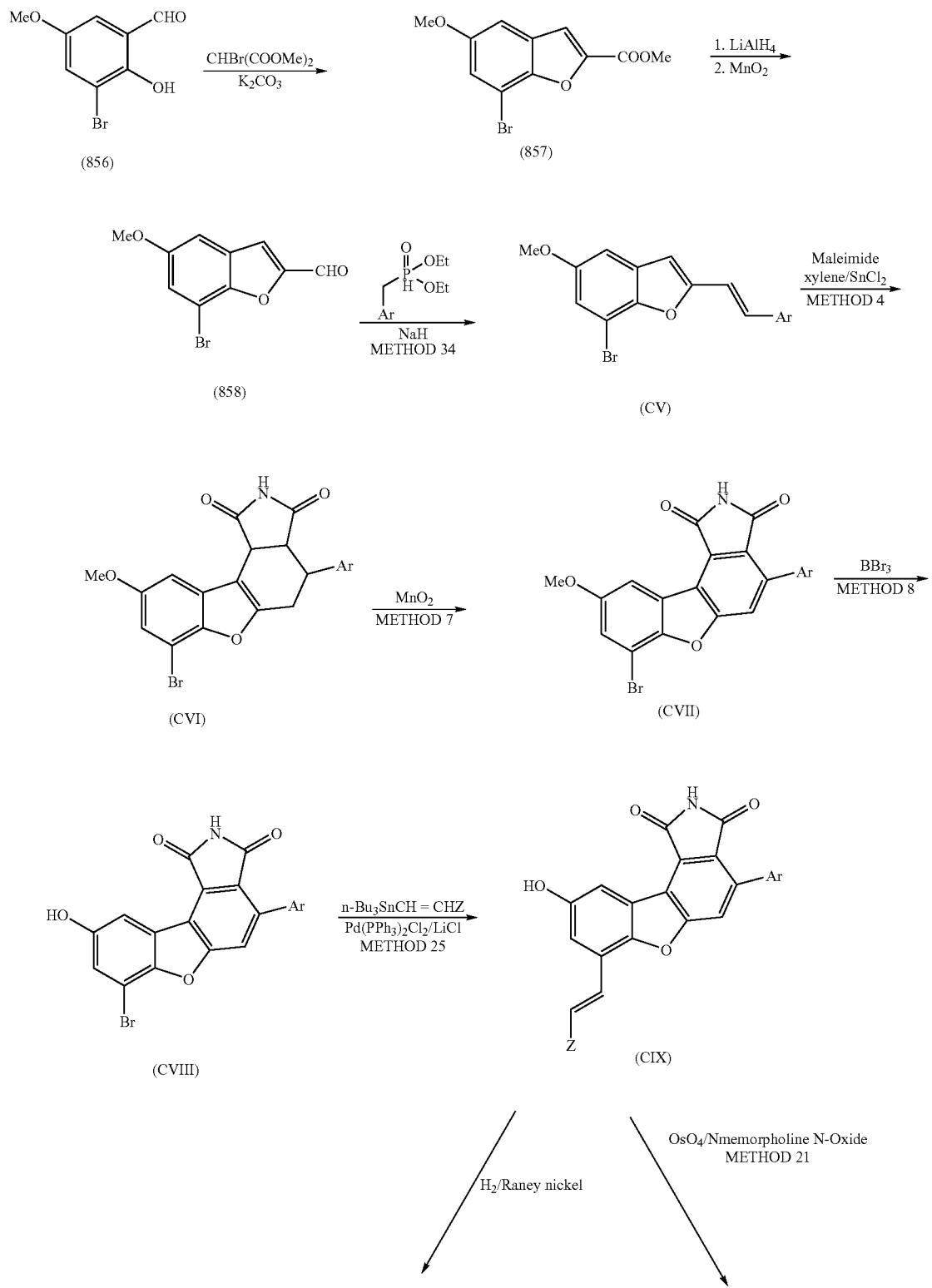
SCHEME 19

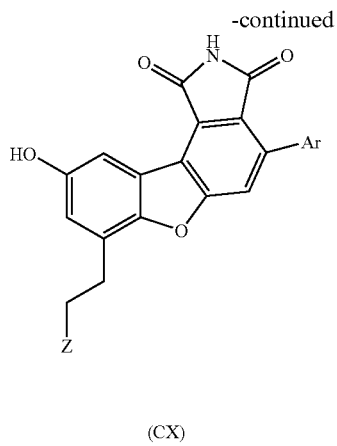

(CX)

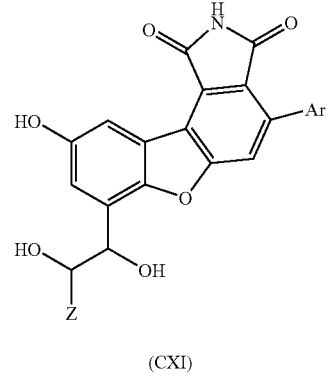

(CXI)

Scheme 19 Procedures

EXAMPLE 437

The Preparation of Methyl 7-bromo-5-methoxy-1-benzofuran-2-carboxylate (856)

To a solution containing 3-Bromo-2-hydroxy-5-methoxybenzaldehyde (94.7 g, 0.410 mol) and dimethyl bromomalonate (103 g, 0.492 mol) in toluene (1.2 L) was added freshly powdered potassium carbonate (85 g, 0.615 mol) and tetra-n-butylammonium bromide (13.2 g, 0.041 mol). The reaction was heated at reflux under a Dean-Stark trap for 48 h. The reaction was concentrated and the residue dissolved with dichloromethane (~0.5 L) and filtered through Celite, washing with dichloromethane (~0.5 L). The filtrate was washed with 1 L of 1M sodium hydroxide and water (2×1 L). The organic phase was then passed through a 400 g pad of silica gel washing with dichloromethane (~1 L) and the filtrate was concentrated to give the desired benzofuran (64 g, 56%) as an orange solid, mp 107–111° C. $^1$H NMR δ (CDCl$_3$) 7.50 (s, 1H), 7.23 (d, 1H), 7.03 (d, 1H), 3.98 (s, 3H), 3.82 (s, 3H).

EXAMPLE 438

The Preparation of 7-Bromo-2-hydroxymethyl-5-methoxybenzofuran and 7-bromo-5-methoxybenzofuran-2-carbaldehyde (858).

A solution containing ester (857) (69 g, 242 mmol) prepared as described in example 856 in anhydrous tetrahydrofuran (2.5 L) was chilled to −78° C. A 1M lithium aluminum hydride solution in tetrahydrofuran (242 mL, 242 mmol) was added over a 30 min period. The reaction was stirred at −78° C. for 1.25 h and was carefully quenched with 50 mL of water. The mixture was poured into 1 L of an ice-cold 1M hydrochloric acid solution and extracted with ethyl acetate (4×500 mL). The combined organic phases were dried (Na$_2$SO$_4$) and concentrated in vacuo to give 67 g of an orange solid. This residue was adsorbed onto 200 g of silica gel and added to a column of silica gel (1 kg, 70–230 mesh) and eluted with 1:9, 1:4, and 1:3 ethyl acetate-heptanes. This gave firstly 25 g (41%) of the final aldehyde (858) as a pale yellow solid, mp 119–121° C. $^1$H NMR δ (CDCl$_3$) 9.90 (s, 1H), 7.55 (s, 1H), 7.38 (d, 1H), 7.10 (s, 1H), 3.85 (s, 3H). Found: C, 47.06; H, 2.66; Br, 31.41. C$_{10}$H$_7$BrO$_3$ requires C, 47.09; H, 2.77; N, 31.33; followed by 20 g (33%) of the expected alcohol. $^1$H NMR δ (CDCl$_3$) 7.08 (m, 1H), 6.9 (m, 1H), 6.68 (s, 1H), 4.78 (s, 2H), 3.85 (s, 3H).

EXAMPLE 439

The Preparation of 7-Bromo-5-methoxybenzofuran-2-carbaldehyde (858)

A solution of the alcohol isolated above (560 mg, 2.18 mmol) prepared as described in example 858, tetrahydrofuran (20 mL) and ether (60 mL) was added manganese dioxide (1.9 g, 21.8 mmol). The reaction was stirred for 2 days and filtered through Celite. The filtrate was concentrated in vacuo and chromatographed on silica give 200 mg (~50%) of the desired aldehyde (858) (spectra as above).

Representative Procedure for Method 34 of Scheme 19

EXAMPLE 440

The Preparation of 7-Bromo-2-[(E)-2-(2-chlorophenyl)ethenyl]-5-methoxy-1-benzofuran (CV; Ar=2-chlorophenyl) (859)

To a solution of diethyl 2-chlorobenzylphosphonate (4.91 g, 0.018 mol) and 7-bromo-5-methoxybenzofuran-2-carbaldehyde (11.27 g, 0.016 mol) in tetrahydrofuran (80 mL) was added sodium hydride (60% dispersion in mineral oil, 0.74 g, 0.0185 mol). After 5 min. the reaction mixture was warmed to 60° C. for 1 h. The reaction mixture was cooled to room temperature, water (10 mL) was carefully added and the tetrahydrofuran was removed. Water (50 mL) was added and the mixture was extracted with ethyl acetate (3×100 mL). The combined ethyl acetate extracts were washed with brine (50 mL), dried over magnesium sulphate, filtered and concentrated to dryness. Trituration with diethyl ether (20 mL) gave solid material which was further washed with diethyl ether (20 ml). The liquors were concentrated and triturated with diethyl ether (10 mL), the solid being collected. The combined solids gave (859) (4.89 g, 84%). $^1$H NMR δ (CDCl$_3$) 7.70 (d, J=16 Hz, 1H), 7.65 (dd, J=7.7, 1.5 Hz, 1H), 7.4 (dd, J=6.0, 1 Hz, 1H), 7.23 (m, 2H), 7.05 (d, J=2.3 Hz, 1H), 6.94 (d, J=16 Hz, 1H), 6.92 (d, J=2.3 Hz, 1H), 6.72 (s, 1H), 3.82 (s, 3H); MH$^+$:364.9, 362.9 MH$_-$: 362.9, 360.9.

EXAMPLE 441

The Preparation of 7-Bromo-4-(2-chlorophenyl)-9-methoxy-3a,4,5,10c-tetrahydro-1H-[1]benzofuro[3,2-e]isoindole-1,3(2H)-dione (CVI; Ar=2-chlorophenyl) (860)

A solution of (859) (4.89 g, 0.0185 mol) prepared as described in example 441, maleimide (1.44 g, 0.02 mol) and tin(II) chloride (2.8 g, 0.02 mol) in xylenes (40 mL) was heated to 150° C. overnight. After the addition of more maleimide (1.44 g, 0.02 mol) and tin(II) chloride (1.44 g, 0.01 mol) the reaction was again heated to 150° C. overnight. The solid which formed was collected and washed with xylenes (20 mL) before dissolving in ethyl acetate (200 mL). Water (50 mL) was added and the mixture was filtered through a pad of Celite. The resulting layers were separated, the organic phase was washed with brine (50 mL) dried over magnesium sulphate, filtered and concentrated to dryness. The product (860) (6.1 g, 71%) was used without further purification. $^1$H NMR δ (CDCl$_3$) 7.60 (d, J=6.5 Hz, 1H), 7.40 (m, 2H), 7.25 (m, 1H), 7.1 (m, 2H), 4.36 (dd, J=7.3, 1 Hz, 1H), 4.0 (m, 1H), 3.86 (s, 3H), 3.81 (m, 1H), 3.45 (m, 1H), 3.10 (dd, J=4.7, 17 Hz, 1H); MH$^+$:462,460.

EXAMPLE 442

The Preparation of 7-Bromo-4-(2-chlorophenyl)-9-methoxy-1H-[1]benzofuro[3,2-e]isoindole-1,3(2H)-dione (CVII; Ar=2-chlorophenyl) (861).

Aromatisation of (860) prepared as described in example 442 with MnO$_2$ using the procedure described in example 79 gave the dibenzofuran (861) as a yellow solid (67%). $^1$H NMR δ [(CD$_3$)$_2$SO] 8.22 (d, J=2.6 Hz, 1H), 8.14 (s, 1H), 7.62 (m, 2H), 7.48 (m, 3H), 3.98 (s, 3H). MH$^-$:458, 457,456,454.

EXAMPLE 443

The Preparation of 7-Bromo-4-(2-chlorophenyl)-9-hydroxy-1H-[1]benzofuro[3,2-e]isoindole-1,3(2H)-dione (CVIII; Ar=2-chlorophenyl) (862)

Demethylation of (861) prepared as described in example 442 with BBr$_3$ using the procedure described in example 80 gave (862) (98%) which was used without further purification. $^1$H NMR δ [(CD$_3$)$_2$SO] 8.04 (d, J=2.3 Hz, 1H), 7.91 (s, 1H), 7.56 (d, J=8 Hz, 1H), 7.45 (m, 3H), 7.2 (d, J=2.5 Hz, 1H). MH$^-$:443.9, 441.9, 439.9.

EXAMPLE 444

The Preparation of 4-(2-Chlorophenyl)-9-hydroxy-7-vinyl-1H-[1]benzofuro[3,2-e]isoindole-1,3(2H)-dione (CVIII; Ar=2-chlorophenyl, Z=H) (863).

Reaction of (862) prepared as described in example 443 with tributylvinyltin using the procedure described in example 309 gave (863) (79%). $^1$H NMR δ [(CD$_3$)$_2$SO] 9.80 (s, 1H), 8.04 (d, J=2.7 Hz, 1H), 7.91 (s, 1H), 7.56 (d, J=8 Hz, 1H), 7.45 (m, 3H), 7.2 (d, J=2.5 Hz, 1H), 6.96 (dd, J=18,1 Hz, 1H), 6.25 (d, J=18 Hz, 1H), 5.52 (d, J=11 Hz, 1H). MH$^-$:390,388.

EXAMPLE 445

The Preparation of 4-(2-Chlorophenyl)-7-ethyl-9-hydroxy-1H-[1]benzofuro[3,2-e]isoindole-1,3(2H)-dione (CX; Ar=2-chlorophenyl, Z=H) (864).

A solution of (863) (0.054 g, 0.167 mmol) prepared as described in example 444 in a methanol:tetrahydrofuran mixture (1:1, 4 mL) was hydrogenated over Raney nickel (100 mg) and hydrogen. The product was purified by column chromatography using a gradient of 0–100% ethyl acetate in dichloromethane to give (864) (0.032 g, 59%). $^1$H NMR δ [(CD$_3$)$_2$SO] 9.65 (s, 1H), 7.92 (m, 1H), 7.56 (d, J=3.0 Hz, 1H), 7.43 (m, 3H), 6.96 (d, J=2.5 Hz, 1H), 2.90 (q, 2H), 1.5 (t, 3H). MH$^-$:392, 390.

EXAMPLE 446

The Preparation of 4-(2-Chlorophenyl)-7-(1,2-dihydroxyethyl)-9-hydroxy-1H-[1]benzofuro[3,2-e]isoindole-1,3(2H)-dione (CXI; Ar=2-chlorophenyl, Z=H) (865)

Reaction of (863) prepared as described in example 444 with OSO$_4$ using the procedure described in example 300 gave (865) (35%). $^1$H NMR δ [(CD$_3$)$_2$SO] 9.68 (s, 1H), 7.96 (d, J=2.5 Hz, 1H), 7.9 (s, 1H), 7.55 (d, J=7.8 Hz, 1H), 7.45, m, 3H), 7.17 (d, J=2.5 Hz, 1H), 5.55 (d, J=4.6 Hz, 1H), 5.06 (m, 1H), 4.87 (t, J=5.7 Hz, 1H), 3.65 (m, 1H), 3.55 (m, 1H). MH$^-$:424,422.

SCHEME 20

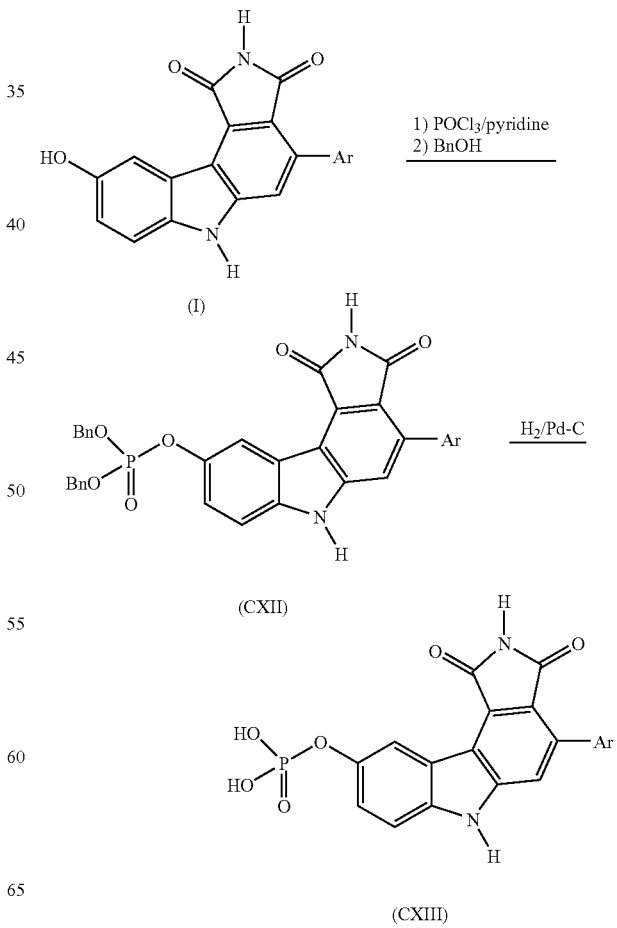

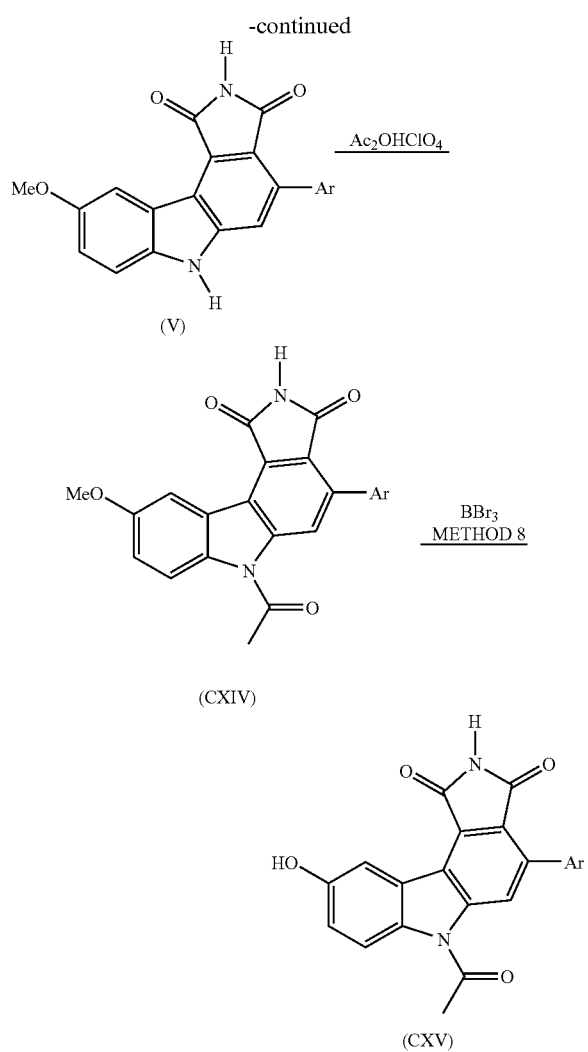

Scheme 20 Procedures

EXAMPLE 447

The Preparation of Dibenzyl 1,3-dioxo-4-phenyl-1,2,3,6-tetrahydropyrrolo[3,4-c]carbazol-9-yl phosphate (CXII; Ar=phenyl) (336)

To a solution of 9-hydroxy-4-phenylpyrrolo[3,4-c]carbazole-1,3(2H,6H)-dione (I; Ar=phenyl) (0.50 g, 1.52 mmol) in pyridine (30 mL) under nitrogen was added phosphorous oxychloride (140 □L, 1.52 mmol) dropwise. After 40 minutes stirring at room temperature a further portion of phosphorous oxychloride (40 □L) was added and then after another 20 minutes, benzyl alcohol (0.66 mL, 6.38 mmol) was added. After 3 hours the reaction mixture was diluted with 1N hydrochloric acid and extraction with ethyl acetate. The organic phase was dried, the drying agent was removed and the solution was concentrated to dryness, before being chromatographed on silica eluting with methanol/dichloromethane (3:97) to give the dibenzyl phosphate (336) (284 mg, 32%) as a pale yellow powder, mp 193–194° C. $^1$H NMR δ [(CD$_3$)$_2$SO] 12.12 (br s, 1H), 11.15 (br s, 1H), 8.81 (br s, 1H), 7.69 (s, 1H), 7.63 (m, 3H), 7.48–7.34 (m, 14H), 5.22 (d, $J_{H-F}$=8.3 Hz, 4H). Found: C, 69.65; H, 4.37; N, 4.88; P, 5.26. C$_{34}$H$_{25}$N$_2$O$_6$P requires: C, 69.38; H, 4.28; N, 4.76; P, 5.26.

EXAMPLE 448

The Preparation of 1,3-Dioxo-4-phenyl-1,2,3,6-tetrahydropyrrolo[3,4-c]carbazol-9-yl dihydrogen phosphate (CXIII; Ar=phenyl) (337)

A solution of the dibenzyl phosphate (336) (100 mg, 0.17 mmol) prepared as described in example 447 in methanol/tetrahydrofuran (3:1, 70 mL) was hydrogenated at 60 psi over Pd-C (5%, catalytic) with stirring for 3 hours. The reaction mixture was then filtered through celite and concentrated in vacuo. Trituration from ethyl acetate/hexane gave the phosphate (337) (49 mg, 71%) as a yellow solid, mp 285–295° C. $^1$H NMR δ [(CD$_3$)$_2$SO] 12.01 (br s, 1H), 11.09 (br s, 1H), 8.66 (br s, 1H), 7.63 (m, 3H), 7.57 (br d, J=8.6 Hz, 1H), 7.50–7.44 (m, 4H). Found: C, 55.19; H, 3.29; N, 6.34; P, 6.84. C$_{20}$H$_{13}$N$_2$O$_6$P.1/2H$_2$O requires: C, 55.18; H, 3.71; N, 6.43; P, 7.12.

EXAMPLE 449

The Preparation of 6-Acetyl-4-(2-chlorophenyl)-9-methoxypyrrolo[3,4-c]carbazole-1,3(2H,6H)-dione (CXIV; Ar=2-chlorophenyl) (338)

To a solution of carbazole (33) (45 mg, 0.12 mmol) prepared as described in example 79 in acetic anhydride (4.0 mL) was added 35% perchloric acid (2 drops). The resulting solution was stirred at room temperature for 30 minutes before being poured onto ice water, basified by the addition of solid potassium bicarbonate and extraction with ethyl acetate. The organic phase was dried, the drying agent was removed and the solution was concentrated to dryness. Chromatography on silica eluting with ethyl acetate/hexane (2:3), followed by trituration from ethyl acetate gave acetamide (338) (40 mg, 80%) as a pale yellow powder, mp 277–280° C. $^1$H NMR δ [(CD$_3$)$_2$SO] 11.46 (br s, 1H), 8.74 (d, J=2.8 Hz, 1H), 8.53 (s, 1H), 8.17 (d, J=9.2 Hz, 1H), 7.60 (m, 1H), 7.54–7.47 (m, 3H), 7.32 (dd, J=9.2, 2.8 Hz, 1H), 3.93 (s, 3H), 2.91 (s, 3H). Found: C, 65.50; H, 3.49; N, 6.61. C$_{23}$H$_{15}$ClN$_2$O$_4$.1/4H$_2$O requires: C, 65.26; H, 3.69; N, 6.62.

EXAMPLE 450

The Preparation of 6-Acetyl-4-(2-chlorophenyl)-9-hydroxypyrrolo[3,4-c]carbazole-1,3(2H,6H)-dione (CXV; Ar=2-chlorophenyl) (339)

Demethylation of acetamide (338) (35 mg, 0.08 mmol) prepared as described in example 449 according to the procedure described in example 80, except that the reaction time was 24 hours and the chromatography was performed eluting with ethyl acetate/hexane (1:2 to 2:1), gave phenol (339) (22 mg, 65%) as a pale yellow powder, mp 258–261° C. $^1$H NMR δ [(CD$_3$)$_2$SO] 11.41 (br s, 1H), 9.80 (br s, 1H), 8.59 (d, J=2.6 Hz, 1H), 8.53 (s, 1H), 8.07 (d, J=9.1 Hz, 1H), 7.59 (m, 1H), 7.53–7.46 (m, 3H), 7.15 (dd, J=9.1, 2.6 Hz, 1H), 2.89 (s, 3H). Found: C, 65.03; H, 3.14; N, 6.68. C$_{22}$H$_{13}$ClN$_2$O$_4$ requires: C, 65.28; H, 3.24; N, 6.92.

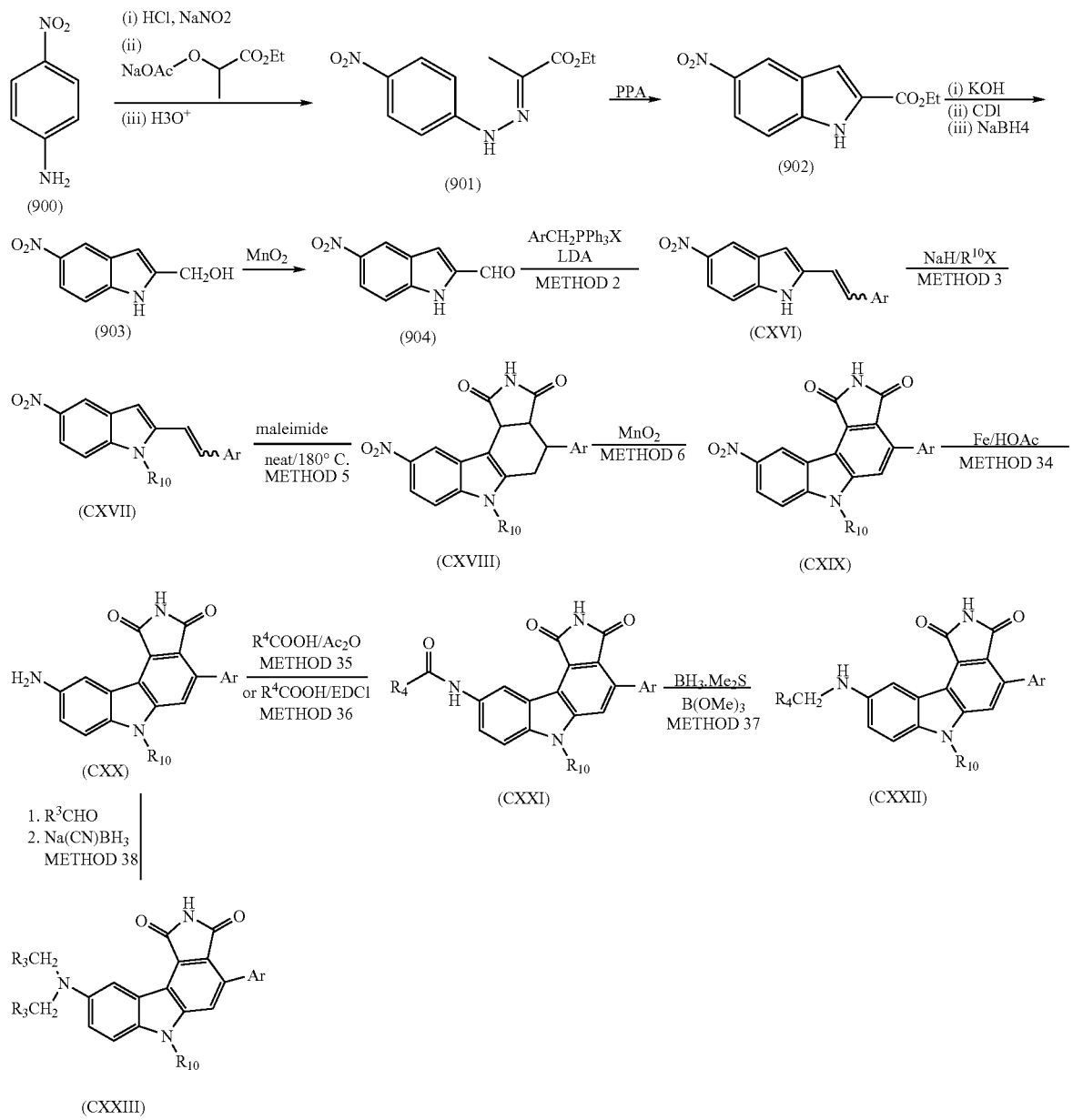

SCHEME 21

Procedures for Scheme 21

EXAMPLE 451

The Preparation of Ethyl (2E)-2-[(4-nitrophenyl)hydrazono]propanoate (901)

A mixture of para-nitroaniline (900) (10.0 g, 72.0 mmol), ice (72 g), and 15% hydrochloric acid (72 mL) was treated with a solution of sodium nitrite (5.4 g, 78.0 mmol) in water (15 mL) at such a rate that the temperature did not exceed 7° C. The reaction mixture was stirred for a further 5 min and then filtered through Celite to give a clear pale yellow/brown solution which was added rapidly to a slurry of sodium acetate (59.0 g, 0.72 mol), ethanol (72 mL), ethyl 2-methylacetoacetate (11.4 mL, 80.0 mmol), and ice (72 g). The resulting red mixture was stirred for 2.5 h and then it was extracted with dichloromethane (3×100 mL). The combined extracts were dried and concentrated to give a red oil (18 g). The red oil was dissolved in ethanol (40 mL) and concentrated hydrochloric acid (15 mL) was added, a fine orange/yellow precipitate formed instantly. The reaction mixture was heated at reflux for 15 min and then it was poured onto ice. The orange/yellow precipitate was collected by filtration and dried to give ethyl (2E)-2-[(4-nitrophenyl)hydrazono]propanoate (901) (15.2 g, 84%). $^1$H NMR δ [(CD$_3$)$_2$SO] 10.50 (s, 1H), 8.20 (m, 2H), 7.40 (m, 2H), 4.23 (q, J=7.2 Hz, 2H), 2.13 (s, 3H), 1.29 (t, J=7 Hz, 3H).

EXAMPLE 452

Ethyl 5-nitro-1H-indole-2-carboxylate (902)

Ethyl (2E)-2-[(4-nitrophenyl)hydrazono]propanoate (901) (10.6 g, 42 mmol) prepared as described in example 451 was heated in polyphosphoric acid (70 g) at 110° C. until no starting material remained by tlc (40 min). Ice (500 g) was added with vigorous stirring, a thick brown precipitate formed which was removed by filtration and dried to give ethyl 5-nitro-1H-indole-2-carboxylate (902) (6.04 g, 61%). This material was used without purification in the next step. $^1$H NMR δ [(CD$_3$)$_2$SO] 12.59 (br, 1H), 8.73 (d, J=2.4 Hz, 1H), 8.13 (dd, J=9.2, 2.4 Hz, 1H), 7.61 (d, J=9.2 Hz, 1H), 7.44 (s, 1H), 4.38 (q, J=7.0 Hz, 2H), 1.36 (t, J=7.0 Hz, 3H).

EXAMPLE 453

The Preparation of (5-Nitro-1H-indol-2-yl)methanol (903)

To a solution of ethyl 5-nitro-1H-indole-2-carboxylate (9.8 g, 42.0 mmol) in methanol (300 mL) was added a solution of 2 M potassium hydroxide (31 mL, 63.0 mmol). The reaction mixture was heated at reflux for 2 h and then the hot solution was filtered, poured onto ice, and acidified. The resultant fine pale brown precipitate was collected by filtration and dried. The crude acid was dissolved in tetrahydrofuran (250 mL) and stirred with 1,1'-carbonyldiimidazole (10.2 g, 63.0 mmol) with gentle warming for 2 h. Water (100 mL) was added and then solid sodium borohydride (7.9 g, 0.21 mol) was added portionwise over 30 min, the reaction mixture was stirred for a further 40 min and then it was quenched with 1 M hydrochloric acid. The tetrahydrofuran was removed at reduced pressure and the residue was dissolved in ethyl acetate, washed, dried, and concentrated to give (5-nitro-1H-indol-2-yl)methanol (903). This material was used without purification in the next step.

EXAMPLE 454

The Preparation of 5-Nitro-1H-indole-2-carbaldehyde (904)

A solution of crude (5-nitro-1H-indol-2-yl)methanol (3.60 g, 18.7 mmol) in chloroform (200 mL) was heated at 50° C. with manganese dioxide (20 g, 0.23 mol) for 3 h. The reaction mixture was then filtered through Celite and concentrated to give 5-nitro-1H-indole-2-carbaldehyde (904) (2.04 g, 57% through two steps). $^1$H NMR δ [(CD$_3$)$_2$SO] 12.64 (br, 1H), 9.96 (s, 1H), 8.83 (d, J=2.3 HZ, 1H), 8.18 (dd, J=9.0 Hz, 2.3 Hz, 1H), 7.69 (d, J=0.7 Hz, 1H), 7.62 (d, J=9.0 Hz, 1H).

EXAMPLE 455

The Preparation of 2-[2-(2-Chlorophenyl)ethenyl]-5-nitro-1H-indole (CXVI; Ar=2-chlorophenyl) (905)

Reaction of the aldehyde (904) prepared as described in example 454 with 2-chlorobenzyltriphenylphosphonium chloride using the procedure described in example 37 (at room temperature) gave the diene (905) as a mixture of E/Z isomers as a yellow solid (95%). Crystallisation from aqueous methanol yielded the pure E-isomer as yellow needles (80%), mp 230–232° C. $^1$H NMR δ [(CD$_3$)$_2$SO] 12.28 (br s, 1H), 8.55 (d, J=2.3 Hz, 1H), 8.03 (dd, J=9.1, 2.3 Hz, 1H), 7.91 (dd, J=7.8, 1.5 Hz, 1H), 7.32–7.61 (m, 6H), 6.92 (s, 1H). Found: C, 64.59; H, 5.68; N, 9.49. C$_{16}$H$_{11}$ClN$_2$O$_2$ requires C, 64.33; H, 5.68; N, 9.49.

EXAMPLE 456

The Preparation of Methyl 2-[2-(5-nitro-1H-indol-2-yl)ethenyl]phenyl ether (CXVI; Ar=2-methoxyphenyl) (906)

Reaction of the aldehyde (904) prepared as described in example 454 with 2-methoxybenzyltriphenylphosphonium bromide using the procedure described in example 37 gave the diene (905) as a mixture of E/Z isomers as a yellow solid (95%) which was used without further purification.

EXAMPLE 457

The Preparation of Methyl 2-[2-(1-methyl-5-nitro-1H-indol-2-yl)ethenyl]phenyl ether (CXVII; Ar=2-methoxyphenyl, R$^{10}$=Me) (907)

Alkylation of diene (906) prepared as described in example 456 with methyl iodide using the procedure described in method3 gave the corresponding diene (908) (94%) as a yellow solid (a mixture of E/Z isomers), which was used without further purification.

EXAMPLE 458

The Preparation of 2-[2-(2-Chlorophenyl)ethenyl]-1-methyl-5-nitro-1H-indole (CXVII; Ar=2-chlorophenyl, R$^{10}$=Me) (908)

Alkylation of diene (905) prepared as described in example 455 with methyl iodide using the procedure described in example 38 gave the corresponding diene (908) (99%) as a yellow solid. A sample was crystallised from methanol as orange needles, mp 161–163° C. $^1$H NMR δ [(CD$_3$)$_2$SO] 8.53 (d, J=2.3 Hz, 1H), 8.05 (dd, J=7.7, 1.6 Hz, 1H), 8.02 (dd, J=9.1, 2.3 Hz, 1H), 7.67 (d, J=9.1 Hz, 1H), 7.46–7.64 (m, 3H), 7.43 (dt, J=7.7, 1.6 Hz, 1H), 7.36 (dt, J=7.7, 1.6 Hz, 1H), 7.22 (s, 1H), 3.95 (s, 3H). Found: C, 65.55; H, 4.19; N, 8.90. C$_{17}$H$_{13}$ClN$_2$O$_2$ requires C, 65.28; H, 4.19; N, 8.96.

EXAMPLE 459

The Preparation of 4-(2-Methoxyphenyl)-6-methyl-9-nitro-4,5,6,10c-tetrahydropyrrolo[3,4-c]carbazole-1,3(2H,3aH)-dione (CXVIII; Ar=2-methoxyphenyl, R$^{10}$=Me) (909)

Reaction of the diene (907) prepared as described in example 457 with maleimide using the procedure described in example 68 gave the adduct (909) (84%) as a glassy solid which was immediately aromatised.

EXAMPLE 460

The Preparation of 4-(2-Chlorophenyl)-6-methyl-9-nitro-4,5,6,10c-tetrahydropyrrolo[3,4-c]carbazole-1,3(2H,3aH)-dione (CXVIII; Ar=2-chlorophenyl, R$^{10}$=Me) (910)

Reaction of the diene (908) prepared as described in example 458 with maleimide using the procedure described in example 68 gave the adduct (910) (88%) as a glassy dark solid which was immediately aromatised.

EXAMPLE 461

The Preparation of 4-(2-Chlorophenyl)-9-nitro-4,5,6,10c-tetrahydropyrrolo[3,4-c]carbazole-1,3(2H,3aH)-dione (CXVIII; Ar=2-chlorophenyl, $R^{10}$=H) (917)

Reaction of the diene (905) prepared as described in example 455 with maleimide using the procedure described in example 68 gave the adduct (917) (74%) as a dark solid which was immediately aromatised.

EXAMPLE 462

The Preparation of 4-(2-Methoxyphenyl)-6-methyl-9-nitropyrrolo[3,4-c]carbazole-1,3(2H,6H)-dione (CXIX; Ar=2-methoxyphenyl, $R^{10}$=Me) (911)

Aromatisation of the adduct (909) prepared as described in example 459 with manganese dioxide using the procedure described in example 79 except that the reaction time was only 4 h gave the nitrocarbazole (911) (50%) as a brown solid mp 320–330° C. (dec.). $^1$H NMR δ [$(CD_3)_2SO$] 11.24 (s, 1H), 9.76 (d, J=2 Hz, 1H), 8.50 (dd, J=9.1, 2.2 Hz, 1H), 7.93 (s, 1H), 7.91 (d, J=9.1 Hz, 1H), 7.46 (t, J=7.3 Hz, 1H), 7.38 (d, J=7.3 Hz, 1H), 7.13 (d, J=7.3 Hz, 1H), 7.08 (t, J=7.3 Hz, 1H), 4.05 (s, 3H), 3.70 (s, 3H). Found: C, 65.76; H, 3.83; N, 9.30. $C_{22}H_{15}N_3O_5$ requires: C, 65.83; H, 3.77; N, 10.47.

EXAMPLE 463

The Preparation of 4-(2-Chlorophenyl)-6-methyl-9-nitropyrrolo[3,4-c]carbazole-1,3(2H,6H)-dione (CXIX; Ar=2-chlorophenyl, $R^{10}$=Me) (912)

Aromatisation of the adduct (910) prepared as described in example 460 with manganese dioxide using the procedure described in example 79 except that the reaction time was only 4 h gave the nitrocarbazole (912) (78%) as an orange solid, mp>320° C. $^1$H NMR δ [$(CD_3)_2SO$] 11.35 (s, 1H) 9.68 (d, J=2.3 Hz, 1H), 8.46 (dd, J=9.1, 2.3 Hz, 1H), 8.00 (s, 1H), 7.88 (d, J=9.1 Hz, 1H) 7.47–7.62 (m, 4H) 4.04 (s, 3H). Found: C, 58.90; H, 3.28; N, 10.30. $C_{21}H_{12}ClN_3O_4 \cdot H_2O$ requires: C, 59.57; H, 3.30; N, 9.93.

EXAMPLE 464

The Preparation of 4-(2-Chlorophenyl)-9-nitropyrrolo[3,4-c]carbazole-1,3(2H,6H)-dione (CXIX; Ar=2-chlorophenyl, $R^{10}$=H (918)

Aromatisation of the adduct (917) prepared as described in example 463 with manganese dioxide using the procedure described in example 79 except that the reaction time was only 4 h gave the nitrocarbazole (918) (84%) as a yellow solid, mp 253–258° C. $^1$H NMR δ [$(CD_3)_2SO$] 12.78 (s, 1H) 11.33 (s, 1H), 9.74 (d, J=2.5 Hz, 1H), 8.45 (dd, J=9.1, 2.5 Hz, 1H), 7.80 (d, J=9.1 Hz, 1H), 7.77 (s, 1H), 7.60 (dd, J=7.2, 1.5 Hz, 1H), 7.45–7.54 (m, 3H). Found: C, 62.39; H, 3.03; N, 10.10. $C_{20}H_{10}ClN_3O_4 \cdot 1/6$ hexane requires: C, 62.22; H, 3.04; N, 10.37

Representative Procedure for Method 34 of Scheme 21

EXAMPLE 465

The Preparation of 9-Amino-4-(2-chlorophenyl)-6-methylpyrrolo[3,4-c]carbazole-1,3(2H,6H)-dione (CXX; Ar=2-chlorophenyl, $R^{10}$=Me) (914)

The nitrocarbazole (912) (0.055 g, 0.14 mmol) prepared as described in example 463 was suspended in a mixture of ethanol:water (4:1, 20 mL) and set at reflux. After 15 min iron powder (0.076 g, 1.4 mmol) was added, followed by acetic acid (0.041 g, 0.70 mmol). The red solution was refluxed for 1 hour, turning a dark colour. The cooled solution was filtered through Celite, washing with ethyl acetate (2×100 mL). The solvent was evaporated under reduced pressure, leaving a brown residue, which was dissolved in ethyl acetate (200 mL). The solution was washed with saturated aqueous sodium bicarbonate and saturated aqueous sodium chloride, then dried and worked up to give the amine (914) as a red solid, mp 208–216° C. $^1$H NMR δ [$(CD_3)_2SO$] 11.00 (s, 1H), 8.15 (d, J=2.2 Hz, 1H), 7.68 (s, 1H), 7.56 (dd, J=7.0, 1.9 Hz, 1H), 7.43–7.49 (m, 4H), 7.02 (dd, J=8.7, 2.2 Hz, 1H), 5.03 (br s, 2H, exchanges with $D_2O$), 3.88 (s, 3H). Found: C, 64.48; H, 3.82; N, 10.32. $C_{21}H_{14}ClN_3O_2 \cdot H_2O$ requires: C, 64.12; H, 4.07; N, 10.68.

EXAMPLE 466

The Preparation of 9-Amino-4-(2-methoxyphenyl)-6-methylpyrrolo[3,4-c]carbazole-1,3(2H,6H)-dione (CXX; Ar=2-methoxyphenyl, $R^{10}$=Me) (913)

The nitrocarbazole (911) prepared as described in example 462 was reduced with iron powder using the procedure described in method 34, to give the amine (913) as a brown solid (74%), mp 188–192° C. $^1$H NMR δ [$(CD_3)_2SO$] 10.87 (s, 1H), 8.14 (d, J=1.7 Hz, 1H), 7.61 (s, 1H), 7.40–7.42 (m, 2H), 7.33 (dd, J=7.3, 1.6 Hz, 1H), 6.98–7.10 (m, 3H), 5.00 (broad s, 2H, exchanges with $D_2O$), 3.86 (s, 3H), 3.68 (s, 3H). Found: C, 69.61; H, 4.66; N, 9.32. $C_{22}H_{17}N_3O_3 \cdot 1/2 C_4H_8O$ requires: C, 69.40; H, 5.06; N, 10.12.

EXAMPLE 467

The Preparation of 9-Amino-4-(2-chlorophenyl)pyrrolo[3,4-c]carbazole-1,3(2H,6H)-dione (CXX; Ar=2-chlorophenyl, $R^{10}$=H) (919)

The nitrocarbazole (918) prepared as described in example 464 was reduced with iron powder using the procedure described in example 465 with a reaction time of 45 min. and the product was precipitated from THF: petroleum ether to give amine (919) as a brown solid (91%), mp 216–222° C. $^1$H NMR δ [$(CD_3)_2SO$] 11.66 (s, 1H), 10.96 (s, 1H), 8.09 (d, J=2.3 Hz, 1H), 7.57 (dd, J=8.1, 1.8 Hz, 1H), 7.40–7.50 (m, 4H), 7.35 (d, J=8.6 Hz, 1H), 6.95 (dd, J=8.6, 2.3 Hz, 1H) 4.95 (br s, 2H). EIMS found: M$^+$=361.0611, 363.0587. $C_{20}H_{12}ClN_3O_2$ requires 361.0818, 363.0589.

Representative Procedure for Method 35 of Scheme 21

EXAMPLE 468

The Preparation of N-[4-(2-Methoxyphenyl)-6-methyl-1,3-dioxo-1,2,3,6-tetrahydropyrrolo[3,4-c]carbazol-9-yl]acetamide (CXXI; Ar=2-methoxyphenyl. $R^{10}$=Me, $R^4$=Me) (916)

Acetic acid (1 mL) and acetic anhydride (1 mL) were mixed under nitrogen at 0° C. and the solution was stirred at 0° C. for 1 hour. A solution of the amine (913) (0.06 g, 0.16 mmol) prepared as described in example 466 in dry dichloromethane was added and the mixture was allowed to warm to room temperature over 2 h and then the solvent evaporated under reduced pressure. The resulting yellow solid was purified by column chromatography on silica gel eluting with petroleum ether:ethyl acetate (100:0 to 0:100). The product (916) was then precipitated from tetrahydrofuran with petroleum ether as a yellow powder (0.044 g, 67%), mp 300–304° C. $^1$H NMR δ [(CD$_3$)$_2$SO] 10.98 (s, 1H), 10.12 (s, 1H), 8.99 (d, J=2.0 Hz, 1H), 7.97 (dd, J=8.8, 2.0 Hz, 1H) 7.74 (s, 1H), 7.66 (d, J=8.8 Hz, 1H), 7.43 (dt, J=7.4, 1.7 Hz, 1H), 7.34 (dd, J=7.4, 1.7 Hz, 1H), 7.12 (d, J=8.1 Hz, 1H), 7.05 (t, J=8.1 Hz, 1H), 3.95 (s, 3H), 3.68 (s, 3H), 2.10 (s, 3H). Found: C, 66.10; H, 4.60; N, 9.44. $C_{24}H_{19}N_3O_4.H_2O$ requires: C, 66.82; H, 4.41; N, 9.74.

EXAMPLE 469

The Preparation of 4-(2-Chlorophenyl)-6-methyl-1, 3-dioxo-1,2,3,6-tetrahydropyrrolo[3,4-c]carbazol-9-ylformamide (CXXI; Ar=2-chlorophenyl, $R^{10}$=Me, $R^4$=H) (920)

Amine (914) prepared as described in example 465 and formic acid were reacted using the procedure described in method35 with a reaction time of 16 h to give the formamide (920) (92%) as a yellow powder, mp 345–348° C. $^1$H NMR δ [(CD$_3$)$_2$SO] 11.16 (s, 0.5H), 11.12 (s, 1H), 10.36 (m, 1.5H), 9.08 (d, J=2.0 Hz, 1H), 8.72 (m, 0.5H), 8.32 (d, J=1.8 Hz, 1H), 7.99 (dd, J=8.8, 2.0 Hz, 1H), 7.85 (s, 0.5H), 7.83 (s, 1H), 7.70–7.73 (m, 1.5H), 7.46–7.60 (m, 7H), 3.98 (s, 1.5H), 3.98 (s, 3H). FABMS found: [M+H]$^+$=404.0790, 406.0779. $C_{22}H_{15}ClN_3O_3$ requires 404.0802, 406.0772.

EXAMPLE 470

The Preparation of 4-(2-Chlorophenyl)-1,3-dioxo-1, 2,3,6-tetrahydropyrrolo[3,4-c]carbazol-9-ylformamide (CXXI; Ar=2-chlorophenyl, $R^{10}$=H, $R^4$=H) (921)

Amine (919) prepared as described in example 467 and formic acid were reacted using the procedure described in example 468 with a reaction time of 4 h to give the formamide (921) (54%) as a yellow powder, mp 293–297° C. $^1$H NMR δ [(CD$_3$)$_2$SO] 12.11 (s, 0.5H), 12.08 (s, 1H), 11.12 (s, 0.5H), 11.08 (s, 1H), 10.34 (s, 1H), 10.30 (s, 0.5H), 9.03 (d, J=1.9 Hz, 1H), 8.69 (m, 0.5H), 8.31 (d, J=1.8 Hz, 1.5H) 7.92 (dd, J=8.8, 1.9 Hz, 1H) 7.42–7.65 (m, 9.5H). Found: C, 64.78; H, 3.53; N, 9.96. $C_{21}H_{12}ClN_3O_3.1/4$ THF requires: C, 64.86; H, 3.44; N, 10.32.

EXAMPLE 471

The Preparation of N-[4-(2-Chlorophenyl)-6-methyl-1,3-dioxo-1,2,3,6-tetrahydropyrrolo[3,4-c]carbazol-9-yl]acetamide (CXXI; Ar=2-chlorophenyl, $R^{10}$=Me, $R^4$=Me) (923)

Amine (914) prepared as described in example 465 and acetic acid were reacted using the procedure described in example 468 with a reaction time of 14 h to give the acetamide (923) (85%) as a yellow powder, mp 338–340° C. $^1$H NMR δ [(CD$_3$)$_2$SO] 11.10 (br s, exchanges with D$_{2O}$, 1H), 10.14 (s, exchanges with D$_2$O, 1H), 9.01 (d, J=2.0 Hz, 1H), 7.99 (dd, J=8.9, 2.0 Hz, 1H), 7.82 (s, 1H), 7.68 (d, J=8.9 Hz, 1H), 7.57 (dd, J=7.2, 1.9 Hz, 1H), 7.44–7.53 (m, 3H), 3.93 (s, 3H), 2.10 (s, 3H). Found: C, 64.44; H, 4.08; N, 8.98. $C_{23}H_{16}ClN_3O_3.1/2CH_3COOH$ requires C, 64.43; H, 4.03; N, 9.39.

EXAMPLE 472

The Preparation of N-[4-(2-Chlorophenyl)-1,3-dioxo-1,2,3,6-tetrahydropyrrolo[3,4-c]carbazol-9-yl] acetamide (CXXI; Ar=2-chlorophenyl, $R^{10}$=H, $R^4$=Me) (926)

Amine (919) prepared as described in example 467 and acetic acid were reacted using the procedure described in example 468 with a reaction time of 4 h to give the acetamide (926) (43%) as a yellow powder, mp 240–245° C. $^1$H NMR δ [(CD$_3$)$_2$SO] 12.04 (br s, 1H), 11.07 (br s, 1H), 10.10 (s, 1H), 8.95 (d, J=2.1 Hz, 1H), 7.90 (dd, J=8.8, 2.1 Hz, 1H), 7.58 (m, 2H), 7.42–7.51 (m, 4H), 2.10 (s, 3H). FABMS found: [M+H]$^+$=404.0787, 406.0776. $C_{22}H_{15}ClN_3O_3$ requires 404.0802, 406.0772.

Representative Procedure for Method 36 of Scheme 21

EXAMPLE 473

The Preparation of N-[4-(2-Chlorophenyl)-6-methyl-1,3-dioxo-1,2,3,6-tetrahydropyrrolo[3,4-c]carbazol-9-yl]-3-(1-piperidinyl)propanamide (CXXI; Ar=2-chlorophenyl, $R^{10}$=Me, $R^4$=3-(1-piperidinyl) propyl) (925)

3-Piperidinylpropanoic acid (0.036 g, 0.23 mmol) and 1-[3-(dimethylamino)propyl]-3-ethylcarbodiimide hydrochloride (0.044g, 0.23 mmol) were combined in dry dimethylformamide (2 mL) at 6° C. under an atmosphere of nitrogen and left to stir for 1 h. A solution of the amine (914) (0.085 g, 0.23 mmol) in dry dimethylformamide (3 mL) was added to the reaction mixture. The solution was allowed to warm to room temperature over 16 h. The solvent was removed under reduced pressure and the residue adsorbed onto silica. Purification by column chromatography eluting with ethyl acetate:methanol:triethylamine (100:0:0 to 75:24:1) yielded (925) as a yellow solid (0.036 g, 30%), mp 241–246° C. $^1$H NMR δ [(CD$_3$)$_2$SO] 11.12 (s, 1H), 10.46 (s, 1H), 9.92 (broad s, 1H), 9.09 (d, J=2.0 Hz, 1H), 7.98 (dd, J=8.9, 2.0 Hz, 1H) 7.83 (s, 1H), 7.71 (d, J=8.9 Hz, 1H), 7.45–7.60 (m, 4H), 3.98 (s, 3H), 3.38 (m, 2H), 3.10 (m, 2H), 2.95 (m, 2H), 1.80 (m, 4H), 1.42 (m, 2H). FABMS found: [M+H]$^+$=515.1842, 517.1833. C$_{29}$H$_{28}$ClN$_4$O$_3$ requires 515.1850, 517.1820.

EXAMPLE 474

The Preparation of N-[4-(2-Chlorophenyl)-6-methyl-1,3-dioxo-1,2,3,6-tetrahydropyrrolo[3,4-c]carbazol-9-yl]-4-(dimethylamino)butanamide hydrochloride (CXXI; Ar=2-chlorophenyl, R$^{10}$=Me, R$^4$=4-dimethylaminobutyl) (928)

Amine (914) prepared as described in example 465 was reacted with EDCI and 4-dimethylaminobutyric acid hydrochloride using the procedure described in example 473 to give the amide (928) (44%) as an orange powder, mp 331–333° C. $^1$H NMR δ [(CD$_3$)$_2$SO] 11.11 (s, 1H), 10.25 (s, 1H), 9.82 (br s, 1H), 9.07 (d, J=2.0 Hz, 1H), 7.98 (dd, J=9.0, 2.0 Hz, 1H), 7.83 (s, 1H), 7.70 (d, J=9.0 Hz, 1H), 7.58 (m, 1H), 7.44–7.52 (m, 3H), 3.97 (s, 3H), 2.99–3.11 (m, 4H), 2.77 (s, 6H), 2.00 (m, 2H). FABMS found: [M+H]$^+$=489.1689, 491.1681. C$_{27}$H$_{26}$ClN$_4$O$_3$ requires 489.1693, 491.1664.

Representative Procedure for Method 37 of Scheme 21

EXAMPLE 475

The Preparation of 4-(2-Chlorophenyl)-6-methyl-9-(methylamino)pyrrolo[3,4-c]carbazole-1,3(2H,6H)-dione (CXXII; Ar=chlorophenyl, R$^{10}$=Me, R$^4$=H) (922)

Borane methylsulphide complex (0.074 mL, 0.78 mmol) and trimethylborate (0.089 mL, 0.78 mmol) were added at 0° C. under an atmosphere of nitrogen to a solution of amide (920) (0.105 g, 0.26 mmol) prepared as described in example 469 dry tetrahydrofuran (10 mL) After stirring at 0° C. for 30 min. the solution was allowed to warm to room temperature over 16 h. Methanol (200 mL) was added and the reaction mixture was stirred for 12 h. The solvent was removed under reduced pressure and the yellow residue was purificatied by column chromatography on silica, eluting with petroleum ether:ethyl acetate (100:0 to 0:100) to give (922) as a red solid (0.053 g, 45%), mp 293–296° C. $^1$H NMR δ [(CD$_3$)$_2$SO] 11.01 (br s, 1H), 8.10 (d, J=2.3 Hz, 1H), 7.69 (s, 1H), 7.57 (dd, J=7.1, 2.0 Hz, 1H), 7.42–7.52 (m, 4H), 7.02 (dd, J=8.8, 2.3 Hz, 1H), 5.61 (q, J=5.2 Hz, 1H), 3.90 (s, 3H), 2.81 (d, J=5.2 Hz, 3H). EIMS found: M$^+$=389.0929, 391.0905. C$_{22}$H$_{16}$ClN$_3$O$_2$ requires 389.0931, 391.0902.

EXAMPLE 476

The Preparation of 4-(2-Chlorophenyl)-9-(ethylamino)-6-methylpyrrolo[3,4-c]carbazole-1,3(2H, 6H)-dione (CXXII; Ar=chlorophenyl, R$^{10}$=Me, R$^4$=Me) (924)

Amide (923) prepared as described in example 471 was reduced with borane methylsulphide complex using the procedure described in method37 to give amine (924) as a red powder, mp 232–236° C. $^1$H NMR δ [(CD$_3$)$_2$SO] 11.00 (s, exchanges with D$_2$O, 1H), 8.13 (d, J=2.2 Hz, 1H), 7.69 (s, 1H), 7.57 (dd, J=7.0, 2.0 Hz, 1H), 7.42–7.51 (m, 4H), 7.05 (dd, J=8.8, 2.2 Hz, 1H), 5.51 (t, J=5.4 Hz, exchanges with D$_2$O, 1H), 3.15 (m, 2H), 1.27 (t, J=7.1 Hz, 3H). EIMS found: M$^+$=403.1080, 405.1061. C$_{23}$H$_{18}$ClN$_3$O$_2$ requires 403.1087, 405.1058.

EXAMPLE 477

The Preparation of 4-(2-chlorophenyl)-9-(methylamino)pyrrolo[3,4-c]carbazole-1,3(2H,6H)-dione (CXXII; Ar=chlorophenyl, R$^{10}$=H, R$^4$=H) (927)

Amide (921) (0.051 g, 0.13 mmol) prepared as described in example 470 was reacted with borane methylsulphide complex using the procedure described in method 37 to give amine (927) (0.021 g, 43%) as an orange powder; m.p. 182–184° C. $^1$H NMR δ [(CD$_3$)$_2$SO] 11.69 (broad s, 1H), 10.97 (broad s, 1H), 8.05 (d, J=2.1 Hz, 1H), 7.40–7.57 (m, 5H), 6.97 (dd, J=8.7, 2.4 Hz, 1H), 5.55 (q, J=4.9 Hz, 1H), 2.80 (d, J=5.2 Hz, 3H). EIMS found: M$^+$=375.0768, 377.0749. C$_{21}$H$_{14}$ClN$_3$O$_2$ requires 375.0774, 377.0745.

Representative Procedure for Method 38 of Scheme 21

EXAMPLE 478

The Preparation of 9-(Dimethylamino)-4-(2-methoxyphenyl)-6-methylpyrrolo[3,4-c]carbazole-1,3(2H,6H)-dione (CXXIII; Ar=methoxyphenyl, R$^{10}$=Me, R$^3$=H) (915)

Amine (913) (0.049 g, 0.13 mmol) prepared as described in example 466 was suspended in methanol (15 m]L) and stirred at 0° C. Formaldehyde (0.01 mL of a 37% aqueous solution, 0.13 mmol) was added followed immediately by sodium cyanoborohydride (0.022 g, 3.5 mmol) portionwise and the mixture was stirred at room temperature for 14 h. The solvent was removed under reduced pressure and the residue dissolved in ethyl acetate (100 mL). The solution was washed with water (2×100 mL), sat. aq. sodium chloride (2×100 mL), then dried over anhydrous sodium sulphate and the solvent evaporated. The residue was chromatographed on silica, eluting with petroleum ether:diethyl ether (100:0 to 0:100) to give (915) as a red solid (0.017 g, 33%), mp 246–251° C. $^1$H NMR δ [(CD$_3$)$_2$SO] 10.92 (s, 1H), 8.39 (d, J=2.5 Hz, 1H), 7.67 (s, 1H), 7.58 (d, J=9.0 Hz, 1H), 7.41 (dt, J=7.4, 1.7 Hz, 1H), 7.37 (dd, J=7.4, 1.7 Hz, 1H), 7.25 (dd, J=9.0, 2.5 Hz, 1H), 7.10 (d, J=7.4 Hz, 1H), 7.04 (t, J=7.4 Hz, 1H) 3.91 (s, 3H), 3.68 (s, 3H), 2.99 (s, 6H). EIMS found M$^+$:399.1580. C$_{24}$H$_{21}$N$_3$O$_3$ requires 399.1583.

SCHEME 22

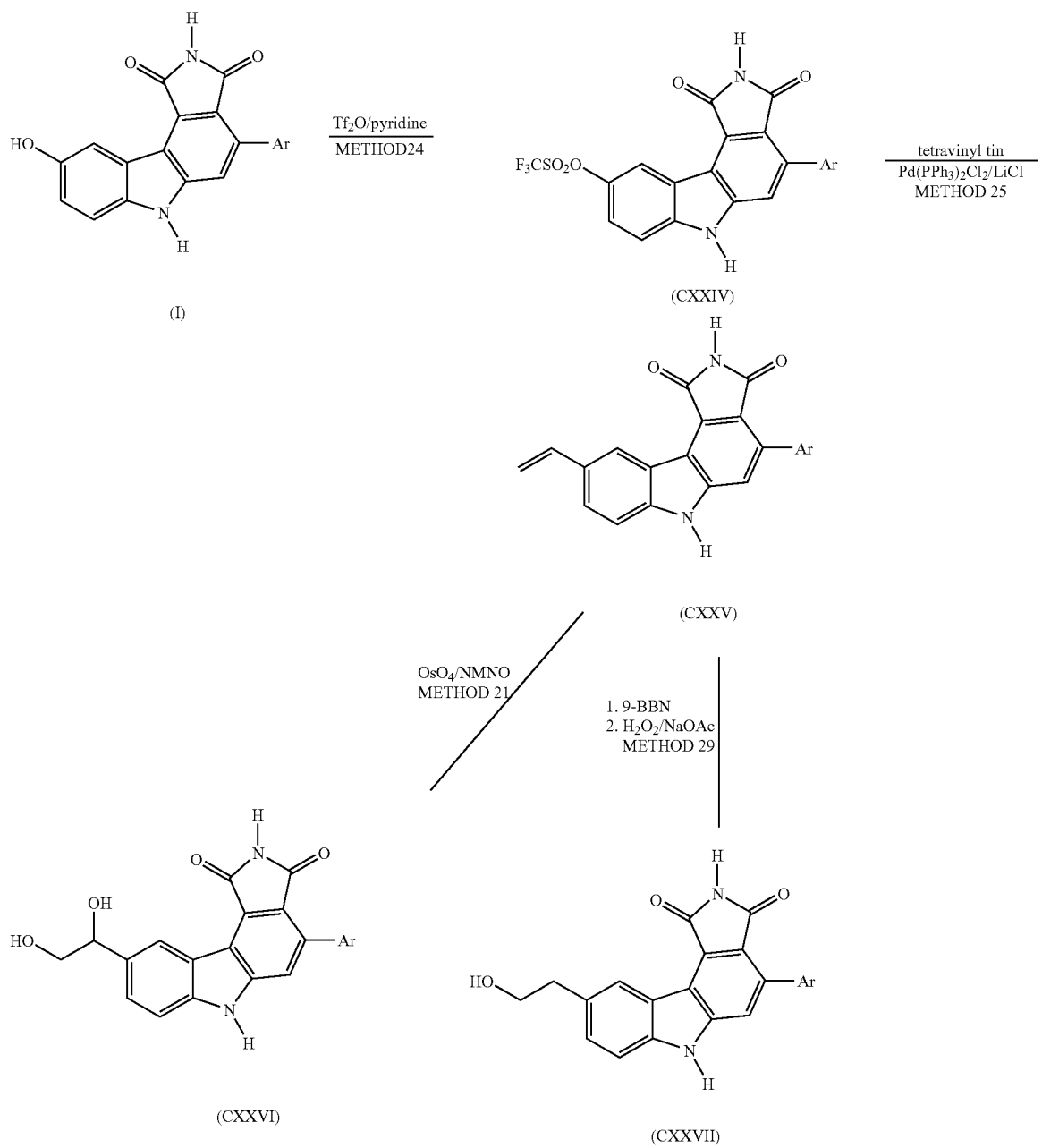

Scheme 22 Procedures

EXAMPLE 479

The Preparation of 4-(2-Chlorophenyl)-1,3-dioxo-1,2,3,6-tetrahydropyrrolo[3,4-c]carbazol-9-yl trifluoromethanesulfonate (CXXIV; Ar=2-chlorophenyl) (615)

Compound (615) was prepared from (9) (I; (Ar=2-chlorophenyl) prepared as described in example 8 using the procedure described in example 307 to give a yellow oil. $^1$H NMR δ [(CD$_3$)$_2$SO] 11.83 (s, 1H), 11.03 (s, 1H), 8.28 (s, 1H), 8.32 (s, 1H), 7.6–7.4 (m, 5H), 7.07 (s, 1H). EIMS found: M$^+$=493.9946. C$_{21}$H$_{10}$ClF$_3$N$_2$SO$_5$ requires 493.9951.

EXAMPLE 480

The Preparation of 4-(2-Chlorophenyl)-9-vinylpyrrolo[3,4-c]carbazole-1,3(2H,6H)-dione (CXXV; Ar=2-chlorophenyl) (616)

Compound (616) was prepared from (615) prepared as described in example 479 (using the procedure described in example 309, with tetraethyl tin as the stannane to give a yellow oil. $^1$H NMR δ [(CD$_3$)$_2$SO] 11.71 (s, 1H), 11.48 (br, 1H), 8.23 (s, 1H), 8.78, (s, 1H), 7.99 (s, 1H), 7.62–7.43 (m, 5H), 7.2–7.1 (m, 1H), 6.10 (d, J=17.6 Hz, 1H), 5.46 (d, J=11.3 Hz, 1H). EIMS found: M$^+$=372.0661. C$_{22}$H$_{13}$ClN$_2$O$_2$ requires 372.0666.

EXAMPLE 481

The Preparation of 4-(2-Chlorophenyl)-9-(1,2-dihydroxyethyl)pyrrolo[3,4-c]carbazole-1,3(2H,6H)-dione (CXXVI; Ar=2-chlorophenyl) (617)

The diol (617) was prepared from (616) prepared as described in example 480 using the procedure described in example 300 to give a yellow solid, mp 265–268° C. $^1$H NMR δ [(CD$_3$)$_2$SO] 12.06 (br, 1H), 11.08 (br, 1H), 8.87 (s, 1H), 7.60–7.40 (m, 7H), 5.32 (d, J=3.8 Hz, 1H), 4.74 (m, 2H), 3.55 (m, 2H). EIMS found: M$^+$=406.0718. C$_{22}$H$_{15}$ClN$_2$O$_4$ requires 406.0720.

EXAMPLE 482

The Preparation of 4-(2-Chlorophenyl)-9-(2-Hydroxyethyl)pyrrolo[3,4-c]carbazole-1,3(2H,6H)-dione (CXXVII; Ar=2-chlorophenyl) (618)

Compound (618) was prepared from (616) prepared as described in example 480 using the procedure described in example 344 to give a yellow solid, mp 253–257° C. $^1$H NMR δ [(CD$_3$)$_2$SO] 12.03 (br, 1H), 11.08 (br, 1H), 8.73 (s, 1H), 7.60–7.40 (m, 6H), 4.69 (t, J=5.2 Hz, 1H), 3.71 (m, 2H), 2.93 (t, J=7.2 Hz, 2H). EINS found: M$^+$=390.0769. C$_{22}$H$_{15}$ClN$_2$O$_3$ requires 390.0771.

EXAMPLE 483

Other Novel Checkpoint Inhibitors

Listed below are other checkpoint inhibitors of the present invention which may be prepared by process known in the art, processes described herein-above, or a combination of said processes. One of skill in the art will understand how each compound is prepared by reference to the disclosure herein.

| COMPOUND NAME | MP (deg C) | APCI (pos) Found Mass |
|---|---|---|
| 4-(4-Amino-2-methoxy-phenyl)-9-hydroxy-6H-pyrrolo[3,4-c]carbazole-1,3-dione | 308–316 | |
| N-[4-(2-Chloro-phenyl)-1,3-dioxo-1,2,3,6-tetrahydro-pyrrolo[3,4-c]carbazol-9-yl]-acetamide | 240–245 | |
| N-[4-(2-Chloro-phenyl)-6-methyl-1,3-dioxo-1,2,3,6-tetrahydro-pyrrolo[3,4-c]carbazol-9-yl]-4-dimethylamino-butyramide | | 488/450 |
| 4-(2-Chloro-phenyl)-9-methylamino-6H-pyrrolo[3,4-c]carbazole-1,3-dione | 182–184 | |
| 9-Hydroxy-4-(2-methoxy-4-nitro-phenyl)-6H-pyrrolo[3,4-c]carbazole-1,3-dione | 242–244 | |
| 4-(2-Chloro-phenyl)-9-hydroxy-8-(4-morpholin-4-yl-butyl)-6H-pyrrolo[3,4-c]carbazole-1,3-dione; hydrochloride salt | 191–193 | |
| 4-(2-Chloro-phenyl)-8-[3-(3,5-dimethyl-piperazin-1-yl)-propoxy]-9-hydroxy-6-methyl-6H-pyrrolo[3,4-c]carbazole-1,3-dione | 252–254 | |
| 4-(2-Chloro-phenyl)-9-hydroxy-8-(3-hydroxy-propoxy)-6-methyl-6H-pyrrolo[3,4-c]carbazole-1,3-dione | 285–288 | |
| 4-(2-Chloro-phenyl)-8-(4-hydroxy-butoxy)-6-methyl-6H-pyrrolo[3,4-c]carbazole-1,3-dione | 221–223 | |
| 4-(2-Chloro-phenyl)-8-(3,4-dihydroxy-butoxy)-6-methyl-6H-pyrrolo[3,4-c]carbazole-1,3-dione | 240–243 | |
| 4-(2-Chloro-phenyl)-6-methyl-8-(4-methylamino-butoxy)-6H-pyrrolo[3,4-c]carbazole-1,3-dione | 204–208 | |
| Acetic acid 4-(2-chloro-phenyl)-1,3-dioxo-1,2,3,6-tetrahydro-pyrrolo[3,4-c]carbazol-9-yl ester | 293–296 | |
| 4-(2-Chloro-phenyl)-9-hydroxy-8-(4-methylamino-butyl)-6H-pyrrolo[3,4-c]carbazole-1,3-dione | 212–214 | |
| 2-(9-Hydroxy-1,3-dioxo-1,2,3,6-tetrahydro-pyrrolo[3,4-c]carbazol-4-yl)-benzamide | 330–334 | |
| 4-(2-Chloro-phenyl)-6-methyl-8-piperidin-3-yl-6H-pyrrolo[3,4-c]carbazole-1,3-dione | | 444.1/446.1 |
| 8-(3-Amino-pyrrolidine-1-carbonyl)-4-(2-chloro-phenyl)-6-methyl-6H-pyrrolo[3,4-c]carbazole-1,3-dione;hydrochloride salt | | 473/475 |
| 4-(2-Chloro-phenyl)-9-pyridin-2-yl-6H-pyrrolo[3,4-c]carbazole-1,3-dione | 295–297 | |
| 4-(2-Chloro-phenyl)-9-pyridin-4-yl-6H-pyrrolo[3,4-c]carbazole-1,3-dione | 266–269 | |
| 4-(2-Chloro-phenyl)-8-(3-dimethylamino-propoxy)-9-hydroxy-6-(2-hydroxy-ethyl)-6H-pyrrolo[3,4-c]carbazole-1,3-dione | 243–245 | |
| 4-(2-Chloro-phenyl)-6-methyl-9-pyridin-2-yl-6H-pyrrolo[3,4-c]carbazole-1,3-dione | 257–259 | |
| 4-(2-Chloro-phenyl)-9-hydroxy-6-(2-hydroxy-ethyl)-8-(3-pyrrolidin-1-yl-propoxy)-6H-pyrrolo[3,4-c]carbazole-1,3-dione | 244–247 | |

| COMPOUND NAME | MP (deg C) | APCI (pos) Found Mass |
|---|---|---|
| N-[4-(2-Chloro-phenyl)-1,3-dioxo-1,2,3,6-tetrahydro-pyrrolo[3,4-c]carbazol-9-yl]-3-piperidin-1-yl-propionamide | 300–310 | |
| 4-(2-Chloro-phenyl)-9-hydroxy-6-methyl-8-(3-methylamino-propoxy)-6H-pyrrolo[3,4-c]carbazole-1,3-dione | 255–258 (dec) | |
| 4-(2-Chloro-phenyl)-8-(4-hydroxy-but-1-enyl)-6-methyl-6H-pyrrolo[3,4-c]carbazole-1,3-dione | 280–283 | |
| 4-(2-Chloro-phenyl)-8-(4-hydroxy-butyl)-6-methyl-H-pyrrolo[3,4-c]carbazole-1,3-dione | 269–272 | |
| 4-(2-Chloro-phenyl)-8-(3-dimethylamino-propoxy)-9-hydroxy-6-(3-hydroxy-propyl)-6H-pyrrolo[3,4-c]carbazole-1,3-dione | 180–183 | |
| 6-(3-Bromo-propyl)-4-(2-chloro-phenyl)-8-(3-dimethylamino-propoxy)-9-hydroxy-6H-pyrrolo[3,4-c]carbazole-1,3-dione | 296–300 (dec) | |
| 4-(2-Chloro-phenyl)-8-(4-dimethylamino-3-hydroxy-butoxy)-6-methyl-6H-pyrrolo[3,4-c]carbazole-1,3-dione;hydrochloride salt | 228–233 | |
| 4-(2-Chloro-phenyl)-8-hydroxy-6-(3-hydroxy-propyl)-6H-pyrrolol[3,4-c]carbazole-1,3-dione | 283–288 | |
| 4-(2-Chloro-phenyl)-8-(4-dimethylamino-butyl)-6-methyl-6H-pyrrolo[3,4-c]carbazole-1,3-dione | 258–262 | |
| 4-(2-Chloro-phenyl)-6-methyl-8-(4-pyrrolidin-1-yl-butyl)-6H-pyrrolo[3,4-c]carbazole-1,3-dione | 231–234 | |
| 4-(2-Chloro-phenyl)-6-methyl-8-(4-methylamino-butyl)-6H-pyrrolo[3,4-c]carbazole-1,3-dione | 232–236 | |
| 4-(2-Chloro-phenyl)-9-hydroxy-6-(3-hydroxy-propyl)-8-(3-pyrrolidin-1-yl-propoxy)-6H-ppyrrolo[3,4-c]carbazole-1,3-dione | 252–254 | |
| 4-(2-Chloro-phenyl)-8-[3-(3,5-dimethyl-piperazin-1-yl)-propoxy]-9-hydroxy-6-(3-hydroxy-propyl)-6H-pyrrolo[3,4-c]carbazole-1,3-dione | 210–215 (dec) | |
| 4-(2-Chloro-phenyl)-9-hydroxy-8-(4-hydroxy-butyl)-6-methyl-6H-pyrrolo[3,4-c]carbazole-1,3-dione | 287–289 | |
| 8-{3-[Bis-(2-hydroxy-ethyl)-amino]-propoxy}-4-(2-chloro-phenyl)-9-hydroxy-6-methyl-6H-pyrrolo[3,4-c]carbazole-1,3-dione | 129–132 | |
| 4-(2-Chloro-phenyl)-9-hydroxy-6-(3-hydroxy-propyl)-8-[3-(4-methyl-piperazin-1-yl)-propoxy]-6H-pyrrolo[3,4-c]carbazole-1,3-dione | 186–191 (dec) | |
| 4-(2-Chloro-phenyl)-6-(3-hydroxy-propyl)-9-nitro-6H-pyrrolo[3,4-c]carbazole-1,3-dione | 268–272 | |
| 9-Amino-4-(2-chloro-phenyl)-6-(3-hydroxy-propyl)-6H-pyrrolo[3,4-c]carbazole-1,3-dione | 230 (dec) | |
| 3-[4-(2-Chloro-phenyl)-9-nitro-1,3-dioxo-2,3-dihydro-1H-pyrrolo[3,4-c]carbazol-6-yl]-propionic acid | 256–258 | |
| 4-(2-Chloro-phenyl)-9-hydroxy-8-(4-hydroxy-butoxy)-6-methyl-6H-pyrrolol3,4-c]carbazole-1,3-dione | 225–227 | |
| 4-(2-Chloro-phenyl)-6-(3-hydroxy-propyl)-8-methoxy-6H-pyrrolo[3,4-c]carbazole-1,3-dione | 255–257 | |
| 4-(2-Chloro-phenyl)-9-fluora-8-methaxy-6-methyl-6H-pyrrola[3,4-c]carbazole-1,3-dione | 347–351 | |
| 4-(2-Chloro-phenyl)-9-fluoro-8-hydroxy-6-methyl-6H-pyrrolo[3,4-c]carbazole-1,3-dione | 305–310 | |
| 4-(2-Chloro-phenyl)-8-(3-dimethylamino-propoxy)-6-(3-hydroxy-propyl)-6H-pyrrolo[3,4-c]carbazole-1,3-dione | 208–211 | |
| 4-(2-Chloro-phenyl)-6-(3-hydroxy-propyl)-8-(3-pyrrolidin-1-yl-propoxy)-6H-pyrrolo[3,4-c]carbazole-1,3-dione | 208–210 | |
| 4-(2-Chloro-phenyl)-9-fluoro-8-(3-hydroxy-propoxy)-6-methyl-6H-pyrrolo[3,4-c]carbazole-1,3-dione | 311–315 | |
| 4-(2-Chloro-phenyl)-9-fluora-6-methyl-8-(3-methylamino-propoxy)-6H-pyrrolo[3,4-c]carbazole-1,3-dione | 317–321 | |
| 4-(2-Chloro-phenyl)-9-hydroxy-6-methyl-8-(4-morpholin-4-yl-butyl)-6H-pyrrolo[3,4-c]carbazole-1,3-dione | 257–260 | |
| 4-(2-Chloro-phenyl)-9-fluoro-6-methyl-8-(3-pyrralidin-1-yl-propoxy)-6H-pyrrolo[3,4-c]carbazole-1,3-dione | 270–273 | |

-continued

| COMPOUND NAME | MP (deg C) | APCI (pos) Found Mass |
|---|---|---|
| 4-(2-Chloro-phenyl)-9-hydroxy-6-(2-hydroxy-ethyl)-8-[3-(4-methyl-piperazin-1-yl)-propoxy]-6H-pyrrolo[3,4-c]carbazole-1,3-dione | 177–183 (dec) | |
| 4-(2-Chloro-phenyl)-8-(3-diethylamino-propoxy)-9-hydroxy-6-(2-hydroxy-ethyl)-6H-pyrrolo[3,4-c]carbazole-1,3-dione | 165–167 (dec) | |
| 4-(2-Chloro-phenyl)-8-(3-dimethylamino-propoxy)-9-fluoro-6-methyl-6H-pyrrolo[3,4-c]carbazole-1,3-dione | 272–275 | |
| N-[4-(2-Chloro-phenyl)-6-(3-hydroxy-propyl)-1-methylene-3-oxo-1,2,3,6-tetrahydra-pyrrolo[3,4-c]carbazal-9-yl]-formamide | 193–196 | |
| 4-(2-Chloro-phenyl)-6-methyl-8-pyridin-4-yl-6H-pyrrolo[3,4-c]carbazole-1,3-dione | | 438.1 |
| 4-(2-Chloro-phenyl)-9-hydroxy-6-(3-hydroxy-propyl)-8-piperidin-4-yl-6H-pyrrolo[3,4-c]carbazole-1,3-dione | | 504/506 |
| 8-(3-(R)-Amino-pyrrolidine-1-carbonyl)-4-(2-chloro-phenyl)-6-methyl-6H-pyrrolo[3,4-c]carbazole-1,3-dione; hydrochloride salt | | 473.1 |
| 8-(3-(S) Amino-pyrrolidine-1-carbonyl)-4-(2-chloro-phenyl)-6-methyl-6H-pyrrolo[3,4-]carbazole-1,3-dione; hydrochloride salt | | 473.1 |
| 4-(2-Chloro-phenyl)-6-methyl-8-piperidin-4-yl-6H-pyrrolo[3,4-c]carbazole-1,3-dione; | | 444.1 |
| 4-(2-Chloro-phenyl)-6-methyl-8-(piperazine-1-carbonyl)-6H-pyrrolo[3,4-c]carbazole-1,3-dione; hydrochloride salt | | 473/475 |
| 4-(2-Chloro-phenyl)-8-(4-dimethylamino-butyl)-9-hydroxy-6-methyl-6H-pyrrolo[3,4-c]carbazole-1,3-dione | 246–250 | |
| 4-(2-Chloro-phenyl)-9-hydroxy-6-methyl-8-(4-pyrrolidin-1-yl-butyl)-6H-pyrrolo[3,4-c]carbazole-1,3-dione | 250–254 | |
| 4-(2-Chloro-phenyl)-9-hydroxy-6-methyl-8-(4-methylamino-butyl)-6H-pyrrolo[3,4-c]carbazole-1,3-dione | 254 (dec) | |
| [4-(2-Chloro-phenyl)-6-methyl-1,3-dioxo-1,2,3,6-tetrahydro-pyrrolo[3,4-c]carbazol-9-yl]-urea | 300 (dec) | |
| 4-(2-Chloro-phenyl)-9-hydroxy-8-(3-hydroxy-2-methyl-propoxy)-6-methyl-6H-pyrrolo[3,4-c]carbazole-1,3-dione | 264–266 | |
| 4-(2-Chloro-phenyl)-8-(4-dimethylamino-butoxy)-9-hydroxy-6-methyl-6H-pyrrolo[3,4-c]carbazole-1,3-dione | 224–226 | |
| 4-(2-Chloro-phenyl)-6-(3-methoxy-propyl)-8-piperidin-3-yl-6H-pyrrolo[3,4-c]carbazole-1,3-dione; hydrochloride salt | | 502.2 |
| 4-(2-Chloro-phenyl)-6-(3-hydroxy-propyl)-8-(3-methylamino-propoxy)-6H-pyrrolo[3,4-c]carbazole-1,3-dione | 208–214 | |
| 9-Bromo-4-(2-chloro-phenyl)-6-(3-hydroxy-propyl)-8-(3-methylamino-propoxy)-6H-pyrrolo[3,4-c]carbazole-1,3-dione | 190–196 | |
| 4-[4-(2-Chloro-phenyl)-6-methyl-1,3-dioxo-1,2,3,6-tetrahydro-pyrrolo[3,4-c]carbazol-8-ylmethyl]-piperidine-1-carboxylic acid tert-butyl ester | 221–224 | |
| 4-(2-Chloro-phenyl)-6-methyl-8-piperidin-4-ylmethyl-6H-pyrrolo[3,4-c]carbazole-1,3-dione | 265–270 | |
| 4-(2-Chloro-phenyl)-6-(3-methoxy-propyl)-8-piperidin-4-yl-6H-pyrrolo[3,4-c]carbazole-1,3-dione; hydrochloride salt | | 502.1 |
| 4-(2-Chloro-phenyl)-6-(3-hydroxy-propyl)-8-piperidin-3-yl-6H-pyrrolo[3,4-c]carbazole-1,3-dione; hydrochloride salt | | 488.2 |
| 4-(2-Chloro-phenyl)-6-(3-hydroxy-propyl)-8-piperidin-4-yl-6H-pyrrolo[3,4-c]carbazole-1,3-dione; hydrochloride salt | | 488.1 |
| 4-(2-Chloro-phenyl)-6-methyl-8-(perhydro-1,4-diazepine-1-carbonyl)-6H-pyrrolo[3,4-c]carbazole-1,3-dione; hydrochloride salt | | 487/489 |
| 4-(2-Chloro-phenyl)-9-hydroxy-6-methyl-8-[4-(4-methyl-piperazin-1-yl)-butyl]-6H-pyrrolo[3,4-c]carbazole-1,3-dione | 247–250 | |

-continued

| COMPOUND NAME | MP (deg C) | APCI (pos) Found Mass |
|---|---|---|
| 4-(2-Chloro-phenyl)-9-hydroxy-6-methyl-8-(4-pyrrolidin-1-yl-butoxy)-6H-pyrrolo[3,4-c]carbazole-1,3-dione | 243–245 (dec) | |
| 4-(2-Chloro-phenyl)-8-[4-(3,5-dimethyl-piperazin-1-yl)-butoxy]-9-hydroxy-6-methyl-6H-pyrrolo[3,4-c]carbazole-1,3-dione | 223–225 | |
| 4-(2-Chloro-phenyl)-6-methyl-1,3-dioxo-1,2,3,6-tetrahydro-pyrrolo[3,4-c]carbazole-8-carboxylic acid (2-dimethylamino-ethyl)-methyl-amide; compound with trifluoro-acetic acid | | 488/490 |
| 8-((S)-3-Amino-pyrrolidine-1-carbonyl)-4-(2-chloro-phenyl)-6-(2-hydroxy-ethyl)-6H-pyrrolo[3,4-c]carbazole-1,3-dione; hydrobromide salt | | 503.1 |
| 4-(2-Chloro-phenyl)-6-(2-hydroxy-ethyl)-8-piperidin-4-yl-6H-pyrrolo[3,4-c]carbazole-1,3-dione; hydrobromide salt | | 474.2 |
| 9-Amino-4-(2-chloro-phenyl)-6-(2-hydroxy-ethyl)-6H-pyrrolo[3,4-c]carbazole-1,3-dione | 221–224 | |
| 4-(2-Chloro-phenyl)-9-hydroxy-6-methyl-8-[3-(4-methyl-piperazin-1-yl)-propoxy]-6H-pyrrolo[3,4-c]carbazole-1,3-dione | 209–212 | |
| 3-[9-Amino-4-(2-chloro-phenyl)-1,3-dioxo-2,3-dihydro-1H-pyrrolo[3,4-c]carbazol-6-yl]-N-(2-dimethylamino-ethyl)-propionamide | >350 | |
| 3-[4-(2-Chloro-phenyl)-9-formylamino-1,3-dioxo-2,3-dihydro-1 H-pyrrolo[3,4-c]carbazol-6-yl]-N-(2-dimethylamino-ethyl)-propionamide | 240–244 | |
| 9-Amino-4-(2-chloro-phenyl)-7-methoxy-6-methyl-6H-pyrrolo[3,4-c]carbazole-1,3-dione | 318–323 | |
| 3-[4-(2-Chloro-phenyl)-9-hydroxy-1,3-dioxo-8-(3-pyrrolidin-1-yl-propoxy)-2,3-dihydro-1H-pyrrolo[3,4-c]carbazol-6-yl]-propionamide | 246–248 | |
| 4-(2-Chloro-phenyl)-6-methyl-8-pyrrolidin-3-yl-6H-pyrrolo[3,4-c]carbazole-1,3-dione; trifluoroacetic acid salt | | 428/430 |
| 4-(2-Chloro-phenyl)-6-methyl-1,3-dioxo-1,2,3,6-tetrahydro-pyrrolo[3,4-c]carbazole-8-carboxylic acid | | 403/405 NB. apcl(neg) |
| N-[4-(2-Chloro-phenyl)-7-methaxy-6-methyl-1,3-dioxo-1,2,3,6-tetrahydro-pyrrolo[3,4-c]carbazol-9-yl]-formamide | 313–317 | |
| 4-(2-Chloro-phenyl)-7-hydroxy-6-methyl-9-nitro-6H-pyrrolo[3,4-c]carbazole-1,3-dione | >300 | |
| 4-(2-Chloro-phenyl)-9-hydroxy-6-methyl-8-[2-(1-methyl-pyrrolidin-2-yl)-ethaxy]-6H-pyrrolo[3,4-c]carbazole-1,3-dione | 232–235 | |
| 4-(2-Chloro-phenyl)-9-hydroxy-6-methyl-8-[4-(4-methyl-piperazin-1-yl)-butaxy]-6H-pyrrolo[3,4-c]carbazole-1,3-dione | 210–212 | |
| 4-(2-Chloro-phenyl)-9-hydroxy-6-methyl-8-(4-morpholin-4-yl-butoxy)-6H-pyrrolo[3,4-c]carbazole-1,3-dione | 212 | |
| N-[4-(2-Chloro-phenyl)-6-(2-hydroxy-ethyl)-1,3-dioxo-1,2,3,6-tetrahydro-pyrrolo[3,4-c]carbazol-9-yl]-formamide | 273–275 | |
| 4-(2-Fluoro-6-methoxy-phenyl)-9-hydroxy-6H-pyrrolo[3,4-c]carbazole-1,3-dione | | 377 |
| N-[4-(2-Chloro-phenyl)-6-(3-hydroxy-propyl)-8-methoxy-1,3-dioxo-1,2,3,6-tetrahydro-pyrrolo[3,4-c]carbazol-9-yl]-acetamide | | 492/494 |
| N-[4-(2-Chloro-phenyl)-6-(3-hydroxy-propyl)-8-methoxy-1,3-dioxo-1,2,3,6-terrahydro-pyrrolo[3,4-c]carbazol-9-yU-formamide | | 478/480 |
| N-[4-(2-Chloro-phenyl)-8-hydroxy-6-(3-hydroxy-propyl)-1,3-dioxo-1,2,3,6-tetrahydro-pyrrolo[3,4-c]carbazol-9-yl]-formamide | | 464/466 |
| 6-Butyl-4-(2-chloro-phenyl)-9-hydroxy-8-(3-pyrrolidin-1-yl-propoxy)-6H-pyrrolo[3,4-c]carbazole-1,3-dione | 222–225 | |
| 8-(3-(S)-Amino-pyrrolidine-1-carbonyl)-4-(2-chloro-phenyl)-6-(3-hydroxy-propyl)-6H-pyrrolo[3,4-c]carbazole-1,3-dione | | 517 |
| 4-(2-Chloro-phenyl)-6-methyl-8-pyrrolidin-2-yl-6H-pyrrolo[3,4-c]carbazole-1,3-dione | | 430/432 |
| 8-(4-Amino-butyl)-4-(2-chloro-phenyl)-6-methyl-6H-pyrrolo[3,4-c]carbazole-1,3-dione | | 432/434 |

-continued

| COMPOUND NAME | MP (deg C) | APCI (pos) Found Mass |
|---|---|---|
| 2-Dimethylamino-ethanesulfonic acid {3-[9-amino-4-(2-chloro-phenyl)-1,3-dioxo-2,3-dihydro-1H-pyrrolo[3,4-c]carbazol-6-yl]-propionyl}-amide | >350 | |
| 2-Dimethylamino-ethanesulfonic acid {3-[4-(2-chloro-phenyl)-9-formylamino-1,3-dioxo-2,3-dihydro-1H-pyrrolo[3,4-c]carbazol-6-yl]-propionyl}-amide | >370 | |
| 4-(2-Chloro-phenyl)-9-hydroxy-6-methyl-8-(2-methyl-3-pyrrolidin-1-yl-propoxy)-6H-pyrrolo[3,4-c]carbazole-1,3-dione | 242–244 | |
| 4-(2-Chloro-phenyl)-9-hydroxy-8-(3-hydroxy-2,2-dimethyl-propoxy)-6-methyl-6H-pyrrolo[3,4-c]carbazole-1,3-dione | 290–293 | |
| 4-(2-Chloro-phenyl)-9-methoxy-6-methyl-1,3-dioxo-1,2,3,6-tetrahydro-pyrrolo[3,4-c]carbazole-8-carboxylic acid | | 435/437 |
| 4-(2-Chloro-phenyl)-9-methoxy-6-methyl-1,3-dioxo-1,2,3,6-tetrahydro-pyrrolo[3,4-c]carbazole-8-carboxylic acid amide | | 434/436 |
| 4-(2-Chloro-phenyl)-9-methoxy-6-methyl-1,3-dioxo-1,2,3,6-tetrahydro-pyrrolo[3,4-c]carbazole-8-carboxylic acid (2-pyrrolidin-1-yl-ethyl)-amide | | 531/533 |
| 4-(2-Chloro-phenyl)-9-hydroxy-6-methyl-1,3-dioxo-1,2,3,6-tetrahydro-pyrrolo[3,4-c]carbazole-8-carboxylic acid | | 419/421 (APCIneg) |
| 4-(2-Chloro-phenyl)-9-hydroxy-6-methyl-1,3-dioxo-1,2,3,6-tetrahydro-pyrrolo[3,4-c]carbazole-8-carboxylic acid amide | | 420/422 |
| 4-(2-Chloro-phenyl)-9-hydroxy-6-methyl-1,3-dioxo-1,2,3,6-tetrahydro-pyrrolo[3,4-c]carbazole-8-carboxylic acid (2-pyrrolidin-1-yl-ethyl)-amide | | 517/519 |
| N-[4-(2-Chloro-phenyl)-7-hydroxy-6-methyl-1,3-dioxo-1,2,3,6-tetrahydro-pyrrolo[3,4-c]carbazol-9-yl]-formamide | >350 | |
| 4-(2-Chloro-phenyl)-6-(2-hydroxy-ethyl)-1,3-dioxo-1,2,3,6-tetrahydro-pyrrolo[3,4-c]carbazole-8-carboxylic acid methyl ester | | 449.1 |
| 4-(2-Chloro-phenyl)-6-methyl-1,3-dioxo-1,2,3,6-tetrahydro-pyrrolo[3,4-c]carbazole-8-carboxylic acid (2-pyrrolidin-1-yl-ethyl)-amide | | 501/503 |
| 3-[4-(2-Chloro-phenyl)-8-(3-dimethylamino-propoxy)-9-hydroxy-1,3-dioxo-2,3-dihydro-1H-pyrrolo[3,4-c]carbazol-6-yl]-propionamide | 235–237 (dec) | |
| 4-(2-Chloro-phenyl)-8-[3-(ethyl-propyl-amino)-propylsulfanyl]-9-hydroxy-6-methyl-6H-pyrrolo[3,4-c]carbazole-1,3-dione | | 520/522 |
| 9-Hydroxy-6-methyl-4-phenyl-8-(3-pyrrolidin-1-yl-propoxy)-6H-pyrrolo[3,4-c]carbazole-1,3-dione | 248–250 | |
| 9-Amino-4-(2-chloro-phenyl)-6-methyl-7-vinyl-6H-pyrrolo[3,4-c]carbazole-1,3-dione | >350 | |
| 4-(2-Chloro-phenyl)-8-(3-(R)dimethylamino-pyrrolidine-1-carbonyl)-6-(2-hydroxy-ethyl)-6H-pyrrolo[3,4-c]carbazole-1,3-dione | | 530.2 |
| N-[4-(2-Chloro-phenyl)-6-methyl-1,3-dioxo-7-vinyl-1,2,3,6-tetrahydro-pyrrolo[3,4-c]carbazol-9-yl]-formamide | 248–254 | |
| N-[4-(2-Chloro-phenyl)-7-(1,2-dihydroxy-ethyl)-6-methyl-1,3-dioxo-1,2,3,6-tetrahydro-pyrrolo[3,4-c]carbazol-9-yl]-formamide | >340 | |
| N-[4-(2-Chloro-phenyl)-9-hydroxy-6-methyl-1,3-dioxo-1,2,3,6-tetrahydro-pyrrolo[3,4-c]carbazole-8-carbonyl]-methanesulfonamide | 310–315 | |
| 2-Dimethylamino-ethanesulfonic acid [4-(2-chloro-phenyl)-9-hydroxy-6-methyl-1,3-dioxo-1,2,3,6-tetrahydro-pyrrolo[3,4-c]carbazole-8-carbonyl]-amide | 285–293 | |
| 4-(2-Chloro-phenyl)-9-hydroxy-6-methyl-1,3-dioxo-1,2,3,6-tetrahydro-pyrrolo[3,4-c]carbazole-8-carboxylic acid dimethylamide | | 448/450 |
| 4-(2-Chloro-phenyl)-9-hydroxy-8-(3-morpholin-4-yl-propoxy)-6H-pyrrolo[3,4-c]carbazole-1,3-dione | 178–184 | |
| 4-(2-Chloro-phenyl)-9-hydroxy-6-methyl-8-(2-pyrrolidin-1-yl-ethoxy)-6H-pyrrolo[3,4-c]carbazole-1,3-dione | 242–244 | |
| 8-(3-Amino-propoxy)-4-(2-chloro-phenyl)-9-hydroxy-6-methyl-6H-pyrrolo[3,4-c]carbazole-1,3-dione; hydrochloride salt | 293–296 | |

-continued

| COMPOUND NAME | MP (deg C) | APCI (pos) Found Mass |
|---|---|---|
| 4-(2-Chloro-phenyl)-9-hydroxy-6-methyl-8-(2-methyl-3-pyrrolidin-1-yl-propoxy)-6H-pyrrolo[3,4-c]carbazole-1,3-dione | 245–248 | |
| 4-(2-Chloro-phenyl)-6-methyl-1,3-dioxo-1,2,3,6-tetrahydro-pyrrolo[3,4-c]carbazole-8-carboxylic acid (2-diethylamino-ethyl)-amide | | 503/505 |
| 4-(2-Chloro-phenyl)-6-methyl-1,3-dioxo-1,2,3,6-tetrahydro-pyrrolo[3,4-c]carbazole-8-carboxylic acid [3-(4-methyl-piperazin-1-yl)-propyl]-amide | | 544/546 |
| 4-(2-Chloro-phenyl)-6-methyl-1,3-dioxo-1,2,3,6-tetrahydro-pyrrolo[3,4-c]carbazole-8-carboxylic acid (3-diethylamino-2-hydroxy-propyl)-amide | | 533/535 |
| 4-(2-Chloro-phenyl)-6-methyl-1,3-dioxo-1,2,3,6-tetrahydro-pyrrolo[3,4-c]carbazole-8-carboxylic acid (3-pyrrolidin-1-yl-propyl)-amide | | 515/517 |
| 4-(2-Chloro-phenyl)-8-(3-(S)-dimethylamino-pyrrolidine-1-carbonyl)-6-(2-hydroxy-ethyl)-6H-pyrrolo[3,4-c]carbazole-1,3-dione; Trifluro acetic acid salt | | 531.2 |
| 4-(2-Chloro-phenyl)-6-(2-hydroxy-ethyl)-1,3-dioxo-1,2,3,6-tetrahydro-pyrrolo[3,4-c]carbazole-8-carboxylic acid (2-pyrrolidin-1-yl-ethyl)-amide | | 531.3 |
| 4-(2-Chloro-phenyl)-6-(2-hydroxy-ethyl)-1,3-dioxo-1,2,3,6-tetrahydro-pyrrolo[3,4-c]carbazole-8-carboxylic acid amide | | 432.1 |
| 4-(2-Chloro-phenyl)-8-(3-dimethylamino-propoxy)-9-hydroxy-6H-pyrrolo[3,4-c]carbazole-1,3-dione | 155–160 (dec) | |
| 4-(2-Chloro-pbenyl)-9-hydroxy-8-[3-(4-methyl-piperazin-1-yl)-propoxy]-6H-pyrrolo[3,4-c]carbazole-1,3-dione | 238–244 | |
| 4-(2-Chloro-phenyl)-9-hydroxy-8-(3-pyrrolidin-1-yl-propoxy)-6H-pyrrolo[3,4-c]carbazole-1,3-dione | 170–175 (dec) | |
| 4-(2-Chloro-phenyl)-9-hydroxy-6-methyl-8-(2-morpholin-4-yl-ethoxy)-6H-pyrrolo[3,4-c]carbazole-1,3-dione | 292–294 | |
| 4-(2-Chloro-phenyl)-9-hydroxy-6-methyl-8-[2-(4-methyl-piperazin-1-yl)-ethoxy]-6H-pyrrolo[3,4-c]carbazole-1,3-dione | 272–274 | |
| N-[4-(2-Chloro-phenyl)-8-methoxy-6-methyl-1,3-dioxo-1,2,3,6-tetrahydro-pyrrolo[3,4-c]carbazol-9-yl]-formamide | 338–342 | |
| 4-(2-Chloro-phenyl)-9-hydroxy-8-(3-hydroxy-propoxy)-6H-pyrrolo[3,4-c]carbazole-1,3-dione | 235–239 | |
| 4-(2-Chloro-phenyl)-9-hydroxy-6-methyl-1,3-dioxo-1,2,3,6-tetrahydro-pyrrolo[3,4-c]carbazole-8-carboxylic acid (2-dimethylamino-ethyl)-methyl-amide | | 505/507 |
| 4-(2-Chloro-phenyl)-9-hydroxy-6-methyl-1,3-dioxo-1,2,3,6-tetrahydro-pyrrolo[3,4-c]carbazole-8-carboxylic acid (1-ethyl-pyrrolidin-2-ylmethyl)-amide | | 531/533 |
| 4-(2-Chloro-phenyl)-9-hydroxy-6-methyl-1,3-dioxo-1,2,3,6-tetrahydro-pyrrolo[3,4-c]carbazole-8-carboxylic acid (3-diethylamino-propyl)-amide | | 533/535 |
| 4-(2-Chloro-phenyl)-9-hydroxy-6-methyl-8-(1H-tetrazol-5-yl)-6H-pyrrolo[3,4-c]carbazole-1,3-dione | | 445/447 |
| 4-(2-Chloro-phenyl)-9-hydroxy-6-methyl-1,3-dioxo-1,2,3,6-tetrahydro-pyrrolo[3,4-c]carbazole-8-carboxylic acid [2-(1-methyl-pyrrolidin-2-yl)-ethyl]-amide | | 531/533 |
| 4-(2-Chloro-phenyl)-9-hydroxy-6-(2-hydroxy-ethyl)-8-(3-[(2-hydroxy-ethyl)-methyl-amino]-propoxy)-6H-pyrrolo[3,4-c]carbazole-1,3-dione | | 538/540 |
| 4-(2-Chloro-phenyl)-9-hydroxy-8-{3-[(2-hydroxy-ethyl)-methyl-amino]-propoxy}-6-methyl-6H-pyrrolo[3,4-c]carbazole-1,3-dione | | 508/510 |
| 4-(2-Chloro-phenyl)-9-hydroxy-6-(2-hydroxy-ethyl)-8-(3-piperidin-1-yl-propoxy)-6H-pyrrolo[3,4-c]carbazole-1,3-dione | | 548/550 |
| 4-(2-Chloro-phenyl)-9-hydroxy-6-methyl-8-(3-piperidin-1-yl-propoxy)-6H-pyrrolo[3,4-c]carbazole-1,3-dione | | 518/520 |
| 8-[3-(Benzyl-methyl-amino)-propoxy]-4-(2-chloro-phenyl)-9-hydroxy-6-(2-hydroxy-ethyl)-6H-pyrrolo[3,4-c]carbazole-1,3-dione | | 584/586 |

-continued

| COMPOUND NAME | MP (deg C) | APCI (pos) Found Mass |
|---|---|---|
| 8-[3-(Benzyl-methyl-amino)-propoxy]-4-(2-chloro-phenyl)-9-hydroxy-6-methyl-6H-pyrrolo[3,4-c]carbazole-1,3-dione | | 554/556 |
| 4-(2-Chloro-phenyl)-9-hydroxy-6-(2-hydroxy-ethyl)-8-[3-(4-pyridin-2-yl-piperazin-1-yl)-propoxy]-6H-pyrrolo[3,4-c]carbazole-1,3-dione | | 626/628 |
| 4-(2-Chloro-phenyl)-9-hydroxy-6-methyl-8-[3-(4-pyridin-2-yl-piperazin-1-yl)-propoxyl-6H-pyrrolo[3,4-c]carbazole-1,3-dione | | 596/598 |
| 4-(2-Chloro-phenyl)-8-(3-dipentylamino-propoxy)-9-hydroxy-6-(2-hydroxy-ethyl)-6H-pyrrolo[3,4-c]carbazole-1,3-dione | | 620/622 |
| 4-(2-Chloro-phenyl)-8-(3-dipentylamino-propoxy)-9-hydroxy-6-methyl-6H-pyrrolo[3,4-c]carbazole-1,3-dione | | 590/592 |
| 4-(2-Chloro-phenyl)-8-{3-[(2-dimethylamino-ethyl)-methyl-amino]-propoxy}-9-hydroxy-6-(2-hydroxy-ethyl)-6H-pyrrolo[3,4-c]carbazole-1,3-dione | | 565/567 |
| 4-(2-Chloro-phenyl)-8-{3-[(2-dimethylamino-ethyl)-methyl-amino]-propoxy}-9-hydroxy-6-methyl-6H-pyrrolo[3,4-c]carbazole-1,3-dione | | 535/537 |
| 4-(2-Chloro-phenyl)-9-hydroxy-6-(2-hydroxy-ethyl)-8-[3-(3-hydroxy-pyrrolidin-1-yl)-propoxy]-6H-pyrrolo[3,4-c]carbazole-1,3-dione | | 550/552 |
| 4-(2-Chloro-phenyl)-9-hydroxy-8-[3-(3-hydroxy-pyrrolidin-1-yl)-propoxyl-6-methyl-6H-pyrrolo[3,4-c]carbazole-1,3-dione | 520/522 | |
| 4-(2-Chloro-phenyl)-8-[3-(cyclohexyl-methyl-amino)-propoxy]-9-hydroxy-6-(2-hydroxy-ethyl)-6H-pyrrolo[3,4-c]carbazole-1,3-dione | | 576/579 |
| 4-(2-Chloro-phenyl)-8-[3-(cyclohexyl-methyl-amino)-propoxy]-9-hydroxy-6-methyl-6H-pyrrolo[3,4-c]carbazole-1,3-dione | | 546/548 |
| 4-(2-Chloro-phenyl)-9-hydroxy-6-(2-hydroxy-ethyl)-8-[3-(2-methyl-piperidin-1-yl)-propoxy]-6H-pyrrolo[3,4-c]carbazole-1,3-dione | | 562/564 |
| 4-(2-Chloro-phenyl)-9-hydroxy-6-methyl-8-[3-(2-methyl-piperidin-1-yl)-propoxy]-6H-pyrrolo[3,4-c]carbazole-1,3-dione | | 532/534 |
| 4-(2-Chloro-phenyl)-9-hydroxy-6-(2-hydroxy-ethyl)-8-[3-(2-hydroxymethyl-piperidin-1-yl)-propoxy]-6H-pyrrolo[3,4-c]carbazole-1,3-dione | | 578/580 |
| 4-(2-Chloro-phenyl)-9-hydroxy-8-[3-(2-hydroxymethyl-piperidin-1-yl)-propoxy]-6-methyl-6H-pyrrolo[3,4-c]carbazole-1,3-dione | | 548/550 |
| 4-(2-Chloro-phenyl)-9-hydroxy-6-(2-hydroxy-ethyl)-8-[3-(methyl-pyridin-3-ylmethyl-amino)-propoxy]-6H-pyrrolo[3,4-c]carbazole-1,3-dione | | 585/587 |
| 4-(2-Chloro-phenyl)-9-hydroxy-6-methyl-8-[3-(methyl-pyridin-3-ylmethyl-amino)-propoxy]-6H-pyrrolo[3,4-c]carbazole-1,3-dione | | 555/557 |
| 4-(2-Chloro-phenyl)-9-hydroxy-6-(2-hydroxy-ethyl)-8-[3-(2-hydroxymethyl-pyrrolidin-1-yl)-propoxy]-6H-pyrrolo[3,4-c]carbazole-1,3-dione | | 564/566 |
| 4-(2-Chloro-phenyl)-9-hydroxy-8-[3-(2-hydroxymethyl-pyrrolidin-1-yl)-propoxy]-6-methyl-6H-pyrrolo[3,4-c]carbazole-1,3-dione | | 534/536 |
| 4-(2-Chloro-phenyl)-8-[3-(ethyl-methyl-amino)-propoxy]-9-hydroxy-6-(2-hydroxy-ethyl)-6H-pyrrolo[3,4-c]carbazole-1,3-dione | | 522/524 |
| 4-(2-Chloro-phenyl)-8-[3-(ethyl-methyl-amino)-propoxy]-9-hydroxy-6-methyl-6H-pyrrolo[3,4-c]carbazole-1,3-dione | | 492/494 |
| 4-(2-Chloro-phenyl)-8-(3-dipropylamino-propoxy)-9-hydroxy-6-(2-hydroxy-ethyl)-6H-pyrrolo[3,4-c]carbazole-1,3-dione | | 564/566 |
| 4-(2-Chloro-phenyl)-8-(3-dipropylamino-propoxy)-9-hydroxy-6-methyl-6H-pyrrolo[3,4-c]carbazole-1,3-dione | | 534/536 |
| 4-(2-Chloro-phenyU-8-(3-diethylamino-propoxy)-9-hydroxy-6-methyl-6H-pyrrolo[3,4-c]carbazole-1,3-dione | | 506/508 |
| 8-{3-[Bis-(3-methyl-butyl)-amino]-propoxy}-4-(2-chloro-phenyl)-9-hydroxy-6-methyl-6H-pyrrolo[3,4-c]carbazole-1,3-dione | | 590/592 |

| COMPOUND NAME | MP (deg C) | APCI (pos) Found Mass |
|---|---|---|
| 4-(2-Chloro-phenyl)-8-[3-(2,6-dimethyl-piperidin-1-yl)-propoxy]-9-hydroxy-6-(2-hydroxy-ethyl)-6H-pyrrolo[3,4-c]carbazole-1,3-dione | | 576/578 |
| 4-(2-Chloro-phenyl)-8-[3-(2,6-dimethyl-piperidin-1-yl)-propoxy]-9-hydroxy-6-methyl-6H-pyrrolo[3,4-c]carbazole-1,3-dione | | 546/548 |
| 9-Hydroxy-6-(2-hydroxy-ethyl)-4-phenyl-8-(3-pyrrolidin-1-yl-propoxy)-6H-pyrrolo[3,4-c]carbazole-1,3-dione | | 500.2 |
| 4-(2-Chloro-phenyl)-8-(3-dicyclohexylamino-propoxy)-9-hydroxy-6-(2-hydroxy-ethyl)-6H-pyrrolo[3,4-c]carbazole-1,3-dione; trifluoro-acetic acid salt | | 644/646 |
| 4-(2-Chloro-phenyl)-8-(3-diisopropylamino-propoxy)-9-hydroxy-6-(2-hydroxy-ethyl)-6H-pyrrolo[3,4-c]carbazole-1,3-dione; trifluoro-acetic acid salt | | 564/566 |
| 9-Amino-4-(2-chloro-phenyl)-6-methyl-8-(3-pyrrolidin-1-yl-propoxy)-6H-pyrrolo[3,4-c]carbazole-1,3-dione | 285–288 | |
| N-[4-(2-Chloro-phenyl)-6-methyl-1,3-dioxo-8-(3-pyrrolidin-1-yl-propoxy)-1,2,3,6-tetrahydro-pyrrolo[3,4-c]carbazol-9-yl]-formamide | 262–264 | |
| 4-(2-Chloro-phenyl)-9-hydroxy-6-methyl-1,3-dioxo-1,2,3,6-tetrahydro-pyrrolo[3,4-c]carbazole-8-sulfonic acid (2-pyrrolidin-1-yl-ethyl)-amide | | 553/555 |
| 4-(2-Chloro-phenyl)-8-(3-cyclohexylamino-propoxy)-9-hydroxy-6-methyl-6H-pyrrolo[3,4-c]carbazole-1,3-dione | | 532/534 |
| 4-(2-Chloro-phenyl)-9-hydroxy-6-methyl-8-(3-pyrrolidin-1-yl-propane-1-sulfinyl)-6H-pyrrolo[3,4-c]carbazole-1,3-dione | 305–312 (dec) | |
| 4-(2-Chloro-phenyl)-9-hydroxy-6-methyl-8-(3-pyrrolidin-1-yl-propane-1-sulfonyl)-6H-pyrrolo[3,4-c]carbazole-1,3-dione | 252–258 (dec) | |
| 4-(2-Chloro-phenyl)-9-hydroxy-6-(2-hydroxy-ethyl)-8-(4-pyrrolidin-1-yl-butyl)-6H-pyrrolo[3,4-c]carbazole-1,3-dione | 198–203 | |
| 4-(2-Chloro-phenyl)-9-hydroxy-6-(2-hydroxy-ethyl)-8-(4-morpholin-4-yl-butyl)-6H-pyrrolo[3,4-c]carbazole-1,3-dione | 269–272 | |
| 4-(2-Chloro-phenyl)-9-hydroxy-6-(2-hydroxy-ethyl)-8-[4-(4-methyl-piperazin-1-yl)-butyl]-6H-pyrrolo[3,4-c]carbazole-1,3-dione | 196–201 | |
| 4-(2-Chloro-phenyl)-8-[3-(ethyl-propyl-amino)-butoxy]-9-hydroxy-6-methyl-6H-pyrrolo[3,4-c]carbazole-1,3-dione | 238–240 | |
| 4-(2-Chloro-phenyl)-9-hydroxy-6-methyl-8-(1-methyl-3-pyrrolidin-1-yl-propoxy)-6H-pyrrolo[3,4-c]carbazole-1,3-dione | 225–227 | |
| 9-Amino-4-(2-chloro-phenyl)-8-(4-hydroxy-butyl)-6-methyl-pyrrolo[3,4-c]carbazole-1,3-dione | 224–227 | |
| N-[4-(2-Chloro-phenyl)-6-methyl-1,3-dioxo-8-(4-pyrrolidin-1-yl-butyl)-1,2,3,6-tetrahydro-pyrrolo[3,4-c]carbazol-9-yl]-formamide | 252–257 | |
| N-{4-(2-Chloro-phenyl)-6-methyl-8-[4-(4-methyl-piperazin-1-yl)-butyl]-1,3-dioxo-1,2,3,6-tetrahydro-pyrrolo[3,4-c]carbazol-9-yl}-formamide | 270–273 | |
| N-[4-(2-Chloro-phenyl)-6-methyl-8-(4-morpholin-4-yl-butyl)-1,3-dioxo-1,2,3,6-tetrahydro-pyrrolo[3,4-c]carbazol-9-yl]-formamide | 205–209 | |
| 9-Amino-4-(2-chloro-phenyl)-7-(4-hydroxy-butyl)-6-methyl-6H-pyrrolo[3,4-c]carbazole-1,3-dione | 202–208 | |
| N-[4-(2-Chloro-phenyl)-7-(4-hydroxy-butyl)-6-methyl-1,3-dioxo-1,2,3,6-tetrahydro-pyrrolo[3,4-c]carbazol-9-yl]-formamide | 230–243 | |
| N-[4-(2-Chloro-phenyl)-6-methyl-7-(4-morpholin-4-yl-butyl)-1,3-dioxo-1,2,3,6-tetrahydro-pyrrolo[3,4-c]carbazol-9-yl]-formamide | 256–260 | |
| N-{4-(2-Chloro-phenyl)-6-methyl-7-[4-(4-methyl-piperazin-1-yl)-butyl]-1,3-dioxo-1,2,3,6-tetrahydro-pyrrolo[3,4-c]carbazol-9-yl}-formamide | 205–209 | |
| N-[4-(2-Chloro-phenyl)-7-(4-dimethylamino-butyl)-6-methyl-1,3-dioxo-1,2,3,6-tetrahydro-pyrrolo[3,4-c]carbazol-9-yl]-formamide | 257–259 | |

-continued

| COMPOUND NAME | MP (deg C) | APCI (pos) Found Mass |
|---|---|---|
| N-[4-(2-Chloro-phenyl)-6-methyl-1,3-dioxo-7-(4-pyrrolidin-1-yl-butyl)-1,2,3,6-tetrahydro-pyrrolo[3,4-c]carbazol-9-yl]-formamide | 238–240 | |
| 9-Amino-4-(2-chloro-phenyl)-6-methyl-7-(4-morpholin-4-yl-butyl)-6H-pyrrolo[3,4-c]carbazole-1,3-dione | 158–162 (dec) | |
| 9-Amino-4-(2-chloro-phenyl)-6-methyl-7-[4-(4-methyl-piperazin-1-yl)-butyl]-6H-pyrrolo[3,4-c]carbazole-1,3-dione | 162–166 (dec) | |
| 9-Amino-4-(2-chloro-phenyl)-7-(4-dimethylamino-butyl)-6-methyl-6H-pyrrolo[3,4-c]carbazole-1,3-dione | 211–215 | |
| 9-Amino-4-(2-chloro-phenyl)-6-methyl-7-(4-pyrrolidin-1-yl-butyl)-6H-pyrrolo[3,4-c]carbazole-1,3-dione | 204–206 | |

EXAMPLE 484

Wee1 Inhibition Filter Binding Assay (OY) to Test for Wee1 Inhibition Activity This assay provides a measure of inhibitory ability of the test compounds against isolated Wee1 kinase.

The Wee1 kinase assay measures enzyme mediated phosphorylation of tyrosine on a synthetic peptide substrate in the presence of compounds being tested. The assay was carried out in 96-well filter microtiter plates (Millipore #MADP NOB10). Compounds were dissolved and diluted in DMSO, 10 µl 3×EDB buffer (150 mM Tris, pH 8.0, 30 mM NaCl, 30 mM $MgCl_2$, 3 mM DTT), 18 µl water, and 2 µl of drug dilution were added to the test wells and mixed thoroughly, 10 µl of enzyme-substrate mixture was added to the wells. The Wee1 enzyme (human Wee1 kinase aa215-647, Onyx Pharmaceuticals, expressed in and purified from a baculovirus protein expression system) concentration was 0.01 µg/µl and the substrate (Poly Ornithine:Tyrosine (4:1), Sigma Chemical Co.) was 0.6 µg/µl in 1×EDB buffer. The plates were mixed thoroughly for 5 minutes at room temperature. The reaction was started by adding 10 µl of 1×EDB buffer containing 47.5 µM ATP (Sigma) and 0.026 µCi/µl $\gamma$-$^{32}$P-ATP (ICN Biomedicals, Inc.) The plates were mixed at room temperature for 20 minutes. The reaction was stopped by adding 50 µl of ice cold 20% TCA with 0.1 M tetrasodium pyro-phosphate. Plates were incubated on ice or refrigerated at 4° C. for 1 hour. Liquid reaction mixture was removed on a vacuum manifold, and the precipitated phosphorylated substrate was rinsed 5 times with 200 µl ice cold 10% TCA with 0.1 M tetrasodium pyrophosphate. 25 µl liquid scintillation cocktail were added to the membrane bound substrate and the plate read in a Microbeta (Perkin-Elmer) plate reader. Activity of compounds was calculated in comparison to uninhibited control determinations in each assay.

The data shown in Table 3 demonstrates activities ($IC_{50}$) of Wee1 less than 0.1 µM ranging up to 1.65 µM. However, Compound X with the highest Wee1 activity on this table is a representative compound from U.S. Pat. No. 4,912,107. Compound X does not fall within the ambit of this invention either structurally or as a checkpoint abrogator of the present invention. The activity of Compound X against Wee1 kinase in this assay is less potent than the upper limit for the preferred compounds. The data in Table 3 shows that the modification of the core structure leads to unexpected potency in the inhibition of Wee1 kinase and a selectivity of at least 10-fold over the inhibition of the PKC enzyme.

The compounds of the present invention are considered to be suitable for use in an animal to treat cell proliferative diseases either alone or in conjunction with one or more other antineoplastic modalities if the Wee1 activity has an $IC_{50}$ of less than 1 µM in the assay described above. Preferably the compounds have an $IC_{50}$ of less than 0.5 µM and most preferably an $IC_{50}$ of less than 0.1 µM

TABLE 3

Wee1, Chk1 and PKC Activity

| | WEE1OY $IC_{50}$ (µM) | CHK1A $IC_{50}$ (µM) | PKC $IC_{50}$ (µM) |
|---|---|---|---|
| Compound X | 1.65 | 0.297 | 3.6 |
| Compound of Example 94 | 0.263 | 0.056 | 1.8 |
| Compound of Example 80 | 0.006 | 0.167 | 1.49 |
| Compound of Example 68 | 0.011 | 0.435 | 0.48 |
| Compound of Example 369 | 0.428 | >10 | >4 |
| Compound of Example 230 | 0.009 | 4.46 | 1.5 |

EXAMPLE 485

Chk1 Enzyme Inhibition Assay

In order to determine the inhibitory activity of the compounds of the present invention against Chk1, the following assay was performed to measure the inhibition of isolated Chk1 enzyme.

The assay was carried out in round bottom polypropylene 96-well plates (Costar). Compounds were tested in serial dilutions beginning with a high concentration of 50 µM followed by up to nine 3-fold dilutions. Compounds were dissolved and diluted in DMSO. 2 µl of drug were spotted on the bottom of the assay plates, then diluted with 58 µl of Chk1 buffer (20 mM Tris, pH 8.0, 50 mM NaCl, 10% Glycerol, 10 mM $MgCl_2$, 5 mM dithiothreitol), and mixed at room temperature for 1 minute. 20 µl of buffer containing 250 ηg/well Chk1 enzyme (Onyx Pharmaceuticals) and 1 µg/well GST-Cdc25 substrate (Onyx) were added. Contents of the wells were mixed for 1 minute and incubated at room temperature for 10 minutes. 20 µl of buffer containing 20 µM ATP and 0.4 µCi ATP [$\gamma$-$^{33}$P] were added. The contents were mixed for 1 minute and incubated at 30° C. for 30 minutes. The reaction was stopped by adding 50 µl of 120 mM EDTA to each well, except the control wells already containing EDTA. 140 µl of the contents of the wells were transferred to the wells of Reacti-Bind Glutathione Coated White 96-Well Plates (Pierce). Contents were mixed for 1 minute and incubated at room temperature for 1 hour. All of the wells were rinsed three times each with 300 µl PBS and air dried. 200 µl MicroScint 20 (Packard) was put in the wells. Plates were sealed with an adhesive cover and counted in a Top Count Microplate Scintillation counter (Packard). Activity of compounds was calculated in comparison to uninhibited control determinations in each assay.

The data shown in Table 4 demonstrates activities ($IC_{50}$) of Chk1 less than 0.002 µM ranging up to 0.297 µM. However, Compound X with the highest Chk1 activity on this table is a representative compound from U.S. Pat. No. 4,912,107. Compound X does not fall within the ambit of this invention either structurally or as a checkpoint abrogator of the present invention. The activity of Compound X against Chk1 kinase in this assay is less potent than the upper limit for the preferred compounds. The data in Table 4 shows that the modification of the core structure leads to unexpected potency in the inhibition of Chk1 kinase and a selectivity of at least 10-fold over the inhibition of the PKC enzyme.

The compounds of the present invention are considered to be suitable for use in an animal to treat cell proliferative diseases in conjunction with another antineoplastic modality if the Chk1 activity has an $IC_{50}$ of less than 0.275 µM in the assay described above. Preferably the compounds have an $IC_{50}$ of less than 0.2 µM and most preferably an $IC_{50}$ of less than 0.1 µM

TABLE 4

Wee1, Chk1 and PKC Activity

| | WEE1OY $IC_{50}$ (µM) | CHK1A $IC_{50}$ (µM) | PKC $IC_{50}$ (µM) |
|---|---|---|---|
| Compound X | 1.65 | 0.297 | 3.6 |
| Compound of Example 198 | 0.193 | 0.013 | 0.132 |
| Compound of Example 214 | 0.295 | 0.002 | 0.171 |

Some of the compounds of the present invention are dual inhibitors, being selective for inhibiting both Wee1 and Chk1 activity. These compounds may be equal in efficacy to the compounds that selectively inhibit either Wee1 or Chk1 even if the activity against either enzyme is higher than that desired for the single inhibitors. Preferably the dual inhibitors have an $IC_{50}$ of less than 1 µM, more preferably less than 500 nM and most preferably less than 100 nM.

TABLE 5

Dual Inhibitors

| | WEE1OY $IC_{50}$ (µM) | CHK1A $IC_{50}$ (µM) |
|---|---|---|
| Compound of Example 363 | 0.057 | 0.02 |
| Compound of Example 366 | 0.075 | 0.014 |

EXAMPLE 486

Myt-1 Inhibition Scintillation Proximity Assay to Test for Myt-1 Inhibition Activity This assay provides a measure of inhibitory activity of the test compounds against isolated Myt-1 kinase.

The assay was carried out in 96-well SPA (Scintillation Proximity Assay) plates from Wallac. The compounds were tested at 50 µM followed by up to nine 3-fold dilutions (i.e., 50, 16.67, 5.56, 1.85, 0.617, etc.). Drugs were dissolved and diluted in DMSO. 2 µl of drug were spotted on the bottom surface of the wells of the SPA plates. 30 µl of MB buffer (50 mM Tris, pH 8.0, 100 mM NaCl, 0.1% Tween 20, 1 mM $MgCl_2$, 100 µM DTT) containing 27 µM cold ATP were added to each well and then 9 µl of MB buffer with 177.8 ηM Myt-1 enzyme (MW=54.6 kDa). Plates were mixed at room temperature for 1 minute, then incubated at room temperature for 5–15 minutes. 9 µl MHKB buffer (50 mM Tris, pH 8.0, 1 mM $MgCl_2$, 100 µM DTT, 0.1 mM $Na_3VO_4$) with 88.9 ηM Cdc2/B (MW=84.5 kDa) were added, mixed at room temperature for 1 minute. The plates were centrifuged up to 2400 RPM, and incubated for 30 minutes at 30° C. 30 µl MHKB buffer containing 1 µM biotinylated histone H1 (Amersham) peptide substrate (stock: 1 mM) and 10 µCi/µl ATP [$\gamma$-$^{33}$P]) were added. The plates were mixed at room temperature for 1 minute, centrifuged up to 2400 RPM, and incubated for 30 minutes at 30° C. The reaction was stopped with 200 µl stop buffer, 5 mM EDTA and 0.1% Triton X-100 (from 10X stock of 50 mM EDTA and 1.0% Triton X-100 diluted with PBS) with at least 20 µg/ml Streptavidin SPA beads (Amersham) and 50 µM ATP. Plates were sealed with an adhesive cover, mixed by inverting 10 times, and incubated for 10 minutes at room temperature. The plates were centrifuged at 2400 RPM for 15 minutes at room temperature and counted in Wallac Microbeta Trilux counter. Activity of compounds was calculated in comparison to uninhibited control determinations in each assay.

None of the compounds of the present invention had $IC_{50}$ for Myt-1 activity in this assay of less than 10 µM. Since phosphorylation of thr 14 on cdc2 (catalyzed by Myt-1 kinase) is also a checkpoint establishing event, a compound that inhibits both Wee1 kinase and Myt-1 kinase may be a checkpoint abrogator due to its dual inhibitory activity. Lack of Myt-1 inhibition, therefore, rules out the contribnution of Myt-1 to check point abrogation. The absence of significant Myt-1 inhibitory activity of the compounds of the present invention demonstrates the selectivity of theses compounds as Wee1 kinase and Chk1 kinase inhibitors.

EXAMPLE 487

Protein Kinase C (PKC) Assay

The PKC assay provides a measure of inhibitory activity of the test compounds against PKC contained in a rat brain preparation.

Enzyme was prepared from a preparation of rat brain (Promega) 0.5 µg diluted with 1.6 ml of 10 mM Hepes buffer pH 7.5. Reaction buffer was comprised of 150 mM Hepes buffer, 4 mM $CaCl_2$, 15 mM $MgCl_2$, 3 mM EDTA, 3.75 mM EGTA at pH 7.5. Histone substrate was made by dissolving histone H1 (Sigma) in water at 1.5 mg/ml. Phosphatidylserine/diolein liposomes were made by mixing 75 µl of 10 mg/ml phosphatidylserine (Sigma) in $CHCl_3$ with 60 µl of 2.5 mg/ml diolein in $CHCl_3$ (Sigma) in a glass vial and evaporating the $CHCl_3$ under $N_2$. The film was suspended in 1 ml water and sonicated 6×15 sec with a microtip probe at room temperature.

To carry out the assay, 50 µl buffer, 20 µl histone, 20 µl liposomes, and inhibitor or solvent control were added to wells of a 96-well filter plate (Millipore) with enough water, if necessary, to make the final volume 110 µl. 20 µl of enzyme preparation solution were added and incubated for 10 minutes at room temperature. This was followed by the addition of 20 µl of $^{32}$P ATP (75 µM ATP in water, labeled ATP at 25 µCi/ml) which was incubated for 15 minutes at room temperature. The reaction was terminated by the addition of 50 µl of 40% (w/v) trichloroacetic acid. The filters were washed by vacuum filtration with 5×125 µl of ice cold 10% (w/v) trichloroacetic acid. The filters were placed in scintillation fluor and counted to determine precipitated labeled phosphate incorporated into substrate. The percent inhibition was calculated in comparison to the uninhibited controls.

EXAMPLE 488

Cell-Based 96-Well Cdc2 Histone H1 Kinase Assay for G2 Checkpoint Abrogation

This cellular assay is a measure of the effect of the test compounds on the activity of the Cdc2/cyclin B complex on one of its physiological substrates, Histone H1.

HT-29 cells 20,000 per well (NUNCLON™ cat no. 163320 96-well plate) were plated in 171 µl media [Dulbecco's Modified Eagle's Medium 4500 mg/L Glucose (DME High Glucose), 1% penicillin and streptomycin, 2% L-Glutamate, 10% FBS]. The plate was incubated at 37° C. for 24 hours. 9 µl of a 5 µM Adriamycin solution was added to each well (250-nM final concentration) and incubated at 37° C. for an additional 16 hours. Next, 20 µl of 500 ng/mL nocodazole was added per well immediately followed by addition of 5 µl test compound. The plate was incubated at 37° C. for 4 hrs. The plate was removed from the incubator and spun in a Beckman GS-6R Centrifuge for 10 minutes, 800 rpm, 4° C. The media was removed and the plate surface dried by blotting. 100 µL of PBS was added to each well. The plate was spun as above. The PBS was removed from plate and the plate surface was dried. 20 µl of lysis buffer (50 mM Hepes pH 7.5, 250 mM NaCl, 0.1% NP 40, 10 mM β-Glycerophosphate,1 mM NaF,1 mM EDTA,1 mM Pefabloc,1 mM DTT, 0.11 mM sodium orthovanadate, 10 µg/ml Aprotinin, 20 µM Leupeptin) was then added to each well followed by medium-speed rocking at 4° C. for 45 minutes. After lysis, 30 µL of kinase assay buffer (50 mM Hepes, 22 mM MgCl$_2$, 1 mM DTT, 166.7 ng/l Histone H1, 83 µM ATP, 0.033 µCi/µl [γ-$^{33}$P]ATP) was added. The plate was incubated on a 32° C. plate warmer for 25 minutes. The kinase reaction was stopped by adding 80 µl of 100 mM EDTA pH 7.8 to each well. The lysate was harvested onto a pre-wetted Wallac P-30 filtermat (Wallac 1450-523, glass fiber filter with negatively charged P30 active groups size 90×120 mm) using 75 mM H$_3$PO$_4$ for 10 seconds, followed by a 10 second aspiration step. The filtermat was placed in a 75 mM H$_3$PO$_4$ bath and shaken gently for 10 minutes at room temperature, then placed within the fold of a single sheet of paper towel, and subjected to microwaves on high power for 2 to 3 minutes, or until filtermat is dry. The filtermat was placed in a sample bag (Wallac 1450-432), 5-mil nonaqueous scintillation fluid was added to the sample bag and the bag was sealed. The samples were read in a Wallac 1450 MicroBeta Liquid Scintillation Counter. The data shown in Table 6 demonstrate the cellular effect of a Wee1 and/or Chk1 inhibitor on a physiological substrate of cdc2/cyclinB which complex is itself a substrate of Wee1 kinase.

TABLE 6

Histone Kinase Assay

|  | WEE1OY IC$_{50}$ (µM) | CHK1A IC$_{50}$ (µM) | Histone Kinase IC$_{50}$ (µM) |
|---|---|---|---|
| Compound of Example 80 | 0.006 | 0.166 | 0.646 |
| Compound of Example 198 | 0.1933 | 0.013 | 0.798 |
| Compound of Example 363 | 0.057 | 0.023 | 0.505 |

EXAMPLE 489

Procedure for Clonogenic Assays in HT-29 Cells±Adriamycin

This cellular assay is a measure of the toxicity of the test compounds in the absence and presence of DNA damage induced by a conventional chemotherapeutic agent.

HT-29 cells were grown in Dulbecco's Modified Eagle Medium with high glucose, supplemented with 1 mM sodium pyruvate, 2 mM L-glutamine, 16 mM HEPES, 8 mM MOPS, and 10% fetal bovine serum. The cells were incubated at 37° C. in an atmosphere of 5% CO$_2$ and 100% relative humidity.

Two or three T-75 tissue culture flasks were seeded at about 50% confluency in 30 ml media and incubated for approximately 24 hours. Adriamycin (ADR) (dissolved at 5 mM in distilled water (dH$_2$O)) was added to the flasks to a final concentration of 1 uM or 500 nM. One flask received no ADR. The cells were allowed to incubate with the ADR for 1 hour. All flasks were then washed twice with 20 ml media allowed to incubate a further 16 hours in 30 ml media.

The stock agar (3.2% Seaplaque GTG Agarose (BioWhittaker Molecular Applications)) was suspended in distilled water and autoclaved for 20 minutes. The agar was melted prior to use in a microwave oven. The bottom agar was a 1:4 dilution of the stock agar in media with enough fetal bovine serum added to bring the solution to 10%. One microliter was plated in each well of 6-well tissue culture plates and the plates allowed to harden. The cloning agar (a 1:8 dilution of stock agar in media with fetal bovine serum added to 10%) was prepared and held at 40° C. until used.

The cells were trypsinized using Trypsin-EDTA and their concentration adjusted to 75,000 cells per microliter with media. One hundred microliters of each cell suspension were placed into sterile 15 ml plastic centrifuge tubes. Twenty-five microliters of each test compound was added to appropriate tubes, followed by addition of 5 ml of warm cloning agar. The tubes were mixed well and 2 ml of the agar/cell suspension were added to duplicate wells of the 6-well plates that were coated with agar earlier. The plates were swirled and placed in the refrigerator for 5 minutes. After the plates returned to room temperature they were incubated for 10 to 14 days, until colonies were visible. The colonies were stained with INT (p-Iodonitrotetrazolium Violet) (dissolved in dH$_2$O at 1 mg/ml and filter sterilized). One milliliter INT was added to each well and the plates incubated overnight at 37° C., 5% CO$_2$, and 100% relative humidity. The colonies were counted using a Hamamatsu video imaging system and ImageQuant software.

TABLE 7

Clonogenic Assay Data

|  | % of Control Colonies With No DNA Damage | % of Control Colonies With DNA Damage |
|---|---|---|
| Compound of Example 366 (250 nM) | 38% | 2.8% |

EXAMPLE 490

Procedures for Western Blot Determination of Phosphotyrosine 15 on Cdc-2 and Mobility Shift of Myt-1.

These western blot assays measure the phosphorylation state of the physiologic substrate of Wee1: tyrosine 15 on Cdc2 kinase. This is accomplished by means of a phospho-specific antibody whose signal is normalized by comparison to the total amount of Cdc2 detected in the samples. The shift of the Myt-1 protein to a lower mobility on a Western blot is used as a measure of progression into M phase of the cell cycle.

A. Procedure for detecting phosphotyrosine 15, Myt-1 shift and total Cdc-2 from cultured HT-29 cells in response to potential check point abrogators±Adriamycin and/or Nocodazole HT-29 cells were grown in Dulbecco's Modified Eagle Medium with high glucose, supplemented with 1 mM sodium pyruvate, 2 mM L-glutamine, 16 mM HEPES, 8 mM MOPS, and 10% fetal bovine serum. The cells were incubated at 37° C., in 5% $CO_2$, and 100% relative humidity.

Cells were grown and treated in 6-well tissue culture plates. Cells were seeded in 3 mL media at a concentration of 200,000 per mL. Once seeded the cells were allowed to attach 24 hours.

All treatments were done in duplicate wells. The wells that were treated with Adriamycin (ADR) were exposed to 1 µM ADR for 1 hour. ADR was dissolved in sterile distilled water. After the 1 hour incubation the cells were washed twice with 2 ml media and then incubated in 3 ml media for 16 hours. After the 16-hour incubation, the cells were treated with various concentrations of abrogator±Nocodazole (NOC) at 50 ng/ml. Abrogators were dissolved in dimethylsulfoxide (DMSO) at a concentration of 10 mM and diluted with growth medium before being added to the cells and NOC was dissolved at 1 mg/mL in DMSO and diluted with growth medium before administration to the cells. The cells were incubated 6 hours with the abrogator and NOC. The duplicate wells were scraped, on ice, and combined in a 15 ml centrifuge tube. The wells were rinsed with Dulbecco's phosphate buffered saline (DPBS) without calcium and magnesium and the rinse combined with the scraped cells. The cells were centrifuged at 200×g at 4° C. for 5 minutes. The supernatant was discarded and the pellets resuspended in 100 µL DPBS. The cell suspension was then transferred to 1.5 ml eppendorf centrifuge tubes and centrifuged at 4° C. for 4 minutes at 4000 rpm. After the supernatant was removed, the pellet was frozen on dry ice and stored at −80° C.

The pellets were thawed on ice prior to lysis. The lysis buffer, ELB (2.5 mM HEPES (7.5), 150 mM NaCl, 25 µM NaF and 0.5% NP40 supplemented with 1 mM AEBSF, 1 mM sodium orthovanadate, and 1 mM dithiothretol, and complete protease inhibitor cocktail tablets (Roche Biochemicals). The tablets were dissolved in 2 mL distilled water and diluted 1:25 in the lysis buffer. The pellets were suspended in 100 µl complete lysis buffer and incubated on ice for 30 minutes. Following lysis, the suspension was centrifuged at 14,000 rpm for 15 minutes at 4° C. The supernatant liquidwas collected and the protein concentration determined using the Pierce BCA protein Assay Kit per manufacturers instructions. The protein concentration was adjusted to 3 mg/mL with DPBS. The samples were then diluted 1:1 with Invitrogen 2×tris-glycine sample buffer supplemented with 50 µl/ml 2-mercaptoethanol, boiled for 3 minutes, and stored frozen at −20° C.

Thirty micrograms of protein per lane were run on Novex pre-cast 12%, 1.5 mm, 10-well, tris-glycine polyacrylimide gels using Novex running buffer and Invitrogen (See Blue Plus 2 molecular weight standards). The gels weare run at 100 volts for 30 minutes then 125 volts for 1.5 hours. The proteins were transferred to 0.45 µm pore nitrocellulose membranes using Novex transfer buffer and the Novex X-Cell II blot module. The nitrocellulose membranes were blocked overnight at room temperature. The blocking buffer was 5 mM Tris (8.0), 150 mM NaCl, 0.1% Tween 20, 1 mM NaF, 10 mM glycerolphosphate, 100 µM sodium orthovanadate, and 3% bovine serum albumen.

After blocking, the gels were cut with a razor blade and the top portion treated with anti Myt-1 antibody diluted 1:5000 with blocking buffer. The lower portion of the gel was treated with biotinylated antiphosphotyrosine 15, also diluted 1:5000 in blocking buffer. The membranes were incubated for 2 hours at room temperature with constant rocking. The antibody solutions were removed and the membranes were washed 3 times for 20 minutes each with TNT buffer. TNT buffer consisted of 50 mM Tris (8.0), 150 mM NaCl, and 0.1% Tween 20. Secondary antibody was then added in blocking buffer. Neutravidin HRP at 1:40,000 was used for the biotinylated phosphotyrosine 15 blots and Bio Rad goat anti rabbit at 1:10,000 was used for the Myt-1 blots. The blots remained in secondary antibody for 1 hour at room temperature followed by three 20-minute washes with TNT buffer. Protein bands were detected using the Amersham Pharmacia ECL detection kit and Kodak Bio Max film per manufacturer's instructions.

The phosphotyrosine 15 membranes were stripped using the Chemicon International Re-Blot kit per manufacturer's instructions. The blots were then washed twice with TNT buffer and once with blocking buffer for 20 minutes each. Anti Cdc-2 (cdk1; Labvision Corporation) were diluted 150 µl per 50 ml blocking buffer and incubated with the blots for 2 hours at room temperature followed by three 20-minute washes in TNT buffer. The secondary antibody was Bio Rad goat antimouse HRP and was diluted 1:10,000 in blocking buffer before a 1 hour incubation with the blots at room temperature. Three 20-minute washes preceded ECL detection.

B. Procedure for detecting MPM 2 in cultured HT-29 cells+/−potential checkpoint abrogators, adriamycin, and nocodazole This assay uses polyclonal antibody to quantitate the M-phase specific histological markers in the determination of a mitotic index (fraction of cells found in mitosis).

HT-29 cells were grown in Dulbecco's Modified Eagle Medium with high glucose, supplemented with 1 mM sodium pyruvate, 2 mM L-glutamine, 16 mM HEPES, 8 mM MOPS, and 10% fetal bovine serum. They were incubated at 37° C. in an atmosphere of 5% $CO_2$ and 100% relative humidity.

Cells were seeded in 96-well tissue culture plates at 100 µl per well at a concentration of 40,000 per ml. The cells were allowed to attach and begin growing for 24 hours. 100 µl of adriamycin (ADR) at 2 µM (final=1 µM) was added to test cells and the cells incubated for 1 hour as above. Following the incubation, the plates were washed 2 times with growth media. The media was replaced with 100 µl fresh media and incubate a further 16 hours. Serial 2-fold dilutions of potential abrogators were added to the test wells. The rows that received nocodazole (NOC) have 2 µl NOC added at 2.5 µg/ml. The plates were then incubated an additional 6 hours. Following the incubation, the plates were centrifuged for 5 minutes at 4° C. at 200 g. One hundred microliters of Carnoy's fixative, 3 parts methanol to 1 part acetic acid, was added directly to each well and left at room temperature for 15 minutes. The media/fixative mixture was removed by suction and replaced with ice cold ethanol: acetic acid in a 20:1 ratio. The plates were stored at 4° C. until stained.

The fixed cells were stained for MPM-2 using the Upstate Biotechnology MPM-2 rhodamine detection kit per manufacturer's instructions. Briefly, the cells were washed with Dulbecco's phosphate buffered saline (DPBS) with calcium and magnesium followed by incubation with blocking buffer consisting of 8% bovine serum albumen (BSA) for a minimum of 1 hour. The cells were then washed with PBS one time and treated overnight at 4° C. with primary antibody at 5 µg/ml (100 µl per well) diluted with DPBS with 1% BSA. The cells were then washed twice for 15 minutes each with DPBS and then incubated with a 1:1000 dilution of rhodamine conjugated goat antimouse IgG in DPBS with 1% BSA for 1 hour. The secondary antibody was washed off in three 30-minute washes with DPBS. The cells were then counterstained using the Molecular Probes Mycoflour kit to stain nuclei following the instructions for the kit.

The stained cells were viewed under fluorescence microscopy using fluorescence filters suitable for detecting rhodamine and DAPI stains. Images were captured using a Spot digital camera and images analyzed using ImageQuant to quantitate total nuclei and to count MPM-2 positive cells.

MPM-2 Assay
(Values are % of cells in M phase)

|  | + Media | + ADR | + NOC | + ADR + NOC |
|---|---|---|---|---|
| Control | 8.4 | 7.0 | 26.4 | 25.9 |
| Compound of Example 363 @ 312.5 nM | 26.4 | 18.9 | 37.2 | 86.2 |

EXAMPLE 491

Procedure for In Vivo Testing of Wee1, Wee1/Chk1 or Chk1 Inhibitors in Combination with Adriamycin or Cisplatin These experiments measured the in vivo modulation of Py15 on Cdc2 in a tumor and assessed the therapeutic effect of Wee1, Wee1/Chk1 or Chk1 inhibitors of the present invention combined with a conventional agent. The therapeutic effect is measured by an increase in life span of treated animals.

In Vivo Experiments

In Vivo Methods

The initial in vivo experiments demonstrate biochemical and physiological evidence of Wee1, Wee1/Chk1 or Chk1 inhibition by examining modulation of the downstream target (i.e., the phosphorylation status of Cdc2 tyrosine 15) and cell cycle effects in L1210 murine leukemia tumor cells. L1210 was chosen for its lack of p53 function, pronounced G2 accumulation in response to DNA damage, ease of propagation in mice, and rapid cycle time. $CD_2F1$ mice weighing 25 to 26 g were inoculated intraperitoneally (ip) with $10^5$ or $5 \times 10^5$ L1210 cells and randomized into treatment groups of 3 mice each. On Day 4, 5, or 6 after tumor implantation, the mice were treated with a single injection of DNA damaging agent (cisplatin, 8 or 6 mg/kg iv), one or more injections of the compound of Example 80 (20 mg/kg ip, sc, or iv), or both agents. The injections of the compound of Example 80 were spaced 3 td 8 hours apart and were started simultaneously with the DNA damaging agent or after a delay of 8 or 16 hours. Control animals received only 0.2 ml saline iv. The DNA damaging agents were dissolved in saline and the compound of Example 80 was dissolved in 1 of 2 vehicles: (1) 10% cremaphor, 10% ethanol, and 80% $H_2O$ or (2) 5% dimethylacetamide, 25% propylene glycol, and 70% polyvinylpyrrolidine (30% w/v in $H_2O$). The mice were sacrificed at several time points ranging from 8 to 40 hours after commencement of treatment and the tumor cells were harvested in phosphate buffered saline containing 1 mM sodium orthovanadate and 5 mM EDTA. The L1210 cells were counted on a Coulter Counter and for each group an aliquot of $2.5 \times 10^7$ cells were centrifuged and frozen as pellets and an aliquot of $2.5 \times 10^6$ was frozen in Vindelov's citrate buffer[1] at $-80°$ C.

The larger pellets were homogenized for 30 seconds with a sonicator in a cold lysis buffer (RIPA) containing 25 mM Tris (base) pH 7.4, 350 mM sodium chloride, 1% nonidet P40, 5 mM EDTA (tetrasodium), 0.5% sodium deoxycholate, 0.1% sodium dodecyl sulfate, 1 mM AEBSF, 1 mM sodium fluoride, 0.5 mM sodium orthovanadate, 15 µg/ml aprotinin, 20 µM leupeptin, 10 mM β-glycerophosphate, and 1 mM DTT in $H_2O$. The lysates were diluted 1:10 with a mixture of 4 parts RIPA and 5 parts 2 times Novex electrophoresis sample buffer which, when diluted to working concentration contained 2% sodium dodecyl sulfate, 0.0025% bromphenol blue, 10% glycerol, and 60 mM dithiothreitol in $H_2O$. The samples were heated at 98° for 5 minutes. Duplicate Novex 4% to 20% polyacrylamide Trisglycine 15-well 1 mm mini-gels were loaded with 15 µl/well and run at 200 V (constant) for 45 minutes. The proteins were transferred to nitrocellulose membranes in Novex transfer buffer at 25 V (constant) for 2 hours. One of each membrane was blotted for total Cdc2 protein with LabVision MS-10P antibodies at 1:200, followed by BioRad 172-1011 goat antimouse IgG-HRP at 1:10,000. The other membrane was blotted for Cdc2 phosphotyrosine 15 (Ptyr15) with biotinylated rabbit polyclonal antibodies supplied by Onyx Pharmaceuticals at 1:5000, followed by Pierce 31001 neutravidin-HRP at 1:20,000 (50 ng/ml). The antibodies were detected with Amersham ECL reagents. The blot images were captured on Kodak BioMax MR film and imaged on a Molecular Dynamics Personal Densitometer SI. Densitometry was performed with Molecular Dynamics Image QuaNT software. The densitometric values for Cdc2 Ptyrl 5 were normalized for total Cdc2 protein (divided by the values for total Cdc2 to obtain a ratio of phospho:total Cdc2) and divided by the ratio of the control samples to obtain percent of control phosphorylation values for each tumor sample.

The smaller pellets were stained for DNA content by the method of Vindelov (Vindeløv LL, Christensen IJ, and Nissen NI. A detergent-trypsin method for the preparation of nuclei for flow cytometric DNA analysis. *Cytometry* 1983;3: 323–327). They were analyzed for propidium iodide fluorescence on a Beckman-Coulter Elite flow cytometer. Cell cycle distributions were estimated by the broadened trapezoid model of Bagwell (Bagwell, C.B. Theoretical aspects of flow cytometry data analysis. In: K.D. Bauer, R.E. Duque, T.V. Shankey, (eds.), Clinical Flow Cytometry: Principles and Application. pp. 41–61. Baltimore: Williams & Wilkins, 1993) as implemented by the Verity Software House program ModFit. LT.

Subsequent in vivo experiments were designed to determine if the addition of a Wee1, Wee1/Chk1 or Chk1 inhibitor to standard chemotherapy with DNA damaging agents results in a therapeutic gain. $CD_2F1$ mice weighing 24 to 26 g were inoculated with 104 L1210 cells ip and randomized into treatment groups of 6 mice each. On Days 3, 7, and 11 after implant, the mice were treated with a single iv injection of 1 of 3 dose levels of a DNA damaging agent (cisplatin or doxorubicin) alone or in combination with 2 ip injections of 1 of 2 dose levels of the compound of Example 80. Control mice received appropriate vehicle in place of active agents. Dose levels were based on mean group body weights. Mortality data were collected over a 3-week span and the median survival times of each group were calculated. Efficacy data (% T/C) are reported as the median life span of the treated animals divided by the median life span of the control animals times 100. The maximal % T/C of the combination groups was then compared with the maximal % T/C of the DNA damage. As shown on Table 9, the only groups to derive a measure of the therapeutic gain were associated with addition of a Wee1, Wee1/Chk1 or Chk1 inhibitor of the present invention.

TABLE 9

| | Cell cycle distribution of L1210 cells | | |
|---|---|---|---|
| | $G_1$ | S | $G_2M$ |
| Saline control | 44.3 | 44.2 | 11.5 |
| Cisplatin 6 mg/kg | 14.0 | 26.4 | 59.6 |
| Compound of Example 80 20 mg/kg | 60.0 | 27.6 | 12.4 |
| Cisplatin + Compound of Example 80 | 82.5 | 13.3 | 4.2 |

Cell cycle distribution of L1210 cells treated in vivo with cisplatin at 6 mg/kg and with the compound of Example 80 at 20 mg/kg. Cells were examined 24 hours after administration of drug and compound. Values are percent of cells examined.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequences of steps of the methods for preparing these compounds.

What is claimed is:

1. A compound of Formula I

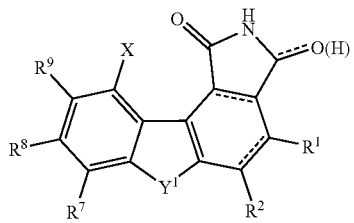

wherein
each dashed line represents an optional bond;
$R^1$ is
an aryl optionally substituted with up to five substituents selected from halogen, alkyl, haloalkyl, hydroxyl, nitro, cyano, C(O)$R^3$, O$R^3$, S(O)$_m R^3$, NR$^3$R$^4$, OC(O)R$^3$, NR$^3$(CO)OR$^4$, CH$_2$NR$^3$R$^4$, CH$_2$OR$^3$, COOR$^3$, CONR$^3$R$^4$, NR$^3$COR$^4$, SO$_2$NR$^3$R$^4$, CONHSO$_2$R$^3$, NR$^3$S(O)$_m R^4$ NHCONR$^3$R$^4$, NR$^3$CONHR$^4$;

m is 0–2;
X is hydrogen or halogen;
$Y^1$ is NR$^{10}$;
$R^9$ is hydroxyl;
r is 0–6;
$R^2$, $R^7$, $R^8$ and $R^{10}$ are in each instance independently selected from ((CR$^5$R$^6$)$_n$T)$_a$(CR$^{11}$R$^{12}$)$_b$)-Z wherein the sum n, a and b is in each instance less than 10; T may be absent, or, when present, is in each instance independently selected from O, CONR$^3$, CONHSO$_2$, S(O)$_m$, NR$^3$, NR$^3$—O, O—S(O)$_m$, S(O)$_m$—O, NR$^3$—S(O)$_2$, or S(O)$_2$—NR$^3$;
n is in each instance independently 0–6;
a is in each instance independently 0–6;
b is in each instance independently 0–6;
Z is selected from hydrogen, halogen, alkyl, haloalkyl, cycloalkyl, cycloalkenyl, heterocyclyl, aryl, heteroaryl, cyano, nitro, hydroxy, C(O)R$^3$, CONHSO$_2$R$^3$, OR$^3$, S(O)$_m R^3$, OSO$_2$R$^3$, NR$^3$R$^4$, CO$_2$R$^3$, CONR$^3$R$^4$, NR$^3$COR$^4$, SO$_2$NR$^3$R$^4$, OPO(OR$^3$)(OR$^4$), CH=CR$^3$R$^4$, CCR$^3$, (C=NR$^3$)NHR$^4$, NH(C=NR$^3$)NHR$^4$, NH(C=NH)NR$^3$R$^4$, wherein the alkyl, cycloalkyl, cycloalkenyl, heterocyclyl, aryl or heteroaryl group may be substituted with up to four groups independently selected from halogen, alkyl, hydroxyl, nitro, cyano, OR$^3$, S(O)$_m R^3$, NR$^3$R$^4$, OC(O)R$^3$, NR$^3$(CO)OR$^4$, C(O)R$^3$, COOR$^3$, CONR$^3$R$^4$, NR$^3$COR$^4$, SO$_2$NR$^3$R$^4$, CONHSO$_2$R$^3$, NR$^3$S(O)$_m R^4$, CH$_2$NR$^3$R$^4$, CH$_2$OR$^3$, NHCONR$^3$R$^4$, NR$^3$CONHR$^4$; R$^5$, R$^6$, R$^{11}$ and R$^{12}$ are in each instance independently selected from hydrogen, hydroxyl, alkyl, haloalkyl, cycloalkyl, cycloalkenyl, aryl, heteroaryl, heterocyclyl, halogen, cyano, nitro, CH$_2$NR$^3$R$^4$, CH$_2$OR$^3$, C(O)R$^3$, OR$^3$, S(O)$_m R^3$, NR$^3$R$^4$, COOR$^3$, CONR$^3$R$^4$, SO$_2$NR$^3$R$^4$, NHCONR$^3$R$^4$, NR$^3$CONHR$^4$; wherein the alkyl, haloalkyl, cycloalkyl, cycloalkenyl, heterocyclyl, aryl or heteroaryl group may be substituted with up to four groups independently selected from halogen, alkyl, hydroxyl, nitro, cyano, OR$^3$, S(O)$_m R^3$, NR$^3$R$^4$, OC(O)R$^3$, NR$^3$(CO)OR$^4$, C(O)R$^3$, COOR$^3$, CONR$^3$R$^4$, NR$^3$COR$^4$, SO$_2$NR$^3$R$^4$, CONHSO$_2$R$^3$, NR$^3$S(O)$_m R^4$, NHCONR$^3$R$^4$, NR$^3$CONHR$^4$;
$R^5$ and $R^6$ or $R^{11}$ and $R^{12}$ together with the carbon atom to which they are attached may form a carbonyl group; or together with the carbon or heteratom to which they are attached may form a cycloalkyl or heterocyclyl group, said carbonyl, cycloalkyl or heterocyclyl group may be substituted with up to four groups independently selected from halogen, hydroxyl, nitro, cyano, alkyl, haloalkyl, alkyl, nitro, cyano, OR$^3$, S(O)$_m R^3$, NR$^3$R$^4$, OC(O)R$^3$, NR$^3$(CO)OR$^4$, C(O)R$^3$, COOR$^3$, CONR$^3$R$^4$, NR$^3$COR$^4$, S(O)$_2$NR$^3$R$^4$, CONHSO$_2$R$^3$, NR$^3$S(O)$_m R^4$, NHCONR$^3$R$^4$, NR$^3$CONHR$^4$;
$R^3$, $R^4$ are independently selected from hydrogen, alkyl, haloalkyl or a substituted or unsubstituted carbocyclic group selected from cycloalkyl, cycloalkenyl, heterocyclyl, aryl, and heteroaryl, wherein the said alkyl, or a substituted group may be substituted with up to 4 groups selected from halogen, hydroxyl, nitro, cyano, alkyl, haloalkyl, alkyloxy, carboxy, COOH, CONH$_2$, NHCOCH$_3$, N(CH$_3$)$_2$, NHCH$_3$, thiomethyl, thioethyl, SOCH$_3$, SO$_2$CH$_3$;
$R^3$ and $R^4$ together with the carbon atom or heteroatom to which they are attached may form a cycloalkyl or heterocyclyl group substituted with up to four groups independently selected from halogen, hydroxyl, nitro, cyano, alkyl, haloalkyl, alkyloxy, formyl, carboxy, acetyl, CH$_2$NH$_2$, CH$_2$OH, COOH, CONH$_2$, NHCOCH$_3$, N(CH$_3$)$_2$, thiomethyl, thioethyl, SOCH$_3$, SO$_2$CH$_3$, alkoxycarbonyl, alkylcarbonyl, alkynylamino, aminoalkyl, aminoalkylcarbonyl, amino, mono- or dialkylamino, or R$^3$ and R$^4$ together with the nitrogen to which they are attached may form a heterocyclic ring containing 3–8 members, up to four of which members are optionally carbonyl groups or heteroatoms independently selected from oxygen, sulfur, S(O), S(O)$_2$, and nitrogen, wherein the carbocyclic group is unsubstituted or substituted with up to four groups independently selected from halogen, hydroxy, hydroxyalkyl, alkyl, haloalkyl, alkoxy, alkoxycarbonyl, alkylcarbonyl, alkynylamino, aminoalkyl, aminoalkylcarbonyl, amino, mono- or dialkylamino.

2. A compound according to claim 1 in which R$^1$ is selected from an unsubstituted aryl ring or an aryl ring substituted with up to 3 substituents selected from the group consisting of halogen, haloalkyl, alkoxy, hydroxyl, nitro, or NR$^3$R$^4$.

3. A compound according to claim 1 wherein R$^9$ is hydroxyl, Y$^1$ is NR$^{10}$, and the bond represented by the dashed line (C—O) is absent.

4. A compound according to claim 1 wherein R$^8$ is not hydrogen.

5. A compound according to claim 1 wherein R$^8$ is ((CR$^5$R$^6$)$_n$T)$_a$(CR$^{11}$R$^{12}$)$_b$)—Z; wherein T may be absent or O and Z is NR$^3$R$^4$.

6. A compound according to claim 1 wherein R$^8$ is ((CR$^5$R$^6$)$_n$T)$_a$(CR$^{11}$R$^{12}$)$_b$)—Z wherein T and Z are absent.

7. A compound according to claim 1 wherein R$^7$ is ((CR$^5$R$^6$)$_n$T)$_a$(CR$^{11}$R$^{12}$)$_b$)—Z.

8. The compounds:

2-(4-(2,6-Dichlorophenyl)-9-hydroxy-1,3-dioxo-2,3-dihydropyrrolo[3,4-c]carbazol-6 (1H)-yl)ethyl methanesulfonate;

2-94-(2-Chlorophenyl)-9-hydroxy-1,3-dioxo-2,3-dihydropyrrolo[3,4-c]carbazol-6 (1H)-yl)ethyl methanesulfonate;

3-(4-(2,6-Dichlorophenyl)-9-hydroxy-1,3-dioxo-2,3-dihydropyrrolo[3,4-c]carbazol-6 (1H)-yl)-N-[2-(dimethylamino)ethyl]propanamide;

3-(4-(2-Chloro-6-methoxyphenyl)-9-hydroxy-1,3-dioxo-2,3-dihydropyrrolo[3,4-c]carbazol-6 (1H)-yl)-N-[2-(dimethylamino)ethyl]propanamide;

3-(4-(2-Chlorophenyl)-9-hydroxy-1,3-dioxo-2,3-dihydropyrrolo[3,4-c]carbazol-6 (1H)-yl)-N-(1H-tetraazol-5-yl) propanamide;

3-(4-(2-Chlorophenyl)-9-hydroxy-1,3-dioxo-2,3-dihydropyrrolo[3,4-c]carbazol-6 (1H)-yl)-N-[2-(1H-imidazol-5-yl)ethyl] propanamide;

3-(4-(2-Chlorophenyl)-9-hydroxy-1,3-dioxo-2,3-dihydropyrrolo[3,4-c]carbazol-6 (1H)-yl)-N-[2-(4-morpholinyl) ethyl] propanamide;

3-(4-(2-Chlorophenyl)-9-hydroxy-1,3-dioxo-2,3-dihydropyrrolo[3,4-c]carbazol-6 (1H)-yl)-N-[2-(dimethylamino)ethyl]propanamide;

3-(4-(2-Chlorophenyl)-9-hydroxy-1,3-dioxo-2,3-dihydropyrrolo[3,4-c]carbazol-6 (1H)-yl) propanenitrile;

3-(4-(2-Chlorophenyl)-9-hydroxy-1,3-dioxo-2,3-dihydropyrrolo[3,4-c]carbazol-6 (1H)-yl) propanoic acid;

3-(9-Hydroxy-1,3-dioxo-4-phenyl-2,3-dihydropyrrolo[3,4-c]carbazol-6 (1H)-yl) propanamide;

3-(9-Hydroxy-1,3-dioxo-4-phenyl-2,3-dihydropyrrolo[3,4-c]carbazol-6 (1H)-yl) propanoic acid;

4-(2,3-Dichlorophenyl)-9-hydroxypyrrolo[3,4-c]carbazole-1,3(2H,6H)-dione;

4-(2-Chloro-5-hydroxyphenyl)-9-hydroxypyrrolo[3,4-c]carbazole-1,3(2H,6H)-dione;

4-(2,6-Dibromophenyl)-9-hydroxypyrrolo[3,4-c]carbazole-1,3(2H,6H)-dione;

4-(2,6-Dichloro-3-hydroxyphenyl)-9-hydroxypyrrolo[3,4-c] carbazole-1,3(2H, 6H)-dione;

4-(2,6-Dichloro-4-hydroxyphenyl)-9-hydroxypyrrolo[3,4-c] carbazole-1,3(2H, 6H)-dione;

4-(2,6-Dichlorophenyl)-9-hydroxy-6-(2-hydroxyethyl) pyrrolo[3,4-c]carbazole-1,3(2H,6H)-dione;

4-(2,6-Dichlorophenyl)-9-hydroxy-6-(3-hydroxypropyl) pyrrolo[3,4-c]carbazole-1,3(2H,6H)-dione;

4-(2,6-Dichlorophenyl)-9-hydroxy-6-[3-(1H-imidazol-1-yl)propyl]pyrrolo[3,4-c]carbazole-1,3(2H,6H)-dione;

4-(2,6-Dichlorophenyl)-9-hydroxypyrrolo[3,4-c]carbazole-1,3(2H,6H)-dione;

4-(2,6-Dimethoxyphenyl)-9-hydroxypyrrolo[3,4-c]carbazole-1,3(2H,6H)-dione;

4-(2-Bromophenyl)-9-hydroxypyrrolo[3,4-c]carbazole-1,3(2H,6H)-dione;

4-(2-Chloro-3-hydroxyphenyl)-9-hydroxypyrrolo[3,4-c] carbazole-1,3(2H,6H)-dione;

4-(2-Chloro-4-hydroxyphenyl)-9-hydroxypyrrolo[3,4-c] carbazole-1,3(2H,6H)-dione;

4-(2-Chloro-6-hydroxyphenyl)-9-hydroxypyrrolo[3,4-c] carbazole-1,3(2H,6H)-dione;

4-(2-Chloro-6-methoxyphenyl)-9-hydroxy-6-(2-hydroxyethyl) pyrrolo[3,4-c]carbazole-1,3(2H,6H)-dione (112);

4-(2-Chloro-6-methoxyphenyl)-9-hydroxy-6-(3-hydroxypropyl) pyrrolo[3,4-c]carbazole-1,3(2H,6H)-dione;

4-(2-Chloro-6-methoxyphenyl)-9-hydroxy-6-[3-(4-morpholinyl) propyl] pyrrolo [3,4-c]carbazole-1,3(2H,6H)-dione;

4-(2-Chloro-6-methoxyphenyl)-9-hydroxypyrrolo[3,4-c] carbazole-1,3(2H,6H)-dione;

4-(2-Chlorophenyl)-6-(2,3-dihydroxypropyl)-9-hydroxypyrrolo[3,4-c]carbazole-1,3(2H,6H)-dione;

4-(2-Chlorophenyl)-6-(2-hydroxyethyl)-9-hydroxypyrrolo[3,4-c]carbazole-1,3 (2H,6H)-dione;

4-(2-Chlorophenyl)-6-(3,4-dihydroxybutyl)-9-hydroxypyrrolo[3,4-c]carbazole-1,3(2H,6H)-dione;

4-(2-Chlorophenyl)-6-ethyl-9-hydroxypyrrolo[3,4-c]carbazole-1,3(2H,6H)-dione;

4-(2-chlorophenyl)-9-hydroxy-6-(2-hydroxypropyl) pyrrolo[3,4-c]carbazole-1,3(2H,6H)dione;

4-(2-Chlorophenyl)-9-hydroxy-6-(3-methoxypropyl) pyrrolo[3,4-c]carbazole-1,3(2H,6H)-dione;

4-(2-Chlorophenyl)-9-hydroxy-6-[(2R)-3-hydroxy-2-methylpropyl]pyrrolo[3,4-c]carbazole-1,3(2H,6H)-dione;

4-(2-chlorophenyl)-9-hydroxy-6-[(2S)-3-hydroxy-2-methylpropyl]pyrrolo[3,4-c]carbazole-1,3(2H,6H)-dione;

4-(2-Chlorophenyl)-9-hydroxy-6-[2-(1H-1,2,4-triazol-5-ylsulfinyl)ethyl]pyrrolo [3,4-c]carbazole-1,3(2H,6H)-dione;

4-(2-Chlorophenyl)-9-hydroxy-6-[2-(1H-1,2,4-triazol-5-ylsulfonyl)ethyl]pyrrolo [3,4-c]carbazole-1,3(2H,6H)-dione;

4-(2-Chlorophenyl)-9-hydroxy-6-[2-(1H-imidazol-2-ylsulfanyl) ethyl]pyrrolo [3,4-c]carbazole-1,3(2H,6H)-dione;

4-(2-Chlorophenyl)-9-hydroxy-6-[2-(1H-imidazol-2-ylsulfinyl)ethyl]pyrrolo[3,4-c]carbazole-1,3(2H,6H)-dione;

4-(2-Chlorophenyl)-9-hydroxy-6-[2-(1H-imidazol-2-yl-sulfonyl)ethyl]pyrrolo[3,4-c]carbazole-1,3(2H,6H)-dione;
4-(2-Chlorophenyl)-9-hydroxy-6-[2-(1H-tetraazol-5-yl)ethyl]pyrrolo[3,4-c]carbazole-1,3(2H,6H)-dione;
4-(2-Chlorophenyl)-9-hydroxy-6-[2-(4H-1,2,4-triazol-3-ylsulfanyl)ethyl]pyrrolo[3,4-c]carbazole-1,3(2H,6H)-dione;
4-(2-Chlorophenyl)-9-hydroxy-6-[2-hydroxy-3-(4-morpholinyl)propyl]pyrrolo [3,4-c]carbazole-1,3(2H,6H)-dione;
4-(2-Chlorophenyl)-9-hydroxy-6-[2-hydroxy-3-(methylamino)propyl]pyrrolo [3,4-c]carbazole-1,3(2H,6H)-dione;
4-(2-Chlorophenyl)-9-hydroxy-6-[3-(1H-imidazol-1-yl)propyl]pyrrolo[3,4-c]carbazole-1,3(2H,6H)-dione;
4-(2-Chlorophenyl)-9-hydroxy-6-[3-(1H-tetraazol-5-yl)propyl]pyrrolo[3,4-c]carbazole-1,3(2H,6H)-dione;
4-(2-Chlorophenyl)-9-hydroxy-6-[3-(methylsulfanyl)propyl]pyrrolo[3,4-c]carbazole-1,3(2H,6H)-dione;
4-(2-Chlorophenyl)-9-hydroxy-6-isopropylpyrrolo[3,4-c]carbazole-1,3(2H,6H)-dione;
4-(2-Chlorophenyl)-9-hydroxy-6-methylpyrrolo[3,4-c]carbazole-1,3(2H,6H)-dione;
4-(2-Chlorophenyl)-9-hydroxypyrrolo[3,4-c]carbazole-1,3(2H,6H)-dione;
4-(3-Amino-2-chlorophenyl)-9-hydroxypyrrolo[3,4-c]carbazole-1,3(2H,6H)-dione;
4-(3-Aminophenyl)-9-hydroxypyrrolo[3,4-c]carbazole-1,3(2H,6H)-dione; 4-(3-Chlorophenyl)-9-hydroxypyrrolo[3,4-c]carbazole-1,3(2H,6H)-dione;
4-(4-(2-Chlorophenyl)-9-hydroxy-1,3-dioxo-2,3-dihydropyrrolo[3,4-c]carbazol-6(1H)-yl)butanenitrile;
4-(4-(2-Chlorophenyl)-9-hydroxy-1,3-dioxo-2,3-dihydropyrrolo[3,4-c]carbazol-6(1H)-yl)butanoic acid;
4-(4-Amino-2-bromophenyl)-9-hydroxypyrrolo[3,4-c]carbazole-1,3(2H,6H)-dione);
4-(4-Amino-2-chlorophenyl)-9-hydroxypyrrolo[3,4-c]carbazole-1,3(2H,6H)-dione;
6-(2-Chloroethyl)-4-(2-chlorophenyl)-9-hydroxypyrrolo[3,4-c]carbazole-1,3(2H,6H)-dione;
6-(3-Bromopropyl)-4-(2,6-dichlorophenyl)-9-hydroxypyrrolo[3,4-c]carbazole-1,3(2H,6H)-dione (233);
6-(3-Bromopropyl)-4-(2-chloro-6-methoxyphenyl)-9-hydroxypyrrolo[3,4-c]carbazole-1,3(2H,6H)-dione;
6-(3-Bromopropyl)-4-(2-chlorophenyl)-9-hydroxypyrrolo[3,4-c]carbazole-1,3(2H,6H)-dione;
6-Acetyl-4-(2-chlorophenyl)-9-hydroxypyrrolo[3,4-c]carbazole-1,3(2H,6H)-dione;
6-Butyl-4-(2-chlorophenyl)-9-hydroxypyrrolo[3,4-c]carbazole-1,3(2H,6H)-dione;
9-Hydroxy-4-(2-hydroxyphenyl)pyrrolo[3,4-c]carbazole-1,3(2H,6H)-dione;9-Hydroxy-4-(2-iodophenyl)pyrrolo[3,4-c]carbazole-1,3(2H,6H)-dione;
9-Hydroxy-4-(2-methoxyphenyl)pyrrolo[3,4-c]carbazole-1,3(2H,6H)-dione;9-Hydroxy-4-(2-nitrophenyl)pyrrolo[3,4-c]carbazole-1,3(2H,6H)-dione;
9-Hydroxy-4-(3-thienyl)pyrrolo[3,4-c]carbazole-1,3(2H,6H)-dione;
9-Hydroxy-4-(4-hydroxyphenyl)pyrrolo[3,4-c]carbazole-1,3(2H,6H)-dione;
9-Hydroxy-4-[2-(methylsulfanyl)phenyl]pyrrolo[3,4-c]carbazole-1,3(2H,6H)-dione;
9-Hydroxy-6-(2-hydroxyethyl)-4-(2-methoxyphenyl)pyrrolo[3,4-c]carbazole-1,3(2H,6H)-dione;
9-Hydroxy-6-(2-hydroxyethyl)-4-phenylpyrrolo[3,4-c]carbazole-1,3(2H,6H)-dione;

9-Hydroxy-6-(3-hydroxypropyl)-4-(2-methoxyphenyl)pyrrolo[3,4-c]carbazole-1,3(2H,6H)-dione;
Methyl 3-(4-(2-chlorophenyl)-9-hydroxy-1,3-dioxo-2,3-dihydropyrrolo[3,4-c]carbazol-6(1H)-yl)propanoate;
N-[3-(4-(2-Chlorophenyl)-9-hydroxy-1,3-dioxo-2,3-dihydropyrrolo[3,4-c]carbazol-6 (1H)-yl)propanoyl]-2-(dimethylamino)ethanesulfonamide;
N-[3-(4-(2-Chlorophenyl)-9-hydroxy-1,3-dioxo-2,3-dihydropyrrolo[3,4-c]carbazol-6 (1H)-yl) propanoyl] benzenesulfonamide;
N-[3-(4-(2-Chlorophenyl)-9-hydroxy-1,3-dioxo-2,3-dihydropyrrolo[3,4-c]carbazol-6 (1H)-yl) propanoyl] methanesulfonamide;
N-[4-(4-(2-Chlorophenyl)-9-hydroxy-1,3-dioxo-2,3-dihydropyrrolo[3,4-c]carbazol-6 (1H)-yl)butanoyl]benzenesulfonamide;
N-[4-(4-(2-Chlorophenyl)-9-hydroxy-1,3-dioxo-2,3-dihydropyrrolo[3,4-c]carbazol-6(1H)-yl)butanoyl]methanesulfonamide;
2-(9-Hydroxy-1,3-dioxo-1,2,3,6-tetrahydropyrrolo[3,4-c]carbazol-4-yl) benzonitrile;
3-(9-Hydroxy-1,3-dioxo-1,2,3,6-tetrahydro-pyrrolo[3,4-c]carbazol-4-yl)-benzonitrile;4-(2,3-Dichlorophenyl)-9-hydroxypyrrolo[3,4-c]carbazole-1,3(2H,6H)-dione;
4-(2-Chloro-5-hydroxyphenyl)-9-hydroxypyrrolo[3,4-c]carbazole-1,3(2H,6H)-dione;
4-(2,6-Dibromophenyl)-9-hydroxypyrrolo[3,4-c]carbazole-1,3(2H,6H)-dione;
4-(2,6-Dichloro-3-hydroxyphenyl)-9-hydroxypyrrolo[3,4-c]carbazole-1,3(2H,6H)-dione;
4-(2,6-Dichloro-4-hydroxyphenyl)-9-hydroxypyrrolo[3,4-c]carbazole-1,3(2H, 6H)-dione;4-(2,6-Dichlorophenyl)-9-hydroxypyrrolo[3,4-c]carbazole-1,3(2H,6H)-dione;
4-(2,6-Dimethoxyphenyl)-9-hydroxypyrrolo[3,4-c]carbazole-1,3(2H,6H)-dione;4-(2,6-Dimethylphenyl)-9-hydroxypyrrolo[3,4-c]carbazole-1,3(2H,6H)-dione;4-(2-Acetyl-phenyl)-9-hydroxy-6H-pyrrolo[3,4-c]carbazole-1,3-dione;
4-(2-Aminophenyl)-9-hydroxypyrrolo[3,4-c]carbazole-1,3(2H,6H)-dione;
4-(2-Bromo-4-nitrophenyl)-9-hydroxypyrrolo[3,4-c]carbazole-1,3(2H,6H)-dione;
4-(2-Bromophenyl)-9-hydroxypyrrolo[3,4-c]carbazole-1,3(2H,6H)-dione;
4-(2-Chloro-3-hydroxyphenyl)-9-hydroxypyrrolo[3,4-c]carbazole-1,3(2H,6H)-dione;
4-(2-Chloro-4-hydroxyphenyl)-9-hydroxypyrrolo[3,4-c]carbazole-1,3(2H,6H)-dione;
4-(2-Chloro-4-nitrophenyl)-9-hydroxypyrrolo[3,4-c]carbazole-1,3(2H,6H)-dione;
4-(2-Chloro-6-hydroxyphenyl)-9-hydroxypyrrolo[3,4-c]carbazole-1,3(2H,6H)-dione;
4-(2-Chloro-6-methoxyphenyl)-9-hydroxypyrrolo[3,4-c]carbazole-1,3(2H,6H)-dione;
4-(2-Ethoxyphenyl)-9-hydroxypyrrolo[3,4-c]carbazole-1,3(2H,6H)-dione;
4-(2-Ethylphenyl)-9-hydroxypyrrolo[3,4-c]carbazole-1,3(2H,6H)-dione;
4-(3-Amino-2-chlorophenyl)-9-hydroxypyrrolo[3,4-c]carbazole-1,3(2H,6H)-dione;
4-(3-Aminophenyl)-9-hydroxypyrrolo[3,4-c]carbazole-1,3(2H,6H)-dione;
4-(3-Chlorophenyl)-9-hydroxypyrrolo[3,4-c]carbazole-1,3(2H,6H)-dione;
4-(4-Amino-2-bromophenyl)-9-hydroxypyrrolo[3,4-c]carbazole-1,3(2H,6H)-dione);

4-(4-Amino-2-chlorophenyl)-9-hydroxypyrrolo[3,4-c] carbazole-1,3(2H,6H)-dione;
4-(4-Aminophenyl)-9-hydroxypyrrolo[3,4-c]carbazole-1, 3(2H,6H)-dione;
4-(4-Chlorophenyl)-9-hydroxypyrrolo[3,4-c]carbazole-1, 3(2H,6H)-dione;
4-(5-Amino-2-methoxyphenyl)-9-hydroxypyrrolo[3,4-c] carbazole-1,3(2H,6H)-dione;
4-[1,1-Bipbenyl]-2-yl-9-hydroxypyrrolo[3,4-c]carbazole-1,3(2H,6H)-dione;
4-Furan-2-yl-9-hydroxy-6H-pyrrolo[3,4-c]carbazole-1,3-dione;
9-Hydroxy-4-(2-hydroxyphenyl)pyrrolo[3,4-c]carbazole-1,3(2H,6H)-dione;
9-Hydroxy-4-(2-iodophenyl)pyrrolo[3,4-c]carbazole-1,3 (2H,6H)-dione;
9-Hydroxy-4-(2-methoxyphenyl)pyrrolo[3,4-c]carbazole-1,3(2H,6H)-dione;
9-Hydroxy-4-(2-methylsulfanyl-phenyl)-6H-pyrrolo[3,4-c]carbazole-1,3-dione;
9-Hydroxy-4-(2-nitrophenyl)pyrrolo[3,4-c]carbazole-1,3 (2H,6H)-dione;
9-Hydroxy-4-(2-thienyl)pyrrolo[3,4-c]carbazole-1,3(2H, 6H)-dione;
9-Hydroxy-4-(2-trifluoromethylphenyl)pyrrolo[3,4-c] carbazole-1,3(2H,6H)-dione;
9-Hydroxy-4-(3-hydroxy-4-methoxyphenyl)pyrrolo[3,4-c]carbazole-1,3(2H,6H)-dione;
9-Hydroxy-4-(3-hydroxymethyl-phenyl)-6H-pyrrolo[3,4-c]carbazole-1,3-dione;
9-Hydroxy-4-(3-hydroxy-phenyl)-6H-pyrrolo[3,4-c]carbazole-1,3-dione;
9-Hydroxy-4-(3-hydroxyphenyl)pyrrolo[3,4-c]carbazole-1,3(2H,6H)-dione;
9-Hydroxy-4-(3-nitrophenyl)pyrrolo[3,4-c]carbazole-1,3 (2H,6H)-dione;
9-Hydroxy-4-(3-thienyl)pyrrolo[3,4-c]carbazole-1,3(2H, 6H)-dione;
9-Hydroxy-4-(3-trifluoromethoxy-phenyl)-6H-pyrrolo[3, 4-c]carbazole-1,3-dione;
9-Hydroxy-4-(4-hydroxymethylphenyl)pyrrolo[3,4-c] carbazole-1,3(2H,6H)-dione;
9-Hydroxy-4-(4-hydroxyphenyl)pyrrolo[3,4-c]carbazole-1,3(2H,6H)-dione;
9-Hydroxy-4-(4-trifluoromethoxy-phenyl)-6H-pyrrolo[3, 4-c]carbazole-1,3-dione;
9-Hydroxy-4-[2-(hydroxymethyl)phenyl]pyrrolo[3,4-c] carbazole-1,3(2H,6H)-dione;
9-Hydroxy-4-[2-(methylsulfanyl)phenyl]pyrrolo[3,4-c] carbazole-1,3(2H,6H)-dione;
9-Hydroxy-4-[2-(methylsulfinyl)phenyl]pyrrolo[3,4-c] carbazole-1,3(2H,6H)-dione;
9-Hydroxy-4-m-tolyl-6H-pyrrolo[3,4-c]carbazole-1,3-dione;
9-Hydroxy-4-o-tolyl-6H-pyrrolo[3,4-c]carbazole-1,3-dione;
4-(2-chlorophenyl)-9-hydroxy-6-propylpyrrolo[3,4-c] carbazole-1,3(2H,6H)-dione;
2-(4-(2-chlorophenyl)-9-hydroxy-1,3-dioxo-2,3-dihydropyrrolo[3,4-c]carbazol-6(1H)-yl)acetamide;
2-{[3-(4-(2-Chlorophenyl)-9-hydroxy-1,3-dioxo-2,3-dihydropyrrolo[3,4-c]carbazol-6(1H)-yl) propyl]amino}benzoic acid;
3-(4-(2,6-Dichlorophenyl)-9-hydroxy-1,3-dioxo-2,3-dihydropyrrolo[3,4-c]carbazol-6(1H)-yl) propanoic acid;
3-(4-(2-chlorophenyl)-9-(formylamino)-1,3-dioxo-2,3-dihydropyrrolo[3,4-c]carbazol-6(1H)-yl)-N-[2-(dimethylamino)ethyl]propanamide;
3-(4-(2-Chlorophenyl)-9-hydroxy-1,3-dioxo-2,3-dihydropyrrolo[3,4-c]carbazol-6(1H)-yl)-N-(2,2,6,6-tetramethyl-4-piperidinyl);
3-(4-(2-Chlorophenyl)-9-hydroxy-1,3-dioxo-2,3-dihydropyrrolo[3,4-c]carbazol-6(1H0-yl)-N-[2-(1H-imidazol-5-yl)ethyl]propanamide;
3-(4-(2-Chlorophenyl)-9-hydroxy-1,3-dioxo-2,3-dihydropyrrolo[3,4-c]carbazol-6(1H)-yl)-N-[2-(dimethylamino)ethyl]-N-methylpropanamide;
3,9-dihydroxy-4-phenyl-3,6-dihydropyrrolo[3,4-c]carbazol-1(2H)-one;
3-{[3-(4-(2-Chlorophenyl)-9-hydroxy-1,3-dioxo-2,3-dihydropyrrolo[3,4-c]carbazol-6 (1H)-yl) propyl]amino}benzoic acid;
4-(2,6-dichlorophenyl)-6-[3-(dimethylamino) propyl]-9-hydroxypyrrolo[3,4-c]carbazole-1,3(2H,6H)-dione;
4-(2,6-Dichlorophenyl)-6-{3-[(cis)-3,5-dimethylpiperazinyl]propyl}-9-hydroxypyrrolo[3,4-c]carbazole-1,3 (2H,6H)-dione;
4-(2,6-dichlorophenyl)-8-[3-(dimethylamino)propoxy]-9-hydroxypyrrolo[3,4-c]carbazole-1,3(2H,6H)-dione;
4-(2,6-dichlorophenyl)-8-[4-(dimethylamino)butyl]-9-hydroxy-6-methylpyrrolo[3,4-c]carbazole-1,3(2H, 6H)-dione;
4-(2,6-dichlorophenyl)-9-hydroxy-6-[2-(4-methyl-1-piperazinyl) ethyl]pyrrolo [3,4-c]carbazole-1,3(2H,6H)-dione;
4-(2,6-dichlorophenyl)-9-hydroxy-6-[2-(4-morpholinyl) ethyl]pyrrolo[3,4-c]carbazole-1,3(2H,6H)-dione;
4-(2,6-dichlorophenyl)-9-hydroxy-6-[3-(1H-imidazol-1-yl) propyl]pyrrolo[3,4-c]carbazole-1,3(2H,6H)-dione;
4-(2,6-dichlorophenyl)-9-hydroxy-6-[3-(4-methyl-1-piperazinyl) propyl]pyrrolo [3,4-c]carbazole-1,3(2H,6H)-dione;
4-(2,6-dichlorophenyl)-9-hydroxy-6-[3-(4-morpholinyl) propyl]pyrrolo[3,4-c]carbazole-1,3(2H,6H)-dione;
4-(2,6-dichlorophenyl)-9-hydroxy-6-[3-(dimethylamino) ethyl]pyrrolo[3,4-c]carbazole-1,3(2H,6H)-dione;
4-(2,6-dichlorophenyl)-9-hydroxy-6-[3-(methylamino) propyl]pyrrolo[3,4-c]carbazole-1,3(2H,6H)-dione;
4-(2,6-dichlorophenyl)-9-hydroxy-6-methyl-8-[3-(methylamino)propoxy]pyrrolo[3,4-c]carbazole-1,3(2H, 6H)-dione;
4-(2,6-dichlorophenyl)-9-hydroxy-8-[4-(methylamino) butyl]pyrrolo[3,4-c]carbazole-1,3(2H,6H)-dione;
4-(2-bromophenyl)-8-[3-(dimethylamino)propoxy]-9-hydroxy-6-methylpyrrolo [3,4-c]carbazole-1,3(2H,6H)-dione;
4-(2-bromophenyl)-8-[3-(dimethylamino)propoxy]-9-hydroxypyrrolo[3,4-c]carbazole-1,3(2H,6H)-dione;
4-(2-bromophenyl)-8-[4-(dimethylamino)butyl]-9-hydroxypyrrolo[3,4-c]carbazole-1,3(2H,6H)-dione;
4-(2-bromophenyl)-9-hydroxy-6-methyl-8-[3-(methylamino)propoxy]pyrrolo [3,4-c]carbazole-1,3(2H,6H)-dione;
4-(2-bromophenyl)-9-hydroxy-8-[3-(methylamino)propoxy]pyrrolo[3,4-c]carbazole-1,3(2H,6H)-dione;
4-(2-bromophenyl)-9-hydroxy-8-[4-(methylamino)butyl] pyrrolo[3,4-c]carbazole-1,3(2H,6H)-dione;
4-(2-Chloro-6-methoxyphenyl)-6-{3-[cis-3,5-dimethylpiperazinyl]propyl}-9-hydroxypyrrolo[3,4-c]carbazole-1,3(2H,6H)-dione;

4-(2-chloro-6-methoxyphenyl)-8-[3-(dimethylamino)propoxy]-9-hydroxy-6-methylpyrrolo[3,4-c]carbazole-1,3(2H,6H)-dione;

4-(2-chloro-6-methoxyphenyl)-8-[3-(dimethylamino)propoxy]-9-hydroxypyrrolo [3,4-c]carbazole-1,3(2H,6H)-dione;

4-(2-chloro-6-methoxyphenyl)-8-[4-(dimethylamino)butyl]-9-hydroxy-6-methylpyrrolo[3,4-c]carbazole-1,3 (2H,6H)-dione;

4-(2-chloro-6-methoxyphenyl)-8-[4-(dimethylamino)butyl]-9-hydroxypyrrolo [3,4-c]carbazole-1,3(2H,6H)-dione;

4-(2-Chloro-6-methoxyphenyl)-9-hydroxy-6-[2-(4-morpholinyl)ethyl]pyrrolo [3,4-c]carbazole-1,3(2H,6H)-dione;

4-(2-chloro-6-methoxyphenyl)-9-hydroxy-6-methyl-8-[3-(methylamino) propoxy]pyrrolo[3,4-c]carbazole-1,3(2H,6H)-dione;

4-(2-chloro-6-methoxyphenyl)-9-hydroxy-8-[3-(methylamino)propoxy]pyrrolo [3,4-c]carbazole-1,3(2H,6H)-dione;

4-(2-chloro-6-methoxyphenyl)-9-hydroxy-8-[4-(methylamino)butyl]pyrrolo[3,4-c]carbazole-1,3(2H,6H)-dione;

4-(2-Chlorophenyl)-1,9-dihydroxy-6-(3-hydroxypropyl)-1,6-dihydropyrrolo[3,4-c]carbazol-3(2H)-one;

4-(2-chlorophenyl)-3,9-dihydroxy-6-(3-hydroxypropyl)-3,6-dihydropyrrolo[3,4-c]carbazol-1(2H)-one;

4-(2-Chlorophenyl)-6-[3-(dimethylamino)-2-hydroxypropyl]-9-hydroxypyrrolo [3,4-c]carbazole-1,3(2H,6H)-dione;

4-(2-chlorophenyl)-6-[3-(dimethylamino)propyl]-9-hydroxypyrrolo[3,4-c]carbazole-1,3(2H,6H)-dione;

4-(2-Chlorophenyl)-6-{3-[(cis)-3,5-dimethylpiperazinyl]propyl}-9-hydroxypyrrolo[3,4-c]carbazole-1,3(2H,6H)-dione;

4-(2-chlorophenyl)-6-cyclopentyl-9-hydroxypyrrolo[3,4-c]carbazole-1,3(2H,6H)-dione;

4-(2-Chloro-phenyl)-8-(3-diethylamino-propoxy)-9-hydroxy-6-(2-hydroxy-ethyl)-6H-pyrrolo[3,4-c]carbazole-1,3-dione;

4-(2-Chloro-phenyl)-8-(3-dimethylamino-propoxy)-9-hydroxy-6-(3-hydroxy-propyl)-6H-pyrrolo[3,4-c]carbazole-1,3-dione;

4-(2-Chlorophenyl)-8-[3-(dimethylamino)propoxy]-9-hydroxy-6-(2-hydroxyethyl) pyrrolo[3,4-c]carbazole-1,3(2H,6H)-dione;

4-(2-chlorophenyl)-8-[3-(dimethylamino)propoxy]-9-hydroxy-6-(3-hydroxypropyl)pyrrolo[3,4-c]carbazole-1,3(2H,6H)-dione;

4-(2-Chlorophenyl)-8-[3-(dimethylamino)propoxy]-9-hydroxy-6-methylpyrrolo[3,4-c]carbazole-1,3(2H,6H)-dione;

4-(2-Chlorophenyl)-8-[3-(dimethylamino)propoxy]-9-hydroxypyrrolo[3,4-c]carbazole-1,3(2H,6H)-dione;

4-(2-chlorophenyl)-8-[4-(dimethylamino)butanoyl]-9-hydroxy-6-methylpyrrolo[3,4-c]carbazole-1,3(2H,6H)-dione;

4-(2-chlorophenyl)-8-[4-(dimethylamino)butyl]-9-hydroxy-6-(2-hydroxyethyl) pyrrolo[3,4-c]carbazole-1,3 (2H,6H)-dione;

4-(2-chlorophenyl)-8-[4-(dimethylamino)butyl]-9-hydroxy-6-(3-hydroxypropyl) pyrrolo[3,4-c]carbazole-1,3(2H,6H)-dione;

4-(2-chlorophenyl)-8-[4-(dimethylamino)butyl]-9-hydroxy-6-(3-hydroxypropyl)pyrrolo[3,4-c]carbazole-1,3(2H,6H)-dione;

4-(2-chlorophenyl)-8-[4-(dimethylamino)butyl]-9-hydroxy-6-methylpyrrolo[3,4-c]carbazole-1,3(2H,6H)-dione;

4-(2-Chlorophenyl)-8-[4-(dimethylamino) butyl]-9-hydroxypyrrolo[3,4-c]carbazole-1,3(2H,6H)-dione;

4-(2-chlorophenyl)-8-{[3-(dimethylamino)propyl]sulfinyl}-9-hydroxy-6-methylpyrrolo[3,4-c]carbazole-1,3 (2H,6H)-dione;

4-(2-chlorophenyl)-8-{3-[(3,5-dimethylpiperazinyl] propoxy}-9-hydroxy-6-methylpyrrolo[3,4-c]carbazole-1,3(2H,6H)-dione;

4-(2-Chlorophenyl)-8-ethyl-9-hydroxy-6-methylpyrrolo [3,4-c]carbazole-1,3(2H,6H)-dione;

4-(2-chlorophenyl)-9-(hydroxymethyl)pyrrolo[3,4-c]carbazole-1,3(2H,6H)-dione;

4-(2-chlorophenyl)-9-hydroxy-6-(2,2,2-trifluoroethyl) pyrrolo[3,4-c]carbazole-1,3(2H,6H)-dione;

4-(2-Chloro-phenyl)-9-hydroxy-6-(2-hydroxy-ethyl)-8-[3-(4-methyl-piperazin-1-yl)-propoxy]-6H-pyrrolo[3,4-c]carbazole-1,3-dione;

4-(2-Chlorophenyl)-9-hydroxy-6-(2-hydroxyethyl)-8-[3-(4-morpholinyl) propoxy]pyrrolo[3,4-c]carbazole-1,3 (2H,6H)-dione;

4-(2-chlorophenyl)-9-hydroxy-6-(2-hydroxyethyl)-8-[3-(methylamino) propoxy]pyrrolo[3,4-c]carbazole-1,3 (2H,6H)-dione;

4-(2-chlorophenyl)-9-hydroxy-6-(2-hydroxyethyl)-8-[4-(methylamino) butyl]pyrrolo[3,4-c]carbazole-1,3(2H, 6H)-dione;

4-(2-chlorophenyl)-9-hydroxy-6-(2-phenylethyl) pyrrolo [3,4-c]carbazole-1,3(2H,6H)-dione;

4-(2-chlorophenyl)-9-hydroxy-6-(2-propynyl)pyrrolo[3, 4-c]carbazole-1,3(2H, 6H)-dione;

4-(2-Chlorophenyl)-9-hydroxy-6-(3-hydroxypropyl)-4,5, 6,10c-tetrahydropyrrolo [3,4-c]carbazole-1,3(2H, 3aH)-dione;

4-(2-Chloro-phenyl)-9-hydroxy-6-(3-hydroxy-propyl)-8-(3-pyrrolidin-1-yl-propoxy)-6H-pyrrolo[3,4-c]carbazole-1,3-dione;

4-(2-chlorophenyl)-9-hydroxy-6-(3-hydroxypropyl)-8-[3-(1-pyrrolidinyl) propoxy]pyrrolo[3,4-c]carbazole-1,3(2H,6H)-dione;

4-(2-Chloro-phenyl)-9-hydroxy-6-(3-hydroxy-propyl)-8-[3-(4-methyl-piperazin-1-yl)-propoxy]-6H-pyrrolo[3,4-c]carbazole-1,3-dione;

4-(2-chlorophenyl)-9-hydroxy-6-(3-hydroxypropyl)-8-[3-(methylamino) propoxy]pyrrolo[3,4-c]carbazole-1,3(2H,6H)-dione;

4-(2-Chloro-phenyl)-9-hydroxy-6-(3-hydroxy-propyl)-8-piperidin-4-yl-6H-pyrrolo[3,4-c]carbazole-1,3-dione;

4-(2-chlorophenyl)-9-hydroxy-6-(4,4,4-trifluorobutyl) pyrrolo[3,4-c]carbazole-1,3(2H,6H)-dione;

4-(2-chlorophenyl)-9-hydroxy-6-(4-pentenyl)pyrrolo[3, 4-c]carbazole-1,3(2H,6H)-dione;

4-(2-Chlorophenyl)-9-hydroxy-6,8-bis (2-hydroxyethyl) pyrrolo[3,4-c]carbazole-1,3(2H,6H)-dione;

4-(2-chlorophenyl)-9-hydroxy-6-[2-(1H-imidazol-1-yl) ethyl]pyrrolo[3,4-c]carbazole-1,3(2H,6H)-dione;

4-(2-chlorophenyl)-9-hydroxy-6-[2-(4-methyl-1-piperazinyl) ethyl]pyrrolo[3,4-c]carbazole-1,3(2H,6H)-dione;

4-(2-chlorophenyl)-9-hydroxy-6-[2-(4-morpholinyl) ethyl]pyrrolo[3,4-c]carbazole-1,3(2H,6H)-dione;

4-(2-Chlorophenyl)-9-hydroxy-6-[2-(phenylsulfanyl) ethyl]pyrrolo[3,4-c]carbazole-1,3(2H,6H)-dione;

4-(2-chlorophenyl)-9-hydroxy-6-[3-(4-methyl-1-piperazinyl) propyl]pyrrolo[3,4-c]carbazole-1,3(2H,6H)-dione;

4-(2-chlorophenyl)-9-hydroxy-6-[3-(4-morpholinyl)propyl]pyrrolo[3,4-c]carbazole-1,3(2H,6H)-dione;

4-(2-chlorophenyl)-9-hydroxy-6-[3-(dimethylamino)ethyl]pyrrolo[3,4-c]carbazole-1,3(2H,6H)-dione;

4-(2-chlorophenyl)-9-hydroxy-6-[3-(methylamino)propyl]pyrrolo[3,4-c]carbazole-1,3(2H,6H)-dione;

4-(2-chlorophenyl)-9-hydroxy-6-isobutylpyrrolo[3,4-c]carbazole-1,3(2H,6H)-dione;

4-(2-chlorophenyl)-9-hydroxy-6-isopentylpyrrolo[3,4-c]carbazole-1,3(2H,6H)-dione;

4-(2-Chloro-phenyl)-9-hydroxy-6-methyl-8-(4-morpholin-4-yl-butyl)-6H-pyrrolo [3,4-c]carbazole-1,3-dione;

4-(2-Chlorophenyl)-9-hydroxy-6-methyl-8-[3-(1-pyrrolidinyl) propoxy]pyrrolo [3,4-c]carbazole-1,3(2H,6H)-dione;

4-(2-Chlorophenyl)-9-hydroxy-6-methyl-8-[3-(4-morpholinyl)propoxy]pyrrolo [3,4-c]carbazole-1,3(2H,6H)-dione;

4-(2-chlorophenyl)-9-hydroxy-6-methyl-8-[3-(methylamino)propoxy]pyrrolo [3,4-c]carbazole-1,3(2H,6H)-dione;

4-(2-chlorophenyl)-9-hydroxy-6-methyl-8-[4-(methylamino)butanoyl]pyrrolo [3,4-c]carbazole-1,3(2H,6H)-dione;

4-(2-chlorophenyl)-9-hydroxy-6-methyl-8-[4-(methylamino)butyl]pyrrolo[3,4-c]carbazole-1,3(2H,6H)-dione;

4-(2-chlorophenyl)-9-hydroxy-6-methyl-8-{[3-(methylamino)propyl]sulfonyl}pyrrolo[3,4-c]carbazole-1,3(2H,6H)-dione;

4-(2-chlorophenyl)-9-hydroxy-6-pentylpyrrolo[3,4-c]carbazole-1,3(2H,6H)-dione;

4-(2-Chlorophenyl)-9-hydroxy-8-(2-hydroxyethyl)-6-methylpyrrolo[3,4-c]carbazole-1,3(2H,6H)-dione;

4-(2-Chloro-phenyl)-9-hydroxy-8-(4-hydroxy-butoxy)-6-methyl-6H-pyrrolo[3,4-c]carbazole-1,3-dione;

4-(2-Chloro-phenyl)-9-hydroxy-8-(4-hydroxy-butyl)-6-methyl-6H-pyrrolo[3,4-c]carbazole-1,3-dione;

4-(2-Chlorophenyl)-9-hydroxy-8-[3-(methylamino)propoxy]pyrrolo[3,4-c]carbazole-1,3(2H,6H)-dione;

4-(2-Chlorophenyl)-9-hydroxy-8-[4-(1-pyrrolidinyl)butyl]pyrrolo[3,4-c]carbazole-1,3(2H,6H)-dione;

4-(2-Chlorophenyl)-9-hydroxy=8-[4-(methylamino) butyl]-6-propylpyrrolo[3,4-c]carbazole-1,3(2H,6H)-dione;

4-(2-Chlorophenyl)-9-hydroxy-8-[4-(methylamino) butyl]pyrrolo[3,4-c]carbazole-1,3(2H,6H)-dione;

4-(5-Amino-2-chlorophenyl)-9-hydroxypyrrolo[3,4-c]carbazole-1,3(2H,6H)-dione;

4-(5-Amino-2-methoxyphenyl)-9-hydroxypyrrolo[3,4-c]carbazole-1,3(2H,6H)-dione;

4-{[3-(4-(2-Chlorophenyl)-9-hydroxy-1,3-dioxo-2,3-dihydropyrrolo[3,4-c]carbazol-6 (1H)-yl) propyl] amino}benzoic acid;

6-(2-aminoethyl)-4-(2-chlorophenyl)-9-hydroxypyrrolo[3,4-c]carbazole-1,3 (2H,6H)-dione;

6-(2-anilinoethyl)-4-(2,6-dichlorophenyl)-9-hydroxypyrrolo[3,4-c]carbazole-1,3(2H,6H)-dione;

6-(2-anilinoethyl)-4-(2-chlorophenyl)-9-hydroxypyrrolo[3,4-c]carbazole-1,3(2H,6H)-dione;

6-(3-aminopropyl)-9-hydroxy-4-phenylpyrrolo[3,4-c]carbazole-1,3(2H,6H)-dione;

6-(3-anilinopropyl)-4-(2,6-dichlorophenyl)-9-hydroxypyrrolo[3,4-c]carbazole-1,3(2H,6H)-dione;

6-(3-anilinopropyl)-4-(2-chlorophenyl)-9-hydroxypyrrolo[3,4-c]carbazole-1,3(2H,6H)-dione;

6-(3-Anilinopropyl)-9-hydroxy-4-phenylpyrrolo[3,4-c]carbazole-1,3(2H,6H)—dione;

6-(3-Bromo-propyl)-4-(2-chloro-phenyl)-8-(3-dimethylamino-propoxy)-9-hydroxy-6H-pyrrolo[3,4-c]carbazole-1,3-dione;

6-(3-butenyl)-4-(2-chlorophenyl)-9-hydroxypyrrolo[3,4-c]carbazole-1,3(2H,6H)-dione;

6-[3-(Benzylamino)propyl]-9-hydroxy-4-phenylpyrrolo[3,4-c]carbazole-1,3(2H,6H)-dione;

6-[3-(diethylamino) propyl]-9-hydroxy-4-phenylpyrrolo[3,4-c]carbazole-1,3(2H,6H)-dione;

6-[6-(dimethylamino)hexyl]-9-hydroxy-4-phenylpyrrolo[3,4-c]carbazole-1,3(2H,6H)-dione;

6-allyl-4-(2-chlorophenyl)-9-hydroxypyrrolo[3,4-c]carbazole-1,3(2H,6H)-dione;

6-Benzyl-4-(2-chlorophenyl)-9-hydroxypyrrolo[3,4-c]carbazole-1,3(2H,6H)-dione;

6-butyl-4-(2,6-dichlorophenyl)-8-[3-(dimethylamino)propoxy]-9-hydroxypyrrolo [3,4-c]carbazole-1,3(2H,6H)-dione;

6-butyl-4-(2,6-dichlorophenyl)-8-[4-(dimethylamino)butyl]-9-hydroxypyrrolo [3,4-c]carbazole-1,3(2H,6H)-dione;

6-butyl-4-(2,6-dichlorophenyl)-9-hydroxy-8-[3-(methylamino) propoxy]pyrrolo [3,4-c]carbazole-1,3(2H,6H)-dione;

6-butyl-4-(2,6-dichlorophenyl)-9-hydroxy-8-[4-(methylamino) butyl]pyrrolo[3,4-c] carbazole-1,3(2H,6H)-dione;

6-butyl-4-6-methoxyphenyl-)-8-[3-(dimethylamino) propoxy]-9-hydroxypyrrolo [3,4-c]carbazole-1,3(2H,6H)-dione;

6-butyl-4-(2-chloro-6-methoxyphenyl)-8-[4-(dimethylamino) butyl]-9-hydroxypyrrolo[3,4-c]carbazole-1,3(2H,6H)-dione;

6-butyl-4-(2-chloro-6-methoxyphenyl)-9-hydroxy-8-[3-(methylamino) propoxy]pyrrolo[3,4-c]carbazole-1,3(2H,6H)-dione;

6-butyl-4-(2-chlorophenyl)-8-[3-(dimethylamino) propoxy]-9-hydroxypyrrolo [3,4-c]carbazole-1,3(2H,6H)-dione;

6-butyl-4-(2-chlorophenyl)-8-[4-(dimethylamino) butyl]-9-hydroxypyrrolo[3,4-c]carbazole-1,3(2H,6H)-dione;

6-butyl-4-(2-chlorophenyl)-9-hydroxy-8-[3-(methylamino) propoxy]pyrrolo[3,4-c]carbazole-1,3(2H,6H)-dione;

6-butyl-4-(2-chlorophenyl)-9-hydroxy-8-[4-(1-pyrrolidinyl) butyl]pyrrolo[3,4-c]carbazole-1,3(2H,6H)-dione;

6-sec-butyl-4-(2-chlorophenyl)-9-hydroxypyrrolo[3,4-c]carbazole-1,3(2H,6H)-dione;

7-(2-Amino-1-hydroxy-ethyl)-4-(2-chlorophenyl)-9-hydroxy-6-oxa-2-aza-[c]fluorene-1,3-dione;

8-(2,3-Dihydroxypropyl)-9-hydroxy-6-methyl-4-phenylpyrrolo[3,4-c]carbazole-1,3(2H,6H)-dione;

8-(4-aminobutyl)-4-(2-chlorophenyl)-9-hydroxy-6-methylpyrrolo[3,4-c]carbazole-1,3(2H,6H)-dione;

8-(4-aminobutyl)-4-(2-chlorophenyl)-9-hydroxypyrrolo[3,4-c]carbazole-1,3(2H,6H)-dione;

8-[2-(Dimethylamino)ethyl]-9-hydroxy-6-methyl-4-phenylpyrrolo[3,4-c]carbazole-1,3(2H,6H)-dione;

8-[3-(Dimethylamino)propoxy]-9-hydroxy-6-methyl-4-phenylpyrrolo[3,4-c]carbazole-1,3(2H,6H)-dione;

8-[3-(Dimethylamino)propyl]-9-hydroxy-6-methyl-4-phenylpyrrolo[3,4-c]carbazole-1,3(2H,6H)-dione;

8-{3-[Bis-(2-hydroxy-ethyl)-amino]-propoxy}-4-(2-chlorophenyl)-9-hydroxy-6-methyl-6H-pyrrolo[3,4-c]carbazole-1,3-dione;

8-Ethyl-9-hydroxy-6-methyl-4-phenylpyrrolo[3,4-c]carbazole-1,3(2H,6H)-dione;

9-Hydroxy-4-(2-hydroxyphenyl)-6-(3-hydroxypropyl)pyrrolo[3,4-c]carbazole-1,3(2H,6H)-dione;

9-Hydroxy-4-(2-methoxyphenyl)-6-[2-(4-morpholinyl)ethyl]pyrrolo[3,4-c]carbazole-1,3(2H,6H)-dione;

9-Hydroxy-4,5-diphenylpyrrolo[3,4-c]carbazole-1,3(2H,6H)-dione;

9-Hydroxy-4-phenyl-6-[3-(1-piperazinyl)propyl]pyrrolo[3,4-c]carbazole-1,3(2H,6H)-dione;

9-hydroxy-4-phenyl-6-[3-(1-piperidinyl)propyl]pyrrolo[3,4-c]carbazole-1,3(2H,6H)-dione;

9-hydroxy-4-phenyl-6-[3-(1-pyrrolidinyl) propyl]pyrrolo[3,4-c]carbazole-1,3(2H,6H)-dione;

9-Hydroxy-5-methyl-4-phenylpyrrolo[3,4-c]carbazole-1,3(2H,6H)-dione;

9-Hydroxy-6-(3-hydroxypropyl)-4-phenylpyrrolo[3,4-c]carbazole-1,3(2H,6H)-dione;

9-Hydroxy-6-(6-hydroxyhexyl)-4-phenylpyrrolo[3,4-c]carbazole-1,3(2H,6H)-dione;

9-Hydroxy-6-[2-(1H-imidazol-1-yl)ethyl]-4-phenylpyrrolo[3,4-c]carbazole-1,3(2H,6H)-dione;

9-Hydroxy-6-[2-(4-morpholinyl) ethyl]-4-phenylpyrrolo[3,4-c]carbazole-1,3(2H,6H)-dione;

9-hydroxy-6-[2-(methylamino)ethyl]-4-phenylpyrrolo[3,4-c]carbazole-1,3(2H,6H)-dione;

9-Hydroxy-6-[3-(1H-imidazol-1-yl) propyl]-4-phenylpyrrolo[3,4-c]carbazole-1,3(2H,6H)-dione;

9-hydroxy-6-[3-(4-methyl-1-piperazinyl)propyl]-4-phenylpyrrolo[3,4-c]carbazole-1,3(2H,6H)-dione;

9-Hydroxy-6-[3-(4-morpholinyl) propyl]-4-phenylpyrrolo[3,4-c]carbazole-1,3(2H,6H)-dione;

9-Hydroxy-6-[3-(niethylamino) propyl]-4-phenylpyrrolo[3,4-c]carbazole-1,3 (2H,6H)-dione;

9-hydroxy-6-[6-(4-methyl-1-piperazinyl)hexyl]-4-phenylpyrrolo[3,4-c]carbazole-1,3(2H,6H)-dione;

9-Hydroxy-6-methyl-4-phenylpyrrolo[3,4-c]carbazole-1,3(2H,6H)-dione;

9-Hydroxy-8-(2-hydroxyethyl)-6-methyl-4-phenylpyrrolo[3,4-c]carbazole-1,3(2H,6H)-dione;

9-Hydroxy-8-(3-hydroxypropyl)-6-methyl-4-phenylpyrrolo[3,4-c]carbazole-1,3(2H,6H)-dione;

N-[2-(Dimethylamino) ethyl]-3-(9-hydroxy-1,3-dioxo-4-phenyl-2,3-dihydropyrrolo[3,4-c]carbazol-6(1H)-yl) propanamide; and N-[2-(Dimethylamino)ethyl]-3-(9-hydroxy-4-(2-methoxyphenyl)-1,3-dioxo-2,3-dihydropyrrolo[3,4-c]carbazol-6 (1H)-yl) propanamide.

9. The compounds:

4-(4-Amino-2-methoxy-phenyl)-9-hydroxy-6H-pyrrolo[3,4-c]carbazole-1,3-dione;

4-(2-Chloro-phenyl)-9-hydroxy-8-(4-morpholin-4-yl-butyl)-6H-pyrrolo[3,4-c]carbazole-1,3-dione; hydrochloride salt;

4-(2-Chloro-phenyl)-8-[3-(3,5-dimethyl-piperazin-1-yl)-propoxy]-9-hydroxy-6-methyl-6H-pyrrolo[3,4-c]carbazole-1,3-dione;

4-(2-Chloro-phenyl)-9-hydroxy-8-(3-hydroxy-propoxy)-6-methyl-6H-pyrrolo [3,4-c]carbazole-1,3-dione;

4-(2-Chloro-phenyl)-9-hydroxy-8-(4-methylamino-butyl)-6H-pyrrolo[3,4-c]carbazole-1,3-dione;

2-(9-Hydroxy-1,3-dioxo-1,2,3,6-tetrahydro-pyrrolo[3,4-c]carbazol-4-yl)-benzamide;

4-(2-Chloro-phenyl)-8-(3-dimethylamino-propoxy)-9-hydroxy-6-(2-hydroxy-ethyl)-6H-pyrrolo[3,4-c]carbazole-1,3-dione;

4-(2-Chloro-phenyl)-9-hydroxy-6-(2-hydroxy-ethyl)-8-(3-pyrrolidin-1-yl-propoxy)-6H-pyrrolo[3,4-c]carbazole-1,3-dione;

4-(2-Chloro-phenyl)-9-hydroxy-6-methyl-8-(3-methylamino-propoxy)-6H-pyrrolo[3,4-c]carbazole-1,3-dione;

4-(2-Chloro-phenyl)-8-(3-dimethylamino-propoxy)-9-hydroxy-6-(3-hydroxy-propyl)-6H-pyrrolo[3,4-c]carbazole-1,3-dione;

6-(3-Bromo-propyl)-4-(2-chloro-phenyl)-8-(3-dimethylamino-propoxy)-9-hydroxy-6H-pyrrolo[3,4-c]carbazole-1,3-dione;

4-(2-Chloro-phenyl)-9-hydroxy-6-(3-hydroxy-propyl)-8-(3-pyrrolidin-1-yl-propoxy)-6H-pyrrolo[3,4-c]carbazole-1,3-dione;

4-(2-Chloro-phenyl)-8-[3-(3,5-dimethyl-piperazin-1-yl)-propoxy]-9-hydroxy-6-(3-hydroxy-propyl)-6H-pyrrolo[3,4-c]carbazole-1,3-dione;

4-(2-Chloro-phenyl)-9-hydroxy-8-(4-hydroxy-butyl)-6-methyl-6H-pyrrolo[3,4-c]carbazole-1,3-dione;

8-{3-[Bis-(2-hydroxy-ethyl)-amino]-propoxy}-4-(2-chloro-phenyl)-9-hydroxy-6-methyl-6H-pyrrolo[3,4-c]carbazole-1,3-dione;

4-(2-Chloro-phenyl)-9-hydroxy-6-(3-hydroxy-propyl)-8-[3-(4-methyl-piperazin-1-yl)-propoxy]-6H-pyrrolo[3,4-c]carbazole-1,3-dione;

4-(2-Chloro-phenyl)-9-hydroxy-8-(4-hydroxy-butoxy)-6-methyl-6H-pyrrolo[3,4-c]carbazole-1,3-dione;

4-(2-Chloro-phenyl)-9-hydroxy-6-methyl-8-(4-morpholin-4-yl-butyl)-6H-pyrrolo[3,4-c]carbazole-1,3-dione;

4-(2-Chloro-phenyl)-9-hydroxy-6-(2-hydroxy-ethyl)-8-[3-(4-methyl-piperazin-1-yl)-propoxy]-6H-pyrrolo[3,4-c]carbazole-1,3-dione;

4-(2-Chloro-phenyl)-8-(3-diethylamino-propoxy)-9-hydroxy-6-(2-hydroxy-ethyl)-6H-pyrrolo[3,4-c]carbazole-1,3-dione;

4-(2-Chloro-phenyl)-9-hydroxy-6-(3-hydroxy-propyl)-8-piperidin-4-yl-6H-pyrrolo[3,4-c]carbazole-1,3-dione;

4-(2-Chloro-phenyl)-8-(4-dimethylamino butyl)-9-hydroxy-6-methyl-6H-pyrrolo[3,4-c]carbazole-1,3-dione;

4-(2-Chloro-phenyl)-9-hydroxy-6-methyl-8-(4-pyrrolidin-1-yl-butyl)-6H-pyrrolo[3,4-c]carbazole-1,3-dione;

4-(2-Chloro-phenyl)-9-hydroxy-6-methyl-8-(4-methylamino-butyl)-6H-pyrrolo[3,4-c]carbazole-1,3-dione;

4-(2-Chloro-phenyl)-9-hydroxy-8-(3-hydroxy-2-methyl-propoxy)-6-methyl-6H-pyrrolo[3,4-c]carbazole-1,3-dione;

4-(2-Chloro-phenyl)-8-(4-dimethylamino-butoxy)-9-hydroxy-6-methyl-6H-pyrrolo[3,4-c]carbazole-1,3-dione;

4-(2-Chloro-phenyl)-9-hydroxy-6-methyl-8-[4-(4-methyl-piperazin-1-yl)-butyl]-6H-pyrrolo[3,4-c]carbazole-1,3-dione;

4-(2-Chloro-phenyl)-9-hydroxy-6-methyl-8-(4-pyrrolidin-1-yl-butoxy)-6H-pyrrolo[3,4-c]carbazole-1,3-dione;

4-(2-Chloro-phenyl)-8-[4-(3,5-dimethyl-piperazin-1-yl)-butoxy]-9-hydroxy-6-methyl-6H-pyrrolo[3,4-c]carbazole-1,3-dione;

4-(2-Chloro-phenyl)-9-hydroxy-6-methyl-8-[3-(4-methyl-piperazin-1-yl)-propoxy]-6H-pyrrolo[3,4-c]carbazole-1,3-dione;

3-[4-(2-Chloro-phenyl)-9-hydroxy-1,3-dioxo-8-(3-pyrrolidin-1-yl-propoxy)-2,3-dihydro-1H-pyrrolo[3,4-c]carbazol-6-yl]-propionamide;

4-(2-Chloro-phenyl)-9-hydroxy-6-methyl-8-[2-(1-methyl-pyrrolidin-2-yl)-ethoxy]-6H-pyrrolo[3,4-c]carbazole-1,3-dione;

4-(2-Chloro-phenyl)-9-hydroxy-6-methyl-8-[4-(4-methyl-piperazin-1-yl)-butoxy]-6H-pyrrolo[3,4-c]carbazole-1,3-dione;

4-(2-Chloro-phenyl)-9-hydroxy-6-methyl-8-(4-morpholin-4-yl-butoxy)-6H-pyrrolo[3,4-c]carbazole-1,3-dione;

4-(2-Fluoro-6-methoxy-phenyl)-9-hydroxy-6H-pyrrolo[3,4-c]carbazole-1,3-dione;

4-(2-Chloro-phenyl)-9-hydroxy-6-methyl-8-(2-methyl-3-pyrrolidin-1-yl-propoxy)-6H-pyrrolo[3,4-c]carbazole-1,3-dione;

4-(2-Chloro-phenyl)-9-hydroxy-8-(3-hydroxy-2,2-dimethyl-propoxy)-6-methyl-6H-pyrrolo[3,4-c]carbazole-1,3-dione;

4-(2-Chloro-phenyl)-9-hydroxy-6-methyl-1,3-dioxo-1,2,3,6-tetrahydro-pyrrolo[3,4-c]carbazole-8-carboxylic acid;

4-(2-Chloro-phenyl)-9-hydroxy-6-methyl-1,3-dioxo-1,2,3,6-tetrahydro-pyrrolo[3,4-c]carbazole-8-carboxylic acid amide;

4-(2-Chloro-phenyl)-9-hydroxy-6-methyl-1,3-dioxo-1,2,3,6-tetrahydro-pyrrolo[3,4-c]carbazole-8-carboxylic acid (2-pyrrolidin-1-yl-ethyl)-amide;

3-[4-(2-Chloro-phenyl)-8-(3-dimethylamino-propoxy)-9-hydroxy-1,3-dioxo-2,3-dihydro-1H-pyrrolo[3,4-c]carbazol-6-yl]-propionamide;

4-(2-Chloro-phenyl)-8-[3-(ethyl-propyl-amino)-propylsulfanyl]-9-hydroxy-6-methyl-6H-pyrrolo[3,4-c]carbazole-1,3-dione;

9-Hydroxy-6-methyl-4-phenyl-8-(3-pyrrolidin-1-yl-propoxy)-6H-pyrrolo[3,4-c]carbazole-1,3-dione;

N-[4-(2-Chloro-phenyl)-9-hydroxy-6-methyl-1,3-dioxo-1,2,3,6-tetrahydro-pyrrolo[3,4-c]carbazole-8-carbonyl]-methanesulfonamide;

2-Dimethylamino-ethanesulfonic acid[4-(2-chloro-phenyl)-9-hydroxy-6-methyl-1,3-dioxo-1,2,3,6-tetrahydro-pyrrolo[3,4-c]carbazole-8-carbonyl]-amide;

4-(2-Chloro-phenyl)-9-hydroxy-6-methyl-1,3-dioxo-1,2,3,6-tetrahydro-pyrrolo[3,4-c]carbazole-8-carboxylic acid dimethylamide;

4-(2-Chloro-phenyl)-9-hydroxy-8-(3-morpholin-4-yl-propoxy)-6H-pyrrolo[3,4-c]carbazole-1,3-dione;

4-(2-Chloro-phenyl)-9-hydroxy-6-methyl-8-(2-pyrrolidin-1-yl-ethoxy)-6H-pyrrolo[3,4-c]carbazole-1,3-dione;

8-(3-Amino-propoxy)-4-(2-chloro-phenyl)-9-hydroxy-6-methyl-6H-pyrrolo[3,4-c]carbazole-1,3-dione hydrochloride salt;

4-(2-Chloro-phenyl)-9-hydroxy-6-methyl-8-(2-methyl-3-pyrrolidin-1-yl-propoxy)-6H-pyrrolo[3,4-c]carbazole-1,3-dione;

4-(2-Chloro-phenyl)-9-hydroxy-8-[3-(4-methyl-piperazin-1-yl)-propoxy]-6H-pyrrolo[3,4-c]carbazole-1,3-dione;

4-(2-Chloro-phenyl)-9-hydroxy-8-(3-pyrrolidin-1-yl-propoxy)-6H-pyrrolo[3,4-c]carbazole-1,3-dione;

4-(2-Chloro-phenyl)-9-hydroxy-6-methyl-8-(2-morpholin-4-yl-ethoxy)-6H-pyrrolo[3,4-c]carbazole-1,3-dione;

4-(2-Chloro-phenyl)-9-hydroxy-6-methyl-8-[2-(4-methyl-piperazin-1-yl)-ethoxy]-6H-pyrrolo[3,4-c]carbazole-1,3-dione;

4-(2-Chloro-phenyl)-9-hydroxy-8-(3-hydroxy-propoxy)-6H-pyrrolo[3,4-c]carbazole-1,3-dione;

4-(2-Chloro-phenyl)-9-hydroxy-6-methyl-1,3-dioxo-1,2,3,6-tetrahydro-pyrrolo[3,4-c]carbazole-8-carboxylic acid (2-dimethylamino-ethyl)-methyl-amide;

4-(2-Chloro-phenyl)-9-hydroxy-6-methyl-1,3-dioxo-1,2,3,6-tetrahydro-pyrrolo[3,4-c]carbazole-8-carboxylic acid (1-ethyl-pyrrolidin-2-ylmethyl)-amide;

4-(2-Chloro-phenyl)-9-hydroxy-6-methyl-1,3-dioxo-1,2,3,6-tetrahydro-pyrrolo[3,4-c]carbazole-8-carboxylic acid (3-diethylamino-propyl)-amide;

4-(2-Chloro-phenyl)-9-hydroxy-6-methyl-8-(1H-tetrazol-5-yl)-6H-pyrrolo[3,4-c]carbazole-1,3-dione;

4-(2-Chloro-phenyl)-9-hydroxy-6-methyl-1,3-dioxo-1,2,3,6-tetrahydro-pyrrolo[3,4-c]carbazole-8-carboxylic acid[2-(1-methyl-pyrrolidin-2-yl)-ethyl]-amide;

4-(2-Chloro-phenyl)-9-hydroxy-6-(2-hydroxy-ethyl)-8-{3-[(2-hydroxy-ethyl)-methyl-amino]-propoxy}-6H-pyrrolo[3,4-c]carbazole-1,3-dione;

4-(2-Chloro-phenyl)-9-hydroxy-8-{3-[(2-hydroxy-ethyl)-methyl-amino]-propoxy}-6-methyl-6H-pyrrolo[3,4-c]carbazole-1,3-dione;

4-(2-Chloro-phenyl)-9-hydroxy-6-(2-hydroxy-ethyl)-8-(3-piperidin-1-yl-propoxy)-6H-pyrrolo[3,4-c]carbazole-1,3-dione;

4-(2-Chloro-phenyl)-9-hydroxy-6-methyl-8-(3-piperidin-1-yl-propoxy)-6H-pyrrolo[3,4-c]carbazole-1,3-dione;

8-[3-(Benzyl-methyl-amino)-propoxy]-4-(2-chloro-phenyl)-9-hydroxy-6-(2-hydroxy-ethyl)-6H-pyrrolo[3,4-c]carbazole-1,3-dione;

8-[3-(Benzyl-methyl-amino)-propoxy]-4-(2-chloro-phenyl)-9-hydroxy-6-methyl-6H-pyrrolo[3,4-c]carbazole-1,3-dione;

4-(2-Chloro-phenyl)-9-hydroxy-6-(2-hydroxy-ethyl)-8-[3-(4-pyridin-2-yl-piperazin-1-yl)-propoxy]-6H-pyrrolo[3,4-c]carbazole-1,3-dione;

4-(2-Chloro-phenyl)-9-hydroxy-6-methyl-8-[3-(4-pyridin-2-yl-piperazin-1-yl)-propoxy]-6H-pyrrolo[3,4-c]carbazole-1,3-dione;

4-(2-Chloro-phenyl)-8-(3-dipentylamino-propoxy)-9-hydroxy-6-(2-hydroxy-ethyl)-6H-pyrrolo[3,4-c]carbazole-1,3-dione;

4-(2-Chloro-phenyl)-8-(3-dipentylamino-propoxy)-9-hydroxy-6-methyl-6H-pyrrolo[3,4-c]carbazole-1,3-dione;

4-(2-Chloro-phenyl)-8-{3-[(2-dimethylamino-ethyl)-methyl-amino]-propoxy}-9-hydroxy-6-(2-hydroxy-ethyl)-6H-pyrrolo[3,4-c]carbazole-1,3-dione;

4-(2-Chloro-phenyl)-8-{3-[(2-dimethyl amino-ethyl)-methyl-amino]-propoxy}-9-hydroxy-6-methyl-6H-pyrrolo[3,4-c]carbazole-1,3-dione;

4-(2-Chloro-phenyl)-9-hydroxy-6-(2-hydroxy-ethyl)-8-[3-(3-hydroxy-pyrrolidin-1-yl)-propoxy]-6H-pyrrolo[3,4-c]carbazole-1,3-dione;

4-(2-Chloro-phenyl)-9-hydroxy-8-[3-(3-hydroxy-pyrrolidin-1-yl)-propoxy]-6-methyl-6H-pyrrolo[3,4-c]carbazole-1,3-dione;

4-(2-Chloro-phenyl)-8-[3-(cyclohexyl-methyl-amino)-propoxy]-9-hydroxy-6-(2-hydroxy-ethyl)-6H-pyrrolo[3,4-c]carbazole-1,3-dione;

4-(2-Chloro-phenyl)-8-[3-(cyclohexyl-methyl-amino)-propoxy]-9-hydroxy-6-methyl-6H-pyrrolo[3,4-c]carbazole-1,3-dione 4-(2-Chloro-phenyl)-9-hydroxy-6-(2-hydroxy-ethyl)-8-[3-(2-methyl-piperidin-1-yl)-propoxy]-6H-pyrrolo[3,4-c]carbazole-1,3-dione;

4-(2-Chloro-phenyl)-9-hydroxy-6-methyl-8-[3-(2-methyl-piperidin-1-yl)-propoxy]-6H-pyrrolo[3,4-c]carbazole-1,3-dione;

4-(2-Chloro-phenyl)-9-hydroxy-6-(2-hydroxy-ethyl)-8-[3-(2-hydroxymethyl-piperidin-1-yl)-propoxy]-6H-pyrrolo[3,4-c]carbazole-1,3-dione;

4-(2-Chloro-phenyl)-9-hydroxy-8-[3-(2-hydroxymethyl-piperidin-1-yl)-propoxy]-6-methyl-6H-pyrrolo[3,4-c]carbazole-1,3-dione;

4-(2-Chloro-phenyl)-9-hydroxy-6-(2-hydroxy-ethyl)-8-[3-(methyl-pyridin-3-ylmethyl-amino)-propoxy]-6H-pyrrolo[3,4-c]carbazole-1,3-dione;

4-(2-Chloro-phenyl)-9-hydroxy-6-methyl-8-[3-(methyl-pyridin-3-ylmethyl-amino)-propoxy]-6H-pyrrolo[3,4-c]carbazole-1,3-dione;

4-(2-Chloro-phenyl)-9-hydroxy-6-(2-hydroxy-ethyl)-8-[3-(2-hydroxymethyl-pyrrolidin-1-yl)-propoxy]-6H-pyrrolo[3,4-c]carbazole-1,3-dione;

4-(2-Chloro-phenyl)-9-hydroxy-8-[3-(2-hydroxymethyl-pyrrolidin-1-yl)-propoxy]-6-methyl-6H-pyrrolo[3,4-c]carbazole-1,3-dione;

4-(2-Chloro-phenyl)-8-[3-(ethyl-methyl-amino)-propoxy]-9-hydroxy-6-(2-hydroxy-ethyl)-6H-pyrrolo[3,4-c]carbazole-1,3-dione;

4-(2-Chloro-phenyl)-8-[3-(ethyl-methyl-amino)-propoxy]-9-hydroxy-6-methyl-6H-pyrrolo[3,4-c]carbazole-1,3-dione;

4-(2-Chloro-phenyl)-8-(3-dipropylamino-propoxy)-9-hydroxy-6-(2-hydroxy-ethyl)-6H-pyrrolo[3,4-c]carbazole-1,3-dione;

4-(2-Chloro-phenyl)-8-(3-dipropylamino-propoxy)-9-hydroxy-6-methyl-6H-pyrrolo[3,4-c]carbazole-1,3-dione;

4-(2-Chloro-phenyl)-8-(3-diethylamino-propoxy)-9-hydroxy-6-methyl-6H-pyrrolo[3,4-c]carbazole-1,3-dione;

8-{3-[Bis-(3-methyl-butyl)-amino]-propoxy}-4-(2-chloro-phenyl)-9-hydroxy-6-methyl-6H-pyrrolo[3,4-c]carbazole-1,3-dione;

4-(2-Chloro-phenyl)-8-[3-(2,6-dimethyl-piperidin-1-yl)-propoxy]-9-hydroxy-6-(2-hydroxy-ethyl)-6H-pyrrolo[3,4-c]carbazole-1,3-dione;

4-(2-Chloro-phenyl)-8-[3-(2,6-dimethyl-piperidin-1-yl)-propoxy]-9-hydroxy-6-methyl-6H-pyrrolo[3,4-c]carbazole-1,3-dione;

9-Hydroxy-6-(2-hydroxy-ethyl)-4-phenyl-8-(3-pyrrolidin-1-yl-propoxy)-6H-pyrrolo[3,4-c]carbazole-1,3-dione;

4-(2-Chloro-phenyl)-8-(3-dicyclohexylamino-propoxy)-9-hydroxy-6-(2-hydroxy-ethyl)-6H-pyrrolo[3,4-c]carbazole-1,3-dione; trifluoro-acetic acid salt;

4-(2-Chloro-phenyl)-8-(3-diisopropylamino-propoxy)-9-hydroxy-6-(2-hydroxy-ethyl)-6H-pyrrolo[3,4-c]carbazole-1,3-dione; trifluoro-acetic acid salt;

4-(2-Chloro-phenyl)-9-hydroxy-6-methyl-1,3-dioxo-1,2,3,6-tetrahydro-pyrrolo[3,4-c]carbazole-8-sulfonic acid (2-pyrrolidin-1-yl-ethyl)-amide;

4-(2-Chloro-phenyl)-8-(3-cyclohexylamino-propoxy)-9-hydroxy-6-methyl-6H-pyrrolo[3,4-c]carbazole-1,3-dione;

4-(2-Chloro-phenyl)-9-hydroxy-6-methyl-8-(3-pyrrolidin-1-yl-propane-1-sulfinyl)-6H-pyrrolo[3,4-c]carbazole-1,3-dione;

4-(2-Chloro-phenyl)-9-hydroxy-6-methyl-8-(3-pyrrolidin-1-yl-propane-1-sulfonyl)-6H-pyrrolo[3,4-c]carbazole-1,3-dione;

4-(2-Chloro-phenyl)-9-hydroxy-6-(2-hydroxy-ethyl)-8-(4-pyrrolidin-1-yl-butyl)-6H-pyrrolo[3,4-c]carbazole-1,3-dione;

4-(2-Chloro-phenyl)-9-hydroxy-6-(2-hydroxy-ethyl)-8-(4-morpholin-4-yl-butyl)-6H-pyrrolo[3,4-c]carbazole-1,3-dione;

4-(2-Chloro-phenyl)-9-hydroxy-6-(2-hydroxy-ethyl)-8-[4-(4-methyl-piperazin-1-yl)-butyl]-6H-pyrrolo[3,4-c]carbazole-1,3-dione;

4-(2-Chloro-phenyl)-8-[3-(ethyl-propyl-amino)-butoxy]-9-hydroxy-6-methyl-6H-pyrrolo[3,4-c]carbazole-1,3-dione; and 4-(2-Chloro-phenyl)-9-hydroxy-6-methyl-8-(1-methyl-3-pyrrolidin-1-yl-propoxy)-6H-pyrrolo[3,4-c]carbazole-1,3-dione.

* * * * *